(12) United States Patent
Renner et al.

(10) Patent No.: US 7,264,810 B2
(45) Date of Patent: *Sep. 4, 2007

(54) MOLECULAR ANTIGEN ARRAY

(75) Inventors: Wolfgang A. Renner, Zürich (CH); Martin Bachmann, Winterthur (CH); Alain Tissot, Zürich (CH); Patrick Maurer, Winterthur (CH); Franziska Lechner, Zürich (CH); Peter Sebbel, Zürich (CH); Christine Piossek, Winterthur (CH)

(73) Assignee: Cytos Biotechnology AG, Zürich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/050,902

(22) Filed: Jan. 18, 2002

(65) Prior Publication Data
US 2003/0175290 A1 Sep. 18, 2003

Related U.S. Application Data

(60) Provisional application No. 60/262,379, filed on Jan. 19, 2001, provisional application No. 60/288,549, filed on May 4, 2001, provisional application No. 60/326,998, filed on Oct. 5, 2001, provisional application No. 60/331,045, filed on Nov. 7, 2001.

(51) Int. Cl.
A61K 39/385 (2006.01)
A61K 9/00 (2006.01)
A61K 39/00 (2006.01)
A61K 47/30 (2006.01)

(52) U.S. Cl. ............... 424/185.1; 424/400; 424/192.1; 424/193.1; 424/194.1; 424/195.11; 424/196.11; 424/198.1; 424/278.1; 424/281.1; 424/282.1

(58) Field of Classification Search ............... 424/400, 424/184.1, 193.1, 196.11, 197.11, 278.1, 424/278.11, 185.1, 194.1, 198.1, 288.1, 195.11, 424/281.1, 192.1, 282.1; 530/403–405, 350
See application file for complete search history.

(56) References Cited

U.S. PATENT DOCUMENTS

| | | | |
|---|---|---|---|
| 4,722,840 A | 2/1988 | Valenzuela et al. | |
| 5,071,651 A | 12/1991 | Sabara et al. | |
| 5,143,726 A | 9/1992 | Thornton et al. | |
| 5,334,394 A | 8/1994 | Kossovsky et al. | |
| 5,374,426 A | 12/1994 | Sabara et al. | |
| 5,580,589 A | 12/1996 | Stoves et al. | |
| 5,580,859 A | 12/1996 | Felgner et al. | |
| 5,698,424 A * | 12/1997 | Mastico et al. | 435/477 |
| 5,739,026 A | 4/1998 | Garoff et al. | |
| 5,766,602 A | 6/1998 | Xiong et al. | |
| 5,770,380 A | 6/1998 | Hamilton et al. | |
| 5,789,245 A | 8/1998 | Dubensky, Jr. et al. | |
| 5,792,462 A | 8/1998 | Johnston et al. | |
| 5,814,482 A | 9/1998 | Dubensky, Jr. et al. | |
| 5,871,747 A | 2/1999 | Gengoux-Sedlik et al. | |
| 5,928,647 A | 7/1999 | Rock | |
| 5,935,821 A | 8/1999 | Chatterjee et al. | |
| 6,004,763 A | 12/1999 | Gengoux et al. | |
| 6,054,312 A | 4/2000 | Larocca et al. | |
| 6,231,864 B1 | 5/2001 | Birkett | |
| 6,380,364 B1 | 4/2002 | Mueller et al. | |
| 2002/0064533 A1 | 5/2002 | Murray | |
| 2002/0081295 A1 * | 6/2002 | Schiller et al. | 424/143.1 |
| 2003/0054010 A1 | 3/2003 | Sebbel et al. | |

FOREIGN PATENT DOCUMENTS

| | | |
|---|---|---|
| EP | 0 259 149 B1 | 12/1993 |
| EP | 0 578 293 A1 | 1/1994 |
| EP | 0 385 610 B1 | 3/1994 |
| EP | 0 465 081 B1 | 4/1994 |
| EP | 0 283 505 B1 | 7/1994 |
| EP | 0 425 082 A1 | 4/1995 |
| WO | WO90/15878 * | 12/1990 |
| WO | WO92/11291 A1 | 7/1992 |
| WO | WO 94/06472 A1 | 3/1994 |
| WO | WO94/06472 A1 | 3/1994 |
| WO | WO94/15585 A1 | 7/1994 |
| WO | WO 94/15585 A1 | 7/1994 |
| WO | WO96/05293 A1 | 2/1996 |
| WO | WO 96/05293 A1 | 2/1996 |
| WO | WO96/30523 A2 | 10/1996 |

(Continued)

OTHER PUBLICATIONS

Li et al (Current Molecular Medicine 3:773-779, 2003).*
Chackerian et al (Proceedings of the National Academy of Sciences USA 96:2373-2378, 1999).*
Witte et al (Cancer and Metastasis Reviews 17:155-161, 1998).*
Abraham, J.M., et al., "An invertible element of DNA controls phase variation of type 1 fimbriae of *Escherichia coli*," Proc. Natl. Acad. Sci. USA 82:5724-5727, National Academy Press (1985).

(Continued)

*Primary Examiner*—Bruce R. Campell
*Assistant Examiner*—Michelle Horning
(74) *Attorney, Agent, or Firm*—Sterne, Kessler, Goldstein & Fox P.L.L.C.

(57) ABSTRACT

The present invention is related to the fields of molecular biology, virology, immunology and medicine. The invention provides a composition comprising an ordered and repetitive antigen or antigenic determinant array. The invention also provides a process for producing an antigen or antigenic determinant in an ordered and repetitive array. The ordered and repetitive antigen or antigenic determinant is useful in the production of vaccines for the treatment of infectious diseases, the treatment of allergies and as a pharmaccine to prevent or cure cancer and to efficiently induce self-specific immune responses, in particular antibody responses.

218 Claims, 54 Drawing Sheets

FOREIGN PATENT DOCUMENTS

| WO | WO97/31948 A1 | 9/1997 |
|---|---|---|
| WO | WO98/15631 A1 | 4/1998 |
| WO | WO99/07839 A2 | 2/1999 |
| WO | WO 99/07839 A2 | 2/1999 |
| WO | WO99/28478 | 6/1999 |
| WO | WO 99/40934 A1 | 8/1999 |
| WO | WO99/40934 A1 | 8/1999 |
| WO | WO9950432 A1 | 10/1999 |
| WO | WO99/57289 | 11/1999 |
| WO | WO 99/67293 A1 | 12/1999 |
| WO | WO99/67293 A1 | 12/1999 |
| WO | WO 00/23955 A1 | 4/2000 |
| WO | WO 00/32227 A1 * | 6/2000 |
| WO | WO 00/32227 A2 | 6/2000 |
| WO | WO 00/50461 | 8/2000 |
| WO | WO 00/59928 A1 | 10/2000 |
| WO | WO 01/62284 A2 | 8/2001 |
| WO | WO 01/85208 A2 | 11/2001 |

OTHER PUBLICATIONS

Abraham, S.N., et al., "Glycerol-Induced Unraveling of the Tight Helical Conformation of *Escherichia coli* Type 1 Fimbriae," *J. Bacteriol.* 174:5145-5148, American Society for Microbiology (1992).

Adhin, M.R., et al., "Nucleotide Sequence from the ssRNA Bacteriophage JP34 Resolves the Discrepancy between Serological and Biophysical Classification," *Virology* 170:238-242, Academic Press, Inc. (1989).

Aguzzi, A., "Prion diseases, blood and the immune system: concerns and reality," *Haematologica* 85:3-10, Il Pensiero Scientifico Editore (Jan. 2000).

Ansel, K.M., et al., "In Vivo-activated CD4 T Cells Upregulate CXC Cheomkine Receptor 5 and Reprogram Their Response to Lymphoid Chemokines," *J. Exp. Med.* 190:1123-1134, The Rockefeller University Press (1999).

Ansel, K.M., et al., "A chemokine-driven positive feedback loop organizes lymphoid follicles," *Nature* 406:309-314, Nature Publishing Group (Jul. 2000).

Antonysamy, M.A., et al., "Evidence for a Role of IL-17 in Organ Allograft Rejection: IL-17 Promotes the Functional Differentiation of Dendritic Cell Progenitors," *J. Immunol.* 162:577-584, The American Association of Immunologists (1999).

Arenberg, D.A., et al., "The murine CC chemokine, 6C-kine, inhibits tumor growth and angiogenesis in a human lung cancer SCID mouse model," *Cancer Immunol. Immunother.* 49:587-592, Springer-Verlag (Jan. 2001).

Arnon, R., et al., "A mimotope peptide-based vaccine against *Schistosoma mansoni*: synthesis and characterization," *Immunology* 101:555-562, Blackwell Science, Ltd. (Dec. 2000).

Bachmann, M.F., and Zinkernagel, R.M., "The influence of virus structure on antibody responses and virus serotype formation," *Immunol. Today* 17:553-558, Elsevier Science, Ltd. (1996).

Bachmann, M.F., and Zinkernagel, R.M., "Neutralizing Antiviral B Cell Responses," *Annu. Rev. Immunol.* 15:235-270, Annual Reviews, Inc. (1997).

Bachmann, M.F., et al., "TRANCE, a Tumor Necrosis Factor Family Member Critical for CD40 Ligand-independent T Helper Cell Activation," *J. Exp. Med.* 189:1025-1031, The Rockefeller University Press (1999).

Banerjee, R.R., and Lazar, M.A., "Dimerization of Resistin and Resistin-like Molecules Is Determined by a Single Cysteine," *J. Biol. Chem.* 276:25970-25973, The American Society for Biochemistry and Molecular Biology, Inc. (Jul. 2001).

Bard, F. et al., "Peripherally administered antibodies against amyloid β-peptide enter the central nervous system and reduce pathology in a mouse model of Alzheimer disease," *Nat. Med.* 6:916-919, Nature Publishing Company (Aug. 2000).

Bass, S., and Yang, M., "Expressing cloned genes in *Escherichia coli*," in *Protein Function: A Practical Approach*, 2nd ed., Creighton, T.E., ed., IRL Press, Oxford, Great Britain, pp. 29-55 (1997).

Bernhagen, J., et al., "Purification, Bioactivity, and Secondary Structure Analysis of Mouse and Human Macrophage Migration Inhibitory Factor (MIF)," *Biochemistry* 33:14144-14155, American Chemical Society (1994).

Biaselle, C.J., and Millar, D.B., "Studies on Triton X-100 detergent micelles," *Biophys. Chem.* 3:355-361, North-Holland Publishing Company (1975).

Bleul, C.C., et al., "The lymphocyte chemoattractant SDF-1 is a ligand for LESTR/fusin and blocks HIV-1 entry," *Nature* 382:829-833, Nature Publishing Group (1996).

Blomfield, I.C., et al., "Type 1 Fimbriation and *fimE* Mutants of *Escherichia coli* K-12," *J. Bacteriol.* 173:5298-5307, American Society for Microbiology (1991).

Blomfield, I.C., et al., "Integration host factor stimulates both FimB- and FimE-mediated site-specific DNA inversion that controls phase variation of type 1 fimbriae expression in *Escherichia coli*," *Mol. Microbiol.* 23:705-717, Blackwell Science, Ltd. (1997).

Boder, E.T., and Wittrup, K.D., "Yeast Surface Display for Directed Evolution of Protein Expression, Affinity, and Stability," *Methods Enzymol.* 328:430-444, Academic Press (Oct. 2000).

Bonci, A., et al., "Relatedness and Phylogeny Within the Family of Periplasmic Chaperones Involved in the Assembly of Pili or Capsule-Like Structures of Gram-Negative Bacteria," *J. Mol. Evol.* 44:299-309, Springer-Verlag (1997).

Brandner, S., et al., "A crucial role for B cells in neuroinvasive scrapie," *Transfus. Clin. Biol.* 6:17-23, Elsevier, Paris (1999).

Brinton, Jr., C.C., "The structure, function, synthesis and genetic control of bacterial pili and a molecular model for DNA and RNA transport in gram negative bacteria," *Trans. N.Y. Acad. Sci.* 27:1003-1054, New York Academy of Sciences (1965).

Brown, K.D., et al., "A family of small inducible proteins secreted by leukocytes are members of a new superfamily that includes leukocyte and fibroblast-derived inflammatory agents, growth factors, and indicators of various activation processes," *J. Immunol.* 142:679-687, The American Association of Immunologists (1989).

Brown, P.M., et al., "A Single-Step Purification of Biologically Active Recombinant Human Interleukin-5 from a Baculovirus Expression System," *Protein Expr. Purif.* 6:63-71, Academic Press, Inc. (1995).

Brown, K.L., et al., "Scrapie replication in lymphoid tissues depends on prion protein-expressing follicular dendritic cells," *Nat. Med.* 11:1308-1312, Nature Publishing Company (1999).

Bullitt, E., et al., "Development of pilus organelle subassemblies *in vitro* depends on chaperone uncapping of a beta zipper," *Proc. Natl. Acad. Sci. USA* 93:12890-12895, National Academy Press (1996).

Bullitt, E., and Makowski, L., "Bacterial Adhesion Pili Are Heterologous Assemblies of Similar Subunits," *Biophys. J.* 74:623-632, Biophysical Society (1998).

Burger, J.A., et al., "Blood-derived nurse-like cells protect chronic lymphocytic leukemia B cells from spontaneous apoptosis through stromal cell-derived factor-1," *Blood* 96:2655-2663, The American Society of Hematology (Oct. 2000).

Burghoff, R.L., et al., "Utilization of the Mouse Large Intestine To Select an *Escherichia coli* F-18 DNA Sequence That Enhances Colonizing Ability and Stimulates Synthesis of Type 1 Fimbriae," *Infect. Immun.* 61:1293-1300, American Society for Microbiology (1993).

Cannon-Carlson S., et al., "Expression, Purification, and Characterization of Recombinant Human Interleukin-13 from NS-O Cells," *Protein Expr. Purif.*12:239-248, Academic Press (1998).

Chabaud, M., et al., "Enhancing Effect of IL-17 on IL-1—Induced IL-6 and Leukemia Inhibitory Factor Production by Rheumatoid Arthritis Synoviocytes and Its Regulation by Th2 Cytokines," *J. Immunol.* 161: 409-414, The American Association of Immunologists (1998).

Chabaud, M., et al., "Human Interleukin-17. A T Cell-Derived Proinflammatory Cytokine Produced by the Rheumatoid Synovium," *Arthritis Rheum.* 42:963-970, Wiley-Liss, Inc. (1999).

Chabaud, M., et al., "Contribution of Interleukin 17 to synovium matrix destruction in rheumatoid arthritis," *Cytokine 12*:1092-1099, Cell Press (Jul. 2000).

Clark, H.F, et al., "Comparative Characterization of a C-Type Virus-Producing Cell Line (VSW) and a Virus-Free Cell-Line (VH2) From *Vipera russelli*," *J. Natl. Cancer Inst. 51*:645-657, Oxford University Press (1973).

Clark-Lewis, I., et al., "Chemical Synthesis, Purification, and Characterization of Two Inflammatory Proteins, Neutrophil Activating Peptide 1 (Interleukin-8) and Neutrophil Activating Peptide 2," *Biochemistry 30*:3128-3135, American Chemical Society (1991).

Coffman, R.L., et al., "Antibody to Interleukin-5 Inhibits Helminth-Induced Eosinophilia in Mice," *Science 245*:308-310, American Association for the Advancement of Science (1989).

Cohen, C., and Parry D.A.D, "α-Helical coiled coils-a widespread motif in proteins," *Trends Biochem. Sci. 11*:245-248, Elsevier Science Publishers B.V. (1986).

Corti, M., et al., "GM1-ganglioside-Triton X-100 mixed micelles: changes of micellar properties studied by laser-light scattering and enzymatic methods," *Chem. Phys. Lipids 28*:197-214, Elsevier/North-Holland Scientific Publishers, Ltd. (1981).

Coutelier, J.-P., et al., "IgG2a Restriction of murine antibodies elicited by viral infections," *J. Exp. Med. 165*:64-69, The Rockefeller University Press (1987).

Crump, M.P., et al., "Solution Structure of Eotaxin, a Chemokine That Selectively Recruits Eosinophils in Allergic Inflammation," *J. Biol. Chem. 273*:22471-22479, The American Society for Biochemistry and Molecular Biology, Inc. (1998).

Davis, N.L., et al., "*In Vitro* Synthesis of Infectious Venezuelan Equine Encephalitis Virus RNA from a cDNA Clone: Analysis of a Viable Deletion Mutant," *Virology 171*:189-204, Academic Press (1989).

Daugherty, P.S., et al., "Development of an optimized expression system for the screening of antibody libraries displayed on the *Escherichia coli* surface," *Protein Eng. 12*:613-621, Oxford University Press (1999).

Dealwis, C., et al., "Crystal structure of chemically synthesized [N33A] stromal cell-drived factor 1α, a potent ligand for the HIV-1 "fusin" coreceptor," *Proc. Natl. Acad. Sci. USA 95*:6941-6946, National Academy Science (Jun. 2001).

Dodson, K.W., et al., "Outer-membrane PapC molecular usher discriminately recognizes periplasmic chaperone-pilus subunit complexes," *Proc. Natl. Acad. Sci. USA 90*:3670-3674, National Academy Press (1993).

Dudler, J., et al., "Effect of interleukin 17 on proteoglycan degradation in murine knee joints," *Ann. Rheum. Dis. 59*:529-532, Bmj Publishing Group (Jul. 2000).

Eckhardt, S.G., et al., "Hepatitis B Virus Core Antigen Has Two Nuclear Localization Sequences in the Arginine-Rich Carboxyl Terminus," *J. Virol. 65*:575-582, American Society for Microbiology (1991).

Eisenmesser, E.Z., et al., "Expression, Purification, Refolding, and Characterization of Recombinant Human Interleukin-13: Utilization of Intracellular Processing," *Protein Expr. Purif. 20*:186-195, Academic Press (Nov. 2000).

Eisenmesser, E.Z., et al., "Solution Structure of Interleukin-13 and Insights into Receptor Engagement," *J. Mol. Biol. 310*:231-241, Academic Press (Jun. 2001).

Eisenstein, B.I., "Phase Variation of Type 1 Fimbriae in *Escherichia coli* Is Under Transcriptional Control," *Science 214*:337-339, American Association for the Advancement of Science (1981).

Elisseeva, E.L., et al., "NMR Studies of Active N-terminal Peptides of Stromal Cell-derived Factor-1," *J. Biol. Chem. 275*:26799-26805, The American Society for Biochemistry and Molecular Biology, Inc. (Sep. 2000).

Eshdat, Y., et al., "Dissociation and Reassembly of *Escherichia coli* Type 1 Pili," *J. Bacterial. 148*:308-314, American Society for Microbiology (1981).

Ettinger, R., et al., "A Critical Role for Lymphotoxin-β Receptor in the Development of Diabetes in Nonobese Diabetic Mice," *J. Exp. Med. 193*:1333-1339, The Rockefeller University Press (Jun. 2001).

Fehr, T., et al., "Role of Repetitive Antigen Patterns for Induction of Antibodies Against Antibodies," *J Exp. Med. 185*:1785-1792, The Rockefeller University Press (1997).

Folkman, J., and Klagsbrun, M., "Angiogenic Factors," *Science 235*:442-447, American Association for the Advancement of Science (1987).

Folkman, J., "Angiogenesis in cancer, vascular, rheumatoid and other disease," *Nat. Med. 1*:27-31, Nature Publishing Company (1995).

Forssmann, U., et al., "Eotaxin-2, a Novel CC Chemokine that Is Selective for the Chemokine Receptor CCR3, and Acts Like Eotaxin on Human Eosinophil and Basophil Leukocytes," *J. Exp. Med. 185*:2171-2176, The Rockefeller University Press (1997).

Fossiez, F., et al., "T Cell Interleukin-17 Induces Stromal Cells to Produce Proinflammatory and Hematopoietic Cytokines," *J. Exp. Med. 183*:2593-2603, The Rockefeller University Press (1996).

Fossiez F., et al., "Interleukin-17," *Intern. Rev. Immunol. 16*:541-551, Harwood Academic Publishers (1998).

Fujiwara, K., et al., "Novel preparation method of immunogen for hydrophobic hapten, enzyme immunoassay for daunomycin and adriamycin," *J. Immunol. Methods 45*:195-203, Elsevier/North-Holland Biomedical Press (1981).

Gally, D.L., et al., "Environmental Regulation of the *fim* Switch Controlling Type 1 Fimbrial Phase Variation in *Escherichia coli* K-12: Effects of Temperature and Media," *J. Bacteriol. 175*:6186-6193, American Society for Microbiology (1993).

Gally, D. L., et al., "Interaction of FimB and FimE with the *fim* switch that controls the phase variation of type 1 fimbriate in *Escherichia coli* K-12," *Mol. Microbiol. 21*:725-738, Blackwell Science, Ltd. (1996).

Gherardi, E. et al., "A single-step procedure for cloning and selection of antibody-secreting hybridomas," *J. Immunol. Methods 126*: 61-68, Elsevier (1990).

Golmohammadi, R., et al., "The crystal structure of bacteriophage Qβ at 3.5Å resolution," *Structure 4*:543-554, Current Biology, Ltd. (1996).

Gunn, M.D., et al., "A B-cell-homing chemokine made in lymphoid follicles activates Burkitt's lymphoma receptor-1," *Nature 391*:799-803, Nature Publishing Group (1998).

Hanes, J., et al., "Picomolar affinity antibodies from a fully synthetic naive library selected and evolved by ribosome display," *Nat. Biotechnol. 18*:1287-1292, Nature Publishing Company (Dec. 2000).

Hanson, M.S., et al., "Purification of the *Escherichia coli* Type 1 Pilin and Minor Pilus Proteins and Partial Characterization of the Adhesin Protein," *J. Bacteriol. 170*:3350-3358, American Society for Microbiology (1988).

Hanson, M.S., and Brinton, Jr., C.C., "Identification and characterization of *E. coli* type-1 pilus tip adhesion protein," *Nature 332*:265-268, Nature Publishing Group (1988).

Harrison, J.L., et al., "Screening of Phage Antibody Libraries," *Methods Enzymol. 267*:83-109, Macmillan Publishers, Ltd. (1996).

Haalam, D.B., et al., "The amino-terminal domain of the P-pilus adhesin determines receptor specificity," *Mol. Microbiol. 14*:399-409, Blackwell Scientific Publications (1994).

Hedrick, J.A., and Zlotnik, A., "Identification and Characterization of a Novel β Chemokine Containing Six Conserved Cysteines," *J. Immunol. 159*: 1589-1593, The American Association of Immunologists (1997).

Heveker, N., et al., Dissociation of the signalling and antiviral properties of SDF-1-derived small peptides, *Curr. Biol. 8*:369-376, Current Biology, Ltd. (1998).

Hirel, P.-H., et al., "Extent of N-terminal methionine excision from *Escherichia coli* proteins is governed by the side-chain length of the penultimate amino acid," *Proc. Natl. Acad. Sci. USA 86*:8247-8251, National Academy Press (1989).

Holmes, W.D., et al., "Solution Studies of Recombinant Human Stromal-Cell-Derived Factor-1," *Prot. Expr. Purif. 21*:367-377, Academic Press (Apr. 2001).

Holmgren, A., et al., "Conserved immunoglobulin-like features in a family of periplasmic pilus chaperones in bacteria," *EMBO J. 11*:1617-1622, Oxford University Press (1992).

Holmgren, A., and Brändén, C.-I., "Crystal structure of chaperone protein PapD reveals an immunoglobulin fold," *Nature* 342:248-251, Nature Publishing Group (1989).

Hultgren, S.J., et al., "The PapG adhesin of uropathogenic *Escherichia coli* contains separate regions for receptor binding and for the incorporation into the pilus," *Proc. Nat. Acad. Sci. USA* 86:4357-4361, National Academy Press (1989).

Hultgren, S.J., et al., "PapD and superfamily of periplasmic immunoglobulin-like pilus chaperones," *Adv. Prot. Chem.* 44:99-123, Academic Press, Inc. (1993).

Hultgren, S.J., et al., "Pilus and Nonpilus Bacterial Adhesins: Assembly and Function in Cell Recognition," *Cell* 73:887-901, Cell Press (1993).

Hultrgen, S.J., et al., "Bacterial Adhesins and Their Assembly," in *Escherichia coli and Salmonella*, Neidhardt, F.C., et al., eds., ASM Press, Washington, D.C. pp. 2730-2756 (1996).

Humbles, A.A., et al., "Kinetics of Ectaxin Generation and Its Relationship to Eosinophil Accumulation in Allergic Airways Disease: Analysis in a Guinea Pig Model In Vvio," *J. Exp. Med.* 186:601-612, The Rockefeller University Press (1997).

Hung, D.L., et al., "Molecular basis of two subfamilies of immunoglobulin-like chaperones," *EMBO J.* 15:3792-3805, Oxford University Press (1996).

Hung, D.L. and Hultgren, S.J., "Pilus Biogenesis via the Chaperone/Usher Pathway: An Integration of Structure and Function," *J. Struct. Biol.* 124:201-220, Academic Press (1998).

Ikeda, T., et al., "Determination of Three Isoforms of the Receptor Activator of Nuclear Factor-κB Ligand and Their Differential Expression in Bone and Thymus," *Endocrinology* 142:1419-1426, The Endocrine Society (Apr. 2001).

Ingley E., et al., "Production and purification of recombinant human interleukin-5 from yeast and baculovirus expression systems," *Eur. J. Biochem.* 196:623-629, Blackwell Science, Ltd. (1991).

Jacob-Dubuisson, F., et al., "PapD chaperone function in pilus biogenesis depends on oxidant and chaperone-like activities of DsbA," *Proc. Natl. Acad. Sci. USA* 91:11552-11556, National Academy Press (1994).

Jacob-Dubuisson, F., et al., "Initiation of assembly and association of the structural elements of a bacterial pilus depend on two specialized tip proteins," *EMBO J.* 12:837-847, Oxford University Press (1993).

Jacob-Dubuisson, F., et al., "Chaperone-assisted Self-assembly of Pili Independent of Cellular Energy," *J. Biol. Chem.* 269:12447-12455, The American Society for Biochemistry and Molecular Biology, Inc. (1994).

Jiang, X., et al., "Norwalk Virus Genome Cloning and Characterization," *Science* 250:1580-1583, American Association for the Advancement of Science (1990).

Jones, C.H., et al., "FimC is a periplasmic PapD-like chaperone that directs assembly of type 1 pili in bacteria," *Proc. Natl. Acad. Sci. USA* 90:8397-8401, National Academy Press (1993).

Jones, C.H., et al., "FimH adhesin of type 1 pili is assembled into a fibrillar tip structure in the Enterbacteriaceae," *Proc. Natl. Acad. Sci. USA* 92:2081-2085, National Academy Press (1995).

Josien, R., et al., "TRANCE, a Tumor Necrosis Factor Family Member, Enhances the Longevity and Adjuvant Properties of Dendritic Cells In Vivo," *J. Exp. Med.* 191: 495-501, The Rockefeller University Press (Feb. 2000).

Jovanovic, D.V., et al., "IL-17 Stimulates the Production and Expression of Proinflammatory Cytokines, IL-β and TNF-α, by Human Macrophages," *J. Immunol.* 160:3513-3521, The American Association of Immunologists (1998).

Kapp, U., et al., "Interleukin 13 Is Secreted by and Stimulates the Growth of Hodgkin and Reed-Sternberg Cells," *J. Exp. Med.* 189:1939-1945, The Rockefeller University Press (1999).

Kastelein, R.A. et al., "Effect of the sequence upstream from the ribosome-binding site on the yield of protein from the cloned gene for phage MS2 coat protein," *Gene* 23:245-254, Elsevier (1983).

Kim, K.J., et al., "Inhibition of vascular endothelial growth factor-induced angiogenesis suppresses tumour growth *in vivo*," *Nature* 362:841-844, Nature Publishing Group (1993).

Kim, K.-H., et al., "A Cysteine-rich Adipose Tissue-specific Secretory Factor Inhibits Adipocyte Differentiation," *J. Biol. Chem.* 276:11252-11256, The American Society for Biochemistry and Molecular Biology, Inc. (Apr. 2001).

Klemm, P., "The *fimA* gene encoding the type-1 fimbrial subunit of *Escherichia coli*. Nucleotide sequence and primary structure of the protein," *Euro. J. Biochem.* 143:395-399, Blackwell Science, Ltd. (1984).

Klemm, P., and Christiansen, G., "Three *fim* genes required for the regulation of length and mediation of adhesion of *Escherichia coli* type 1 fimbriae," Mol. Gen. Genet. 208:439-445, Springer-Verlag (1987).

Klemm, P., et al., "The major subunit of *Escherichia coli* type 1 fimbriate is not required for D-mannose-specific adhesion," *Mol. Microbiol.* 4:553-559, Blackwell Scientific Publications (1990).

Klemm, P., and Christiansen, G., "The *fimD* gene required for cell surface localization of *Escherichia coli* type 1 fimbriae," *Mol. Gen. Genet.* 220:334-338, Springer-Verlag (1990).

Klemm, P., "FimC, a chaperone-like periplasmic protein of *Escherichia coli* involved in biogenesis of type 1 fimbriae," *Res. Microbiol.* 143:831-838, Institut Pasteur/Elsevier (1992).

Klemm, P., and Krogfelt, K.A., "Type 1 Fimbriae of *Escherichia coli*," in *Fimbriae*, Klemm, P., ed., CRC Press, Inc., Boca Raton, FL., pp. 9-26 (1994).

Kodama, S., et al., "Characterization of recombinant murine interleukin 5 expressed in Chinese hamster ovary cells," *Glycobiology* 2:419-427, Oxford University Press (1992).

Kodama, S., et al., "Carbohydrate Structures of Human Interleukin 5 Expressed in Chinese Hamster Ovary Cells," *J. Biochem.* (Tokyo) 110:693-701, Japanese Biochemical Society (1991).

Kopf, M., et al., "IL-5-Deficient Mice Have a Developmental Defect in CD5+ B-1 Cells and Lack Eosinophilia but have Normal Antibody and Cytotoxic T Cell Responses," *Immunity* 4:15-24, Cell Press (1996).

Koschel, M., et al., "Extensive Mutagenesis of the Hepatitis B Virus Core Gene and Mapping of Mutations That Allow Capsid Formation," *J. Virol* 73:2153-2160, American Society for Microbiology (1999).

Koths, K., et al., "Structure-Function Studies on Human Macrophage Colony-Stimulating Factor (M-CSF)," *Mol. Reprod. Dev.* 46:31-38, Wiley-Liss, Inc. (1997).

Kozlovska, T.M., et al., "Recombinant RNA phage Qβ capsid particles synthesized and self-assembled in *Escherichia coli,"Gene* 137:133-137, Elsevier Science Publishers B.V. (1993).

Kozlovskaya, T.M., et al., "Formation of capsid-like structures as a result of the expression of a cloned envelope protein from RNA-containing bacteriophage fr," *Dokl. Akad. Nauk. SSSR* 287: 452-455, Erivan Akademiia Nauk Armianskoi Ssr (1986).

Kozlovskaya, T.M., et al., "Formation of capsid-like structures as a result of the expression of a cloned envelope protein gene from RNA-containing bacteriophage fr," STNEasy, Accession No. 1986:219892, CAplus English abstract (1986) (Document AT37).

Krogfelt, K.A., et al., "Direct Evidence that the FimH Protein Is the Mannose-Specific Adhesin of *Escherichia coli* Type 1 Fimbriae," *Infect. Immun.* 58:1995-1998, American Society for Microbiology (1990).

Kuehn, M.J., et al., "Structural Basis of Pilus Subunit Recognition by the PapD Chaperone," *Science* 262:1234-1241, American Association for the Advancement of Science (1993).

Kunimoto, D.Y, et al., "High-level production of murine interleukin-5 (IL-5) utilizing recombinant baculovirus expression. Purification of the rIL-5 and its use in assessing the biologic role of IL-5 glycosylation," *Cytokine* 3:224-230, W.B. Saunders Company (1991).

Landschulz, W.H., et al., "The Leucine Zipper: A Hypothetical Structure Common to a New Class of DNA Binding Proteins," *Science* 240:1759-1764, American Association for the Advancement of Science (1988).

Leake, C.J., et al., "Cytopathic Effect and Plaque Formation by Arboviruses in a Continuous Cell Line (XTC-2) from the Toad *Xenopus laevis*," *J. gen. Virol.* 35:335-339, Cambridge University Press (1977).

Lee, K.H., et al., "Two-Dimensional Electrophoresis of Proteins as a Tool in the Metabolic Engineering of Cell Cycle Regulation," *Biotech. Bioeng.* 50:336-340, John Wiley & Sons, Inc. (1996).

Leech, M., et al., "Involvement of macrophage migration inhibitory factor in the evolution of rat adjuvant arthitis," *Arthritis Rheum.* 41:910-917, Arthritis Foundation (1998).

Leech, M., et al. "Regulation of macrophage migration inhibitory factor by endogenous glucocorticoid in rat adjuvant-induced arthritis," *Arthritis Rheum.* 43:827-833, Arthritis Foundation (Apr. 2000).

Liljeström, P., and Garoff, H., "A new generation of animal cell expression vectors based on the semliki forest virus replicon," *Bio/technology* 9:1356-1361, Nature Publishing Company (1991).

Liljeström, P., "Alphavirus expression systems," *Curr. Opin. Biotechnol.* 5:495-500, Current Biology, Ltd. (1994).

Lim, F., et al., "The RNA-binding Site of Bacteriophage Qβ Coat Protein," *J. Biol. Chem.* 271:31839-31845, The American Society for Biochemistry and Molecular Biology, Inc. (1996)

Lin, E.Y., et al., "Colony-stimulating Factor 1 Promotes Progression of Mammary Tumors to Malignancy," *J. Exp. Med.* 193:727-739, The Rockefeller University Press (Mar. 2001).

Lindberg, F., et al., "PapD, a Periplasmic Transport Protein in P-Pilus Biogenesis," *J. Bacteriol.* 171:6052-6058, American Society for Microbiology (1989).

Lo-Man, R., et al., "A recombinant virus-like particle system derived from parvovirus as an efficient antigen carrier to elicit a polarized Th1 immune response without adjuvant," *Eur. J. Immunol.* 28:1401-1407, Wiley-VCH Verlag GmbH (1998).

López, O., et al., "Direct formation of mixed micelles in the solubilization of phospholipid liposomes by Triton X-100," *FEBS Lett.* 426:314-318, Elsevier (1998).

Lowe, M.A., et al., "Immunoelectron Microscopic Analysis of Elongation of Type 1 Fimbriae in *Escherichia coli,*" *J. Bacteriol.* 169:157-163, American Society for Microbiology (1987).

Lu, D., et al., "Identification of the Residues in the Extracellular Region of KDR Important for Interaction with Vascular Endothelial Growth Factor and Neutralizing Anti-KDR Antibodies," *J. Biol. Chem.* 275:14321-14330, The American Society for Biochemistry and Molecular Biology, Inc. (May 2000).

Lum, L., et al., "Evidence for a Role of a Tumor Necrosis Factor-α(TNF-α)—converting Enzyme-like Protease in Shedding of TRANCE, a TNF Family Member Involved in Osteoclastogenesis and Dendritic Cell Survival," *J. Biol. Chem.* 274:13613-13618, The American Society for Biochemistry and Molecular Biology, Inc. (1999).

Lundstrom, K., "Alphaviruses as expression vectors," *Curr. Opin. Biotechnol.* 8:578-582, Current Biology, Ltd. (1997).

Luther, S.A., et al., "BLC Expression in Pancreatic Islets Causes B Cell Recruitment and Lymphotoxin-Dependent Lymphoid Neogenesis," *Immunity* 12:471-481, Cell Press (May 2000).

Mackay, J.L., and Browning, J.L., "Turning off follicular dendritic cells," *Nature* 395:26-27, Macmillan Magazines, Ltd. (1998).

Martiny-Baron, G., and Marmé, D., "VEGF-mediated tumour angiogenesis: a new target for cancer therapy," *Curr. Opin. Biotechnol.* 6:675-680, Current Biology, Ltd. (1995).

Matsui, S.M., et al., "The Isolation and Characterization of a Norwalk Virus-Specific cDNA," *J. Clin. Invest.* 87:1456-1461, The AMerican Society for Clinical Investigation, Inc. (1991).

Matsumoto, M., et al., "Role of Lymphotoxin and the Type 1 TNF Receptor in the Formaion of Germinal Centers," *Science* 271:1289-1291, American Association for the Advancement of Science (1996).

Matthews, W., et al., "A receptor tyrosine kinase cDNA isolated from a population of enriched primitive hematopoietic cells and exhibiting close genetic linkage to *c-kit,*" *Proc. Natl. Acad. Sci. USA* 88:9026-9030, National Academy Press (1991).

Matusevicius, , D., et al., "Interleukin-17 mRNA expression in blood and CSF mononuclear cells is augmented in multiple sclerosis," *Mult. Scler.* 5:101-104, Stockton Press (1999).

Mayer, K.l., and Stone, M.J., "NMR Solution Structure and Receptor Peptide Binding of the CC Chemokine Eotaxin-2," *Biochemistry* 39:8382-8395, American Chemical Society (Jul. 2000).

McClain, M.S., et al., "Roles of *fimB* and *fimE* in Site-Specific DNA Inversion Associated with Phase Variation of Type 1 Fimbriae in *Escherichia coli,*" *J. Bacteriol.* 173:5308-5314, American Society for Microbiology (1991).

McPherson, P.S., "Regulatory Role of SH3 Domain-mediated Protein-Protein Interactions in Synaptic Vesicle Endocytosis," *Cell Signal* 11:229-238, Elsevier Science, Inc. (1999).

Mikulowska, A., et al., "Macrophage Migration Inhibitory Factor Is Involved in the Pathogenesis of Collagen Type II-Induced Arthritis in Mice," *J. Immunol.* 158:5514-5517, The American Association of Immunoglists (1997)

Millauer, B., et al., "Glioblastoma growth inhibited *in vivo* by a dominant-negative Flk-1 mutant," *Nature* 367:576-579, Nature Publishing Group (1994).

Min, H., et al., "Osteoprotegerin Reverses Osteoporosis by Inhibiting Endosteal Osteoclasts and Prevents Vascular Calcification by Blocking a Process Resembling Osteoclastogenesis," *J. Exp. Med.* 192:463-474, The Rockefeller University Press (Aug. 2000).

Mitchell, D.L., et al., "Purification and characterization of recombinant murine interleukin-5 glycoprotein, from a Baculovirus expression system," *Biochem. Soc. Trans.* 21:332S, Portland Press (1993).

Montrasio, F. et al., "Impaired Prion Replication in Spleens of Mice Lacking Functional Follicular Dendritic Cells," *Science* 288:1257-1259, American Association for the Advancement of Science (May 2000).

Morein, B., et al., "Iscom, a novel structure for antigenic presentation of membrane proteins from enveloped viruses," *Nature* 308:457-460, Nature Publishing Group (1984).

Moriya, C., et al., "Large quantity production with extreme convenience of human SDF-1α and SDF-1β by a Sendai virus vector," *FEBS Lett.* 425:105-111, Amsterdam Elsevier Science B.V. (1998).

Müller, A., et al., "Involvement of chemokine receptors in breast cancer metastasis," *Nature* 410:50-56, Nature Publishing Group (Mar. 2001).

Murphy, Jr., K.P., et al., "Expression of Human Interleukin-17 in *Pichia pastoris*: Pyrification and Characterization," *Protein Expr. Purif.* 12:208-214, Academic Press (1998).

Nagira, M., et al., "Molecular Cloning of a Novel Human CC Chemokine Secondary Lymphoid-Tissue Chemokine That Is a Potent Chemoattractant for Lymphocytes and Mapped to Chromosome 9p13," *J. Biol. Chem.* 272:19518-19524, The American Society for Biochemistry and Molecular Biology, Inc. (1997).

Nanki, T., et al., "Stromal Cell-Derived Factor-1-CXC Chemokine Receptor 4 Interactions Play a Central Role in CD4$^+$ T Cell Accumlation in Rheumatoid Arthritis Synovium," *J. Immuno.* 165:6590-6598, The American Association of Immunologists (Dec. 2000).

Naureckiene, S., and Uhlin., B.E., "*In vitro* analysis of mRNA processing by Rnase E in the pap operon of *Escherichia coli,*" *Mol. Microbiol.* 21:55-68, Blackwell Science, Ltd. (1996).

Neirynck, S., et al., "A universal influenza A vaccine based on the extracellular domain of the M2 protein," *Nat. Med.* 5:1157-1163, Nature Publishing Company (1999).

Newman, J.V., et al., "Stimulation of *Escherichia coli* F-18Col$^-$ Type-1 fimbriae synthesis by *leuX,*" *FEMS Microbiol. Lett.* 122:281-287, Elsevier (1994).

Ni, C.-Z., et al., "Crystal structure of the coat protein from the GA bacteriophage: Model of the unassembled dimer," *Protein Sci.* 5:2485-2493, Cambridge University Press (1996).

Nilsson, P., et al., "Mutations Affecting mRNA Processing and Fimbrial Biogenesis in the *Escherichia coli pap* Operon," *J. Bacterial.* 178:683-690, American Society for Microbiology (1996).

Oberlin, E., et al., "The CXC chemokine SDF-1 is the ligand for LESTR/fusin and prevents infection by T-cell-line-adapted HIV-1," *Nature* 382:833-835, Nature Publishing Group (1996).

Ohnishi, Y., et al., "Crystal Structure of Recombinant Native SDF-1α with Additional Mutagenesis Studies: An Attempt at a More Comprehensive Interpretation of Accumulated Structure-Activity Relationship Data," *J. Interferon Cytokine Res.* 20:691-700, Mary Ann Liebert, Inc. (Aug. 2000).

Olszewska, W., et al., "Protection against Measles Virus-Induced Encephalitis by Anti-mimotope Antibodies: The Role of Antibody Affinity," *Virology* 272:98-105, Academic Press (Jun. 2000).

Orndorff, P.E., and Falkow, S., "Identification and Characterization of a Gene Product That Regulates Type 1 Piliation in *Escherichia coli,*" *J. Bacteriol.* 160:61-66, American Society for Microbiology (1984).

Orndorff, P.E., and Falkow, S., "Nucleotide Sequence of *pilA*, the Gene Encoding the Structural Component of Type 1 Pili in *Escherichia coli,*" *J. Bacteriol.* 162:454-457, American Society for Microbiology (1985).

O'Shea, E.K., et al., "Evidence That the Leucine Zipper Is a Coiled Coil," *Science* 243:538-542, American for the Advancement of Science (1989).

O'Shea, E.K., et al., "Mechanism of Specificity in the Fos-Jun Oncoprotein Heterodimer," *Cell* 68:699-708, Cell Press (1992).

Pandit, J., et al., "Three-dimensional Structure of Dimeric Human Recombinant Macrophage Colony-Stimulating Factor," *Science* 258:1358-1362, American Association for the Advancement of Science (1992).

Pierrot, C., et al., "Expression of Rat Interleukin-5 and Generation of Neutralizing Antiserum: a Comparative Study of Rat IL-5 Produced in *Escherichia coli* and Insect Cells," *Biochem. Biophys. Res. Commun.* 253:756-760, Academic Press (1998).

Pierson-Mullany, L.K., et al. "Characterization of polyclonal allergen-specific IgE responses by affinity distributions," *Mol. Immunol.* 37:613-620, Elsevier Science, Ltd. (Aug. 2000).

Piossek, C., et al., "Vascular Endothelial Growth Factor (VEGF) Receptor II-derived Peptides Inhibit VEGF," *J. Biol. Chem.* 274:5612-5619, The American Society for Biochemistry and Molecular Biology, Inc. (1999).

Presta, L.G., et al., "Humanization of an Anti-Vascular Endothelial Growth Factor Monoclonal Antibody for the Therapy of Solid Tumors and Other Disorders," *Cancer Res.* 57:4593-4599, The American Association for Cancer Research (1997).

Priano, C., et al., "A Complete Plasmid-based Complementation System for RNA Coliphage Qβ: Three Proteins of Bacteriophage Qβ (Group III) and SP (Group IV) can be Interchanged," *J. Mol. Biol.* 249:283-297, Academic Press, Ltd. (1995).

Proudfoot, A.E.I., et al., "Preparation and characterization of human interleukin-5 expressed in recombinant *Escherichia coli,*" *Biochem. J.* 270:357-361, Portland Press, Ltd. (1990).

Renner, W.A., et al., "Recombinant Cyclin E Expression Activates Proliferation and Obviates Surface Attachment of Chinese Hamster Ovary (CHO) Cells in Protein-Free Medium," *Biotech. Bioeng.* 47:476-482, John Wiley & Sons, Inc. (1995).

Risau, W., "Mechanisms of angiogenesis," *Nature* 386:671-674, Nature Publishing Group (1997).

Ritter, A., et al., "The Pai-associated *leuX* specific tRNA$_5^{Leu}$ affects type 1 fimbriation in pathogenic *Escherichia coli* by control of FimB recombinase expression," *Mol. Microbiol.* 25:871-882, Blackwell Science, Ltd. (1997).

Roesch, P.L., and Blomfield, I.C., "Leucine alters the interaction of the leucine-responsive recombination in *Escherichia coli,*" *Mol. Microbiol.* 27:751-761, Blackwell Science, Ltd. (1998).

Roher, A.E., et al., "Isolation and Chemical Characterization of Alzheimer's Disease Paired Helical Filament Cytoskeletons: Differentiation from Amyloid Plaque Core Protein," *J. Cell Biol.* 107:2703-2716, The Rockefeller University Press (1988).

Roher, A.E., et al., "Morphological and Biochemical Analyses of Amyloid Plaque Core Proteins Purified from Alzheimer Disease Brain Tissue," *J. Neurochem.* 61:1916-1926, Raven Press, Ltd. (1993).

Romagnani, S., "The Th1/Th2 paradigm," *Immunol. Today* 18:263-266, Elsevier Science, Ltd. (1997).

Rothenberg, M.E., et al., "Targeted Disruption of the Chemokine Eotaxin Partially Reduces Antigen-induced Tissue Eosinophilia," *J. Exp. Med.* 185:785-790, The Rockefeller University Press (1997).

Rusconi, S., et al., "In vitro inhibition of HIV-1 by Met-SDF-1β alone or in combination with antiretroviral drugs," *Antivir. Ther.* 5:199-204, International Medical Press (Sep. 2000).

Russell, P.W., and Orndorff, P.E., "Lesions in Two *Escherichia coli* Type 1 Pilus Genes Alter Pilus Number and Length without Affecting Receptor Binding," *J. Bacteriol.* 174:5923-5935, American Society for Microbiology (1992).

Santos, L., et al., "Role of macrophage migration inhibitory factor (MIF) in murine antigen-induced arthritis: interaction with glucocorticoids," *Clin. Exp. Immunol.* 123:309-314, Blackwell Science (Feb. 2001).

Saulino, E.T., et al., "Ramifications of kinetic partitioning on usher-mediated pilus biogenesis," *EMBO J.* 17:2177-2185, Oxford University Press (1998).

Schenk, D., et al., "Immunization with amyloid-β attenuates Alzheimer-disease-like pathology in the PDAPP mouse," *Nature* 400:173-177, Nature Publishing Group (1999).

Schlesinger, S., "Alphaviruses—vectors for the expression of heterologous genes," *Trends Biotechnol.* 11:18-22, Elsevier Science Publishers, Ltd. (1993).

Selkoe, D.J., "Translating cell biology into therapeutic advances in Alzheimer's disease," *Nature* 399:A23-A31, Nature Publishing Group (1999).

Slonim, L.N., et al., "Interactive surface in the PapD chaperone cleft is conserved in pilus chaperone superfamily and essential in subunit recognition and assembly," *EMBO J.* 11:4747-4756, Oxford University Press (1992).

Smyth, C.J., et al., "Fimbrial adhesins: similarities and variations in structure and biogenesis," *FEMS Immun. Med. Microbiol.* 16:127-139, Elsevier (1996).

Soto, H., et al., "The CC chemokine 6Ckine binds the CXC chemokine receptor CXCR3," *Proc. Natl. Acad. Sci. USA* 95:8205-8210, National Academy Press (1998).

Soto, G.E., et al., "Periplasmic chaperone recognition motif of subunits mediates quaternary interactions in the pilus," *EMBO J.* 17:6155-6167, Oxford University Press (1998).

Soto, G.E., and Hultgren, S.J., "Bacterial Adhesins: Common Themes and Variations in Architecture and Assembly," *J. Bacteriol.* 181:1059-1071, American Society for Mircobiology (1999).

Steppan, C.M., et al., "The hormone resistin links obesity to diabetes," *Nature* 409:307-312, Nature Publishing Group (Jan. 2001).

Stollar, V., "Togaviruses in Cultured Arthropod Cells," in *The Togaviruses. Biology, Structure, Replication*, Schlesinger, R.W., ed., Academic Press, Inc. New York, N.Y., pp. 583-621 (1980).

Strauss, J., and Strauss, E.G., "The Alphaviruses: Gene Expression, Replication and Evolution," *Microbiol. Rev.* 58:491-562, American Society for Microbiology (1994).

Striker, R.T., et al., "Stable Fiber-forming and Non-fiber-forming Chaperone-Subunit Complexes in Pilus Biogenesis," *J. Biol. Chem.* 269:12233-12239, The American Society for Biochemistry and Molecular Biology, Inc. (1994).

Sturchler-Pierrat, C., et al., "Two amyloid precursor protein transgenic mouse models with Alzheimer disease-like pathology," *Proc. Natl. Acad. Sci. USA* 94:13287-13292, National Academy Press (1997).

Sun, H.-W., et al., "Crystal structure at the 2.6-Å resolution of human macrophage migration inhibitory factor," *Proc. Natl. Acad. Sci. USA* 93:5191-5196, National Academy Press (1996).

Tang, J.-L., et al., "Interleukin-17 antagonism inhibits but not chronic vascular rejection," *Transplantation* 72:348-350, Lippincott Williams & Wilkens , (Jul. 2001).

Tanimori, H., et al., "Enzyme immunoassay of neocarzinostatin using β-galactosidase as label," *J. Pharm. Dyn.* 4:812-819, Pharmaceutical Society of Japan (1981).

Teixeira, M.M., et al., "Chemokine-induced Eosinophil Recruitment. Evidence of a Role for Endogenous Eotaxin in an In Vivo Allergy Model in Mouse Skin," *J. Clin. Invest.* 100:1657-1666, The AMerican Society for Clinical Investigation, Inc. (1997).

Tewari, R., et al., "Neurophil Activation by Nascent FimH Subunits of Type I Fimbriae Purified from the Periplasm of *Escherichia coli,*" *J. Biol. Chem.* 268:3009-3015, The American Society for Biochemistry and Molecular Biology, Inc. (1993).

Teunissen, M.B.M., et al., "Interleukin-17 and Interferon-γ Synergize in the Enhancement of Proinflammatory Cytokine by Human Keratinocytes," *J. Invest. Dermatol.* 111:645-649, The Society for Investigative Dermatology, Inc. (1998).

Thanassi, D.G., et al., "The PapC usher forms an oligomeric channel: Implications for pilus biogenesis across the outer membrane," *Proc. Natl. Acad. Sci. USA* 95:3146-3151, National Academy Press (1998).

De Togni, P., et al., "Abnormal Development of Peripheral Lymphoid Organs in Mice Deficient in Lymphotoxin," *Science* 264:703-707, American Association for the Advancement of Science (1994).

Topchieva, I., and Karezin, K., "Self-Assembled Supramolecular Micellar Structures Based on Non-ionic Surfactants and Cyclodextrins," *J. Colloid Interface Sci.* 213:29-35, Academic Press (1999).

Twomey, T., et al., "Structure and immunogenicity of experimental foot-and-mouth disease and poliomyelitis vaccines," *Vaccine* 13:1603-1610, Elsevier Science, Ltd. (1995).

Ulrich, R., et al., "Core particles of hepatitis B virus as carrier for foreign epitopes," *Adv. Virus Res.* 50:141-182, Academic Press (1998).

Vicari, A.P., et al., "Antitumor Effects of the Mouse Chemokine 6Ckine/SLC Through Angiostatic and Immunobiological Mechanisms," *J. Immunol.* 165:1992-2000, The American Association of Immunologists (Aug. 2000).

Visintin, M. et al., "Selection of antibodies for intracellular function using a two-hybrid *in vivo* systems," *Proc. Natl. Acad. Sci. USA* 96:11723-11728, National Academy Press (1999).

Walse, B., et al., "Transferred nuclear Overhauser effect spectroscopy study of a peptide from PapG pilus subunit bound by the *Escherichia coli* PapD chaperone," *FEBS Lett.* 412:115-120, Elsevier Science B.V. (1997).

Warnes, A., et al., "Expression of the measles virus nucleoprotein gene in *Eshcerichia coli* and assembly of nucleocapsid-like structures," *Gene* 160:173-178, Elsevier Science B.V. (1995).

Watson, E., et al., "Structure determination of the intact major sialylated oligosaccharide chains of recombinant human erythropoietin expressed in Chinese hamster ovary cells," *Glycobiology* 4:227-237, Oxford University Press (1994).

Wei, Y.Q., et al., "Immunotherapy to tumors with xenogeneic endothelial cells as a vaccine," *Nat. Med.* 6:1160-1166, Nature Publishing Company (Oct. 2000).

Witherell, G.W., and Uhlenbeck, O.C., "Specific RNA Binding by Qβ Coat Protein," *Biochemistry* 28:71-76, American Chemical Society (1989).

Wong, C.K., et al., "Elevation of proinflammatory cytosine (IL-18, IL-17, IL-12) and Th2 cytokine (IL-4) concentrations in patients with systemic lupus erythematosus," *Lupus* 9:589-593, Macmillan Publishers Ltd. (2000).

Wu, Q., et al. "Reversal of Spontaneous Autoimmune Insulitis in Nonobese Diabetic Mice by Soluble Lymphotoxin Receptor," *J. Exp. Med.* 193:1327-1332, The Rockefeller University Press (Jun. 2001).

Wuttke, M., et al., "Structural Characterization of Human Recombinant and Bone-derived Bone Sialoprotein," *J. Biol. Chem.* 276:36839-36848, The American Society for Biochemistry and Molecular Biology, Inc. (2001).

Wynne, S.A., et al., "The Crystal Structure of the Human Hepatitis B Virus Capsid," *Mol. Cell* 3:771-780, Cell Press (1999).

Xiong, C., et al., "Sinbis Virus: An Efficient, Broad Host Range Vector for Gene Expression in Animal Cells," *Science* 243:1188-1191, American Association for the Advancement of Science (1989).

Yao, Z., et al., "Human IL-17: A Novel Cytokine Derived from T Cells," *J. Immunol.* 155:5483-5485, The American Association of Immunologists (1995).

Yao, Z., et al., "Molecular characterization of the human interleukin (IL)-17 receptor," *Cytokine* 9:794-800, Academic Press, Ltd. (1997).

Yone, K., et al., "Epitopic Regions for Antibodies against Tumor Necrosis Factor α," *J. Biol. Chem.* 270:19509-19515, The American Society for Biochemistry and Molecular Biology, Inc. (1995).

Yuan, T-T., et al., "Subtype-Independent Immature Secretion and Subtype-Dependent Replication Deficiency of a Highly Frequent, Naturally Occuring Mutation of Human Hepatitis B Virus Core Antigen," *J. Virol.* 73:10122-10128, American Society for Microbiology (1999).

Zang, M., et al., "Production of Recombinant Proteins in Chinese Hamster Ovary Cells Using A Protein-Free Cell Culture Medium," *Bio/Technology* 13:389-392, Nature Publishing Company (1995).

Zhou, S., and Standring, D.N., "Cys Residues of the Hepatitis B Virus Capsid Protein Are Not Essential for the Assembly of Viral Core Particles but Can Influence Their Stability," *J. Virol.* 66:5393-5398, American Society for Microbiology (1992).

Zimmermann, N., et al., "Murine Eotaxin-2: A Constitutive Eosinophil Chemokine Induced by Allergen Challenge and IL-4 Overexpression," *J. Immunol.* 165:5839-5846, The American Association of Immunologists (Nov. 2000).

Ziolkowska, M., et al., "High Levels of IL-17 in Rheumatoid Arthritis Patients: IL-15 Triggers In Vitro IL-17 Production Via Cyclosporin A-Sensitive Mechanism," *J. Immunol.* 164:2832-2838, The American Association of Immunologists (Mar. 2000).

Zuercher, A.W., et al., "Oral anti-IgE immunization with epitope-displaying phage," *Eur. J. Immunol.* 30:128-135, Wiley-Vch Verlag GmbH (Jan. 2000).

Co-pending U.S. Appl. No. 09/449,631, inventors Renner et al., filed Nov. 30, 1999.

Co-pending U.S. Appl. No. 10/050,898, inventors Renner et al., filed Jan. 18, 2002.

Fehr, T., et al., "T cell-independent type I antibody response against B cell epitopes expressed repetitively on recombinant virus particles," *Proc. Natl. Acad. Sci. USA* 95:9477-9481, National Academy Press (1998).

Frenkel, D., et al., "Generation of auto-antibodies towards Alzheimer's disease vaccination," *Vaccine* 19:2615-2619, Elsevier Science, Ltd. (Mar. 2001).

International Search Report for International Application No. PCT/IB02/00166 mailed on Oct. 29, 2002.

International Search Report for International Application No. PCT/IB02/00168 mailed on Nov. 4, 2002.

NCBI Entrez, GenBank Report, Accession No. P03153, from Seeger, C., et al. (Jan. 1990).

NCBI Entrez, GenBank Report, Accession No. X59397, from Jordan, C.T., et al. (Nov. 1991).

NCBI Entrez, GenBank Report, Accession No. 711678A, from Shipolini, R.A., et al. (Jul. 1992).

NCBI Entrez, GenBank Report, Accession No. M27603, from Orndorff, P.E., and Falkow, S. (Apr. 1993).

NCBI Entrez, GenBank Report, Accession No. M20706, from Nassal M. (Apr. 1993).

NCBI Entrez, GenBank Report, Accession No. AAA37490, from Rouvier E. (Jul. 1993).

NCBI Entrez, GenBank Report, Accession No. M90520, from Kew, M.C., et al. (Aug. 1993).

NCBI Entrez, GenBank Report, Accession No. X00981, from Klemm, P. (Sep. 1993).

NCBI Entrez, GenBank Report, Accession No. VCBPQB, from Maita, T., and Konigsberg, W. (Dec. 1993).

NCBI Entrez, GenBank Report, Accession No. AAA16663, from Kozlovska, T.M., et al. (Mar. 1994).

NCBI Entrez, GenBank Report, Accession No. X02514, from Yanisch-Perron, C., et al. (May 1994).

NCBI Entrez, GenBank Report, Accession No. X85256, from Lai, M.E., et al. (Apr. 1995).

NCBI Entrez, GenBank Report, Accession No. X85259, from Lai, M.E., et al., (Apr. 1995).

NCBI Entrez, GenBank Report, Accession No. X85260, from Lai, M.E., et al. (Apr. 1995).

NCBI Entrez, GenBank Report, Accession No. X85272, from Lai, M.E., et al. (Apr. 1995).

NCBI Entrez, GenBank Report, Accession No. X85275, from Lai, M.E., et al. (Apr. 1995).

NCBI Entrez, GenBank Report, Accession No. X85284, from Lai, M.E., et al. (Apr. 1995).

NCBI Entrez, GenBank Report, Accession No. X85285, from Lai, M.E., et al. (Apr. 1995).

NCBI Entrez, GenBank Report, Accession No. X85286, from Lai, M.E., et al. (Apr. 1995).
NCBI Entrez, GenBank Report, Accession No. X85287, from Lai, M.E., et al. (Apr. 1995).
NCBI Entrez, GenBank Report, Accession No. X85291, from Lai, M.E., et al. (Apr. 1995).
NCBI Entrez, GenBank Report, Accession No. X85293, from Lai, M.E., et al. (Apr. 1995).
NCBI Entrez, GenBank Report, Accession No. X85295, from Lai, M.E., et al. (Apr. 1995).
NCBI Entrez, GenBank Report, Accession No. X85296, from Lai, M.E., et al. (Apr. 1995).
NCBI Entrez, GenBank Report, Accession No. X85297, from Lai, M.E., et al. (Apr. 1995).
NCBI Entrez, GenBank Report, Accession No. X85298, from Lai, M.E., et al. (Apr. 1995).
NCBI Entrez, GenBank Report, Accession No. X85299, from Lai, M.E., et al. (Apr. 1995).
NCBI Entrez, GenBank Report, Accession No. X85301, from Lai, M.E., et al. (Apr. 1995).
NCBI Entrez, GenBank Report, Accession No. X85302, from Lai, M.E., et al. (Apr. 1995).
NCBI Entrez, GenBank Report, Accession No. X85303, from Lai, M.E., et al. (Apr. 1995).
NCBI Entrez, GenBank Report, Accession No. X85305, from Lai, M.E., et al. (Apr. 1995).
NCBI Entrez, GenBank Report, Accession No. X85307, from Lai, M.E., et al. (Apr. 1995).
NCBI Entrez, GenBank Report, Accession No. X85311, from Lai, M.E., et al. (Apr. 1995).
NCBI Entrez, GenBank Report, Accession No. X85314, from Lai, M.E., et al. (Apr. 1995).
NCBI Entrez, GenBank Report, Accession No. X85315, from Lai, M.E., et al. (Apr. 1995).
NCBI Entrez, GenBank Report, Accession No. X85316, from Lai, M.E., et al. (Apr. 1995).
NCBI Entrez, GenBank Report, Accession No. X85317, from Lai, M.E., et al. (Apr. 1995).
NCBI Entrez, GenBank Report, Accession No. X85319, from Lai, M.E., et al. (Apr. 1995).
NCBI Entrez, GenBank Report, Accession No. X80925, from Karayiannis, P. (Dec. 1995).
NCBI Entrez, GenBank Report, Accession No. AAC50341, from Yao, Z., et al. (Jan. 1996).
NCBI Entrez, GenBank Report, Accession No. X72702, from Preisler-Adams, S., et al. (Feb. 1996).
NCBI Entrez, GenBank Report, Accession No. VCBPR7, from Weber, K., et al. (Apr. 1996).
NCBI Entrez, GenBank Report, Accession No. 1604193A, from Gomez, F., et al. (Oct. 1996).
NCBI Entrez, GenBank Report, Accession No. B56338, from Hoffman, D.R. (May 1997).
NCBI Entrez, GenBank Report, Accession No. U95551, from Rao, B.S., et al. (Jun. 1997).
NCBI Entrez, GenBank Report, Accession No. S14764, from Vandermeers, A., et al. (Oct. 1997).
NCBI Entrez, GenBank Report, Accession No. P03611, from Weber, K., et al. (Nov. 1997).
NCBI Entrez, GenBank Report, Accession No. AAC14699, from Beekwilder, M.J., et al. (Apr. 1998).
NCBI Entrez, GenBank Report, Accession No. AAC14704, from Beekwilder, M.J., et al. (Apr. 1998).
NCBI Entrez, GenBank Report, Accession No. AF043593, from Gunther, S., et al. (May 1998).
NCBI Entrez, GenBank Report, Accession No. 1POC, from Scott, D.L., et al. (Sep. 1998).
NCBI Entrez, GenBank Report, Accession No. CAA30374, from Inokuchi, Y., et al. (Feb. 1999).
NCBI Entrez, GenBank Report, Accession No. X02496, from Bichko, V., et al. (Apr. 1999).
NCBI Entrez, GenBank Report, Accession No. MFIV62, from Cox, N.J., et al. (Jul. 1999).
NCBI Entrez, GenBank Report, Accession No. VCBPFR, from Wittman-Liebold, B., et al. (Jul. 1999).
NCBI Entrez, GenBank Report, Accession No. A59055, from Hoffman, D.R., and Schmidt, J.O. (Aug. 1999).
NCBI Entrez, GenBank Report, Accession No. B59055, from Hoffman, D.R., and Schmidt, J.O. (Aug. 1999).
NCBI Entrez, GenBank Report, Accession No. AF051814, from Boyd, E.F., and Hartl, D.L. (Sep. 1999).
NCBI Entrez, GenBank Report, Accession No. AF051815, from Boyd, E.F., and Hartl, D.L. (Sep. 1999).
NCBI Entrez, GenBank Report, Accession No. AF110999, from Chang, S.F., et al. (Oct. 1999).
NCBI Entrez, GenBank Report, Accession No. AB033559, from Okamoto, H., et al. (Oct. 1999).
NCBI Entrez, GenBank Report, Accession No. AB010289, from Koseki, T., et al. (Dec. 1999).
NCBI Entrez, GenBank Report, Accession No. AJ132364, from Graupner, S., et al. (Apr. 2000).
NCBI Entrez, GenBank Report, Accession No. AF237482, from Johnson, J.R., et al. (May 2000).
NCBI Entrez, GenBank Report, Accession No. M32138, from Tong, S.P., et al. (Jul. 2000).
NCBI Entrez, GenBank Report, Accession No. AF229646, from Skerker, J.M., and Shapiro, L. (Aug. 2000).
NCBI Entrez, GenBank Report, Accession No. M95589, from Shi, H., et al (Jan. 2001).
NCBI Entrez, GenBank Report, Accession No. VCBPM2, from Min Jou, W., et al. (Jan. 2001).
NCBI Entrez, GenBank Report, Accession No. AF323080, from Steppan, C.M., et al. (Jan. 2001).
NCBI Entrez, GenBank Report, Accession No. AF323081, from Steppan, C.M., et al. (Jan. 2001).
NCBI Entrez, GenBank Report, Accession No. U14003, from Plunket, G., III, et al. (Jan. 2001).
NCBI Entrez, GenBank Report, Accession No. AF121239, from Hannoun, C., et al. (Feb. 2001).
NCBI Entrez, GenBank Report, Accession No. AF121240, from Hannoun, C., et al. (Feb. 2001).
NCBI Entrez, GenBank Report, Accession No. AF121242, from Hannoun, C., et al. (Feb. 2001).
NCBI Entrez, GenBank Report, Accession No. X59795, from Lai, M.E., et al. (Mar. 2001).
NCBI Entrez, GenBank Report, Accession No. X65257, from Lai, M.E., et al. (Mar. 2001).
NCBI Entrez, GenBank Report, Accession No. X65258, from Lai, M.E., et al. (Mar. 2001).
NCBI Entrez, GenBank Report, Accession No. AF151735, from Gerner, P., et al. (Apr. 2001).
NCBI Entrez, GenBank Report, Accession No. AJ000636, from Gousset, N., et al. (Nov. 2001).
NCBI Entrez, GenBank Report, Accession No. AAB59424, from Kenten, J.H., et al. (Feb. 2002).
NCBI Entrez, GenBank Report, Accession No. AAC06250, from Beekwilder, M.J., et al. (Mar. 2002).
NCBI Entrez, GenBank Report, Accession No. L09137, from Yanisch-Perron, C., et al. (May 2002).
NCBI Entrez, GenBank Report, Accession No. O09006, from Hromas, R., et al. (Jun. 2002).
NCBI Entrez, GenBank Report, Accession No. P40224, from Nagasawa, T., et al. (Jun. 2002).
NCBI Entrez, GenBank Report, Accession No. P34884, from Bernhagen, J., et al. (Jun. 2002).
NCBI Entrez, GenBank Report, Accession No. P06821, from Winter, G., et al. (Jun. 2002).
NCBI Entrez, GenBank Report, Accession No. P30904, from Sakai, M., et al. (Jun. 2002).
NCBI Entrez, GenBank Report, Accession No. NP_040754, from Inokuchi, Y., et al. (Jun. 2003).
NCBI Entrez, GenBank Report, Accession No. NP_061354, from Ishikawa, S., et al. (Sep. 2003).
NCBI Entrez, GenBank Report, Accession No. NP_031804, from Lenda, D.M., et al. (Sep. 2003).

NCBI Entrez, GenBank Report, Accession No. NP_006410, from Luther, S.A., et al. (Sep. 2003).
NCBI Entrez, GenBank Report, Accession No. NP_000748, from Yao, G.Q., et al. (Sep. 2003).
NCBI Entrez, GenBank Report, Accession No. P03069, from Hinnebusch, A.G., et al. (Sep. 2003).
NCBI Entrez, GenBank Report, Accession No. O00585, from Hromas, R., et al. (Sep. 2003).
NCBI Entrez, GenBank Report, Accession No. P14174, from Weiser, W.Y., et al. (Sep. 2003).
NCBI Entrez, GenBank Report, Accession No. P48061, from Spotila, L.D., et al. (Sep. 2003).
NCBI Entrez, GenBank Report, Accession No. P80003, from Vandermeers, A., et al. (Sep. 2003).
Swiss-Prot/TrEMBL, TN11_Mouse, Primary Accession No. O35235, entered in Swiss-Prot in Oct. 2001.
Swiss-Prot/TrEMBL, TN11_Human, Primary Accession No. O14788, entered in Swiss-Prot in Oct. 2001.
Co-pending U.S. Appl. No. 10/622,064, inventors Bachmann et al., filed Jul. 18, 2003 (Not Published).
Co-pending U.S. Appl. No. 10/617,876, inventors Bachmann et al., filed Jul. 14, 2003 (Not Published).
Co-pending U.S. Appl. No. 10/622,087, inventors Bachmann et al., filed Jul. 18, 2003 (Not Published).
Co-pending U.S. Appl. No. 10/622,124, inventors Bachmann et al., filed Jul. 18, 2003 (Not Published).
Jegerlehner, A., et al., "A molecular assembly system that renders antigens of choice highly repetitive for induction of protective B cell responses," *Vaccine* 20:3104-3112, Elsevier Science, Ltd. (Aug. 2002).
*The Biology of Animal Viruses*, 2nd ed., Fenner, F., et al., eds., Academic Press, New York, NY, pp. 117-119 (1974).
NCBI Entrez, PubMed Abstract, PMID: 2205968, Diallo, A., et al., "Morbillivirus group: genome organization and proteins," *Vet. Microbiol.* 23:155-163 (1990).
Kozlovska, T.M., et al., "RNA Phage Qβ Coat Protein as a Carrier for Foreign Epitopes," *Intervirology* 39:9-15, S. Karger AG (1996).
Kratz, P.A., et al., "Native display of complete foreign protein domains on the surface of hepatitis B virus capsids," *Proc. Natl. Acad. Sci. USA* 96:1915-1920, National Academy of Sciences (1999).
Nieland, J.D., et al., "Chimeric Papillomavirus Virus-like Particles Induce a Murine Self-Antigen-Specific Protective and Therapeutic Antitumor Immune Response," *J. Cell. Biochem.* 73:145-152, Wiley-Liss, Inc. (1999).
Slepushkin, V.A., et al., "Protection of mice against influenza A virus challenge by vaccination with baculovirus-expressed M2 protein," *Vaccine* 13:1399-1402, Elsevier Science Ltd. (1995).
Vasiljeva, I., et al., "Mosaic Qβ coats as a new presentation model," *FEBS Lett.* 431:7-11, Federation of European Biochemical Societies (1998).
International Search Report for International Application No. PCT/IB 02/00166, mailed Jan. 31, 2003.
Baba, T.W., et al., "Pathogenicity of Live, Attenuated SIV After Mucosal Infection of Neonatal Macaques," *Science* 267:1820-1825, American Association for the Advancement of Science (1995).
Bachmann, M.F., et al., "Dendritic cells process exogenous viral proteins and virus-like particles for Class I presentation to CD8+ cytotoxic T lymphocytes," *Eur. J. Immunol.* 26:2595-2600, VCH Verlagsgesellschaft mbH (1996).
Boorsma, M., et al., "A temperature-regulated replicon-based DNA expression system," *Nat. Biotechnol.* 18:429-432, Nature America, Inc. (Apr. 2000).
Borisova, G., et al., "Hybrid Hepatitis B Virus Nucleocapsid Bearing an Immunodominant Region from Hepatitis B Virus Surface Antigen," *J. Virol.* 67:3696-3701, American Society for Microbiology (1993).
Cesareni, G., "Peptide display on filamentous phage capsids: A new powerful tool to study protein-ligand interaction," *FEBS Lett.* 307:66-70, Elsevier Science Publishers B.V. (1992).
Connor, R.I., et al., "Immunological and Virological and Virological Analyses of Persons Infected by Human Immunodeficiency Virus Type 1 while Participating in Trials of Recombinant gp120 Subunit Vaccines," *J. Virol.* 72:1552-1576, American Society for Microbiology (1998).
Crameri, R. and Suter, M., "Display of biologically active proteins on the surface of filamentous phages: a cDNA cloning system for selection of functional gene products linked to the genetic information responsible for their production," *Gene* 137:69-75, Elsevier Science Publishers B.V. (1993).
Daniel, M.D., et al., "Protective Effects of a Live Attenuated SIV Vaccine with a Deletion in the *nef* Gene," *Science* 258:1938-1941, American Association for the Advancement of Science (1992).
de la Cruz, V.F., et al., "Immunogenicity and Epitope Mapping of Foreign Sequences via Genetically Engineered Filamentous Phage," *J. Biol. Chem.* 263:4318-4322, The American Society for Biochemistry and Molecular Biology, Inc. (1988).
Donnelly, J.J., et al., "DNA Vaccines," *Annu. Rev. Immunol.* 15:617-648, Annual Reviews, Inc. (1997).
Ebina, S., et al., "Chemical Modification of Bovine Pancreatic Trypsin Inhibitor for Single Site Coupling of Immunogenic Peptides for NMR Conformational Analysis," *J. Biol. Chem.* 264:7882-7888, The American Society for Biochemistry and Molecular Biology, Inc. (1989).
Esposito, G., et al., "Conformational study of a short *Pertussis* toxin T cell epitope incorporated in a multiple antigen peptide template by CD and two-dimensional NMR: Analysis of the structural effects on the activity of synthetic immunogens," *Eur. J. Biochem.* 217:171-187, Blackwell Science Ltd. on behalf of the Federation of European Biochemical Societies (1993).
Förster, E., et al., "Natural and recombinant enzymatically active or inactive bee venom phospholipase $A_2$ has the same potency to release histamine from basophils in patients with Hymenoptera allergy," *J. Allergy Clin. Immunol.* 95:1229-1235, Mosby-Year Book, Inc. (1995).
Frolov, I., et al., "Alphavirus-based expression vectors: Strategies and applications," *Proc. Natl. Acad. Sci. USA* 93:11371-11377, National Academy Press (1996).
Gilbert, S.C., et al., "A protein particle vaccine containing multiple malaria epitopes," *Nat. Biotechnol.* 15:1280-1284, Nature America Publishing (1997).
Greenstone, H.L., et al., "Chimeric paillomavirus virus-like particles elicit antitumor immunity against the E7 oncoprotein in an HPV16 tumor model," *Proc. Natl. Acad. Sci. USA* 95:1800-1805, National Academy Press (1998).
Hahn, C.S., et al., "Infectious Sindbis virus transient expression vectors for studying antigen processing and presentation," *Proc. Natl. Acad. Sci. USA* 89:2679-2683, National Academy Press (1992).
Harding, C.V., and Song, R., "Phagocytic Processing of Exogenous Particulate Antigens by Macrophages for Presentation by Class I MHC Molecules," *J. Immunol.* 153:4925-4933, The American Association of Immunologists (1994).
Hilleman, M.R., "Six decades of vaccine development—a personal history," *Nat. Med Vaccine Suppl.* 4:507-514 (May 1998).
Hui, E. K-W. et al., "Hepatitis B viral core proteins with an N-terminal extension can assemble into core-like particles but cannot be enveloped," *J. Gen. Virol.* 80:2647-2659, Society for General Microbiology (1999).
Iannolo, G., et al., "Construction, Exploitation and Evolution of a New Peptide Library Displayed at High Density by Fusion to the Major Coat Protein of Filamentous Phage," *Biol. Chem.* 378:517-521, Walter de Gruyter & Co. (1997).
Iannolo, G., et al., "Modifying Filamentous Phage Capsid: Limits in the Size of the Major Capsid Protein," *J. Mol. Biol.* 248:835-844, Academic Press, Ltd. (1995).
Ikram, H., and Prince, A.M., "A method for coupling the Hepatitis B surface antigen to aldehyde-fixed erythrocytes for use in passive hemagglutination," *J. Virol. Methods* 2:269-275, Elsevier/North-Holland Biomedical Press (1981).
Kovacsovics-Bankowski, M., et al., "Efficient major histocompatibility complex class I presentation of exogenous antigen upon phagocytosis by macrophages," *Proc. Natl. Acad. Sci. USA* 90:4942-4946, National Academy Press (1993).

Lo, K. K-W., et al., "Surface-modified mutants of cytochrome P450cam: enzymatic properties and electromchemistry," *FEBS Lett.* 451:342-346, Elsevier Science B.V. on behalf of the Federation of European Biochemical Societies (1999).

Minenkova, O.O., et al., "Design of specific immunogens using filamentous phage as the carrier," *Gene* 128:85-88, Elsevier Science Publishers B.V. (1993).

Neurath, A.R., et al., "Hepatitis B Virus surface antigen (HBsAg) as carrier for synthetic peptides having an attached hydrophobic tail," *Mol. Immunol.* 26:53-62, Pergamon Press (1989).

Perham, R.N., et al., "Engineering a peptide epitope display system on filamentous bacteriophage," *FEMS Microbiol. Rev.* 17:25-31, Elsevier Science Publishers on behalf of the Federation of European Microbiological Societies (1995).

Petrenko, V.A., et al., "A library of organic landscapes on filamentous phage," *Protein Engin.* 9:797-801, Oxford University Press (1996).

Pumpens, P. and Grens, E., "Hepatitis B core particles as a universal display model: a structure-function basis for development," *FEBS Lett.* 442:1-6, Elsevier Science B.V. on behalf of the Federation of European Biochemical Societies (1999).

Quash, G., et al., "The preparation of latex particles with covalently bound polyamines IgG and measles agglutinins and their use in visual agglutination tests," *J. Immunol. Methods* 22:165-174, Elsevier/North-Holland Biomedical Press (1978).

Raychaudhuri, S., and Rock, K.L., "Fully mobilizing host defense: Building better vaccines," *Nat. Biotechnol.* 16:1025-1031, Nature America, Inc. (1998).

Redfield, R.R., et al., "Disseminated vaccinia in a military recruit with Human Immunodeficiency Virus (HIV) disease," *N. Eng. J. Med.* 316:673-676, Massachusetts Medical Society (1987).

Rudolf, M.P., et al., Molecular Basis for Nonanaphylactogenicty of a Monoclonal Anti-IgE Antibody, *J. Immunol.* 165:813-819, The American Association of Immunologists (2000).

Sedlik, C., et al., "Recombinant parvovirus-like particles as an antigen carrier: A novel nonreplicative exogenous antigen to elicit protective antiviral cytotoxic T cells," *Proc. Natl. Acad. Sci. USA* 94:7503-7508, National Academy Press (1997).

Shen, L., et al., "Recombinant Virus Vaccine-Induced SIV-Specific $CD8^+$ Cytotoxic T Lymphocytes," *Science* 252:440-443, American Association for the Advancement of Science (1991).

Tanimori, H., et al., "Enzyme Immunoassay of Neocarzinostatin Using β-Galactosidase as Label," *J. Pharm. Dyn.* 4:812-819, Pharmaceutical Society of Japan (1981).

Townsend, A., and Bodmer, H., "Antigen recognition by class I-restricted T lymphocytes," *Ann. Rev. Immunol.* 7:601-624, Annual Reviews, Inc. (1989).

VanCott, T.C., et al., "Antibodies with Specificity to Native gp120 and Neutralization Activity against Primary Human Immunodeficiency Virus Type 1 Isolates Elicited by Immunization with Oligomeric gp160," *J. Virol.* 71:4319-4330, American Society for Microbiology (1997).

Watkins, S.J., et al., "The 'adenobody' approach to viral targeting: specific and enhanced adenoviral gene delivery," *Gene Ther.* 4:1004-1012, Stockton Press (1997).

Willis, A.E., et al., "Immunologists properties of foreign peptides in multiple display on a filamentous bacteriophage," *Gene* 128:79-83, Elsevier Science Publishers B.V. (1993).

Dialogue File 351, Accession No. 7431992, Derwent WPI English language abstract for WO 94/06472 (Document AP3).

International Preliminary Examination Report for International Application No. PCT/IB99/01925, European Patent Office, Munich (Aug. 2000) (not for publication).

Artelt, P., et al., "Vectors for efficient expression in mammalian fibroblastoid, myeloid and lymphoid cells via transfection or infection," *Gene* 68:213-219, Elsevier Science Publishers B.V. (1988).

Kilby, J.M., et al., "Potent suppression of HIV-1 replication in humans by T-20, a peptide inhibitor of gp41-mediated virus entry," *Nat. Med.* 4:1302-1307, Nature America, Inc. (1998).

McReynolds, L., et al., "Sequence of chicken ovalbumin mRNA," *Nature* 273:723-728, Macmillan Magazines, Ltd. (1978).

Wild, C., et al., "Letter to the Editor: A Synthetic Peptide from HIV-1 gp41 Is a Potent Inhibitor of Virus-Mediated Cell-Cell Fusion," *AIDS Res. Hum. Retroviruses* 9:1051-1053, Mary Ann Liebert, Inc. (1993).

Invitrogen Manual, "Sindbis Expression System Version C," from internet web page http://www.invitrogen.com/manuals.html, Catalog No. K750-01 (1996).

International Search Report for International Application No. PCT/IB01/00741 mailed Mar. 5, 2002.

Office Action for related U.S. Appl. No. 08/848,616, mailed Aug. 30, 2002.

Office Action for related U.S. Appl. No. 08/848,616, mailed Feb. 7, 2003.

Office Action for related U.S. Application No. 08/848,616, mailed Oct. 31, 2003.

Baba, T.W., et al., "Pathogenicity of Live, Attenuated SIV After Mucosal Infection of Neonatal Macaques," *Science* 267: 1820-1825, American Association for the Advancemant of Science (1995).

Bachmann, M.F., et al., "Dendritic cells process exogenous viral proteins and virus-like particles for class I presentation to $CD8^+$cytotoxic T lymphocytes," *Eur. J. Immunol.* 26:2595-2600, VCH Verlagsgesellschaft mbH (1996).

Boorsma, M., et al., "A temperature-regulated replicon-based DNA expression system," *Nat. Biotechnol.* 18:429-432, Nature America, Inc. (Apr. 2000).

Borisova, G., et al., "Hybrid Hepatitis B Virus Nucleocapsid Bearing an Immunodominant Region from Hepatitis B Virus Surface Antigen," *J. Virol.* 67:3696-3701, American Society for Microbiology (1993).

Cesareni, G., "Peptide display on filamentous phage capsids; A new powerful tool to study protein-ligand interaction," *FEBS Lett.* 307:66-70, Elsevier Science Publishers B.V. (1992).

Connor, R.I., et al., "Immunological and Virological Analyses of Persons Infected by Human Immunodeficiency Virus Type 1, while Participating in Trials of Recombinant gp120 Subunit Vaccines," *J. Virol.* 72:1552-1575, American Society for Microbiology (1998).

Crameri, R. and Suter, M., "Display of biologically active proteins on the surface of filamentous phages: a cDNA cloning system for selection of functional gene products linked to the genetic information responsible for their production," *Gene* 137:69-75, Elsevier Science Publishers B.V. (1993).

Daniel, M.D., et al., "Protective Effects of a Live Attenuated SIV Vaccine with a Deletion in the nef Gene," *Science* 258:1938-1941, American Association for the Advancement of Science (1992).

de la Cruz, V.F., et al., "Immunogenicity and Epitope Mapping of Foreign Sequences via Genetically Engineered Filamentous Phage," *J. Biol. Chem.* 263:4318-4322, The American Society for Biochemistry and Molecular Biology, Inc. (1988).

Donnelly, J.J., et al., "DNA Vaccines," *Ann. Rev. Immunol.* 15:617-648, Annual Reviews, Inc. (1997).

Ebina, S., et al., "Chemical Modification of Bovine Pancreatic Trypsin Inhibitor for Single Site Coupling of Immunogenic Peptides for NMR Conformational Analysis," *J. Biol. Chem.* 264:7882-7888, The American Society for Biochemistry and Molecular Biology, Inc. (1989).

Esposito, G., et al., "Conformational study of a short *Pertussis* toxin T cell epitope incorporated in a multiple antigen peptide template by CD and two-dimensional NMR: Analysis of the structural effects on the activity of synthetic immunogens," *Eur. J. Biochem.* 217:171-187, Blackwell Science Ltd. on behalf of the Federation of European Biochemical Societies (1993).

Förster, E., et al., "Natural and recombinant enzymatically active or inactive bee venom phospholipase $A_2$has the same potency to release histamine from basophils in patients with Hymenoptera allergy," *J. Allergy Clin. Immunol.* 95:1229-1235, Mosby-Year Book, In. (1995).

Frolov, I., et al., "Alphavirus-based expression vectors: Strategies and applications," *Proc. Natl. Acad. Sci, USA* 93:11371-11377, National Academy Press (1996).

Gilbert, S.C., et al., "A protein particle vaccine containing multiple malaria epitopes," *Nat. Biotechnol.* 15:1280-1284, Nature America Publishing (1997).

Greenstone, H.L., et al., "Chimeric paillomavirus virus-like particles elicit antitumor immunity against the E7 oncoprotein in an HPV16 tumor model," Proc. Natl. Acad. Sci, USA 95:1800-1805, National Academy Press (1998).

Hahn, C.S., et al., "Infectious Sindbis virus transient expression vectors for studying antigen processing and presentation," Proc. Natl. Acad. Sci. USA 89:2679-2683, National Academy Press (1992).

Harding, C.V., and Song, R., "Phagocytic Processing of Exogenous Particulate Antigens by Macrophages for Presentation by Class I MHC Molecules," J. Immunol. 153:4925-4933, The American Association of Immunologists (1994).

Hilleman, M.R., "Six decades of vaccine development - a personal history," Nat. Med. Vaccine Suppl. 4:507-514 (May 1998).

Hui, E. K-W. et al., "Hepatitis B viral core proteins with an N-terminal extension can assemble into core-like particles but cannot be enveloped," J. Gen. Virol. 80:2647-2659, Society for General Microbiology (1999).

Iannolo, G., et al., "Construction, Exploitation and Evolution of a New Peptide Library Displayed at High Density by Fusion to the Major Coat Protein of Filamentous Phage," Biol. Chem. 378:517-521, Walter de Gruyter & Co. (1997).

Iannolo, G., et al., "Modifying Filamentous Phage, Capsid: Limits in the Size of the Major Capsid Protein," J. Mol. Biol. 248:835-844, Academic Press, Ltd. (1995).

Ikram, H., and Prince, A.M., "A method for coupling the Hepatitis B surface antigen to aldehyde-fixed erythrocytes for use in passive hemagglutination," J. Virol. Methods 2:269-275, Elsevier/North-Holland Biomedical Press (1981).

Kovacsovics-Bankowski, M., et al., "Efficient major histocompatibility complex class I presentation of exogenous, antigen upon phagocytosis by macrophages," Proc. Natl. Acad. Sci. USA 90:4942-4946, National Academy Press (1993).

Lo, K. K-W., et al., "Surface-modified mutants of cytochrome P450cam: enzymatic properties and electrochemistry," FEBS Lett. 451:342-346, Elsevier Science B.V. on behalf of the Federation of European Biochemical Societies (1999).

Minenkova, O.O., et al., "Design of specific immunogens using filamentous phage as the carrier," Gene 128:85-88, Elsevier Science Publishers B.V. (1993).

Neurath, A.R., et al., "Hepatitis B Virus surface antigen (HBsAg) as carrier for synthetic peptides having an attached hydrophobic tail," Mol. Immunol. 26:53-62, Pergamon Press (1989).

Perham, R.N., et al., "Engineering a peptide epitope display system on filamentous bacteriophage," FEMS Microbiol. Rev. 17:25-31, Elsevier Science Publishers on behalf of the Federation of European Microbiological Societies (1995).

Petrenko, V.A., et al., "A library of organic landscapes on filamentous phage," Protein Engin. 9:797-801, Oxford University Press (1996).

Pumpens, P. and Grens, E., "Hepatitis B core particles as a universal display model: a structure-function basis for development," FEBS Lett. 442:1-6, Elsevier Science B.V. on behalf fo the Federation of European Biochemical Societies (1999).

Quash, G., et al., "The preparation of latex particles with covalently bound polyamines IgG and measles agglutinins and their use in visual agglutination tests," J. Immunol. Methods 22:165-174, Elsevier/North-Holland Biomedical Press (1978).

Raychaudhuri, S., and Rock, K.L., "Fully mobilizing host defense: Building better vaccines," Nat. Biotechnol. 16:1025-1031, Nature America, Inc. (1998).

Redfield, R.R., et al., "Disseminated vaccinia in a military recruit with Human Immunodeficiency Virus (HIV) disease," N. Eng. J. Med. 316:673-676, Massachusetts Medical Society (1987).

Rudolf, M.P., et al., Molecular Basis for Nonanaphylactogenicty of a Monoclonal Anti - IgE Antibody, J. Immunol. 165:813-819, The American Association of Immunologists (2000).

Sedlik, C., et al., "Recombinant parvovirus-like particles as an antigen carrier: A novel nonreplicative exogenous antigen to elicit protective antiviral cytotoxic T cells," Proc. Natl. Acad. Sci. USA 94:7503-7508, National Academy Press (1997).

Shen, L., et al., "Recombinant Virus Vaccine-Induced SIV-Specific CD8* Cytotoxic T Lymphocytes," Science 252:440-443, American Association for the Advancement of Science (1991).

Tanimori, H., et al., "Enzyme Immunoassay of Neocarzinostatin Using β-Galactosidase as Label," J. Pharm. Dyn. 4:812-819, Pharmaceutical Society of Japan (1981).

Townsend, A., and Bodmer, H., "Antigen recognition by class I-restricted T lymphocytes," Ann. Rev. Immunol. 7:601-624, Annual Reviews, Inc. (1989).

VanCott, T.C., et al., "Antibodies with Specificity to Native gp120 and Neutralization Activity against Primary Human Immunodeficiency Virus Type 1 Isolates Elicited by Immunization with Oligomeric gp160," J. Virol. 71:4319-4330, American Society for Microbiology (1997).

Watkins, S.J., et al., "The 'adenobody' approach to viral targeting: specific and enhanced adenoviral gene delivery," Gene Ther. 4:1004-1012, Stockton Press (1997).

Willis, A.E., et al., "Immunological properties of foreign peptides in multiple display on a filamentous bacteriophage," Gene 128:79-83, Elsevier Science Publishers B.V. (1993).

Dialog File 315, Accession No. 7431992, Deerwent WPI English language abstract for WO 94/06472 (Document AP3).

International Preliminary Examination Report for International Application No. PCT/IB99/01925, European Patent Office, Munich (Aug. 2000) (not for publication).

International Search Report for International Application No. PCT/IB99/01925, European Patent Office, Netherland (Jun. 2000) (not for publication).

Office Action for related U.S. Appl. No. 10/050,892, mailed Dec. 19, 2006.

Janus, C., "Vaccines for Alzheimer's disease: how close are we?, " CNS Drugs17(7):457-474 (2003).

Gilman, S., et al., "Clinical effects of Abeta immunization (AN1792) in patients with AD in an interrupted trial," Neurology 641553-1562 (2005).

Masliah, E., et al., Aβ vaccination effects on plaque pathology in the absence of encephalitis in Alzheimer disease, Neurology 64129-131 (2005).

* cited by examiner

```
                                                Nhe I              Linker
  1    GAT CCA GCA GCT GGG CTC GAG GTG CTA GCG GGA GGG GGT GGA TGT GGG
        D   P   A   A   G   L   E   V   L   A   G   G   G   G   C   G Xa
         Factor Xa         ↓ Hind III                hu IgG1
 49    ATC GAA GGT CGC AAG CTT ACT CAC ACA TGC CCA CCG TGC CCA GCA CCT
        I   E   G   R   K   L   T   H   T   C   P   P   C   P   A   P 97    GAA GCC GAG GGG GCA CCG TCA GTC TTC CTC TTC CCC CCA AAA CCC AAG
        E   A   E   G   A   P   S   V   F   L   F   P   P   K   P   K 145    GAC ACC CTC ATG ATC TCC CGG ACC CCT GAG GTC ACA TGC GTG GTG GTG
        D   T   L   M   I   S   R   T   P   E   V   T   C   V   V   V 193    GAC GTG AGC CAC GAA GAC CCT GAG GTC AAG TTC AAC TGG TAC GTG GAC
        D   V   S   H   E   D   P   E   V   K   F   N   W   Y   V   D 241    GGC GTG GAG GTG CAT AAT GCC AAG ACA AAG CCG CGG GAG GAG CAG TAC
        G   V   E   V   H   N   A   K   T   K   P   R   E   E   Q   Y 289    AAC AGC ACG TAC CGT GTG GTC AGC GTC CTC ACC GTC CTG CAC CAG GAC
        N   S   T   Y   R   V   V   S   V   L   T   V   L   H   Q   D 337    TGG CTG AAT GGC AAG GAG TAC AAG TGC AAG GTC TCC AAC AAA GCC CTC
        W   L   N   G   K   E   Y   K   C   K   V   S   N   K   A   L 385    CCA GCC TCC ATC GAG AAA ACC ATC TCC AAA GCC AAA GGG CAG CCC CGA
        P   A   S   I   E   K   T   I   S   K   A   K   G   Q   P   R 433    GAA CCA CAG GTG TAC ACC CTG CCC CCA TCC CGG GAT GAG CTG ACC AAG
        E   P   Q   V   Y   T   L   P   P   S   R   D   E   L   T   K 481    AAC CAG GTC AGC CTG ACC TGC CTG GTC AAA GGC TTC TAT CCC AGC GAC
        N   Q   V   S   L   T   C   L   V   K   G   F   Y   P   S   D 529    ATC GCC GTG GAG TGG GAG AGC AAT GGG CAG CCG GAG AAC AAC TAC AAG
        I   A   V   E   W   E   S   N   G   Q   P   E   N   N   Y   K 577    ACC ACG CCT CCC GTG TTG GAC TCC GAC GGC TCC TTC TTC CTC TAC AGC
        T   T   P   P   V   L   D   S   D   G   S   F   F   L   Y   S 625    AAG CTC ACC GTG GAC AAG AGC AGG TGG CAG CAG GGG AAC GTC TTC TCA
        K   L   T   V   D   K   S   R   W   Q   Q   G   N   V   F   S 673    TGC TCC GTG ATG CAT GAG GCT CTG CAC AAC CAC TAC ACG CAG AAG AGC
        C   S   V   M   H   E   A   L   H   N   H   Y   T   Q   K   S 721    CTC TCC CTG TCT CCG GGT AAA TGA C
        L   S   L   S   P   G   K   -
```

FIG. 1A

```
  1 GGA TCC GGG ATG AAG AAC CTT TCA TTT CCC CTC CTT TTC CTT TTC TTC CTT
                M   K   N   L   S   F   P   L   L   F   L   F   F   L
 52 GTC CCT GAA CTG CTG GGC TCC AGC ATG CCA CTG TGT CCC ATC GAT GAA GCC
     V   P   E   L   L   G   S   S   M   P   L   C   P   I   D   E   A
103 ATC GAC AAG AAG ATC AAA CAA GAC TTC AAC TCC CTG TTT CCA AAT GCA ATA
     I   D   K   K   I   K   Q   D   F   N   S   L   F   P   N   A   I
154 AAG AAC ATT GGC TTA AAT TGC TGG ACA GTC TCC TCC AGA GGG AAG TTG GCC
     K   N   I   G   L   N   C   W   T   V   S   S   R   G   K   L   A
205 TCC TGC CCA GAA GGC ACA GCA GTC TTG AGC TGC TCC TGT GGC TCT GCC TGT
     S   C   P   E   G   T   A   V   L   S   C   S   C   G   S   A   C
256 GGC TCG TGG GAC ATT CGT GAA GAA AAA GTG TGT CAC TGC CAG TGT GCA AGG
     G   S   W   D   I   R   E   E   K   V   C   H   C   Q   C   A   R
307 ATA GAC TGG ACA GCA GCC CGC TGC TGT AAG CTG CAG GTC GCT TCC TCT CTA
     I   D   W   T   A   A   R   C   C   K   L   Q   V   A   S   S   L
358 GCG GGA GGG GGT GGA TGT GGG ATC GAA GGT CGC AAG CTT ACT
     A   G   G   G   G   C   G   I   E   G   R   K   L   T
```

FIG. 2A

```
  1 GGA TCC GGG ATG AAG AAC CTT TCA TTT CCC CTC CTT TTC CTT TTC TTC CTT
                M   K   N   L   S   F   P   L   L   F   L   F   F   L
 52 GTC CCT GAA CTG CTG GGC TCC AGC ATG CCA CTG TGT CCC ATC GAT GAA GCC
     V   P   E   L   L   G   S   S   M   P   L   C   P   I   D   E   A
103 ATC GAC AAG AAG ATC AAA CAA GAC TTC AAC TCC CTG TTT CCA AAT GCA ATA
     I   D   K   K   I   K   Q   D   F   N   S   L   F   P   N   A   I
154 AAG AAC ATT GGC TTA AAT TGC TGG ACA GTC TCC TCC AGA GGG AAG TTG GCC
     K   N   I   G   L   N   C   W   T   V   S   S   R   G   K   L   A
205 TCC TGC CCA GAA GGC ACA GCA GTC TTG AGC TGC TCC TGT GGC TCT GCC TGT
     S   C   P   E   G   T   A   V   L   S   C   S   C   G   S   A   C
256 GGC TCG TGG GAC ATT CGT GAA GAA AAA GTG TGT CAC TGC CAG TGT GCA AGG
     G   S   W   D   I   R   E   E   K   V   C   H   C   Q   C   A   R
307 ATA GAC TGG ACA GCA GCC CGC TGC TGT AAG CTG CAG GTC GCT TCC TCT CTA
     I   D   W   T   A   A   R   C   C   K   L   Q   V   A   S   S   L
358 GCG GGA GGG GGT GGA TGT GGG GAC GAT GAC GAC AAG CTT ACT
     A   G   G   G   G   C   G   D   D   D   D   K   L   T
```

FIG. 2B

SEQUENCE LISTING

<160> NUMBER OF SEQ ID NOS: 350

<210> SEQ ID NO 1
<211> LENGTH: 41
<212> TYPE: DNA
<213> ORGANISM: Artificial Sequence
<220> FEATURE:
<223> OTHER INFORMATION: Primer

<400> SEQUENCE: 1
ggggacgcgt gcagcaggta accaccgtta aagaaggcac c          41

<210> SEQ ID NO 2
<211> LENGTH: 44
<212> TYPE: DNA
<213> ORGANISM: Artificial Sequence
<220> FEATURE:
<223> OTHER INFORMATION: Primer

<400> SEQUENCE: 2
cggtggttac ctgctgcacg cgttgcttaa gcgacatgta gcgg        44

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ccatgaggcc tacgataccc                                  20

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4

```
ggcactcacg gcgcgcttta caggc                                          25

<210> SEQ ID NO 5
<211> LENGTH: 47
<212> TYPE: DNA
<213> ORGANISM: Artificial Sequence
<220> FEATURE:
<223> OTHER INFORMATION: Primer

<400> SEQUENCE: 5
ccttctttaa cggtggttac ctgctggcaa ccaacgtggt tcatgac                  47

<210> SEQ ID NO 6
<211> LENGTH: 40
<212> TYPE: DNA
<213> ORGANISM: Artificial Sequence
<220> FEATURE:
<223> OTHER INFORMATION: Primer

<400> SEQUENCE: 6
aagcatgctg cacgcgtgtg cggtggtcgg atcgcccggc                          40

<210> SEQ ID NO 7
<211> LENGTH: 90
<212> TYPE: DNA
<213> ORGANISM: Artificial Sequence
<220> FEATURE:
<223> OTHER INFORMATION: Primer

<400> SEQUENCE: 7
gggtctagat tcccaaccat tcccttatcc aggcttttg acaacgctat gctccgcgcc    60
catcgtctgc accagctggc ctttgacacc                                     90

<210> SEQ ID NO 8
<211> LENGTH: 108
<212> TYPE: DNA
<213> ORGANISM: Artificial Sequence
<220> FEATURE:
<223> OTHER INFORMATION: Primer

<400> SEQUENCE: 8
gggtctagaa ggaggtaaaa aacgatgaaa aagacagcta tcgcgattgc agtggcactg   60
gctggtttcg ctaccgtagc gcaggccttc ccaaccattc ccttatcc                108

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
cccgaattcc tagaagccac agctgccctc c                                   31

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
cctgcggtgg tctgaccgac accc                                           24
```

<210> SEQ ID NO 11
<211> LENGTH: 41
<212> TYPE: DNA
<213> ORGANISM: Artificial Sequence
<220> FEATURE:
<223> OTHER INFORMATION: Primer

<400> SEQUENCE: 11
ccgcggaaga gccaccgcaa ccaccgtgtg ccgccaggat g                          41

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
ctatcatcta gaatgaatag aggattcttt aac                                   33

<210> SEQ ID NO 13
<211> LENGTH: 15
<212> TYPE: DNA
<213> ORGANISM: Artificial Sequence
<220> FEATURE:
<223> OTHER INFORMATION: Modified ribosome binding site

<400> SEQUENCE: 13
aggaggtaaa aaacg                                                       15

<210> SEQ ID NO 14
<211> LENGTH: 21
<212> TYPE: PRT
<213> ORGANISM: Artificial Sequence
<220> FEATURE:
<223> OTHER INFORMATION: signal peptide

<400> SEQUENCE: 14

Met Lys Lys Thr Ala Ile Ala Ile Ala Val Ala Leu Ala Gly Phe Ala
 1               5                  10                  15

Thr Val Ala Gln Ala
            20

<210> SEQ ID NO 15
<211> LENGTH: 46
<212> TYPE: PRT
<213> ORGANISM: Artificial Sequence
<220> FEATURE:
<223> OTHER INFORMATION: modified Fos construct

<400> SEQUENCE: 15

Cys Gly Gly Leu Thr Asp Thr Leu Gln Ala Glu Thr Asp Gln Val Glu
 1               5                  10                  15

Asp Glu Lys Ser Ala Leu Gln Thr Glu Ile Ala Asn Leu Leu Lys Glu
            20                  25                  30

Lys Glu Lys Leu Glu Phe Ile Leu Ala Ala His Gly Gly Cys
        35                  40                  45

<210> SEQ ID NO 16
<211> LENGTH: 6
<212> TYPE: PRT
<213> ORGANISM: Artificial Sequence
<220> FEATURE:
<223> OTHER INFORMATION: peptide linker -continued

```
<400> SEQUENCE: 16

Ala Ala Ala Ser Gly Gly
  1               5

<210> SEQ ID NO 17
<211> LENGTH: 6
<212> TYPE: PRT
<213> ORGANISM: Artificial Sequence
<220> FEATURE:
<223> OTHER INFORMATION: peptide linker

<400> SEQUENCE: 17

Gly Gly Ser Ala Ala Ala
  1               5

<210> SEQ ID NO 18
<211> LENGTH: 256
<212> TYPE: DNA
<213> ORGANISM: Artificial Sequence
<220> FEATURE:
<223> OTHER INFORMATION: Fos fusion construct

<400> SEQUENCE: 18
gaattcagga ggtaaaaaac gatgaaaaag acagctatcg cgattgcagt ggcactggct     60
ggtttcgcta ccgtagcgca ggcctgggtg ggggcggccg cttctggtgg ttgcggtggt   120
ctgaccgaca ccctgcaggc ggaaaccgac caggtggaag acgaaaaatc cgcgctgcaa   180
accgaaatcg cgaacctgct gaaagaaaaa gaaaagctgg agttcatcct ggcggcacac   240
ggtggttgct aagctt                                                    256

<210> SEQ ID NO 19
<211> LENGTH: 52
<212> TYPE: PRT
<213> ORGANISM: Artificial Sequence
<220> FEATURE:
<223> OTHER INFORMATION: Fos fusion construct

<400> SEQUENCE: 19

Ala Ala Ala Ser Gly Gly Cys Gly Gly Leu Thr Asp Thr Leu Gln Ala
  1               5                  10                  15

Glu Thr Asp Gln Val Glu Asp Glu Lys Ser Ala Leu Gln Thr Glu Ile
             20                  25                  30

Ala Asn Leu Leu Lys Glu Lys Glu Lys Leu Glu Phe Ile Leu Ala Ala
         35                  40                  45

His Gly Gly Cys
     50

<210> SEQ ID NO 20
<211> LENGTH: 261
<212> TYPE: DNA
<213> ORGANISM: Artificial Sequence
<220> FEATURE:
<223> OTHER INFORMATION: Fos fusion construct
<220> FEATURE:
<221> NAME/KEY: CDS
<222> LOCATION: (22)..(240)

<400> SEQUENCE: 20
gaattcagga ggtaaaaaac g atg aaa aag aca gct atc gcg att gca gtg    51
                        Met Lys Lys Thr Ala Ile Ala Ile Ala Val
                         1               5                  10 gca ctg gct ggt ttc gct acc gta gcg cag gcc tgc ggt ggt ctg acc    99
Ala Leu Ala Gly Phe Ala Thr Val Ala Gln Ala Cys Gly Gly Leu Thr
```

```
                15                  20                  25
gac acc ctg cag gcg gaa acc gac cag gtg gaa gac gaa aaa tcc gcg       147
Asp Thr Leu Gln Ala Glu Thr Asp Gln Val Glu Asp Glu Lys Ser Ala
            30                  35                  40 ctg caa acc gaa atc gcg aac ctg ctg aaa gaa aaa gaa aag ctg gag       195
Leu Gln Thr Glu Ile Ala Asn Leu Leu Lys Glu Lys Glu Lys Leu Glu
        45                  50                  55 ttc atc ctg gcg gca cac ggt ggt tgc ggt ggt tct gcg gcc gct           240
Phe Ile Leu Ala Ala His Gly Gly Cys Gly Gly Ser Ala Ala Ala
    60                  65                  70 gggtgtgggg atatcaagct t                                               261
```

<210> SEQ ID NO 21
<211> LENGTH: 73
<212> TYPE: PRT
<213> ORGANISM: Artificial Sequence
<220> FEATURE:
<223> OTHER INFORMATION: Fos fusion construct

<400> SEQUENCE: 21

```
Met Lys Lys Thr Ala Ile Ala Ile Ala Val Ala Leu Ala Gly Phe Ala
1               5                   10                  15

Thr Val Ala Gln Ala Cys Gly Gly Leu Thr Asp Thr Leu Gln Ala Glu
            20                  25                  30

Thr Asp Gln Val Glu Asp Glu Lys Ser Ala Leu Gln Thr Glu Ile Ala
        35                  40                  45

Asn Leu Leu Lys Glu Lys Glu Lys Leu Glu Phe Ile Leu Ala Ala His
    50                  55                  60

Gly Gly Cys Gly Gly Ser Ala Ala Ala
65                  70
```

<210> SEQ ID NO 22
<211> LENGTH: 196
<212> TYPE: DNA
<213> ORGANISM: Artificial Sequence
<220> FEATURE:
<223> OTHER INFORMATION: Fos fusion construct
<220> FEATURE:
<221> NAME/KEY: CDS
<222> LOCATION: (34)..(189)

<400> SEQUENCE: 22

```
gaattcagga ggtaaaaaga tatcgggtgt ggg gcg gcc gct tct ggt ggt tgc      54
                                    Ala Ala Ala Ser Gly Gly Cys
                                                    1           5 ggt ggt ctg acc gac acc ctg cag gcg gaa acc gac cag gtg gaa gac      102
Gly Gly Leu Thr Asp Thr Leu Gln Ala Glu Thr Asp Gln Val Glu Asp
        10                  15                  20 gaa aaa tcc gcg ctg caa acc gaa atc gcg aac ctg ctg aaa gaa aaa      150
Glu Lys Ser Ala Leu Gln Thr Glu Ile Ala Asn Leu Leu Lys Glu Lys
    25                  30                  35 gaa aag ctg gag ttc atc ctg gcg gca cac ggt ggt tgc taagctt          196
Glu Lys Leu Glu Phe Ile Leu Ala Ala His Gly Gly Cys
40                  45                  50
```

<210> SEQ ID NO 23
<211> LENGTH: 52
<212> TYPE: PRT
<213> ORGANISM: Artificial Sequence
<220> FEATURE:
<223> OTHER INFORMATION: Fos fusion construct

<400> SEQUENCE: 23

```
Ala Ala Ala Ser Gly Gly Cys Gly Gly Leu Thr Asp Thr Leu Gln Ala
 1               5                  10                  15

Glu Thr Asp Gln Val Glu Asp Glu Lys Ser Ala Leu Gln Thr Glu Ile
             20                  25                  30

Ala Asn Leu Leu Lys Glu Lys Glu Lys Leu Glu Phe Ile Leu Ala Ala
         35                  40                  45

His Gly Gly Cys
         50

<210> SEQ ID NO 24
<211> LENGTH: 204
<212> TYPE: DNA
<213> ORGANISM: Artificial Sequence
<220> FEATURE:
<223> OTHER INFORMATION: Fos fusion construct

<400> SEQUENCE: 24
gaattcagga ggtaaaaaac gatggcttgc ggtggtctga ccgacaccct gcaggcggaa      60
accgaccagg tggaagacga aaaatccgcg ctgcaaaccg aaatcgcgaa cctgctgaaa     120 gaaaagaaa agctggagtt catcctggcg gcacacggtg gttgcggtgg ttctgcggcc     180
gctgggtgtg gggatatcaa gctt                                            204

<210> SEQ ID NO 25
<211> LENGTH: 56
<212> TYPE: PRT
<213> ORGANISM: Artificial Sequence
<220> FEATURE:
<223> OTHER INFORMATION: Fos fusion construct

<400> SEQUENCE: 25

Lys Thr Met Ala Cys Gly Gly Leu Thr Asp Thr Leu Gln Ala Glu Thr
 1               5                  10                  15

Asp Gln Val Glu Asp Glu Lys Ser Ala Leu Gln Thr Glu Ile Ala Asn
             20                  25                  30

Leu Leu Lys Glu Lys Glu Lys Leu Glu Phe Ile Leu Ala Ala His Gly
         35                  40                  45

Gly Cys Gly Gly Ser Ala Ala Ala
     50                  55

<210> SEQ ID NO 26
<211> LENGTH: 26
<212> TYPE: PRT
<213> ORGANISM: Homo sapiens

<400> SEQUENCE: 26

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala
             20                  25

<210> SEQ ID NO 27
<211> LENGTH: 262
<212> TYPE: DNA
<213> ORGANISM: Artificial Sequence
<220> FEATURE:
<223> OTHER INFORMATION: Fos fusion construct

<400> SEQUENCE: 27
gaattcaggc ctatggctac aggctcccgg acgtccctgc tcctggcttt tggcctgctc      60
```

```
tgcctgccct ggcttcaaga gggcagcgct gggtgtgggg cggccgcttc tggtggttgc    120
ggtggtctga ccgacaccct gcaggcgaaa accgaccagg tggaagacga aaaatccgcg    180
ctgcaaaccg aaatcgcgaa cctgctgaaa gaaaagaaa agctggagtt catcctggcg    240
gcacacggtg gttgctaagc tt                                             262
```

```
<210> SEQ ID NO 28
<211> LENGTH: 52
<212> TYPE: PRT
<213> ORGANISM: Artificial Sequence
<220> FEATURE:
<223> OTHER INFORMATION: Fos fusion construct

<400> SEQUENCE: 28

Ala Ala Ala Ser Gly Gly Cys Gly Gly Leu Thr Asp Thr Leu Gln Ala
  1               5                  10                  15

Glu Thr Asp Gln Val Glu Asp Glu Lys Ser Ala Leu Gln Thr Glu Ile
             20                  25                  30

Ala Asn Leu Leu Lys Glu Lys Glu Lys Leu Glu Phe Ile Leu Ala Ala
         35                  40                  45

His Gly Gly Cys
         50
```

```
<210> SEQ ID NO 29
<211> LENGTH: 261
<212> TYPE: DNA
<213> ORGANISM: Artificial Sequence
<220> FEATURE:
<223> OTHER INFORMATION: Fos fusion construct
<220> FEATURE:
<221> NAME/KEY: CDS
<222> LOCATION: (7)..(240)

<400> SEQUENCE: 29 gaattc atg gct aca ggc tcc cgg acg tcc ctg ctc ctg gct ttt ggc      48
       Met Ala Thr Gly Ser Arg Thr Ser Leu Leu Leu Ala Phe Gly
         1               5                  10 ctg ctc tgc ctg ccc tgg ctt caa gag ggc agc gct tgc ggt ggt ctg     96
Leu Leu Cys Leu Pro Trp Leu Gln Glu Gly Ser Ala Cys Gly Gly Leu
 15                  20                  25                  30 acc gac acc ctg cag gcg gaa acc gac cag gtg gaa gac gaa aaa tcc    144
Thr Asp Thr Leu Gln Ala Glu Thr Asp Gln Val Glu Asp Glu Lys Ser
                 35                  40                  45 gcg ctg caa acc gaa atc gcg aac ctg ctg aaa gaa aaa gaa aag ctg    192
Ala Leu Gln Thr Glu Ile Ala Asn Leu Leu Lys Glu Lys Glu Lys Leu
             50                  55                  60 gag ttc atc ctg gcg gca cac ggt ggt tgc ggt ggt tct gcg gcc gct    240
Glu Phe Ile Leu Ala Ala His Gly Gly Cys Gly Gly Ser Ala Ala Ala
 65                  70                  75 gggtgtggga ggcctaagct t                                             261
```

```
<210> SEQ ID NO 30
<211> LENGTH: 78
<212> TYPE: PRT
<213> ORGANISM: Artificial Sequence
<220> FEATURE:
<223> OTHER INFORMATION: Fos fusion construct

<400> SEQUENCE: 30

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Cys Gly Gly Leu Thr Asp
```

```
                  20                  25                  30
Thr Leu Gln Ala Glu Thr Asp Gln Val Glu Asp Glu Lys Ser Ala Leu
         35                  40                  45

Gln Thr Glu Ile Ala Asn Leu Leu Lys Glu Lys Glu Lys Leu Glu Phe
         50                  55                  60

Ile Leu Ala Ala His Gly Gly Cys Gly Gly Ser Ala Ala Ala
         65                  70                  75
```

<210> SEQ ID NO 31
<211> LENGTH: 44
<212> TYPE: DNA
<213> ORGANISM: Artificial Sequence
<220> FEATURE:
<223> OTHER INFORMATION: Primer

<400> SEQUENCE: 31
cctgggtggg ggcggccgct tctggtggtt gcggtggtct gacc            44

<210> SEQ ID NO 32
<211> LENGTH: 44
<212> TYPE: DNA
<213> ORGANISM: Artificial Sequence
<220> FEATURE:
<223> OTHER INFORMATION: Primer

<400> SEQUENCE: 32
ggtgggaatt caggaggtaa aaagatatcg ggtgtggggc ggcc            44

<210> SEQ ID NO 33
<211> LENGTH: 47
<212> TYPE: DNA
<213> ORGANISM: Artificial Sequence
<220> FEATURE:
<223> OTHER INFORMATION: Primer

<400> SEQUENCE: 33
ggtgggaatt caggaggtaa aaaacgatgg cttgcggtgg tctgacc         47

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
gcttgcggtg gtctgacc                                         18

<210> SEQ ID NO 35
<211> LENGTH: 27
<212> TYPE: DNA
<213> ORGANISM: Artificial Sequence
<220> FEATURE:
<223> OTHER INFORMATION: Primer

<400> SEQUENCE: 35
ccaccaagct tagcaaccac cgtgtgc                               27

<210> SEQ ID NO 36
<211> LENGTH: 54
<212> TYPE: DNA
<213> ORGANISM: Artificial Sequence
<220> FEATURE:
<223> OTHER INFORMATION: Primer

```
<400> SEQUENCE: 36
ccaccaagct tgatatcccc acacccagcg gccgcagaac caccgcaacc accg      54

<210> SEQ ID NO 37
<211> LENGTH: 32
<212> TYPE: DNA
<213> ORGANISM: Artificial Sequence
<220> FEATURE:
<223> OTHER INFORMATION: Primer

<400> SEQUENCE: 37
ccaccaagct taggcctccc acacccagcg gc                              32

<210> SEQ ID NO 38
<211> LENGTH: 29
<212> TYPE: DNA
<213> ORGANISM: Artificial Sequence
<220> FEATURE:
<223> OTHER INFORMATION: Primer

<400> SEQUENCE: 38
ggtgggaatt caggaggtaa aaacgatg                                   29

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
ggtgggaatt caggcctatg gctacaggct cc                              32

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
ggtgggaatt catggctaca ggctccc                                    27

<210> SEQ ID NO 41
<211> LENGTH: 59
<212> TYPE: DNA
<213> ORGANISM: Artificial Sequence
<220> FEATURE:
<223> OTHER INFORMATION: Primer

<400> SEQUENCE: 41
gggtctagaa tggctacagg ctcccggacg tccctgctcc tggcttttgg cctgctctg  59

<210> SEQ ID NO 42
<211> LENGTH: 58
<212> TYPE: DNA
<213> ORGANISM: Artificial Sequence
<220> FEATURE:
<223> OTHER INFORMATION: Primer

<400> SEQUENCE: 42
cgcaggcctc ggcactgccc tcttgaagcc agggcaggca gagcaggcca aaagccag   58

<210> SEQ ID NO 43
<211> LENGTH: 402
```

```
<212> TYPE: DNA
<213> ORGANISM: Artificial Sequence
<220> FEATURE:
<223> OTHER INFORMATION: Modified bee venom phospholipase A2
<220> FEATURE:
<221> NAME/KEY: CDS
<222> LOCATION: (1)..(402)

<400> SEQUENCE: 43 atc atc tac cca ggt act ctg tgg tgt ggt cac ggc aac aaa tct tct      48
Ile Ile Tyr Pro Gly Thr Leu Trp Cys Gly His Gly Asn Lys Ser Ser
 1               5                  10                  15 ggt ccg aac gaa ctc ggc cgc ttt aaa cac acc gac gca tgc tgt cgc      96
Gly Pro Asn Glu Leu Gly Arg Phe Lys His Thr Asp Ala Cys Cys Arg
                20                  25                  30 acc cag gac atg tgt ccg gac gtc atg tct gct ggt gaa tct aaa cac     144
Thr Gln Asp Met Cys Pro Asp Val Met Ser Ala Gly Glu Ser Lys His
            35                  40                  45 ggg tta act aac acc gct tct cac acg cgt ctc agc tgc gac tgc gac     192
Gly Leu Thr Asn Thr Ala Ser His Thr Arg Leu Ser Cys Asp Cys Asp
        50                  55                  60 gac aaa ttc tac gac tgc ctt aag aac tcc gcc gat acc atc tct tct     240
Asp Lys Phe Tyr Asp Cys Leu Lys Asn Ser Ala Asp Thr Ile Ser Ser
 65                  70                  75                  80 tac ttc gtt ggt aaa atg tat ttc aac ctg atc gat acc aaa tgt tac     288
Tyr Phe Val Gly Lys Met Tyr Phe Asn Leu Ile Asp Thr Lys Cys Tyr
                 85                  90                  95 aaa ctg gaa cac ccg gta acc ggc tgc ggc gaa cgt acc gaa ggt cgc     336
Lys Leu Glu His Pro Val Thr Gly Cys Gly Glu Arg Thr Glu Gly Arg
            100                 105                 110 tgc ctg cac tac acc gtt gac aaa tct aaa ccg aaa gtt tac cag tgg     384
Cys Leu His Tyr Thr Val Asp Lys Ser Lys Pro Lys Val Tyr Gln Trp
        115                 120                 125 ttc gac ctg cgc aaa tac                                             402
Phe Asp Leu Arg Lys Tyr
    130

<210> SEQ ID NO 44
<211> LENGTH: 134
<212> TYPE: PRT
<213> ORGANISM: Artificial Sequence
<220> FEATURE:
<223> OTHER INFORMATION: Modified bee venom phospholipase A2

<400> SEQUENCE:

Phe Asp Leu Arg Lys Tyr
       130

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
ccatcatcta cccaggtac                                              19

<210> SEQ ID NO 46
<211> LENGTH: 34
<212> TYPE: DNA
<213> ORGANISM: Artificial Sequence
<220> FEATURE:
<223> OTHER INFORMATION: Primer

<400> SEQUENCE: 46
cccacaccca gcggccgcgt atttgcgcag gtcg                             34

<210> SEQ ID NO 47
<211> LENGTH: 36
<212> TYPE: DNA
<213> ORGANISM: Artificial Sequence
<220> FEATURE:
<223> OTHER INFORMATION: Primer

<400> SEQUENCE: 47
cggtggttct gcggccgcta tcatctaccc aggtac                           36

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
ttagtatttg cgcaggtcg                                              19

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49
ccggctccat cggtgcag                                               18

<210> SEQ ID NO 50
<211> LENGTH: 36
<212> TYPE: DNA
<213> ORGANISM: Artificial Sequence
<220> FEATURE:
<223> OTHER INFORMATION: Primer

<400> SEQUENCE: 50
accaccagaa gcggccgcag gggaaacaca tctgcc                           36

<210> SEQ ID NO 51
<211> LENGTH: 35

```
<212> TYPE: DNA
<213> ORGANISM: Artificial Sequence
<220> FEATURE:
<223> OTHER INFORMATION: Primer

<400> SEQUENCE: 51
cggtggttct gcggccgctg gctccatcgg tgcag                              35

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
ttaaggggaa acacatctgc c                                            21

<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53
actagtctag aatgagagtg aaggagaaat atc                               33

<210> SEQ ID NO 54
<211> LENGTH: 42
<212> TYPE: DNA
<213> ORGANISM: Artificial Sequence
<220> FEATURE:
<223> OTHER INFORMATION: Primer

<400> SEQUENCE: 54
tagcatgcta gcaccgaatt tatctaattc caataattct tg                     42

<210> SEQ ID NO 55
<211> LENGTH: 51
<212> TYPE: DNA
<213> ORGANISM: Artificial Sequence
<220> FEATURE:
<223> OTHER INFORMATION: Primer

<400> SEQUENCE: 55
gtagcaccca ccaaggcaaa gctgaaagct acccagctcg agaaactggc a            51

<210> SEQ ID NO 56
<211> LENGTH: 48
<212> TYPE: DNA
<213> ORGANISM: Artificial Sequence
<220> FEATURE:
<223> OTHER INFORMATION: Primer

<400> SEQUENCE: 56
caaagctcct attcccactg ccagtttctc gagctgggta gctttcag               48

<210> SEQ ID NO 57
<211> LENGTH: 36
<212> TYPE: DNA
<213> ORGANISM: Artificial Sequence
<220> FEATURE:
<223> OTHER INFORMATION: Primer

<400> SEQUENCE: 57
```

```
ttcggtgcta gcggtggctg cggtggtctg accgac                    36
```

<210> SEQ ID NO 58
<211> LENGTH: 37
<212> TYPE: DNA
<213> ORGANISM: Artificial Sequence
<220> FEATURE:
<223> OTHER INFORMATION: Primer

<400> SEQUENCE: 58

```
gatgctgggc ccttaaccgc aaccaccgtg tgccgcc                   37
```

<210> SEQ ID NO 59
<211> LENGTH: 46
<212> TYPE: PRT
<213> ORGANISM: Artificial Sequence
<220> FEATURE:
<223> OTHER INFORMATION: JUN amino acid sequence

<400> SEQUENCE: 59

```
Cys Gly Gly Arg Ile Ala Arg Leu Glu Glu Lys Val Lys Thr Leu Lys
 1               5                  10                  15
Ala Gln Asn Ser Glu Leu Ala Ser Thr Ala Asn Met Leu Arg Glu Gln
            20                  25                  30
Val Ala Gln Leu Lys Gln Lys Val Met Asn His Val Gly Cys
        35                  40                  45
```

<210> SEQ ID NO 60
<211> LENGTH: 46
<212> TYPE: PRT
<213> ORGANISM: Artificial Sequence
<220> FEATURE:
<223> OTHER INFORMATION: FOS amino acid sequence

<400> SEQUENCE: 60

```
Cys Gly Gly Leu Thr Asp Thr Leu Gln Ala Glu Thr Asp Gln Val Glu
 1               5                  10                  15
Asp Glu Lys Ser Ala Leu Gln Thr Glu Ile Ala Asn Leu Leu Lys Glu
            20                  25                  30
Lys Glu Lys Leu Glu Phe Ile Leu Ala Ala His Gly Gly Cys
        35                  40                  45
```

<210> SEQ ID NO 61
<211> LENGTH: 33
<212> TYPE: DNA
<213> ORGANISM: Artificial Sequence
<220> FEATURE:
<223> OTHER INFORMATION: Primer

<400> SEQUENCE: 61

```
ccggaattca tgtgcggtgg tcggatcgcc cgg                       33
```

<210> SEQ ID NO 62
<211> LENGTH: 39
<212> TYPE: DNA
<213> ORGANISM: Artificial Sequence
<220> FEATURE:
<223> OTHER INFORMATION: Primer

<400> SEQUENCE: 62

```
gtcgctaccc gcggctccgc aaccaacgtg gttcatgac                 39
```

<210> SEQ ID NO 63
<211> LENGTH: 50
<212> TYPE: DNA

<210> SEQ ID NO 63
<211> LENGTH: 50
<212> TYPE: DNA
<213> ORGANISM: Artificial Sequence
<220> FEATURE:
<223> OTHER INFORMATION: Primer

<400> SEQUENCE: 63
gttggttgcg gagccgcggg tagcgacatt gacccttata aagaatttgg     50

<210> SEQ ID NO 64
<211> LENGTH: 38
<212> TYPE: DNA
<213> ORGANISM: Artificial Sequence
<220> FEATURE:
<223> OTHER INFORMATION: Primer

<400> SEQUENCE: 64
cgcgtcccaa gcttctacgg aagcgttgat aggatagg     38

<210> SEQ ID NO 65
<211> LENGTH: 33
<212> TYPE: DNA
<213> ORGANISM: Artificial Sequence
<220> FEATURE:
<223> OTHER INFORMATION: Primer

<400> SEQUENCE: 65
ctagccgcgg gttgcggtgg tcggatcgcc cgg     33

<210> SEQ ID NO 66
<211> LENGTH: 38
<212> TYPE: DNA
<213> ORGANISM: Artificial Sequence
<220> FEATURE:
<223> OTHER INFORMATION: Primer

<400> SEQUENCE: 66
cgcgtcccaa gcttttagca accaacgtgg ttcatgac     38

<210> SEQ ID NO 67
<211> LENGTH: 31
<212> TYPE: DNA
<213> ORGANISM: Artificial Sequence
<220> FEATURE:
<223> OTHER INFORMATION: Primer

<400> SEQUENCE: 67
ccggaattca tggacattga cccttataaa g     31

<210> SEQ ID NO 68
<211> LENGTH: 45
<212> TYPE: DNA
<213> ORGANISM: Artificial Sequence
<220> FEATURE:
<223> OTHER INFORMATION: Primer

<400> SEQUENCE: 68
ccgaccaccg caacccgcgg ctagcggaag cgttgatagg atagg     45

<210> SEQ ID NO 69
<211> LENGTH: 47
<212> TYPE: DNA
<213> ORGANISM: Artificial Sequence
<220> FEATURE:
<223> OTHER INFORMATION: Primer

<400> SEQUENCE: 69
ctaatggatc cggtgggggc tgcggtggtc ggatcgcccg gctcgag     47

<210> SEQ ID NO 70
<211> LENGTH: 39
<212> TYPE: DNA
<213> ORGANISM: Artificial Sequence
<220> FEATURE:
<223> OTHER INFORMATION: Primer

<400> SEQUENCE: 70
gtcgctaccc gcggctccgc aaccaacgtg gttcatgac                    39

<210> SEQ ID NO 71
<211> LENGTH: 31
<212> TYPE: DNA
<213> ORGANISM: Artificial Sequence
<220> FEATURE:
<223> OTHER INFORMATION: Primer

<400> SEQUENCE: 71
ccggaattca tggacattga cccttataaa g                            31

<210> SEQ ID NO 72
<211> LENGTH: 48
<212> TYPE: DNA
<213> ORGANISM: Artificial Sequence
<220> FEATURE:
<223> OTHER INFORMATION: Primer

<400> SEQUENCE: 72
ccgaccaccg cagcccccac cggatccatt agtacccacc caggtagc          48

<210> SEQ ID NO 73
<211> LENGTH: 45
<212> TYPE: DNA
<213> ORGANISM: Artificial Sequence
<220> FEATURE:
<223> OTHER INFORMATION: Primer

<400> SEQUENCE: 73
gttggttgcg gagccgcggg tagcgaccta gtagtcagtt atgtc             45

<210> SEQ ID NO 74
<211> LENGTH: 38
<212> TYPE: DNA
<213> ORGANISM: Artificial Sequence
<220> FEATURE:
<223> OTHER INFORMATION: Primer

<400> SEQUENCE: 74
cgcgtcccaa gcttctacgg aagcgttgat aggatagg                     38

<210> SEQ ID NO 75
<211> LENGTH: 33
<212> TYPE: DNA
<213> ORGANISM: Artificial Sequence
<220> FEATURE:
<223> OTHER INFORMATION: Primer

<400> SEQUENCE: 75
ctagccgcgg gttgcggtgg tcggatcgcc cgg                          33

<210> SEQ ID NO 76
<211> LENGTH: 38
<212> TYPE: DNA
<213> ORGANISM: Artificial Sequence
<220> FEATURE:

```
<223> OTHER INFORMATION: Primer

<400> SEQUENCE: 76
cgcgtcccaa gcttttagca accaacgtgg ttcatgac                               38

<210> SEQ ID NO 77
<211> LENGTH: 30
<212> TYPE: DNA
<213> ORGANISM: Artificial Sequence
<220> FEATURE:
<223> OTHER INFORMATION: Primer

<400> SEQUENCE: 77
ccggaattca tggccacact tttaaggagc                                        30

<210> SEQ ID NO 78
<211> LENGTH: 38
<212> TYPE: DNA
<213> ORGANISM: Artificial Sequence
<220> FEATURE:
<223> OTHER INFORMATION: Primer

<400> SEQUENCE: 78
cgcgtcccaa gcttttagca accaacgtgg ttcatgac                               38

<210> SEQ ID NO 79
<211> LENGTH: 31
<212> TYPE: DNA
<213> ORGANISM: Artificial Sequence
<220> FEATURE:
<223> OTHER INFORMATION: Primer

<400> SEQUENCE: 79
ccggaattca tggacattga cccttataaa g                                      31

<210> SEQ ID NO 80
<211> LENGTH: 51
<212> TYPE: DNA
<213> ORGANISM: Artificial Sequence
<220> FEATURE:
<223> OTHER INFORMATION: Primer

<400> SEQUENCE: 80
cctagagcca cctttgccac catcttctaa attagtaccc acccaggtag c                51

<210> SEQ ID NO 81
<211> LENGTH: 48
<212> TYPE: DNA
<213> ORGANISM: Artificial Sequence
<220> FEATURE:
<223> OTHER INFORMATION: Primer

<400> SEQUENCE: 81
gaagatggtg gcaaaggtgg ctctagggac ctagtagtca gttatgtc                    48

<210> SEQ ID NO 82
<211> LENGTH: 38
<212> TYPE: DNA
<213> ORGANISM: Artificial Sequence
<220> FEATURE:
<223> OTHER INFORMATION: Primer

<400> SEQUENCE: 82
cgcgtcccaa gcttctaaac aacagtagtc tccggaag                               38
```

<210> SEQ ID NO 83
<211> LENGTH: 36
<212> TYPE: DNA
<213> ORGANISM: Artificial Sequence
<220> FEATURE:
<223> OTHER INFORMATION: Primer

<400> SEQUENCE: 83
gccgaattcc tagcagctag caccgaattt atctaa                                36

<210> SEQ ID NO 84
<211> LENGTH: 33
<212> TYPE: DNA
<213> ORGANISM: Artificial Sequence
<220> FEATURE:
<223> OTHER INFORMATION: Primer

<400> SEQUENCE: 84
ggttaagtcg acatgagagt gaaggagaaa tat                                   33

<210> SEQ ID NO 85
<211> LENGTH: 30
<212> TYPE: DNA
<213> ORGANISM: Artificial Sequence
<220> FEATURE:
<223> OTHER INFORMATION: Primer

<400> SEQUENCE: 85
taaccgaatt caggaggtaa aaagatatgg                                       30

<210> SEQ ID NO 86
<211> LENGTH: 35
<212> TYPE: DNA
<213> ORGANISM: Artificial Sequence
<220> FEATURE:
<223> OTHER INFORMATION: Primer

<400> SEQUENCE: 86
gaagtaaagc ttttaaccac cgcaaccacc agaag                                 35

<210> SEQ ID NO 87
<211> LENGTH: 33
<212> TYPE: DNA
<213> ORGANISM: Artificial Sequence
<220> FEATURE:
<223> OTHER INFORMATION: Primer

<400> SEQUENCE: 87
tcgaatgggc cctcatcttc gtgtgctagt cag                                   33

<210> SEQ ID NO 88
<211> LENGTH: 4
<212> TYPE: PRT
<213> ORGANISM: Artificial Sequence
<220> FEATURE:
<223> OTHER INFORMATION: Fos fusion construct

<400> SEQUENCE: 88

Glu Phe Arg Arg
 1

<210> SEQ ID NO 89
<211> LENGTH: 183
<212> TYPE: PRT
<213> ORGANISM: Hepatitis B virus

<400> SEQUENCE: 89

-continued

```
Met Asp Ile Asp Pro Tyr Lys Glu Phe Gly Ala Thr Val Glu Leu Leu
  1               5                  10                  15

Ser Phe Leu Pro Ser Asp Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Gly Asn Leu Glu Asp Pro Ile
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Gly Ser Gln Cys
            180
```

<210> SEQ ID NO 90
<211> LENGTH: 183
<212> TYPE: PRT
<213> ORGANISM: Hepatitis B virus

<400> SEQUENCE: 90

```
Met Asp Ile Asp Pro Tyr Lys Glu Phe Gly Ala Thr Val Glu Leu Leu
  1               5                  10                  15

Ser Phe Leu Pro Ser Asp Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Gly Asn Leu Glu Asp Pro Thr
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
                115                 120                 125

Pro Pro Ala Tyr Arg Pro Thr Asn Ala Pro Ile Leu Ser Thr Leu Pro
        130                 135                 140

Glu Thr Cys Val Ile Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Gly Ser Gln Cys
```

```
                180

<210> SEQ ID NO 91
<211> LENGTH: 212
<212> TYPE: PRT
<213> ORGANISM: Hepatitis B virus

<400> SEQUENCE: 91

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Gly Asn Leu Glu Asp Pro Ile Ser Arg Asp
             100                 105                 110

Leu Val Val Ser Tyr Val Asn Thr Asn Met Gly Leu Lys Phe Arg Gln
         115                 120                 125

Leu Leu Trp Phe His Ile Ser Cys Leu Thr Phe Gly Arg Glu Thr Val
     130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                 165                 170                 175

Val Val Arg Arg Arg Gly Arg Ser Pro Arg Arg Arg Thr Pro Ser Pro
             180                 185                 190

Arg Arg Arg Arg Ser Gln Ser Pro Arg Arg Arg Arg Ser Gln Ser Arg
         195                 200                 205

Glu Ser Gln Cys
    210

<210> SEQ ID NO 92
<211> LENGTH: 212
<212> TYPE: PRT
<213> ORGANISM: Hepatitis B virus

<400> SEQUENCE: 92

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Asn Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Gly Asn Leu Glu Asp Pro Ile Ser Arg Asp
```

```
                  100                 105                 110
Leu Val Val Ser Tyr Val Asn Thr Asn Met Gly Leu Lys Phe Arg Gln
            115                 120                 125
Leu Leu Trp Phe His Ile Ser Cys Leu Thr Phe Gly Arg Glu Thr Val
        130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
            180                 185                 190
Arg Arg Arg Arg Ser Gln Ser Pro Arg Arg Arg Arg Ser Gln Ser Arg
        195                 200                 205
Glu Ser Gln Cys
    210

<210> SEQ ID NO 93
<211> LENGTH: 183
<212> TYPE: PRT
<213> ORGANISM: Hepatitis B virus

<400> SEQUENCE: 93

Met Asp Ile Asp Pro Tyr Lys Glu Phe Gly Ala Thr Val Glu Leu Leu
1               5                   10                  15
Ser Phe Leu Pro Thr Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Val Asn Leu Glu Asp Pro Ala
65                  70                  75                  80
Ser Arg Asp Leu Val Val Ser Tyr Val Asn Thr Asn Met Gly Leu Lys
                85                  90                  95
Phe Arg Gln Leu Leu Trp Phe His Ile Ser Cys Leu Thr Phe Gly Arg
            100                 105                 110
Glu Thr Val Ile Glu Tyr Leu Val Ser Phe Gly Val Trp Ile Arg Thr
        115                 120                 125
Pro Pro Ala Tyr Arg Pro Pro Asn Ala Pro Ile Leu Ser Thr Leu Pro
    130                 135                 140
Glu Thr Cys Val Val Arg Arg Arg Gly Arg Ser Pro Arg Arg Arg Thr
145                 150                 155                 160
Pro Ser Pro Arg Arg Arg Arg Ser Gln Ser Pro Arg Arg Arg Arg Ser
                165                 170                 175
Gln Ser Arg Glu Ser Gln Cys
            180

<210> SEQ ID NO 94
<211> LENGTH: 212
<212> TYPE: PRT
<213> ORGANISM: Hepatitis B virus

<400> SEQUENCE: 94

Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Gly Met Asp Ile
```

-continued

```
                20                  25                  30
Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Thr
                 85                  90                  95

Leu Ala Thr Trp Val Gly Gly Asn Leu Glu Asp Pro Val Ser Arg Asp
                100                 105                 110

Leu Val Val Ser Tyr Val Asn Thr Asn Val Gly Leu Lys Phe Arg Gln
                115                 120                 125

Leu Leu Trp Phe His Ile Ser Cys Leu Thr Phe Gly Arg Glu Thr Val
                130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Arg Ser Gln Ser Arg
                195                 200                 205

Glu Ser Gln Cys
        210
```

<210> SEQ ID NO 95
<211> LENGTH: 212
<212> TYPE: PRT
<213> ORGANISM: Hepatitis B virus

<400> SEQUENCE: 95

```
Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Asp Met Asp Ile
                 20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Thr
                 85                  90                  95

Leu Ala Thr Trp Val Gly Gly Asn Leu Glu Asp Pro Val Ser Arg Asp
                100                 105                 110

Leu Val Val Ser Tyr Val Asn Thr Asn Val Gly Leu Lys Phe Arg Gln
                115                 120                 125

Leu Leu Trp Phe His Ile Ser Cys Leu Thr Phe Gly Arg Glu Thr Val
                130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175
```

```
Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
        210

<210> SEQ ID NO 96
<211> LENGTH: 212
<212> TYPE: PRT
<213> ORGANISM: Hepatitis B virus

<400> SEQUENCE: 96

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
                 20                  25                  30

Asp Pro Tyr Lys Glu Phe Gly Ala Thr Val Glu Leu Leu Ser Phe Leu
             35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro Gln
 65                  70                  75                  80

His Thr Ala Leu Arg Gln Ala Ile Leu Cys Trp Gly Glu Leu Met Thr
                 85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
        210

<210> SEQ ID NO 97
<211> LENGTH: 212
<212> TYPE: PRT
<213> ORGANISM: Hepatitis B virus

<400> SEQUENCE: 97

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
                 20                  25                  30

Asp Pro Tyr Lys Glu Phe Gly Ala Thr Val Glu Leu Leu Ser Phe Leu
             35                  40                  45

Pro Ser Asp Phe Phe Pro Ser Val Arg Asp Leu Leu Asp Thr Ala Ser
 50                  55                  60
```

```
Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Lys Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Arg Ser Gln Ser Arg
                195                 200                 205

Gly Ser Gln Cys
        210

<210> SEQ ID NO 98
<211> LENGTH: 183
<212> TYPE: PRT
<213> ORGANISM: Hepatitis B virus

<400> SEQUENCE: 98

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
                 20                  25                  30

Thr Ala Ser Ala Leu Phe Arg Asp Ala Leu Glu Ser Pro Glu His Cys
             35                  40                  45

Ser Pro His His Thr Ala Leu Arg Gln Ala Ile Leu Cys Trp Gly Glu
         50                  55                  60

Leu Met Thr Leu Ala Thr Trp Val Gly Gly Asn Leu Glu Asp Pro Ala
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Asp Thr Val Ile Glu Tyr Leu Val Ser Phe Gly Val Trp Ile Arg Thr
        115                 120                 125

Pro Pro Ala Tyr Arg Pro Ser Asn Ala Pro Ile Leu Ser Thr Leu Pro
    130                 135                 140

Glu Thr Cys Val Val Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 99
<211> LENGTH: 183
<212> TYPE: PRT
<213> ORGANISM: Hepatitis B virus
```

<400> SEQUENCE: 99

```
Met Asp Ile Asp Pro Tyr Lys Glu Phe Gly Ala Thr Val Glu Leu Leu
  1               5                  10                  15
Ser Phe Leu Pro Ser Asp Phe Phe Pro Ser Val Arg Asp Leu Leu Asp
                 20                  25                  30
Thr Ala Ser Ala Leu Tyr Arg Glu Ala Leu Glu Ser Pro Glu His Cys
             35                  40                  45
Ser Pro His His Thr Ala Leu Arg Gln Ala Ile Leu Cys Trp Gly Glu
         50                  55                  60
Leu Met Thr Leu Ala Thr Trp Val Gly Val Asn Leu Glu Asp Pro Ala
 65                  70                  75                  80
Ser Arg Asp Leu Val Val Ser Tyr Val Asn Thr Asn Met Gly Leu Lys
                 85                  90                  95
Phe Arg Gln Leu Leu Trp Phe His Ile Ser Cys Leu Thr Phe Gly Arg
            100                 105                 110
Glu Thr Val Ile Glu Tyr Leu Val Ser Phe Gly Val Trp Ile Arg Thr
            115                 120                 125
Pro Pro Ala Tyr Arg Pro Pro Asn Ala Pro Ile Leu Ser Thr Leu Pro
        130                 135                 140
Glu Thr Thr Val Val Arg Arg Arg Gly Arg Ser Pro Arg Arg Arg Thr
145                 150                 155                 160
Pro Ser Pro Arg Arg Arg Arg Ser Gln Ser Pro Arg Arg Arg Arg Ser
                165                 170                 175
Gln Ser Arg Glu Ser Gln Cys
            180
```

<210> SEQ ID NO 100
<211> LENGTH: 212
<212> TYPE: PRT
<213> ORGANISM: Hepatitis B virus

<400> SEQUENCE: 100

```
Met Gln Leu Phe His Leu Cys Leu Ile Ile Ser Cys Ser Cys Pro Thr
  1               5                  10                  15
Val Gln Ala Ser Lys Leu Cys Leu Gly Trp Leu Trp Gly Met Asp Ile
                 20                  25                  30
Asp Pro Tyr Lys Glu Phe Gly Ala Thr Val Glu Leu Leu Ser Phe Leu
             35                  40                  45
Pro Ser Asp Phe Phe Pro Ser Val Arg Asp Leu Leu Asp Thr Ala Ser
         50                  55                  60
Ala Leu Tyr Arg Glu Ala Leu Glu Ser Pro Glu His Cys Ser Pro His
 65                  70                  75                  80
His Thr Ala Leu Arg His Ala Ile Leu Cys Trp Gly Asp Leu Arg Thr
                 85                  90                  95
Leu Ala Thr Trp Val Gly Gly Asn Leu Glu Asp Pro Ile Ser Arg Asp
            100                 105                 110
Leu Val Val Ser Tyr Val Asn Thr Asn Met Gly Leu Lys Phe Arg Gln
            115                 120                 125
Leu Leu Trp Phe His Ile Ser Cys Leu Thr Phe Gly Arg Glu Thr Val
        130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
```

```
Val Val Arg Arg Arg Gly Arg Ser Pro Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

<210> SEQ ID NO 101
<211> LENGTH: 212
<212> TYPE: PRT
<213> ORGANISM: Hepatitis B virus

<400> SEQUENCE: 101

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Phe Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Ala Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Gln Ala
145                 150                 155                 160

Tyr Arg Pro Pro Asn Ala Pro Ile Leu Ser Thr Leu Pro Glu Thr Cys
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

<210> SEQ ID NO 102
<211> LENGTH: 183
<212> TYPE: PRT
<213> ORGANISM: Artificial Sequence
<220> FEATURE:
<223> OTHER INFORMATION: synthetic human Hepatitis B construct

<400> SEQUENCE: 102

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45
```

```
Ser Pro His His Thr Ala Leu Arg Gln Ala Ile Leu Cys Trp Gly Glu
 50                  55                  60
Leu Met Thr Leu Ala Thr Trp Val Gly Val Asn Leu Glu Asp Pro Ala
 65                  70                  75                  80
Ser Arg Asp Leu Val Val Ser Tyr Val Asn Thr Asn Met Gly Leu Lys
                 85                  90                  95
Phe Arg Gln Leu Leu Trp Phe His Ile Ser Cys Leu Thr Phe Gly Arg
                100                 105                 110
Glu Thr Val Leu Glu Tyr Leu Val Ser Phe Gly Val Trp Ile Arg Thr
                115                 120                 125
Pro Pro Ala Tyr Arg Pro Pro Asn Ala Pro Ile Leu Ser Thr Leu Pro
130                 135                 140
Glu Thr Thr Val Val Arg Arg Gly Arg Ser Pro Arg Arg Arg Thr
145                 150                 155                 160
Pro Ser Pro Arg Arg Arg Ser Gln Ser Pro Arg Arg Arg Ser
                165                 170                 175
Gln Ser Arg Glu Ser Gln Cys
                180

<210> SEQ ID NO 103
<211> LENGTH: 212
<212> TYPE: PRT
<213> ORGANISM: Hepatitis B virus

<400> SEQUENCE: 103

Met Gln Leu Phe His Leu Cys Leu Ile Ile Ser Cys Ser Cys Pro Thr
  1               5                  10                  15
Val Gln Ala Ser Lys Leu Cys Leu Gly Trp Leu Trp Gly Met Asp Ile
                 20                  25                  30
Asp Pro Tyr Lys Glu Phe Gly Ala Thr Val Glu Leu Leu Ser Phe Leu
                 35                  40                  45
Pro Ser Asp Phe Phe Pro Ser Val Arg Asp Leu Leu Asp Thr Ala Ser
 50                  55                  60
Ala Leu Tyr Arg Glu Ala Leu Glu Ser Pro Glu His Cys Ser Pro His
 65                  70                  75                  80
His Thr Ala Leu Arg Gln Ala Ile Leu Cys Trp Gly Asp Leu Met Ser
                 85                  90                  95
Leu Ala Thr Trp Val Gly Val Asn Leu Glu Asp Pro Ile Ser Arg Asp
                100                 105                 110
Leu Val Val Ser Tyr Val Asn Thr Asn Met Gly Leu Lys Phe Arg Gln
                115                 120                 125
Leu Leu Trp Phe His Ile Ser Cys Leu Thr Phe Gly Arg Glu Thr Val
130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
                180                 185                 190
Arg Arg Arg Arg Ser Gln Ser Pro Arg Arg Arg Arg Ser Gln Ser Arg
                195                 200                 205
Glu Ser Gln Cys
210

<210> SEQ ID NO 104
```

```
<211> LENGTH: 183
<212> TYPE: PRT
<213> ORGANISM: Hepatitis B virus

<400> SEQUENCE: 104

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 105
<211> LENGTH: 183
<212> TYPE: PRT
<213> ORGANISM: Hepatitis B virus

<400> SEQUENCE: 105

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160
```

```
Pro Ser Pro Arg Arg Arg Ser Gln Ser Pro Arg Arg Arg Ser
            165                 170                 175

Gln Ser Arg Glu Ser Gln Cys
            180

<210> SEQ ID NO 106
<211> LENGTH: 183
<212> TYPE: PRT
<213> ORGANISM: Hepatitis B virus

<400> SEQUENCE: 106

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Ala Asn Leu Glu Asp Pro Ala
 65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Thr Pro Arg Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
            180

<210> SEQ ID NO 107
<211> LENGTH: 212
<212> TYPE: PRT
<213> ORGANISM: Hepatitis B virus

<400> SEQUENCE: 107

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
                20                  25                  30

Asp Pro Tyr Lys Glu Phe Gly Ala Thr Val Glu Leu Leu Ser Phe Leu
            35                  40                  45

Pro Ser Asp Phe Phe Pro Ser Val Arg Asp Leu Leu Asp Thr Ala Ser
        50                  55                  60

Ala Leu Tyr Arg Asp Ala Leu Glu Ser Pro Glu His Cys Ser Pro His
 65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110
```

```
Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
                180                 185                 190

Arg Arg Arg Arg Ser Gln Ser Pro Arg Arg Arg Ser Gln Ser Arg
            195                 200                 205

Glu Ser Gln Cys
    210
```

```
<210> SEQ ID NO 108
<211> LENGTH: 212
<212> TYPE: PRT
<213> ORGANISM: Hepatitis B virus

<400> SEQUENCE: 108

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
                180                 185                 190

Arg Arg Arg Arg Ser Gln Ser Pro Arg Arg Arg Ser Gln Ser Arg
            195                 200                 205

Glu Ser Gln Cys
    210
```

```
<210> SEQ ID NO 109
<211> LENGTH: 212
<212> TYPE: PRT
<213> ORGANISM: Hepatitis B virus

<400> SEQUENCE: 109
```

-continued

```
Met Gln Leu Phe His Leu Cys Leu Ile Ile Ser Cys Thr Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
                100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
130                 135                 140

Ile Glu Tyr Leu Val Ala Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Arg Ser Gln Ser Arg
            195                 200                 205

Glu Ser Gln Cys
        210

<210> SEQ ID NO 110
<211> LENGTH: 212
<212> TYPE: PRT
<213> ORGANISM: Hepatitis B virus

<400> SEQUENCE: 110

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Phe Glu Cys Ser Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Gly Asn Leu Glu Asp Pro Ile Ser Arg Asp
                100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
```

```
                145                 150                 155                 160
Tyr Arg Pro Pro Asn Ala Pro Ile Leu Ser Thr Leu Pro Glu Thr Thr
                    165                 170                 175
Val Val Arg Arg Arg Gly Arg Ser Pro Arg Arg Thr Pro Ser Pro
                180                 185                 190
Arg Arg Arg Arg Ser Gln Ser Pro Arg Arg Arg Arg Ser Gln Ser Arg
            195                 200                 205
Glu Ser Gln Cys
        210

<210> SEQ ID NO 111
<211> LENGTH: 212
<212> TYPE: PRT
<213> ORGANISM: Hepatitis B virus
<220> FEATURE:
<221> NAME/KEY: UNSURE
<222> LOCATION: 28
<223> OTHER INFORMATION: Xaa may be any amino acid.

<400> SEQUENCE: 111

Met Gln Leu Phe His Leu Cys Leu Ile Ile Ser Cys Ser Cys Pro Thr
 1               5                  10                  15
Val Gln Ala Ser Lys Leu Cys Leu Gly Trp Leu Xaa Asp Met Asp Ile
                20                  25                  30
Asp Pro Tyr Lys Glu Phe Gly Ala Thr Val Glu Leu Leu Ser Phe Leu
            35                  40                  45
Pro Ser Asp Phe Phe Pro Ser Val Arg Asp Leu Leu Asp Thr Ala Ser
    50                  55                  60
Ala Leu Tyr Arg Glu Ala Leu Glu Ser Pro Glu His Cys Ser Pro His
65                  70                  75                  80
His Thr Ala Leu Arg Gln Ala Ile Leu Cys Trp Gly Asp Leu Ile Thr
                85                  90                  95
Leu Ser Thr Trp Val Gly Gly Asn Leu Glu Asp Pro Thr Ser Arg Asp
            100                 105                 110
Leu Val Val Ser Tyr Val Asn Thr Asn Met Gly Leu Lys Phe Arg Gln
        115                 120                 125
Leu Leu Trp Phe His Ile Ser Cys Leu Thr Phe Gly Arg Glu Thr Val
    130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
            180                 185                 190
Arg Arg Arg Arg Ser Gln Ser Pro Arg Arg Arg Arg Thr Gln Ser Arg
        195                 200                 205
Glu Ser Gln Cys
        210

<210> SEQ ID NO 112
<211> LENGTH: 212
<212> TYPE: PRT
<213> ORGANISM: Hepatitis B virus

<400> SEQUENCE: 112

Met Gln Leu Phe His Leu Cys Leu Ile Ile Ser Cys Ser Cys Pro Thr
 1               5                  10                  15
```

-continued

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 113
<211> LENGTH: 212
<212> TYPE: PRT
<213> ORGANISM: Hepatitis B virus

<400> SEQUENCE: 113

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Cys Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

```
Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
    210
```

<210> SEQ ID NO 114
<211> LENGTH: 212
<212> TYPE: PRT
<213> ORGANISM: Hepatitis B virus

<400> SEQUENCE: 114

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
            35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Ser Gln Ser Arg
            195                 200                 205

Glu Pro Gln Cys
    210
```

<210> SEQ ID NO 115
<211> LENGTH: 212
<212> TYPE: PRT
<213> ORGANISM: Hepatitis B virus

<400> SEQUENCE: 115

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
            35                  40                  45

Pro Ser Asp Phe Phe Pro Ser Val Arg Asp Leu Leu Ser Thr Ala Ser
    50                  55                  60
```

-continued

```
Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 116
<211> LENGTH: 212
<212> TYPE: PRT
<213> ORGANISM: Hepatitis B virus

<400> SEQUENCE: 116

```
Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
                 20                  25                  30

Asp Pro Tyr Lys Glu Phe Gly Ala Thr Val Glu Leu Leu Ser Phe Leu
             35                  40                  45

Pro Ser Asp Phe Phe Pro Ser Val Arg Asp Leu Leu Asp Thr Ala Ser
         50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
```

<210> SEQ ID NO 117
<211> LENGTH: 212
<212> TYPE: PRT
<213> ORGANISM: Hepatitis B virus

<400> SEQUENCE: 117

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Lys Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 118
<211> LENGTH: 212
<212> TYPE: PRT
<213> ORGANISM: Hepatitis B virus

<400> SEQUENCE: 118

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Thr Asn Leu Glu Asp Pro Ala Ser Arg Asp

```
            100                 105                 110
Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
            130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                    165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
        210
```

<210> SEQ ID NO 119
<211> LENGTH: 183
<212> TYPE: PRT
<213> ORGANISM: Hepatitis B virus

<400> SEQUENCE: 119

```
Met Asp Ile Asp Pro Tyr Lys Glu Phe Gly Ala Ser Met Glu Leu Leu
1               5                   10                  15

Ser Phe Leu Pro Ser Asp Phe Tyr Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Thr Pro His His Thr Ala Leu Arg Gln Ala Ile Leu Cys Trp Gly Glu
    50                  55                  60

Leu Met Thr Leu Ala Thr Trp Val Gly Gly Asn Leu Gln Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Val Ser Cys Leu Thr Phe Gly Arg
            100                 105                 110

Glu Thr Val Val Glu Tyr Leu Val Ser Phe Gly Val Trp Ile Arg Thr
        115                 120                 125

Pro Gln Ala Tyr Arg Pro Pro Asn Ala Pro Ile Leu Ser Thr Leu Pro
    130                 135                 140

Glu Thr Cys Val Val Arg Arg Gly Arg Ser Pro Arg Arg Arg Thr
145                 150                 155                 160

Pro Ser Pro Arg Arg Arg Ser Gln Ser Pro Arg Arg Arg Arg Ser
                165                 170                 175

Gln Ser Arg Glu Ser Gln Cys
            180
```

<210> SEQ ID NO 120
<211> LENGTH: 183
<212> TYPE: PRT
<213> ORGANISM: Hepatitis B virus

<400> SEQUENCE: 120

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
```

-continued

```
                    20                  25                  30
Thr Ala Ser Ala Leu Tyr Arg Glu Ala Leu Glu Ser Pro Glu His Cys
            35                  40                  45

Ser Pro His His Thr Ala Leu Arg His Val Phe Leu Cys Trp Gly Asp
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 121
<211> LENGTH: 212
<212> TYPE: PRT
<213> ORGANISM: Hepatitis B virus

<400> SEQUENCE: 121

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Thr Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205
```

```
Glu Ser Gln Cys
    210

<210> SEQ ID NO 122
<211> LENGTH: 212
<212> TYPE: PRT
<213> ORGANISM: Hepatitis B virus

<400> SEQUENCE: 122

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Ile Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
        195                 200                 205

Glu Ser Gln Cys
    210

<210> SEQ ID NO 123
<211> LENGTH: 183
<212> TYPE: PRT
<213> ORGANISM: Hepatitis B virus

<400> SEQUENCE: 123

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Val
65                  70                  75                  80

Ser Arg Asp Leu Val Val Ser Tyr Val Asn Thr Asn Val Gly Leu Lys
                85                  90                  95
```

```
Phe Arg Gln Leu Leu Trp Phe His Ile Ser Cys Leu Thr Phe Gly Arg
                100                 105                 110
Glu Thr Val Ile Glu Tyr Leu Val Ser Phe Gly Val Trp Ile Arg Thr
            115                 120                 125
Pro Pro Ala Tyr Arg Pro Asn Ala Pro Ile Leu Ser Thr Leu Pro
        130                 135                 140
Glu Thr Thr Val Val Arg Arg Arg Gly Arg Ser Pro Arg Arg Arg Thr
145                 150                 155                 160
Pro Ser Pro Ala Arg Arg Arg Ser Gln Ser Pro Arg Arg Arg Arg Ser
                165                 170                 175
Gln Ser Arg Glu Ser Gln Cys
            180

<210> SEQ ID NO 124
<211> LENGTH: 212
<212> TYPE: PRT
<213> ORGANISM: Hepatitis B virus

<400> SEQUENCE: 124

Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Gly Met Asp Ile
            20                  25                  30
Asp Pro Tyr Lys Glu Phe Gly Ala Thr Val Glu Leu Leu Ser Phe Leu
        35                  40                  45
Pro Ser Asp Phe Phe Pro Ser Val Arg Asp Leu Leu Asp Thr Ala Ser
    50                  55                  60
Ala Leu Tyr Arg Glu Ala Leu Glu Ser Pro Glu His Cys Ser Pro His
65                  70                  75                  80
His Thr Ala Leu Arg Gln Ala Ile Leu Cys Trp Gly Asp Leu Met Asn
                85                  90                  95
Leu Ala Thr Trp Val Gly Gly Asn Leu Glu Asp Pro Val Ser Arg Asp
            100                 105                 110
Leu Val Val Gly Tyr Val Asn Thr Thr Val Gly Leu Lys Phe Arg Gln
        115                 120                 125
Leu Leu Trp Phe His Ile Ser Cys Leu Thr Phe Gly Arg Glu Thr Val
    130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
            180                 185                 190
Arg Arg Arg Arg Ser Gln Ser Pro Arg Arg Arg Arg Ser Gln Ser Arg
        195                 200                 205
Glu Ser Gln Cys
    210

<210> SEQ ID NO 125
<211> LENGTH: 183
<212> TYPE: PRT
<213> ORGANISM: Hepatitis B virus

<400> SEQUENCE: 125

Met Asp Ile Asp Pro Tyr Lys Glu Phe Gly Ala Thr Val Glu Leu Leu
1               5                   10                  15
```

-continued

```
Ser Phe Leu Pro Ser Asp Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Thr Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 126
<211> LENGTH: 212
<212> TYPE: PRT
<213> ORGANISM: Hepatitis B virus

<400> SEQUENCE: 126

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Ala Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Ile Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205
```

Glu Ser Gln Cys
    210

<210> SEQ ID NO 127
<211> LENGTH: 212
<212> TYPE: PRT
<213> ORGANISM: Hepatitis B virus

<400> SEQUENCE: 127

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Thr Arg Asp
            100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 128
<211> LENGTH: 212
<212> TYPE: PRT
<213> ORGANISM: Hepatitis B virus

<400> SEQUENCE: 128

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Arg Ile Leu Cys Trp Gly Glu Leu Met Thr
                85                  90                  95

```
Leu Ala Thr Trp Val Gly Val Asn Leu Glu Asp Pro Ala Ser Arg Asp
                100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Thr Arg Ser Gln Ser Arg
            195                 200                 205

Glu Ser Gln Cys
    210

<210> SEQ ID NO 129
<211> LENGTH: 212
<212> TYPE: PRT
<213> ORGANISM: Hepatitis B virus

<400> SEQUENCE: 129

Met Gln Leu Phe His Leu Cys Leu Val Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Asn Asn Leu Glu Asp Pro Ala Ser Arg Asp
                100                 105                 110

Leu Val Val Asn Tyr Val Asn Thr Asn Met Gly Leu Lys Ile Arg Gln
            115                 120                 125

Leu Leu Trp Phe His Ile Ser Cys Leu Thr Phe Gly Arg Glu Thr Val
        130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

<210> SEQ ID NO 130
<211> LENGTH: 212
<212> TYPE: PRT
```

<213> ORGANISM: Hepatitis B virus

<400> SEQUENCE: 130

| Met | Gln | Leu | Phe | His | Leu | Cys | Leu | Ile | Ile | Ser | Cys | Ser | Cys | Pro | Thr |
|---|---|---|---|---|---|---|---|---|---|---|---|---|---|---|---|
| 1 | | | | 5 | | | | | 10 | | | | | 15 | |

Val Gln Ala Ser Lys Leu Cys Leu Gly Trp Leu Trp Gly Met Asp Ile
            20              25              30

Asp Pro Tyr Lys Glu Phe Gly Ala Thr Val Glu Leu Leu Ser Phe Leu
    35                  40              45

Pro Ser Ala Phe Phe Pro Ser Val Arg Asp Leu Leu Asp Thr Ala Ser
 50                  55              60

Ala Leu Tyr Arg Glu Ala Leu Glu Ser Pro Glu His Cys Ser Pro His
 65              70              75              80

His Thr Ala Leu Arg Gln Ala Ile Leu Cys Trp Gly Asp Leu Met Thr
            85              90              95

Leu Ala Thr Trp Val Gly Val Asn Leu Glu Asp Pro Ala Ser Arg Asp
          100             105           110

Leu Val Val Ser Tyr Val Asn Thr Asn Met Gly Leu Lys Phe Arg Gln
          115             120           125

Leu Leu Trp Phe His Ile Ser Cys Leu Thr Phe Gly Arg Glu Thr Val
130                135             140

Ile Glu Tyr Leu Val Ser Phe Gly Val Trp Ile Arg Thr Pro Pro Ala
145              150              155           160

Tyr Arg Pro Pro Asn Ala Pro Ile Leu Ser Thr Leu Pro Glu Thr Thr
          165             170           175

Val Val Arg Arg Arg Gly Arg Ser Pro Arg Arg Thr Pro Ser Pro
          180             185           190

Arg Arg Arg Ser Gln Ser Pro Arg Arg Arg Ser Gln Ser Arg
          195             200           205

Glu Ser Gln Cys
210

<210> SEQ ID NO 131
<211> LENGTH: 183
<212> TYPE: PRT
<213> ORGANISM: Hepatitis B virus

<400> SEQUENCE: 131

Met Asp Ile Asp Pro Tyr Lys Glu Phe Gly Ala Thr Val Glu Leu Leu
1                 5                 10              15

Ser Phe Leu Pro Ser Asp Phe Phe Pro Ser Val Arg Asp Leu Leu Asp
          20             25           30

Thr Ala Ala Leu Tyr Arg Glu Ala Leu Glu Ser Pro Glu His Cys
          35             40           45

Ser Pro His His Thr Ala Leu Arg Gln Ala Ile Leu Cys Trp Gly Glu
 50                  55              60

Leu Met Thr Leu Ala Thr Trp Val Gly Asn Asn Leu Glu Asp Pro Ala
 65               70              75              80

Ser Arg Asp Leu Val Val Asn Tyr Val Asn Thr Asn Met Gly Leu Lys
            85              90              95

Ile Arg Gln Leu Leu Trp Phe His Ile Ser Cys Leu Thr Phe Gly Arg
          100             105           110

Glu Thr Val Leu Glu Tyr Leu Val Ser Phe Gly Val Trp Ile Arg Thr
          115             120           125

Pro Pro Ala Tyr Arg Pro Pro Asn Ala Pro Ile Leu Ser Thr Leu Pro

```
                130                 135                 140
Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 132
<211> LENGTH: 183
<212> TYPE: PRT
<213> ORGANISM: Hepatitis B virus

<400> SEQUENCE: 132

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Gly Ser Gln Cys
            180

<210> SEQ ID NO 133
<211> LENGTH: 3221
<212> TYPE: DNA
<213> ORGANISM: Hepatitis B virus
<220> FEATURE:
<221> NAME/KEY: CDS
<222> LOCATION: (1901)..(2458)

<400> SEQUENCE: 133
ttccactgcc ttccaccaag ctctgcagga ccccagagtc aggggtctgt attttcctgc    60
tggtggctcc agttcaggaa cagtaaaccc tgctccgaat attgcctctc acatctcgtc   120
aatctccgcg aggactgggg accctgtgac gaacatggag aacatcacat caggattcct   180
aggacccctg ctcgtgttac aggcggggtt tttattgttg acaagaatcc tcacaatacc   240
gcagagtcta gactcgtggt ggacttctct caatttttata ggggatcac ccgtgtgtct   300 tggccaaaat tcgcagtccc caacctccaa tcactcacca acctcctgtc tccaatttg   360 tcctggttat cgctggatgt gtctgcggcg ttttatcata ttcctcttca tcctgctgct   420
```

-continued

```
atgcctcatc ttcttattgg ttcttctgga ttatcaaggt atgttgcccg tttgtcctct    480
aattccagga tcaacaacaa ccagtacggg accatgcaaa acctgcacga ctcctgctca    540
aggcaactct atgtttccct catgttgctg tacaaaacct acggttggaa attgcacctg    600
tattcccatc ccatcgtcct gggctttcgc aaaataccta tgggagtggg cctcagtccg    660
tttctcttgg ctcagtttac tagtgccatt tgttcagtgg ttcgtagggc tttcccccac    720
tgtttggctt tcagctatat ggatgatgtg gtattggggg ccaagtctgt acagcatcgt    780
gagtcccttt ataccgctgt taccaattt cttttgtctc tgggtataca tttaaaccct    840
aacaaaacaa aaagatgggg ttattcccta aacttcatgg gttacataat tggaagttgg    900
ggaacattgc cacaggatca tattgtacaa aagatcaaac actgttttag aaaacttcct    960
gttaacaggc ctattgattg gaaagtatgt caaagaattg tgggtctttt gggctttgct   1020
gctccattta cacaatgtgg atatcctgcc ttaatgcctt tgtatgcatg tatacaggct   1080
aaacaggctt tcactttctc gccaacttac aaggcctttc taagtaaaca gtacatgaac   1140
ctttaccccg ttgctcggca acggcctggt ctgtgccaag tgtttgctga cgcaaccccc   1200
actggttggg gcttggccat aggccatcag cgcatgagtg gaacctttgt ggctcctctg   1260
ccgatccata ctgcggaact cctagccgct tgtattgctc gcagccggtc tggagcaaag   1320
ctcatcggaa ctgacaattc tgtcgtcctc tcgcggaaat atacatcgtt tccatggctg   1380
ctaggctgta ctgccaactg gatccttcgc gggacgtcct ttgtttacgt cccgtcggcg   1440
ctgaatcccg cggacgaccc ctctcggggc cgcttgggac tctatcgtcc ccttctccgt   1500
ctgccgttcc agccgaccac ggggcgcacc tctctttacg cggtctcccc gtctgtgcct   1560
tctcatctgc cggtccgtgt gcacttcgct tcacctctgc acgttgcatg gagaccaccg   1620
tgaacgccca tcagatcctg cccaaggtct tacataagag gactcttgga ctcccagcaa   1680
tgtcaacgac cgaccttgag gcctacttca agactgtgt gtttaaggac tgggaggagc   1740
tgggggagga gattaggtta aaggtctttg tattaggagg ctgtaggcat aaattggtct   1800
gcgcaccagc accatgcaac ttttcacct ctgcctaatc atctcttgta catgtcccac   1860
tgttcaagcc tccaagctgt gccttgggtg gctttgggc atg gac att gac cct    1915
                                            Met Asp Ile Asp Pro
                                              1               5 tat aaa gaa ttt gga gct act gtg gag tta ctc tcg ttt ttg cct tct    1963
Tyr Lys Glu Phe Gly Ala Thr Val Glu Leu Leu Ser Phe Leu Pro Ser
         10                  15                  20 gac ttc ttt cct tcc gtc aga gat ctc cta gac acc gcc tca gct ctg    2011
Asp Phe Phe Pro Ser Val Arg Asp Leu Leu Asp Thr Ala Ser Ala Leu
     25                  30                  35 tat cga gaa gcc tta gag tct cct gag cat tgc tca cct cac cat act    2059
Tyr Arg Glu Ala Leu Glu Ser Pro Glu His Cys Ser Pro His His Thr
 40                  45                  50 gca ctc agg caa gcc att ctc tgc tgg ggg gaa ttg atg act cta gct    2107
Ala Leu Arg Gln Ala Ile Leu Cys Trp Gly Glu Leu Met Thr Leu Ala
     55                  60                  65 acc tgg gtg ggt aat aat ttg gaa gat cca gca tcc agg gat cta gta    2155
Thr Trp Val Gly Asn Asn Leu Glu Asp Pro Ala Ser Arg Asp Leu Val
 70                  75                  80                  85 gtc aat tat gtt aat act aac atg ggt tta aag atc agg caa cta ttg    2203
Val Asn Tyr Val Asn Thr Asn Met Gly Leu Lys Ile Arg Gln Leu Leu
         90                  95                 100 tgg ttt cat ata tct tgc ctt act ttt gga aga gag act gta ctt gaa    2251
Trp Phe His Ile Ser Cys Leu Thr Phe Gly Arg Glu Thr Val Leu Glu
```

```
                    105                 110                 115
tat ttg gtc tct ttc gga gtg tgg att cgc act cct cca gcc tat aga    2299
Tyr Leu Val Ser Phe Gly Val Trp Ile Arg Thr Pro Pro Ala Tyr Arg
            120                 125                 130 cca cca aat gcc cct atc tta tca aca ctt ccg gaa act act gtt gtt    2347
Pro Pro Asn Ala Pro Ile Leu Ser Thr Leu Pro Glu Thr Thr Val Val
135                 140                 145 aga cga cgg gac cga ggc agg tcc cct aga aga aga act ccc tcg cct    2395
Arg Arg Arg Asp Arg Gly Arg Ser Pro Arg Arg Arg Thr Pro Ser Pro
150                 155                 160                 165 cgc aga cgc aga tct caa tcg ccg cgt cgc aga aga tct caa tct cgg    2443
Arg Arg Arg Arg Ser Gln Ser Pro Arg Arg Arg Ser Gln Ser Arg
                170                 175                 180 gaa tct caa tgt tag tattccttgg actcataagg tgggaaactt tactgggctt    2498
Glu Ser Gln Cys
            185 tattcctcta cagtacctat ctttaatcct gaatggcaaa ctccttcctt tcctaagatt    2558 catttacaag aggacattat tgataggtgt caacaatttg tgggccctct cactgtaaat    2618 gaaaagagaa gattgaaatt aattatgcct gctagattct atcctaccca cactaaatat    2678 ttgcccttag acaaggaat taaaccttat tatccagatc aggtagttaa tcattacttc    2738 caaaccagac attatttaca tactctttgg aaggctggta ttctatataa gagggaaacc    2798 acacgtagcg catcattttg cgggtcacca tattcttggg aacaagagct acagcatggg    2858 aggttggtca ttaaaacctc gcaaaggcat ggggacgaat ctttctgttc caacccctct    2918 gggattcttt cccgatcatc agttggaccc tgcattcgga gccaactcaa acaatccaga    2978 ttgggacttc aacccatca aggaccactg gccagcagcc aaccaggtag gagtgggagc    3038 attcgggcca gggctcaccc ctccacacgg cggtattttg gggtggagcc ctcaggctca    3098 gggcatattg accacagtgt caacaattcc tcctcctgcc tccaccaatc ggcagtcagg    3158 aaggcagcct actcccatct ctccacctct aagagacagt catcctcagg ccatgcagtg    3218 gaa                                                                3221

<210> SEQ ID NO 134
<211> LENGTH: 185
<212> TYPE: PRT
<213> ORGANISM: Hepatitis B virus

<400> SEQUENCE: 134

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
         50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125
```

Pro Pro Ala Tyr Arg Pro Pro Asn Ala Pro Ile Leu Ser Thr Leu Pro
        130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185

<210> SEQ ID NO 135
<211> LENGTH: 188
<212> TYPE: PRT
<213> ORGANISM: Woodchuck hepatitis B virus

<400> SEQUENCE: 135

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Thr Asn Cys
            180                 185

<210> SEQ ID NO 136
<211> LENGTH: 217
<212> TYPE: PRT
<213> ORGANISM: Ground squirrel hepatitis virus

<400> SEQUENCE: 136

Met Tyr Leu Phe His Leu Cys Leu Val Phe Ala Cys Val Pro Cys Pro
1               5                   10                  15

Thr Val Gln Ala Ser Lys Leu Cys Leu Gly Trp Leu Trp Asp Met Asp
            20                  25                  30

Ile Asp Pro Tyr Lys Glu Phe Gly Ser Ser Tyr Gln Leu Leu Asn Phe
        35                  40                  45

Leu Pro Leu Asp Phe Phe Pro Asp Leu Asn Ala Leu Val Asp Thr Ala
    50                  55                  60

Ala Ala Leu Tyr Glu Glu Glu Leu Thr Gly Arg Glu His Cys Ser Pro
65                  70                  75                  80

-continued

His His Thr Ala Ile Arg Gln Ala Leu Val Cys Trp Glu Leu Thr
                85                  90                  95

Arg Leu Ile Thr Trp Met Ser Glu Asn Thr Thr Glu Val Arg Arg
            100                 105                 110

Ile Ile Val Asp His Val Asn Asn Thr Trp Gly Leu Lys Val Arg Gln
        115                 120                 125

Thr Leu Trp Phe His Leu Ser Cys Leu Thr Phe Gly Gln His Thr Val
    130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
            180                 185                 190

Arg Thr Pro Ser Pro Arg Arg Arg Ser Gln Ser Pro Arg Arg Arg
        195                 200                 205

Arg Ser Gln Ser Pro Ala Ser Asn Cys
    210                 215

<210> SEQ ID NO 137
<211> LENGTH: 262
<212> TYPE: PRT
<213> ORGANISM: Snow Goose Hepatitis B Virus

<400> SEQUENCE: 137

Met Asp Val Asn Ala Ser Arg Ala Leu Ala Asn Val Tyr Asp Leu Pro
1               5                   10                  15

Asp Asp Phe Phe Pro Lys Ile Glu Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ala Ile Arg Ala Val Ile Pro Pro
65                  70                  75                  80

Thr Thr Ala Pro Val Pro Ser Gly Tyr Leu Ile Gln His Asp Glu Ala
                85                  90                  95

Glu Glu Ile Pro Leu Gly Asp Leu Phe Lys Glu Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val Ala Gln Gly Gly Arg Lys Thr Ser Thr Ala Thr Arg Lys
        195                 200                 205

Pro Arg Gly Leu Glu Pro Arg Arg Lys Val Lys Thr Thr Val Val
    210                 215                 220

Tyr Gly Arg Arg Arg Ser Lys Ser Arg Glu Arg Arg Ala Ser Ser Pro

```
                225                 230                 235                 240
Gln Arg Ala Gly Ser Pro Leu Pro Arg Ser Ser Ser His His Arg
                    245                 250                 255

Ser Pro Ser Pro Arg Lys
                260

<210> SEQ ID NO 138
<211> LENGTH: 305
<212> TYPE: PRT
<213> ORGANISM: Duck hepatitis B virus

<400> SEQUENCE: 138

Met Trp Asp Leu Arg Leu His Pro Ser Pro Phe Gly Ala Ala Cys Gln
  1               5                  10                  15

Gly Ile Phe Thr Ser Ser Leu Leu Phe Leu Val Thr Val Pro Leu
             20                  25                  30

Val Cys Thr Ile Val Tyr Asp Ser Cys Leu Cys Met Asp Ile Asn Ala
                 35                  40                  45

Ser Arg Ala Leu Ala Asn Val Tyr Asp Leu Pro Asp Asp Phe Phe Pro
         50                  55                  60

Lys Ile Asp Asp Leu Val Arg Asp Ala Lys Asp Ala Leu Glu Pro Tyr
 65                  70                  75                  80

Trp Arg Asn Asp Ser Ile Lys Lys His Val Leu Ile Ala Thr His Phe
                 85                  90                  95

Val Asp Leu Ile Glu Asp Phe Trp Gln Thr Thr Gln Gly Met His Glu
            100                 105                 110

Ile Ala Glu Ala Leu Arg Ala Ile Ile Pro Ala Thr Thr Ala Pro Val
        115                 120                 125

Pro Gln Gly Phe Leu Val Gln His Glu Glu Ala Glu Ile Pro Leu
    130                 135                 140

Gly Glu Leu Phe Arg Tyr Gln Glu Glu Arg Leu Thr Asn Phe Gln Pro
145                 150                 155                 160

Asp Tyr Pro Val Thr Ala Arg Ile His Ala His Leu Lys Ala Tyr Ala
                165                 170                 175

Lys Ile Asn Glu Glu Ser Leu Asp Arg Ala Arg Arg Leu Leu Trp Trp
            180                 185                 190

His Tyr Asn Cys Leu Leu Trp Gly Glu Pro Asn Val Thr Asn Tyr Ile
        195                 200                 205

Ser Arg Leu Arg Thr Trp Leu Ser Thr Pro Glu Lys Tyr Arg Gly Lys
    210                 215                 220

Asp Ala Pro Thr Ile Glu Ala Ile Thr Arg Pro Ile Gln Val Ala Gln
225                 230                 235                 240

Gly Gly Arg Asn Lys Thr Gln Gly Val Arg Lys Ser Arg Gly Leu Glu
                245                 250                 255

Pro Arg Arg Arg Arg Val Lys Thr Thr Ile Val Tyr Gly Arg Arg
                260                 265                 270

Ser Lys Ser Arg Glu Arg Arg Ala Pro Thr Pro Gln Arg Ala Gly Ser
        275                 280                 285

Pro Leu Pro Arg Thr Ser Arg Asp His His Arg Ser Pro Ser Pro Arg
    290                 295                 300

Glu
305

<210> SEQ ID NO 139
<211> LENGTH: 212
```

```
<212> TYPE: PRT
<213> ORGANISM: Haemophilus influenzae

<400> SEQUENCE: 139

Met Lys Lys Thr Leu Leu Gly Ser Leu Ile Leu Leu Ala Phe Ala Gly
  1               5                  10                  15

Asn Val Gln Ala Ala Ala Asn Ala Asp Thr Ser Gly Thr Val Thr Phe
             20                  25                  30

Phe Gly Lys Val Val Glu Asn Thr Cys Gln Val Asn Gln Asp Ser Glu
         35                  40                  45

Tyr Glu Cys Asn Leu Asn Asp Val Gly Lys Asn His Leu Ser Gln Gln
     50                  55                  60

Gly Tyr Thr Ala Met Gln Thr Pro Phe Thr Ile Thr Leu Glu Asn Cys
 65                  70                  75                  80

Asn Val Thr Thr Thr Asn Asn Lys Pro Lys Ala Thr Lys Val Gly Val
                 85                  90                  95

Tyr Phe Tyr Ser Trp Glu Ile Ala Asp Lys Asp Asn Lys Tyr Thr Leu
            100                 105                 110

Lys Asn Ile Lys Glu Asn Thr Gly Thr Asn Asp Ser Ala Asn Lys Val
        115                 120                 125

Asn Ile Gln Leu Leu Glu Asp Asn Gly Thr Ala Glu Ile Lys Val Val
130                 135                 140

Gly Lys Thr Thr Thr Asp Phe Thr Ser Glu Asn His Asn Gly Ala Gly
145                 150                 155                 160

Ala Asp Pro Val Ala Thr Asn Lys His Ile Ser Ser Leu Thr Pro Leu
                165                 170                 175

Asn Asn Gln Asn Ser Ile Asn Leu His Tyr Ile Ala Gln Tyr Tyr Ala
            180                 185                 190

Thr Gly Val Ala Glu Ala Gly Lys Val Pro Ser Ser Val Asn Ser Gln
        195                 200                 205

Ile Ala Tyr Glu
        210

<210> SEQ ID NO 140
<211> LENGTH: 139
<212> TYPE: PRT
<213> ORGANISM: Pseudomonas stutzeri

<400> SEQUENCE: 140

Met Lys Ala Gln Met Gln Lys Gly Phe Thr Leu Ile Glu Leu Met Ile
  1               5                  10                  15

Val Val Ala Ile Ile Gly Ile Leu Ala Ala Ile Ala Leu Pro Ala Tyr
             20                  25                  30

Gln Asp Tyr Thr Val Arg Ser Asn Ala Ala Ala Ala Leu Ala Glu Ile
         35                  40                  45

Thr Pro Gly Lys Ile Gly Phe Glu Gln Ala Ile Asn Glu Gly Lys Thr
     50                  55                  60

Pro Ser Leu Thr Ser Thr Asp Glu Gly Tyr Ile Gly Ile Thr Asp Ser
 65                  70                  75                  80

Thr Ser Tyr Cys Asp Val Asp Leu Asp Thr Ala Ala Asp Gly His Ile
                 85                  90                  95

Glu Cys Thr Ala Lys Gly Gly Asn Ala Gly Lys Phe Asp Gly Lys Thr
            100                 105                 110

Ile Thr Leu Asn Arg Thr Ala Asp Gly Glu Trp Ser Cys Ala Ser Thr
        115                 120                 125
```

Leu Asp Ala Lys Tyr Lys Pro Gly Lys Cys Ser
       130                 135

<210> SEQ ID NO 141
<211> LENGTH: 59
<212> TYPE: PRT
<213> ORGANISM: Caulobacter crescentus

<400> SEQUENCE: 141

Met Thr Lys Phe Val Thr Arg Phe Leu Lys Asp Glu Ser Gly Ala Thr
 1               5                  10                  15

Ala Ile Glu Tyr Gly Leu Ile Val Ala Leu Ile Ala Val Val Ile Val
            20                  25                  30

Thr Ala Val Thr Thr Leu Gly Thr Asn Leu Arg Thr Ala Phe Thr Lys
        35                  40                  45

Ala Gly Ala Ala Val Ser Thr Ala Ala Gly Thr
    50                  55

<210> SEQ ID NO 142
<211> LENGTH: 173
<212> TYPE: PRT
<213> ORGANISM: Escherichia coli

<400> SEQUENCE: 142

Met Ala Val Val Ser Phe Gly Val Asn Ala Ala Pro Thr Ile Pro Gln
 1               5                  10                  15

Gly Gln Gly Lys Val Thr Phe Asn Gly Thr Val Val Asp Ala Pro Cys
            20                  25                  30

Ser Ile Ser Gln Lys Ser Ala Asp Gln Ser Ile Asp Phe Gly Gln Leu
        35                  40                  45

Ser Lys Ser Phe Leu Glu Ala Gly Gly Val Ser Lys Pro Met Asp Leu
    50                  55                  60

Asp Ile Glu Leu Val Asn Cys Asp Ile Thr Ala Phe Lys Gly Gly Asn
 65                  70                  75                  80

Gly Ala Gln Lys Gly Thr Val Lys Leu Ala Phe Thr Gly Pro Ile Val
                85                  90                  95

Asn Gly His Ser Asp Glu Leu Asp Thr Asn Gly Gly Thr Gly Thr Ala
           100                 105                 110

Ile Val Val Gln Gly Ala Gly Lys Asn Val Val Phe Asp Gly Ser Glu
       115                 120                 125

Gly Asp Ala Asn Thr Leu Lys Asp Gly Glu Asn Val Leu His Tyr Thr
   130                 135                 140

Ala Val Val Lys Lys Ser Ser Ala Val Gly Ala Ala Val Thr Glu Gly
145                 150                 155                 160

Ala Phe Ser Ala Val Ala Asn Phe Asn Leu Thr Tyr Gln
               165                 170

<210> SEQ ID NO 143
<211> LENGTH: 173
<212> TYPE: PRT
<213> ORGANISM: Escherichia coli

<400> SEQUENCE: 143

Met Ala Val Val Ser Phe Gly Val Asn Ala Ala Pro Thr Ile Pro Gln
 1               5                  10                  15

Gly Gln Gly Lys Val Thr Phe Asn Gly Thr Val Val Asp Ala Pro Cys
            20                  25                  30

Ser Ile Ser Gln Lys Ser Ala Asp Gln Ser Ile Asp Phe Gly Gln Leu

```
            35                  40                  45
Ser Lys Ser Phe Leu Glu Ala Gly Gly Val Ser Lys Pro Met Asp Leu
        50                  55                  60

Asp Ile Glu Leu Val Asn Cys Asp Ile Thr Ala Phe Lys Gly Gly Asn
 65                  70                  75                  80

Gly Ala Gln Lys Gly Thr Val Lys Leu Ala Phe Thr Gly Pro Ile Val
                85                  90                  95

Asn Gly His Ser Asp Glu Leu Asp Thr Asn Gly Gly Thr Gly Thr Ala
            100                 105                 110

Ile Val Val Gln Gly Ala Gly Lys Asn Val Val Phe Asp Gly Ser Glu
        115                 120                 125

Gly Asp Ala Asn Thr Leu Lys Asp Gly Glu Asn Val Leu His Tyr Thr
130                 135                 140

Ala Val Val Lys Lys Ser Ser Ala Val Gly Ala Ala Val Thr Glu Gly
145                 150                 155                 160

Ala Phe Ser Ala Val Ala Asn Phe Asn Leu Thr Tyr Gln
                165                 170
```

<210> SEQ ID NO 144
<211> LENGTH: 172
<212> TYPE: PRT
<213> ORGANISM: Escherichia coli

<400> SEQUENCE: 144

```
Met Ala Val Val Ser Phe Gly Val Asn Ala Ala Pro Thr Thr Pro Gln
 1               5                  10                  15

Gly Gln Gly Arg Val Thr Phe Asn Gly Thr Val Val Asp Ala Pro Cys
                20                  25                  30

Ser Ile Ser Gln Lys Ser Ala Asp Gln Ser Ile Asp Phe Gly Gln Leu
            35                  40                  45

Ser Lys Ser Phe Leu Ala Asn Asp Gly Gln Ser Lys Pro Met Asn Leu
        50                  55                  60

Asp Ile Glu Leu Val Asn Cys Asp Ile Thr Ala Phe Lys Asn Gly Asn
 65                  70                  75                  80

Ala Lys Thr Gly Ser Val Lys Leu Ala Phe Thr Gly Pro Thr Val Ser
                85                  90                  95

Gly His Pro Ser Glu Leu Ala Thr Asn Gly Pro Gly Thr Ala Ile
            100                 105                 110

Met Ile Gln Ala Ala Gly Lys Asn Val Pro Phe Asp Gly Thr Glu Gly
        115                 120                 125

Asp Pro Asn Leu Leu Lys Asp Gly Asp Asn Val Leu His Tyr Thr Thr
130                 135                 140

Val Gly Lys Lys Ser Ser Asp Gly Asn Ala Gln Ile Thr Glu Gly Ala
145                 150                 155                 160

Phe Ser Gly Val Ala Thr Phe Asn Leu Ser Tyr Gln
                165                 170
```

<210> SEQ ID NO 145
<211> LENGTH: 853
<212> TYPE: DNA
<213> ORGANISM: Escherichia coli
<220> FEATURE:
<221> NAME/KEY: CDS
<222> LOCATION: (281)..(829)

<400> SEQUENCE: 145
acgtttctgt ggctcgacgc atcttcctca ttcttctctc caaaaaccac ctcatgcaat      60

```
ataaacatct ataaataaag ataacaaata gaatattaag ccaacaaata aactgaaaaa      120
gtttgtccgc gatgctttac ctctatgagt caaaatggcc ccaatgtttc atcttttggg      180
ggaaactgtg cagtgttggc agtcaaactc gttgacaaac aaagtgtaca gaacgactgc      240
ccatgtcgat ttagaaatag ttttttgaaa ggaaagcagc atg aaa att aaa act        295
                                              Met Lys Ile Lys Thr
                                                1               5 ctg gca atc gtt gtt ctg tcg gct ctg tcc ctc agt tct acg acg gct        343
Leu Ala Ile Val Val Leu Ser Ala Leu Ser Leu Ser Ser Thr Thr Ala
             10                  15                  20 ctg gcc gct gcc acg acg gtt aat ggt ggg acc gtt cac ttt aaa ggg        391
Leu Ala Ala Ala Thr Thr Val Asn Gly Gly Thr Val His Phe Lys Gly
         25                  30                  35 gaa gtt gtt aac gcc gct tgc gca gtt gat gca ggc tct gtt gat caa        439
Glu Val Val Asn Ala Ala Cys Ala Val Asp Ala Gly Ser Val Asp Gln
     40                  45                  50 acc gtt cag tta gga cag gtt cgt acc gca tcg ctg gca cag gaa gga        487
Thr Val Gln Leu Gly Gln Val Arg Thr Ala Ser Leu Ala Gln Glu Gly
 55                  60                  65 gca acc agt tct gct gtc ggt ttt aac att cag ctg aat gat tgc gat        535
Ala Thr Ser Ser Ala Val Gly Phe Asn Ile Gln Leu Asn Asp Cys Asp
 70                  75                  80                  85 acc aat gtt gca tct aaa gcc gct gtt gcc ttt tta ggt acg gcg att        583
Thr Asn Val Ala Ser Lys Ala Ala Val Ala Phe Leu Gly Thr Ala Ile
                 90                  95                 100 gat gcg ggt cat acc aac gtt ctg gct ctg cag agt tca gct gcg ggt        631
Asp Ala Gly His Thr Asn Val Leu Ala Leu Gln Ser Ser Ala Ala Gly
            105                 110                 115 agc gca aca aac gtt ggt gtg cag atc ctg gac aga acg ggt gct gcg        679
Ser Ala Thr Asn Val Gly Val Gln Ile Leu Asp Arg Thr Gly Ala Ala
        120                 125                 130 ctg acg ctg gat ggt gcg aca ttt agt tca gaa aca acc ctg aat aac        727
Leu Thr Leu Asp Gly Ala Thr Phe Ser Ser Glu Thr Thr Leu Asn Asn
    135                 140                 145 gga acc aat acc att ccg ttc cag gcg cgt tat ttt gca acc ggg gcc        775
Gly Thr Asn Thr Ile Pro Phe Gln Ala Arg Tyr Phe Ala Thr Gly Ala
150                 155                 160                 165 gca acc ccg ggt gct gct aat gcg gat gcg acc ttc aag gtt cag tat        823
Ala Thr Pro Gly Ala Ala Asn Ala Asp Ala Thr Phe Lys Val Gln Tyr
                170                 175                 180 caa taa cctacctagg ttcagggacg ttca                                     853
Gln

<210> SEQ ID NO 146
<211> LENGTH: 182
<212> TYPE: PRT
<213> ORGANISM: Escherichia coli

<400> SEQUENCE: 146

Met Lys Ile Lys Thr Leu Ala Ile Val Val Leu Ser Ala Leu Ser Leu
 1               5                  10                  15

Ser Ser Thr Thr Ala Leu Ala Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
```

```
            65                  70                  75                  80
Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175

Phe Lys Val Gln Tyr Gln
            180
```

<210> SEQ ID NO 147
<211> LENGTH: 11
<212> TYPE: PRT
<213> ORGANISM: Artificial Sequence
<220> FEATURE:
<223> OTHER INFORMATION: FLAG peptide

<400> SEQUENCE: 147

```
Cys Gly Gly Asp Tyr Lys Asp Asp Asp Lys
  1               5                  10
```

<210> SEQ ID NO 148
<211> LENGTH: 31
<212> TYPE: DNA
<213> ORGANISM: Artificial Sequence
<220> FEATURE:
<223> OTHER INFORMATION: primer

<400> SEQUENCE: 148
ccggaattca tggacattga cccttataaa g                                    31

<210> SEQ ID NO 149
<211> LENGTH: 37
<212> TYPE: DNA
<213> ORGANISM: Artificial Sequence
<220> FEATURE:
<223> OTHER INFORMATION: primer

<400> SEQUENCE: 149
gtgcagtatg gtgaggtgag gaatgctcag gagactc                              37

<210> SEQ ID NO 150
<211> LENGTH: 37
<212> TYPE: DNA
<213> ORGANISM: Artificial Sequence
<220> FEATURE:
<223> OTHER INFORMATION: primer

<400> SEQUENCE: 150
gsgtctcctg agcattcctc acctcaccat actgcac                              37

<210> SEQ ID NO 151
<211> LENGTH: 33
<212> TYPE: DNA
<213> ORGANISM: Artificial Sequence
<220> FEATURE:
<223> OTHER INFORMATION: primer

<400> SEQUENCE: 151
cttccaaaag tgagggaaga aatgtgaaac cac                               33

<210> SEQ ID NO 152
<211> LENGTH: 47
<212> TYPE: DNA
<213> ORGANISM: Artificial Sequence
<220> FEATURE:
<223> OTHER INFORMATION: primer

<400> SEQUENCE: 152
cgcgtcccaa gcttctaaac aacagtagtc tccggaagcg ttgatag                47

<210> SEQ ID NO 153
<211> LENGTH: 33
<212> TYPE: DNA
<213> ORGANISM: Artificial Sequence
<220> FEATURE:
<223> OTHER INFORMATION: primer

<400> SEQUENCE: 153
gtggtttcac atttcttccc tcacttttgg aag                               33

<210> SEQ ID NO 154
<211> LENGTH: 281
<212> TYPE: PRT
<213> ORGANISM: Saccharomyces cerevisiae

<400> SEQUENCE: 154

```
Met Ser Glu Tyr Gln Pro Ser Leu Phe Ala Leu Asn Pro Met Gly Phe
  1               5                  10                  15

Ser Pro Leu Asp Gly Ser Lys Ser Thr Asn Glu Asn Val Ser Ala Ser
             20                  25                  30

Thr Ser Thr Ala Lys Pro Met Val Gly Gln Leu Ile Phe Asp Lys Phe
         35                  40                  45

Ile Lys Thr Glu Glu Asp Pro Ile Ile Lys Gln Asp Thr Pro Ser Asn
     50                  55                  60

Leu Asp Phe Asp Phe Ala Leu Pro Gln Thr Ala Thr Ala Pro Asp Ala
 65                  70                  75                  80

Lys Thr Val Leu Pro Ile Pro Glu Leu Asp Asp Ala Val Val Glu Ser
                 85                  90                  95

Phe Phe Ser Ser Ser Thr Asp Ser Thr Pro Met Phe Glu Tyr Glu Asn
            100                 105                 110

Leu Glu Asp Asn Ser Lys Glu Trp Thr Ser Leu Phe Asp Asn Asp Ile
        115                 120                 125

Pro Val Thr Thr Asp Asp Val Ser Leu Ala Asp Lys Ala Ile Glu Ser
    130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Lys Ser His His Val
            180                 185                 190

Gly Lys Asp Asp Glu Ser Arg Leu Asp His Leu Gly Val Val Ala Tyr
        195                 200                 205

Asn Arg Lys Gln Arg Ser Ile Pro Leu Ser Pro Ile Val Pro Glu Ser
    210                 215                 220
```

```
Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                245                 250                 255

Val Glu Glu Leu Leu Ser Lys Asn Tyr His Leu Glu Asn Glu Val Ala
            260                 265                 270

Arg Leu Lys Lys Leu Val Gly Glu Arg
        275                 280

<210> SEQ ID NO 155
<211> LENGTH: 181
<212> TYPE: PRT
<213> ORGANISM: Escherichia coli

<400> SEQUENCE: 155

Met Lys Ile Lys Thr Leu Ala Ile Val Val Leu Ser Ala Leu Ser Leu
1               5                   10                  15

Ser Ser Thr Ala Ala Leu Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Gly Ala Ala Thr Pro Gly Ala Ala Asn Ala Asp Ala Thr Phe
                165                 170                 175

Lys Val Gln Tyr Gln
            180

<210> SEQ ID NO 156
<211> LENGTH: 447
<212> TYPE: DNA
<213> ORGANISM: Hepatitis B
<220> FEATURE:
<221> NAME/KEY: CDS
<222> LOCATION: (1)..(447)

<400> SEQUENCE: 156 atg gac att gac cct tat aaa gaa ttt gga gct act gtg gag tta ctc    48
Met Asp Ile Asp Pro Tyr Lys Glu Phe Gly Ala Thr Val Glu Leu Leu
1               5                   10                  15 tcg ttt ttg cct tct gac ttc ttt cct tcc gta cga gat ctt cta gat    96
Ser Phe Leu Pro Ser Asp Phe Phe Pro Ser Val Arg Asp Leu Leu Asp
            20                  25                  30 acc gcc gca gct ctg tat cgg gat gcc tta gag tct cct gag cat tgt   144
Thr Ala Ala Ala Leu Tyr Arg Asp Ala Leu Glu Ser Pro Glu His Cys
        35                  40                  45
```

```
tca cct cac cat act gca ctc agg caa gca att ctt tgc tgg gga gac        192
Ser Pro His His Thr Ala Leu Arg Gln Ala Ile Leu Cys Trp Gly Asp
 50                  55                  60 tta atg act cta gct acc tgg gtg ggt act aat tta gaa gat cca gca        240
Leu Met Thr Leu Ala Thr Trp Val Gly Thr Asn Leu Glu Asp Pro Ala
 65                  70                  75                  80 tct agg gac cta gta gtc agt tat gtc aac act aat gtg ggc cta aag        288
Ser Arg Asp Leu Val Val Ser Tyr Val Asn Thr Asn Val Gly Leu Lys
                 85                  90                  95 ttc aga caa tta ttg tgg ttt cac att tct tgt ctc act ttt gga aga        336
Phe Arg Gln Leu Leu Trp Phe His Ile Ser Cys Leu Thr Phe Gly Arg
            100                 105                 110 gaa acg gtt cta gag tat ttg gtc tct ttt gga gtg tgg att cgc act        384
Glu Thr Val Leu Glu Tyr Leu Val Ser Phe Gly Val Trp Ile Arg Thr
        115                 120                 125 cct cca gcc tat aga cca cca aat gcc cct atc cta tca acg ctt ccg        432
Pro Pro Ala Tyr Arg Pro Pro Asn Ala Pro Ile Leu Ser Thr Leu Pro
130                 135                 140 gag act act gtt gtt                                                    447
Glu Thr Thr Val Val
145
```

<210> SEQ ID NO 157
<211> LENGTH: 149
<212> TYPE: PRT
<213> ORGANISM: Hepatitis B

<400> SEQUENCE: 157

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
             20                  25                  30

Thr Ala Ala Leu Tyr Arg Asp Ala Leu Glu Ser Pro Glu His Cys
         35                  40                  45

Ser Pro His His Thr Ala Leu Arg Gln Ala Ile Leu Cys Trp Gly Asp
 50                  55                  60

Leu Met Thr Leu Ala Thr Trp Val Gly Thr Asn Leu Glu Asp Pro Ala
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val
145

<210> SEQ ID NO 158
<211> LENGTH: 152
<212> TYPE: PRT
<213> ORGANISM: Hepatitis B

<400> SEQUENCE: 158

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
             20                  25                  30

```
Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
                100                 105                 110

Phe Gly Arg Glu Thr Val Leu Glu Tyr Leu Val Ser Phe Gly Val Trp
            115                 120                 125

Ile Arg Thr Pro Pro Ala Tyr Arg Pro Pro Asn Ala Pro Ile Leu Ser
    130                 135                 140

Thr Leu Pro Glu Thr Thr Val Val
145                 150

<210> SEQ ID NO 159
<211> LENGTH: 132
<212> TYPE: PRT
<213> ORGANISM: Bacteriophage Q Beta

<400> SEQUENCE: 159

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
                100                 105                 110

Ala Ala Leu Leu Ala Ser Pro Leu Leu Ile Asp Ala Ile Asp Gln Leu
            115                 120                 125

Asn Pro Ala Tyr
    130

<210> SEQ ID NO 160
<211> LENGTH: 129
<212> TYPE: PRT
<213> ORGANISM: Bacteriophage R 17

<400> SEQUENCE: 160

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60
```

```
Pro Lys Val Ala Thr Gln Thr Val Gly Gly Val Glu Leu Pro Val Ala
 65                  70                  75                  80

Ala Trp Arg Ser Tyr Leu Asn Met Glu Leu Thr Ile Pro Ile Phe Ala
                 85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 161
<211> LENGTH: 130
<212> TYPE: PRT
<213> ORGANISM: Bacteriophage fr

<400> SEQUENCE: 161

Met Ala Ser Asn Phe Glu Glu Phe Val Leu Val Asp Asn Gly Gly Thr
  1               5                  10                  15

Gly Asp Val Lys Val Ala Pro Ser Asn Phe Ala Asn Gly Val Ala Glu
                 20                  25                  30

Trp Ile Ser Ser Asn Ser Arg Ser Gln Ala Tyr Lys Val Thr Cys Ser
             35                  40                  45

Val Arg Gln Ser Ser Ala Asn Asn Arg Lys Tyr Thr Val Lys Val Glu
 50                  55                  60

Val Pro Lys Val Ala Thr Gln Val Gln Gly Gly Val Glu Leu Pro Val
 65                  70                  75                  80

Ala Ala Trp Arg Ser Tyr Met Asn Met Glu Leu Thr Ile Pro Val Phe
                 85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130

<210> SEQ ID NO 162
<211> LENGTH: 130
<212> TYPE: PRT
<213> ORGANISM: Bacteriophage GA

<400> SEQUENCE: 162

Met Ala Thr Leu Arg Ser Phe Val Leu Val Asp Asn Gly Gly Thr Gly
  1               5                  10                  15

Asn Val Thr Val Val Pro Val Ser Asn Ala Asn Gly Val Ala Glu Trp
                 20                  25                  30

Leu Ser Asn Asn Ser Arg Ser Gln Ala Tyr Arg Val Thr Ala Ser Tyr
             35                  40                  45

Arg Ala Ser Gly Ala Asp Lys Arg Lys Tyr Ala Ile Lys Leu Glu Val
 50                  55                  60

Pro Lys Ile Val Thr Gln Val Val Asn Gly Val Glu Leu Pro Gly Ser
 65                  70                  75                  80

Ala Trp Lys Ala Tyr Ala Ser Ile Asp Leu Thr Ile Pro Ile Phe Ala
                 85                  90                  95

Ala Thr Asp Asp Val Thr Val Ile Ser Lys Ser Leu Ala Gly Leu Phe
            100                 105                 110
```

```
Lys Val Gly Asn Pro Ile Ala Glu Ala Ile Ser Ser Gln Ser Gly Phe
        115                 120                 125

Tyr Ala
    130

<210> SEQ ID NO 163
<211> LENGTH: 132
<212> TYPE: PRT
<213> ORGANISM: Bacteriophage SP

<400> SEQUENCE: 163

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130

<210> SEQ ID NO 164
<211> LENGTH: 130
<212> TYPE: PRT
<213> ORGANISM: Bacteriophage MS2

<400> SEQUENCE: 164

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 165
<211> LENGTH: 133
```

```
<212> TYPE: PRT
<213> ORGANISM: Bacteriophage M11

<400> SEQUENCE: 165

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
        115                 120                 125

Leu Asn Pro Ala Tyr
    130

<210> SEQ ID NO 166
<211> LENGTH: 133
<212> TYPE: PRT
<213> ORGANISM: Bacteriophage MX1

<400> SEQUENCE: 166

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
            100                 105                 110

Leu Lys Ala Leu Leu Ala Asp Pro Met Leu Ile Asp Ala Ile Asp Asn
        115                 120                 125

Leu Asn Pro Ala Tyr
    130

<210> SEQ ID NO 167
<211> LENGTH: 330
<212> TYPE: PRT
<213> ORGANISM: Bacteriophage NL95

<400> SEQUENCE: 167

Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
```

```
                20                  25                  30
Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 168
<211> LENGTH: 134
<212> TYPE: PRT
<213> ORGANISM: Apis mellifera

<400> SEQUENCE: 168

Ile Ile Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
            20                  25                  30

Thr His Asp Met Cys Pro Asp Val Met Ser Ala Gly Glu Ser Lys His
        35                  40                  45

Gly Leu Thr Asn Thr Ala Ser His Thr Arg Leu Ser Cys Asp Cys Asp
    50                  55                  60
```

```
Asp Lys Phe Tyr Asp Cys Leu Lys Asn Ser Ala Asp Thr Ile Ser Ser
 65                  70                  75                  80

Tyr Phe Val Gly Lys Met Tyr Phe Asn Leu Ile Asp Thr Lys Cys Tyr
                 85                  90                  95

Lys Leu Glu His Pro Val Thr Gly Cys Gly Glu Arg Thr Glu Gly Arg
            100                 105                 110

Cys Leu His Tyr Thr Val Asp Lys Ser Lys Pro Lys Val Tyr Gln Trp
            115                 120                 125

Phe Asp Leu Arg Lys Tyr
            130

<210> SEQ ID NO 169
<211> LENGTH: 129
<212> TYPE: PRT
<213> ORGANISM: Apis mellifera

<400> SEQUENCE: 169

Ile Ile Tyr Pro Gly Thr Leu Trp Cys Gly His Gly Asn Lys Ser Ser
 1               5                  10                  15

Gly Pro Asn Glu Leu Gly Arg Phe Lys His Thr Asp Ala Cys Cys Arg
             20                  25                  30

Thr His Asp Met Cys Pro Asn Val Met Ser Ala Gly Glu Ser Lys His
         35                  40                  45

Gly Leu Thr Asp Thr Ala Ser Arg Leu Ser Cys Asn Asp Asn Asp Leu
     50                  55                  60

Phe Tyr Lys Asp Ser Ala Asp Thr Ile Ser Ser Tyr Phe Val Gly Lys
 65                  70                  75                  80

Met Tyr Phe Asn Leu Ile Asn Thr Lys Cys Tyr Lys Leu Glu His Pro
                 85                  90                  95

Val Thr Gly Cys Gly Glu Arg Thr Glu Gly Arg Cys Leu His Tyr Thr
            100                 105                 110

Val Asp Lys Ser Lys Pro Lys Val Tyr Gln Trp Phe Asp Leu Arg Lys
            115                 120                 125

Tyr

<210> SEQ ID NO 170
<211> LENGTH: 134
<212> TYPE: PRT
<213> ORGANISM: Apis dorsata

<400> SEQUENCE: 170

Ile Ile Tyr Pro Gly Thr Leu Trp Cys Gly His Gly Asn Val Ser Ser
 1               5                  10                  15

Ser Pro Asp Glu Leu Gly Arg Phe Lys His Thr Asp Ser Cys Cys Arg
             20                  25                  30

Ser His Asp Met Cys Pro Asp Val Met Ser Ala Gly Glu Ser Lys His
         35                  40                  45

Gly Leu Thr Asn Thr Ala Ser His Thr Arg Leu Ser Cys Asp Cys Asp
     50                  55                  60

Asp Lys Phe Tyr Asp Cys Leu Lys Asn Ser Ser Asp Thr Ile Ser Ser
 65                  70                  75                  80

Tyr Phe Val Gly Glu Met Tyr Phe Asn Ile Leu Asp Thr Lys Cys Tyr
                 85                  90                  95

Lys Leu Glu His Pro Val Thr Gly Cys Gly Lys Arg Thr Glu Gly Arg
            100                 105                 110

Cys Leu Asn Tyr Thr Val Asp Lys Ser Lys Pro Lys Val Tyr Gln Trp
```

Phe Asp Leu Arg Lys Tyr
    130

<210> SEQ ID NO 171
<211> LENGTH: 134
<212> TYPE: PRT
<213> ORGANISM: Apis cerana

<400> SEQUENCE: 171

Ile Ile Tyr Pro Gly Thr Leu Trp Cys Gly His Gly Asn Val Ser Ser
1               5                   10                  15

Gly Pro Asn Glu Leu Gly Arg Phe Lys His Thr Asp Ala Cys Cys Arg
            20                  25                  30

Thr His Asp Met Cys Pro Asp Val Met Ser Ala Gly Glu Ser Lys His
        35                  40                  45

Gly Leu Thr Asn Thr Ala Ser His Thr Arg Leu Ser Cys Asp Cys Asp
    50                  55                  60

Asp Thr Phe Tyr Asp Cys Leu Lys Asn Ser Gly Glu Lys Ile Ser Ser
65                  70                  75                  80

Tyr Phe Val Gly Lys Met Tyr Phe Asn Leu Ile Asp Thr Lys Cys Tyr
                85                  90                  95

Lys Leu Glu His Pro Val Thr Gly Cys Gly Glu Arg Thr Glu Gly Arg
            100                 105                 110

Cys Leu Arg Tyr Thr Val Asp Lys Ser Lys Pro Lys Val Tyr Gln Trp
        115                 120                 125

Phe Asp Leu Arg Lys Tyr
    130

<210> SEQ ID NO 172
<211> LENGTH: 136
<212> TYPE: PRT
<213> ORGANISM: Bombus pennsylvanicus

<400> SEQUENCE: 172

Ile Ile Tyr Pro Gly Thr Leu Trp Cys Gly Asn Gly Asn Ile Ala Asn
1               5                   10                  15

Gly Thr Asn Glu Leu Gly Leu Trp Lys Glu Thr Asp Ala Cys Cys Arg
            20                  25                  30

Thr His Asp Met Cys Pro Asp Ile Ile Glu Ala His Gly Ser Lys His
        35                  40                  45

Gly Leu Thr Asn Pro Ala Asp Tyr Thr Arg Leu Asn Cys Glu Cys Asp
    50                  55                  60

Glu Glu Phe Arg His Cys Leu His Asn Ser Gly Asp Ala Val Ser Ala
65                  70                  75                  80

Ala Phe Val Gly Arg Thr Tyr Phe Thr Ile Leu Gly Thr Gln Cys Phe
                85                  90                  95

Arg Leu Asp Tyr Pro Ile Val Lys Cys Lys Val Lys Ser Thr Ile Leu
            100                 105                 110

Arg Glu Cys Lys Glu Tyr Glu Phe Asp Thr Asn Ala Pro Gln Lys Tyr
        115                 120                 125

Gln Trp Phe Asp Val Leu Ser Tyr
    130                 135

<210> SEQ ID NO 173
<211> LENGTH: 142
<212> TYPE: PRT

<213> ORGANISM: Heloderma suspectum

<400> SEQUENCE: 173

Gly Ala Phe Ile Met Pro Gly Thr Leu Trp Cys Gly Ala Gly Asn Ala
1               5                   10                  15

Ala Ser Asp Tyr Ser Gln Leu Gly Thr Glu Lys Asp Thr Asp Met Cys
            20                  25                  30

Cys Arg Asp His Asp His Cys Ser Asp Thr Met Ala Ala Leu Glu Tyr
        35                  40                  45

Lys His Gly Met Arg Asn Tyr Arg Pro His Thr Val Ser His Cys Asp
    50                  55                  60

Cys Asp Asn Gln Phe Arg Ser Cys Leu Met Asn Val Lys Asp Arg Thr
65                  70                  75                  80

Ala Asp Leu Val Gly Met Thr Tyr Phe Thr Val Leu Lys Ile Ser Cys
                85                  90                  95

Phe Glu Leu Glu Glu Gly Glu Gly Cys Val Asp Asn Asn Phe Ser Gln
            100                 105                 110

Gln Cys Thr Lys Ser Glu Ile Met Pro Val Ala Lys Leu Val Ser Ala
        115                 120                 125

Ala Pro Tyr Gln Ala Gln Ala Glu Thr Gln Ser Gly Glu Gly
    130                 135                 140

<210> SEQ ID NO 174
<211> LENGTH: 143
<212> TYPE: PRT
<213> ORGANISM: Heloderma suspectum

<400> SEQUENCE: 174

Gly Ala Phe Ile Met Pro Gly Thr Leu Trp Cys Gly Ala Gly Asn Ala
1               5                   10                  15

Ala Ser Asp Tyr Ser Gln Leu Gly Thr Glu Lys Asp Thr Asp Met Cys
            20                  25                  30

Cys Arg Asp His Asp His Cys Glu Asn Trp Ile Ser Ala Leu Glu Tyr
        35                  40                  45

Lys His Gly Met Arg Asn Tyr Tyr Pro Ser Thr Ile Ser His Cys Asp
    50                  55                  60

Cys Asp Asn Gln Phe Arg Ser Cys Leu Met Lys Leu Lys Asp Gly Thr
65                  70                  75                  80

Ala Asp Tyr Val Gly Gln Thr Tyr Phe Asn Val Leu Lys Ile Pro Cys
                85                  90                  95

Phe Glu Leu Glu Glu Gly Gly Cys Val Asp Trp Asn Phe Trp Leu
            100                 105                 110

Glu Cys Thr Glu Ser Lys Ile Met Pro Val Ala Lys Leu Val Ser Ala
        115                 120                 125

Ala Pro Tyr Gln Ala Gln Ala Glu Thr Gln Ser Gly Glu Gly Arg
    130                 135                 140

<210> SEQ ID NO 175
<211> LENGTH: 142
<212> TYPE: PRT
<213> ORGANISM: Heloderma suspectum

<400> SEQUENCE: 175

Gly Ala Phe Ile Met Pro Gly Thr Leu Trp Cys Gly Ala Gly Asn Ala
1               5                   10                  15

Ala Ser Asp Tyr Ser Gln Leu Gly Thr Glu Lys Asp Thr Asp Met Cys
            20                  25                  30

-continued

Cys Arg Asp His Asp His Cys Glu Asn Trp Ile Ser Ala Leu Glu Tyr
             35                  40                  45

Lys His Gly Met Arg Asn Tyr Tyr Pro Ser Thr Ile Ser His Cys Asp
 50                  55                  60

Cys Asp Asn Gln Phe Arg Ser Cys Leu Met Lys Leu Lys Asp Gly Thr
65                  70                  75                  80

Ala Asp Tyr Val Gly Gln Thr Tyr Phe Asn Val Leu Lys Ile Pro Cys
                 85                  90                  95

Phe Glu Leu Glu Glu Gly Glu Gly Cys Val Asp Trp Asn Phe Trp Leu
                100                 105                 110

Glu Cys Thr Glu Ser Lys Ile Met Pro Val Ala Lys Leu Val Ser Ala
            115                 120                 125

Ala Pro Tyr Gln Ala Gln Ala Glu Thr Gln Ser Gly Glu Gly
        130                 135                 140

<210> SEQ ID NO 176
<211> LENGTH: 574
<212> TYPE: PRT
<213> ORGANISM: IgE heavy chain

<400> SEQUENCE: 176

Met Asp Trp Thr Trp Ile Leu Phe Leu Val Ala Ala Thr Arg Val
1               5                   10                  15

His Ser Gln Thr Gln Leu Val Gln Ser Gly Ala Glu Val Arg Lys Pro
             20                  25                  30

Gly Ala Ser Val Arg Val Ser Cys Lys Ala Ser Gly Tyr Thr Phe Ile
         35                  40                  45

Asp Ser Tyr Ile His Trp Ile Arg Gln Ala Pro Gly His Gly Leu Glu
 50                  55                  60

Trp Val Gly Trp Ile Asn Pro Asn Ser Gly Gly Thr Asn Tyr Ala Pro
65                  70                  75                  80

Arg Phe Gln Gly Arg Val Thr Met Thr Arg Asp Ala Ser Phe Ser Thr
                 85                  90                  95

Ala Tyr Met Asp Leu Arg Ser Leu Arg Ser Asp Ser Ala Val Phe
                100                 105                 110

Tyr Cys Ala Lys Ser Asp Pro Phe Trp Ser Asp Tyr Tyr Asn Phe Asp
            115                 120                 125

Tyr Ser Tyr Thr Leu Asp Val Trp Gly Gln Gly Thr Thr Val Thr Val
        130                 135                 140

Ser Ser Ala Ser Thr Gln Ser Pro Ser Val Phe Pro Leu Thr Arg Cys
145                 150                 155                 160

Cys Lys Asn Ile Pro Ser Asn Ala Thr Ser Val Thr Leu Gly Cys Leu
                165                 170                 175

Ala Thr Gly Tyr Phe Pro Glu Pro Val Met Val Thr Trp Asp Thr Gly
            180                 185                 190

Ser Leu Asn Gly Thr Thr Met Thr Leu Pro Ala Thr Thr Leu Thr Leu
        195                 200                 205

Ser Gly His Tyr Ala Thr Ile Ser Leu Leu Thr Val Ser Gly Ala Trp
    210                 215                 220

Ala Lys Gln Met Phe Thr Cys Arg Val Ala His Thr Pro Ser Ser Thr
225                 230                 235                 240

Asp Trp Val Asp Asn Lys Thr Phe Ser Val Cys Ser Arg Asp Phe Thr
                245                 250                 255

Pro Pro Thr Val Lys Ile Leu Gln Ser Ser Cys Asp Gly Gly Gly His

-continued

```
                    260                 265                 270
        Phe Pro Pro Thr Ile Gln Leu Leu Cys Leu Val Ser Gly Tyr Thr Pro
                275                 280                 285
        Gly Thr Ile Asn Ile Thr Trp Leu Glu Asp Gly Gln Val Met Asp Val
                290                 295                 300
        Asp Leu Ser Thr Ala Ser Thr Thr Gln Glu Gly Glu Leu Ala Ser Thr
        305                 310                 315                 320
        Gln Ser Glu Leu Thr Leu Ser Gln Lys His Trp Leu Ser Asp Arg Thr
                        325                 330                 335
        Tyr Thr Cys Gln Val Thr Tyr Gln Gly His Thr Phe Glu Asp Ser Thr
                    340                 345                 350
        Lys Lys Cys Ala Asp Ser Asn Pro Arg Gly Val Ser Ala Tyr Leu Ser
                        355                 360                 365
        Arg Pro Ser Pro Phe Asp Leu Phe Ile Arg Lys Ser Pro Thr Ile Thr
                    370                 375                 380
        Cys Leu Val Val Asp Leu Ala Pro Ser Lys Gly Thr Val Asn Leu Thr
        385                 390                 395                 400
        Trp Ser Arg Ala Ser Gly Lys Pro Val Asn His Ser Thr Arg Lys Glu
                        405                 410                 415
        Glu Lys Gln Arg Asn Gly Thr Leu Thr Val Thr Ser Thr Leu Pro Val
                    420                 425                 430
        Gly Thr Arg Asp Trp Ile Glu Gly Glu Thr Tyr Gln Cys Arg Val Thr
                    435                 440                 445
        His Pro His Leu Pro Arg Ala Leu Met Arg Ser Thr Thr Lys Thr Ser
                    450                 455                 460
        Gly Pro Arg Ala Ala Pro Glu Val Tyr Ala Phe Ala Thr Pro Glu Trp
        465                 470                 475                 480
        Pro Gly Ser Arg Asp Lys Arg Thr Leu Ala Cys Leu Ile Gln Asn Phe
                        485                 490                 495
        Met Pro Glu Asp Ile Ser Val Gln Trp Leu His Asn Glu Val Gln Leu
                    500                 505                 510
        Pro Asp Ala Arg His Ser Thr Thr Gln Pro Arg Lys Thr Lys Gly Ser
                    515                 520                 525
        Gly Phe Phe Val Phe Ser Arg Leu Glu Val Thr Arg Ala Glu Trp Glu
                530                 535                 540
        Gln Lys Asp Glu Phe Ile Cys Arg Ala Val His Glu Ala Ala Ser Pro
        545                 550                 555                 560
        Ser Gln Thr Val Gln Arg Ala Val Ser Val Asn Pro Gly Lys
                        565                 570

<210> SEQ ID NO 177

<400> SEQUENCE: 177

000

<210> SEQ ID NO 178
<211> LENGTH: 13
<212> TYPE: PRT
<213> ORGANISM: IgE Peptides

<400> SEQUENCE: 178

Cys Gly Gly Val Asn Leu Thr Trp Ser Arg Ala Ser Gly
1               5                   10

<210> SEQ ID NO 179
```

```
<211> LENGTH: 8
<212> TYPE: PRT
<213> ORGANISM: IgE Mimotype

<400> SEQUENCE: 179

Ile Asn His Arg Gly Tyr Trp Val
1               5

<210> SEQ ID NO 180
<211> LENGTH: 8
<212> TYPE: PRT
<213> ORGANISM: IgE Mimotype

<400> SEQUENCE: 180

Arg Asn His Arg Gly Tyr Trp Val
1               5

<210> SEQ ID NO 181
<211> LENGTH: 10
<212> TYPE: PRT
<213> ORGANISM: IgE Mimotype

<400> SEQUENCE: 181

Arg Ser Arg Ser Gly Gly Tyr Trp Leu Trp
1               5                   10

<210> SEQ ID NO 182
<211> LENGTH: 10
<212> TYPE: PRT
<213> ORGANISM: IgE Mimotype

<400> SEQUENCE: 182

Val Asn Leu Thr Trp Ser Arg Ala Ser Gly
1               5                   10

<210> SEQ ID NO 183
<211> LENGTH: 10
<212> TYPE: PRT
<213> ORGANISM: IgE Mimotype

<400> SEQUENCE: 183

Val Asn Leu Pro Trp Ser Arg Ala Ser Gly
1               5                   10

<210> SEQ ID NO 184
<211> LENGTH: 10
<212> TYPE: PRT
<213> ORGANISM: IgE Mimotype

<400> SEQUENCE: 184

Val Asn Leu Thr Trp Ser Phe Gly Leu Glu
1               5                   10

<210> SEQ ID NO 185
<211> LENGTH: 10
<212> TYPE: PRT
<213> ORGANISM: IgE Mimotype

<400> SEQUENCE: 185

Val Asn Leu Pro Trp Ser Phe Gly Leu Glu
1               5                   10

<210> SEQ ID NO 186
<211> LENGTH: 10
<212> TYPE: PRT
```

<213> ORGANISM: IgE Mimotype

<400> SEQUENCE: 186

Val Asn Arg Pro Trp Ser Phe Gly Leu Glu
1               5                   10

<210> SEQ ID NO 187
<211> LENGTH: 10
<212> TYPE: PRT
<213> ORGANISM: IgE Mimotype

<400> SEQUENCE: 187

Val Lys Leu Pro Trp Arg Phe Tyr Gln Val
1               5                   10

<210> SEQ ID NO 188
<211> LENGTH: 10
<212> TYPE: PRT
<213> ORGANISM: IgE Mimotype

<400> SEQUENCE: 188

Val Trp Thr Ala Cys Gly Tyr Gly Arg Met
1               5                   10

<210> SEQ ID NO 189
<211> LENGTH: 7
<212> TYPE: PRT
<213> ORGANISM: IgE Mimotype

<400> SEQUENCE: 189

Gly Thr Val Ser Thr Leu Ser
1               5

<210> SEQ ID NO 190
<211> LENGTH: 7
<212> TYPE: PRT
<213> ORGANISM: IgE Mimotype

<400> SEQUENCE: 190

Leu Leu Asp Ser Arg Tyr Trp
1               5

<210> SEQ ID NO 191
<211> LENGTH: 7
<212> TYPE: PRT
<213> ORGANISM: IgE Mimotype

<400> SEQUENCE: 191

Gln Pro Ala His Ser Leu Gly
1               5

<210> SEQ ID NO 192
<211> LENGTH: 7
<212> TYPE: PRT
<213> ORGANISM: IgE Mimotype

<400> SEQUENCE: 192

Leu Trp Gly Met Gln Gly Arg
1               5

<210> SEQ ID NO 193
<211> LENGTH: 15
<212> TYPE: PRT
<213> ORGANISM: IgE Mimotype -continued

```
<400> SEQUENCE: 193

Leu Thr Leu Ser His Pro His Trp Val Leu Asn His Phe Val Ser
1               5                   10                  15

<210> SEQ ID NO 194
<211> LENGTH: 9
<212> TYPE: PRT
<213> ORGANISM: IgE Mimotype

<400> SEQUENCE: 194

Ser Met Gly Pro Asp Gln Thr Leu Arg
1               5

<210> SEQ ID NO 195
<211> LENGTH: 6
<212> TYPE: PRT
<213> ORGANISM: IgE Mimotype

<400> SEQUENCE: 195

Val Asn Leu Thr Trp Ser
1               5

<210> SEQ ID NO 196
<211> LENGTH: 56
<212> TYPE: DNA
<213> ORGANISM: Oligonucleotide Primer

<400> SEQUENCE: 196
tagatgatta cgccaagctt ataatagaaa tagttttttg aaaggaaagc agcatg        56

<210> SEQ ID NO 197
<211> LENGTH: 45
<212> TYPE: DNA
<213> ORGANISM: Oligonucleotide Primer

<400> SEQUENCE: 197
gtcaaaggcc ttgtcgacgt tattccatta cgcccgtcat tttgg                    45

<210> SEQ ID NO 198
<211> LENGTH: 4623
<212> TYPE: DNA
<213> ORGANISM: pFIMAIC

<400> SEQUENCE: 198
agacgaaagg gcctcgtgat acgcctattt ttataggtta atgtcatgat aataatggtt     60
tcttagacgt caggtggcac ttttcgggga atgtgcgcg  gaaccccctat tgtttatttt   120 ttctaaatac attcaaatat gtatccgctc atgagacaat aaccctgata aatgcttcaa   180
taatattgaa aaaggaagag tatgagtatt caacatttcc gtgtcgccct tattcccttt   240
tttgcggcat tttgccttcc tgttttttgct cacccagaaa cgctggtgaa agtaaaagat   300
gctgaagatc agttgggtgc acgagtgggt tacatcgaac tggatctcaa cagcggtaag   360
atccttgaga gttttcgccc cgaagaacgt tttccaatga tgagcacttt taaagttctg   420
ctatgtggcg cggtattatc ccgtattgac gccgggcaag agcaactcgg tcgccgcata   480
cactattctc agaatgactt ggttgagtac tcaccagtca cagaaaagca tcttacggat   540
ggcatgacag taagagaatt atgcagtgct gccataacca tgagtgataa cactgcggcc   600
aacttacttc tgacaacgat cggaggaccg aaggagctaa ccgcttttttt gcacaacatg   660 ggggatcatg taactcgcct tgatcgttgg gaaccggagc tgaatgaagc cataccaaac   720
```

```
gacgagcgtg acaccacgat gcctgtagca atggcaacaa cgttgcgcaa actattaact      780
ggcgaactac ttactctagc ttcccggcaa caattaatag actggatgga ggcggataaa      840
gttgcaggac cacttctgcg ctcggccctt ccggctggct ggtttattgc tgataaatct      900
ggagccggtg agcgtgggtc tcgcggtatc attgcagcac tggggccaga tggtaagccc      960
tcccgtatcg tagttatcta cacgacgggg agtcaggcaa ctatggatga acgaaataga     1020
cagatcgctg agataggtgc ctcactgatt aagcattggt aactgtcaga ccaagtttac     1080
tcatatatac tttagattga tttaaaactt catttttaat ttaaaaggat ctaggtgaag     1140
atcctttttg ataatctcat gaccaaaatc ccttaacgtg agttttcgtt ccactgagcg     1200
tcagaccccg tagaaagat caaaggatct tcttgagatc ctttttttct gcgcgtaatc      1260
tgctgcttgc aaacaaaaaa accaccgcta ccagcggtgg tttgtttgcc ggatcaagag     1320
ctaccaactc tttttccgaa ggtaactggc ttcagcagag cgcagatacc aaatactgtc     1380
cttctagtgt agccgtagtt aggccaccac ttcaagaact ctgtagcacc gcctacatac     1440
ctcgctctgc taatcctgtt accagtggct gctgccagtg gcgataagtc gtgtcttacc     1500
gggttggact caagacgata gttaccggat aaggcgcagc ggtcgggctg aacggggggt     1560
tcgtgcacac agcccagctt ggagcgaacg acctacaccg aactgagata cctacagcgt     1620
gagctatgag aaagcgccac gcttcccgaa gggagaaagg cggacaggta ccggtaagc     1680 ggcagggtcg gaacaggaga gcgcacgagg gagcttccag ggggaaacgc ctggtatctt     1740
tatagtcctg tcgggtttcg ccacctctga cttgagcgtc gatttttgtg atgctcgtca     1800 gggggcgga gcctatggaa aaacgccagc aacgcggcct ttttacggtt cctggccttt      1860
tgctggcctt tgctcacat gttctttcct gcgttatccc ctgattctgt ggataaccgt      1920
attaccgcct ttgagtgagc tgataccgct cgccgcagcc gaacgaccga gcgcagcgag     1980
tcagtgagcg aggaagcgga agagcgccca atacgcaaac cgcctctccc cgcgcgttgg     2040
ccgattcatt aatgcagctg gcacgacagg tttcccgact ggaaagcggg cagtgagcgc     2100
aacgcaatta atgtgagtta gctcactcat taggcacccc aggctttaca ctttatgctt     2160
ccggctcgta tgttgtgtgg aattgtgagc ggataacaat ttcacacagg aaacagctat     2220
gaccatgatt acgccaagct tataatagaa atagtttttt gaaaggaaag cagcatgaaa     2280
attaaaactc tggcaatcgt tgttctgtcg gctctgtccc tcagttctac agcggctctg     2340
gccgctgcca cgacggttaa tggtgggacc gttcacttta aagggaagt tgttaacgcc     2400 gcttgcgcag ttgatgcagg ctctgttgat caaaccgttc agtaggaca ggttcgtacc      2460 gcatcgctgg cacaggaagg agcaaccagt tctgctgtcg gttttaacat tcagctgaat     2520
gattgcgata ccaatgttgc atctaaagcc gctgttgcct ttttaggtac ggcgattgat     2580
gcgggtcata ccaacgttct ggctctgcag agttcagctg cgggtagcgc aacaaacgtt     2640
ggtgtgcaga tcctggacag aacgggtgct gcgctgacgc tggatggtgc gacatttagt     2700
tcagaaacaa ccctgaataa cggaaccaat accattccgt tccaggcgcg ttattttgca     2760
accggggccg caaccccggg tgctgctaat gcggatgcga ccttcaaggt tcagtatcaa     2820
taacctaccc aggttcaggg acgtcattac gggcagggat gcccacccct gtgcgataaa     2880
aataacgatg aaaggaaga gattatttct attagcgtcg ttgctgccaa tgtttgctct     2940
ggccggaaat aaatggaata ccacgttgcc cggcggaaat atgcaatttc agggcgtcat     3000
tattgcggaa acttgccgga ttgaagccgg tgataaacaa atgacggtca atatgggca     3060 aatcagcagt aaccggtttc atgcggttgg ggaagatagc gcaccggtgc cttttgttat     3120
```

```
tcatttacgg gaatgtagca cggtggtgag tgaacgtgta ggtgtggcgt ttcacggtgt    3180
cgcggatggt aaaaatccgg atgtgctttc cgtgggagag gggccaggga tagccaccaa    3240
tattggcgta gcgttgtttg atgatgaagg aaacctcgta ccgattaatc gtcctccagc    3300
aaactggaaa cggctttatt caggctctac ttcgctacat ttcatcgcca aatatcgtgc    3360
taccgggcgt cgggttactg gcggcatcgc caatgcccag gcctggttct ctttaaccta    3420
tcagtaattg ttcagcagat aatgtgataa caggaacagg acagtgagta ataaaaacgt    3480
caatgtaagg aaatcgcagg aaataacatt ctgcttgctg gcaggtatcc tgatgttcat    3540
ggcaatgatg gttgccggac gcgctgaagc gggagtggcc ttaggtgcga ctcgcgtaat    3600
ttatccggca gggcaaaaac aagagcaact tgccgtgaca ataatgatg aaaatagtac     3660 ctatttaatt caatcatggg tggaaaatgc cgatggtgta aaggatggtc gttttatcgt    3720
gacgcctcct ctgtttgcga tgaagggaaa aaaagagaat accttacgta ttcttgatgc    3780
aacaaataac caattgccac aggaccggga agtttattc tggatgaacg ttaaagcgat     3840
tccgtcaatg gataaatcaa aattgactga gaatacgcta cagctcgcaa ttatcagccg    3900
cattaaactg tactatcgcc cggctaaatt agcgttgcca cccgatcagg ccgcagaaaa    3960
attaagattt cgtcgtagcg cgaattctct gacgctgatt aacccgacac cctattacct    4020
gacggtaaca gagttgaatg ccggaacccg ggttcttgaa aatgcattgg tgcctccaat    4080
gggcgaaagc acggttaaat tgccttctga tgcaggaagc aatattactt accgaacaat    4140
aaatgattat ggcgcactta cccccaaaat gacgggcgta atggaataac gtcgactcta    4200
gaggatcccc gggtaccgag ctcgaattca ctggccgtcg ttttacaacg tcgtgactgg    4260
gaaaaccctg gcgttaccca acttaatcgc cttgcagcac atccccctt cgccagctgg    4320 cgtaatagcg aagaggcccg caccgatcgc ccttcccaac agttgcgcag cctgaatggc    4380
gaatggcgcc tgatgcggta ttttctcctt acgcatctgt gcggtatttc acaccgcata    4440
tggtgcactc tcagtacaat ctgctctgat gccgcatagt taagccagcc ccgacacccg    4500
ccaacacccg ctgacgcgcc ctgacgggct tgtctgctcc cggcatccgc ttacagacaa    4560
gctgtgaccg tctccgggag ctgcatgtgt cagaggtttt caccgtcatc accgaaacgc    4620
gcg                                                                  4623

<210> SEQ ID NO 199
<211> LENGTH: 42
<212> TYPE: DNA
<213> ORGANISM: Oligonucleotide Primer

<400> SEQUENCE: 199
aagatcttaa gctaagcttg aattctctga cgctgattaa cc                        42

<210> SEQ ID NO 200
<211> LENGTH: 41
<212> TYPE: DNA
<213> ORGANISM: Oligonucleotide Primer

<400> SEQUENCE: 200
acgtaaagca tttctagacc gcggatagta atcgtgctat c                         41

<210> SEQ ID NO 201
<211> LENGTH: 5681
<212> TYPE: DNA
<213> ORGANISM: pFIMD
```

<400> SEQUENCE: 201

```
tcaccgtcat caccgaaacg cgcgagacga aagggcctcg tgatacgcct attttatag        60
gttaatgtca tgataataat ggtttcttag acgtcaggtg gcacttttcg gggaaatgtg       120
cgcggaaccc ctatttgttt attttttctaa atacattcaa atatgtatcc gctcatgaga      180
caataaccct gataaatgct tcaataatat tgaaaaagga agagtatgag tattcaacat       240
ttccgtgtcg cccttattcc cttttttgcg gcattttgcc ttcctgtttt tgctcaccca       300
gaaacgctgg tgaaagtaaa agatgctgaa gatcagttgg gtgcacgagt gggttacatc       360
gaactggatc tcaacagcgg taagatcctt gagagttttc gccccgaaga acgttttcca       420
atgatgagca cttttaaagt tctgctatgt ggcgcggtat tatcccgtat tgacgccggg       480
caagagcaac tcggtcgccg catacactat tctcagaatg acttggttga gtactcacca       540
gtcacagaaa agcatcttac ggatggcatg acagtaagag aattatgcag tgctgccata       600
accatgagtg ataacactgc ggccaactta cttctgacaa cgatcggagg accgaaggag       660
ctaaccgctt ttttgcacaa catgggggat catgtaactc gccttgatcg ttgggaaccg       720
gagctgaatg aagccatacc aaacgacgag cgtgacacca cgatgcctgt agcaatggca       780
acaacgttgc gcaaactatt aactggcgaa ctacttactc tagcttcccg gcaacaatta       840
atagactgga tggaggcgga taagttgca ggaccacttc tgcgctcggc ccttccggct        900
ggctggttta ttgctgataa atctggagcc ggtgagcgtg ggtctcgcgg tatcattgca       960
gcactggggc cagatggtaa gccctcccgt atcgtagtta tctacacgac ggggagtcag      1020
gcaactatgg atgaacgaaa tagacagatc gctgagatag gtgcctcact gattaagcat      1080
tggtaactgt cagaccaagt ttactcatat atactttaga ttgatttaaa acttcatttt      1140
taatttaaaa ggatctaggt gaagatcctt tttgataatc tcatgaccaa atcccttaa       1200
cgtgagtttt cgttccactg agcgtcagac cccgtagaaa agatcaaagg atcttcttga      1260
gatccttttt ttctgcgcgt aatctgctgc ttgcaaacaa aaaaaccacc gctaccagcg      1320
gtggtttgtt tgccggatca agagctacca actctttttc cgaaggtaac tggcttcagc      1380
agagcgcaga taccaaatac tgtccttcta gtgtagccgt agttaggcca ccacttcaag      1440
aactctgtag caccgcctac atacctcgct ctgctaatcc tgttaccagt ggctgctgcc      1500
agtggcgata agtcgtgtct taccgggttg gactcaagac gatagttacc ggataaggcg      1560
cagcggtcgg gctgaacggg gggttcgtgc acacagccca gcttggagcg aacgacctac      1620
accgaactga gatacctaca gcgtgagcta tgagaaagcg ccacgcttcc cgaagggaga      1680
aaggcggaca ggtatccggt aagcggcagg gtcggaacag gagagcgcac gagggagctt      1740
ccagggggaa acgcctggta tctttatagt cctgtcgggt ttcgccacct ctgacttgag      1800
cgtcgatttt tgtgatgctc gtcagggggg cggagcctat ggaaaaacgc cagcaacgcg      1860
gcctttttac ggttcctggc cttttgctgg ccttttgctc acatgttctt tcctgcgtta      1920
tcccctgatt ctgtggataa ccgtattacc gcctttgagt gagctgatac cgctcgccgc      1980
agccgaacga ccgagcgcag cgagtcagtg agcgaggaag cggaagagcg cccaatacgc      2040
aaaccgcctc tccccgcgcg ttggccgatt cattaatgca gctggcacga caggtttccc      2100
gactggaaag cgggcagtga gcgcaacgca attaatgtga gttagctcac tcattaggca      2160
ccccaggctt tacactttat gcttccggct cgtatgttgt gtggaattgt gagcggataa      2220
caatttcaca caggaaacag ctatgaccat gattacgcca agcttgaatt ctctgacgct      2280
gattaacccg acaccctatt acctgacggt aacagagttg aatgccggaa cccgggttct      2340
```

-continued

```
tgaaaatgca ttggtgcctc caatgggcga agcacggtt aaattgcctt ctgatgcagg    2400
aagcaatatt acttaccgaa cataaatga ttatggcgca cttaccccca aaatgacggg    2460
cgtaatggaa taacgcaggg ggaattttc gcctgaataa aaagaattga ctgccggggt    2520
gattttaagc cggaggaata atgtcatatc tgaatttaag actttaccag cgaaacacac    2580
aatgcttgca tattcgtaag catcgtttgg ctggttttt tgtccgactc gttgtcgcct    2640
gtgcttttgc cgcacaggca cctttgtcat ctgccgacct ctattttaat ccgcgctttt    2700
tagcggatga tccccaggct gtggccgatt tatcgcgttt tgaaaatggg caagaattac    2760
cgccagggac gtatcgcgtc gatatctatt tgaataatgg ttatatggca acgcgtgatg    2820
tcacatttaa tacgggcgac agtgaacaag ggattgttcc ctgcctgaca cgcgcgcaac    2880
tcgccagtat ggggctgaat acggcttctg tcgccggtat gaatctgctg gcggatgatg    2940
cctgtgtgcc attaaccaca atggtccagg acgctactgc gcatctggat gttggtcagc    3000
agcgactgaa cctgacgatc cctcaggcat ttatgagtaa tcgcgcgcgt ggttatattc    3060
ctcctgagtt atgggatccc ggtattaatg ccggattgct caattataat ttcagcggaa    3120
atagtgtaca gaatcggatt ggggtaaca gccattatgc atatttaaac ctacagagtg    3180
ggttaaatat tggtgcgtgg cgtttacgcg acaataccac ctggagttat aacagtagcg    3240
acagatcatc aggtagcaaa aataaatggc agcatatcaa tacctggctt gagcgagaca    3300
taataccgtt acgttcccgg ctgacgctgg gtgatggtta tactcagggc gatattttcg    3360
atggtattaa ctttcgcggc gcacaattgg cctcagatga caatatgtta cccgatagtc    3420
aaagaggatt tgccccggtg atccacggta ttgctcgtgg tactgcacag gtcactatta    3480
aacaaaatgg gtatgacatt tataatagta cggtgccacc ggggccttt accatcaacg    3540 atatctatgc cgcaggtaat agtggtgact gcaggtaac gatcaaagag ctgacggca    3600 gcacgcagat ttttaccgta ccctattcgt cagtcccgct tttgcaacgt gaagggcata    3660
ctcgttattc cattacggca ggagaatacc gtagtggaaa tgcgcagcag gaaaaaaccc    3720
gcttttccca gagtacatta ctccacggcc ttccggctgg ctggacaata tatggtggaa    3780
cgcaactggc ggatcgttat cgtgcttta atttcggtat cgggaaaaac atgggggcac    3840
tgggcgctct gtctgtggat atgacgcagg ctaattccac acttcccgat gacagtcagc    3900
atgacggaca atcggtgcgt tttctctata acaaatcgct caatgaatca ggcacgaata    3960
ttcagttagt gggttaccgt tattcgacca gcggatattt taatttcgct gatacaacat    4020
acagtcgaat gaatggctac aacattgaaa cacaggacgg agttattcag gttaagccga    4080
aattcaccga ctattacaac ctcgcttata caaacgcgg gaaattacaa ctcaccgtta    4140
ctcagcaact cgggcgcaca tcaacactgt atttgagtgg tagccatcaa acttattggg    4200
gaacgagtaa tgtcgatgag caattccagg ctggattaaa tactgcgttc gaagatatca    4260
actggacgct cagctatagc ctgacgaaaa acgcctggca aaaggacgg gatcagatgt    4320 tagcgcttaa cgtcaatatt cctttcagcc actggctgcg ttctgacagt aaatctcagt    4380
ggcgacatgc cagtgccagc tacagcatgt cacacgatct caacggtcgg atgaccaatc    4440
tggctggtgt atacgtacg ttgctggaag acaacaacct cagctatagc gtgcaaaccg    4500
gctatgccgg gggaggcgat ggaaatagcg gaagtacagg ctacgccacg ctgaattatc    4560
gcggtggtta cggcaatgcc aatatcggtt acagccatag cgatgatatt aagcagctct    4620
attacggagt cagcggtggg gtactggctc atgccaatgg cgtaacgctg gggcagccgt    4680
```

```
taaacgatac ggtggtgctt gttaaagcgc ctggcgcaaa agatgcaaaa gtcgaaaacc    4740 agacggggt gcgtaccgac tggcgtggtt atgccgtgct gccttatgcc actgaatatc    4800
gggaaaatag agtggcgctg ataccaata ccctggctga taacgtcgat ttagataacg    4860
cggttgctaa cgttgttccc actcgtgggg cgatcgtgcg agcagagttt aaagcgcgcg    4920
ttgggataaa actgctcatg acgctgaccc acaataataa gccgctgccg tttggggcga    4980
tggtgacatc agagagtagc cagagtagcg gcattgttgc ggataatggt caggtttacc    5040
tcagcggaat gcctttagcg ggaaaagttc aggtgaaatg gggagaagag gaaaatgctc    5100
actgtgtcgc caattatcaa ctgccaccag agagtcagca gcagttatta acccagctat    5160
cagctgaatg tcgttaaggg ggcgtgatga gaaacaaacc ttttttatcttct ctgtgcgctt    5220 ttttgtggct ggcggtgagt cacgcttttgg ctgcggatag cacgattact atccgcggtc    5280
tagaggatcc ccgggtaccg agctcgaatt cactggccgt cgttttacaa cgtcgtgact    5340 gggaaaccc tggcgttacc caacttaatc gccttgcagc acatcccct ttcgccagct    5400 ggcgtaatag cgaagaggcc cgcaccgatc gcccttccca acagttgcgc agcctgaatg    5460
gcgaatggcg cctgatgcgg tattttctcc ttacgcatct gtgcggtatt tcacaccgca    5520
tatggtgcac tctcagtaca atctgctctg atgccgcata gttaagccag ccccgacacc    5580
cgccaacacc cgctgacgcg ccctgacggg cttgtctgct cccggcatcc gcttacagac    5640
aagctgtgac cgtctccggg agctgcatgt gtcagaggtt t                      5681

<210> SEQ ID NO 202
<211> LENGTH: 40
<212> TYPE: DNA
<213> ORGANISM: Oligonucleotide Primer

<400> SEQUENCE: 202
aattacgtga gcaagcttat gagaaacaaa ccttttttatc                            40

<210> SEQ ID NO 203
<211> LENGTH: 41
<212> TYPE: DNA
<213> ORGANISM: Oligonucleotide Primer

<400> SEQUENCE: 203
gactaaggcc tttctagatt attgataaac aaaagtcacg c                         41

<210> SEQ ID NO 204
<211> LENGTH: 4637
<212> TYPE: DNA
<213> ORGANISM: pFIMFGH

<400> SEQUENCE: 204
aaagggcctc gtgatacgcc tattttttata ggttaatgtc atgataataa tggtttctta    60
gacgtcaggt ggcacttttc ggggaaatgt gcgcggaacc cctatttgtt tattttttcta   120 aatacattca aatatgtatc cgctcatgag acaataaccc tgataaatgc ttcaataata   180
ttgaaaaagg aagagtatga gtattcaaca tttccgtgtc gcccttattc ccttttttgc   240
ggcattttgc cttcctgttt ttgctcaccc agaaacgctg gtgaaagtaa agatgctga    300 agatcagttg ggtgcacgag tgggttacat cgaactggat ctcaacagcg gtaagatcct   360
tgagagtttt cgccccgaag aacgttttcc aatgatgagc acttttaaag ttctgctatg   420
tggcgcggta ttatcccgta ttgacgccgg gcaagagcaa ctcggtcgcc gcatacacta   480
ttctcagaat gacttggttg agtactcacc agtcacagaa aagcatctta cggatggcat   540
```

-continued

```
gacagtaaga gaattatgca gtgctgccat aaccatgagt gataacactg cggccaactt    600
acttctgaca acgatcggag gaccgaagga gctaaccgct ttttttgcaca acatgggga    660
tcatgtaact cgccttgatc gttgggaacc ggagctgaat gaagccatac caaacgacga   720
gcgtgacacc acgatgcctg tagcaatggc aacaacgttg cgcaaactat taactggcga   780
actacttact ctagcttccc ggcaacaatt aatagactgg atggaggcgg ataaagttgc    840
aggaccactt ctgcgctcgg cccttccggc tggctggttt attgctgata atctggagc    900
cggtgagcgt gggtctcgcg gtatcattgc agcactgggg ccagatggta agccctcccg    960
tatcgtagtt atctacacga cggggagtca ggcaactatg gatgaacgaa atagacagat   1020
cgctgagata ggtgcctcac tgattaagca ttggtaactg tcagaccaag tttactcata   1080
tatactttag attgatttaa aacttcattt ttaatttaaa aggatctagg tgaagatcct   1140
ttttgataat ctcatgacca aaatccctta acgtgagttt tcgttccact gagcgtcaga   1200
ccccgtagaa aagatcaaag gatcttcttg agatcctttt tttctgcgcg taatctgctg   1260
cttgcaaaca aaaaaaccac cgctaccagc ggtggtttgt ttgccggatc aagagctacc   1320
aactcttttt ccgaaggtaa ctggcttcag cagagcgcag ataccaaata ctgtccttct   1380
agtgtagccg tagttaggcc accacttcaa gaactctgta gcaccgccta catacctcgc   1440
tctgctaatc ctgttaccag tggctgctgc cagtggcgat aagtcgtgtc ttaccgggtt   1500
ggactcaaga cgatagttac cggataaggc gcagcggtcg ggctgaacgg ggggttcgtg   1560
cacacagccc agcttggagc gaacgaccta caccgaactg agatacctac agcgtgagct   1620
atgagaaagc gccacgcttc ccgaagggag aaaggcggac aggtatccgg taagcggcag   1680
ggtcggaaca ggagagcgca cgagggagct tccaggggga aacgcctggt atctttatag   1740
tcctgtcggg tttcgccacc tctgacttga gcgtcgattt ttgtgatgct cgtcaggggg   1800
gcggagccta tggaaaaacg ccagcaacgc ggcctttttta cggttcctgg ccttttgctg   1860
gccttttgct cacatgttct ttcctgcgtt atccctgat tctgtggata accgtattac   1920
cgcctttgag tgagctgata ccgctcgccg cagccgaacg accgagcgca gcgagtcagt   1980
gagcgaggaa gcggaagagc gcccaatacg caaaccgcct ctccccgcgc gttggccgat   2040
tcattaatgc agctggcacg acaggtttcc cgactggaaa gcgggcagtg agcgcaacgc   2100
aattaatgtg agttagctca ctcattaggc accccaggct ttacacttta tgcttccggc   2160
tcgtatgttg tgtggaattg tgagcggata acaatttcac acaggaaaca gctatgacca   2220
tgattacgcc aagcttatga gaaacaaacc ttttttatctt ctgtgcgctt ttttgtggct   2280
ggcggtgagt cacgctttgg ctgcggatag cacgattact atccgcggct atgtcaggga   2340
taacggctgt agtgtggccg ctgaatcaac caatttttact gttgatctga tggaaaacgc   2400
ggcgaagcaa tttaacaaca ttggcgcgac gactcctgtt gttccatttc gtatttttgct   2460
gtcaccctgt ggtaatgccg tttctgccgt aaaggttggg tttactggcg ttgcagatag   2520
ccacaatgcc aacctgcttg cacttgaaaa tacggtgtca gcggcttcgg gactgggaat   2580
acagcttctg aatgagcagc aaaatcaaat accccttaat gctccatcgt ccgcgctttc   2640
gtggacgacc ctgacgccgg gtaaaccaaa tacgctgaat ttttacgccc ggctaatggc   2700
gacacaggtg cctgtcactg cggggcatat caatgccacg gctaccttca ctcttgaata   2760
tcagtaactg gagatgctca tgaaatggtg caaacgtggg tatgtattgg cggcaatatt   2820
ggcgctcgca agtgcgacga tacaggcagc cgatgtcacc atcacggtga acggtaaggt   2880
```

| | |
|---|---|
| cgtcgccaaa ccgtgtacgg tttccaccac caatgccacg gttgatctcg gcgatcttta | 2940 |
| ttctttcagt cttatgtctg ccggggcggc atcggcctgg catgatgttg cgcttgagtt | 3000 |
| gactaattgt ccggtgggaa cgtcgagggt cactgccagc ttcagcgggg cagccgacag | 3060 |
| taccggatat tataaaaacc aggggaccgc gcaaaacatc cagttagagc tacaggatga | 3120 |
| cagtggcaac acattgaata ctggcgcaac caaaacagtt caggtggatg attcctcaca | 3180 |
| atcagcgcac ttcccgttac aggtcagagc attgacagta aatggcggag ccactcaggg | 3240 |
| aaccattcag gcagtgatta gcatcaccta tacctacagc tgaacccgaa gagatgattg | 3300 |
| taatgaaacg agttattacc ctgtttgctg tactgctgat gggctggtcg gtaaatgcct | 3360 |
| ggtcattcgc ctgtaaaacc gccaatggta ccgctatccc tattggcggt ggcagcgcca | 3420 |
| atgtttatgt aaaccttgcg cccgtcgtga atgtggggca aaacctggtc gtggatcttt | 3480 |
| cgacgcaaat cttttgccat aacgattatc cggaaaccat tacagactat gtcacactgc | 3540 |
| aacgaggctc ggcttatggc ggcgtgttat ctaattttc cgggaccgta aaatatagtg | 3600 |
| gcagtagcta tccatttcct accaccagcg aaacgccgcg cgttgtttat aattcgagaa | 3660 |
| cggataagcc gtggccggtg gcgctttatt tgacgcctgt gagcagtgcg ggcggggtgg | 3720 |
| cgattaaagc tggctcatta attgccgtgc ttattttgcg acagaccaac aactataaca | 3780 |
| gcgatgattt ccagtttgtg tggaatattt acgccaataa tgatgtggtg gtgcctactg | 3840 |
| gcggctgcga tgtttctgct cgtgatgtca ccgttactct gccggactac cctggttcag | 3900 |
| tgccaattcc tcttaccgtt tattgtgcga aaagccaaaa cctggggtat acctctccg | 3960 |
| gcacaaccgc agatgcgggc aactcgattt tcaccaatac cgcgtcgttt tcacctgcac | 4020 |
| agggcgtcgg cgtacagttg acgcgcaacg gtacgcattat tccagcgaat aacacggtat | 4080 |
| cgttaggagc agtagggact tcggcggtga gtctgggatt aacggcaaat tatgcacgta | 4140 |
| ccggagggca ggtgactgca gggaatgtgc aatcgattat tggcgtgact tttgtttatc | 4200 |
| aataatctag aggatccccg ggtaccgagc tcgaattcac tggccgtcgt tttacaacgt | 4260 |
| cgtgactggg aaaaccctgg cgttacccaa cttaatcgcc ttgcagcaca tccccctttc | 4320 |
| gccagctggc gtaatagcga agaggcccgc accgatcgcc cttcccaaca gttgcgcagc | 4380 |
| ctgaatggcg aatggcgcct gatgcggtat tttctcctta cgcatctgtg cggtatttca | 4440 |
| caccgcatat ggtgcactct cagtacaatc tgctctgatg ccgcatagtt aagccagccc | 4500 |
| cgacacccgc caacacccgc tgacgcgccc tgacgggctt gtctgctccc ggcatccgct | 4560 |
| tacagacaag ctgtgaccgt ctccgggagc tgcatgtgtc agaggttttc accgtcatca | 4620 |
| ccgaaacgcg cgagacg | 4637 |

<210> SEQ ID NO 205
<211> LENGTH: 9299
<212> TYPE: DNA
<213> ORGANISM: pFIMAICDFGH

<400> SEQUENCE: 205

| | |
|---|---|
| cgagacgaaa gggcctcgtg atacgcctat tttataggt taatgtcatg ataataatgg | 60 |
| tttcttagac gtcaggtggc acttttcggg gaaatgtgcg cggaacccct atttgtttat | 120 |
| ttttctaaat acattcaaat atgtatccgc tcatgagaca ataaccctga taatgcttc | 180 |
| aataatattg aaaaaggaag agtatgagta ttcaacattt ccgtgtcgcc cttattccct | 240 |
| ttttttgcggc attttgcctt cctgtttttg ctcacccaga aacgctggtg aaagtaaaag | 300 |
| atgctgaaga tcagttgggt gcacgagtgg gttacatcga actggatctc aacagcggta | 360 |

-continued

```
agatccttga gagttttcgc cccgaagaac gttttccaat gatgagcact tttaaagttc    420
tgctatgtgg cgcggtatta tcccgtattg acgccgggca agagcaactc ggtcgccgca    480
tacactattc tcagaatgac ttggttgagt actcaccagt cacagaaaag catcttacgg    540
atggcatgac agtaagagaa ttatgcagtg ctgccataac catgagtgat aacactgcgg    600
ccaacttact tctgacaacg atcggaggac cgaaggagct aaccgctttt ttgcacaaca    660
tgggggatca tgtaactcgc cttgatcgtt gggaaccgga gctgaatgaa gccataccaa    720
acgacgagcg tgacaccacg atgcctgtag caatggcaac aacgttgcgc aaactattaa    780
ctggcgaact acttactcta gcttcccggc aacaattaat agactggatg gaggcggata    840
aagttgcagg accacttctg cgctcggccc ttccggctgg ctggtttatt gctgataaat    900
ctggagccgg tgagcgtggg tctcgcggta tcattgcagc actggggcca gatggtaagc    960
cctcccgtat cgtagttatc tacacgacgg gagtcaggc aactatggat gaacgaaata    1020
gacagatcgc tgagataggt gcctcactga ttaagcattg gtaactgtca gaccaagttt    1080
actcatatat actttagatt gatttaaaac ttcatttta atttaaaagg atctaggtga    1140 agatccttt tgataatctc atgaccaaaa tcccttaacg tgagttttcg ttccactgag    1200
cgtcagaccc cgtagaaaag atcaaaggat cttcttgaga tcctttttt ctgcgcgtaa    1260 tctgctgctt gcaaacaaaa aaccaccgc taccagcggt ggtttgtttg ccggatcaag    1320
agctaccaac tctttttccg aaggtaactg gcttcagcag agcgcagata ccaaatactg    1380
tccttctagt gtagccgtag ttaggccacc acttcaagaa ctctgtagca ccgcctacat    1440
acctcgctct gctaatcctg ttaccagtgg ctgctgccag tggcgataag tcgtgtctta    1500
ccgggttgga ctcaagacga tagttaccgg ataaggcgca gcggtcgggc tgaacggggg    1560
gttcgtgcac acagcccagc ttggagcgaa cgacctacac cgaactgaga tacctacagc    1620
gtgagctatg agaaagcgcc acgcttcccg aagggagaaa ggcggacagg tatccggtaa    1680
gcggcagggt cggaacagga gagcgcacga gggagcttcc agggggaaac gcctggtatc    1740
tttatagtcc tgtcgggttt cgccacctct gacttgagcg tcgatttttg tgatgctcgt    1800
caggggggcg gagcctatgg aaaaacgcca gcaacgcggc cttttacgg ttcctggcct    1860 tttgctggcc ttttgctcac atgttctttc ctgcgttatc ccctgattct gtggataacc    1920
gtattaccgc ctttgagtga gctgataccg ctcgccgcag ccgaacgacc gagcgcagcg    1980
agtcagtgag cgaggaagcg gaagagcgcc caatacgcaa accgcctctc cccgcgcgtt    2040
ggccgattca ttaatgcagc tggcacgaca ggtttcccga ctggaaagcg ggcagtgagc    2100
gcaacgcaat taatgtgagt tagctcactc attaggcacc ccaggcttta cactttatgc    2160
ttccggctcg tatgttgtgt ggaattgtga gcggataaca atttcacaca ggaaacagct    2220
atgaccatga ttacgccaag cttataatag aaatagtttt ttgaaaggaa agcagcatga    2280
aaattaaaac tctggcaatc gttgttctgt cggctctgtc cctcagttct acagcggctc    2340
tggccgctgc cacgacggtt aatggtggga ccgttcactt taaagggaa gttgttaacg    2400 ccgcttcgc agttgatgca ggctctgttg atcaaaccgt tcagttagga caggttcgta    2460
ccgcatcgct ggcacaggaa ggagcaacca gttctgctgt cggttttaac attcagctga    2520
atgattgcga taccaatgtt gcatctaaag ccgctgttgc cttttaggt acggcgattg    2580 atgcgggtca taccaacgtt ctggctctgc agagttcagc tgcgggtagc gcaacaaacg    2640
ttggtgtgca gatcctggac agaacgggtg ctgcgctgac gctggatggt gcgacattta    2700
```

```
gttcagaaac aaccctgaat aacggaacca ataccattcc gttccaggcg cgttattttg    2760
caaccggggc cgcaaccccg ggtgctgcta atgcggatgc gaccttcaag gttcagtatc    2820
aataacctac ccaggttcag ggacgtcatt acgggcaggg atgcccaccc ttgtgcgata    2880
aaaataacga tgaaaaggaa gagattattt ctattagcgt cgttgctgcc aatgtttgct    2940
ctggccggaa ataaatggaa taccacgttg cccggcggaa atatgcaatt tcagggcgtc    3000
attattgcgg aaacttgccg gattgaagcc ggtgataaac aaatgacggt caatatgggg    3060
caaatcagca gtaaccggtt tcatgcggtt ggggaagata gcgcaccggt gccttttgtt    3120
attcatttac gggaatgtag cacggtggtg agtgaacgtg taggtgtggc gtttcacggt    3180
gtcgcggatg gtaaaaatcc ggatgtgctt ccgtgggag agggccagg gatagccacc    3240 aatattggcg tagcgttgtt tgatgatgaa ggaaacctcg taccgattaa tcgtcctcca    3300
gcaaactgga aacggcttta ttcaggctct acttcgctac atttcatcgc caaatatcgt    3360
gctaccgggc gtcgggttac tggcggcatc gccaatgccc aggcctggtt ctctttaacc    3420
tatcagtaat tgttcagcag ataatgtgat aacaggaaca ggacagtgag taataaaaac    3480
gtcaatgtaa ggaaatcgca ggaaataaca ttctgcttgc tggcaggtat cctgatgttc    3540
atggcaatga tggttgccgg acgcgctgaa gcgggagtgg ccttaggtgc gactcgcgta    3600
atttatccgg cagggcaaaa acaagagcaa cttgccgtga caataatga tgaaaatagt    3660 acctatttaa ttcaatcatg ggtggaaaat gccgatggtg taaaggatgg tcgttttatc    3720
gtgacgcctc ctctgtttgc gatgaaggga aaaaagaga ataccttacg tattcttgat    3780
gcaacaaata accaattgcc acaggaccgg gaaagtttat tctggatgaa cgttaaagcg    3840
attccgtcaa tggataaatc aaaattgact gagaatacgc tacagctcgc aattatcagc    3900
cgcattaaac tgtactatcg cccggctaaa ttagcgttgc cacccgatca ggccgcagaa    3960
aaattaagat ttcgtcgtag cgcgaattct ctgacgctga ttaacccgac accctattac    4020
ctgacggtaa cagagttgaa tgccggaacc cgggttcttg aaaatgcatt ggtgcctcca    4080
atgggcgaaa gcacggttaa attgccttct gatgcaggaa gcaatattac ttaccgaaca    4140
ataaatgatt atggcgcact taccccccaaa atgacgggcg taatgaaata acgcaggggg    4200
aatttttcgc ctgaataaaa agaattgact gccggggtga ttttaagccg gaggaataat    4260
gtcatatctg aatttaagac tttaccagcg aaacacacaa tgcttgcata ttcgtaagca    4320
tcgtttggct ggttttttg tccgactcgt tgtcgcctgt gcttttgccg cacaggcacc    4380
tttgtcatct gccgacctct attttaatcc gcgcttttta gcggatgatc cccaggctgt    4440
ggccgattta tcgcgttttg aaaatgggca agaattaccg ccaggacgt atcgcgtcga    4500 tatctatttg aataatggtt atatggcaac gcgtgatgtc acatttaata cgggcgacag    4560
tgaacaaggg attgttccct gcctgacacg cgcgcaactc gccagtatgg ggctgaatac    4620
ggcttctgtc gccggtatga atctgctggc ggatgatgcc tgtgtgccat taccacaat    4680 ggtccaggac gctactgcgc atctggatgt tggtcagcag cgactgaacc tgacgatccc    4740
tcaggcattt atgagtaatc gcgcgcgtgg ttatattcct cctgagttat gggatcccgg    4800
tattaatgcc ggattgctca attataattt cagcggaaat agtgtacaga atcggattgg    4860
gggtaacagc cattatgcat atttaaacct acagagtggg ttaaatattg gtgcgtggcg    4920
tttacgcgac aataccacct ggagttataa cagtagcgac agatcatcag gtagcaaaaa    4980 taaatgcag catatcaata cctggcttga gcgagacata ataccgttac gttcccggct    5040
gacgctgggt gatggttata ctcagggcga tattttcgat ggtattaact ttcgcggcgc    5100
```

```
acaattggcc tcagatgaca atatgttacc cgatagtcaa agaggatttg ccccggtgat    5160
ccacggtatt gctcgtggta ctgcacaggt cactattaaa caaaatgggt atgacattta    5220
taatagtacg gtgccaccgg ggccttttac catcaacgat atctatgccg caggtaatag    5280
tggtgacttg caggtaacga tcaaagaggc tgacggcagc acgcagattt ttaccgtacc    5340
ctattcgtca gtcccgcttt tgcaacgtga agggcatact cgttattcca ttacggcagg    5400
agaataccgt agtggaaatg cgcagcagga aaaaacccgc ttttccaga gtacattact     5460 ccacggcctt ccggctggct ggacaatata tggtggaacg caactggcgg atcgttatcg    5520 tgctttaat ttcggtatcg ggaaaaacat gggggcactg ggcgctctgt ctgtggatat     5580
gacgcaggct aattccacac ttcccgatga cagtcagcat gacggacaat cggtgcgttt    5640
tctctataac aaatcgctca atgaatcagg cacgaatatt cagttagtgg gttaccgtta    5700
ttcgaccagc ggatatttta atttcgctga tacaacatac agtcgaatga atggctacaa    5760
cattgaaaca caggacggag ttattcaggt taagccgaaa ttcaccgact attacaacct    5820
cgcttataac aaacgcggga aattacaact caccgttact cagcaactcg ggcgcacatc    5880
aacactgtat ttgagtggta gccatcaaac ttattgggga acgagtaatg tcgatgagca    5940
attccaggct ggattaaata ctgcgttcga agatatcaac tggacgctca gctatagcct    6000
gacgaaaaac gcctggcaaa aaggacggga tcagatgtta cgcttaacg tcaatattcc     6060 tttcagccac tggctgcgtt ctgacagtaa atctcagtgg cgacatgcca gtgccagcta    6120
cagcatgtca cacgatctca acggtcggat gaccaatctg gctggtgtat acggtacgtt    6180
gctggaagac aacaacctca gctatagcgt gcaaaccggc tatgccgggg gaggcgatgg    6240
aaatagcgga agtacaggct acgccacgct gaattatcgc ggtggttacg gcaatgccaa    6300
tatcggttac agccatagcg atgatattaa gcagctctat tacggagtca gcggtggggt    6360
actggctcat gccaatggcg taacgctggg gcagccgtta aacgatacgg tggtgcttgt    6420
taaagcgcct ggcgcaaaag atgcaaaagt cgaaaccag acggggtgc gtaccgactg      6480 gcgtggttat gccgtgctgc cttatgccac tgaatatcgg gaaaatagag tggcgctgga    6540
taccaatacc ctggctgata acgtcgattt agataacgcg gttgctaacg ttgttcccac    6600
tcgtggggcg atcgtgcgag cagagtttaa agcgcgcgtt gggataaaac tgctcatgac    6660
gctgacccac aataataagc cgctgccgtt tggggcgatg gtgacatcag agagtagcca    6720
gagtagcggc attgttgcgg ataatggtca ggtttacctc agcggaatgc ctttagcggg    6780
aaaagttcag gtgaaatggg gagaagagga aaatgctcac tgtgtcgcca attatcaact    6840
gccaccagag agtcagcagc agttattaac ccagctatca gctgaatgtc gttaaggggg    6900
cgtgatgaga aacaaacctt tttatcttct gtgcgctttt ttgtggctgg cggtgagtca    6960
cgctttggct gcggatagca cgattactat ccgcggctat gtcagggata acggctgtag    7020
tgtggccgct gaatcaacca attttactgt tgatctgatg gaaaacgcgg cgaagcaatt    7080
taacaacatt ggcgcgacga ctcctgttgt tccatttcgt attttgctgt caccctgtgg    7140
taatgccgtt tctgccgtaa aggttgggtt tactggcgtt gcagatagcc acaatgccaa    7200
cctgcttgca cttgaaaata cggtgtcagc ggcttcggga ctgggaatac agcttctgaa    7260
tgagcagcaa aatcaaatac cccttaatgc tccatcgtcc gcgctttcgt ggacgaccct    7320
gacgccgggt aaaccaaata cgctgaattt ttacgcccgg ctaatggcga cacaggtgcc    7380
tgtcactgcg gggcatatca atgccacggc taccttcact cttgaatatc agtaactgga    7440
```

| | |
|---|---|
| gatgctcatg aaatggtgca aacgtgggta tgtattggcg gcaatattgg cgctcgcaag | 7500 |
| tgcgacgata caggcagccg atgtcaccat cacggtgaac ggtaaggtcg tcgccaaacc | 7560 |
| gtgtacggtt tccaccacca atgccacggt tgatctcggc gatctttatt ctttcagtct | 7620 |
| tatgtctgcc ggggcggcat cggcctgcca tgatgttgcg cttgagttga ctaattgtcc | 7680 |
| ggtgggaacg tcgagggtca ctgccagctt cagcggggca gccgacagta ccggatatta | 7740 |
| taaaaaccag gggaccgcgc aaaacatcca gttagagcta caggatgaca gtggcaacac | 7800 |
| attgaatact ggcgcaacca aaacagttca ggtggatgat tcctcacaat cagcgcactt | 7860 |
| cccgttacag gtcagagcat tgacagtaaa tggcggagcc actcagggaa ccattcaggc | 7920 |
| agtgattagc atcacctata cctacagctg aacccgaaga gatgattgta atgaaacgag | 7980 |
| ttattaccct gtttgctgta ctgctgatgg gctggtcggt aaatgcctgg tcattcgcct | 8040 |
| gtaaaaccgc caatggtacc gctatcccta ttggcggtgg cagcgccaat gtttatgtaa | 8100 |
| accttgcgcc cgtcgtgaat gtggggcaaa acctggtcgt ggatctttcg acgcaaatct | 8160 |
| tttgccataa cgattatccg gaaaccatta cagactatgt cacactgcaa cgaggctcgg | 8220 |
| cttatggcgg cgtgttatct aattttttccg ggaccgtaaa atatagtggc agtagctatc | 8280 |
| catttcctac caccagcgaa acgccgcgcg ttgtttataa ttcgagaacg gataagccgt | 8340 |
| ggccggtggc gctttatttg acgcctgtga gcagtgcggg cggggtggcg attaaagctg | 8400 |
| gctcattaat tgccgtgctt attttgcgac agaccaacaa ctataacagc gatgatttcc | 8460 |
| agtttgtgtg gaatatttac gccaataatg atgtggtggt gcctactggc ggctgcgatg | 8520 |
| tttctgctcg tgatgtcacc gttactctgc cggactaccc tggttcagtg ccaattcctc | 8580 |
| ttaccgttta ttgtgcgaaa agccaaaacc tggggtatta cctctccggc acaaccgcag | 8640 |
| atgcgggcaa ctcgattttc accaataccg cgtcgttttc acctgcacag ggcgtcggcg | 8700 |
| tacagttgac gcgcaacggt acgattattc cagcgaataa cacggtatcg ttaggagcag | 8760 |
| tagggacttc ggcggtgagt ctgggattaa cggcaaatta tgcacgtacc ggagggcagg | 8820 |
| tgactgcagg gaatgtgcaa tcgattattg gcgtgacttt tgtttatcaa taatctagaa | 8880 |
| ggatccccgg gtaccgagct cgaattcact ggccgtcgtt ttacaacgtc gtgactggga | 8940 |
| aaaccctggc gttacccaac ttaatcgcct tgcagcacat ccccctttcg ccagctggcg | 9000 |
| taatagcgaa gaggcccgca ccgatcgccc ttcccaacag ttgcgcagcc tgaatggcga | 9060 |
| atggcgcctg atgcggtatt ttctccttac gcatctgtgc ggtatttcac accgcatatg | 9120 |
| gtgcactctc agtacaatct gctctgatgc cgcatagtta agccagcccc gacacccgcc | 9180 |
| aacacccgct gacgcgccct gacgggcttg tctgctcccg gcatccgctt acagacaagc | 9240 |
| tgtgaccgtc tccgggagct gcatgtgtca gaggttttca ccgtcatcac cgaaacgcg | 9299 |

<210> SEQ ID NO 206
<211> LENGTH: 8464
<212> TYPE: DNA
<213> ORGANISM: pFIMAICDFG

<400> SEQUENCE: 206

| | |
|---|---|
| cgagacgaaa gggcctcgtg atacgcctat ttttataggt taatgtcatg ataataatgg | 60 |
| tttcttagac gtcaggtggc acttttcggg gaaatgtgcg cggaacccct atttgtttat | 120 |
| ttttctaaat acattcaaat atgtatccgc tcatgagaca ataaccctga taaatgcttc | 180 |
| aataatattg aaaaaggaag agtatgagta ttcaacattt ccgtgtcgcc cttattccct | 240 |
| tttttgcggc attttgcctt cctgtttttg ctcacccaga aacgctggtg aaagtaaaag | 300 |

-continued

```
atgctgaaga tcagttgggt gcacgagtgg gttacatcga actggatctc aacagcggta      360
agatccttga gagttttcgc cccgaagaac gttttccaat gatgagcact tttaaagttc      420
tgctatgtgg cgcggtatta tcccgtattg acgccgggca agagcaactc ggtcgccgca      480
tacactattc tcagaatgac ttggttgagt actcaccagt cacagaaaag catcttacgg      540
atggcatgac agtaagagaa ttatgcagtg ctgccataac catgagtgat aacactgcgg      600
ccaacttact tctgacaacg atcggaggac cgaaggagct aaccgctttt ttgcacaaca      660
tgggggatca tgtaactcgc cttgatcgtt gggaaccgga gctgaatgaa gccataccaa      720
acgacgagcg tgacaccacg atgcctgtag caatggcaac aacgttgcgc aaactattaa      780
ctggcgaact acttactcta gcttcccggc aacaattaat agactggatg gaggcggata      840
aagttgcagg accacttctg cgctcggccc ttccggctgg ctggtttatt gctgataaat      900
ctggagccgg tgagcgtggg tctcgcggta tcattgcagc actggggcca gatggtaagc      960
cctcccgtat cgtagttatc tacacgacgg ggagtcaggc aactatggat gaacgaaata     1020
gacagatcgc tgagataggt gcctcactga ttaagcattg gtaactgtca gaccaagttt     1080
actcatatat actttagatt gatttaaaac ttcatttttta atttaaaagg atctaggtga     1140
agatcctttt tgataatctc atgaccaaaa tcccttaacg tgagttttcg ttccactgag     1200
cgtcagaccc cgtagaaaag atcaaaggat cttcttgaga tccttttttt ctgcgcgtaa     1260
tctgctgctt gcaaacaaaa aaccaccgc taccagcggt ggtttgtttg ccggatcaag     1320
agctaccaac tctttttccg aaggtaactg gcttcagcag agcgcagata ccaaatactg     1380
tccttctagt gtagccgtag ttaggccacc acttcaagaa ctctgtagca ccgcctacat     1440
acctcgctct gctaatcctg ttaccagtgg ctgctgccag tggcgataag tcgtgtctta     1500
ccgggttgga ctcaagacga tagttaccgg ataaggcgca gcggtcgggc tgaacggggg     1560
gttcgtgcac acagcccagc ttggagcgaa cgacctacac cgaactgaga tacctacagc     1620
gtgagctatg agaaagcgcc acgcttcccg aagggagaaa ggcggacagg tatccggtaa     1680
gcggcagggt cggaacagga gagcgcacga gggagcttcc agggggaaac gcctggtatc     1740
tttatagtcc tgtcgggttt cgccacctct gacttgagcg tcgatttttg tgatgctcgt     1800
caggggggcg gagcctatgg aaaaacgcca gcaacgcggc ctttttacgg ttcctggcct     1860
tttgctggcc ttttgctcac atgttctttc ctgcgttatc ccctgattct gtggataacc     1920
gtattaccgc ctttgagtga gctgataccg ctcgccgcag ccgaacgacc gagcgcagcg     1980
agtcagtgag cgaggaagcg gaagagcgcc caatacgcaa accgcctctc cccgcgcgtt     2040
ggccgattca ttaatgcagc tggcacgaca ggtttcccga ctggaaagcg ggcagtgagc     2100
gcaacgcaat taatgtgagt tagctcactc attaggcacc ccaggcttta cactttatgc     2160
ttccggctcg tatgttgtgt ggaattgtga gcggataaca atttcacaca ggaaacagct     2220
atgaccatga ttacgccaag cttataatag aaatagtttt ttgaaaggaa agcagcatga     2280
aaattaaaac tctggcaatc gttgttctgt cggctctgtc cctcagttct acagcggctc     2340
tggccgctgc cacgacggtt aatggtggga ccgttcactt taaagggaa gttgttaacg     2400 ccgcttcgcg agttgatgca ggctctgttg atcaaaccgt tcagtaggga caggttcgta     2460
ccgcatcgct ggcacaggaa ggagcaacca gttctgctgt cggttttaac attcagctga     2520
atgattgcga taccaatgtt gcatctaaag ccgctgttgc cttttttaggt acggcgattg     2580 atgcgggtca taccaacgtt ctggctctgc agagttcagt tgcgggtagc gcaacaaacg     2640
```

```
ttggtgtgca gatcctggac agaacgggtg ctgcgctgac gctggatggt gcgacattta   2700
gttcagaaac aaccctgaat aacggaacca ataccattcc gttccaggcg cgttattttg   2760
caaccgggc cgcaaccccg ggtgctgcta atgcggatgc gaccttcaag gttcagtatc   2820
aataacctac ccaggttcag ggacgtcatt acgggcaggg atgcccaccc ttgtgcgata   2880
aaaataacga tgaaaaggaa gagattattt ctattagcgt cgttgctgcc aatgtttgct   2940
ctggccggaa ataaatggaa taccacgttg cccggcggaa atatgcaatt tcagggcgtc   3000
attattgcgg aaacttgccg gattgaagcc ggtgataaac aaatgacggt caatatgggg   3060
caaatcagca gtaaccggtt tcatgcggtt ggggaagata gcgcaccggt gccttttgtt   3120
attcatttac gggaatgtag cacggtggtg agtgaacgtg taggtgtggc gtttcacggt   3180
gtcgcggatg gtaaaaatcc ggatgtgctt tccgtgggag aggggccagg gatagccacc   3240
aatattggcg tagcgttgtt tgatgatgaa ggaaacctcg taccgattaa tcgtcctcca   3300
gcaaactgga aacggcttta ttcaggctct acttcgctac atttcatcgc caaatatcgt   3360
gctaccgggc gtcgggttac tggcggcatc gccaatgccc aggcctggtt ctctttaacc   3420
tatcagtaat tgttcagcag ataatgtgat aacaggaaca ggacagtgag taataaaaac   3480
gtcaatgtaa ggaaatcgca ggaaataaca ttctgcttgc tggcaggtat cctgatgttc   3540
atggcaatga tggttgccgg acgcgctgaa gcgggagtgg ccttaggtgc gactcgcgta   3600
atttatccgg caggcaaaa acaagagcaa cttgccgtga caaataatga tgaaaatagt   3660
acctatttaa ttcaatcatg ggtggaaaat gccgatggtg taaaggatgg tcgttttatc   3720
gtgacgcctc ctctgtttgc gatgaaggga aaaaagaga ataccttacg tattcttgat   3780
gcaacaaata accaattgcc acaggaccgg gaaagtttat tctggatgaa cgttaaagcg   3840
attccgtcaa tggataaatc aaaattgact gagaatacgc tacagctcgc aattatcagc   3900
cgcattaaac tgtactatcg cccggctaaa ttagcgttgc cacccgatca ggccgcagaa   3960
aaattaagat ttcgtcgtag cgcgaattct ctgacgctga ttaacccgac accctattac   4020
ctgacggtaa cagagttgaa tgccggaacc cgggttcttg aaaatgcatt ggtgcctcca   4080
atgggcgaaa gcacggttaa attgccttct gatgcaggaa gcaatattac ttaccgaaca   4140
ataaatgatt atggcgcact tacccccaaa atgacgggcg taatggaata acgcaggggg   4200
aatttttcgc ctgaataaaa agaattgact gccggggtga ttttaagccg gaggaataat   4260
gtcatatctg aatttaagac tttaccagcg aaacacacaa tgcttgcata ttcgtaagca   4320
tcgtttggct ggttttttg tccgactcgt tgtcgcctgt gcttttgccg cacaggcacc   4380
tttgtcatct gccgacctct attttaatcc gcgcttttta gcggatgatc cccaggctgt   4440
ggccgattta tcgcgttttg aaaatgggca agaattaccg ccaggacgt atcgcgtcga   4500
tatctatttg aataatggtt atatggcaac gcgtgatgtc acatttaata cgggcgacag   4560
tgaacaaggg attgttccct gcctgacacg cgcgcaactc gccagtatgg ggctgaatac   4620
ggcttctgtc gccggtatga atctgctggc ggatgatgcc tgtgtgccat taccacaat   4680
ggtccaggac gctactgcgc atctggatgt tggtcagcag cgactgaacc tgacgatccc   4740
tcaggcattt atgagtaatc gcgcgcgtgg ttatattcct cctgagttat gggatcccgg   4800
tattaatgcc ggattgctca attataattt cagcggaaat agtgtacaga atcggattgg   4860
gggtaacagc cattatgcat atttaaacct acagagtggg ttaaatattg gtgcgtggcg   4920
tttacgcgac aataccacct ggagttataa cagtagcgac agatcatcag gtagcaaaaa   4980
taaatggcag catatcaata cctggcttga gcgagacata ataccgttac gttcccggct   5040
```

-continued

```
gacgctgggt gatggttata ctcagggcga tattttcgat ggtattaact ttcgcggcgc    5100
acaattggcc tcagatgaca atatgttacc cgatagtcaa agaggatttg ccccggtgat    5160
ccacggtatt gctcgtggta ctgcacaggt cactattaaa caaaatgggt atgacattta    5220
taatagtacg gtgccaccgg ggccttttac catcaacgat atctatgccg caggtaatag    5280
tggtgacttg caggtaacga tcaaagaggc tgacggcagc acgcagattt ttaccgtacc    5340
ctattcgtca gtcccgcttt tgcaacgtga agggcatact cgttattcca ttacggcagg    5400
agaataccgt agtggaaatg cgcagcagga aaaaacccgc tttttccaga gtacattact    5460
ccacggcctt ccggctggct ggacaatata tggtggaacg caactggcgg atcgttatcg    5520
tgcttttaat ttcggtatcg ggaaaaacat gggggcactg ggcgctctgt ctgtggatat    5580
gacgcaggct aattccacac ttcccgatga cagtcagcat gacggacaat cggtgcgttt    5640
tctctataac aaatcgctca atgaatcagg cacgaatatt cagttagtgg gttaccgtta    5700
ttcgaccagc ggatatttta atttcgctga tacaacatac agtcgaatga atggctacaa    5760
cattgaaaca caggacggag ttattcaggt taagccgaaa ttcaccgact attacaacct    5820
cgcttataac aaacgcggga aattacaact caccgttact cagcaactcg ggcgcacatc    5880
aacactgtat ttgagtggta gccatcaaac ttattgggga acgagtaatg tcgatgagca    5940
attccaggct ggattaaata ctgcgttcga agatatcaac tggacgctca gctatagcct    6000
gacgaaaaac gcctggcaaa aaggacggga tcagatgtta gcgcttaacg tcaatattcc    6060
tttcagccac tggctgcgtt ctgacagtaa atctcagtgg cgacatgcca gtgccagcta    6120
cagcatgtca cacgatctca acggtcggat gaccaatctg gctggtgtat acggtacgtt    6180
gctggaagac aacaacctca gctatagcgt gcaaaccggc tatgccgggg gaggcgatgg    6240
aaatagcgga agtacaggct acgccacgct gaattatcgc ggtggttacg gcaatgccaa    6300
tatcggttac agccatagcg atgatattaa gcagctctat tacggagtca gcggtggggt    6360
actggctcat gccaatggcg taacgctggg gcagccgtta acgatacgg tggtgcttgt    6420 taaagcgcct ggcgcaaaag atgcaaaagt cgaaaaccag acgggggtgc gtaccgactg    6480
gcgtggttat gccgtgctgc cttatgccac tgaatatcgg gaaaatagag tggcgctgga    6540
taccaatacc ctggctgata acgtcgattt agataacgcg gttgctaacg ttgttcccac    6600
tcgtggggcg atcgtgcgag cagagtttaa agcgcgcgtt gggataaaac tgctcatgac    6660
gctgacccac aataataagc cgctgccgtt tggggcgatg gtgacatcag agagtagcca    6720
gagtagcggc attgttgcgg ataatggtca ggtttacctc agcggaatgc ctttagcggg    6780
aaaagttcag gtgaaatggg gagaagagga aaatgctcac tgtgtcgcca attatcaact    6840
gccaccagag agtcagcagc agttattaac ccagctatca gctgaatgtc gttaagggg    6900 cgtgatgaga acaaaccttt tttatcttct gtgcgctttt ttgtggctgg cggtgagtca    6960
cgctttggct gcggatagca cgattactat ccgcggctat gtcagggata acggctgtag    7020
tgtggccgct gaatcaacca atttttactgt tgatctgatg gaaaacgcgg cgaagcaatt    7080
taacaacatt ggcgcgacga ctcctgttgt tccatttcgt attttgctgt cacccctgtgg    7140 taatgccgtt tctgccgtaa aggttgggtt tactggcgtt gcagatagcc acaatgccaa    7200
cctgcttgca cttgaaaata cggtgtcagc ggcttcggga ctgggaatac agcttctgaa    7260
tgagcagcaa aatcaaatac cccttaatgc tccatcgtcc cgcgctttcgt ggacgaccct    7320 gacgccgggt aaaccaaata cgctgaattt ttacgcccgg ctaatggcga cacaggtgcc    7380
```

-continued

```
tgtcactgcg gggcatatca atgccacggc taccttcact cttgaatatc agtaactgga    7440
gatgctcatg aaatggtgca aacgtgggta tgtattggcg gcaatattgg cgctcgcaag    7500
tgcgacgata caggcagccg atgtcaccat cacggtgaac ggtaaggtcg tcgccaaacc    7560
gtgtacggtt tccaccacca atgccacggt tgatctcggc gatctttatt ctttcagtct    7620
tatgtctgcc ggggcggcat cggcctggca tgatgttgcg cttgagttga ctaattgtcc    7680
ggtgggaacg tcgagggtca ctgccagctt cagcggggca gccgacagta ccggatatta    7740
taaaaaccag gggaccgcgc aaaacatcca gttagagcta caggatgaca gtggcaacac    7800
attgaatact ggcgcaacca aaacagttca ggtggatgat tcctcacaat cagcgcactt    7860
cccgttacag gtcagagcat tgacagtaaa tggcggagcc actcagggaa ccattcaggc    7920
agtgattagc atcacctata cctacagctg aacccgaaga gatgattgta atgaaacgag    7980
ttattaccct gtttgctgta ctgctgatgg gctggtcggt aaatgcctgg tcattcgcct    8040
gtaaaaccgc caatggtacc gagctcgaat tcactggccg tcgttttaca acgtcgtgac    8100
tgggaaaacc ctggcgttac ccaacttaat cgccttgcag cacatccccc tttcgccagc    8160
tggcgtaata gcgaagaggc ccgcaccgat cgcccttccc aacagttgcg cagcctgaat    8220
ggcgaatggc gcctgatgcg gtattttctc cttacgcatc tgtgcggtat ttcacaccgc    8280
atatggtgca ctctcagtac aatctgctct gatgccgcat agttaagcca gccccgacac    8340
ccgccaacac ccgctgacgc gccctgacgg gcttgtctgc tcccggcatc cgcttacaga    8400
caagctgtga ccgtctccgg gagctgcatg tgtcagaggt tttcaccgtc atcaccgaaa    8460
cgcg                                                                 8464
```

<210> SEQ ID NO 207
<211> LENGTH: 13
<212> TYPE: PRT
<213> ORGANISM: Ce3epitope

<400> SEQUENCE: 207

Cys Gly Gly Val Asn Leu Thr Trp Ser Arg Ala Ser Gly
1               5                   10

<210> SEQ ID NO 208
<211> LENGTH: 13
<212> TYPE: PRT
<213> ORGANISM: Ce3mimotope

<400> SEQUENCE: 208

Cys Gly Gly Val Asn Leu Pro Trp Ser Phe Gly Leu Glu
1               5                   10

<210> SEQ ID NO 209
<211> LENGTH: 9
<212> TYPE: PRT
<213> ORGANISM: Bee venom phospholipase A2 cloning vector

<400> SEQUENCE: 209

Ala Ala Ala Ser Gly Gly Cys Gly Gly
1               5

<210> SEQ ID NO 210
<211> LENGTH: 145
<212> TYPE: PRT
<213> ORGANISM: PLA2 fusion protein

<400> SEQUENCE: 210

```
Met Ala Ile Ile Tyr Pro Gly Thr Leu Trp Cys Gly His Gly Asn Lys
1               5                   10                  15

Ser Ser Gly Pro Asn Glu Leu Gly Arg Phe Lys His Thr Asp Ala Cys
            20                  25                  30

Cys Arg Thr Gln Asp Met Cys Pro Asp Val Met Ser Ala Gly Glu Ser
                35                  40                  45

Lys His Gly Leu Thr Asn Thr Ala Ser His Thr Arg Leu Ser Cys Asp
        50                  55                  60

Cys Asp Asp Lys Phe Tyr Asp Cys Leu Lys Asn Ser Ala Asp Thr Ile
65                  70                  75                  80

Ser Ser Tyr Phe Val Gly Lys Met Tyr Phe Asn Leu Ile Asp Thr Lys
                85                  90                  95

Cys Tyr Lys Leu Glu His Pro Val Thr Gly Cys Gly Glu Arg Thr Glu
                100                 105                 110

Gly Arg Cys Leu His Tyr Thr Val Asp Lys Ser Lys Pro Lys Val Tyr
            115                 120                 125

Gln Trp Phe Asp Leu Arg Lys Tyr Ala Ala Ala Ser Gly Gly Cys Gly
        130                 135                 140

Gly
145

<210> SEQ ID NO 211
<211> LENGTH: 17
<212> TYPE: PRT
<213> ORGANISM: Ce4mimotope

<400> SEQUENCE: 211

Gly Glu Phe Cys Ile Asn His Arg Gly Tyr Trp Val Cys Gly Asp Pro
1               5                   10                  15

Ala

<210> SEQ ID NO 212
<211> LENGTH: 27
<212> TYPE: PRT
<213> ORGANISM: Synthetic M2 Peptide

<400> SEQUENCE: 212

Ser Leu Leu Thr Glu Val Glu Thr Pro Ile Arg Asn Glu Trp Gly Cys
1               5                   10                  15

Arg Cys Asn Gly Ser Ser Asp Gly Gly Gly Cys
            20                  25

<210> SEQ ID NO 213
<211> LENGTH: 97
<212> TYPE: PRT
<213> ORGANISM: Matrix protein M2

<400> SEQUENCE: 213

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80
```

-continued

Gln Ser Ala Val Asp Ala Asp Asp Gly His Phe Val Ser Ile Glu Leu
                85                  90                  95

Glu

<210> SEQ ID NO 214
<211> LENGTH: 42
<212> TYPE: DNA
<213> ORGANISM: Oligonucleotide

<400> SEQUENCE: 214
taaccgaatt caggaggtaa aaacatatgg ctatcatcta cc                        42

<210> SEQ ID NO 215
<211> LENGTH: 129
<212> TYPE: PRT
<213> ORGANISM: Bacteriophage f2

<400> SEQUENCE: 215

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 216
<211> LENGTH: 17
<212> TYPE: PRT
<213> ORGANISM: Circular Mimotope

<400> SEQUENCE: 216

Gly Glu Phe Cys Ile Asn His Arg Gly Tyr Trp Val Cys Gly Asp Pro
1               5                   10                  15

Ala

<210> SEQ ID NO 217
<211> LENGTH: 329
<212> TYPE: PRT
<213> ORGANISM: Bacteriophage Q-beta

<400> SEQUENCE: 217

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

-continued

Val Thr Val Ser Val Ser Gln Pro Ser Arg Asn Arg Lys Asn Tyr Lys
            50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
            115                 120                 125

Leu Asn Pro Ala Tyr Trp Thr Leu Leu Ile Ala Gly Gly Gly Ser Gly
            130                 135                 140

Ser Lys Pro Asp Pro Val Ile Pro Asp Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
            195                 200                 205

Gly Asn Thr Lys Trp Arg Asp Trp Asp Ser Arg Leu Ser Tyr Thr Thr
            210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
            275                 280                 285

Ala Asp Gly Val Ile Val Gly Phe Trp Arg Asp Pro Ser Ser Gly Gly
290                 295                 300

Ala Ile Pro Phe Asp Phe Thr Lys Phe Asp Lys Thr Lys Cys Pro Ile
305                 310                 315                 320

Gln Ala Val Ile Val Pro Arg Ala
                325

<210> SEQ ID NO 218
<211> LENGTH: 770
<212> TYPE: PRT
<213> ORGANISM: Amyloid-Beta Protein (Homo Sapiens)

<400> SEQUENCE: 218

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
            50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn

-continued

```
                85                  90                  95
Trp Cys Lys Arg Gly Arg Lys Gln Cys Lys Thr His Pro His Phe Val
            100                 105                 110
Ile Pro Tyr Arg Cys Leu Val Gly Glu Phe Val Ser Asp Ala Leu Leu
            115                 120                 125
Val Pro Asp Lys Cys Lys Phe Leu His Gln Glu Arg Met Asp Val Cys
            130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
            195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
            275                 280                 285
Glu Val Cys Ser Glu Gln Ala Glu Thr Gly Pro Cys Arg Ala Met Ile
            290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
            355                 360                 365
Ala Ser Thr Pro Asp Ala Val Asp Lys Tyr Leu Glu Thr Pro Gly Asp
            370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
            435                 440                 445
Glu Arg Gln Gln Leu Val Glu Thr His Met Ala Arg Val Glu Ala Met
            450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
            485                 490                 495
Tyr Val Arg Ala Glu Gln Lys Asp Arg Gln His Thr Leu Lys His Phe
            500                 505                 510
```

```
Glu His Val Arg Met Val Asp Pro Lys Lys Ala Ala Gln Ile Arg Ser
            515                 520                 525

Gln Val Met Thr His Leu Arg Val Ile Tyr Glu Arg Met Asn Gln Ser
        530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
                595                 600                 605

Val Asn Gly Glu Phe Ser Leu Asp Asp Leu Gln Pro Trp His Ser Phe
                610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
                675                 680                 685

Val Phe Phe Ala Glu Asp Val Gly Ser Asn Lys Gly Ala Ile Ile Gly
                690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
                755                 760                 765

Gln Asn
    770

<210> SEQ ID NO 219
<211> LENGTH: 82
<212> TYPE: PRT
<213> ORGANISM: Beta-Amyloid Peptide Precursor (Homo Sapiens)

<400> SEQUENCE: 219

Gly Ser Gly Leu Thr Asn Ile Lys Thr Glu Glu Ile Ser Glu Val Lys
1               5                   10                  15

Met Asp Ala Glu Phe Arg His Asp Ser Gly Tyr Glu Val His His Gln
                20                  25                  30

Lys Leu Val Phe Phe Ala Glu Asp Val Gly Ser Asn Lys Gly Ala Ile
            35                  40                  45

Ile Gly Leu Met Val Gly Gly Val Val Ile Ala Thr Val Ile Ile Ile
        50                  55                  60

Thr Leu Val Met Leu Lys Lys Gln Tyr Thr Ser Asn His His Gly Val
65                  70                  75                  80

Val Glu

<210> SEQ ID NO 220
```

<211> LENGTH: 42
<212> TYPE: PRT
<213> ORGANISM: Amyloid Beta Peptide

<400> SEQUENCE: 220

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

<210> SEQ ID NO 221
<211> LENGTH: 249
<212> TYPE: PRT
<213> ORGANISM: Homo sapiens

<400> SEQUENCE: 221

```
Tyr Phe Arg Ala Gln Met Asp Pro Asn Arg Ile Ser Glu Asp Gly Thr
1               5                   10                  15

His Cys Ile Tyr Arg Ile Leu Arg Leu His Glu Asn Ala Asp Phe Gln
            20                  25                  30

Asp Thr Thr Leu Glu Ser Gln Asp Thr Lys Leu Ile Pro Asp Ser Cys
        35                  40                  45

Arg Arg Ile Lys Gln Ala Phe Gln Gly Ala Val Gln Lys Glu Leu Gln
    50                  55                  60

His Ile Val Gly Ser Gln His Ile Arg Ala Glu Lys Ala Met Val Asp
65                  70                  75                  80

Gly Ser Trp Leu Asp Leu Ala Lys Arg Ser Lys Leu Glu Ala Gln Pro
                85                  90                  95

Phe Ala His Leu Thr Ile Asn Ala Thr Asp Ile Pro Ser Gly Ser His
            100                 105                 110

Lys Val Ser Leu Ser Ser Trp Tyr His Asp Arg Gly Trp Ala Lys Ile
        115                 120                 125

Ser Asn Met Thr Phe Ser Asn Gly Lys Leu Ile Val Asn Gln Asp Gly
    130                 135                 140

Phe Tyr Tyr Leu Tyr Ala Asn Ile Cys Phe Arg His His Glu Thr Ser
145                 150                 155                 160

Gly Asp Leu Ala Thr Glu Tyr Leu Gln Leu Met Val Tyr Val Thr Lys
                165                 170                 175

Thr Ser Ile Lys Ile Pro Ser Ser His Thr Leu Met Lys Gly Gly Ser
            180                 185                 190

Thr Lys Tyr Trp Ser Gly Asn Ser Glu Phe His Phe Tyr Ser Ile Asn
        195                 200                 205

Val Gly Gly Phe Phe Lys Leu Arg Ser Gly Glu Glu Ile Ser Ile Glu
    210                 215                 220

Val Ser Asn Pro Ser Leu Leu Asp Pro Asp Gln Asp Ala Thr Tyr Phe
225                 230                 235                 240

Gly Ala Phe Lys Val Arg Asp Ile Asp
                245
```

<210> SEQ ID NO 222
<211> LENGTH: 244
<212> TYPE: PRT
<213> ORGANISM: Homo sapiens

<400> SEQUENCE: 222

```
Met Asp Pro Asn Arg Ile Ser Glu Asp Gly Thr His Cys Ile Tyr Arg
1               5                   10                  15

Ile Leu Arg Leu His Glu Asn Ala Asp Phe Gln Asp Thr Thr Leu Glu
            20                  25                  30

Ser Gln Asp Thr Lys Leu Ile Pro Asp Ser Cys Arg Arg Ile Lys Gln
        35                  40                  45

Ala Phe Gln Gly Ala Val Gln Lys Glu Leu Gln His Ile Val Gly Ser
    50                  55                  60

Gln His Ile Arg Ala Glu Lys Ala Met Val Asp Gly Ser Trp Leu Asp
65                  70                  75                  80

Leu Ala Lys Arg Ser Lys Leu Glu Ala Gln Pro Phe Ala His Leu Thr
                85                  90                  95

Ile Asn Ala Thr Asp Ile Pro Ser Gly Ser His Lys Val Ser Leu Ser
            100                 105                 110

Ser Trp Tyr His Asp Arg Gly Trp Ala Lys Ile Ser Asn Met Thr Phe
            115                 120                 125

Ser Asn Gly Lys Leu Ile Val Asn Gln Asp Gly Phe Tyr Tyr Leu Tyr
        130                 135                 140

Ala Asn Ile Cys Phe Arg His His Glu Thr Ser Gly Asp Leu Ala Thr
145                 150                 155                 160

Glu Tyr Leu Gln Leu Met Val Tyr Val Thr Lys Thr Ser Ile Lys Ile
                165                 170                 175

Pro Ser Ser His Thr Leu Met Lys Gly Gly Ser Thr Lys Tyr Trp Ser
            180                 185                 190

Gly Asn Ser Glu Phe His Phe Tyr Ser Ile Asn Val Gly Gly Phe Phe
        195                 200                 205

Lys Leu Arg Ser Gly Glu Glu Ile Ser Ile Glu Val Ser Asn Pro Ser
    210                 215                 220

Leu Leu Asp Pro Asp Gln Asp Ala Thr Tyr Phe Gly Ala Phe Lys Val
225                 230                 235                 240

Arg Asp Ile Asp

<210> SEQ ID NO 223
<211> LENGTH: 247
<212> TYPE: PRT
<213> ORGANISM: Mus musculus

<400> SEQUENCE: 223

Tyr Phe Arg Ala Gln Met Asp Pro Asn Arg Ile Ser Glu Asp Ser Thr
1               5                   10                  15

His Cys Phe Tyr Arg Ile Leu Arg Leu His Glu Asn Ala Gly Leu Gln
            20                  25                  30

Asp Ser Thr Leu Glu Ser Glu Asp Thr Leu Pro Asp Ser Cys Arg Arg
        35                  40                  45

Met Lys Gln Ala Phe Gln Gly Ala Val Gln Lys Glu Leu Gln His Ile
    50                  55                  60

Val Gly Pro Gln Arg Phe Ser Gly Ala Pro Ala Met Met Glu Gly Ser
65                  70                  75                  80

Trp Leu Asp Val Ala Gln Arg Gly Lys Pro Glu Ala Gln Pro Phe Ala
                85                  90                  95

His Leu Thr Ile Asn Ala Ala Ser Ile Pro Ser Gly Ser His Lys Val
            100                 105                 110

Thr Leu Ser Ser Trp Tyr His Asp Arg Gly Trp Ala Lys Ile Ser Asn
            115                 120                 125
```

```
Met Thr Leu Ser Asn Gly Lys Leu Arg Val Asn Gln Asp Gly Phe Tyr
            130                 135                 140

Tyr Leu Tyr Ala Asn Ile Cys Phe Arg His His Glu Thr Ser Gly Ser
145                 150                 155                 160

Val Pro Thr Asp Tyr Leu Gln Leu Met Val Tyr Val Lys Thr Ser
                165                 170                 175

Ile Lys Ile Pro Ser Ser His Asn Leu Met Lys Gly Gly Ser Thr Lys
                180                 185                 190

Asn Trp Ser Gly Asn Ser Glu Phe His Phe Tyr Ser Ile Asn Val Gly
            195                 200                 205

Gly Phe Phe Lys Leu Arg Ala Gly Glu Glu Ile Ser Ile Gln Val Ser
        210                 215                 220

Asn Pro Ser Leu Leu Asp Pro Asp Gln Asp Ala Thr Tyr Phe Gly Ala
225                 230                 235                 240

Phe Lys Val Gln Asp Ile Asp
                245

<210> SEQ ID NO 224
<211> LENGTH: 199
<212> TYPE: PRT
<213> ORGANISM: Mus musculus

<400> SEQUENCE: 224

Met Lys Gln Ala Phe Gln Gly Ala Val Gln Lys Glu Leu Gln His Ile
1               5                   10                  15

Val Gly Pro Gln Arg Phe Ser Gly Ala Pro Ala Met Met Glu Gly Ser
            20                  25                  30

Trp Leu Asp Val Ala Gln Arg Gly Lys Pro Glu Ala Gln Pro Phe Ala
        35                  40                  45

His Leu Thr Ile Asn Ala Ala Ser Ile Pro Ser Gly Ser His Lys Val
    50                  55                  60

Thr Leu Ser Ser Trp Tyr His Asp Arg Gly Trp Ala Lys Ile Ser Asn
65                  70                  75                  80

Met Thr Leu Ser Asn Gly Lys Leu Arg Val Asn Gln Asp Gly Phe Tyr
                85                  90                  95

Tyr Leu Tyr Ala Asn Ile Cys Phe Arg His His Glu Thr Ser Gly Ser
            100                 105                 110

Val Pro Thr Asp Tyr Leu Gln Leu Met Val Tyr Val Lys Thr Ser
        115                 120                 125

Ile Lys Ile Pro Ser Ser His Asn Leu Met Lys Gly Gly Ser Thr Lys
    130                 135                 140

Asn Trp Ser Gly Asn Ser Glu Phe His Phe Tyr Ser Ile Asn Val Gly
145                 150                 155                 160

Gly Phe Phe Lys Leu Arg Ala Gly Glu Glu Ile Ser Ile Gln Val Ser
                165                 170                 175

Asn Pro Ser Leu Leu Asp Pro Asp Gln Asp Ala Thr Tyr Phe Gly Ala
            180                 185                 190

Phe Lys Val Gln Asp Ile Asp
        195

<210> SEQ ID NO 225
<211> LENGTH: 114
<212> TYPE: PRT
<213> ORGANISM: Rattus sp.

<400> SEQUENCE: 225

Pro Met Phe Ile Val Asn Thr Asn Val Pro Arg Ala Ser Val Pro Glu
```

```
                1               5                  10                 15
Gly Phe Leu Ser Glu Leu Thr Gln Gln Leu Ala Gln Ala Thr Gly Lys
                20                 25                 30

Pro Ala Gln Tyr Ile Ala Val His Val Val Pro Asp Gln Leu Met Thr
            35                 40                 45

Phe Ser Gly Thr Ser Asp Pro Cys Ala Leu Cys Ser Leu His Ser Ile
        50                 55                 60

Gly Lys Ile Gly Gly Ala Gln Asn Arg Asn Tyr Ser Lys Leu Leu Cys
65                  70                 75                  80

Gly Leu Leu Ser Asp Arg Leu His Ile Ser Pro Asp Arg Val Tyr Ile
                85                 90                 95

Asn Tyr Tyr Asp Met Asn Ala Ala Asn Val Gly Trp Asn Gly Ser Thr
                100                105                110

Phe Ala

<210> SEQ ID NO 226
<211> LENGTH: 114
<212> TYPE: PRT
<213> ORGANISM: Mus musculus

<400> SEQUENCE: 226

Pro Met Phe Ile Val Asn Thr Asn Val Pro Arg Ala Ser Val Pro Glu
1               5                  10                 15

Gly Phe Leu Ser Glu Leu Thr Gln Gln Leu Ala Gln Ala Thr Gly Lys
                20                 25                 30

Pro Ala Gln Tyr Ile Ala Val His Val Val Pro Asp Gln Leu Met Thr
            35                 40                 45

Phe Ser Gly Thr Asn Asp Pro Cys Ala Leu Cys Ser Leu His Ser Ile
        50                 55                 60

Gly Lys Ile Gly Gly Ala Gln Asn Arg Asn Tyr Ser Lys Leu Leu Cys
65                  70                 75                  80

Gly Leu Leu Ser Asp Arg Leu His Ile Ser Pro Asp Arg Val Tyr Ile
                85                 90                 95

Asn Tyr Tyr Asp Met Asn Ala Ala Asn Val Gly Trp Asn Gly Ser Thr
                100                105                110

Phe Ala

<210> SEQ ID NO 227
<211> LENGTH: 114
<212> TYPE: PRT
<213> ORGANISM: Homo sapiens

<400> SEQUENCE: 227

Pro Met Phe Ile Val Asn Thr Asn Val Pro Arg Ala Ser Val Pro Asp
1               5                  10                 15

Gly Phe Leu Ser Glu Leu Thr Gln Gln Leu Ala Gln Ala Thr Gly Lys
                20                 25                 30

Pro Pro Gln Tyr Ile Ala Val His Val Val Pro Asp Gln Leu Met Ala
            35                 40                 45

Phe Gly Gly Ser Ser Glu Pro Cys Ala Leu Cys Ser Leu His Ser Ile
        50                 55                 60

Gly Lys Ile Gly Gly Ala Gln Asn Arg Ser Tyr Ser Lys Leu Leu Cys
65                  70                 75                  80

Gly Leu Leu Ala Glu Arg Leu Arg Ile Ser Pro Asp Arg Val Tyr Ile
                85                 90                 95
```

```
Asn Tyr Tyr Asp Met Asn Ala Ala Asn Val Gly Trp Asn Asn Ser Thr
                100                 105                 110
Phe Ala

<210> SEQ ID NO 228
<211> LENGTH: 155
<212> TYPE: PRT
<213> ORGANISM: Homo sapiens

<400> SEQUENCE: 228

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
                100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 229
<211> LENGTH: 158
<212> TYPE: PRT
<213> ORGANISM: Mus musculus

<400> SEQUENCE: 229

Met Ser Pro Gly Arg Ala Ser Ser Val Ser Leu Met Leu Leu Leu Leu
1               5                   10                  15

Leu Ser Leu Ala Ala Thr Val Lys Ala Ala Ile Ile Pro Gln Ser Ser
                20                  25                  30

Ser Ala Cys Pro Asn Thr Glu Ala Lys Asp Phe Leu Gln Asn Val Lys
            35                  40                  45

Val Asn Leu Lys Val Phe Asn Ser Leu Gly Ala Lys Val Ser Ser Arg
    50                  55                  60

Arg Pro Ser Asp Tyr Leu Asn Arg Ser Thr Ser Pro Trp Thr Leu His
65                  70                  75                  80

Arg Asn Glu Asp Pro Asp Arg Tyr Pro Ser Val Ile Trp Glu Ala Gln
                85                  90                  95

Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
    115                 120                 125

Pro Glu Ser Cys Pro Phe Thr Phe Arg Val Glu Lys Met Leu Val Gly
130                 135                 140

Val Gly Cys Thr Cys Val Ala Ser Ile Val Arg Gln Ala Ala
```

```
                145                 150                 155

<210> SEQ ID NO 230
<211> LENGTH: 132
<212> TYPE: PRT
<213> ORGANISM: Homo sapiens

<400> SEQUENCE: 230

Met Ala Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130

<210> SEQ ID NO 231
<211> LENGTH: 112
<212> TYPE: PRT
<213> ORGANISM: Homo sapiens

<400> SEQUENCE: 231

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

<210> SEQ ID NO 232
<211> LENGTH: 111
<212> TYPE: PRT
<213> ORGANISM: Mus musculus

<400> SEQUENCE: 232

Gly Pro Val Pro Arg Ser Val Ser Leu Pro Leu Thr Leu Lys Glu Leu
1               5                   10                  15

Ile Glu Glu Leu Ser Asn Ile Thr Gln Asp Gln Thr Pro Leu Cys Asn
            20                  25                  30
```

```
Gly Ser Met Val Trp Ser Val Asp Leu Ala Ala Gly Gly Phe Cys Val
            35                  40                  45

Ala Leu Asp Ser Leu Thr Asn Ile Ser Asn Cys Asn Ala Ile Tyr Arg
 50                  55                  60

Thr Gln Arg Ile Leu His Gly Leu Cys Asn Arg Lys Ala Pro Thr Thr
 65                  70                  75                  80

Val Ser Ser Leu Pro Asp Thr Lys Ile Glu Val Ala His Phe Ile Thr
                 85                  90                  95

Lys Leu Leu Ser Tyr Thr Lys Gln Leu Phe Arg His Gly Pro Phe
                100                 105                 110

<210> SEQ ID NO 233
<211> LENGTH: 134
<212> TYPE: PRT
<213> ORGANISM: Homo sapiens

<400> SEQUENCE: 233

Met Arg Met Leu Leu His Leu Ser Leu Leu Ala Leu Gly Ala Ala Tyr
 1               5                  10                  15

Val Tyr Ala Ile Pro Thr Glu Ile Pro Thr Ser Ala Leu Val Lys Glu
             20                  25                  30

Thr Leu Ala Leu Leu Ser Thr His Arg Thr Leu Leu Ile Ala Asn Glu
         35                  40                  45

Thr Leu Arg Ile Pro Val Pro Val His Lys Asn His Gln Leu Cys Thr
     50                  55                  60

Glu Glu Ile Phe Gln Gly Ile Gly Thr Leu Glu Ser Gln Thr Val Gln
 65                  70                  75                  80

Gly Gly Thr Val Glu Arg Leu Phe Lys Asn Leu Ser Leu Ile Lys Lys
                 85                  90                  95

Tyr Ile Asp Gly Gln Lys Lys Lys Cys Gly Glu Glu Arg Arg Arg Val
                100                 105                 110

Asn Gln Phe Leu Asp Tyr Leu Gln Glu Phe Leu Gly Val Met Asn Thr
            115                 120                 125

Glu Trp Ile Ile Glu Ser
        130

<210> SEQ ID NO 234
<211> LENGTH: 115
<212> TYPE: PRT
<213> ORGANISM: Homo sapiens

<400> SEQUENCE: 234

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
             20                  25                  30

Ile Pro Val Pro Val His Lys Asn His Gln Leu Cys Thr Glu Glu Ile
         35                  40                  45

Phe Gln Gly Ile Gly Thr Leu Glu Ser Gln Thr Val Gln Gly Gly Thr
     50                  55                  60

Val Glu Arg Leu Phe Lys Asn Leu Ser Leu Ile Lys Lys Tyr Ile Asp
 65                  70                  75                  80

Gly Gln Lys Lys Lys Cys Gly Glu Glu Arg Arg Arg Val Asn Gln Phe
                 85                  90                  95

Leu Asp Tyr Leu Gln Glu Phe Leu Gly Val Met Asn Thr Glu Trp Ile
                100                 105                 110
```

Ile Glu Ser
        115

<210> SEQ ID NO 235
<211> LENGTH: 113
<212> TYPE: PRT
<213> ORGANISM: Mus musculus

<400> SEQUENCE: 235

Met Glu Ile Pro Met Ser Thr Val Val Lys Glu Thr Leu Thr Gln Leu
1               5                   10                  15

Ser Ala His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
        35                  40                  45

Gly Leu Asp Ile Leu Lys Asn Gln Thr Val Arg Gly Thr Val Glu
    50                  55                  60

Met Leu Phe Gln Asn Leu Ser Leu Ile Lys Lys Tyr Ile Asp Arg Gln
65                  70                  75                  80

Lys Glu Lys Cys Gly Glu Glu Arg Arg Arg Thr Arg Gln Phe Leu Asp
                85                  90                  95

Tyr Leu Gln Glu Phe Leu Gly Val Met Ser Thr Glu Trp Ala Met Glu
            100                 105                 110

Gly

<210> SEQ ID NO 236
<211> LENGTH: 111
<212> TYPE: PRT
<213> ORGANISM: Homo sapiens

<400> SEQUENCE: 236

Ser Asp Gly Gly Ala Gln Asp Cys Cys Leu Lys Tyr Ser Gln Arg Lys
1               5                   10                  15

Ile Pro Ala Lys Val Val Arg Ser Tyr Arg Lys Gln Glu Pro Ser Leu
            20                  25                  30

Gly Cys Ser Ile Pro Ala Ile Leu Phe Leu Pro Arg Lys Arg Ser Gln
        35                  40                  45

Ala Glu Leu Cys Ala Asp Pro Lys Glu Leu Trp Val Gln Gln Leu Met
    50                  55                  60

Gln His Leu Asp Lys Thr Pro Ser Pro Gln Lys Pro Ala Gln Gly Cys
65                  70                  75                  80

Arg Lys Asp Arg Gly Ala Ser Lys Thr Gly Lys Lys Gly Lys Gly Ser
                85                  90                  95

Lys Gly Cys Lys Arg Thr Glu Arg Ser Gln Thr Pro Lys Gly Pro
            100                 105                 110

<210> SEQ ID NO 237
<211> LENGTH: 110
<212> TYPE: PRT
<213> ORGANISM: Mus musculus

<400> SEQUENCE: 237

Ser Asp Gly Gly Gly Gln Asp Cys Cys Leu Lys Tyr Ser Gln Lys Lys
1               5                   10                  15

Ile Pro Tyr Ser Ile Val Arg Gly Tyr Arg Lys Gln Glu Pro Ser Leu
            20                  25                  30

Gly Cys Pro Ile Pro Ala Ile Leu Phe Ser Pro Arg Lys His Ser Lys

```
                35                  40                  45
Pro Glu Leu Cys Ala Asn Pro Glu Gly Trp Val Gln Asn Leu Met
 50                  55                  60

Arg Arg Leu Asp Gln Pro Pro Ala Pro Gly Lys Gln Ser Pro Gly Cys
 65                  70                  75                  80

Arg Lys Asn Arg Gly Thr Ser Lys Ser Gly Lys Gly Lys Gly Ser
                 85                  90                  95

Lys Gly Cys Lys Arg Thr Glu Gln Thr Gln Pro Ser Arg Gly
            100                 105                 110

<210> SEQ ID NO 238
<211> LENGTH: 74
<212> TYPE: PRT
<213> ORGANISM: Homo sapiens

<400> SEQUENCE: 238

Asp Gly Lys Pro Val Ser Leu Ser Tyr Arg Cys Pro Cys Arg Phe Phe
  1               5                  10                  15

Glu Ser His Val Ala Arg Ala Asn Val Lys His Leu Lys Ile Leu Asn
                 20                  25                  30

Thr Pro Asn Cys Ala Leu Gln Ile Val Ala Arg Leu Lys Asn Asn Asn
             35                  40                  45

Arg Gln Val Cys Ile Asp Pro Lys Leu Lys Trp Ile Gln Glu Tyr Leu
 50                  55                  60

Glu Lys Ala Leu Asn Lys Arg Phe Lys Met
 65                  70

<210> SEQ ID NO 239
<211> LENGTH: 70
<212> TYPE: PRT
<213> ORGANISM: Mus musculus

<400> SEQUENCE: 239

Asp Gly Lys Pro Val Ser Leu Ser Tyr Arg Cys Pro Cys Arg Phe Phe
  1               5                  10                  15

Glu Ser His Ile Ala Arg Ala Asn Val Lys His Leu Lys Ile Leu Asn
                 20                  25                  30

Thr Pro Asn Cys Ala Leu Gln Ile Val Ala Arg Leu Lys Asn Asn Asn
             35                  40                  45

Arg Gln Val Cys Ile Asp Pro Lys Leu Lys Trp Ile Gln Glu Tyr Leu
 50                  55                  60

Glu Lys Ala Leu Asn Lys
 65                  70

<210> SEQ ID NO 240
<211> LENGTH: 109
<212> TYPE: PRT
<213> ORGANISM: Homo sapiens

<400> SEQUENCE: 240

Met Lys Phe Ile Ser Thr Ser Leu Leu Leu Met Leu Leu Val Ser Ser
  1               5                  10                  15

Leu Ser Pro Val Gln Gly Val Leu Glu Val Tyr Tyr Thr Ser Leu Arg
                 20                  25                  30

Cys Arg Cys Val Gln Glu Ser Ser Val Phe Ile Pro Arg Arg Phe Ile
             35                  40                  45

Asp Arg Ile Gln Ile Leu Pro Arg Gly Asn Gly Cys Pro Arg Lys Glu
 50                  55                  60
```

```
Ile Ile Val Trp Lys Lys Asn Lys Ser Ile Val Cys Val Asp Pro Gln
 65                  70                  75                  80

Ala Glu Trp Ile Gln Arg Met Met Glu Val Leu Arg Lys Arg Ser Ser
                 85                  90                  95

Ser Thr Leu Pro Val Pro Val Phe Lys Arg Lys Ile Pro
            100                 105

<210> SEQ ID NO 241
<211> LENGTH: 109
<212> TYPE: PRT
<213> ORGANISM: Mus musculus

<400> SEQUENCE: 241

Met Arg Leu Ser Thr Ala Thr Leu Leu Leu Leu Ala Ser Cys Leu
 1               5                  10                  15

Ser Pro Gly His Gly Ile Leu Glu Ala His Tyr Thr Asn Leu Lys Cys
                 20                  25                  30

Arg Cys Ser Gly Val Ile Ser Thr Val Val Gly Leu Asn Ile Ile Asp
             35                  40                  45

Arg Ile Gln Val Thr Pro Pro Gly Asn Gly Cys Pro Lys Thr Glu Val
 50                  55                  60

Val Ile Trp Thr Lys Met Lys Lys Val Ile Cys Val Asn Pro Arg Ala
 65                  70                  75                  80

Lys Trp Leu Gln Arg Leu Leu Arg His Val Gln Ser Lys Ser Leu Ser
                 85                  90                  95

Ser Thr Pro Gln Ala Pro Val Ser Lys Arg Arg Ala Ala
            100                 105

<210> SEQ ID NO 242
<211> LENGTH: 97
<212> TYPE: PRT
<213> ORGANISM: Homo sapiens

<400> SEQUENCE: 242

Met Lys Val Ser Ala Ala Leu Leu Trp Leu Leu Leu Ile Ala Ala Ala
 1               5                  10                  15

Phe Ser Pro Gln Gly Leu Ala Gly Pro Ala Ser Val Pro Thr Thr Cys
                 20                  25                  30

Cys Phe Asn Leu Ala Asn Arg Lys Ile Pro Leu Gln Arg Leu Glu Ser
             35                  40                  45

Tyr Arg Arg Ile Thr Ser Gly Lys Cys Pro Gln Lys Ala Val Ile Phe
 50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                 85                  90                  95

Pro

<210> SEQ ID NO 243
<211> LENGTH: 119
<212> TYPE: PRT
<213> ORGANISM: Homo sapiens

<400> SEQUENCE: 243

Met Ala Gly Leu Met Thr Ile Val Thr Ser Leu Leu Phe Leu Gly Val
 1               5                  10                  15

Cys Ala His His Ile Ile Pro Thr Gly Ser Val Val Ile Pro Ser Pro
```

```
                20                  25                  30

Cys Cys Met Phe Phe Val Ser Lys Arg Ile Pro Glu Asn Arg Val Val
        35                  40                  45

Ser Tyr Gln Leu Ser Ser Arg Ser Thr Cys Leu Lys Ala Gly Val Ile
 50                  55                  60

Phe Thr Thr Lys Lys Gly Gln Gln Phe Cys Gly Asp Pro Lys Gln Glu
 65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cys
            115

<210> SEQ ID NO 244
<211> LENGTH: 94
<212> TYPE: PRT
<213> ORGANISM: Homo sapiens

<400> SEQUENCE: 244

Met Met Gly Leu Ser Leu Ala Ser Ala Val Leu Leu Ala Ser Leu Leu
 1                   5                  10                  15

Ser Leu His Leu Gly Thr Ala Thr Arg Gly Ser Asp Ile Ser Lys Thr
                20                  25                  30

Cys Cys Phe Gln Tyr Ser His Lys Pro Leu Pro Trp Thr Trp Val Arg
            35                  40                  45

Ser Tyr Glu Phe Thr Ser Asn Ser Cys Ser Gln Arg Ala Val Ile Phe
 50                  55                  60

Thr Thr Lys Arg Gly Lys Lys Val Cys Thr His Pro Arg Lys Lys Trp
 65                  70                  75                  80

Val Gln Lys Tyr Ile Ser Leu Leu Lys Thr Pro Lys Gln Leu
                85                  90

<210> SEQ ID NO 245
<211> LENGTH: 97
<212> TYPE: PRT
<213> ORGANISM: Mus musculus

<400> SEQUENCE: 245

Met Gln Ser Ser Thr Ala Leu Leu Phe Leu Leu Thr Val Thr Ser
 1                   5                  10                  15

Phe Thr Ser Gln Val Leu Ala His Pro Gly Ser Ile Pro Thr Ser Cys
                20                  25                  30

Cys Phe Ile Met Thr Ser Lys Lys Ile Pro Asn Thr Leu Leu Lys Ser
            35                  40                  45

Tyr Lys Arg Ile Thr Asn Asn Arg Cys Thr Leu Lys Ala Ile Val Phe
 50                  55                  60

Lys Thr Arg Leu Gly Lys Glu Ile Cys Ala Asp Pro Lys Lys Lys Trp
 65                  70                  75                  80

Val Gln Asp Ala Thr Lys His Leu Asp Gln Lys Leu Gln Thr Pro Lys
                85                  90                  95

Pro

<210> SEQ ID NO 246
<211> LENGTH: 119
<212> TYPE: PRT
<213> ORGANISM: Mus musculus
```

```
<400> SEQUENCE: 246

Met Ala Gly Ser Ala Thr Ile Val Ala Gly Leu Leu Leu Val Ala
1               5                   10                  15

Cys Ala Cys Cys Ile Phe Pro Ile Asp Ser Val Thr Ile Pro Ser Ser
            20                  25                  30

Cys Cys Thr Ser Phe Ile Ser Lys Lys Ile Pro Glu Asn Arg Val Val
        35                  40                  45

Ser Tyr Gln Leu Ala Asn Gly Ser Ile Cys Pro Lys Ala Gly Val Ile
    50                  55                  60

Phe Ile Thr Lys Lys Gly His Lys Ile Cys Thr Asp Pro Lys Leu Leu
65                  70                  75                  80

Trp Val Gln Arg His Ile Gln Lys Leu Asp Ala Lys Lys Asn Gln Pro
                85                  90                  95

Ser Lys Gly Ala Lys Ala Val Arg Thr Lys Phe Ala Val Gln Arg Arg
            100                 105                 110

Arg Gly Asn Ser Thr Glu Val
            115

<210> SEQ ID NO 247
<211> LENGTH: 553
<212> TYPE: PRT
<213> ORGANISM: Homo sapiens

<400> SEQUENCE: 247

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240
```

```
Leu His Thr Val Asp Pro Gly Ser Ala Lys Gln Arg Pro Pro Arg Ser
            245                 250                 255

Thr Cys Gln Ser Phe Glu Pro Glu Thr Pro Val Val Lys Asp Ser
        260                 265                 270

Thr Ile Gly Gly Ser Pro Gln Pro Arg Pro Ser Val Gly Ala Phe Asn
            275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
                340                 345                 350

Ser Ala Lys Gly Gln Gln Pro Ala Asp Val Thr Gly Thr Ala Leu Pro
            355                 360                 365

Arg Val Gly Pro Val Arg Pro Thr Gly Gln Asp Trp Asn His Thr Pro
370                 375                 380

Gln Lys Thr Asp His Pro Ser Ala Leu Leu Arg Asp Pro Pro Glu Pro
385                 390                 395                 400

Gly Ser Pro Arg Ile Ser Ser Pro Arg Pro Gln Gly Leu Ser Asn Pro
                405                 410                 415

Ser Thr Leu Ser Ala Gln Pro Gln Leu Ser Arg Ser His Ser Ser Gly
                420                 425                 430

Ser Val Leu Pro Leu Gly Glu Leu Glu Gly Arg Arg Ser Thr Arg Asp
            435                 440                 445

Arg Arg Ser Pro Ala Glu Pro Glu Gly Gly Pro Ala Ser Glu Gly Ala
            450                 455                 460

Ala Arg Pro Leu Pro Arg Phe Asn Ser Val Pro Leu Thr Asp Thr His
465                 470                 475                 480

Glu Arg Gln Ser Glu Gly Ser Ser Ser Pro Gln Leu Gln Glu Ser Val
                485                 490                 495

Phe His Leu Leu Val Pro Ser Val Ile Leu Val Leu Leu Ala Val Gly
                500                 505                 510

Gly Leu Leu Phe Tyr Arg Trp Arg Arg Ser His Gln Glu Pro Gln
            515                 520                 525

Arg Ala Asp Ser Pro Leu Glu Gln Pro Glu Gly Ser Pro Leu Thr Gln
    530                 535                 540

Asp Asp Arg Gln Val Glu Leu Pro Val
545                 550

<210> SEQ ID NO 248
<211> LENGTH: 552
<212> TYPE: PRT
<213> ORGANISM: Mus musculus

<400> SEQUENCE: 248

Met Thr Ala Arg Gly Ala Ala Gly Arg Cys Pro Ser Ser Thr Trp Leu
1               5                   10                  15

Gly Ser Arg Leu Leu Leu Val Cys Leu Leu Met Ser Arg Ser Ile Ala
            20                  25                  30

Lys Glu Val Ser Glu His Cys Ser His Met Ile Gly Asn Gly His Leu
        35                  40                  45

Lys Val Leu Gln Gln Leu Ile Asp Ser Gln Met Glu Thr Ser Cys Gln
```

-continued

```
            50                  55                  60
Ile Ala Phe Glu Phe Val Asp Gln Glu Gln Leu Asp Asp Pro Val Cys
 65                  70                  75                  80

Tyr Leu Lys Lys Ala Phe Phe Leu Val Gln Asp Ile Ile Asp Glu Thr
                     85                  90                  95

Met Arg Phe Lys Asp Asn Thr Pro Asn Ala Asn Ala Thr Glu Arg Leu
                    100                 105                 110

Gln Glu Leu Ser Asn Asn Leu Asn Ser Cys Phe Thr Lys Asp Tyr Glu
                115                 120                 125

Glu Gln Asn Lys Ala Cys Val Arg Thr Phe His Glu Thr Pro Leu Gln
            130                 135                 140

Leu Leu Glu Lys Ile Lys Asn Phe Phe Asn Glu Thr Lys Asn Leu Leu
145                 150                 155                 160

Glu Lys Asp Trp Asn Ile Phe Thr Lys Asn Cys Asn Asn Ser Phe Ala
                    165                 170                 175

Lys Cys Ser Ser Arg Asp Val Val Thr Lys Pro Asp Cys Asn Cys Leu
                180                 185                 190

Tyr Pro Lys Ala Thr Pro Ser Ser Asp Pro Ala Ser Ala Ser Pro His
            195                 200                 205

Gln Pro Pro Ala Pro Ser Met Ala Pro Leu Ala Gly Leu Ala Trp Asp
        210                 215                 220

Asp Ser Gln Arg Thr Glu Gly Ser Ser Leu Leu Pro Ser Glu Leu Pro
225                 230                 235                 240

Leu Arg Ile Glu Asp Pro Gly Ser Ala Lys Gln Arg Pro Pro Arg Ser
                    245                 250                 255

Thr Cys Gln Thr Leu Glu Ser Thr Glu Gln Pro Asn His Gly Asp Arg
                260                 265                 270

Leu Thr Glu Asp Ser Gln Pro His Pro Ser Ala Gly Gly Pro Val Pro
            275                 280                 285

Gly Val Glu Asp Ile Leu Glu Ser Ser Leu Gly Thr Asn Trp Val Leu
        290                 295                 300

Glu Glu Ala Ser Gly Glu Ala Ser Glu Gly Phe Leu Thr Gln Glu Ala
305                 310                 315                 320

Lys Phe Ser Pro Ser Thr Pro Val Gly Gly Ser Ile Gln Ala Glu Thr
                    325                 330                 335

Asp Arg Pro Arg Ala Leu Ser Ala Ser Pro Phe Pro Lys Ser Thr Glu
                340                 345                 350

Asp Gln Lys Pro Val Asp Ile Thr Asp Arg Pro Leu Thr Glu Val Asn
            355                 360                 365

Pro Met Arg Pro Ile Gly Gln Thr Gln Asn Asn Thr Pro Glu Lys Thr
        370                 375                 380

Asp Gly Thr Ser Thr Leu Arg Glu Asp His Gln Glu Pro Gly Ser Pro
385                 390                 395                 400

His Ile Ala Thr Pro Asn Pro Gln Arg Val Ser Asn Ser Ala Thr Pro
                    405                 410                 415

Val Ala Gln Leu Leu Leu Pro Lys Ser His Ser Trp Gly Ile Val Leu
                420                 425                 430

Pro Leu Gly Glu Leu Glu Gly Lys Arg Ser Thr Arg Asp Arg Arg Ser
            435                 440                 445

Pro Ala Glu Leu Glu Gly Gly Ser Ala Ser Glu Gly Ala Ala Arg Pro
        450                 455                 460

Val Ala Arg Phe Asn Ser Ile Pro Leu Thr Asp Thr Gly His Val Glu
465                 470                 475                 480
```

-continued

```
Gln His Glu Gly Ser Ser Asp Pro Gln Ile Pro Glu Ser Val Phe His
                485                 490                 495
Leu Leu Val Pro Gly Ile Ile Leu Val Leu Leu Thr Val Gly Gly Leu
            500                 505                 510
Leu Phe Tyr Lys Trp Lys Trp Arg Ser His Arg Asp Pro Gln Thr Leu
            515                 520                 525
Asp Ser Ser Val Gly Arg Pro Glu Asp Ser Ser Leu Thr Gln Asp Glu
            530                 535                 540
Asp Arg Gln Val Glu Leu Pro Val
545                 550

<210> SEQ ID NO 249
<211> LENGTH: 108
<212> TYPE: PRT
<213> ORGANISM: Homo sapiens

<400> SEQUENCE: 249

Met Lys Ala Leu Cys Leu Leu Leu Pro Val Gly Leu Leu Val
1               5                   10                  15
Ser Ser Lys Thr Leu Cys Ser Met Glu Glu Ala Ile Asn Glu Arg Ile
            20                  25                  30
Gln Glu Val Ala Gly Ser Leu Ile Phe Arg Ala Ile Ser Ser Ile Gly
        35                  40                  45
Leu Glu Cys Gln Ser Val Thr Ser Arg Gly Asp Leu Ala Thr Cys Pro
    50                  55                  60
Arg Gly Phe Ala Val Thr Gly Cys Thr Cys Gly Ser Ala Cys Gly Ser
65                  70                  75                  80
Trp Asp Val Arg Ala Glu Thr Thr Cys His Cys Gln Cys Ala Gly Met
                85                  90                  95
Asp Trp Thr Gly Ala Arg Cys Cys Arg Val Gln Pro
            100                 105

<210> SEQ ID NO 250
<211> LENGTH: 114
<212> TYPE: PRT
<213> ORGANISM: Mus musculus

<400> SEQUENCE: 250

Met Lys Asn Leu Ser Phe Pro Leu Leu Phe Leu Phe Leu Val Pro
1               5                   10                  15
Glu Leu Leu Gly Ser Ser Met Pro Leu Cys Pro Ile Asp Glu Ala Ile
            20                  25                  30
Asp Lys Lys Ile Lys Gln Asp Phe Asn Ser Leu Phe Pro Asn Ala Ile
            35                  40                  45
Lys Asn Ile Gly Leu Asn Cys Trp Thr Val Ser Ser Arg Gly Lys Leu
    50                  55                  60
Ala Ser Cys Pro Glu Gly Thr Ala Val Leu Ser Cys Ser Cys Gly Ser
65                  70                  75                  80
Ala Cys Gly Ser Trp Asp Ile Arg Glu Glu Lys Val Cys His Cys Gln
                85                  90                  95
Cys Ala Arg Ile Asp Trp Thr Ala Ala Arg Cys Cys Lys Leu Gln Val
            100                 105                 110
Ala Ser

<210> SEQ ID NO 251
<211> LENGTH: 174
```

```
<212> TYPE: PRT
<213> ORGANISM: Homo sapiens

<400> SEQUENCE: 251

Gln Asp Gln Gly Gly Leu Val Thr Glu Thr Ala Asp Pro Gly Ala Gln
1               5                   10                  15

Ala Gln Gln Gly Leu Gly Phe Gln Lys Leu Pro Glu Glu Pro Glu
            20                  25                  30

Thr Asp Leu Ser Pro Gly Leu Pro Ala Ala His Leu Ile Gly Ala Pro
        35                  40                  45

Leu Lys Gly Gln Gly Leu Gly Trp Glu Thr Thr Lys Glu Gln Ala Phe
50                  55                  60

Leu Thr Ser Gly Thr Gln Phe Ser Asp Ala Glu Gly Leu Ala Leu Pro
65                  70                  75                  80

Gln Asp Gly Leu Tyr Tyr Leu Tyr Cys Leu Val Gly Tyr Arg Gly Arg
                85                  90                  95

Ala Pro Pro Gly Gly Asp Pro Gln Gly Arg Ser Val Thr Leu Arg
            100                 105                 110

Ser Ser Leu Tyr Arg Ala Gly Gly Ala Tyr Gly Pro Gly Thr Pro Glu
            115                 120                 125

Leu Leu Leu Glu Gly Ala Glu Thr Val Thr Pro Val Leu Asp Pro Ala
    130                 135                 140

Arg Arg Gln Gly Tyr Gly Pro Leu Trp Tyr Thr Ser Val Gly Phe Gly
145                 150                 155                 160

Gly Leu Val Gln Leu Arg Arg Gly Glu Arg Val Tyr Val Asn
                165                 170

<210> SEQ ID NO 252
<211> LENGTH: 258
<212> TYPE: PRT
<213> ORGANISM: Mus musculus

<400> SEQUENCE: 252

Gln Asp Gln Gly Arg Arg Val Glu Lys Ile Ile Gly Ser Gly Ala Gln
1               5                   10                  15

Ala Gln Lys Arg Leu Asp Asp Ser Lys Pro Ser Cys Ile Leu Pro Ser
            20                  25                  30

Pro Ser Ser Leu Ser Glu Thr Pro Asp Pro Arg Leu His Pro Gln Arg
        35                  40                  45

Ser Asn Ala Ser Arg Asn Leu Ala Ser Thr Ser Gln Gly Pro Val Ala
50                  55                  60

Gln Ser Ser Arg Glu Ala Ser Ala Trp Met Thr Ile Leu Ser Pro Ala
65                  70                  75                  80

Ala Asp Ser Thr Pro Asp Pro Gly Val Gln Gln Leu Pro Lys Gly Glu
                85                  90                  95

Pro Glu Thr Asp Leu Asn Pro Glu Leu Pro Ala Ala His Leu Ile Gly
            100                 105                 110

Ala Trp Met Ser Gly Gln Gly Leu Ser Trp Glu Ala Ser Gln Glu Glu
            115                 120                 125

Ala Phe Leu Arg Ser Gly Ala Gln Phe Ser Pro Thr His Gly Leu Ala
    130                 135                 140

Leu Pro Gln Asp Gly Val Tyr Tyr Leu Tyr Cys His Val Gly Tyr Arg
145                 150                 155                 160

Gly Arg Thr Pro Pro Ala Gly Arg Ser Arg Ala Arg Ser Leu Thr Leu
                165                 170                 175
```

-continued

```
Arg Ser Ala Leu Tyr Arg Ala Gly Gly Ala Tyr Gly Arg Gly Ser Pro
            180                 185                 190

Glu Leu Leu Glu Gly Ala Glu Thr Val Thr Pro Val Val Asp Pro
            195                 200                 205

Ile Gly Tyr Gly Ser Leu Trp Tyr Thr Ser Val Gly Phe Gly Gly Leu
            210                 215                 220

Ala Gln Leu Arg Ser Gly Glu Arg Val Tyr Val Asn Ile Ser His Pro
225                 230                 235                 240

Asp Met Val Asp Tyr Arg Arg Gly Lys Thr Phe Phe Gly Ala Val Met
                245                 250                 255

Val Gly

<210> SEQ ID NO 253
<211> LENGTH: 128
<212> TYPE: PRT
<213> ORGANISM: RNA-phage PP7

<400> SEQUENCE: 253

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

<210> SEQ ID NO 254
<211> LENGTH: 330
<212> TYPE: PRT
<213> ORGANISM: RNA-phage SP A1 protein

<400> SEQUENCE: 254

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
        35                  40                  45

Thr Val Ser Val Ala Gln Pro Ser Arg Asn Arg Lys Asn Phe Lys Val
    50                  55                  60

Gln Ile Lys Leu Gln Asn Pro Thr Ala Cys Thr Arg Asp Ala Cys Asp
65                  70                  75                  80

Pro Ser Val Thr Arg Ser Ala Phe Ala Asp Val Thr Leu Ser Phe Thr
                85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
```

-continued

```
                115                 120                 125
Pro Ala Tyr Trp Ala Ala Leu Leu Val Ala Ser Ser Gly Gly Gly Asp
    130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205

Gly Asn Thr Asn Trp Arg Asn Trp Asp Gln Arg Leu Ser Asp Tyr Asp
    210                 215                 220

Ile Ala Asn Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser Leu
                325                 330

<210> SEQ ID NO 255
<211> LENGTH: 132
<212> TYPE: PRT
<213> ORGANISM: QB 240

<400> SEQUENCE: 255

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 256
<211> LENGTH: 132
```

-continued

```
<212> TYPE: PRT
<213> ORGANISM: Qb 243

<400> SEQUENCE: 256

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 257
<211> LENGTH: 132
<212> TYPE: PRT
<213> ORGANISM: Qb 250

<400> SEQUENCE: 257

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 258
<211> LENGTH: 132
<212> TYPE: PRT
<213> ORGANISM: Qb 259

<400> SEQUENCE: 258

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
```

```
                  20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 259
<211> LENGTH: 132
<212> TYPE: PRT
<213> ORGANISM: Qb 251

<400> SEQUENCE: 259

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 260
<211> LENGTH: 20
<212> TYPE: DNA
<213> ORGANISM: PH19

<400> SEQUENCE: 260
taagtcctct gccacgtacc                                              20

<210> SEQ ID NO 261
<211> LENGTH: 20
<212> TYPE: DNA
<213> ORGANISM: PH20

<400> SEQUENCE: 261
tggaaaccac gctcacttcc                                              20
```

-continued

```
<210> SEQ ID NO 262
<211> LENGTH: 30
<212> TYPE: DNA
<213> ORGANISM: PH21

<400> SEQUENCE: 262
cgggatccgg gatgaagaac ctttcatttc                                          30

<210> SEQ ID NO 263
<211> LENGTH: 31
<212> TYPE: DNA
<213> ORGANISM: PH22

<400> SEQUENCE: 263
gcctctagag aggaagcgac ctgcagctta c                                        31

<210> SEQ ID NO 264
<211> LENGTH: 46
<212> TYPE: DNA
<213> ORGANISM: PH29

<400> SEQUENCE: 264
ctagcgggag ggggtggatg tggggacgac tacaaggatg acgaca                        46

<210> SEQ ID NO 265
<211> LENGTH: 46
<212> TYPE: DNA
<213> ORGANISM: PH30

<400> SEQUENCE: 265
agcttgtcgt catccttgta gtcgtcccca catccacccc ctcccg                        46

<210> SEQ ID NO 266
<211> LENGTH: 45
<212> TYPE: DNA
<213> ORGANISM: PH31

<400> SEQUENCE: 266
agcttactca cacatgccca ccgtgcccag cacctgaagc cgagg                         45

<210> SEQ ID NO 267
<211> LENGTH: 38
<212> TYPE: DNA
<213> ORGANISM: PH32

<400> SEQUENCE: 267
cggcttcagg tgctgggcac ggtgggcatg tgtgagta                                 38

<210> SEQ ID NO 268
<211> LENGTH: 37
<212> TYPE: DNA
<213> ORGANISM: PH35

<400> SEQUENCE: 268
ctagcgggag ggggtggatg tgggatcgaa ggtcgca                                  37

<210> SEQ ID NO 269
<211> LENGTH: 37
<212> TYPE: DNA
<213> ORGANISM: PH36

<400> SEQUENCE: 269
agcttgcgac cttcgatccc acatccaccc cctcccg                                  37
```

```
<210> SEQ ID NO 270
<211> LENGTH: 43
<212> TYPE: DNA
<213> ORGANISM: PH37

<400> SEQUENCE: 270
cgggatccag cagctgggct cgaggtgcta gctttgttta aac            43

<210> SEQ ID NO 271
<211> LENGTH: 55
<212> TYPE: DNA
<213> ORGANISM: PH38

<400> SEQUENCE: 271
gatcgtttaa acaaacaaag ctagcacctc gagcccagct gctggatccc ggtac    55

<210> SEQ ID NO 272
<211> LENGTH: 37
<212> TYPE: DNA
<213> ORGANISM: PH39

<400> SEQUENCE: 272
ctagcgggag ggggtggatg tggggacgat gacgaca                   37

<210> SEQ ID NO 273
<211> LENGTH: 37
<212> TYPE: DNA
<213> ORGANISM: PH40

<400> SEQUENCE: 273
agcttgtcgt catcgtcccc acatccaccc cctcccg                   37

<210> SEQ ID NO 274
<211> LENGTH: 30
<212> TYPE: DNA
<213> ORGANISM: PH41

<400> SEQUENCE: 274
catggagaca gacacactcc tgctatgggt                           30

<210> SEQ ID NO 275
<211> LENGTH: 39
<212> TYPE: DNA
<213> ORGANISM: PH42

<400> SEQUENCE: 275
gcagtaccca tagcaggagt gtgtctgtct ccatggtac                 39

<210> SEQ ID NO 276
<211> LENGTH: 37
<212> TYPE: DNA
<213> ORGANISM: PH43

<400> SEQUENCE: 276
actgctgctc tgggttccag gttccactgg tgacgcg                   37

<210> SEQ ID NO 277
<211> LENGTH: 36
<212> TYPE: DNA
<213> ORGANISM: PH44

<400> SEQUENCE: 277
gatccgcgtc accagtggaa cctggaaccc agagca                    36
```

<210> SEQ ID NO 278
<211> LENGTH: 40
<212> TYPE: DNA
<213> ORGANISM: SU7

<400> SEQUENCE: 278
agcttgcgga tccaggatat cggctcgagg ttctagagtg        40

<210> SEQ ID NO 279
<211> LENGTH: 40
<212> TYPE: DNA
<213> ORGANISM: SU8

<400> SEQUENCE: 279
ggcccactct agaacctcga gccgatatcc tggatccgca        40

<210> SEQ ID NO 280
<211> LENGTH: 107
<212> TYPE: PRT
<213> ORGANISM: Artificial Sequence
<220> FEATURE:
<223> OTHER INFORMATION: Resistin-C-Xa construct

<400> SEQUENCE: 280

Ser Ser Met Pro Leu Cys Pro Ile Asp Glu Ala Ile Asp Lys Lys Ile
1               5                   10                  15

Lys Gln Asp Phe Asn Ser Leu Phe Pro Asn Ala Ile Lys Asn Ile Gly
            20                  25                  30

Leu Asn Cys Trp Thr Val Ser Ser Arg Gly Lys Leu Ala Ser Cys Pro
        35                  40                  45

Glu Gly Thr Ala Val Leu Ser Cys Ser Cys Gly Ser Ala Cys Gly Ser
    50                  55                  60

Trp Asp Ile Arg Glu Glu Lys Val Cys His Cys Gln Cys Ala Arg Ile
65                  70                  75                  80

Asp Trp Thr Ala Ala Arg Cys Cys Lys Leu Gln Val Ala Ser Ser Leu
                85                  90                  95

Ala Gly Gly Gly Gly Cys Gly Ile Glu Gly Arg
            100                 105

<210> SEQ ID NO 281
<211> LENGTH: 107
<212> TYPE: PRT
<213> ORGANISM: Artificial Sequence
<220> FEATURE:
<223> OTHER INFORMATION: Resistin-C-EK construct

<400> SEQUENCE: 281

Ser Ser Met Pro Leu Cys Pro Ile Asp Glu Ala Ile Asp Lys Lys Ile
1               5                   10                  15

Lys Gln Asp Phe Asn Ser Leu Phe Pro Asn Ala Ile Lys Asn Ile Gly
            20                  25                  30

Leu Asn Cys Trp Thr Val Ser Ser Arg Gly Lys Leu Ala Ser Cys Pro
        35                  40                  45

Glu Gly Thr Ala Val Leu Ser Cys Ser Cys Gly Ser Ala Cys Gly Ser
    50                  55                  60

Trp Asp Ile Arg Glu Glu Lys Val Cys His Cys Gln Cys Ala Arg Ile
65                  70                  75                  80

Asp Trp Thr Ala Ala Arg Cys Cys Lys Leu Gln Val Ala Ser Ser Leu
                85                  90                  95

```
Ala Gly Gly Gly Gly Cys Gly Asp Asp Asp Asp
            100                 105
```

<210> SEQ ID NO 282
<211> LENGTH: 103
<212> TYPE: PRT
<213> ORGANISM: Artificial Sequence
<220> FEATURE:
<223> OTHER INFORMATION: Resistin-GCG construct

<400> SEQUENCE: 282

```
Ser Ser Met Pro Leu Cys Pro Ile Asp Glu Ala Ile Asp Lys Lys Ile
1               5                   10                  15

Lys Gln Asp Phe Asn Ser Leu Phe Pro Asn Ala Ile Lys Asn Ile Gly
            20                  25                  30

Leu Asn Cys Trp Thr Val Ser Ser Arg Gly Lys Leu Ala Ser Cys Pro
        35                  40                  45

Glu Gly Thr Ala Val Leu Ser Cys Ser Cys Gly Ser Ala Cys Gly Ser
    50                  55                  60

Trp Asp Ile Arg Glu Glu Lys Val Cys His Cys Gln Cys Ala Arg Ile
65                  70                  75                  80

Asp Trp Thr Ala Ala Arg Cys Cys Lys Leu Gln Val Ala Ser Ser Leu
                85                  90                  95

Ala Gly Gly Gly Gly Cys Gly
            100
```

<210> SEQ ID NO 283
<211> LENGTH: 10285
<212> TYPE: DNA
<213> ORGANISM: Artificial Sequence
<220> FEATURE:
<223> OTHER INFORMATION: pCep-Xa-Fc construct
<220> FEATURE:
<221> NAME/KEY: misc_feature
<222> LOCATION: (9872)..(9872)
<223> OTHER INFORMATION: n is a, c, g, or t

<400> SEQUENCE: 283

```
gccccgccgc cggacgaact aaacctgact acggcatctc tgcccttct tcgctggtac      60
gaggagcgct tttgttttgt attcggggca gtgcatgtaa tcccttcagt tggttggtac    120
aacttgccaa ctgggccctg ttccacatgt gacacggggg gggaccaaac acaaagggt     180
tctctgactg tagttgacat ccttataaat ggatgtgcac atttgccaac actgagtggc    240
tttcatcctg gagcagactt tgcatgctgt ggactgcaac acaacattgc ctttatgtgt    300
aactcttggc tgaagctctt acaccaatgc tggggacat gtacctccca ggggcccagg     360
aagactacgg gaggctacac caacgtcaat cagagggcc tgtgtagcta ccgataagcg     420
gaccctcaag agggcattag caatagtgtt tataaggccc ccttgttaac cctaaacggg    480
tagcatatgc ttcccgggta gtagtatata ctatccagac taaccctaat tcaatagcat    540
atgttaccca acgggaagca tatgctatcg aattagggtt agtaaaaggg tcctaaggaa    600
cagcgatatc tcccaccca tgagctgtca cggtttatt tacatgggt caggattcca      660
cgagggtagt gaaccatttt agtcacaagg gcagtggctg aagatcaagg agcgggcagt    720
gaactctcct gaatcttcgc ctgcttcttc attctccttc gtttagctaa tagaataact    780
gctgagttgt gaacagtaag gtgtatgtga ggtgctcgaa acaaggtttt caggtgacgc    840
ccccagaata aaatttggac gggggggttca gtggtggcat tgtgctatga caccaatata   900
```

-continued

| | |
|---|---|
| accctcacaa accccttggg caataaatac tagtgtagga atgaaacatt ctgaatatct | 960 |
| ttaacaatag aaatccatgg ggtggggaca agccgtaaag actggatgtc catctcacac | 1020 |
| gaatttatgg ctatgggcaa cacataatcc tagtgcaata tgatactggg gttattaaga | 1080 |
| tgtgtcccag gcagggacca agacaggtga accatgttgt tacactctat ttgtaacaag | 1140 |
| gggaaagaga gtggacgccg acagcagcgg actccactgg ttgtctctaa caccccgaa | 1200 |
| aattaaacgg ggctccacgc caatgggccc cataaacaaa gacaagtggc cactcttttt | 1260 |
| tttgaaattg tggagtgggg gcacgcgtca gcccccacac gccgccctgc ggttttggac | 1320 |
| tgtaaaataa gggtgtaata acttggctga ttgtaacccc gctaaccact gcggtcaaac | 1380 |
| cacttgccca caaaccact aatggcaccc cggggaatac ctgcataagt aggtgggcgg | 1440 |
| gccaagatag gggcgcgatt gctgcgatct ggaggacaaa ttacacacac ttgcgcctga | 1500 |
| gcgccaagca cagggttgtt ggtcctcata ttcacgaggt cgctgagagc acggtgggct | 1560 |
| aatgttgcca tgggtagcat atactaccca aatatctgga tagcatatgc tatcctaatc | 1620 |
| tatatctggg tagcataggc tatcctaatc tatatctggg tagcatatgc tatcctaatc | 1680 |
| tatatctggg tagtatatgc tatcctaatt tatatctggg tagcataggc tatcctaatc | 1740 |
| tatatctggg tagcatatgc tatcctaatc tatatctggg tagtatatgc tatcctaatc | 1800 |
| tgtatccggg tagcatatgc tatcctaata gagattaggg tagtatatgc tatcctaatt | 1860 |
| tatatctggg tagcatatac tacccaaata tctggatagc atatgctatc ctaatctata | 1920 |
| tctgggtagc atatgctatc ctaatctata tctgggtagc ataggctatc ctaatctata | 1980 |
| tctgggtagc atatgctatc ctaatctata tctgggtagt atatgctatc ctaatttata | 2040 |
| tctgggtagc ataggctatc ctaatctata tctgggtagc atatgctatc ctaatctata | 2100 |
| tctgggtagt atatgctatc ctaatctgta tccgggtagc atatgctatc ctcatgcata | 2160 |
| tacagtcagc atatgatacc cagtagtaga gtgggagtgc tatcctttgc atatgccgcc | 2220 |
| acctcccaag ggggcgtgaa ttttcgctgc ttgtcctttt cctgcatgct ggttgctccc | 2280 |
| attcttaggt gaatttaagg aggccaggct aaagccgtcg catgtctgat tgctcaccag | 2340 |
| gtaaatgtcg ctaatgtttt ccaacgcgag aaggtgttga gcgcggagct gagtgacgtg | 2400 |
| acaacatggg tatgcccaat tgccccatgt tgggaggacg aaaatggtga caagacagat | 2460 |
| ggccagaaat acaccaacag cacgcatgat gtctactggg gatttattct ttagtgcggg | 2520 |
| ggaatacacg gcttttaata cgattgaggg cgtctcctaa caagttacat cactcctgcc | 2580 |
| cttcctcacc ctcatctcca tcacctcctt catctccgtc atctccgtca tcaccctccg | 2640 |
| cggcagcccc ttccaccata ggtggaaacc agggaggcaa atctactcca tcgtcaaagc | 2700 |
| tgcacacagt caccctgata ttgcaggtag gagcgggctt tgtcataaca aggtccttaa | 2760 |
| tcgcatcctt caaaacctca gcaaatatat gagtttgtaa aaagaccatg aaataacaga | 2820 |
| caatggactc cctagcgggg ccaggttgtg ggccgggtcc aggggccatt ccaaagggga | 2880 |
| gacgactcaa tggtgtaaga cgacattgtg gaatagcaag ggcagttcct cgccttaggt | 2940 |
| tgtaaaggga ggtcttacta cctccatata cgaacacacc ggcgacccaa gttccttcgt | 3000 |
| cggtagtcct ttctacgtga ctcctagcca ggagagctct taaaccttct gcaatgttct | 3060 |
| caaatttcgg gttggaacct ccttgaccac gatgctttcc aaaccaccct ccttttttgc | 3120 |
| gcctgcctcc atcaccctga ccccggggtc cagtgcttgg gccttctcct gggtcatctg | 3180 |
| cggggccctg ctctatcgct cccgggggca cgtcaggctc accatctggg ccaccttctt | 3240 |
| ggtggtattc aaaataatcg gcttcccta cagggtggaa aaatggcctt ctacctggag | 3300 |

```
ggggcctgcg cggtggagac ccggatgatg atgactgact actgggactc ctgggcctct   3360
tttctccacg tccacgacct ctcccctgg ctctttcacg acttcccccc ctggctcttt     3420
cacgtcctct accccggcgg cctccactac ctcctcgacc ccggcctcca ctacctcctc   3480
gaccccggcc tccactgcct cctcgacccc ggcctccacc tcctgctcct gcccctcctg   3540
ctcctgcccc tcctcctgct cctgcccctc ctgcccctcc tgctcctgcc cctcctgccc   3600
ctcctgctcc tgcccctcct gccctcctg ctcctgcccc tcctgcccct cctcctgctc     3660
ctgcccctcc tgcccctcct cctgctcctg cccctcctgc cctcctgct cctgcccctc     3720
ctgcccctcc tgctcctgcc cctcctgccc ctcctgctcc tgcccctcct gctcctgccc   3780
ctcctgctcc tgcccctcct gctcctgccc ctcctgcccc tcctgcccct cctcctgctc   3840
ctgcccctcc tgctcctgcc cctcctgccc ctcctgcccc tcctgctcct gcccctcctc   3900
ctgctcctgc cctcctgcc cctcctgccc ctcctcctgc tcctgcccct cctgcccctc     3960
ctcctgctcc tgcccctcct cctgctcctg cccctcctgc cctcctgcc cctcctcctg     4020
ctcctgcccc tcctgcccct cctcctgctc ctgcccctcc tcctgctcct gcccctcctg   4080
cccctcctgc ccctcctcct gctcctgccc ctcctcctgc tcctgcccct cctgcccctc   4140
ctgcccctcc tgcccctcct cctgctcctg cccctcctcc tgctcctgcc cctcctgctc   4200
ctgcccctcc cgctcctgct cctgctcctg ttccaccgtg ggtcccttg cagccaatgc     4260
aacttggacg ttttttgggt ctccggacac catctctatg tcttggccct gatcctgagc   4320
cgccccgggc tcctggtctt ccgcctcctc gtcctcgtcc tcttccccgt cctcgtccat   4380
ggttatcacc ccctcttctt tgaggtccac tgccgccgga gccttctggt ccagatgtgt   4440
ctcccttctc tcctaggcca tttccaggtc ctgtacctgg cccctcgtca gacatgattc   4500
acactaaaag agatcaatag acatctttat tagacgacgc tcagtgaata cagggagtgc   4560
agactcctgc cccctccaac agccccccca ccctcatccc cttcatggtc gctgtcagac   4620
agatccaggt ctgaaaattc cccatcctcc gaaccatcct cgtcctcatc accaattact   4680
cgcagcccga aaactcccg ctgaacatcc tcaagatttg cgtcctgagc ctcaagccag   4740
gcctcaaatt cctcgtcccc cttttttgctg gacggtaggg atggggattc tcgggacccc   4800
tcctcttcct cttcaaggtc accagacaga gatgctactg gggcaacgga agaaaagctg   4860
ggtgcggcct gtgaggatca gcttatcgat gataagctgt caaacatgag aattcttgaa   4920
gacgaagggg cctcgtgata cgcctatttt tataggttaa tgtcatgata ataatggttt   4980
cttagacgtc aggtggcact tttcggggaa atgtgcgcgg aaccctatt tgtttatttt       5040
tctaaataca ttcaaatatg tatccgctca tgagacaata accctgataa atgcttcaat   5100
aatattgaaa aggaagagt atgagtattc aacatttccg tgtcgccctt attccctttt       5160
ttgcggcatt ttgccttcct gtttttgctc acccagaaac gctggtgaaa gtaaaagatg   5220
ctgaagatca gttgggtgca cgagtgggtt acatcgaact ggatctcaac agcggtaaga   5280
tccttgagag ttttcgcccc gaagaacgtt ttccaatgat gagcactttt aaagttctgc   5340
tatgtggcgc ggtattatcc cgtgttgacg ccgggcaaga gcaactcggt cgccgcatac   5400
actattctca gaatgacttg gttgagtact caccagtcac agaaaagcat cttacggatg   5460
gcatgacagt aagagaatta tgcagtgctg ccataaccat gagtgataac actgcggcca   5520
acttacttct gacaacgatc ggaggaccga aggagctaac cgcttttttg cacaacatgg   5580
gggatcatgt aactcgcctt gatcgttggg aaccggagct gaatgaagcc ataccaaacg   5640
```

```
acgagcgtga caccacgatg cctgcagcaa tggcaacaac gttgcgcaaa ctattaactg    5700
gcgaactact tactctagct tcccggcaac aattaataga ctggatggag gcggataaag    5760
ttgcaggacc acttctgcgc tcggcccttc cggctggctg gtttattgct gataaatctg    5820
gagccggtga gcgtgggtct cgcggtatca ttgcagcact ggggccagat ggtaagccct    5880
cccgtatcgt agttatctac acgacgggga gtcaggcaac tatggatgaa cgaaatagac    5940
agatcgctga gataggtgcc tcactgatta agcattggta actgtcagac caagtttact    6000
catatatact ttagattgat ttaaaacttc attttttaatt taaaaggatc taggtgaaga    6060
tcctttttga taatctcatg accaaaatcc cttaacgtga gttttcgttc cactgagcgt    6120
cagaccccgt agaaaagatc aaaggatctt cttgagatcc ttttttttctg cgcgtaatct    6180 gctgcttgca acaaaaaaa ccaccgctac cagcggtggt ttgtttgccg gatcaagagc    6240
taccaactct ttttccgaag gtaactggct tcagcagagc gcagatacca aatactgtcc    6300
ttctagtgta gccgtagtta ggccaccact tcaagaactc tgtagcaccg cctacatacc    6360
tcgctctgct aatcctgtta ccagtggctg ctgccagtgg cgataagtcg tgtcttaccg    6420
ggttggactc aagacgatag ttaccggata aggcgcagcg gtcgggctga acggggggtt    6480
cgtgcacaca gcccagcttg gagcgaacga cctacaccga actgagatac ctacagcgtg    6540
agctatgaga aagcgccacg cttcccgaag ggagaaaggc ggacaggtat ccggtaagcg    6600
gcagggtcgg aacaggagag cgcacgaggg agcttccagg gggaaacgcc tggtatcttt    6660
atagtcctgt cgggtttcgc cacctctgac ttgagcgtcg atttttgtga tgctcgtcag    6720
gggggcggag cctatggaaa aacgccagca acgcggcctt tttacggttc ctggccttttt    6780 gctgcgccgc gtgcggctgc tggagatggc ggacgcgatg gatatgttct gccaagggtt    6840
ggtttgcgca ttcacagttc tccgcaagaa ttgattggct ccaattcttg gagtggtgaa    6900
tccgttagcg aggccatcca gcctcgcgtc gaactagatg atccgctgtg gaatgtgtgt    6960
cagttagggt gtggaaagtc cccaggctcc ccagcaggca gaagtatgca aagcatgcat    7020
ctcaattagt cagcaaccag gtgtggaaag tccccaggct ccccagcagg cagaagtatg    7080
caaagcatgc atctcaatta gtcagcaacc atagtcccgc ccctaactcc gcccatcccg    7140
cccctaactc cgcccagttc cgcccattct ccgccccatg gctgactaat ttttttttatt    7200 tatgcagagg ccgaggccgc ctcggcctct gagctattcc agaagtagtg aggaggcttt    7260
tttggagggt gaccgccacg accggtgccg ccaccatccc ctgacccacg cccctgaccc    7320
ctcacaagga gacgaccttc catgaccgag tacaagccca cggtgcgcct cgccacccgc    7380
gacgacgtcc ccgggccgt acgcaccctc gccgccgcgt tcgccgacta ccccgccacg    7440
cgccacaccg tcgaccccga ccgccacatc gaacgcgtca ccgagctgca agaactcttc    7500
ctcacgcgcg tcgggctcga catcggcaag gtgtgggtcg cggacgacgg cgccgcggtg    7560
gcggtctgga ccacgccgga gagcgtcgaa gcggggggcg tgttcgccga gatcggcccg    7620
cgcatggccg agttgagcgg ttcccggctg gccgcgcagc aacagatgga aggcctcctg    7680
gcgccgcacc ggcccaagga gcccgcgtgg ttcctggcca ccgtcggcgt ctcgcccgac    7740
caccagggca agggtctggg cagcgccgtc gtgctccccg gagtggaggc ggccgagcgc    7800 gccgggggtgc ccgccttcct ggagacctcc gcgccccgca acctccccctt ctacgagcgg    7860 ctcggcttca ccgtcaccgc cgacgtcgag tgcccgaagg accgcgcgac ctggtgcatg    7920
acccgcaagc ccggtgcctg acgcccgccc cacgacccgc agcgcccgac cgaaaggagc    7980
gcacgacccg gtccgacggc ggcccacggg tcccagggg gtcgacctcg aaacttgttt    8040
```

-continued

```
attgcagctt ataatggtta caaataaagc aatagcatca caaatttcac aaataaagca      8100
ttttttttcac tgcattctag ttgtggtttg tccaaactca tcaatgtatc ttatcatgtc      8160
tggatcgatc cgaacccctt cctcgaccaa ttctcatgtt tgacagctta tcatcgcaga      8220
tccgggcaac gttgttgcat tgctgcaggc gcagaactgg taggtatgga agatctatac      8280
attgaatcaa tattggcaat tagccatatt agtcattggt tatatagcat aaatcaatat      8340
tggctattgg ccattgcata cgttgtatct atatcataat atgtacattt atattggctc      8400
atgtccaata tgaccgccat gttgacattg attattgact agttattaat agtaatcaat      8460
tacgggtca ttagttcata gcccatatat ggagttccgc gttacataac ttacggtaaa       8520
tggcccgcct ggctgaccgc ccaacgaccc ccgcccattg acgtcaataa tgacgtatgt      8580
tcccatagta acgccaatag ggactttcca ttgacgtcaa tgggtggagt atttacggta      8640
aactgcccac ttggcagtac atcaagtgta tcatatgcca gtccgcccc ctattgacgt       8700
caatgacggt aaatggcccg cctggcatta tgcccagtac atgaccttac gggactttcc      8760
tacttggcag tacatctacg tattagtcat cgctattacc atggtgatgc ggttttggca      8820
gtacaccaat gggcgtggat agcggtttga ctcacgggga tttccaagtc tccacccat      8880
tgacgtcaat gggagtttgt tttggcacca aaatcaacgg gactttccaa aatgtcgtaa      8940
taacccgcc ccgttgacgc aaatgggcgg taggcgtgta cggtgggagg tctatataag       9000
cagagctcgt ttagtgaacc gtcagatctc tagaagctgg gtaccgggat ccagcagctg      9060
ggctcgaggt gctagcggga gggggtggat gtgggatcga aggtcgcaag cttactcaca      9120
catgcccacc gtgcccagca cctgaagccg aggggcacc gtcagtcttc ctcttcccc        9180
caaaacccaa ggacaccctc atgatctccc ggacccctga ggtcacatgc gtggtggtgg      9240
acgtgagcca cgaagaccct gaggtcaagt tcaactggta cgtggacggc gtggaggtgc      9300
ataatgccaa gacaaagccg cgggaggagc agtacaacag cacgtaccgt gtggtcagcg      9360
tcctcaccgt cctgcaccag gactggctga atggcaagga gtacaagtgc aaggtctcca      9420
acaaagccct cccagcctcc atcgagaaaa ccatctccaa agccaaaggg cagccccgag      9480
aaccacaggt gtacaccctg cccccatccc gggatgagct gaccaagaac caggtcagcc      9540
tgacctgcct ggtcaaaggc ttctatccca gcgacatcgc cgtggagtgg gagagcaatg      9600
ggcagccgga gaacaactac aagaccacgc ctcccgtgtt ggactccgac ggctccttct      9660
tcctctacag caagctcacc gtggacaaga gcaggtggca gcaggggaac gtcttctcat      9720
gctccgtgat gcatgaggct ctgcacaacc actacacgca gaagagcctc tccctgtctc      9780
cgggtaaatg actcgaggcc cgaacaaaaa ctcatctcag aagaggatct gaatagcgcc      9840
gtcgaccatc atcatcatca tcattgagtt tnaacgatcc agacatgata agatacattg      9900
atgagtttgg acaaaccaca actagaatgc agtgaaaaaa atgctttatt tgtgaaattt      9960
gtgatgctat tgctttattt gtaaccatta taagctgcaa taaacaagtt aacaacaaca     10020
attgcattca ttttatgttt caggttcagg gggaggtggg gaggttttt aaagcaagta      10080
aaacctctac aaatgtggta tggctgatta tgatccggct gcctcgcgcg tttcggtgat     10140
gacggtgaaa acctctgaca catgcagctc ccggagacgg tcacagcttg tctgtaagcg     10200
gatgccggga gcagacaagc ccgtcagggc gcgtcagcgg tgttggcgg gtgtcgggc       10260
gcagccatga ccggtcgact ctaga                                           10285
```

<210> SEQ ID NO 284

```
<211> LENGTH: 19
<212> TYPE: DNA
<213> ORGANISM: Artificial Sequence
<220> FEATURE:
<223> OTHER INFORMATION: 5'LT oligonucleotide

<400> SEQUENCE: 284
cttggtgccg caggatcag                                                    19

<210> SEQ ID NO 285
<211> LENGTH: 19
<212> TYPE: DNA
<213> ORGANISM: Artificial Sequence
<220> FEATURE:
<223> OTHER INFORMATION: 3'LT oligonucleotide

<400> SEQUENCE: 285
cagatggctg tcaccccac                                                    19

<210> SEQ ID NO 286
<211> LENGTH: 37
<212> TYPE: DNA
<213> ORGANISM: Artificial Sequence
<220> FEATURE:
<223> OTHER INFORMATION: 5'LT long-NheI oligonucleotide

<400> SEQUENCE: 286
gcccgctagc ctgcggtggt caggatcagg gacgtcg                                37

<210> SEQ ID NO 287
<211> LENGTH: 37
<212> TYPE: DNA
<213> ORGANISM: Artificial Sequence
<220> FEATURE:
<223> OTHER INFORMATION: 5'LT short-NheI oligonucleotide

<400> SEQUENCE: 287
gcccgctagc ctgcggtggt tctccagctg cggattc                                37

<210> SEQ ID NO 288
<211> LENGTH: 33
<212> TYPE: DNA
<213> ORGANISM: Artificial Sequence
<220> FEATURE:
<223> OTHER INFORMATION: 3'LT stop-NotI oligonucleotide

<400> SEQUENCE: 288
caatgactgc ggccgcttac cccaccatca ccg                                    33

<210> SEQ ID NO 289
<211> LENGTH: 504
<212> TYPE: PRT
<213> ORGANISM: Artificial Sequence
<220> FEATURE:
<223> OTHER INFORMATION: GST-EK-C-LT-beta-49-306 fusion protein

<400> SEQUENCE: 289

Ala Pro Leu Val Met Ser Pro Ile Leu Gly Tyr Trp Lys Ile Lys Gly
 1               5                  10                  15

Leu Val Gln Pro Thr Arg Leu Leu Leu Glu Tyr Leu Glu Glu Lys Tyr
            20                  25                  30

Glu Glu His Leu Tyr Glu Arg Asp Glu Gly Asp Lys Trp Arg Asn Lys
        35                  40                  45

Lys Phe Glu Leu Gly Leu Glu Phe Pro Asn Leu Pro Tyr Tyr Ile Asp
    50                  55                  60
```

-continued

```
Gly Asp Val Lys Leu Thr Gln Ser Met Ala Ile Ile Arg Tyr Ile Ala
 65                  70                  75                  80

Asp Lys His Asn Met Leu Gly Gly Cys Pro Lys Glu Arg Ala Glu Ile
                 85                  90                  95

Ser Met Leu Glu Gly Ala Val Leu Asp Ile Arg Tyr Gly Val Ser Arg
            100                 105                 110

Ile Ala Tyr Ser Lys Asp Phe Glu Thr Leu Lys Val Asp Phe Leu Ser
        115                 120                 125

Lys Leu Pro Glu Met Leu Lys Met Phe Glu Asp Arg Leu Cys His Lys
    130                 135                 140

Thr Tyr Leu Asn Gly Asp His Val Thr His Pro Asp Phe Met Leu Tyr
145                 150                 155                 160

Asp Ala Leu Asp Val Val Leu Tyr Met Asp Pro Met Cys Leu Asp Ala
                165                 170                 175

Phe Pro Lys Leu Val Cys Phe Lys Lys Arg Ile Glu Ala Ile Pro Gln
            180                 185                 190

Ile Asp Lys Tyr Leu Lys Ser Ser Lys Tyr Ile Ala Trp Pro Leu Gln
        195                 200                 205

Gly Trp Gln Ala Thr Phe Gly Gly Asp His Pro Pro Lys Ala Ser
    210                 215                 220

Met Thr Gly Gly Gln Gln Met Gly Arg Asp Leu Tyr Asp Asp Asp
225                 230                 235                 240

Lys Leu Ala Cys Gly Gly Gln Asp Gln Gly Arg Arg Val Glu Lys Ile
                245                 250                 255

Ile Gly Ser Gly Ala Gln Ala Gln Lys Arg Leu Asp Asp Ser Lys Pro
        260                 265                 270

Ser Cys Ile Leu Pro Ser Pro Ser Leu Ser Glu Thr Pro Asp Pro
    275                 280                 285

Arg Leu His Pro Gln Arg Ser Asn Ala Ser Arg Asn Leu Ala Ser Thr
    290                 295                 300

Ser Gln Gly Pro Val Ala Gln Ser Ser Arg Glu Ala Ser Ala Trp Met
305                 310                 315                 320

Thr Ile Leu Ser Pro Ala Ala Asp Ser Thr Pro Asp Pro Gly Val Gln
                325                 330                 335

Gln Leu Pro Lys Gly Glu Pro Glu Thr Asp Leu Asn Pro Glu Leu Pro
            340                 345                 350

Ala Ala His Leu Ile Gly Ala Trp Met Ser Gly Gln Gly Leu Ser Trp
        355                 360                 365

Glu Ala Ser Gln Glu Glu Ala Phe Leu Arg Ser Gly Ala Gln Phe Ser
    370                 375                 380

Pro Thr His Gly Leu Ala Leu Pro Gln Asp Gly Val Tyr Tyr Leu Tyr
385                 390                 395                 400

Cys His Val Gly Tyr Arg Gly Arg Thr Pro Ala Gly Arg Ser Arg
                405                 410                 415

Ala Arg Ser Leu Thr Leu Arg Ser Ala Leu Tyr Arg Ala Gly Gly Ala
            420                 425                 430

Tyr Gly Arg Gly Ser Pro Glu Leu Leu Leu Glu Gly Ala Glu Thr Val
        435                 440                 445

Thr Pro Val Val Asp Pro Ile Gly Tyr Gly Ser Leu Trp Tyr Thr Ser
    450                 455                 460

Val Gly Phe Gly Gly Leu Ala Gln Leu Arg Ser Gly Glu Arg Val Tyr
465                 470                 475                 480
```

-continued

```
Val Asn Ile Ser His Pro Asp Met Val Asp Tyr Arg Arg Gly Lys Thr
                485                 490                 495
Phe Phe Gly Ala Val Met Val Gly
            500

<210> SEQ ID NO 290
<211> LENGTH: 427
<212> TYPE: PRT
<213> ORGANISM: Artificial Sequence
<220> FEATURE:
<223> OTHER INFORMATION: GST-EK-C-LT_126-306 fusion protein

<400> SEQUENCE: 290

Ala Pro Leu Val Met Ser Pro Ile Leu Gly Tyr Trp Lys Ile Lys Gly
1               5                   10                  15
Leu Val Gln Pro Thr Arg Leu Leu Leu Glu Tyr Leu Glu Glu Lys Tyr
                20                  25                  30
Glu Glu His Leu Tyr Glu Arg Asp Glu Gly Asp Lys Trp Arg Asn Lys
            35                  40                  45
Lys Phe Glu Leu Gly Leu Glu Phe Pro Asn Leu Pro Tyr Tyr Ile Asp
    50                  55                  60
Gly Asp Val Lys Leu Thr Gln Ser Met Ala Ile Ile Arg Tyr Ile Ala
65                  70                  75                  80
Asp Lys His Asn Met Leu Gly Gly Cys Pro Lys Glu Arg Ala Glu Ile
                85                  90                  95
Ser Met Leu Glu Gly Ala Val Leu Asp Ile Arg Tyr Gly Val Ser Arg
            100                 105                 110
Ile Ala Tyr Ser Lys Asp Phe Glu Thr Leu Lys Val Asp Phe Leu Ser
        115                 120                 125
Lys Leu Pro Glu Met Leu Lys Met Phe Glu Asp Arg Leu Cys His Lys
    130                 135                 140
Thr Tyr Leu Asn Gly Asp His Val Thr His Pro Asp Phe Met Leu Tyr
145                 150                 155                 160
Asp Ala Leu Asp Val Val Leu Tyr Met Asp Pro Met Cys Leu Asp Ala
                165                 170                 175
Phe Pro Lys Leu Val Cys Phe Lys Lys Arg Ile Glu Ala Ile Pro Gln
            180                 185                 190
Ile Asp Lys Tyr Leu Lys Ser Ser Lys Tyr Ile Ala Trp Pro Leu Gln
        195                 200                 205
Gly Trp Gln Ala Thr Phe Gly Gly Gly Asp His Pro Pro Lys Ala Ser
    210                 215                 220
Met Thr Gly Gly Gln Gln Met Gly Arg Asp Leu Tyr Asp Asp Asp Asp
225                 230                 235                 240
Lys Leu Ala Cys Gly Gly Ser Pro Ala Ala Asp Ser Thr Pro Asp Pro
                245                 250                 255
Gly Val Gln Gln Leu Pro Lys Gly Glu Pro Glu Thr Asp Leu Asn Pro
            260                 265                 270
Glu Leu Pro Ala Ala His Leu Ile Gly Ala Trp Met Ser Gly Gln Gly
        275                 280                 285
Leu Ser Trp Glu Ala Ser Gln Glu Glu Ala Phe Leu Arg Ser Gly Ala
    290                 295                 300
Gln Phe Ser Pro Thr His Gly Leu Ala Leu Gln Asp Gly Val Tyr Tyr
305                 310                 315                 320
Tyr Leu Tyr Cys His Val Gly Tyr Arg Gly Arg Thr Pro Pro Ala Gly
                325                 330                 335
```

```
Arg Ser Arg Ala Arg Ser Leu Thr Leu Arg Ser Ala Leu Tyr Arg Ala
            340                 345                 350

Gly Gly Ala Tyr Gly Arg Gly Ser Pro Glu Leu Leu Leu Glu Gly Ala
            355                 360                 365

Glu Thr Val Thr Pro Val Val Asp Pro Ile Gly Tyr Gly Ser Leu Trp
            370                 375                 380

Tyr Thr Ser Val Gly Phe Gly Gly Leu Ala Gln Leu Arg Ser Gly Glu
385                 390                 395                 400

Arg Val Tyr Val Asn Ile Ser His Pro Asp Met Val Asp Tyr Arg Arg
            405                 410                 415

Gly Lys Thr Phe Phe Gly Ala Val Met Val Gly
            420                 425

<210> SEQ ID NO 291
<211> LENGTH: 311
<212> TYPE: PRT
<213> ORGANISM: Artificial Sequence
<220> FEATURE:
<223> OTHER INFORMATION: his-myc-EK-C-LT_49-306 fusion protein

<400> SEQUENCE: 291

Ala Pro Leu Val His His His His His Gly Pro Leu Val Asp Val
1               5                   10                  15

Ala Ser Asn Glu Gln Lys Leu Ile Ser Glu Asp Leu Ala Ser Met
            20                  25                  30

Thr Gly Gly Gln Gln Met Gly Arg Asp Leu Tyr Asp Asp Asp Lys
            35                  40                  45

Leu Ala Cys Gly Gly Gln Asp Gln Gly Arg Arg Val Glu Lys Ile Ile
    50                  55                  60

Gly Ser Gly Ala Gln Ala Gln Lys Arg Leu Asp Asp Ser Lys Pro Ser
65                  70                  75                  80

Cys Ile Leu Pro Ser Pro Ser Ser Leu Ser Glu Thr Pro Asp Pro Arg
                85                  90                  95

Leu His Pro Gln Arg Ser Asn Ala Ser Arg Asn Leu Ala Ser Thr Ser
            100                 105                 110

Gln Gly Pro Val Ala Gln Ser Ser Arg Glu Ala Ser Ala Trp Met Thr
            115                 120                 125

Ile Leu Ser Pro Ala Ala Asp Ser Thr Pro Asp Pro Gly Val Gln Gln
    130                 135                 140

Leu Pro Lys Gly Glu Pro Glu Thr Asp Leu Asn Pro Glu Leu Pro Ala
145                 150                 155                 160

Ala His Leu Ile Gly Ala Trp Met Ser Gly Gln Gly Leu Ser Trp Glu
                165                 170                 175

Ala Ser Gln Glu Glu Ala Phe Leu Arg Ser Gly Ala Gln Phe Ser Pro
            180                 185                 190

Thr His Gly Leu Ala Leu Pro Gln Asp Gly Val Tyr Tyr Leu Tyr Cys
            195                 200                 205

His Val Gly Tyr Arg Gly Arg Thr Pro Pro Ala Gly Arg Ser Arg Ala
    210                 215                 220

Arg Ser Leu Thr Leu Arg Ser Ala Leu Tyr Arg Ala Gly Gly Ala Tyr
225                 230                 235                 240

Gly Arg Gly Ser Pro Glu Leu Leu Leu Glu Gly Ala Glu Thr Val Thr
                245                 250                 255

Pro Val Val Asp Pro Ile Gly Tyr Gly Ser Leu Trp Tyr Thr Ser Val
            260                 265                 270
```

```
Gly Phe Gly Gly Leu Ala Gln Leu Arg Ser Gly Glu Arg Val Tyr Val
        275                 280                 285

Asn Ile Ser His Pro Asp Met Val Asp Tyr Arg Arg Gly Lys Thr Phe
    290                 295                 300

Phe Gly Ala Val Met Val Gly
305                 310

<210> SEQ ID NO 292
<211> LENGTH: 234
<212> TYPE: PRT
<213> ORGANISM: Artificial Sequence
<220> FEATURE:
<223> OTHER INFORMATION: his-myc-EK-C-LT_126-306 fusion protein

<400> SEQUENCE: 292

Ala Pro Leu Val His His His His His Gly Pro Leu Val Asp Val
1               5                   10                  15

Ala Ser Asn Glu Gln Lys Leu Ile Ser Glu Glu Asp Leu Ala Ser Met
            20                  25                  30

Thr Gly Gly Gln Gln Met Gly Arg Asp Leu Tyr Asp Asp Asp Asp Lys
        35                  40                  45

Leu Ala Cys Gly Gly Ser Pro Ala Ala Asp Ser Thr Pro Asp Pro Gly
    50                  55                  60

Val Gln Gln Leu Pro Lys Gly Glu Pro Glu Thr Asp Leu Asn Pro Glu
65                  70                  75                  80

Leu Pro Ala Ala His Leu Ile Gly Ala Trp Met Ser Gly Gln Gly Leu
                85                  90                  95

Ser Trp Glu Ala Ser Gln Glu Glu Ala Phe Leu Arg Ser Gly Ala Gln
            100                 105                 110

Phe Ser Pro Thr His Gly Leu Ala Leu Pro Gln Asp Gly Val Tyr Tyr
        115                 120                 125

Leu Tyr Cys His Val Gly Tyr Arg Gly Arg Thr Pro Pro Ala Gly Arg
    130                 135                 140

Ser Arg Ala Arg Ser Leu Thr Leu Arg Ser Ala Leu Tyr Arg Ala Gly
145                 150                 155                 160

Gly Ala Tyr Gly Arg Gly Ser Pro Glu Leu Leu Leu Glu Gly Ala Glu
                165                 170                 175

Thr Val Thr Pro Val Val Asp Pro Ile Gly Tyr Gly Ser Leu Trp Tyr
            180                 185                 190

Thr Ser Val Gly Phe Gly Gly Leu Ala Gln Leu Arg Ser Gly Glu Arg
        195                 200                 205

Val Tyr Val Asn Ile Ser His Pro Asp Met Val Asp Tyr Arg Arg Gly
    210                 215                 220

Lys Thr Phe Phe Gly Ala Val Met Val Gly
225                 230

<210> SEQ ID NO 293
<211> LENGTH: 43
<212> TYPE: DNA
<213> ORGANISM: Artificial Sequence
<220> FEATURE:
<223> OTHER INFORMATION: MCS-1F primer

<400> SEQUENCE: 293
tatggatccg gctagcgctc gagggtttaa acggcggccg cat                    43

<210> SEQ ID NO 294
<211> LENGTH: 45
```

<212> TYPE: DNA
<213> ORGANISM: Artificial Sequence
<220> FEATURE:
<223> OTHER INFORMATION: MCS-1R primer

<400> SEQUENCE: 294
tcgaatgcgg ccgccgttta aaccctcgag cgctagccgg atcca         45

<210> SEQ ID NO 295
<211> LENGTH: 58
<212> TYPE: DNA
<213> ORGANISM: Artificial Sequence
<220> FEATURE:
<223> OTHER INFORMATION: Bamhis6-EK-Nhe-F oligonucleotide

<400> SEQUENCE: 295
gatccacacc accaccacca ccacggttct ggtgacgacg atgacaaagc gctagccc      58

<210> SEQ ID NO 296
<211> LENGTH: 58
<212> TYPE: DNA
<213> ORGANISM: Artificial Sequence
<220> FEATURE:
<223> OTHER INFORMATION: Bamhis6-EK-Nhe-R oligonucleotide

<400> SEQUENCE: 296
tcgagggcta gcgctttgtc atcgtcgtca ccagaaccgt ggtggtggtg gtggtgtg      58

<210> SEQ ID NO 297
<211> LENGTH: 42
<212> TYPE: DNA
<213> ORGANISM: Artificial Sequence
<220> FEATURE:
<223> OTHER INFORMATION: oligo1F-C-glycine-linker

<400> SEQUENCE: 297
tcgagggtgg tggtggtggt tgcggttaat aagtttaaac gc         42

<210> SEQ ID NO 298
<211> LENGTH: 42
<212> TYPE: DNA
<213> ORGANISM: Artificial Sequence
<220> FEATURE:
<223> OTHER INFORMATION: oligo1R-C-glycine-linker

<400> SEQUENCE: 298
ggccgcgttt aaacttatta accgcaacca ccaccaccac cc         42

<210> SEQ ID NO 299
<211> LENGTH: 51
<212> TYPE: DNA
<213> ORGANISM: Artificial Sequence
<220> FEATURE:
<223> OTHER INFORMATION: oligo1F-C-gamma1-linker

<400> SEQUENCE: 299
tcgaggataa aacccacacc tctccgccgt gtggttaata gtttaaacg c         51

<210> SEQ ID NO 300
<211> LENGTH: 51
<212> TYPE: DNA
<213> ORGANISM: Artificial Sequence
<220> FEATURE:
<223> OTHER INFORMATION: oligo1R-C-gamma1-linker

<400> SEQUENCE: 300
ggccgcgttt aaacttatta accacacggc ggagaggtgt gggttttatc c          51

<210> SEQ ID NO 301
<211> LENGTH: 36
<212> TYPE: DNA
<213> ORGANISM: Artificial Sequence
<220> FEATURE:
<223> OTHER INFORMATION: oligo1FA-C-gamma3-linker

<400> SEQUENCE: 301
tcgagccgaa accgtctacc ccgccgggtt cttctg                          36

<210> SEQ ID NO 302
<211> LENGTH: 38
<212> TYPE: DNA
<213> ORGANISM: Artificial Sequence
<220> FEATURE:
<223> OTHER INFORMATION: oligo1RA-C-gamma3-linker

<400> SEQUENCE: 302
caccaccaga agaacccggc ggggtagacg gtttcggc                        38

<210> SEQ ID NO 303
<211> LENGTH: 39
<212> TYPE: DNA
<213> ORGANISM: Artificial Sequence
<220> FEATURE:
<223> OTHER INFORMATION: oligo2FB-C-gamma3-linker

<400> SEQUENCE: 303
gtggtgctcc gggtggttgc ggttaataag tttaaacgc                       39

<210> SEQ ID NO 304
<211> LENGTH: 37
<212> TYPE: DNA
<213> ORGANISM: Artificial Sequence
<220> FEATURE:
<223> OTHER INFORMATION: oligo2RB-C-gamma3-linker

<400> SEQUENCE: 304
ggccgcgttt aaacttatta accgcaacca cccggag                         37

<210> SEQ ID NO 305
<211> LENGTH: 33
<212> TYPE: DNA
<213> ORGANISM: Artificial Sequence
<220> FEATURE:
<223> OTHER INFORMATION: rMIF-F oligonucleotide

<400> SEQUENCE: 305
ggaattccat atgcctatgt tcatcgtgaa cac                             33

<210> SEQ ID NO 306
<211> LENGTH: 29
<212> TYPE: DNA
<213> ORGANISM: Artificial Sequence
<220> FEATURE:
<223> OTHER INFORMATION: rMIF-Xho-R oligonucleotide

<400> SEQUENCE: 306
cccgctcgag agcgaaggtg gaaccgttc                                  29

<210> SEQ ID NO 307
<211> LENGTH: 124
<212> TYPE: PRT
<213> ORGANISM: Artificial Sequence

```
<220> FEATURE:
<223> OTHER INFORMATION: rMIF-C1

<400> SEQUENCE: 307

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Gly
            20                  25                  30

Lys Pro Ala Gln Tyr Ile Ala Val His Val Val Pro Asp Gln Leu Met
        35                  40                  45

Thr Phe Ser Gly Thr Ser Asp Pro Cys Ala Leu Cys Ser Leu His Ser
    50                  55                  60

Ile Gly Lys Ile Gly Gly Ala Gln Asn Arg Asn Tyr Ser Lys Leu Leu
65                  70                  75                  80

Cys Gly Leu Leu Ser Asp Arg Leu His Ile Ser Pro Asp Arg Val Tyr
                85                  90                  95

Ile Asn Tyr Tyr Asp Met Asn Ala Ala Asn Val Gly Trp Asn Gly Ser
            100                 105                 110

Thr Phe Ala Leu Glu Gly Gly Gly Gly Cys Gly
        115                 120

<210> SEQ ID NO 308
<211> LENGTH: 127
<212> TYPE: PRT
<213> ORGANISM: Artificial Sequence
<220> FEATURE:
<223> OTHER INFORMATION: rMIF-C2

<400> SEQUENCE: 308

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Gly
            20                  25                  30

Lys Pro Ala Gln Tyr Ile Ala Val His Val Val Pro Asp Gln Leu Met
        35                  40                  45

Thr Phe Ser Gly Thr Ser Asp Pro Cys Ala Leu Cys Ser Leu His Ser
    50                  55                  60

Ile Gly Lys Ile Gly Gly Ala Gln Asn Arg Asn Tyr Ser Lys Leu Leu
65                  70                  75                  80

Cys Gly Leu Leu Ser Asp Arg Leu His Ile Ser Pro Asp Arg Val Tyr
                85                  90                  95

Ile Asn Tyr Tyr Asp Met Asn Ala Ala Asn Val Gly Trp Asn Gly Ser
            100                 105                 110

Thr Phe Ala Leu Glu Asp Lys Thr His Thr Ser Pro Pro Cys Gly
        115                 120                 125

<210> SEQ ID NO 309
<211> LENGTH: 135
<212> TYPE: PRT
<213> ORGANISM: Artificial Sequence
<220> FEATURE:
<223> OTHER INFORMATION: rMIF-C3

<400> SEQUENCE: 309

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Gly
            20                  25                  30
```

-continued

```
Lys Pro Ala Gln Tyr Ile Ala Val His Val Pro Asp Gln Leu Met
        35                  40                  45

Thr Phe Ser Gly Thr Ser Asp Pro Cys Ala Leu Cys Ser Leu His Ser
    50                  55                  60

Ile Gly Lys Ile Gly Gly Ala Gln Asn Arg Asn Tyr Ser Lys Leu Leu
65                  70                  75                  80

Cys Gly Leu Leu Ser Asp Arg Leu His Ile Ser Pro Asp Arg Val Tyr
                85                  90                  95

Ile Asn Tyr Tyr Asp Met Asn Ala Ala Asn Val Gly Trp Asn Gly Ser
            100                 105                 110

Thr Phe Ala Leu Glu Pro Lys Pro Ser Thr Pro Pro Gly Ser Ser Gly
        115                 120                 125

Gly Ala Pro Gly Gly Cys Gly
        130                 135

<210> SEQ ID NO 310
<211> LENGTH: 124
<212> TYPE: PRT
<213> ORGANISM: Homo sapiens

<400> SEQUENCE: 310

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala Leu Glu Gly Gly Gly Gly Gly Cys Gly
        115                 120

<210> SEQ ID NO 311
<211> LENGTH: 123
<212> TYPE: PRT
<213> ORGANISM: Homo sapiens

<400> SEQUENCE: 311

Pro Met Phe Ile Val Asn Thr Asn Val Pro Arg Ala Ser Val Pro Asp
1               5                   10                  15

Gly Phe Leu Ser Glu Leu Thr Gln Gln Leu Ala Gln Ala Thr Gly Lys
            20                  25                  30

Pro Pro Gln Tyr Ile Ala Val His Val Pro Asp Gln Leu Met Ala
        35                  40                  45

Phe Gly Gly Ser Ser Glu Pro Cys Ala Leu Cys Ser Leu His Ser Ile
    50                  55                  60

Gly Lys Ile Gly Gly Ala Gln Asn Arg Ser Tyr Ser Lys Leu Leu Cys
65                  70                  75                  80

Gly Leu Leu Ala Glu Arg Leu Arg Ile Ser Pro Asp Arg Val Tyr Ile
                85                  90                  95
```

Asn Tyr Tyr Asp Met Asn Ala Ala Asn Val Gly Trp Asn Asn Ser Thr
                100                 105                 110

Phe Ala Leu Glu Gly Gly Gly Cys Gly
            115             120

<210> SEQ ID NO 312
<211> LENGTH: 127
<212> TYPE: PRT
<213> ORGANISM: Homo sapiens

<400> SEQUENCE: 312

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
            35                  40                  45

Ala Phe Gly Gly Ser Ser Glu Pro Cys Ala Leu Cys Ser Leu His Ser
        50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
                100                 105                 110

Thr Phe Ala Leu Glu Asp Lys Thr His Thr Ser Pro Pro Cys Gly
            115                 120                 125

<210> SEQ ID NO 313
<211> LENGTH: 126
<212> TYPE: PRT
<213> ORGANISM: Homo sapiens

<400> SEQUENCE: 313

Pro Met Phe Ile Val Asn Thr Asn Val Pro Arg Ala Ser Val Pro Asp
1               5                   10                  15

Gly Phe Leu Ser Glu Leu Thr Gln Gln Leu Ala Gln Ala Thr Gly Lys
            20                  25                  30

Pro Pro Gln Tyr Ile Ala Val His Val Val Pro Asp Gln Leu Met Ala
            35                  40                  45

Phe Gly Gly Ser Ser Glu Pro Cys Ala Leu Cys Ser Leu His Ser Ile
        50                  55                  60

Gly Lys Ile Gly Gly Ala Gln Asn Arg Ser Tyr Ser Lys Leu Leu Cys
65                  70                  75                  80

Gly Leu Leu Ala Glu Arg Leu Arg Ile Ser Pro Asp Arg Val Tyr Ile
                85                  90                  95

Asn Tyr Tyr Asp Met Asn Ala Ala Asn Val Gly Trp Asn Asn Ser Thr
                100                 105                 110

Phe Ala Leu Glu Asp Lys Thr His Thr Ser Pro Pro Cys Gly
            115                 120                 125

<210> SEQ ID NO 314
<211> LENGTH: 135
<212> TYPE: PRT
<213> ORGANISM: Homo sapiens

<400> SEQUENCE: 314

Met Pro Met Phe Ile Val Asn Thr Asn Val Pro Arg Ala Ser Val Pro

```
                  1               5                  10                 15
Asp Gly Phe Leu Ser Glu Leu Thr Gln Gln Leu Ala Gln Ala Thr Gly
                 20                  25                  30
Lys Pro Pro Gln Tyr Ile Ala Val His Val Pro Asp Gln Leu Met
             35                  40                  45
Ala Phe Gly Gly Ser Ser Glu Pro Cys Ala Leu Cys Ser Leu His Ser
         50                  55                  60
Ile Gly Lys Ile Gly Gly Ala Gln Asn Arg Ser Tyr Ser Lys Leu Leu
65                  70                  75                  80
Cys Gly Leu Leu Ala Glu Arg Leu Arg Ile Ser Pro Asp Arg Val Tyr
                 85                  90                  95
Ile Asn Tyr Tyr Asp Met Asn Ala Ala Asn Val Gly Trp Asn Asn Ser
                100                 105                 110
Thr Phe Ala Leu Glu Pro Lys Pro Ser Thr Pro Pro Gly Ser Ser Gly
            115                 120                 125
Gly Ala Pro Gly Gly Cys Gly
        130                 135
```

<210> SEQ ID NO 315
<211> LENGTH: 134
<212> TYPE: PRT
<213> ORGANISM: Homo sapiens

<400> SEQUENCE: 315

```
Pro Met Phe Ile Val Asn Thr Asn Val Pro Arg Ala Ser Val Pro Asp
1               5                  10                  15
Gly Phe Leu Ser Glu Leu Thr Gln Gln Leu Ala Gln Ala Thr Gly Lys
                20                  25                  30
Pro Pro Gln Tyr Ile Ala Val His Val Pro Asp Gln Leu Met Ala
            35                  40                  45
Phe Gly Gly Ser Ser Glu Pro Cys Ala Leu Cys Ser Leu His Ser Ile
        50                  55                  60
Gly Lys Ile Gly Gly Ala Gln Asn Arg Ser Tyr Ser Lys Leu Leu Cys
65                  70                  75                  80
Gly Leu Leu Ala Glu Arg Leu Arg Ile Ser Pro Asp Arg Val Tyr Ile
                85                  90                  95
Asn Tyr Tyr Asp Met Asn Ala Ala Asn Val Gly Trp Asn Asn Ser Thr
               100                 105                 110
Phe Ala Leu Glu Pro Lys Pro Ser Thr Pro Pro Gly Ser Ser Gly Gly
           115                 120                 125
Ala Pro Gly Gly Cys Gly
       130
```

<210> SEQ ID NO 316
<211> LENGTH: 62
<212> TYPE: DNA
<213> ORGANISM: Artificial Sequence
<220> FEATURE:
<223> OTHER INFORMATION: RANKL-UP oligonucleotide

<400> SEQUENCE: 316
ctgccagggg cccgggtgcg gcggtggcca tcatcaccac catcaccagc gcttctcagg    60
ag    62

<210> SEQ ID NO 317
<211> LENGTH: 35
<212> TYPE: DNA

―continued

```
<213> ORGANISM: Artificial Sequence
<220> FEATURE:
<223> OTHER INFORMATION: RANKL-down oligonucleotide

<400> SEQUENCE: 317
ccgctcgagt tagtctatgt cctgaacttt gaaag                               35

<210> SEQ ID NO 318
<211> LENGTH: 419
<212> TYPE: PRT
<213> ORGANISM: Artificial Sequence
<220> FEATURE:
<223> OTHER INFORMATION: GST-PS-C-RANKL construct

<400> SEQUENCE: 318

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Gly Cys Gly Gly His His His His His His Gln
225                 230                 235                 240

Arg Phe Ser Gly Ala Pro Ala Met Met Glu Gly Ser Trp Leu Asp Val
                245                 250                 255

Ala Gln Arg Gly Lys Pro Glu Ala Gln Pro Phe Ala His Leu Thr Ile
            260                 265                 270

Asn Ala Ala Ser Ile Pro Ser Gly Ser His Lys Val Thr Leu Ser Ser
        275                 280                 285

Trp Tyr His Asp Arg Gly Trp Ala Lys Ile Ser Asn Met Thr Leu Ser
    290                 295                 300

Asn Gly Lys Leu Arg Val Asn Gln Asp Gly Phe Tyr Tyr Leu Tyr Ala
305                 310                 315                 320

Asn Ile Cys Phe Arg His His Glu Thr Ser Gly Ser Val Pro Thr Asp
```

```
                       325                 330                 335
Tyr Leu Gln Leu Met Val Tyr Val Lys Thr Ser Ile Lys Ile Pro
                340                 345                 350

Ser Ser His Asn Leu Met Lys Gly Gly Ser Thr Lys Asn Trp Ser Gly
                355                 360                 365

Asn Ser Glu Phe His Phe Tyr Ser Ile Asn Val Gly Gly Phe Phe Lys
            370                 375                 380

Leu Arg Ala Gly Glu Glu Ile Ser Ile Gln Val Ser Asn Pro Ser Leu
385                 390                 395                 400

Leu Asp Pro Asp Gln Asp Ala Thr Tyr Phe Gly Ala Phe Lys Val Gln
                405                 410                 415

Asp Ile Asp

<210> SEQ ID NO 319
<211> LENGTH: 1269
<212> TYPE: DNA
<213> ORGANISM: Artificial Sequence
<220> FEATURE:
<223> OTHER INFORMATION: GST-PS-C-RANKL construct

<400> SEQUENCE: 319
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300 gatattgat  acggtgtttc gagaattgca tatagtaaag actttgaaac tctcaaagtt     360 gatttctta  gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aaaatcggat     660
ctggaagttc tgttccaggg gcccgggtgc ggcggtggcc atcatcacca ccatcaccag     720
cgcttctcag gagctccagc tatgatggaa ggctcatggt tggatgtggc ccagcgaggc     780
aagcctgagg cccagccatt tgcacacctc accatcaatg ctgccagcat cccatcgggt     840
tcccataaag tcactctgtc ctcttggtac cacgatcgag gctgggccaa gatctctaac     900
atgacgttaa gcaacggaaa actaagggtt aaccaagatg gcttctatta cctgtacgcc     960
aacatttgct ttcggcatca tgaaacatcg ggaagcgtac ctacagacta tcttcagctg    1020
atggtgtatg tcgttaaaac cagcatcaaa atcccaagtt ctcataacct gatgaaagga    1080
gggagcacga aaaactggtc gggcaattct gaattccact tttattccat aaatgttggg    1140
ggatttttca agctccgagc tggtgaagaa attagcattc aggtgtccaa cccttccctg    1200
ctggatccgg atcaagatgc gacgtacttt ggggctttca agttcagga  catagactaa    1260 ctcgagcgg                                                            1269

<210> SEQ ID NO 320
<211> LENGTH: 185
<212> TYPE: PRT
<213> ORGANISM: Homo sapiens
```

```
<400> SEQUENCE: 320

Gly Cys Gly Gly Gly Gln His Ile Arg Ala Glu Lys Ala Met Val Asp
1               5                   10                  15

Gly Ser Trp Leu Asp Leu Ala Lys Arg Ser Lys Leu Glu Ala Gln Pro
                20                  25                  30

Phe Ala His Leu Thr Ile Asn Ala Thr Asp Ile Pro Ser Gly Ser His
            35                  40                  45

Lys Val Ser Leu Ser Ser Trp Tyr His Asp Arg Gly Trp Ala Lys Ile
    50                  55                  60

Ser Asn Met Thr Phe Ser Asn Gly Lys Leu Ile Val Asn Gln Asp Gly
65                  70                  75                  80

Phe Tyr Tyr Leu Tyr Ala Asn Ile Cys Phe Arg His His Glu Thr Ser
                85                  90                  95

Gly Asp Leu Ala Thr Glu Tyr Leu Gln Leu Met Val Tyr Val Thr Lys
            100                 105                 110

Thr Ser Ile Lys Ile Pro Ser Ser His Thr Leu Met Lys Gly Gly Ser
            115                 120                 125

Thr Lys Tyr Trp Ser Gly Asn Ser Glu Phe His Phe Tyr Ser Ile Asn
130                 135                 140

Val Gly Gly Phe Phe Lys Leu Arg Ser Gly Glu Glu Ile Ser Ile Glu
145                 150                 155                 160

Val Ser Asn Pro Ser Leu Leu Asp Pro Asp Gln Asp Ala Thr Tyr Phe
                165                 170                 175

Gly Ala Phe Lys Val Arg Asp Ile Asp
            180                 185

<210> SEQ ID NO 321
<211> LENGTH: 29
<212> TYPE: DNA
<213> ORGANISM: Artificial Sequence
<220> FEATURE:
<223> OTHER INFORMATION: Primer 5'PrP-BamHI

<400> SEQUENCE: 321
cgggatccca ccatggtggg gggccttgg                                    29

<210> SEQ ID NO 322
<211> LENGTH: 24
<212> TYPE: DNA
<213> ORGANISM: Artificial Sequence
<220> FEATURE:
<223> OTHER INFORMATION: Primer 3'PrP-NheI

<400> SEQUENCE: 322
ctagctagcc tggatcttct cccg                                         24

<210> SEQ ID NO 323
<211> LENGTH: 350
<212> TYPE: PRT
<213> ORGANISM: Artificial Sequence
<220> FEATURE:
<223> OTHER INFORMATION: mPrPt-EK-Fc construct

<400> SEQUENCE: 323

Met Val Gly Gly Leu Gly Gly Tyr Met Leu Gly Ser Ala Met Ser Arg
1               5                   10                  15

Pro Met Ile His Phe Gly Asn Asp Trp Glu Asp Arg Tyr Tyr Arg Glu
                20                  25                  30

Asn Met Tyr Arg Tyr Pro Asn Gln Val Tyr Tyr Arg Pro Val Asp Gln
```

```
                    35                  40                  45
Tyr Ser Asn Gln Asn Asn Phe Val His Asp Cys Val Asn Ile Thr Ile
     50                  55                  60

Lys Gln His Thr Val Thr Thr Thr Lys Gly Glu Asn Phe Thr Glu
 65                  70                  75                  80

Thr Asp Val Lys Met Met Glu Arg Val Val Glu Gln Met Cys Val Thr
                 85                  90                  95

Gln Tyr Gln Lys Glu Ser Gln Ala Tyr Tyr Asp Gly Arg Ser Arg Leu
                100                 105                 110

Ala Gly Gly Gly Cys Gly Asp Asp Asp Lys Leu Thr His Thr
                115                 120                 125

Cys Pro Pro Cys Pro Ala Pro Glu Ala Glu Gly Ala Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
                180                 185                 190

Lys Pro Arg Glu Glu Gln Tyr Asn Ser Thr Tyr Arg Val Val Ser Val
                195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
                260                 265                 270

Lys Gly Phe Tyr Pro Ser Asp Ile Ala Val Glu Trp Glu Ser Asn Gly
                275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
                340                 345                 350

<210> SEQ ID NO 324
<211> LENGTH: 124
<212> TYPE: PRT
<213> ORGANISM: Artificial Sequence
<220> FEATURE:
<223> OTHER INFORMATION: mPrPt construct

<400> SEQUENCE: 324

Met Val Gly Gly Leu Gly Gly Tyr Met Leu Gly Ser Ala Met Ser Arg
 1               5                  10                  15

Pro Met Ile His Phe Gly Asn Asp Trp Glu Asp Arg Tyr Tyr Arg Glu
                 20                  25                  30

Asn Met Tyr Arg Tyr Pro Asn Gln Val Tyr Tyr Arg Pro Val Asp Gln
                 35                  40                  45

Tyr Ser Asn Gln Asn Asn Phe Val His Asp Cys Val Asn Ile Thr Ile
```

```
                    50                  55                  60
Lys Gln His Thr Val Thr Thr Thr Lys Gly Glu Asn Phe Thr Glu
 65                  70                  75                  80

Thr Asp Val Lys Met Met Glu Arg Val Val Glu Gln Met Cys Val Thr
                     85                  90                  95

Gln Tyr Gln Lys Glu Ser Gln Ala Tyr Tyr Asp Gly Arg Ser Arg Leu
                    100                 105                 110

Ala Gly Gly Gly Gly Cys Gly Asp Asp Asp Lys
                    115                 120
```

<210> SEQ ID NO 325
<211> LENGTH: 102
<212> TYPE: PRT
<213> ORGANISM: Artificial Sequence
<220> FEATURE:
<223> OTHER INFORMATION: human resistin-C-Xa construct

<400> SEQUENCE: 325

```
Ser Ser Lys Thr Leu Cys Ser Met Glu Glu Ala Ile Asn Glu Arg Ile
 1               5                  10                  15

Gln Glu Val Ala Gly Ser Leu Ile Phe Arg Ala Ile Ser Ser Ile Gly
                 20                  25                  30

Leu Glu Cys Gln Ser Val Thr Ser Arg Gly Asp Leu Ala Thr Cys Pro
             35                  40                  45

Arg Gly Phe Ala Val Thr Gly Cys Thr Cys Gly Ser Ala Cys Gly Ser
         50                  55                  60

Trp Asp Val Arg Ala Glu Thr Thr Cys His Cys Gln Cys Ala Gly Met
 65                  70                  75                  80

Asp Trp Thr Gly Ala Arg Cys Cys Arg Val Gln Pro Gly Gly Gly Gly
                 85                  90                  95

Cys Gly Ile Glu Gly Arg
                100
```

<210> SEQ ID NO 326
<211> LENGTH: 103
<212> TYPE: PRT
<213> ORGANISM: Artificial Sequence
<220> FEATURE:
<223> OTHER INFORMATION: human resistin-C-EK construct

<400> SEQUENCE: 326

```
Ser Ser Lys Thr Leu Cys Ser Met Glu Glu Ala Ile Asn Glu Arg Ile
 1               5                  10                  15

Gln Glu Val Ala Gly Ser Leu Ile Phe Arg Ala Ile Ser Ser Ile Gly
                 20                  25                  30

Leu Glu Cys Gln Ser Val Thr Ser Arg Gly Asp Leu Ala Thr Cys Pro
             35                  40                  45

Arg Gly Phe Ala Val Thr Gly Cys Thr Cys Gly Ser Ala Cys Gly Ser
         50                  55                  60

Trp Asp Val Arg Ala Glu Thr Thr Cys His Cys Gln Cys Ala Gly Met
 65                  70                  75                  80

Asp Trp Thr Gly Ala Arg Cys Cys Arg Val Gln Pro Gly Gly Gly Gly
                 85                  90                  95

Cys Gly Asp Asp Asp Asp Lys
                100
```

<210> SEQ ID NO 327
<211> LENGTH: 98

```
<212> TYPE: PRT
<213> ORGANISM: Artificial Sequence
<220> FEATURE:
<223> OTHER INFORMATION: human resisitin-C construct

<400> SEQUENCE: 327

Ser Ser Lys Thr Leu Cys Ser Met Glu Glu Ala Ile Asn Glu Arg Ile
1               5                   10                  15

Gln Glu Val Ala Gly Ser Leu Ile Phe Arg Ala Ile Ser Ile Gly
            20                  25                  30

Leu Glu Cys Gln Ser Val Thr Ser Arg Gly Asp Leu Ala Thr Cys Pro
            35                  40                  45

Arg Gly Phe Ala Val Thr Gly Cys Thr Cys Gly Ser Ala Cys Gly Ser
            50                  55                  60

Trp Asp Val Arg Ala Glu Thr Thr Cys His Cys Gln Cys Ala Gly Met
65                  70                  75                  80

Asp Trp Thr Gly Ala Arg Cys Cys Arg Val Gln Pro Gly Gly Gly Gly
                85                  90                  95

Cys Gly

<210> SEQ ID NO 328
<211> LENGTH: 132
<212> TYPE: PRT
<213> ORGANISM: Artificial Sequence
<220> FEATURE:
<223> OTHER INFORMATION: mouse C-IL-13-F construct

<400> SEQUENCE: 328

Ala Asp Pro Gly Cys Gly Gly Gly Gly Leu Ala Gly Pro Val Pro
1               5                   10                  15

Arg Ser Val Ser Leu Pro Leu Thr Leu Lys Glu Leu Ile Glu Leu
            20                  25                  30

Ser Asn Ile Thr Gln Asp Gln Thr Pro Leu Cys Asn Gly Ser Met Val
            35                  40                  45

Trp Ser Val Asp Leu Ala Ala Gly Gly Phe Cys Val Ala Leu Asp Ser
    50                  55                  60

Leu Thr Asn Ile Ser Asn Cys Asn Ala Ile Tyr Arg Thr Gln Arg Ile
65                  70                  75                  80

Leu His Gly Leu Cys Asn Arg Lys Ala Pro Thr Thr Val Ser Ser Leu
                85                  90                  95

Pro Asp Thr Lys Ile Glu Val Ala His Phe Ile Thr Lys Leu Leu Ser
            100                 105                 110

Tyr Thr Lys Gln Leu Phe Arg His Gly Pro Phe Leu Glu Val Leu Ala
            115                 120                 125

Ile Glu Gly Arg
    130

<210> SEQ ID NO 329
<211> LENGTH: 119
<212> TYPE: PRT
<213> ORGANISM: Artificial Sequence
<220> FEATURE:
<223> OTHER INFORMATION: mouse C-IL-13-S construct

<400> SEQUENCE: 329

Leu Ala Cys Gly Gly Gly Gly Gly Pro Val Pro Arg Ser Val Ser
1               5                   10                  15

Leu Pro Leu Thr Leu Lys Glu Leu Ile Glu Glu Leu Ser Asn Ile Thr
            20                  25                  30
```

-continued

```
Gln Asp Gln Thr Pro Leu Cys Asn Gly Ser Met Val Trp Ser Val Asp
        35                  40                  45

Leu Ala Ala Gly Gly Phe Cys Val Ala Leu Asp Ser Leu Thr Asn Ile
 50                  55                  60

Ser Asn Cys Asn Ala Ile Tyr Arg Thr Gln Arg Ile Leu His Gly Leu
 65                  70                  75                  80

Cys Asn Arg Lys Ala Pro Thr Thr Val Ser Ser Leu Pro Asp Thr Lys
                 85                  90                  95

Ile Glu Val Ala His Phe Ile Thr Lys Leu Leu Ser Tyr Thr Lys Gln
             100                 105                 110

Leu Phe Arg His Gly Pro Phe
            115
```

<210> SEQ ID NO 330
<211> LENGTH: 133
<212> TYPE: PRT
<213> ORGANISM: Artificial Sequence
<220> FEATURE:
<223> OTHER INFORMATION: human C-IL-13-F construct

<400> SEQUENCE: 330

```
Ala Asp Pro Gly Cys Gly Gly Gly Gly Leu Ala Gly Pro Val Pro
 1               5                  10                  15

Pro Ser Thr Ala Leu Arg Glu Leu Ile Glu Glu Leu Val Asn Ile Thr
             20                  25                  30

Gln Asn Gln Lys Ala Pro Leu Cys Asn Gly Ser Met Val Trp Ser Ile
         35                  40                  45

Asn Leu Thr Ala Gly Met Tyr Cys Ala Ala Leu Glu Ser Leu Ile Asn
 50                  55                  60

Val Ser Gly Cys Ser Ala Ile Glu Lys Thr Gln Arg Met Leu Ser Gly
 65                  70                  75                  80

Phe Cys Pro His Lys Val Ser Ala Gly Gln Phe Ser Ser Leu His Val
                 85                  90                  95

Arg Asp Thr Lys Ile Glu Val Ala Gln Phe Val Lys Asp Leu Leu Leu
             100                 105                 110

His Leu Lys Lys Leu Phe Arg Glu Gly Arg Phe Asn Leu Glu Val Leu
         115                 120                 125

Ala Ile Glu Gly Arg
        130
```

<210> SEQ ID NO 331
<211> LENGTH: 120
<212> TYPE: PRT
<213> ORGANISM: Artificial Sequence
<220> FEATURE:
<223> OTHER INFORMATION: human C-IL-13-S construct

<400> SEQUENCE: 331

```
Leu Ala Cys Gly Gly Gly Gly Gly Pro Val Pro Pro Ser Thr Ala
 1               5                  10                  15

Leu Arg Glu Leu Ile Glu Glu Leu Val Asn Ile Thr Gln Asn Gln Lys
             20                  25                  30

Ala Pro Leu Cys Asn Gly Ser Met Val Trp Ser Ile Asn Leu Thr Ala
         35                  40                  45

Gly Met Tyr Cys Ala Ala Leu Glu Ser Leu Ile Asn Val Ser Gly Cys
     50                  55                  60

Ser Ala Ile Glu Lys Thr Gln Arg Met Leu Ser Gly Phe Cys Pro His
```

```
                65                  70                  75                  80
Lys Val Ser Ala Gly Gln Phe Ser Ser Leu His Val Arg Asp Thr Lys
                    85                  90                  95
Ile Glu Val Ala Gln Phe Val Lys Asp Leu Leu His Leu Lys Lys
                100                 105                 110
Leu Phe Arg Glu Gly Arg Phe Asn
            115                 120

<210> SEQ ID NO 332
<211> LENGTH: 136
<212> TYPE: PRT
<213> ORGANISM: Artificial Sequence
<220> FEATURE:
<223> OTHER INFORMATION: mouse C-IL-5-E construct

<400> SEQUENCE: 332

Ala Leu Val Gly Cys Gly Gly Pro Lys Pro Ser Thr Pro Pro Gly Ser
1               5                   10                  15
Ser Gly Gly Ala Pro Ala Ser Met Glu Ile Pro Met Ser Thr Val Val
                20                  25                  30
Lys Glu Thr Leu Thr Gln Leu Ser Ala His Arg Ala Leu Leu Thr Ser
            35                  40                  45
Asn Glu Thr Met Arg Leu Pro Val Pro Thr His Lys Asn His Gln Leu
    50                  55                  60
Cys Ile Gly Glu Ile Phe Gln Gly Leu Asp Ile Leu Lys Asn Gln Thr
65                  70                  75                  80
Val Arg Gly Gly Thr Val Glu Met Leu Phe Gln Asn Leu Ser Leu Ile
                85                  90                  95
Lys Lys Tyr Ile Asp Arg Gln Lys Glu Lys Cys Gly Glu Glu Arg Arg
                100                 105                 110
Arg Thr Arg Gln Phe Leu Asp Tyr Leu Gln Glu Phe Leu Gly Val Met
            115                 120                 125
Ser Thr Glu Trp Ala Met Glu Gly
    130                 135

<210> SEQ ID NO 333
<211> LENGTH: 134
<212> TYPE: PRT
<213> ORGANISM: Artificial Sequence
<220> FEATURE:
<223> OTHER INFORMATION: mouse C-IL-5-F construct

<400> SEQUENCE: 333

Ala Asp Pro Gly Cys Gly Gly Gly Gly Leu Ala Met Glu Ile Pro
1               5                   10                  15
Met Ser Thr Val Val Lys Glu Thr Leu Thr Gln Leu Ser Ala His Arg
                20                  25                  30
Ala Leu Leu Thr Ser Asn Glu Thr Met Arg Leu Pro Val Pro Thr His
            35                  40                  45
Lys Asn His Gln Leu Cys Ile Gly Glu Ile Phe Gln Gly Leu Asp Ile
    50                  55                  60
Leu Lys Asn Gln Thr Val Arg Gly Gly Thr Val Glu Met Leu Phe Gln
65                  70                  75                  80
Asn Leu Ser Leu Ile Lys Lys Tyr Ile Asp Arg Gln Lys Glu Lys Cys
                85                  90                  95
Gly Glu Glu Arg Arg Arg Thr Arg Gln Phe Leu Asp Tyr Leu Gln Glu
                100                 105                 110
```

```
Phe Leu Gly Val Met Ser Thr Glu Trp Ala Met Glu Gly Leu Glu Val
            115                 120                 125

Leu Ala Ile Glu Gly Arg
        130
```

<210> SEQ ID NO 334
<211> LENGTH: 121
<212> TYPE: PRT
<213> ORGANISM: Artificial Sequence
<220> FEATURE:
<223> OTHER INFORMATION: mouse C-IL-5-S construct

<400> SEQUENCE: 334

```
Leu Ala Cys Gly Gly Gly Gly Met Glu Ile Pro Met Ser Thr Val
1               5                   10                  15

Val Lys Glu Thr Leu Thr Gln Leu Ser Ala His Arg Ala Leu Leu Thr
            20                  25                  30

Ser Asn Glu Thr Met Arg Leu Pro Val Pro Thr His Lys Asn His Gln
        35                  40                  45

Leu Cys Ile Gly Glu Ile Phe Gln Gly Leu Asp Ile Leu Lys Asn Gln
    50                  55                  60

Thr Val Arg Gly Gly Thr Val Glu Met Leu Phe Gln Asn Leu Ser Leu
65                  70                  75                  80

Ile Lys Lys Tyr Ile Asp Arg Gln Lys Glu Lys Cys Gly Glu Glu Arg
                85                  90                  95

Arg Arg Thr Arg Gln Phe Leu Asp Tyr Leu Gln Glu Phe Leu Gly Val
            100                 105                 110

Met Ser Thr Glu Trp Ala Met Glu Gly
            115                 120
```

<210> SEQ ID NO 335
<211> LENGTH: 138
<212> TYPE: PRT
<213> ORGANISM: Artificial Sequence
<220> FEATURE:
<223> OTHER INFORMATION: human C-IL-5-E construct

<400> SEQUENCE: 335

```
Ala Leu Val Gly Cys Gly Gly Pro Lys Pro Ser Thr Pro Pro Gly Ser
1               5                   10                  15

Ser Gly Gly Ala Pro Ala Ser Ile Pro Thr Glu Ile Pro Thr Ser Ala
            20                  25                  30

Leu Val Lys Glu Thr Leu Ala Leu Leu Ser Thr His Arg Thr Leu Leu
        35                  40                  45

Ile Ala Asn Glu Thr Leu Arg Ile Pro Val Pro Val His Lys Asn His
    50                  55                  60

Gln Leu Cys Thr Glu Glu Ile Phe Gln Gly Ile Gly Thr Leu Glu Ser
65                  70                  75                  80

Gln Thr Val Gln Gly Gly Thr Val Glu Arg Leu Phe Lys Asn Leu Ser
                85                  90                  95

Leu Ile Lys Lys Tyr Ile Asp Gly Gln Lys Lys Lys Cys Gly Glu Glu
            100                 105                 110

Arg Arg Arg Val Asn Gln Phe Leu Asp Tyr Leu Gln Glu Phe Leu Gly
        115                 120                 125

Val Met Asn Thr Glu Trp Ile Ile Glu Ser
    130                 135
```

<210> SEQ ID NO 336

```
<211> LENGTH: 136
<212> TYPE: PRT
<213> ORGANISM: Artificial Sequence
<220> FEATURE:
<223> OTHER INFORMATION: human C-IL-5-F construct

<400> SEQUENCE: 336

Ala Asp Pro Gly Cys Gly Gly Gly Gly Leu Ala Ile Pro Thr Glu
1               5                   10                  15

Ile Pro Thr Ser Ala Leu Val Lys Glu Thr Leu Ala Leu Leu Ser Thr
                20                  25                  30

His Arg Thr Leu Leu Ile Ala Asn Glu Thr Leu Arg Ile Pro Val Pro
            35                  40                  45

Val His Lys Asn His Gln Leu Cys Thr Glu Glu Ile Phe Gln Gly Ile
    50                  55                  60

Gly Thr Leu Glu Ser Gln Thr Val Gln Gly Thr Val Glu Arg Leu
65                  70                  75                  80

Phe Lys Asn Leu Ser Leu Ile Lys Lys Tyr Ile Asp Gly Gln Lys Lys
                85                  90                  95

Lys Cys Gly Glu Glu Arg Arg Arg Val Asn Gln Phe Leu Asp Tyr Leu
            100                 105                 110

Gln Glu Phe Leu Gly Val Met Asn Thr Glu Trp Ile Ile Glu Ser Leu
        115                 120                 125

Glu Val Leu Ala Ile Glu Gly Arg
        130                 135

<210> SEQ ID NO 337
<211> LENGTH: 123
<212> TYPE: PRT
<213> ORGANISM: Artificial Sequence
<220> FEATURE:
<223> OTHER INFORMATION: human C-IL-5-S construct

<400> SEQUENCE: 337

Leu Ala Cys Gly Gly Gly Gly Ile Pro Thr Glu Ile Pro Thr Ser
1               5                   10                  15

Ala Leu Val Lys Glu Thr Leu Ala Leu Leu Ser Thr His Arg Thr Leu
                20                  25                  30

Leu Ile Ala Asn Glu Thr Leu Arg Ile Pro Val Pro Val His Lys Asn
            35                  40                  45

His Gln Leu Cys Thr Glu Glu Ile Phe Gln Gly Ile Gly Thr Leu Glu
    50                  55                  60

Ser Gln Thr Val Gln Gly Gly Thr Val Glu Arg Leu Phe Lys Asn Leu
65                  70                  75                  80

Ser Leu Ile Lys Lys Tyr Ile Asp Gly Gln Lys Lys Lys Cys Gly Glu
                85                  90                  95

Glu Arg Arg Arg Val Asn Gln Phe Leu Asp Tyr Leu Gln Glu Phe Leu
            100                 105                 110

Gly Val Met Asn Thr Glu Trp Ile Ile Glu Ser
        115                 120

<210> SEQ ID NO 338
<211> LENGTH: 27
<212> TYPE: PRT
<213> ORGANISM: Artificial Sequence
<220> FEATURE:
<223> OTHER INFORMATION: primer NheIL13-F

<400> SEQUENCE: 338
```

```
Cys Thr Ala Gly Cys Thr Ala Gly Cys Cys Gly Gly Cys Cys Gly
1               5                   10                  15

Gly Thr Gly Cys Cys Ala Ala Gly Ala Thr Cys
            20                  25
```

<210> SEQ ID NO 339
<211> LENGTH: 26
<212> TYPE: DNA
<213> ORGANISM: Artificial Sequence
<220> FEATURE:
<223> OTHER INFORMATION: primer XhoIL13-R

<400> SEQUENCE: 339
tttctcgagg aagggccgt ggcgaa        26

<210> SEQ ID NO 340
<211> LENGTH: 55
<212> TYPE: DNA
<213> ORGANISM: Artificial Sequence
<220> FEATURE:
<223> OTHER INFORMATION: primer Spelinker3-F1

<400> SEQUENCE: 340
ccccgccggg ttcttctggc ggtgctccgg ctagcatgga gattcccatg agcac        55

<210> SEQ ID NO 341
<211> LENGTH: 52
<212> TYPE: DNA
<213> ORGANISM: Artificial Sequence
<220> FEATURE:
<223> OTHER INFORMATION: Primer SpeNlinker3-F2

<400> SEQUENCE: 341
ttttactagt tggttgcggc ggcccgaaac cgagcacccc gccgggttct tc        52

<210> SEQ ID NO 342
<211> LENGTH: 49
<212> TYPE: DNA
<213> ORGANISM: Artificial Sequence
<220> FEATURE:
<223> OTHER INFORMATION: Primer IL5StopXho-R

<400> SEQUENCE: 342
ttttgcggcc gcgtttaaac tcgagttatt agccttccat tgcccactc        49

<210> SEQ ID NO 343
<211> LENGTH: 25
<212> TYPE: DNA
<213> ORGANISM: Artificial Sequence
<220> FEATURE:
<223> OTHER INFORMATION: Primer BamH1-FLK1-F

<400> SEQUENCE: 343
cgcggatcca ttcatcgcct ctgtc        25

<210> SEQ ID NO 344
<211> LENGTH: 26
<212> TYPE: DNA
<213> ORGANISM: Artificial Sequence
<220> FEATURE:
<223> OTHER INFORMATION: Primer Nhe1-FLK1-B

<400> SEQUENCE: 344
ctagctagct tgtgtgaac tcggac        26

```
<210> SEQ ID NO 345
<211> LENGTH: 205
<212> TYPE: PRT
<213> ORGANISM: Artificial Sequence
<220> FEATURE:
<223> OTHER INFORMATION: mVEGFR-2 (2-3) fragment

<400> SEQUENCE: 345

Pro Phe Ile Ala Ser Val Ser Asp Gln His Gly Ile Val Tyr Ile Thr
1               5                   10                  15

Glu Asn Lys Asn Lys Thr Val Val Ile Pro Cys Arg Gly Ser Ile Ser
            20                  25                  30

Asn Leu Asn Val Ser Leu Cys Ala Arg Tyr Pro Glu Lys Arg Phe Val
        35                  40                  45

Pro Asp Gly Asn Arg Ile Ser Trp Asp Ser Glu Ile Gly Phe Thr Leu
    50                  55                  60

Pro Ser Tyr Met Ile Ser Tyr Ala Gly Met Val Phe Cys Glu Ala Lys
65                  70                  75                  80

Ile Asn Asp Glu Thr Tyr Gln Ser Ile Met Tyr Ile Val Val Val
                85                  90                  95

Gly Tyr Arg Ile Tyr Asp Val Ile Leu Ser Pro Pro His Glu Ile Glu
                100                 105                 110

Leu Ser Ala Gly Glu Lys Leu Val Leu Asn Cys Thr Ala Arg Thr Glu
        115                 120                 125

Leu Asn Val Gly Leu Asp Phe Thr Trp His Ser Pro Pro Ser Lys Ser
    130                 135                 140

His His Lys Lys Ile Val Asn Arg Asp Val Lys Pro Phe Pro Gly Thr
145                 150                 155                 160

Val Ala Lys Met Phe Leu Ser Thr Leu Thr Ile Glu Ser Val Thr Lys
                165                 170                 175

Ser Asp Gln Gly Glu Tyr Thr Cys Val Ala Ser Ser Gly Arg Met Ile
            180                 185                 190

Lys Arg Asn Arg Thr Phe Val Arg Val His Thr Lys Pro
        195                 200                 205

<210> SEQ ID NO 346
<211> LENGTH: 263
<212> TYPE: PRT
<213> ORGANISM: Artificial Sequence
<220> FEATURE:
<223> OTHER INFORMATION: human C-LT_49-306 fragment

<400> SEQUENCE: 346

Leu Ala Cys Gly Gly Gln Asp Gln Gly Arg Arg Val Glu Lys Ile Ile
1               5                   10                  15

Gly Ser Gly Ala Gln Ala Gln Lys Arg Leu Asp Ser Lys Pro Ser
            20                  25                  30

Cys Ile Leu Pro Ser Pro Ser Ser Leu Ser Glu Thr Pro Asp Pro Arg
        35                  40                  45

Leu His Pro Gln Arg Ser Asn Ala Ser Arg Asn Leu Ala Ser Thr Ser
    50                  55                  60

Gln Gly Pro Val Ala Gln Ser Ser Arg Glu Ala Ser Ala Trp Met Thr
65                  70                  75                  80

Ile Leu Ser Pro Ala Ala Asp Ser Thr Pro Asp Pro Gly Val Gln Gln
                85                  90                  95

Leu Pro Lys Gly Glu Pro Glu Thr Asp Leu Asn Pro Glu Leu Pro Ala
            100                 105                 110
```

```
Ala His Leu Ile Gly Ala Trp Met Ser Gly Gln Gly Leu Ser Trp Glu
        115                 120                 125

Ala Ser Gln Glu Glu Ala Phe Leu Arg Ser Gly Ala Gln Phe Ser Pro
130                 135                 140

Thr His Gly Leu Ala Leu Pro Gln Asp Gly Val Tyr Tyr Leu Tyr Cys
145                 150                 155                 160

His Val Gly Tyr Arg Gly Arg Thr Pro Pro Ala Gly Arg Ser Arg Ala
                165                 170                 175

Arg Ser Leu Thr Leu Arg Ser Ala Leu Tyr Arg Ala Gly Ala Tyr
            180                 185                 190

Gly Arg Gly Ser Pro Glu Leu Leu Glu Gly Ala Glu Thr Val Thr
            195                 200                 205

Pro Val Val Asp Pro Ile Gly Tyr Gly Ser Leu Trp Tyr Thr Ser Val
210                 215                 220

Gly Phe Gly Gly Leu Ala Gln Leu Arg Ser Gly Glu Arg Val Tyr Val
225                 230                 235                 240

Asn Ile Ser His Pro Asp Met Val Asp Tyr Arg Arg Gly Lys Thr Phe
                245                 250                 255

Phe Gly Ala Val Met Val Gly
            260
```

```
<210> SEQ ID NO 347
<211> LENGTH: 186
<212> TYPE: PRT
<213> ORGANISM: Artificial Sequence
<220> FEATURE:
<223> OTHER INFORMATION: human C-LT_126-306 fragment

<400> SEQUENCE: 347
```

```
Leu Ala Cys Gly Gly Ser Pro Ala Ala Asp Ser Thr Pro Asp Pro Gly
1               5                   10                  15

Val Gln Leu Pro Lys Gly Glu Pro Glu Thr Asp Leu Asn Pro Glu
            20                  25                  30

Leu Pro Ala Ala His Leu Ile Gly Ala Trp Met Ser Gly Gln Gly Leu
            35                  40                  45

Ser Trp Glu Ala Ser Gln Glu Glu Ala Phe Leu Arg Ser Gly Ala Gln
 50                  55                  60

Phe Ser Pro Thr His Gly Leu Ala Leu Pro Gln Asp Gly Val Tyr Tyr
65                  70                  75                  80

Leu Tyr Cys His Val Gly Tyr Arg Gly Arg Thr Pro Pro Ala Gly Arg
                85                  90                  95

Ser Arg Ala Arg Ser Leu Thr Leu Arg Ser Ala Leu Tyr Arg Ala Gly
            100                 105                 110

Gly Ala Tyr Gly Arg Gly Ser Pro Glu Leu Leu Leu Glu Gly Ala Glu
        115                 120                 125

Thr Val Thr Pro Val Val Asp Pro Ile Gly Tyr Gly Ser Leu Trp Tyr
130                 135                 140

Thr Ser Val Gly Phe Gly Gly Leu Ala Gln Leu Arg Ser Gly Glu Arg
145                 150                 155                 160

Val Tyr Val Asn Ile Ser His Pro Asp Met Val Asp Tyr Arg Arg Gly
                165                 170                 175

Lys Thr Phe Phe Gly Ala Val Met Val Gly
            180                 185
```

```
<210> SEQ ID NO 348
<211> LENGTH: 117
```

-continued

```
<212> TYPE: PRT
<213> ORGANISM: Artificial Sequence
<220> FEATURE:
<223> OTHER INFORMATION: Modified human prion protein fragment

<400> SEQUENCE: 348

Val Gly Gly Leu Gly Gly Tyr Met Leu Gly Ser Ala Met Ser Arg Pro
1               5                   10                  15

Ile Ile His Phe Gly Ser Asp Tyr Glu Asp Arg Tyr Tyr Arg Glu Asn
            20                  25                  30

Met His Arg Tyr Pro Asn Gln Val T

-continued

```
                     20                  25                  30
Met Tyr Arg Tyr Pro Asn Gln Val Tyr Tyr Arg Pro Val Asp Arg Tyr
        35                  40                  45

Ser Asn Gln Asn Asn Phe Val His Asp Cys Val Asn Ile Thr Val Lys
    50                  55                  60

Gln His Thr Val Thr Thr Thr Lys Gly Glu Asn Phe Thr Glu Thr
65                  70                  75                  80

Asp Ile Lys Ile Met Glu Arg Val Val Glu Gln Met Cys Ile Thr Gln
                85                  90                  95

Tyr Gln Arg Glu Ser Gln Ala Tyr Tyr Gln Arg Gly Arg Leu Ala Gly
            100                 105                 110

Gly Gly Gly Cys Gly
            115
```

MOLECULAR ANTIGEN ARRAY

This application claims priority benefit of U.S. provisional application No. 60/262,379, filed Jan. 19, 2001, U.S. provisional application No. 60/288,549, filed May 4, 2001, U.S. provisional application No. 60/326,998, filed Oct. 5, 2001, and U.S. provisional application No. 60/331,045, filed Nov. 7, 2001, which are incorporated herein by reference in their entireties.

BACKGROUND OF THE INVENTION

1. Field of the Invention

The present invention is related to the fields of molecular biology, virology, immunology and medicine. The invention provides a composition comprising an ordered and repetitive antigen or antigenic determinant array. The invention also provides a process for producing an antigen or antigenic determinant in an ordered and repetitive array. The ordered and repetitive antigen or antigenic determinant is useful in the production of vaccines for the treatment of infectious diseases, the treatment of allergies and as a pharmaccine to prevent or cure cancer and to efficiently induce self-specific immune responses, in particular antibody responses.

2. Background Art

WO 00/3227 describes compositions and processes for the production of ordered and repetitive antigen or antigenic determinant arrays. The compositions are useful for the production of vaccines for the prevention of infectious diseases, the treatment of allergies and the treatment of cancers. The compositions comprise a core particle, such as a virus or a virus-like particle, to which at least one antigen or one antigenic determinant, is associated by way of at least one non-peptide bond leading to the ordered and repetitive antigen array.

Virus-like particles (VLPs) are being exploited in the area of vaccine production because of both their structural properties and their non-infectious nature. VLPs are supermolecular structures built in a symmetric manner from many protein molecules of one or more types. They lack the viral genome and, therefore, are noninfectious. VLPs can often be produced in large quantities by heterologous expression and can be easily purified.

Examples of VLPs include the capsid proteins of Hepatitis B virus (Ulrich, et al., *Virus Res.* 50:141–182 (1998)), measles virus (Warnes, et al., *Gene* 160:173–178 (1995)), Sindbis virus, rotavirus (U.S. Pat. No. 5,071,651 and U.S. Pat. No. 5,374,426), foot-and-mouth-disease virus (Twomey, et al., *Vaccine* 13:1603–1610, (1995)), Norwalk virus (Jiang, X., et al., *Science* 250:1580–1583 (1990); Matsui, S. M., et al., *J. Clin. Invest.* 87:1456–1461 (1991)), the retroviral GAG protein (WO 96/30523), the retrotransposon Ty protein p1, the surface protein of Hepatitis B virus (WO 92/11291) and human papilloma virus (WO 98/15631).

It is generally difficult to induce immune responses against self-molecules due to immunological tolerance. Specifically, lymphocytes with a specificity for self-molecules are usually hypo- or even unresponsive if triggered by conventional vaccination strategies.

The amyloid B peptide ($A\beta_{1-42}$) has a central role in the neuropathology of Alzheimers disease. Region specific, extracellular accumulation of $A\beta$ peptide is accompanied by microgliosis, cytoskeletal changes, dystrophic neuritis and synaptic loss. These pathological alterations are thought to be linked to the cognitive decline that defines the disease.

In a mouse model of Alzheimer disease, transgenic animals engineered to produce $A\beta_{1-42}$ (PDAPP-mice), develop plaques and neuron damage in their brains. Recent work has shown immunization of young PDAPP-mice, using $A\beta_{1-42}$, resulted in inhibition of plaque formation and associated dystrophic neuritis (Schenk, D. et al., *Nature* 400:173–77 (1999)).

Furthermore immunization of older PDAPP mice that had already developed AD-like neuropathologies, reduced the extent and progression of the neuropathologies. The immunization protocol for these studies was as follows; peptide was dissolved in aqueous buffer and mixed 1:1 with complete Freunds adjuvant (for primary dose) to give a peptide concentration of 100 µg/dose. Subsequent boosts used incomplete Freunds adjuvant. Mice received 11 immunizations over an 11 month period. Antibodies titres greater than 1:10 000 were achieved and maintained. Hence, immunization may be an effective prophylactic and therapeutic action against Alzheimer disease.

In another study, peripherally administered antibodies raised against $A\beta_{1-42}$, were able to cross the blood-brain barrier, bind $A\beta$ peptide, and induce clearance of pre-existing amyloid (Bard, F. et al., *Nature Medicine* 6:916–19 (2000)). This study utilized either polyclonal antibodies raised against $A\beta_{1-42}$, or monoclonal antibodies raised against synthetic fragments derived from different regions of $A\beta$. Thus induction of antibodies can be considered as a potential therapeutic treatment for Alzheimer disease.

It is well established that the administration of purified proteins alone is usually not sufficient to elicit a strong immune response; isolated antigen generally must be given together with helper substances called adjuvants. Within these adjuvants, the administered antigen is protected against rapid degradation, and the adjuvant provides an extended release of a low level of antigen.

As indicated, one of the key events in Alzheimer's Disease (AD) is the deposition of amyloid as insoluble fibrous masses (amyloidogenesis) resulting in extracellular neuritic plaques and deposits around the walls of cerebral blood vessels (for review see Selkoe, D. J. (1999) Nature. 399, A23–31). The major constituent of the neuritic plaques and congophilic angiopathy is amyloid $\beta$ ($A\beta$), although these deposits also contain other proteins such as glycosaminoglycans and apolipoproteins. $A\beta$ is proteolytically cleaved from a much larger glycoprotein known as Amyloid Precursor Proteins (APPs), which comprises isoforms of 695–770 amino acids with a single hydrophobic transmembrane region. $A\beta$ forms a group of peptides up to 43 amino acids in length showing considerable amino- and carboxy-terminal heterogeneity (truncation) as well as modifications (Roher, A. E., Palmer, K. C., Chau, V., & Ball, M. J. (1988) J. Cell Biol. 107, 2703–2716. Roher, A. E., Palmer, K. C., Yurewicz, E. C., Ball, M. J., & Greenberg, B. D. (1993) J. Neurochem. 61, 1916–1926). Prominent isoforms are A• 1–40 and 1–42. It has a high propensity to form 1-sheets aggregating into fibrils, which ultimately leads to the amyloid. Recent studies demonstrated that a vaccination-induced reduction in brain amyloid deposits resulted in cognitive improvements (Schenk, D., Barbour, R., Dunn, W., Gordon, G., Grajeda, H., Guido, T., Hu, K., Huang, J., Johnson-Wood, K., Khan, K., et al. (1999) Nature. 400, 173–177).

We have surprisingly found that self-molecules or self-antigens presented in a highly ordered and repetitive array were able to efficiently induce self-specific immune responses, in particular antibody responses. Moreover, such responses could even be induced in the absence of adjuvants that otherwise non-specifically activate antigen presenting cells and other immune cells.

BRIEF SUMMARY OF THE INVENTION

The present invention provides compositions, which comprises highly ordered and repetitive antigen or antigenic determinant arrays, as well as the processes for their production and their uses. Thus, the compositions of the invention are useful for the production of vaccines for the prevention of infectious diseases, the treatment of allergies and cancers, and to efficiently induce self-specific immune responses, in particular antibody responses.

In a first aspect, the present invention provides a novel composition comprising, or alternatively consisting of, (A) a non-natural molecular scaffold and (B) an antigen or antigenic determinant. The non-natural molecular scaffold comprises, or alternatively consists of, (i) a core particle selected from the group consisting of (1) a core particle of non-natural origin and (2) a core particle of natural origin; and (ii) an organizer comprising at least one first attachment site, wherein said organizer is connected to said core particle by at least one covalent bond. The antigen or antigenic determinant is a self antigen or a fragment thereof and has at least one second attachment site which is selected from the group consisting of (i) an attachment site not naturally occurring with said antigen or antigenic determinant; and (ii) an attachment site naturally occurring with said antigen or antigenic determinant. The invention provides for an ordered and repetitive self antigen array through an association of the second attachment site to the first attachment site by way of at least one non-peptide bond. Thus, the self antigen or self antigenic determinant and the non-natural molecular scaffold are brought together through this association of the first and the second attachment site to form an ordered and repetitive antigen array.

In a second aspect, the present invention provides a novel composition comprising, or alternatively consisting of, (A) a non-natural molecular scaffold and (B) an antigen or antigenic determinant. The non-natural molecular scaffold comprises, or alternatively consists of, (i) a core particle and (ii) an organizer comprising at least one first attachment site, wherein said core particle is a virus-like particle comprising recombinant proteins, or fragments thereof, of a bacteriophage, and wherein said organizer is connected to said core particle by at least one covalent bond. The antigen or antigenic determinant has at least one second attachment site which is selected from the group consisting of (i) an attachment site not naturally occurring with said antigen or antigenic determinant; and (ii) an attachment site naturally occurring with said antigen or antigenic determinant. The invention provides for an ordered and repetitive antigen array through an association of the second attachment site to the first attachment site by way of at least one non-peptide bond.

In a third aspect, the present invention provides a novel composition comprising, or alternatively consisting of, (A) a non-natural molecular scaffold and (B) an antigen or antigenic determinant. The non-natural molecular scaffold comprises, or alternatively consists of, (i) a core particle selected from the group consisting of (1) a core particle of non-natural origin and (2) a core particle of natural origin; and (ii) an organizer comprising at least one first attachment site, wherein said organizer is connected to said core particle by at least one covalent bond. The antigen or antigenic determinant is an amyloid beta peptide ($A\beta_{1-42}$) or a fragment thereof, and has at least one second attachment site which is selected from the group consisting of (i) an attachment site not naturally occurring with said antigen or antigenic determinant; and (ii) an attachment site naturally occurring with said antigen or antigenic determinant. The invention provides for an ordered and repetitive antigen array through an association of the second attachment site to the first attachment site by way of at least one non-peptide bond.

In a fourth aspect, the present invention provides a novel composition comprising, or alternatively consisting of, (A) a non-natural molecular scaffold and (B) an antigen or antigenic determinant. The non-natural molecular scaffold comprises, or alternatively consists of, (i) a core particle selected from the group consisting of (1) a core particle of non-natural origin and (2) a core particle of natural origin; and (ii) an organizer comprising at least one first attachment site, wherein said organizer is connected to said core particle by at least one covalent bond. The antigen or antigenic determinant is an anti-idiotypic antibody or an anti-idiotypic antibody fragment and has at least one second attachment site which is selected from the group consisting of (i) an attachment site not naturally occurring with said antigen or antigenic determinant; and (ii) an attachment site naturally occurring with said antigen or antigenic determinant. The invention provides for an ordered and repetitive antigen array through an association of the second attachment site to the first attachment site by way of at least one non-peptide bond.

Further aspects as well as preferred embodiments and advantages of the present invention will become apparent in the following as well as, in particular, in the light of the detailed description, the examples and the accompanying claims.

In a preferred embodiment of the present invention, the core particle is a virus-like particle comprising recombinant proteins of a RNA-phage, preferably selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; and l) bacteriophage PP7. Most preferred are bacteriophage Qβ and bacteriophage fr.

In another preferred embodiment of the invention, the recombinant proteins of the RNA-phages comprise wild type coat proteins.

In further preferred embodiment of the invention, the recombinant proteins of the RNA-phages comprise mutant coat proteins.

In yet another embodiment, the core particle comprises, or alternatively consists of, one or more different Hepatitis core (capsid) proteins (HBcAgs). In a related embodiment, one or more cysteine residues of these HBcAgs are either deleted or substituted with another amino acid residue (e.g., a serine residue). In a specific embodiment, the cysteine residues of the HBcAg used to prepare compositions of the invention which correspond to amino acid residues 48 and 107 in SEQ ID NO:134 are either deleted or substituted with another amino acid residue (e.g., a serine residue).

Further, the HBcAg variants used to prepare compositions of the invention will generally be variants which retain the ability to associate with other HBcAgs to form dimeric or multimeric structures that present ordered and repetitive antigen or antigenic determinant arrays.

In another embodiment, the non-natural molecular scaffold comprises, or alternatively consists of, pili or pilus-like structures that have been either produced from pilin proteins or harvested from bacteria. When pili or pilus-like structures are used to prepare compositions of the invention, they may be formed from products of pilin genes which are naturally resident in the bacterial cells but have been modified by genetically engineered (e.g., by homologous recombination) or pilin genes which have been introduced into these cells.

In a related embodiment, the core particle comprises, or alternatively consists of, pili or pilus-like structures that have been either prepared from pilin proteins or harvested from bacteria. These core particles may be formed from products of pilin genes naturally resident in the bacterial cells.

In a particular embodiment, the organizer may comprise at least one first attachment site. The first and the second attachment sites are particularly important elements of compositions of the invention. In various embodiments of the invention, the first and/or the second attachment site may be an antigen and an antibody or antibody fragment thereto; biotin and avidin; streptavidin and biotin; a receptor and its ligand; a ligand-binding protein and its ligand; interacting leucine zipper polypeptides; an amino group and a chemical group reactive thereto; a carboxyl group and a chemical group reactive thereto; a sulfhydryl group and a chemical group reactive thereto; or a combination thereof.

In a further preferred embodiment, the composition further comprises an amino acid linker. Preferably the amino acid linker comprises, or alternatively consists of, the second attachment site. The second attachment site mediates a directed and ordered association and binding, respectively, of the antigen to the core particle. An important function of the amino acid linker is to further ensure proper display and accessibility of the second attachment site, and thus to facilitate the binding of the antigen to the core particle, in particular by way of chemical cross-linking. Another important property of the amino acid linker is to further ensure optimal accessibility and, in particular, reactivity of the second attachment site. These properties of the amino acid linker are of even more importance for protein antigens.

In another preferred embodiment, the amino acid linker is selected from the group consisting of (a) CGG; (b) N-terminal gamma 1-linker; (c) N-terminal gamma 3-linker; (d) Ig hinge regions; (e) N-terminal glycine linkers; (f) $(G)_kC(G)_n$ with n=0–12 and k=0–5; (g) N-terminal glycine-serine linkers; (h) $(G)_kC(G)_m(S)1(GGGGS)_n$ with n=0–3, k=0–5, m=0–10, 1=0–2 (SEQ ID NO:424; (i) GGC; (k) GGC-NH2; (1) C-terminal gamma 1-linker; (m) C-terminal gamma 3-linker; (n) C-terminal glycine linkers; (o) $(G)_nC(G)_k$ with n=0–12 and k=0–5; (p) C-terminal glycine-serine linkers; (q) $(G)_m(S)1(GGGGS)_n(G)_oC(G)_k$ with n=0–3, k=0–5, m=0–10, 1=0–2, and o=0–8 (SEQ ID NO:425).

An important property of glycine and glycine serine linkers is their flexibility, in particular their structural flexibility, allowing a wide range of conformations and disfavoring folding into structures precluding accessibility of the second attachment site. As glycine and glycine serine linkers contain either no or a limited amount of side chain residues, they have limited tendency for engagement into extensive interactions with the antigen, thus, further ensuring accessibility of the second attachment site. Serine residues within the glycine serine linkers confer improved solubility properties to these linkers. Accordingly, the insertion of one or two amino acids either in tandem or isolation, and in particular of polar or charged amino acid residues, in the glycine or glycine serine amino acid linker, is also encompassed by the teaching of the invention.

In a further preferred embodiment, the amino acid linker is either GGC-NH2, GGC-NMe, GGC-N(Me)2, GGC-NHET or GGC-N(Et)2, in which the C-terminus of the cysteine residue of GGC is amidated. These amino acid linkers are preferred in particular for peptide antigens, and in particular for embodiments, in which the antigen or antigenic determinant with said second attachment site comprises Aβ peptides or fragments thereof. Particular preferred is GGC-NH2. In another embodiment, the amino acid linker is an Immunoglobulin (Ig) hinge region. Fragments of Ig hinge regions are also within the scope of the invention, as well as Ig hinge regions modified with glycine residues. Preferably, the Ig hinge regions contain only one cysteine residue. It is to be understood, that the single cysteine residue of the Ig hinge region amino acid linker can be located at several positions within the linker sequence, and a man skilled in the art would know how to select them with the guidance of the teachings of this invention.

In one embodiment, the invention provides the coupling of almost any antigen of choice to the surface of a virus, bacterial pilus, structure formed from bacterial pilin, bacteriophage, virus-like particle or viral capsid particle. By bringing an antigen into a quasi-crystalline 'virus-like' structure, the invention exploits the strong antiviral immune reaction of a host for the production of a highly efficient immune response, i.e., a vaccination, against the displayed antigen.

In yet another embodiment, the antigen may be selected from the group consisting of: (1) a protein suited to induce an immune response against cancer cells; (2) a protein suited to induce an immune response against infectious diseases; (3) a protein suited to induce an immune response against allergens; (4) a protein suited to induce an improved response against self-antigens; and (5) a protein suited to induce an immune response in farm animals or pets. In another embodiment, the first attachment site and/or the second attachment site are selected from the group comprising: (1) a genetically engineered lysine residue and (2) a genetically engineered cysteine residue, two residues that may be chemically linked together.

In a yet further preferred embodiment, first attachment site comprises or is an amino group and said second attachment site comprises or is a sulfhydryl group. Preferably, the first attachment site comprises or is a lysine residue and said second attachment site comprises or is a cysteine residue.

The invention also includes embodiments where the organizer particle has only a single first attachment site and the antigen or antigenic determinant has only a single second attachment site. Thus, when an ordered and repetitive antigen array is prepared using such embodiments, each organizer will be bound to a single antigen or antigenic determinant.

In a further aspect, the invention provides compositions comprising, or alternatively consisting of, (a) a non-natural molecular scaffold comprising (i) a core particle selected from the group consisting of a core particle of non-natural origin and a core particle of natural origin, and (ii) an organizer comprising at least one first attachment site, wherein the core particle comprises, or alternatively consists of, a virus-like particle, a bacterial pilus, a pilus-like structure, or a modified HBcAg, or fragment thereof, and wherein the organizer is connected to the core particle by at least one covalent bond, and (b) an antigen or antigenic determinant with at least one second attachment site, the second attachment site being selected from the group consisting of (i) an attachment site not naturally occurring with the antigen or antigenic determinant and (ii) an attachment site naturally occurring with the antigen or antigenic determinant, wherein the second attachment site is capable of association through at least one non-peptide bond to the first attachment site, and wherein the antigen or antigenic determinant and the scaffold interact through the association to form an ordered and repetitive antigen array.

Other embodiments of the invention include processes for the production of compositions of the invention and a methods of medical treatment using vaccine compositions described herein.

It is to be understood that both the foregoing general description and the following detailed description are exemplary and explanatory only and are intended to provide further explanation of the invention as claimed.

In a still further aspect, the present invention provides a composition comprising a bacteriophage Qβ coat protein attached by a covalent bond to phospholipase A$_2$ protein, or a fragment thereof. In a preferred embodiment, the phospholipase A$_2$ protein, or a fragment thereof, and the bacteriophage Qβ coat protein interact through the covalent bond to form an ordered and repetitive antigen array. In another preferred embodiment, the covalent bond is not a peptide bond. In another preferred embodiment, the phospholipase A$_2$ protein includes an amino acid selected from the group consisting of the amino acid sequence of SEQ ID NO:168, the amino acid sequence of SEQ ID NO:169, the amino acid sequence of SEQ ID NO:170, the amino acid sequence of SEQ ID NO:171, the amino acid sequence of SEQ ID NO:172, the amino acid sequence of SEQ ID NO:173, the amino acid sequence of SEQ ID NO:174, and the amino acid sequence of SEQ ID NO:175.

The present invention also provides a method of making the composition comprising combining the bacteriophage Qβ coat protein and the phospholipase A$_2$ protein, wherein the bacteriophage Qβ coat protein and the phospholipase A$_2$ protein interact to form an antigen array.

In another aspect, the present invention also provides a composition comprising a non-natural molecular scaffold comprising a bacteriophage Qβ coat protein, and an organizer comprising at least one first attachment site, wherein the organizer is connected to the bacteriophage Qβ coat protein by at least one covalent bond; and phospholipase A$_2$ protein, or a fragment thereof, or a variant thereof with at least one second attachment site, the second attachment site being selected from the group consisting of: an attachment site not naturally occurring with the a phospholipase A$_2$ protein, or a fragment thereof; and an attachment site naturally occurring with the a phospholipase A$_2$ protein, or a fragment thereof, wherein the second attachment site associates through at least one non-peptide bond to the first attachment site, and wherein the antigen or antigenic determinant and the scaffold interact through the association to form an ordered and repetitive antigen array. In a preferred embodiment, the phospholipase A$_2$ protein includes an amino acid selected from the group consisting of the amino acid sequence of SEQ ID NO:168, the amino acid sequence of SEQ ID NO:169, the amino acid sequence of SEQ ID NO:170, the amino acid sequence of SEQ ID NO:171, the amino acid sequence of SEQ ID NO:172, the amino acid sequence of SEQ ID NO:173, the amino acid sequence of SEQ ID NO:174,, and the amino acid sequence of SEQ ID NO:175.

The present invention also provides a method of making the composition comprising combining the bacteriophage Qβ coat protein and the phospholipase A$_2$ protein, wherein the bacteriophage Qβ coat protein and the phospholipase A$_2$ protein interact to form an antigen array. Preferably, the antigen array is ordered and/or repetitive.

The present invention also provides a pharmaceutical composition comprising a phospholipase A$_2$ protein, and a pharmaceutically acceptable carrier. The present invention also provides a vaccine composition comprising a phospholipase A$_2$ protein. In a preferred embodiment, the vaccine composition of claim 31, further comprising at least one adjuvant.

The present invention also provides a method of treating an allergy to bee venom, comprising administering the pharmaceutical composition or the vaccine composition to a subject. As a result of such administration the subject exhibits a decreased immune response to the venom.

The invention also relates to a vaccine for the prevention of prion-mediated diseases by induction of anti-lymphotoxinβ, anti-lymphotoxinα or anti-lymphotoxinβ-receptor antibodies. The vaccine contains protein carries foreign to the immunized human or animal coupled to lymphotoxinβ or fragments thereof, lymphotoxinα or fragments thereof or the lymphotoxinβ receptor or fragments thereof. The vaccine is injected in humans or animals in order to induce antibodies specific for endogenous lymphotoxinβ, lymphotoxinα or lymphotoxinβ receptor. These induced anti-lymphotoxinβ, lymphotoxinα or anti-lymphotoxinβ receptor antibodies reduce or eliminate the pool of follicular dendritic cells present in lymphoid organs. Since prion-replication in lymphoid organs and transport to the central nervous system are impaired in the absence of follicular dendritic cells, this treatment inhibits progression of prion-mediated disease. In addition, blocking lymphotoxinβ is beneficial for patients with autoimmune diseases such as diabetes type I.

BRIEF DESCRIPTION OF THE FIGURES

FIG. 1A–1C Modular eukaryotic expression vectors for expression of antigens according to the invention (FIG. 1A:SEQ ID NO:426; FIG. 1B:SEQ ID NO:427; FIG. 1C:SEQ ID NO:428);

FIG. 2A–2C Cloning, expression and coupling of resistin to Qβ capsid protein (FIG. 2A, SEQ ID NO:429; FIG 2B, SEQ ID NO:430);

DETAILED DESCRIPTION OF THE INVENTION

1. Definitions

Figure 1B:
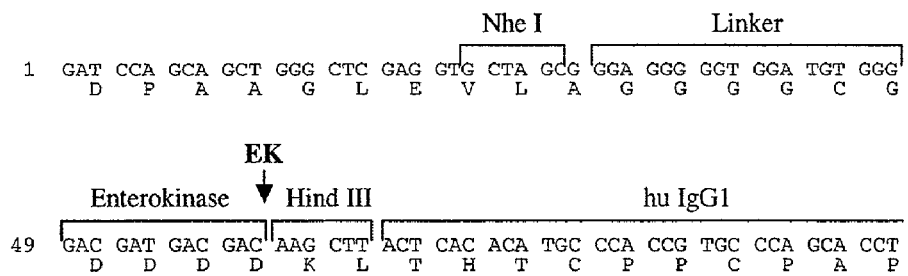

Alphavirus: As used herein, the term "alphavirus" refers to any of the RNA viruses included within the genus *Alphavirus*. Descriptions of the members of this genus are contained in Strauss and Strauss, *Microbiol. Rev.*, 58:491–562 (1994). Examples of alphaviruses include Aura virus, Bebaru virus, Cabassou virus, Chikungunya virus, Easter equine encephalomyelitis virus, Fort morgan virus, Getah virus, Kyzylagach virus, Mayoaro virus, Middleburg virus, Mucambo virus, Ndumu virus, Pixuna virus, Tonate virus, Triniti virus, Una virus, Western equine encephalomyelitis virus, Whataroa virus, Sindbis virus (SIN), Semliki forest virus (SFV), Venezuelan equine encephalomyelitis virus (VEE), and Ross River virus.

Antigen: As used herein, the term "antigen" is a molecule capable of being bound by an antibody. An antigen is additionally capable of inducing a humoral immune response and/or cellular immune response leading to the production of B- and/or T-lymphocytes. An antigen may have one or more epitopes (B- and T-epitopes). The specific reaction referred to above is meant to indicate that the antigen will react, in a highly selective manner, with its corresponding antibody and not with the multitude of other antibodies which may be evoked by other antigens.

Antigenic determinant: As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors.

Association: As used herein, the term "association" as it applies to the first and second attachment sites, refers to at least one non-peptide bond. The nature of the association may be covalent, ionic, hydrophobic, polar or any combination thereof.

Attachment Site, First: As used herein, the phrase "first attachment site" refers to an element of the "organizer", itself bound to the core particle in a non-random fashion, to which the second attachment site located on the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. Multiple first attachment sites are present on the surface of the non-natural molecular scaffold in a repetitive configuration.

Attachment Site, Second: As used herein, the phrase "second attachment site" refers to an element associated with the antigen or antigenic determinant to which the first attachment site of the "organizer" located on the surface of the non-natural molecular scaffold may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is not naturally occurring within the antigen or antigenic determinant, these antigen or antigenic constructs comprise an "amino acid linker". Such an amino acid linker, or also just termed "linker" within this specification, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker is, preferably, composed of naturally occuring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1–C6 alkyl-, cycloalkyl (C5,C6), aryl or heteroaryl moiety. Association between the antigen or antigenic determinant or optionally the second attachment site and the amino acid linker is preferably by way of at least one covalent bond, more preferably by way of at least one peptide bond.

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled," "fused" and "attached".

Core particle: As used herein, the term "core particle" refers to a rigid structure with an inherent repetitive organization that provides a foundation for attachment of an "organizer". A core particle as used herein may be the product of a synthetic process or the product of a biological process.

Coat protein(s): As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qb comprise the "Qβ CP" as well as the A1 protein.

C is-acting: As used herein, the phrase "cis-acting" sequence refers to nucleic acid sequences to which a replicase binds to catalyze the RNA-dependent replication of RNA molecules. These replication events result in the replication of the full-length and partial RNA molecules and, thus, the alphavirus subgenomic promoter is also a "cis-acting" sequence. C is-acting sequences may be located at or near the 5' end, 3' end, or both ends of a nucleic acid molecule, as well as internally.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

Heterologous sequence: As used herein, the term "heterologous sequence" refers to a second nucleotide sequence present in a vector of the invention. The term "heterologous sequence" also refers to any amino acid or RNA sequence encoded by a heterologous DNA sequence contained in a vector of the invention. Heterologous nucleotide sequences can encode proteins or RNA molecules normally expressed in the cell type in which they are present or molecules not normally expressed therein (e.g., Sindbis structural proteins).

Isolated: As used herein, when the term "isolated" is used in reference to a molecule, the term means that the molecule has been removed from its native environment. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

Immunotherapeutic: As used herein, the term "immunotherapeutic" is a composition for the treatment of diseases or disorders. More specifically, the term is used to refer to a method of treatment for allergies or a method of treatment for cancer.

Individual: As used herein, the term "individual" refers to multicellular organisms and includes both plants and animals. Preferred multicellular organisms are animals, more preferred are vertebrates, even more preferred are mammals, and most preferred are humans.

Low or undetectable: As used herein, the phrase "low or undetectable," when used in reference to gene expression level, refers to a level of expression which is either significantly lower than that seen when the gene is maximally induced (e.g., at least five fold lower) or is not readily detectable by the methods used in the following examples section.

Lectin: As used herein, proteins obtained particularly from the seeds of leguminous plants, but also from many other plant and animal sources, that have binding sites for specific mono- or oligosaccharides. Examples include concanavalin A and wheat-germ agglutinin, which are widely used as analytical and preparative agents in the study of glycoprotein.

Mimotope: As used herein, the term "mimotope" refers to a substance which induces an immune response to an antigen or antigenic determinant. Generally, the term mimotope will be used with reference to a particular antigen. For example, a peptide which elicits the production of antibodies to a phospholipase $A_2$ ($PLA_2$) is a mimotope of the antigenic determinant to which the antibodies bind. A mimotope may or may not have substantial structural similarity to or share structural properties with an antigen or antigenic determinant to which it induces an immune response. Methods for generating and identifying mimotopes which induce immune responses to particular antigens or antigenic determinants are known in the art and are described elsewhere herein.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Non-natural molecular scaffold: As used herein, the phrase "non-natural molecular scaffold" refers to any product made by the hand of man that may serve to provide a rigid and repetitive array of first attachment sites. Ideally but not necessarily, these first attachment sites are in a geometric order. The non-natural molecular scaffold may be organic or non-organic and may be synthesized chemically or through a biological process, in part or in whole. The non-natural molecular scaffold is comprised of: (a) a core particle, either of natural or non-natural origin; and (b) an organizer, which itself comprises at least one first attachment site and is connected to a core particle by at least one covalent bond. In a particular embodiment, the non-natural molecular scaffold may be a virus, virus-like particle, a bacterial pilus, a virus capsid particle, a phage, a recombinant form thereof, or synthetic particle.

Ordered and repetitive antigen or antigenic determinant array: As used herein, the term "ordered and repetitive antigen or antigenic determinant array" generally refers to a repeating pattern of antigen or antigenic determinant, characterized by a uniform spacial arrangement of the antigens or antigenic determinants with respect to the non-natural molecular scaffold. In one embodiment of the invention, the repeating pattern may be a geometric pattern. Examples of suitable ordered and repetitive antigen or antigenic determinant arrays are those which possess strictly repetitive paracrystalline orders of antigens or antigenic determinants with spacings of 5 to 15 nanometers.

Organizer: As used herein, the term "organizer" is used to refer to an element bound to a core particle in a non-random fashion that provides a nucleation site for creating an ordered and repetitive antigen array. An organizer is any element comprising at least one first attachment site that is bound to a core particle by at least one covalent bond. An organizer may be a protein, a polypeptide, a peptide, an amino acid (i.e., a residue of a protein, a polypeptide or peptide), a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. Therefore, the organizer further ensures formation of an ordered and repetitive antigen array in accordance with the present invention. In typical embodiments of the invention, the core particle is modified, e.g. by way of genetic engineering or chemical reaction, so as to generate a non-natural molecular scaffold comprising the core particle and the organizer, the latter being connected to the core particle by at least one covalent bond. In certain embodiments of the invention, however, the organizer is selected as being part of the core particle. Therefore, for those embodiments modification of the core particle is not necessarily needed to generate a non-natural molecular scaffold comprising the core particle and the organizer and to ensure the formation of an ordered and repetitive antigen array.

Permissive temperature: As used herein, the phrase "permissive temperature" refers to temperatures at which an enzyme has relatively high levels of catalytic activity.

Pili: As used herein, the term "pili" (singular being "pilus") refers to extracellular structures of bacterial cells composed of protein monomers (e.g., pilin monomers) which are organized into ordered and repetitive patterns. Further, pili are structures which are involved in processes such as the attachment of bacterial cells to host cell surface receptors, inter-cellular genetic exchanges, and cell-cell recognition. Examples of pili include Type-1 pili, P-pili, F1C pili, S-pili, and 987P-pili. Additional examples of pili are set out below.

Pilus-like structure: As used herein, the phrase "pilus-like structure" refers to structures having characteristics similar to that of pili and composed of protein monomers. One example of a "pilus-like structure" is a structure formed by a bacterial cell which expresses modified pilin proteins that do not form ordered and repetitive arrays that are essentially identical to those of natural pili.

Polypeptide: As used herein the term "polypeptide" refers to a polymer composed of amino acid residues, generally natural amino acid residues, linked together through peptide bonds. Although a polypeptide may not necessarily be limited in size, the term polypeptide is often used in conjunction with peptide of a size of about ten to about 50 amino acids.

Protein: As used herein, the term protein refers to a polypeptide generally of a size of above 20, more particularly of above 50 amino acid residues. Proteins generally have a defined three dimensional structure although they do not necessarily need to, and are often referred to as folded, in opposition to peptides and polypeptides which often do not possess a defined three-dimensional structure, but rather can adopt a large number of different conformations, and are referred to as unfolded. The defined three-dimensional structures of proteins is especially important for the association between the core particle and the antigen, mediated by the second attachment site, and in particular by way of chemical cross-linking between the first and second attachment site using a chemical cross-linker. The amino acid linker is also intimately related to the structural properties of proteins in some aspects of the invention.

Purified: As used herein, when the term "purified" is used in reference to a molecule, it means that the concentration of the molecule being purified has been increased relative to molecules associated with it in its natural environment. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules.

Receptor: As used herein, the term "receptor" refers to proteins or glycoproteins or fragments thereof capable of interacting with another molecule, called the ligand. The ligand may belong to any class of biochemical or chemical compounds. The receptor need not necessarily be a membrane-bound protein. Soluble protein, like e.g., maltose binding protein or retinol binding protein are receptors as well.

Residue: As used herein, the term "residue" is meant to mean a specific amino acid in a polypeptide backbone or side chain.

Recombinant host cell: As used herein, the term "recombinant host cell" refers to a host cell into which one ore more nucleic acid molecules of the invention have been introduced.

Recombinant virus: As used herein, the phrase "recombinant virus" refers to a virus that is genetically modified by the hand of man. The phrase covers any virus known in the art. More specifically, the phrase refers to a an alphavirus genetically modified by the hand of man, and most specifically, the phrase refers to a Sinbis virus genetically modified by the hand of man.

Restrictive temperature: As used herein, the phrase "restrictive temperature" refers to temperatures at which an enzyme has low or undetectable levels of catalytic activity. Both "hot" and "cold" sensitive mutants are known and, thus, a restrictive temperature may be higher or lower than a permissive temperature.

RNA-dependent RNA replication event: As used herein, the phrase "RNA-dependent RNA replication event" refers to processes which result in the formation of an RNA molecule using an RNA molecule as a template.

RNA-Dependent RNA polymerase: As used herein, the phrase "RNA-Dependent RNA polymerase" refers to a polymerase which catalyzes the production of an RNA molecule from another RNA molecule. This term is used herein synonymously with the term "replicase."

RNA-phage: As used herein, the term "RNA-phage" refers to RNA viruses infecting bacteria, preferably to single-stranded positive-sense RNA viruses infecting bacteria.

Self antigen: As used herein, the tern "self antigen" refers to proteins encoded by the host's DNA and products generated by proteins or RNA encoded by the host's DNA are defined as self. In addition, proteins that result from a combination of two or several self-molecules or that represent a fraction of a self-molecule and proteins that have a high homology to self-molecules as defined above (>95%) may also be considered self.

Temperature-sensitive: As used herein, the phrase "temperature-sensitive" refers to an enzyme which readily catalyzes a reaction at one temperature but catalyzes the same reaction slowly or not at all at another temperature. An example of a temperature-sensitive enzyme is the replicase protein encoded by the pCYTts vector, which has readily detectable replicase activity at temperatures below 34° C. and has low or undetectable activity at 37° C.

Transcription: As used herein, the term "transcription" refers to the production of RNA molecules from DNA templates catalyzed by RNA polymerase.

Untranslated RNA: As used herein, the phrase "untranslated RNA" refers to an RNA sequence or molecule which does not encode an open reading frame or encodes an open reading frame, or portion thereof, but in a format in which an amino acid sequence will not be produced (e.g., no initiation codon is present). Examples of such molecules are tRNA molecules, rRNA molecules, and ribozymes.

Vector: As used herein, the term "vector" refers to an agent (e.g., a plasmid or virus) used to transmit genetic material to a host cell. A vector may be composed of either DNA or RNA.

Virus-like particle: As used herein, the term "virus-like particle" refers to a structure resembling a virus particle. Moreover, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

Virus particle: The term "virus particle" as used herein refers to the morphological form of a virus. In some virus types it comprises a genome surrounded by a protein capsid; others have additional structures (e.g., envelopes, tails, etc.).

one, a, or an: When the terms "one," "a," or "an" are used in this disclosure, they mean "at least one" or "one or more," unless otherwise indicated.

2. Compositions of Ordered and Repetitive Antigen or Antigenic Determinant Arrays and Methods to Make the Same The disclosed invention provides compositions comprising an ordered and repetitive antigen or antigenic determinant array. Furthermore, the invention conveniently enables the practitioner to construct ordered and repetitive antigen or antigenic determinant arrays for various treatment purposes, which includes the prevention of infectious diseases, the treatment of allergies and the treatment of cancers.

Compositions of the invention essentially comprise, or alternatively consist of, two elements: (1) a non-natural molecular scaffold; and (2) an antigen or antigenic determinant with at least one second attachment site capable of association through at least one non-peptide bond to said first attachment site.

Compositions of the invention also comprise, or alternatively consist of, bacterial pilus proteins to which antigens or antigenic determinants are directly linked.

The non-natural molecular scaffold comprises, or alternatively consists of: (a) a core particle selected from the group consisting of (1) a core particle of non-natural origin and (2) a core particle of natural origin; and (b) an organizer comprising at least one first attachment site, wherein said organizer is connected to said core particle by at least one covalent bond.

Compositions of the invention also comprise, or alternatively consist of, core particles to which antigens or antigenic determinants are directly linked.

The antigen or antigenic determinant has at least one second attachment site which is selected from the group consisting of (a) an attachment site not naturally occurring with said antigen or antigenic determinant; and (b) an attachment site naturally occurring with said antigen or antigenic determinant.

The invention provides for an ordered and repetitive antigen array through an association of the second attachment site to the first attachment site by way of at least one non-peptide bond. Thus, the antigen or antigenic determinant and the non-natural molecular scaffold are brought together through this association of the first and the second attachment site to form an ordered and repetitive antigen array.

The practioner may specifically design the antigen or antigenic determinant and the second attachment site such that the arrangement of all the antigens or antigenic determinants bound to the non-natural molecular scaffold or, in certain embodiments, the core particle will be uniform. For example, one may place a single second attachment site on the antigen or antigenic determinant at the carboxyl or amino terminus, thereby ensuring through design that all antigen or antigenic determinant molecules that are attached to the non-natural molecular scaffold are positioned in a uniform way. Thus, the invention provides a convenient means of placing any antigen or antigenic determinant onto a non-natural molecular scaffold in a defined order and in a manner which forms a repetitive pattern.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and may be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, $2^{nd}$ edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," Meth. Enzymol. 128, Academic Press San Diego (1990); Scopes, R. K., "Protein Purification Principles and Practice," $3^{rd}$ ed., Springer-Verlag, New York (1994)) are also adequately described in the literature, all of which are incorporated herein by reference.

A. Core Particles and Non-Natural Molecular Scaffolds

One element in certain compositions of the invention is a non-natural molecular scaffold comprising, or alternatively consisting of, a core particle and an organizer. As used herein, the phrase "non-natural molecular scaffold" refers to any product made by the hand of man that may serve to provide a rigid and repetitive array of first attachment sites. More specifically, the non-natural molecular scaffold comprises, or alternatively consists of, (a) a core particle selected from the group consisting of (1) a core particle of non-natural origin and (2) a core particle of natural origin; and (b) an organizer comprising at least one first attachment site, wherein said organizer is connected to said core particle by at least one covalent bond.

As will be readily apparent to those skilled in the art, the core particle of the non-natural molecular scaffold of the invention is not limited to any specific form. The core particle may be organic or non-organic and may be synthesized chemically or through a biological process.

In one embodiment, a non-natural core particle may be a synthetic polymer, a lipid micelle or a metal. Such core particles are known in the art, providing a basis from which to build the novel non-natural molecular scaffold of the invention. By way of example, synthetic polymer or metal core particles are described in U.S. Pat. No. 5,770,380, which discloses the use of a calixarene organic scaffold to which is attached a plurality of peptide loops in the creation of an 'antibody mimic', and U.S. Pat. No. 5,334,394 describes nanocrystalline particles used as a viral decoy that are composed of a wide variety of inorganic materials, including metals or ceramics. Suitable metals include chromium, rubidium, iron, zinc, selenium, nickel, gold, silver, platinum. Suitable ceramic materials in this embodiment include silicon dioxide, titanium dioxide, aluminum oxide, ruthenium oxide and tin oxide. The core particles of this embodiment may be made from organic materials including carbon (diamond). Suitable polymers include polystyrene, nylon and nitrocellulose. For this type of nanocrystalline particle, particles made from tin oxide, titanium dioxide or carbon (diamond) are may also be used. A lipid micelle may be prepared by any means known in the art. For example micelles may be prepared according to the procedure of Baiselle and Millar (Biophys. Chem. 4:355–361 (1975)) or Corti et al. (Chem. Phys. Lipids 38:197–214 (1981)) or Lopez et al. (FEBS Lett. 426:314–318 (1998)) or Topchieva and Karezin (J. Colloid Interface Sci. 213:29–35 (1999)) or Morein et al., (Nature 308:457–460 (1984)), which are all incorporated herein by reference.

The core particle may also be produced through a biological process, which may be natural or non-natural. By way of example, this type of embodiment may includes a core particle comprising, or alternatively consisting of, a virus, virus-like particle, a bacterial pilus, a phage, a viral capsid particle or a recombinant form thereof. In a more specific embodiment, the core particle may comprise, or alternatively consist of, recombinant proteins of Rotavirus, recombinant proteins of Norwalk virus, recombinant proteins of Alphavirus, recombinant proteins which form bacterial pili or pilus-like structures, recombinant proteins of Foot and Mouth Disease virus, recombinant proteins of Retrovirus, recombinant proteins of Hepatitis B virus (e.g., a HBcAg), recombinant proteins of Tobacco mosaic virus, recombinant proteins of Flock House Virus, and recombinant proteins of human Papillomavirus. The core particle may further comprise, or alternatively consist of, one or more fragments of such proteins, as well as variants of such proteins which retain the ability to associate with each other to form ordered and repetitive antigen or antigenic determinant arrays.

As explained in more below, variants of proteins which retain the ability to associate with each other to form ordered and repetitive antigen or antigenic determinant arrays may share, for example, at least 80%, 85%, 90%, 95%, 97%, or 99% identity at the amino acid level with their wild-type counterparts. Using the HBcAg having the amino acid sequence shown in SEQ ID NO:89 for illustration, the invention includes vaccine compositions comprising HBcAg polypeptides comprising, or alternatively consisting of, amino acid sequences which are at least 80%, 85%, 90%, 95%, 97%, or 99% identical to the amino acid sequence shown in SEQ ID NO:89, and forms of this protein which have been processed, where appropriate, to remove N-terminal leader sequence. These variants will generally be capable of associating to form dimeric or multimeric structures. Methods which can be used to determine whether proteins form such structures comprise gel filtration, agarose gel electrophoresis, sucrose gradient centrifugation and electron microscopy (e.g., Koschel, M. et al., *J. Virol* 73: 2153–2160 (1999)).

Fragments of proteins which retain the ability to associate with each other to form ordered and repetitive antigen or antigenic determinant arrays may comprise, or alternatively consist of, polypeptides which are 15, 20, 25, 30, 35, 40, 45, 50, 55, 60, 65, 70, 75, 80, 85, 90, 95, 100, 110, 120, 130, 140, 150, 160, 170, 180, 190, or 200 amino acids in length. Examples of such protein fragments include fragments of proteins discussed herein which are suitable for the preparation of core particles and/or non-natural molecular scaffolds.

Whether natural or non-natural, the core particle of the invention will generally have an organizer that is attached to the natural or non-natural core particle by at least one covalent bond. The organizer is an element bound to a core particle in a non-random fashion that provides a nucleation site for creating an ordered and repetitive antigen array. Ideally, but not necessarily, the organizer is associated with the core particle in a geometric order. Minimally, the organizer comprises a first attachment site.

In some embodiments of the invention, the ordered and repetitive array is formed by association between (1) either core particles or non-natural molecular scaffolds and (2) either (a) an antigen or antigenic determinant or (b) one or more antigens or antigenic determinants. For example, bacterial pili or pilus-like structures are formed from proteins which are organized into ordered and repetitive structures. Thus, in many instances, it will be possible to form ordered arrays of antigens or antigenic determinants by linking these constituents to bacterial pili or pilus-like structures either directly or through an organizer.

As previously stated, the organizer may be any element comprising at least one first attachment site that is bound to a core particle by at least one covalent bond. An organizer may be a protein, a polypeptide, a peptide, an amino acid (i.e., a residue of a protein, a polypeptide or peptide), a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. In a more specific embodiment, the organizer may comprise a first attachment site comprising an antigen, an antibody or antibody fragment, biotin, avidin, streptavidin, a receptor, a receptor ligand, a ligand, a ligand-binding protein, an interacting leucine zipper polypeptide, an amino group, a chemical group reactive to an amino group; a carboxyl group, chemical group reactive to a carboxyl group, a sulfhydryl group, a chemical group reactive to a sulfhydryl group, or a combination thereof.

In one embodiment, the core particle of the non-natural molecular scaffold comprises a virus, a bacterial pilus, a structure formed from bacterial pilin, a bacteriophage, a virus-like particle, a viral capsid particle or a recombinant form thereof. Any virus known in the art having an ordered and repetitive coat and/or core protein structure may be selected as a non-natural molecular scaffold of the invention; examples of suitable viruses include sindbis and other alphaviruses, rhabdoviruses (e.g. vesicular stomatitis virus), picornaviruses (e.g., human rhino virus, Aichi virus), togaviruses (e.g., rubella virus), orthomyxoviruses (e.g., Thogoto virus, Batken virus, fowl plague virus), polyomaviruses (e.g., polyomavirus BK, polyomavirus JC, avian polyomavirus BFDV), parvoviruses, rotaviruses, bacteriophage Qβ, bacteriophage R17, bacteriophage M11, bacteriophage MX1, bacteriophage NL95, bacteriophage fr, bacteriophage GA, bacteriophage SP, bacteriophage MS2, bacteriophage f2, bacteriophage PP7, Norwalk virus, foot and mouth disease virus, a retrovirus, Hepatitis B virus, Tobacco mosaic virus, Flock House Virus, and human Papilomavirus (for example, see Table 1 in Bachman, M. F. and Zinkernagel, R. M., *Immunol. Today* 17:553–558 (1996)).

In one embodiment, the invention utilizes genetic engineering of a virus to create a fusion between an ordered and repetitive viral envelope protein and an organizer comprising a heterologous protein, peptide, antigenic determinant or a reactive amino acid residue of choice. Other genetic manipulations known to those in the art may be included in the construction of the non-natural molecular scaffold; for example, it may be desirable to restrict the replication ability of the recombinant virus through genetic mutation. The viral protein selected for fusion to the organizer (i.e., first attachment site) protein should have an organized and repetitive structure. Such an organized and repetitive structure include paracrystalline organizations with a spacing of 5–15 nm on the surface of the virus. The creation of this type of fusion protein will result in multiple, ordered and repetitive organizers on the surface of the virus. Thus, the ordered and repetitive organization of the first attachment sites resulting therefrom will reflect the normal organization of the native viral protein.

As will be discussed in more detail herein, in another embodiment of the invention, the non-natural molecular scaffold is a recombinant alphavirus, and more specifically, a recombinant Sinbis virus. Alphaviruses are positive stranded RNA viruses that replicate their genomic RNA entirely in the cytoplasm of the infected cell and without a DNA intermediate (Strauss, J. and Strauss, E., *Microbiol. Rev.* 58:491–562 (1994)). Several members of the alphavirus family, Sindbis (Xiong, C. et al., *Science* 243:1188–1191 (1989); Schlesinger, S., *Trends Biotechnol.* 11:18–22

(1993)), Semliki Forest Virus (SFV) (Liljeström, P. & Garoff, H., *Bio/Technology* 9:1356–1361 (1991)) and others (Davis, N. L. et al., *Virology* 171:189–204 (1989)), have received considerable attention for use as virus-based expression vectors for a variety of different proteins (Lundstrom, K., *Curr. Opin. Biotechnol.* 8:578–582 (1997); Liljeström, P., *Curr. Opin. Biotechnol.* 5:495–500 (1994)) and as candidates for vaccine development. Recently, a number of patents have issued directed to the use of alphaviruses for the expression of heterologous proteins and the development of vaccines (see U.S. Pat. Nos. 5,766,602; 5,792,462; 5,739, 026; 5,789,245 and 5,814,482). The construction of the alphaviral scaffold of the invention may be done by means generally known in the art of recombinant DNA technology, as described by the aforementioned articles, which are incorporated herein by reference.

A variety of different recombinant host cells can be utilized to produce a viral-based core particle for antigen or antigenic determinant attachment. For example, Alphaviruses are known to have a wide host range; Sindbis virus infects cultured mammalian, reptilian, and amphibian cells, as well as some insect cells (Clark, H., *J. Natl. Cancer Inst.* 51:645 (1973); Leake, C., *J. Gen. Virol.* 35:335 (1977); Stollar, V. in THE TOGAVIRUSES, R. W. Schlesinger, Ed., Academic Press, (1980), pp. 583–621). Thus, numerous recombinant host cells can be used in the practice of the invention. BHK, COS, Vero, HeLa and CHO cells are particularly suitable for the production of heterologous proteins because they have the potential to glycosylate heterologous proteins in a manner similar to human cells (Watson, E. et al., *Glycobiology* 4:227, (1994)) and can be selected (Zang, M. et al., *Bio/Technology* 13:389 (1995)) or genetically engineered (Renner W. et al., *Biotech. Bioeng.* 4:476 (1995); Lee K. et al. *Biotech. Bioeng.* 50:336 (1996)) to grow in serum-free medium, as well as in suspension.

Introduction of the polynucleotide vectors into host cells can be effected by methods described in standard laboratory manuals (see, e.g., Sambrook, J. et al., eds., MOLECULAR CLONING, A LABORATORY MANUAL, 2nd. edition, Cold Spring Harbor Laboratory Press, Cold Spring Harbor, N.Y. (1989), Chapter 9; Ausubel, F. et al., eds., CURRENT PROTOCOLS IN MOLECULAR BIOLOGY, John H. Wiley & Sons, Inc. (1997), Chapter 16), including methods such as electroporation, DEAE-dextran mediated transfection, transfection, microinjection, cationic lipid-mediated transfection, transduction, scrape loading, ballistic introduction, and infection. Methods for the introduction of exogenous DNA sequences into host cells are discussed in Felgner, P. et al., U.S. Pat. No. 5,580,859.

Packaged RNA sequences can also be used to infect host cells. These packaged RNA sequences can be introduced to host cells by adding them to the culture medium. For example, the preparation of non-infective alphaviral particles is described in a number of sources, including "Sindbis Expression System", Version C (Invitrogen Catalog No. K750–1).

When mammalian cells are used as recombinant host cells for the production of viral-based core particles, these cells will generally be grown in tissue culture. Methods for growing cells in culture are well known in the art (see, e.g., Celis, J., ed., CELL BIOLOGY, Academic Press, 2$^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

As will be understood by those in the art, the first attachment site may be or be a part of any suitable protein, polypeptide, sugar, polynucleotide, peptide (amino acid), natural or synthetic polymer, a secondary metabolite or combination thereof that may serve to specifically attach the antigen or antigenic determinant of choice to the non-natural molecular scaffold. In one embodiment, the attachment site is a protein or peptide that may be selected from those known in the art. For example, the first attachment site may selected from the following group: a ligand, a receptor, a lectin, avidin, streptavidin, biotin, an epitope such as an HA or T7 tag, Myc, Max, immunoglobulin domains and any other amino acid sequence known in the art that would be useful as a first attachment site.

It should be further understood by those in the art that with another embodiment of the invention, the first attachment site may be created secondarily to the organizer (i.e., protein or polypeptide) utilized in constructing the in-frame fusion to the capsid protein. For example, a protein may be utilized for fusion to the envelope protein with an amino acid sequence known to be glycosylated in a specific fashion, and the sugar moiety added as a result may then serve at the first attachment site of the viral scaffold by way of binding to a lectin serving as the secondary attachment site of an antigen. Alternatively, the organizer sequence may be biotinylated in vivo and the biotin moiety may serve as the first attachment site of the invention, or the organizer sequence may be subjected to chemical modification of distinct amino acid residues in vitro, the modification serving as the first attachment site.

In another embodiment of the invention, the first attachment site is selected to be the JUN-FOS leucine zipper protein domain that is fused in frame to the Hepatitis B capsid (core) protein (HBcAg). However, it will be clear to all individuals in the art that other viral capsid proteins may be utilized in the fusion protein construct for locating the first attachment site in the non-natural molecular scaffold of the invention.

In another embodiment of the invention, the first attachment site is selected to be a lysine or cysteine residue that is fused in frame to the HBcAg. However, it will be clear to all individuals in the art that other viral capsid or virus-like particles may be utilized in the fusion protein construct for locating the first attachment in the non-natural molecular scaffold of the invention.

The JUN amino acid sequence utilized for the first attachment site is the following:

CGGRIARLEEKVKTLKAQNSELASTANM-
    LREQVAQLKQKVMNHVGC          (SEQ ID NO:59)

In this instance, the anticipated second attachment site on the antigen would be the FOS leucine zipper protein domain and the amino acid sequence would be the following:

CGGLTDTLQAETDQVEDEKSALQTEIAN-
    LLKEKEKLEFILAAHGGC          (SEQ ID NO:60)

These sequences are derived from the transcription factors JUN and FOS, each flanked with a short sequence containing a cysteine residue on both sides. These sequences are known to interact with each other. The original hypothetical structure proposed for the JUN-FOS dimer assumed that the hydrophobic side chains of one monomer interdigitate with the respective side chains of the other monomer in a zipper-like manner (Landschulz et al., *Science* 240:1759–1764 (1988)). However, this hypothesis proved to be wrong, and these proteins are known to form an α-helical coiled coil (O'Shea et al., *Science* 243:538–542 (1989); O'Shea et al., Cell 68:699–708 (1992); Cohen & Parry, *Trends Biochem. Sci.* 11:245–248 (1986)). Thus, the term "leucine zipper" is frequently used to refer to these protein domains for more historical than structural reasons. Throughout this patent, the term "leucine zipper" is used to refer to the sequences depicted above or sequences essentially similar to the ones depicted above. The terms JUN and FOS are used for the respective leucine zipper domains rather than the entire JUN and FOS proteins.

As previously stated, the invention includes viral-based core particles which comprise, or alternatively consist of, a virus, virus-like particle, a phage, a viral capsid particle or a recombinant form thereof. Skilled artisans have the knowledge to produce such core particles and attach organizers thereto. The production of Hepatitis B virus-like particles and measles viral capsid particles as core particles is disclosed in Examples 17 to 22 of WO 00/32227, which is explicitly incorporated by reference. In such embodiments, the JUN leucine zipper protein domain or FOS leucine zipper protein domain may be used as an organizer, and hence as a first attachment site, for the non-natural molecular scaffold of the invention.

Examples 23–29 provide details of the production of Hepatitis B core particles carrying an in-frame fused peptide with a reactive lysine residue and antigens carrying a genetically fused cysteine residue, as first and second attachment site, respectively.

1 In other embodiments, the core particles used in compositions of the invention are composed of a Hepatitis B capsid (core) protein (HBcAg), a fragment of a HBcAg, or other protein or peptide which can form ordered arrays, which have been modified to either eliminate or reduce the number of free cysteine residues. Zhou et al. (*J. Virol.* 66:5393–5398 (1992)) demonstrated that HBcAgs which have been modified to remove the naturally resident cysteine residues retain the ability to associate and form multimeric structures. Thus, core particles suitable for use in compositions of the invention include those comprising modified HBcAgs, or fragments thereof, in which one or more of the naturally resident cysteine residues have been either deleted or substituted with another amino acid residue (e.g., a serine residue).

2 The HBcAg is a protein generated by the processing of a Hepatitis B core antigen precursor protein. A number of isotypes of the HBcAg have been identified. For example, the HBcAg protein having the amino acid sequence shown in SEQ ID NO:132 is 183 amino acids in length and is generated by the processing of a 212 amino acid Hepatitis B core antigen precursor protein. This processing results in the removal of 29 amino acids from the N-terminus of the Hepatitis B core antigen precursor protein. Similarly, the HBcAg protein having the amino acid sequence shown in SEQ ID NO:134 is 185 amino acids in length and is generated by the processing of a 214 amino acid Hepatitis B core antigen precursor protein. The amino acid sequence shown in SEQ ID NO:134, as compared to the amino acid sequence shown in SEQ ID NO:132, contains a two amino acid insert at positions 152 and 153 in SEQ ID NO:134.

In most instances, vaccine compositions of the invention will be prepared using the processed form of a HBcAg (i.e., a HBcAg from which the N-terminal leader sequence (e.g., the first 29 amino acid residues shown in SEQ ID NO:134) of the Hepatitis B core antigen precursor protein have been removed).

Further, when HBcAgs are produced under conditions where processing will not occur, the HBcAgs will generally be expressed in "processed" form. For example, bacterial systems, such as *E. coli*, generally do not remove the leader sequences, also referred to as "signal peptides," of proteins which are normally expressed in eukaryotic cells. Thus, when an *E. coli* expression system is used to produce HBcAgs of the invention, these proteins will generally be expressed such that the N-terminal leader sequence of the Hepatitis B core antigen precursor protein is not present.

In one embodiment of the invention, a modified HBcAg comprising the amino acid sequence shown in SEQ ID NO:134, or subportion thereof, is used to prepare non-natural molecular scaffolds. In particular, modified HBcAgs suitable for use in the practice of the invention include proteins in which one or more of the cysteine residues at positions corresponding to positions 48, 61, 107 and 185 of a protein having the amino acid sequence shown in SEQ ID NO:134 have been either deleted or substituted with other amino acid residues (e.g., a serine residue). As one skilled in the art would recognize, cysteine residues at similar locations in HBcAg variants having amino acids sequences which differ from that shown in SEQ ID NO:134 could also be deleted or substituted with other amino acid residues. The modified HBcAg variants can then be used to prepare vaccine compositions of the invention.

The present invention also includes HBcAg variants which have been modified to delete or substitute one or more additional cysteine residues which are not found in polypeptides having the amino acid sequence shown in SEQ ID NO:134. Examples of such HBcAg variants have the amino acid sequences shown in SEQ ID NOs:90 and 132. These variant contain cysteines residues at a position corresponding to amino acid residue 147 in SEQ ID NO:134. Thus, the vaccine compositions of the invention include compositions comprising HBcAgs in which cysteine residues not present in the amino acid sequence shown in SEQ ID NO:134 have been deleted.

Under certain circumstances (e.g., when a heterobifunctional cross-linking reagent is used to attach antigens or antigenic determinants to the non-natural molecular scaffold), the presence of free cysteine residues in the HBcAg is believed to lead to covalent coupling of toxic components to core particles, as well as the cross-linking of monomers to form undefined species.

Further, in many instances, these toxic components may not be detectable with assays performed on compositions of the invention. This is so because covalent coupling of toxic components to the non-natural molecular scaffold would result in the formation of a population of diverse species in which toxic components are linked to different cysteine residues, or in some cases no cysteine residues, of the HBcAgs. In other words, each free cysteine residue of each HBcAg will not be covalently linked to toxic components. Further, in many instances, none of the cysteine residues of particular HBcAgs will be linked to toxic components. Thus, the presence of these toxic components may be difficult to detect because they would be present in a mixed population of molecules. The administration to an individual of HBcAg species containing toxic components, however, could lead to a potentially serious adverse reaction.

It is well known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. Detection of such toxic products in antigen-capsid conjugates would be difficult using capsids prepared using HBcAgs containing free cysteines and heterobifunctional cross-linkers, since a distribution of products with a broad range of molecular weight would be generated. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached to the non-natural molecular scaffold would be reduced in number or eliminated altogether. Further, a high concentration of cross-linker can be used to produce highly decorated particles without the drawback of generating a plurality of undefined cross-linked species of HBcAg monomers (i.e., a diverse mixture of cross-linked monomeric HbcAgs).

A number of naturally occurring HBcAg variants suitable for use in the practice of the present invention have been identified. Yuan et al., (*J. Virol.* 73:10122–10128 (1999)), for example, describe variants in which the isoleucine residue at position corresponding to position 97 in SEQ ID NO:134 is replaced with either a leucine residue or a phenylalanine residue. The amino acid sequences of a number of HBcAg variants, as well as several Hepatitis B core antigen precursor variants, are disclosed in GenBank reports AAF121240 (SEQ ID NO:89), AF121239 (SEQ ID NO:90), X85297 (SEQ ID NO:91), X02496 (SEQ ID NO:92), X85305 (SEQ ID NO:93), X85303 (SEQ ID NO:94), AF151735 (SEQ ID NO:95), X85259 (SEQ ID NO:96), X85286 (SEQ ID NO:97), X85260 (SEQ ID NO:98), X85317 (SEQ ID NO:99), X85298 (SEQ ID NO:100), AF043593 (SEQ ID NO:101), M20706 (SEQ ID NO:102), X85295 (SEQ ID NO:103), X80925 (SEQ ID NO:104), X85284 (SEQ ID NO:105), X85275 (SEQ ID NO:106), X72702 (SEQ ID NO:107), X85291 (SEQ ID NO:108), X65258 (SEQ ID NO:109), X85302 (SEQ ID NO:110), M32138 (SEQ ID NO:111), X85293 (SEQ ID NO:112), X85315 (SEQ ID NO:113), U95551 (SEQ ID NO:114), X85256 (SEQ ID NO:115), X85316 (SEQ ID NO:116), X85296 (SEQ ID NO:117), AB033559 (SEQ ID NO:118), X59795 (SEQ ID NO:119), X85299 (SEQ ID NO:120), X85307 (SEQ ID NO:121), X65257 (SEQ ID NO:122), X85311 (SEQ ID NO:123), X85301 (SEQ ID NO:124), X85314 (SEQ ID NO:125), X85287 (SEQ ID NO:126), X85272 (SEQ ID NO:127), X85319 (SEQ ID NO:128), AB010289 (SEQ ID NO:129), X85285 (SEQ ID NO:130), AB010289 (SEQ ID NO:131), AF121242 (SEQ ID NO:132), M90520 (SEQ ID NO:135), $PO_{3153}$ (SEQ ID NO:136), AF110999 (SEQ ID NO:137), and M95589 (SEQ ID NO:138), the disclosures of each of which are incorporated herein by reference. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:134.

HBcAgs suitable for use in the present invention may be derived from any organism so long as they are able to associate to form an ordered and repetitive antigen array.

As noted above, generally processed HBcAgs (i.e., those which lack leader sequences) will be used in the vaccine compositions of the invention. Thus, when HBcAgs having amino acid sequence shown in SEQ ID NOs:136, 137, or 138 are used to prepare vaccine compositions of the invention, generally 30, 35–43, or 35–43 amino acid residues at the N-terminus, respectively, of each of these proteins will be omitted.

The present invention includes vaccine compositions, as well as methods for using these compositions, which employ the above described variant HBcAgs for the preparation of non-natural molecular scaffolds.

Further included within the scope of the invention are additional HBcAg variants which are capable of associating to form dimeric or multimeric structures. Thus, the invention further includes vaccine compositions comprising HBcAg polypeptides comprising, or alternatively consisting of, amino acid sequences which are at least 80%, 85%, 90%, 95%, 97%, or 99% identical to any of the amino acid sequences shown in SEQ ID NOs:89–132 and 134–138, and forms of these proteins which have been processed, where appropriate, to remove the N-terminal leader sequence.

Whether the amino acid sequence of a polypeptide has an amino acid sequence that is at least 80%, 85%, 90%, 95%, 97%, or 99% identical to one of the amino acid sequences shown in SEQ ID NOs:89–132 and 134–138, or a subportion thereof, can be determined conventionally using known computer programs such the Bestfit program. When using Bestfit or any other sequence alignment program to determine whether a particular sequence is, for instance, 95% identical to a reference amino acid sequence according to the present invention, the parameters are set such that the percentage of identity is calculated over the full length of the reference amino acid sequence and that gaps in homology of up to 5% of the total number of amino acid residues in the reference sequence are allowed.

The HBcAg variants and precursors having the amino acid sequences set out in SEQ ID NOs:89–132 and 134–136 are relatively similar to each other. Thus, reference to an amino acid residue of a HBcAg variant located at a position which corresponds to a particular position in SEQ ID NO:134, refers to the amino acid residue which is present at that position in the amino acid sequence shown in SEQ ID NO:134. The homology between these HBcAg variants is for the most part high enough among Hepatitis B viruses that infect mammals so that one skilled in the art would have little difficulty reviewing both the amino acid sequence shown in SEQ ID NO:134 and that of a particular HBcAg variant and identifying "corresponding" amino acid residues. For example, the HBcAg amino acid sequence shown in SEQ ID NO:135, which shows the amino acid sequence of a HBcAg derived from a virus which infect woodchucks, has enough homology to the HBcAg having the amino acid sequence shown in SEQ ID NO:134 that it is readily apparent that a three amino acid residue insert is present in SEQ ID NO:135 between amino acid residues 155 and 156 of SEQ ID NO:134.

The HBcAgs of Hepatitis B viruses which infect snow geese and ducks differ enough from the amino acid sequences of HBcAgs of Hepatitis B viruses which infect mammals that alignment of these forms of this protein with the amino acid sequence shown in SEQ ID NO:134 is difficult. However, the invention includes vaccine compositions which comprise HBcAg variants of Hepatitis B viruses which infect birds, as wells as vaccine compositions which comprise fragments of these HBcAg variants. HBcAg fragments suitable for use in preparing vaccine compositions of the invention include compositions which contain polypeptide fragments comprising, or alternatively consisting of, amino acid residues selected from the group consisting of 36–240, 36–269, 44–240, 44–269, 36–305, and 44–305 of SEQ ID NO:137 or 36–240, 36–269, 44–240, 44–269, 36–305, and 44–305 of SEQ ID NO:138. As one skilled in the art would recognize, one, two, three or more of the cysteine residues naturally present in these polypeptides (e.g., the cysteine residues at position 153 is SEQ ID NO:137 or positions 34, 43, and 196 in SEQ ID NO:138) could be either substituted with another amino acid residue or deleted prior to their inclusion in vaccine compositions of the invention.

In one embodiment, the cysteine residues at positions 48 and 107 of a protein having the amino acid sequence shown in SEQ ID NO:134 are deleted or substituted with another amino acid residue but the cysteine at position 61 is left in place. Further, the modified polypeptide is then used to prepare vaccine compositions of the invention.

As set out below in Example 31, the cysteine residues at positions 48 and 107, which are accessible to solvent, may be removed, for example, by site-directed mutagenesis. Further, the inventors have found that the Cys-48-Ser, Cys-107-Ser HBcAg double mutant constructed as described in Example 31 can be expressed in *E. coli*.

As discussed above, the elimination of free cysteine residues reduces the number of sites where toxic components can bind to the HBcAg, and also eliminates sites where cross-linking of lysine and cysteine residues of the same or of neighboring HBcAg molecules can occur. The cysteine at position 61, which is involved in dimer formation and forms a disulfide bridge with the cysteine at position 61 of another HBcAg, will normally be left intact for stabilization of HBcAg dimers and multimers of the invention.

As shown in Example 32, cross-linking experiments performed with (1) HBcAgs containing free cysteine residues and (2) HBcAgs whose free cysteine residues have been made unreactive with iodacetamide, indicate that free cysteine residues of the HBcAg are responsible for cross-linking between HBcAgs through reactions between heterobifunctional cross-linker derivatized lysine side chains, and free cysteine residues. Example 32 also indicates that cross-linking of HBcAg subunits leads to the formation of high molecular weight species of undefined size which cannot be resolved by SDS-polyacrylamide gel electrophoresis.

When an antigen or antigenic determinant is linked to the non-natural molecular scaffold through a lysine residue, it may be advantageous to either substitute or delete one or both of the naturally resident lysine residues located at positions corresponding to positions 7 and 96 in SEQ ID NO:134, as well as other lysine residues present in HBcAg variants. The elimination of these lysine residues results in the removal of binding sites for antigens or antigenic determinants which could disrupt the ordered array and should improve the quality and uniformity of the final vaccine composition.

In many instances, when both of the naturally resident lysine residues at positions corresponding to positions 7 and 96 in SEQ ID NO:134 are eliminated, another lysine will be introduced into the HBcAg as an attachment site for an antigen or antigenic determinant. Methods for inserting such a lysine residue are set out, for example, in Example 23 below. It will often be advantageous to introduce a lysine residue into the HBcAg when, for example, both of the naturally resident lysine residues at positions corresponding to positions 7 and 96 in SEQ ID NO:134 are altered and one seeks to attach the antigen or antigenic determinant to the non-natural molecular scaffold using a heterobifunctional cross-linking agent.

The C-terminus of the HBcAg has been shown to direct nuclear localization of this protein. (Eckhardt et al., *J. Virol.* 65:575–582 (1991).) Further, this region of the protein is also believed to confer upon the HBcAg the ability to bind nucleic acids.

In some embodiments, vaccine compositions of the invention will contain HBcAgs which have nucleic acid binding activity (e.g., which contain a naturally resident HBcAg nucleic acid binding domain). HBcAgs containing one or more nucleic acid binding domains are useful for preparing vaccine compositions which exhibit enhanced T-cell stimulatory activity. Thus, the vaccine compositions of the invention include compositions which contain HBcAgs having nucleic acid binding activity. Further included are vaccine compositions, as well as the use of such compositions in vaccination protocols, where HBcAgs are bound to nucleic acids. These HBcAgs may bind to the nucleic acids prior to administration to an individual or may bind the nucleic acids after administration.

In other embodiments, vaccine compositions of the invention will contain HBcAgs from which the C-terminal region (e.g., amino acid residues 145–185 or 150–185 of SEQ ID NO:134) has been removed and do not bind nucleic acids. Thus, additional modified HBcAgs suitable for use in the practice of the present invention include C-terminal truncation mutants. Suitable truncation mutants include HBcAgs where 1, 5, 10, 15, 20, 25, 30, 34, 35, 36, 37, 38, 39 40, 41, 42 or 48 amino acids have been removed from the C-terminus.

HBcAgs suitable for use in the practice of the present invention also include N-terminal truncation mutants. Suitable truncation mutants include modified HBcAgs where 1, 2, 5, 7, 9, 10, 12, 14, 15, or 17 amino acids have been removed from the N-terminus.

Further HBcAgs suitable for use in the practice of the present invention include N- and C-terminal truncation mutants. Suitable truncation mutants include HBcAgs where 1, 2, 5, 7, 9, 10, 12, 14, 15, and 17 amino acids have been removed from the N-terminus and 1, 5, 10, 15, 20, 25, 30, 34, 35, 36, 37, 38, 39 40, 41, 42 or 48 amino acids have been removed from the C-terminus.

The invention further includes vaccine compositions comprising HBcAg polypeptides comprising, or alternatively consisting of, amino acid sequences which are at least 80%, 85%, 90%, 95%, 97%, or 99% identical to the above described truncation mutants.

As discussed above, in certain embodiments of the invention, a lysine residue is introduced as a first attachment site into a polypeptide which forms the non-natural molecular scaffold. In preferred embodiments, vaccine compositions of the invention are prepared using a HBcAg comprising, or alternatively consisting of, amino acids 1–144 or amino acids 1–149 of SEQ ID NO:134 which is modified so that the amino acids corresponding to positions 79 and 80 are replaced with a peptide having the amino acid sequence of Gly-Gly-Lys-Gly-Gly (SEQ ID NO:158) and the cysteine residues at positions 48 and 107 are either deleted or substituted with another amino acid residue, while the cysteine at position 61 is left in place. The invention further includes vaccine compositions comprising corresponding fragments of polypeptides having amino acid sequences shown in any of SEQ ID NOs:89–132 and 135–136 which also have the above noted amino acid alterations.

The invention further includes vaccine compositions comprising fragments of a HBcAg comprising, or alternatively consisting of, an amino acid sequence other than that shown in SEQ ID NO:134 from which a cysteine residue not present at corresponding location in SEQ ID NO:134 has been deleted. One example of such a fragment would be a polypeptide comprising, or alternatively consisting of, amino acids amino acids 1–149 of SEQ ID NO:132 where the cysteine residue at position 147 has been either substituted with another amino acid residue or deleted.

The invention further includes vaccine compositions comprising HBcAg polypeptides comprising, or alternatively consisting of, amino acid sequences which are at least 80%, 85%, 90%, 95%, 97%, or 99% identical to amino acids 1–144 or 1–149 of SEQ ID NO:134 and corresponding subportions of a polypeptide comprising an amino acid sequence shown in any of SEQ ID NOs:89–132 or 134–136, as well as to amino acids 1–147 or 1–152 of SEQ ID NO:158.

The invention also includes vaccine compositions comprising HBcAg polypeptides comprising, or alternatively consisting of, amino acid sequences which are at least 80%, 85%, 90%, 95%, 97%, or 99% identical to amino acids 36–240, 36–269, 44–240, 44–269, 36–305, and 44–305 of SEQ ID NO:137 or 36–240, 36–269,44–240,44–269, 36–305, and 44–305 of SEQ ID NO:138.

Vaccine compositions of the invention may comprise mixtures of different HBcAgs. Thus, these vaccine compositions may be composed of HBcAgs which differ in amino acid sequence. For example, vaccine compositions could be prepared comprising a "wild-type" HBcAg and a modified HBcAg in which one or more amino acid residues have been altered (e.g., deleted, inserted or substituted). In most applications, however, only one type of a HBcAg, or at least HBcAgs having essentially equivalent first attachment sites, will be used because vaccines prepared using such HBcAgs will present highly ordered and repetitive arrays of antigens or antigenic determinants. Further, preferred vaccine compositions of the invention are those which present highly ordered and repetitive antigen array The invention further includes vaccine compositions where the non-natural molecular scaffold is prepared using a HBcAg fused to another protein. As discussed above, one example of such a fusion protein is a HBcAg/FOS fusion. Other examples of HBcAg fusion proteins suitable for use in vaccine compositions of the invention include fusion proteins where an amino acid sequence has been added which aids in the formation and/or stabilization of HBcAg dimers and multimers. This additional amino acid sequence may be fused to either the N- or C-terminus of the HBcAg. One example, of such a fusion protein is a fusion of a HBcAg with the GCN4 helix region of *Saccharomyces cerevisiae* (GenBank Accession No. $PO_{3069}$ (SEQ ID NO:154)).

The helix domain of the GCN4 protein forms homodimers via non-covalent interactions which can be used to prepare and stabilize HBcAg dimers and multimers.

In one embodiment, the invention provides vaccine compositions prepared using HBcAg fusions proteins comprising a HBcAg, or fragment thereof, with a GCN4 polypeptide having the sequence of amino acid residues 227 to 276 in SEQ ID NO:154 fused to the C-terminus. This GCN4 polypeptide may also be fused to the N-terminus of the HbcAg.

HBcAg/src homology 3 (SH3) domain fusion proteins could also be used to prepare vaccine compositions of the invention. SH3 domains are relatively small domains found in a number of proteins which confer the ability to interact with specific proline-rich sequences in protein binding partners (see McPherson, *Cell Signal* 11:229–238 (1999). HBcAg/SH3 fusion proteins could be used in several ways.

First, the SH3 domain could form a first attachment site which interacts with a second attachment site of the antigen or antigenic determinant. Similarly, a proline rich amino acid sequence could be added to the HBcAg and used as a first attachment site for an SH3 domain second attachment site of an antigen or antigenic determinant. Second, the SH3 domain could associate with proline rich regions introduced into HBcAgs. Thus, SH3 domains and proline rich SH3 interaction sites could be inserted into either the same or different HBcAgs and used to form and stabilized dimers and multimers of the invention.

In other embodiments, a bacterial pilin, a subportion of a bacterial pilin, or a fusion protein which contains either a bacterial pilin or subportion thereof is used to prepare vaccine compositions of the invention. Examples of pilin proteins include pilins produced by *Escherichia coli, Haemophilus influenzae, Neisseria meningitidis, Neisseria gonorrhoeae, Caulobacter crescentus, Pseudomonas stutzeri*, and *Pseudomonas aeruginosa*. The amino acid sequences of pilin proteins suitable for use with the present invention include those set out in GenBank reports AJ000636 (SEQ ID NO:139), AJ132364 (SEQ ID NO:140), AF229646 (SEQ ID NO:141), AF051814 (SEQ ID NO:142), AF051815 (SEQ ID NO:143), and X00981 (SEQ ID NO:155), the entire disclosures of which are incorporated herein by reference.

Bacterial pilin proteins are generally processed to remove N-terminal leader sequences prior to export of the proteins into the bacterial periplasm. Further, as one skilled in the art would recognize, bacterial pilin proteins used to prepare vaccine compositions of the invention will generally not have the naturally present leader sequence.

One specific example of a pilin protein suitable for use in the present invention is the P-pilin of *E. coli* (GenBank report AF237482 (SEQ ID NO:144)). An example of a Type-1 *E. coli* pilin suitable for use with the invention is a pilin having the amino acid sequence set out in GenBank report $PO_{4128}$ (SEQ ID NO:146), which is encoded by nucleic acid having the nucleotide sequence set out in GenBank report M27603 (SEQ ID NO:145). The entire disclosures of these GenBank reports are incorporated herein by reference. Again, the mature form of the above referenced protein would generally be used to prepare vaccine compositions of the invention.

Bacterial pilins or pilin subportions suitable for use in the practice of the present invention will generally be able to associate to form non-natural molecular scaffolds.

Methods for preparing pili and pilus-like structures in vitro are known in the art. Bullitt et al., *Proc. Natl. Acad. Sci. USA* 93:12890–12895 (1996), for example, describe the in vitro reconstitution of *E. coli* P-pili subunits. Further, Eshdat et al., *J. Bacteriol*. 148:308–314 (1981) describe methods suitable for dissociating Type-1 pili of *E. coli* and the reconstitution of pili. In brief, these methods are as follows: pili are dissociated by incubation at 37° C. in saturated guanidine hydrochloride. Pilin proteins are then purified by chromatography, after which pilin dimers are formed by dialysis against 5 MM tris(hydroxymethyl) aminomethane hydrochloride (pH 8.0). Eshdat et al. also found that pilin dimers reassemble to form pili upon dialysis against the 5 mM tris(hydroxymethyl) aminomethane (pH 8.0) containing 5 mM $MgCl_2$.

Further, using, for example, conventional genetic engineering and protein modification methods, pilin proteins may be modified to contain a first attachment site to which an antigen or antigenic determinant is linked through a second attachment site. Alternatively, antigens or antigenic determinants can be directly linked through a second attachment site to amino acid residues which are naturally resident in these proteins. These modified pilin proteins may then be used in vaccine compositions of the invention.

Bacterial pilin proteins used to prepare vaccine compositions of the invention may be modified in a manner similar to that described herein for HBcAg. For example, cysteine and lysine residues may be either deleted or substituted with other amino acid residues and first attachment sites may be added to these proteins. Further, pilin proteins may either be expressed in modified form or may be chemically modified after expression. Similarly, intact pili may be harvested from bacteria and then modified chemically.

In another embodiment, pili or pilus-like structures are harvested from bacteria (e.g., *E. coli*) and used to form vaccine compositions of the invention. One example of pili suitable for preparing vaccine compositions is the Type-1 pilus of *E. coli*, which is formed from pilin monomers having the amino acid sequence set out in SEQ ID NO:146.

A number of methods for harvesting bacterial pili are known in the art. Bullitt and Makowski (*Biophys. J.* 74:623–632 (1998)), for example, describe a pilus purification method for harvesting P-pili from *E. coli*. According to this method, pili are sheared from hyperpiliated *E. coli* containing a P-pilus plasmid and purified by cycles of solubilization and $MgCl_2$ (1.0 M) precipitation. A similar purification method is set out below in Example 33.

Once harvested, pili or pilus-like structures may be modified in a variety of ways. For example, a first attachment site can be added to the pili to which antigens or antigen determinants may be attached through a second attachment site. In other words, bacterial pili or pilus-like structures can be harvested and modified to form non-natural molecular scaffolds.

Pili or pilus-like structures may also be modified by the attachment of antigens or antigenic determinants in the absence of a non-natural organizer. For example, antigens or antigenic determinants could be linked to naturally occurring cysteine resides or lysine residues. In such instances, the high order and repetitiveness of a naturally occurring amino acid residue would guide the coupling of the antigens or antigenic determinants to the pili or pilus-like structures. For example, the pili or pilus-like structures could be linked to the second attachment sites of the antigens or antigenic determinants using a heterobifunctional cross-linking agent.

When structures which are naturally synthesized by organisms (e.g., pili) are used to prepare vaccine compositions of the invention, it will often be advantageous to genetically engineer these organisms so that they produce structures having desirable characteristics. For example, when Type-1 pili of *E. coli* are used, the *E. coli* from which these pili are harvested may be modified so as to produce structures with specific characteristics. Examples of possible modifications of pilin proteins include the insertion of one or more lysine residues, the deletion or substitution of one or more of the naturally resident lysine residues, and the deletion or substitution of one or more naturally resident cysteine residues (e.g., the cysteine residues at positions 44 and 84 in SEQ ID NO:146).

Further, additional modifications can be made to pilin genes which result in the expression products containing a first attachment site other than a lysine residue (e.g., a FOS or JUN domain). Of course, suitable first attachment sites will generally be limited to those which do not prevent pilin proteins from forming pili or pilus-like structures suitable for use in vaccine compositions of the invention.

Pilin genes which naturally reside in bacterial cells can be modified in vivo (e.g., by homologous recombination) or pilin genes with particular characteristics can be inserted into these cells. For examples, pilin genes could be introduced into bacterial cells as a component of either a replicable cloning vector or a vector which inserts into the bacterial chromosome. The inserted pilin genes may also be linked to expression regulatory control sequences (e.g., a lac operator).

In most instances, the pili or pilus-like structures used in vaccine compositions of the invention will be composed of single type of a pilin subunit. Pili or pilus-like structures composed of identical subunits will generally be used because they are expected to form structures which present highly ordered and repetitive antigen arrays.

However, the compositions of the invention also include vaccines comprising pili or pilus-like structures formed from heterogenous pilin subunits. The pilin subunits which form these pili or pilus-like structures can be expressed from genes naturally resident in the bacterial cell or may be introduced into the cells. When a naturally resident pilin gene and an introduced gene are both expressed in a cell which forms pili or pilus-like structures, the result will generally be structures formed from a mixture of these pilin proteins. Further, when two or more pilin genes are expressed in a bacterial cell, the relative expression of each pilin gene will typically be the factor which determines the ratio of the different pilin subunits in the pili or pilus-like structures.

When pili or pilus-like structures having a particular composition of mixed pilin subunits is desired, the expression of at least one of the pilin genes can be regulated by a heterologous, inducible promoter. Such promoters, as well as other genetic elements, can be used to regulate the relative amounts of different pilin subunits produced in the bacterial cell and, hence, the composition of the pili or pilus-like structures.

In additional, while in most instances the antigen or antigenic determinant will be linked to bacterial pili or pilus-like structures by a bond which is not a peptide bond, bacterial cells which produce pili or pilus-like structures used in the compositions of the invention can be genetically engineered to generate pilin proteins which are fused to an antigen or antigenic determinant. Such fusion proteins which form pili or pilus-like structures are suitable for use in vaccine compositions of the invention.

As already discussed, viral capsids may be used for (1) the presentation or antigen or antigenic determinants and (2) the preparation of vaccine compositions of the invention. Particularly, useful in the practice of the invention are viral capsid proteins, also referred to herein as "coat proteins," which upon expression form capsids or capsid-like structures. Thus, these capsid proteins can form core particles and non-natural molecular scaffolds. Generally, these capsids or capsid-like structures form ordered and repetitive arrays which can be used for the presentation of antigens or antigenic determinants and the preparation of vaccine compositions of the invention.

One or more (e.g., one, two, three, four, five, etc.) antigens or antigenic determinants may be attached by any number of means to one or more (e.g., one, two, three, four, five, etc.) proteins which form viral capsids or capsid-like structures (e.g., bacteriophage coat proteins), as well as other proteins. For example, antigens or antigenic determinants may be attached to core particles using first and second attachment sites. Further, one or more (e.g., one, two, three, four, five, etc.) heterobifunctional crosslinkers can be used to attach antigens or antigenic determinants to one or more proteins which form viral capsids or capsid-like structures.

Viral capsid proteins, or fragments thereof may be used, for example, to prepare core particles and vaccine compositions of the invention. Bacteriophage Qβ coat proteins, for example, can be expressed recombinantly in E. coli. Further, upon such expression these proteins spontaneously form capsids. Additionally, these capsids form ordered and repetitive antigen or antigenic determinant arrays which can be used for antigen presentation and the preparation of vaccine compositions. As described below in Example 38, bacteriophage Qβ coat proteins can be used to prepare vaccine compositions which elicit immunological responses to antigenic determinants.

Specific examples of bacteriophage coat proteins which can be used to prepare compositions of the invention include the coat proteins of RNA bacteriophages such as bacteriophage Qβ (SEQ ID NO:159; PIR Database, Accession No. VCBPQβ referring to Qβ CP and SEQ ID NO: 217; Accession No. AAA16663 referring to Qβ A1 protein), bacteriophage R17 (SEQ ID NO:160; PIR Accession No. VCBPR7), bacteriophage fr (SEQ ID NO:161; PIR Accession No. VCBPFR), bacteriophage GA (SEQ ID NO:162; GenBank Accession No. NP-040754), bacteriophage SP (SEQ ID NO:163; GenBank Accession No. CAA30374 referring to SP CP and SEQ ID NO: 254; Accession No. referring to SP A1 protein), bacteriophage MS2 (SEQ ID NO:164; PIR Accession No. VCBPM2), bacteriophage M11 (SEQ ID NO:165; GenBank Accession No. AAC06250), bacteriophage MX1 (SEQ ID NO:166; GenBank Accession No. AAC14699), bacteriophage NL95 (SEQ ID NO:167; GenBank Accession No. AAC14704), bacteriophage f2 (SEQ ID NO: 215; GenBank Accession No. $PO_{3611}$), bacteriophage PP7 (SEQ ID NO: 253), As one skilled in the art would recognize, any protein which forms capsids or capsid-like structures can be used for the preparation of vaccine compositions of the invention. Furthermore, the A1 protein of bacteriophage Qβ or C-terminal truncated forms missing as much as 100, 150 or 180 amino acids from its C-terminus may be incorporated in a capsid assembly of Qβ coat proteins. The A1 protein may also be fused to an organizer and hence a first attachment site, for attachment of Antigens containing a second attachment site. Generally, the percentage of A1 protein relative to Qβ CP in the capsid assembly will be limited, in order to insure capsid formation. A1 protein accession No. AAA16663 (SEQ ID NO: 217).

Qβ coat protein has also been found to self-assemble into capsids when expressed in E. coli (Kozlovska T M. et al., GENE 137: 133–137 (1993)). The obtained capsids or virus-like particles showed an icosahedral phage-like capsid structure with a diameter of 25 nm and T=3 quasi symmetry. Further, the crystal structure of phage Qβ has been solved. The capsid contains 180 copies of the coat protein, which are linked in covalent pentamers and hexamers by disulfide bridges (Golmohammadi, R. et al., Structure 4: 543–5554 (1996)). Other RNA phage coat proteins have also been shown to self-assemble upon expression in a bacterial host (Kastelein, R A. et al., Gene 23: 245–254 (1983), Kozlovskaya, T M. et al., Dokl. Akad. Nauk SSSR 287: 452–455 (1986), Adhin, M R. et al., Virology 170: 238–242 (1989), Ni, C Z., et al., Protein Sci. 5: 2485–2493 (1996), Priano, C. et al., J. Mol. Biol. 249: 283–297 (1995)). The Qβ phage capsid contains, in addition to the coat protein, the so called read-through protein A1 and the maturation protein A2. A1 is generated by suppression at the UGA stop codon and has a length of 329 aa. The capsid of phage Qβ recombinant coat protein used in the invention is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. Biochemistry 28: 71–76 (1989); Lim F. et al., J. Biol. Chem. 271: 31839–31845 (1996)). The stem loop and RNA in general are known to be involved in the virus assembly (Golmohammadi, R. et al., Structure 4: 543–5554 (1996))

Proteins or protein domains may affect the structure and assembly of the particle even more then a short peptide. As an example, proper folding of antigens comprising disulfide bridges will generally not be possible in the cytoplasm of E. coli, where the Qβ particles are expressed. Likewise, glycosylation is generally not possible in prokaryotic expression systems. It is therefore an advantage of the contemplated invention described here to attach the antigen to the particle by starting with the already assembled particle and the isolated antigen. This allows expression of both the particle and the antigen in an expression host guaranteeing proper folding of the antigen, and proper folding and assembly of the particle.

It is a finding of this invention, that one or several several antigen molecules may be attached to one subunit of the capsid of RNA phages coat proteins. A specific feature of the capsid of the coat protein of RNA phages and in particular of Qβ capsid is thus the possibility to couple several antigens per subunit. This allows for the generation of a dense antigen array. Other viral capsids used for covalent attachment of antigens by way of chemical cross-linking, such for example a HBcAg modified with a lysine residue in its major immunodominant region (MIR; WO 00/32227), show coupling density of maximally 0.5 antigens per subunit. The distance between the spikes (corresponding to the MIR) of HBcAg is 50 A (Wynne, S A. et al., Mol. Cell 3: 771–780 (1999)), and therefore an antigen array with distances shorter than 50 A cannot be generated Capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, and not to the interior where the lysine residues interact with RNA. Capsids of other RNA phage coat proteins also have a defined number of lysine residues on their surface and a defined topology of these lysine residues. Another advantage of the capsids derived from RNA phages is their high expression yield in bacteria, that allows to produce large quantities of material at affordable cost.

Another feature of the capsid of Qβ coat protein is its stability. Qβ subunits are bound via disulfide bridges to each other, covalently linking the subunits. Qβ capsid protein also shows unusual resistance to organic solvents and denaturing agents. Surprisingly, we have observed that DMSO and acetonitrile concentrations as high as 30%, and Guanidinium concentrations as high as 1 M could be used without affecting the stability or the ability to form antigen arrays of the capsid. Thus, theses organic solvents may be used to couple hydrophobic peptides. The high stability of the capsid of Qβ coat protein is an important feature pertaining to its use for immunization and vaccination of mammals and humans in particular. The resistance of the capsid to organic solvent allows the coupling of antigens not soluble in aqueous buffers.

Insertion of a cysteine residue into the N-terminal β-hairpin of the coat protein of the RNA phage MS-2 has been described in the patent application U.S. Pat. No. 5,698,424. We note however, that the presence of an exposed free cysteine residue in the capsid may lead to oligomerization of capsids by way of disulfide bridge formation. Other attachments contemplated in patent application U.S. Pat. No. 5,698,424 involve the formation of disulfide bridges between the antigen and the Qβ particle. Such attachments are labile to sulfhydryl-moiety containing molecules.

The reaction between an initial disulfide bridge formed with a cys-residue on Qβ, and the antigen containing a free sulfhydryl residue releases sulfhydryl containing species other than the antigen. These newly formes sulfhydryl containing species can react again with other disulfide bridges present on the particle, thus establishing an equilibrium. Upon reaction with the disulfide bridge formed on the particle, the antigen may either form a disulfide bridge with the cys-residue from the particle, or with the cys-residue of the leaving group molecule which was forming the initial disulfide bridge on the particle. Moreover, the other method of attachment described, using a hetero-bifunctional cross-linker reacting with a cysteine on the Qβ particle on one side, and with a lysine residue on the antigen on the other side, leads to a random orientation of the antigens on the particle.

We further note that, in contrast to the capsid of the Qβ and Fr coat proteins, recombinant MS-2 described in patent application U.S. Pat. No. 5,698,424 is essentially free of nucleic acids, while RNA is packaged inside the two capsids mentioned above.

We describe new and inventive compositions allowing the formation of robust antigen arrays with variable antigen density. We show that much higher epitope density can be achieved than usually obtained with other VLPs. We also disclose compositions with simultaneous display of several antigens with appropriate spacing, and compositions wherein the addition of accessory molecules, enhancing solubility or modifying the capsid in a suitable and desired way.

The preparation of compositions of capsids of RNA phage coat proteins with a high epitope density is disclosed in this application. As a skilled artisan in the Art would know, the conditions for the assembly of the ordered and repetitive antigen array depend for a good part on the antigen and on the selection of a second attachment site on the antigen. In the case of the absence of a useful second attachment site, such a second attachment has to be engineered to the antigen.

A prerequisite in designing a second attachment site, is the choice of the position at which it should be fused, inserted or generally engineered. A skilled artisan would know how to find guidance in selecting the position of the second attachment site. A crystal structure of the antigen may provide information on the availability of the C- or N-termini of the molecule (determined for example from their accessibility to solvent), or on the exposure to solvent of residues suitable for use as second attachment sites, such as cysteine residues. Exposed disulfide bridges, as is the case for Fab fragments, may also be a source of a second attachment site, since they can be generally converted to single cysteine residues through mild reduction. In general, in the case where immunization with a self-antigen is aiming at inhibiting the interaction of this self-antigen with its natural ligands, the second attachment site will be added such that it allows generation of antibodies against the site of interaction with the natural ligands. Thus, the location of the second attachment site will selected such, that steric hindrance from the second attachment site or any amino acid linker containing it, is avoided. In further embodiments, an antibody response directed at a site distinct from the interaction site of the self-antigen with its natural ligand is desired. In such embodiments, the second attachment site may be selected such that it prevents generation of antibodies against the interaction site of the self-antigen with its natural ligands.

Other criteria in selecting the position of the second attachment site include the oligomerization state of the antigen, the site of oligomerization, the presence of a cofactor, and the availability of experimental evidence disclosing sites in the antigen structure and sequence where modification of the antigen is compatible with the function of the self-antigen, or with the generation of antibodies recognizing the self-antigen.

In some embodiments, engineering of a second attachment site onto the antigen requires the fusion of an amino acid linker containing an amino acid suitable as second attachment site according to the disclosures of this invention. In a preferred embodiment, the amino acid is cysteine. The selection of the amino acid linker will be dependent on the nature of the self-antigen, on its biochemical properties, such as pI, charge distribution, glycosylation. In general, flexible amino acid linkers are favored. Examples of amino acid linkers are the hinge region of Immunoglobulins, glycine seine linkers (GGGGS)$_n$ (SEQ ID NO:407), and glycine linkers (G)$_n$ all further containing a cysteine residue as second attachment site and optionally further glycine residues. (In the following are examples of said amino acid linkers:

N-terminal gamma 1: CGDKTHTSPP (SEQ ID NO:408)
C-terminal gamma 1: DKTHTSPPCG (SEQ ID) NO:409)
N-terminal gamma 3: CGGPKPSTPPGSSGGAP (SEQ ID NO:410)
C-terminal gamma 3: PKPSTPPGSSGGAPGGCG (SEQ ID NO:411)
N-terminal glycine linker: GCGGGG (SEQ ID NO:412)
C-terminal glycine linker: GGGGCG (SEQ ID NO:413))

For peptides, GGCG (SEQ ID NO:414) linkers at the C-terminus of the peptide, or CGG at its N-terminus have shown to be useful. In general, glycine residues will be inserted between bulky amino acids and the cysteine to be used as second attachment site.

A particularly favored method of attachment of antigens to VLPs, and in particular to capsids of RNA phage coat proteins is the linking of a lysine residue on the surface of the capsid of RNA phage coat proteins with a cysteine residue on the antigen. To be effective as second attachment site, a sulfhydryl group must be available for coupling. Thus, a cysteine residue has to be in its reduced state, that is a free cysteine or a cysteine residue with a free sulfhydryl group has to be available. In the instant where the cysteine residue to function as second attachment site is in an oxidized form, for example if it is forming a disulfide bridge, reduction of this disulfide bridge with e.g. DTT, TCEP or β-mercaptoethanol is required.

It is a finding of this application that epitope density on the capsid of RNA phage coat proteins can be modulated by the choice of cross-linker and other reaction conditions. For example, the cross-linkers Sulfo-GMBS and SMPH allow reaching higher epitope density than the cross-linker Sulfo-MBS under the same reaction conditions. Derivatization is positively influenced by high concentration of reactants, and manipulation of the reaction conditions can be used to control the number of antigens coupled to RNA phages capsid proteins, and in particular to Qβ capsid protein.

From theoretical calculation, the maximally achievable number of globular protein antigens of a size of 17 kDa does not exceed 0.5. Thus, several of the lysine residues of the capsid of Qβ coat protein will be derivatized with a cross-linker molecule, yet be devoid of antigen. This leads to the disappearance of a positive charge, which may be detrimental to the solubility and stability of the conjugate. By replacing some of the lysine residues with arginines, such is the case in the disclosed Qβ coat protein mutant, we prevent the excessive disappearance of positive charges since the arginine residues do not react with the cross-linker.

In further embodiments, we disclose a Qβ mutant coat protein with additional lysine residues, suitable for obtaining high density arrays of antigens.

The crystal structure of several RNA bacteriophages has been determined (Golmohammadi, R. et al., Structure 4:543–554 (1996)). Using such information, one skilled in the art could readily identify surface exposed residues and modify bacteriophage coat proteins such that one or more reactive amino acid residues can be inserted. Thus, one skilled in the art could readily generate and identify modified forms of bacteriophage coat proteins which can be used in the practice of the invention. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2) can also be used to prepare vaccine compositions of the invention.

Although the sequence of the variants proteins discussed above will differ from their wild-type counterparts, these variant proteins will generally retain the ability to form capsids or capsid-like structures. Thus, the invention further includes vaccine compositions which contain variants of proteins which form capsids or capsid-like structures, as well as methods for preparing such vaccine compositions, individual protein subunits used to prepare such vaccine compositions, and nucleic acid molecules which encode these protein subunits. Thus, included within the scope of the invention are variant forms of wild-type proteins which form ordered and repetitive antigen arrays (e.g., variants of proteins which form capsids or capsid-like structures) and retain the ability to associate and form capsids or capsid-like structures.

As a result, the invention further includes vaccine compositions comprising proteins comprising, or alternatively consisting of, amino acid sequences which are at least 80%, 85%, 90%, 95%, 97%, or 99% identical to wild-type proteins which form ordered arrays. In many instances, these proteins will be processed to remove signal peptides (e.g., heterologous signal peptides).

Further included within the scope of the invention are nucleic acid molecules which encode proteins used to prepare vaccine compositions of the invention.

In particular embodiments, the invention further includes vaccine compositions comprising proteins comprising, or alternatively consisting of, amino acid sequences which are at least 80%, 85%, 90%, 95%, 97%, or 99% identical to any of the amino acid sequences shown in SEQ ID NOs: 159–167, and forms of these proteins which have been processed, where appropriate, to remove the N-terminal leader sequence.

Proteins suitable for use in the practice of the present invention also include C-terminal truncation mutants of proteins which form capsids or capsid-like structures, as well as other ordered arrays. Specific examples of such truncation mutants include proteins having an amino acid sequence shown in any of SEQ ID NOs:159–167 where 1, 2, 5, 7, 9, 10, 12, 14, 15, or 17 amino acids have been removed from the C-terminus. Normally, C-terminal truncation mutants used in the practice of the invention will retain the ability to form capsids or capsid-like structures.

Further proteins suitable for use in the practice of the present invention also include N-terminal truncation mutants of proteins which form capsids or capsid-like structures. Specific examples of such truncation mutants include proteins having an amino acid sequence shown in any of SEQ ID NOs:159–167 where 1, 2, 5, 7, 9, 10, 12, 14, 15, or 17 amino acids have been removed from the N-terminus. Normally, N-terminal truncation mutants used in the practice of the invention will retain the ability to form capsids or capsid-like structures.

Additional proteins suitable for use in the practice of the present invention include—and C-terminal truncation mutants which form capsids or capsid-like structures. Suitable truncation mutants include proteins having an amino acid sequence shown in any of SEQ ID NOs:159–167 where 1, 2, 5, 7, 9, 10, 12, 14, 15, or 17 amino acids have been removed from the N-terminus and 1, 2, 5, 7, 9, 10, 12, 14, 15, or 17 amino acids have been removed from the C-terminus. Normally, N-terminal and C-terminal truncation mutants used in the practice of the invention will retain the ability to form capsids or capsid-like structures.

The invention further includes vaccine compositions comprising proteins comprising, or alternatively consisting of, amino acid sequences which are at least 80%, 85%, 90%, 95%, 97%, or 99% identical to the above described truncation mutants.

The invention thus includes vaccine compositions prepared from proteins which form ordered arrays, methods for preparing vaccine compositions from individual protein subunits, methods for preparing these individual protein subunits, nucleic acid molecules which encode these subunits, and methods for vaccinating and/or eliciting immunological responses in individuals using vaccine compositions of the invention.

B. Construction of an Antigen or Antigenic Determinant with a Second Attachment Site The second element in the compositions of the invention is an antigen or antigenic determinant possessing at least one second attachment site capable of association through at least one non-peptide bond to the first attachment site of the non-natural molecular scaffold. The invention provides for compositions that vary according to the antigen or antigenic determinant selected in consideration of the desired therapeutic effect. Other compositions are provided by varying the molecule selected for the second attachment site.

However, when bacterial pili, or pilus-like structures, pilin proteins are used to prepare vaccine compositions of the invention, antigens or antigenic determinants may be attached to pilin proteins by the expression of pilin/antigen fusion proteins. Similarly, when proteins other than pilin proteins (e.g., viral capsid proteins) are used to prepare vaccine compositions of the invention, antigens or antigenic determinants may be attached to these non-pilin proteins by the expression of non-pilin protein/antigen fusion proteins. Antigens or antigenic determinants may also be attached to bacterial pili, pilus-like structures, pilin proteins, and other proteins which form ordered arrays through non-peptide bonds.

Antigens of the invention may be selected from the group consisting of the following: (a) proteins suited to induce an immune response against cancer cells; (b) proteins suited to induce an immune response against infectious diseases; (c) proteins suited to induce an immune response against allergens,(d) proteins suited to induce an immune response in farm animals, and (e) fragments (e.g., a domain) of any of the proteins set out in (a)-(d).

In one specific embodiment of the invention, the antigen or antigenic determinant is one that is useful for the prevention of infectious disease. Such treatment will be useful to treat a wide variety of infectious diseases affecting a wide range of hosts, eg., human, cow, sheep, pig, dog, cat, other mammalian species and non-mammalian species as well. Treatable infectious diseases are well known to those skilled in the art, examples include infections of viral etiology such as HIV, influenza, Herpes, viral hepatitis, Epstein Bar, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc. Thus, antigens or antigenic determinants selected for the compositions of the invention will be well known to those in the medical art; examples of antigens or antigenic determinants include the following: the HIV antigens gp140 and gp160; the influenaza antigens hemagglutinin, M2 protein and neuramimidase, Hepatitis B surface antigen, circumsporozoite protein of malaria.

In specific embodiments, the invention provides vaccine compositions suitable for use in methods for preventing and/or attenuating diseases or conditions which are caused or exacerbated by "self" gene products (e.g., tumor necrosis factors). Thus, vaccine compositions of the invention include compositions which lead to the production of antibodies that prevent and/or attenuate diseases or conditions caused or exacerbated by "self" gene products. Examples of such diseases or conditions include graft versus host disease, IgE-mediated allergic reactions, anaphylaxis, adult respiratory distress syndrome, Crohn's disease, allergic asthma, acute lymphoblastic leukemia (ALL), non-Hodgkin's lymphoma (NHL), Graves' disease, systemic lupus erythematosus (SLE), inflammatory autoimmune diseases, myasthenia gravis, immunoproliferative disease lymphadenopathy (IPL), angioimmunoproliferative lymphadenopathy (AIL), immunoblastive lymphadenopathy (IBL), rheumatoid arthritis, diabetes, multiple sclerosis, Alzheimer disease and osteoporosis.

In related specific embodiments, compositions of the invention are an immunotherapeutic that may be used for the treatment of allergies or cancer.

The selection of antigens or antigenic determinants for the preparation of compositions and for use in methods of treatment for allergies would be known to those skilled in the medical arts treating such disorders. Representative examples of such antigens or antigenic determinants include the following: bee venom phospholipase $A_2$, Bet v I (birch pollen allergen), 5 Dol m V (white-faced hornet venom allergen), Mellitin and Der p I (House dust mite allergen), as well as fragments of each which can be used to elicit immunological responses.

As indicated, a preferred antigen or antigenic determinant is Der p I. Der p I is a 25 kD protease found in house dust mite faecal particles. Der p I represents the major allergic molecule of house dust mite. Accordingly, 80% of mite allergic patients have anti-Der p I IgE antibodies. In particular, the peptides p52–72 and p 117–133, among others, are known to comprise epitopes, which are recognized by antibodies specific for the native Der p I. IgE antibodies raised in a polyclonal response to the whole antigen bind with high affinity to the peptide region 59–94 (L. Pierson-Mullany et al. (2000) Molecular Immunology). Other regions also bind IgE with high affinity. The peptide p117–133 contains a free cysteine at its N-terminus, preferably representing the second attachment site in accordance with the invention. 3D model assigns peptides p52–72 and p117–133 to the surface of the whole protein. However, other fragments of the Der p I protein may comprise B cell epitopes being preferably suitable for the present invention.

The selection of antigens or antigenic determinants for compositions and methods of treatment for cancer would be known to those skilled in the medical arts treating such disorders. Representative examples of such types of antigens or antigenic determinants include the following: Her2 (breast cancer), GD2 (neuroblastoma), EGF-R (malignant glioblastoma), CEA (medullary thyroid cancer), and CD52 (leukemia), human melanoma protein gp100, human melanoma protein melan-A/MART-1, tyrosinase, NA17-A nt protein, MAGE-3 protein, p53 protein, HPV16 E7 protein, as well as fragments of each which can be used to elicit immunological responses. Further preferred antigenic determinants useful for compositions and methods of treatment for cancer are molecules and antigenic determinants involved in angiogenesis. Angiogenesis, the formation of new blood vessels, plays an essential role in physiological and pathophysiological processes such as wound healing and solid tumor growth, respectively (Folkman, J. (1995) Nat. medicine 1, 27–31; Folkman, J., and Klagsbrun, M. (1987) Science 235, 442–446; Martiny-Baron, G., and Marmé, D. (1995) Curr. Opin. Biotechnol. 6, 675–680; Risau, W. (1997) Nature 386, 671–674). Rapidly growing tumors initiate and depend on the formation of blood vessels to provide the required blood supply. Thus, antiangiogenic agents might be effective as an anticancer therapy.

Among several putative angiogenic factors that have been identified so far vascular endothelial growth factor (VEGF) is a potent endothelial cell specific mitogen and a primary stimulant of the vascularization of many solid tumors. Although recent findings implicate that a set of angiogenic factors must be perfectly orchestrated to form functional vessels, it seems that the blockade of even a single growth factor might limit disease-induced vascular growth. Thus, blockade of VEGF may be a premium target for intervention in tumor induced angiogenesis. To target the endothelium rather than the tumor itself has recently emerged as a novel strategy to fight tumors (Millauer, B., Shawver, L. K., Plate, K. H., Risau, W., and Ullrich, A. (1994) Nature 367, 576–579; Kim, J., Li, B., Winer, J., Armanini, M., Gillett, N., Phillip, H. S., Ferrara, N. (1993) Nature 362, 841–844). In contrast to tumors, which easily mutate target structures recognized by the immune system, endothelial cells do not usually escape the immune system or other therapeutic regimens.

An anti-VEGFR-II antibody (IMC-1C11) and an anti-VEGF antibody have been disclosed (Lu, D., Kussie, P., Pytowski, B., Persaud, K., Bohlen, P., Witte, L., Zhu, Z. (2000) J. Biol. Chem. 275, 14321–14330; Presta, L. G, Chen, H., O'Connor, S J., Chisholm, V., Meng, Y G., Krummen, L., Winkler, M., Ferrara N. (1997) Cancer Res. 47, 4593–4599). The former neutralizing monoclonal anti-VEGFR-2 antibody recognizes an epitope that has been identified as putative VEGF/VEGFR-II binding site (Piossek, C., Schneider-Mergener, J., Schimer, M., Vakalopoulou, E., Germeroth, L., Thierauch, K. H. (1999) J. Biol. Chem. 274, 5612–5619).

Thus, in another preferred embodiment of the invention, the antigen or antigenic determinant is a peptide derived from the VEGFR-II contact site. This provides a composition and a vaccine composition in accordance with the invention, which may have antiangiogenic properties useful for the treatment of cancer. Inhibition of tumor growth in mice using sera specific for VEGFR-2 has been demonstrated (Wei, Y Q., Wang, Q R., Zhao, X., Yang, L., Tian, L., Lu, Y., Kang, B., Lu, C J., Huang, M J., Lou, Y Y., Xiao, F., He, Q M., Shu, J M., Xie, X J., Mao, Y Q., Lei, S., Luo, F., Zhou, L Q., Liu, C E., Zhou, H., Jiang, Y., Peng, F., Yuan, L P., Li, Q., Wu, Y., Liu, J Y. (2000) Nature Medicine 6, 1160–1165). Therefore, further preferred antigenic determinants suitable for inventive compositions and antiangiogenic vaccine compositions in accordance with the invention comprise either the human VEGFR-II derived peptide with the sequence CTARTELNVGIDFNWEYPSSKHQHKK (SEQ ID NO:351), and/or the murine VEGFR-II derived peptide having the sequence CTARTELNVGLDFTWH-SPPSKSHHKK (SEQ ID NO:352), and/or the relevant extracellular globular domains 1–3 of the VEGFR-II.

Therefore, in a preferred embodiment of the invention, the vaccine composition comprises a core particle selected from a virus-like particle or a bacterial pilus and a VEGFR-II derived peptide or a fragment thereof as an antigen or antigenic determinant in accordance with the present invention.

The selection of antigens or antigenic determinants for compositions and methods of treatment for other diseases or conditions associated with self antigens would be also known to those skilled in the medical arts treating such disorders. Representative examples of such antigens or antigenic determinants are, for example, lymphotoxins (e.g. Lymphotoxin α (LT α), Lymphotoxin β (LT β)), and lymphotoxin receptors, Receptor activator of nuclear factor kB ligand (RANKL), vascular endothelial growth factor (VEGF), vascular endothelial growth factor receptor (VEGF-R), Interleukin-5, Interleukin-17, Interleukin-13, CCL21, CXCL12, SDF-1, MCP-1, Endoglin, Resistin, GHRH, LHRH, TRH, MIF, Eotaxin, Bradykinin, BLC, Tumor Necrosis Factor α and amyloid beta peptide (A$\beta_{1-42}$) (SEQ ID NO: 220), as well as fragments of each which can be used to elicit immunological responses. In a preferred embodiment, the antigen is the amyloid beta peptide (A$\beta_{1-42}$) (DAEFRHDSGYEVHHQKL VFFAEDVGSNK-GAIIGLMVGGVVIA (SEQ ID NO: 220), or a fragment thereof. The amyloid beta protein is SEQ ID NO: 218. The amyloid beta precursor protein is SEQ ID NO: 219.

In another preferred embodiment of the invention, the antigen or antigenic determinant is an angiotensin peptide or a fragment thereof. The term "angiotensin peptide" as used herein, shall encompass any peptide comprising the sequence, or fragments thereof, of angiotensinogen, angiotensin I or angiotensin II. The sequences are as follows: Angiotensinogen: DRVYIHPFHLVIHN (SEQ ID NO:353); Angiotensin I: DRVYIHPFHL (SEQ ID NO:354); Angiotensin II: DRVYIHPF (SEQ ID NO:355). Typically, one or more additional amino acids are added either at the C- or at the N-terminus of the angiotensin peptide sequences. The sequence of the angiotensin peptides corresponds to the human sequence, which is identical to the murine sequence. Therefore, immunization of a human or a mouse with vaccines or compositions, respectively, comprising such angiotensin peptides as antigenic determinant in accordance with the invention, is a vaccination against a self-antigen. Those additional amino acids are, in particular, valuable for an oriented and ordered association to the core particle.

Preferably, the angiotensin peptide has an amino acid sequence selected from the group consisting of a) the amino acid sequence of CGGDRVYIHPF (SEQ ID NO:380); b) the amino acid sequence of CGGDRVYIHPFHL (SEQ ID NO:381); c) the amino acid sequence of DRVYIHPF-HLGGC (SEQ ID NO:382); and d) the amino acid sequence of CDRVYIHPFH (SEQ ID NO:383).

A vaccine in accordance with the present invention comprising at least one angiotensin peptide may be used for the treatment of hypertension.

In a particular embodiment of the invention, the antigen or antigenic determinant is selected from the group consisting of: (a) a recombinant protein of HIV, (b) a recombinant protein of Influenza virus (e.g., an Influenza virus M2 protein or a fragment thereof), (c) a recombinant protein of Hepatitis C virus, (d) a recombinant protein of Toxoplasma, (e) a recombinant protein of *Plasmodium falciparum*, (f) a recombinant protein of *Plasmodium vivax*, (g) a recombinant protein of *Plasmodium ovale*, (h) a recombinant protein of *Plasmodium malariae*, (i) a recombinant protein of breast cancer cells, (j) a recombinant protein of kidney cancer cells, (k) a recombinant protein of prostate cancer cells, (l) a recombinant protein of skin cancer cells, (m) a recombinant protein of brain cancer cells, (n) a recombinant protein of leukemia cells, (o) a recombinant profiling, (p) a recombinant protein of bee sting allergy, (q) a recombinant proteins of nut allergy, (r) a recombinant proteins of food allergies, (s) recombinant proteins of asthma, (t) a recombinant protein of Chlamydia, and (u) a fragment of any of the proteins set out in (a)-(t).

Once the antigen or antigenic determinant of the composition is chosen, at least one second attachment site may be added to the molecule in preparing to construct the organized and repetitive array associated with the non-natural molecular scaffold of the invention. Knowledge of what will constitute an appropriate second attachment site will be known to those skilled in the art. Representative examples of second attachment sites include, but are not limited to, the following: an antigen, an antibody or antibody fragment, biotin, avidin, streptavidin, a receptor, a receptor ligand, a ligand, a ligand-binding protein, an interacting leucine zipper polypeptide, an amino group, a chemical group reactive to an amino group; a carboxyl group, chemical group reactive to a carboxyl group, a sulfhydryl group, a chemical group reactive to a sulfhydryl group, or a combination thereof.

The association between the first and second attachment sites will be determined by the characteristics of the respective molecules selected but will comprise at least one non-peptide bond. Depending upon the combination of first and second attachment sites, the nature of the association may be covalent, ionic, hydrophobic, polar, or a combination thereof.

In one embodiment of the invention, the second attachment site may be the FOS leucine zipper protein domain or the JUN leucine zipper protein domain.

In a more specific embodiment of the invention, the second attachment site selected is the FOS leucine zipper protein domain, which associates specifically with the JUN leucine zipper protein domain of the non-natural molecular scaffold of the invention. The association of the JUN and FOS leucine zipper protein domains provides a basis for the formation of an organized and repetitive antigen or antigenic determinant array on the surface of the scaffold. The FOS leucine zipper protein domain may be fused in frame to the antigen or antigenic determinant of choice at either the amino terminus, carboxyl terminus or internally located in the protein if desired.

Several FOS fusion constructs are provided for exemplary purposes. Human growth hormone (Example 4), bee venom phospholipase $A_2$ ($PLA_2$) (Example 9), ovalbumin (Example 10) and HIV gp140 (Example 12).

In order to simplify the generation of FOS fusion constructs, several vectors are disclosed that provide options for antigen or antigenic determinant design and construction (see Example 6). The vectors pAV1–4 were designed for the expression of FOS fusion in *E. coli*; the vectors pAV5 and pAV6 were designed for the expression of FOS fusion proteins in eukaryotic cells. Properties of these vectors are briefly described:

1. pAV1: This vector was designed for the secretion of fusion proteins with FOS at the C-terminus into the *E. coli* periplasmic space. The gene of interest (g.o.i.) may be ligated into the StuI/NotI sites of the vector.

2. pAV2: This vector was designed for the secretion of fusion proteins with FOS at the N-terminus into the *E. coli* periplasmic space. The gene of interest (g.o.i.) ligated into the NotI/EcoRV (or NotI/HindIII) sites of the vector.

3. pAV3: This vector was designed for the cytoplasmic production of fusion proteins with FOS at the C-terminus in *E. coli*. The gene of interest (g.o.i.) may be ligated into the EcoRV/NotI sites of the vector.

4. pAV4: This vector is designed for the cytoplasmic production of fusion proteins with FOS at the N-terminus in *E. coli*. The gene of interest (g.o.i.) may be ligated into the NotI/EcoRV (or NotI/HindIII) sites of the vector. The N-terminal methionine residue is proteolytically removed upon protein synthesis (Hirel et al., *Proc. Natl. Acad. Sci. USA* 86:8247–8251 (1989)).

5. pAV5: This vector was designed for the eukaryotic production of fusion proteins with FOS at the C-terminus. The gene of interest (g.o.i.) may be inserted between the sequences coding for the hGH signal sequence and the FOS domain by ligation into the Eco47III/NotI sites of the vector. Alternatively, a gene containing its own signal sequence may be fused to the FOS coding region by ligation into the StuI/NotI sites.

6. pAV6: This vector was designed for the eukaryotic production of fusion proteins with FOS at the N-terminus. The gene of interest (g.o.i.) may be ligated into the NotI/StuI (or NotI/HindIII) sites of the vector.

As will be understood by those skilled in the art, the construction of a FOS-antigen or -antigenic determinant fusion protein may include the addition of certain genetic elements to facilitate production of the recombinant protein. Example 4 provides guidance for the addition of certain *E. coli* regulatory elements for translation, and Example 7 provides guidance for the addition of a eukaryotic signal sequence. Other genetic elements may be selected, depending on the specific needs of the practioner.

The invention is also seen to include the production of the FOS-antigen or FOS-antigenic determinant fusion protein either in bacterial (Example 5) or eukaryotic cells (Example 8). The choice of which cell type in which to express the fusion protein is within the knowledge of the skilled artisan, depending on factors such as whether post-translational modifications are an important consideration in the design of the composition.

As noted previously, the invention discloses various methods for the construction of a FOS-antigen or FOS-antigenic determinant fusion protein through the use of the pAV vectors. In addition to enabling prokaryotic and eukaryotic expression, these vectors allow the practitioner to choose between N- and C-terminal addition to the antigen of the FOS leucine zipper protein domain. Specific examples are provided wherein N- and C-terminal FOS fusions are made to $PLA_2$ (Example 9) and ovalbumin (Example 10). Example 11 demonstrates the purification of the $PLA_2$ and ovalbumin FOS fusion proteins.

In a more specific embodiment, the invention is drawn to an antigen or antigenic determinant encoded by the HIV genome. More specifically, the HIV antigen or antigenic determinant is gp140. As provided for in Examples 11–15, HIV gp140 may be created with a FOS leucine zipper protein domain and the fusion protein synthesized and purified for attachment to the non-natural molecular scaffold of the invention. As one skilled in the art would know, other HIV antigens or antigenic determinants may be used in the creation of a composition of the invention.

In another more specific embodiment, the invention is drawn to vaccine compositions comprising at least one antigen or antigenic determinant encoded by an Influenza viral nucleic acid, and the use of such vaccine compositions to elicit immune responses. In an even more specific embodiment, the Influenza antigen or antigenic determinant may be an M2 protein (e.g., an M2 protein having the amino acids shown in SEQ ID NO:213, GenBank Accession No. $PO_{6821}$, or in SEQ ID NO: 212, PIR Accession No. MFIV62, or fragment thereof (e.g., amino acids from about 2 to about 24 in SEQ ID NO:213, the amino acid sequence in SEQ ID NO:212). Further, influenza antigens or antigenic determinants may be coupled to non-natural molecular scaffolds or core particles through either peptide or non-peptide bonds. When Influenza antigens or antigenic determinants are coupled to non-natural molecular scaffolds or core particles through peptide bonds, the molecules which form order and repetitive arrays will generally be prepared as fusion protein expression products. The more preferred embodiment is however a composition, wherein the M2 peptide is coupled by chemical cross-linking, to Qβ capsid protein HBcAg capsid protein or Pili according to the disclosures of the invention.

Portions of an M2 protein (e.g., an M2 protein having the amino acid sequence in SEQ ID NO:213), as well as other proteins against which an immunological response is sought, suitable for use with the invention may comprise, or alternatively consist of, peptides of any number of amino acids in length but will generally be at least 6 amino acids in length (e.g., peptides 6, 7, 8, 9, 10, 12, 15, 18, 20, 25, 30, 35, 40, 45, 50, 55, 60, 65, 70, 75, 80, 85, 90, 95, or 97 amino acids in length).

In another specific embodiment of the invention, the second attachment site selected is a cysteine residue, which associates specifically with a lysine residue of the non-natural molecular scaffold or core particle of the invention, or the second attachment site selected is a lysine residue, which associates specifically with a cysteine residue of the non-natural molecular scaffold or core particle of the invention. The chemical linkage of the lysine residue (Lys) and cysteine residue (Cys) provides a basis for the formation of an organized and repetitive antigen or antigenic determinant array on the surface of the scaffold or core particle. The cysteine or lysine residue may be engineered in frame to the antigen or antigenic determinant of choice at either the amino terminus, carboxyl terminus or internally located in the protein if desired. By way of example, $PLA_2$ and HIV gp14O are provided with a cysteine residue for linkage to a lysine residue first attachment site. In additional specific embodiments, the invention provides vaccine compositions suitable for use in methods for preventing and/or attenuating allergic reactions, such as allergic reactions which lead to anaphylaxis. Thus, vaccine compositions of the invention include compositions which lead to the production of antibodies that prevent and/or attenuate allergic reactions. Thus, in certain embodiments, vaccine compositions of the invention include compositions which elicit an immunological response against an allergen. Examples of such allergens include phospholipases such as the phospholipase A$_2$ (PLA$_2$) proteins of *Apis mellifera* (SEQ ID NO:168, GenBank Accession No. 443189; SEQ ID NO:169, GenBank Accession No. 229378), *Apis dorsata* (SEQ ID NO:170, GenBank Accession No. B59055), *Apis cerana* (SEQ ID NO:171, GenBank Accession No. A59055), *Bombus pennsylvanicus* (SEQ ID NO:172 GenBank Accession No. B56338), and *Heloderma suspectum* (SEQ ID NO:173, GenBank Accession No. P80003; SEQ ID NO:174, GenBank Accession No. S14764; SEQ ID NO:175, GenBank Accession No. 226711).

Using the amino acid sequence of a PLA$_2$ protein of *Apis mellifera* (SEQ ID NO:168) for illustration, peptides of at least about 60 amino acids in length, which represent any portion of the whole PLA$_2$ sequence, may also be used in compositions for preventing and/or attenuating allergic reactions. Examples of such peptides include peptides which comprise amino acids 1–60 in SEQ ID NO:168, amino acids 1–70 in SEQ ID NO:168, amino acids 10–70 in SEQ ID NO:168, amino acids 20–80 in SEQ ID NO:168, amino acids 30–90 in SEQ ID NO:168, amino acids 40–100 in SEQ ID NO:168, amino acids 47–99 in SEQ ID NO:168, amino acids 50–110 in SEQ ID NO:168, amino acids 60–120 in SEQ ID NO:168, amino acids 70–130 in SEQ ID NO:168, or amino acids 90–134 in SEQ ID NO:168, as well corresponding portions of other PLA$_2$ proteins (e.g., PLA$_2$ proteins described above). Further examples of such peptides include peptides which comprise amino acids 1–10 in SEQ ID NO:168, amino acids 5–15 in SEQ ID NO:168, amino acids 10–20 in SEQ ID NO:168, amino acids 20–30 in SEQ ID NO:168, amino acids 30–40 in SEQ ID NO:168, amino acids 40–50 in SEQ ID NO:168, amino acids 50–60 in SEQ ID NO:168, amino acids 60–70 in SEQ ID NO:168, amino acids 70–80 in SEQ ID NO:168, amino acids 80–90 in SEQ ID NO:168, amino acids 90–100 in SEQ ID NO:168, amino acids 100–110 in SEQ ID NO:168, amino acids 110–120 in SEQ ID NO:168, or amino acids 120–130 in SEQ ID NO:168, as well corresponding portions of other PLA$_2$ proteins (e.g., PLA$_2$ proteins described above).

Portions of PLA$_2$, as well as portions of other proteins against which an immunological response is sought, suitable for use with the invention may comprise, or alternatively consist of, peptides which are generally at least 6 amino acids in length (e.g., peptides 6, 7, 8, 9, 10, 12, 15, 18, 20, 25, 30, 35, 40, 45, 50, 55, 60, 65, 70 75, 80, 85, 90,95, or 100 amino acids in length).

PLA$_2$ peptides (e.g., the full length PLA$_2$ proteins discussed above, as well as subportions of each) may also be coupled to any substance (e.g., a Qβ capsid protein or fragment thereof) which allows for the formation of ordered and repetitive antigen arrays.

In another aspect of the present invention, the invention provides compositions being particularly suitable for treating and/or preventing conditions caused or exacerbated by "self" gene products.

In a preferred embodiment of the invention, the antigenic determinant is RANKL (Receptor activator of NFkB Ligand). RANKL is also known as TRANCE (TNF-related activation induced cytokine), ODF (Osteoclast differentiation factor) or OPGL (Osteoprotegerin ligand). The amino acid sequence of the extracellular part of human RANKL is shown in SEQ ID No: 221 (RANKL_human: TrEMBL: 014788), while the amino acid sequence of a human isoform is shown in SEQ ID No: 222. Sequences for the extracellular part of murine RANKL and an isoform are shown in SEQ ID No.223 (RANKL_mouse: TrEMBL:O35235), and in SEQ ID No.224 (RANKL_mouse splice forms: TrEMBL: Q9JJK8 and TrEMBL:Q9JJK9), respectively.

It has been shown that RANKL is an essential factor in osteoclastogenesis. Inhibition of the interaction of RANKL with its receptor RANK can lead to a suppression of osteoclastogenesis and thus provide a means to stop excessive bone resorption as seen in osteoporosis and other conditions. The RANKL/RANK interaction was inhibited either by a RANK-Fc fusion protein or the soluble decoy receptor of RANKL, termed osteoprotegerin OPG.

In the immune system RANKL is expressed on T cells while RANK is found on antigen-presenting cells. The RANKL-RANK interaction was shown to be critical for CD40L-independent T-helper cell activation (Bachmann et al., *J. Exp. Med.* 7:1025 (1999)) and enhance the longevity and adjuvant properties of dendritic cells (Josien et al., *J Exp Med.* 191: 495 (2000)).

In bone RANKL is expressed on stromal cells or osteoblasts, while RANK is expressed on the osteoclast precursor. The interaction of RANK and RANKL is crucial for the development of osteoclast precursors to mature osteoclasts. The interaction can be blocked by osteoprotegerin.

OPG-deficient mice develop osteoporosis that can be rescued by injection of recombinant OPG. This means that OPG is able to reverse osteoporosis. Thus, inhibition of the RANK-RANKL interaction by way of injecting this specific embodiment of the invention may reverse osteoporosis.

In addition, arterial calcification was observed in OPG k.o. mice which could be reversed by injection of OPG (Min et al., *J. Exp. Med.* 4: 463 (2000)). In an adjuvant-induced arthritis model OPG injection was able to prevent bone loss and cartilage destruction, but not inflammation (paw swelling). It is assumed that activated T cells lead to a RANKL-mediated increase of osteoclastogenesis and bone loss. OPG inhibits prostate cancer-induced osteoclastogenesis and prevents prostate tumor growth in the bone of mice. OPG diminishes advanced bone cancer pain in mice.

RANKL is a transmembrane protein of 245 aa belonging to the TNF-superfamily. Part of the extracellular region (178 aa) can be shed by a TACE-like protease (Lum et al., *J. Biol. Chem.* 274:13613 (1999)). In addition splice variants lacking the transmembrane domain have been described (Ikeda et al., *Endocrinology*142: 1419 (2001)). The shed part contains the domain highly homologous to soluble TNF-α. This extracellular domain of RANKL forms homotrimers as seen for TNF-α. The C-terminus seems to be involved in the trimer contact site. One cysteine is present in this region of the sequence.

We have built a model for the 3-dimensional structure of the corresponding region of RANKL and found that the naturally present cysteine may not be accessible in the folded structure for interaction with a first attachment site on the carrier in accordance with the present invention. The N-terminus is preferred for attaching a second attachment site comprising an amino acid linker with an additional cysteine residue. A human-RANKL construct with an N terminal amino acid linker containing a cysteine residue fused to the extracellular part of RANKL is a very preferred embodiment of the invention. However, an amino-acid linker containing a cysteine residue as second attachment site and being fused at the C-terminus of the RANKL sequence or the extracellular part of RANKL leads to further preferred embodiments of the invention.

Human-RANKL constructs, such as the one identified in SEQ ID NO:320, are generated according to the teachings disclosed in EXAMPLE 6, and the man skilled in the art are able to compare murine and human RANKL sequences in a protein sequence alignment to identify the part of the sequence of human-RANKL to be cloned in the vectors described in EXAMPLE 6. Fragments containing amino acids 138–317 and corresponding to the C-terminal region of the extracellular domain of human RANKL, are particularly favored embodiments of the invention, and can be modified for coupling to VLPs and Pili as required according to the teaching of the present invention. However, other suitable vectors may also be used for expression in the suitable host described below. Further human-RANKL constructs, and in particular, the ones comprising the part of the extracellular region (178 aa), —or fragments thereof—that can be shed by a TACE-like protease (Lum et al., *J Biol. Chem.* 274:13613 (1999)), or comprising the sequence corresponding to the alternative splice variants lacking the transmembrane domain, as well as conservative fragments thereof, are intended to be encompassed within the scope of the present invention. Human C-terminal fragments comprising amino acids 165–317 are also embodiments of the invention. Alternatively, fragments which encompass the entire extracellular region (amino acids 71–317) and can be modified for coupling to VLPs and Pili as required according to the teaching of the present invention, are also within the scope of the invention.

RANKL has been expressed in different systems (*E.coli*, insect cells, mammalian cells) and shown to be active, and therefore several expression systems can be used for production of the antigen of the composition. In the case where expression of the protein is directed to the periplasm of *E. coli*, the signal peptide of RANKL, or of RANKL constructs consisting of the extracellular part of the protein, and both possibly modified to comprise a second attachment site in accordance with the invention, is replaced with a bacterial signal peptide. For expression of the protein in the cytoplasm of *E. coli*, RANKL constructs are devoid of signal peptide.

In another preferred embodiment of the invention, the antigenic determinant is MIF or a fragment thereof. MIF is a cytokine that has been first described in 1966 by its function as an inhibitor of macrophage migration. It is also known as delayed early response protein 6 (DER6), glycosylation inhibiting factor or phenylpyruvate tautomerase. The latter name originates from enzymatic activity of MIF, however the endogenous substrate has not been identified.

MIF has been shown to be implicated in a wide range of conditions. MIF (mRNA and protein) is upregulated in delayed type hypersensitivity (DTH) reaction induced by tuberculin, and anti-MIF antibody inhibits this DTH reaction. MIF is also upregulated in renal allograft rejection. In a model for ocular autoimmune disease, experimental autoimmune uveoretinitis (EAU), anti-MIF treatment caused delay of EAU development. In patients, there is an increase in serum of MIF, which is also the case in Behcet's disease patients and patients suffering from iridocyclitis. Immunization against MIF may provide a way of treatment against rheumatoid arthritis.

High serum MIF concentration has been found in atopic dermatitis patients. In skin lesions, MIF is diffusely expressed instead of being found in the basal cell layer in controls. MIF concentration is decreasing after steroid treatment, consistent with a role of MIF in inflammation. MIF has also been found to contribute to the establishment of glomerulonephritis. Animals treated with anti-MIF Antibody show significantly reduced glomerulonephritis. MIF is pituitary derived, secreted e.g. upon LPS stimulation, and potentiates endotoxemia. Accordingly, anti-MIF mAb inhibits endotoxemia and septic shock, while recombinant MIF markedly increases lethality of peritonitis. MIF is also a glucocorticoid-induced modulator of cytokine production, and promotes inflammation.

MIF is produced by T-cells (Th2), supports proliferation of T-cells, and anti-MIF-treatment reduces T-cell proliferation and IgG levels. There is an increased MIF concentration in the cerebrospinal fluid of multiple sclerosis and neuro-Behcet's disease patients. High MIF levels were also found in sera of patients with extended psoriasis. High MIF levels are found in sera of ulcerative colitis patients but not Crohn's disease patients.

High MIF levels have been found in sera of patients with bronchic asthma. MIF is also upregulated in synovial fluid of rheumatoid arthritis patients. Anti-MIF treatment was effectively decreasing rheumatoid arthritis in mouse and rat models (Mikulowska et al., *J. Immunol.* 158:5514–7(1997); Leech et al., *Arthritis Rheum.* 41:910–7 (1998), Leech et al. *Arthritis Rheum.* 43:827–33 (2000), Santos et al., *Clin. Exp. Immunol.* 123:309–14 (2001)). Thus, treatment directed at inhibiting MIF activity using a composition comprising MIF as an antigenic determinant may be beneficial for the conditions mentioned above.

MIF from mouse, rat and human consists of 114 amino acid and contains three conserved cysteines, as shown in SEQ ID No 225 (MIF_rat: SwissProt), in SEQ ID No 226 (MIF_mouse: SwissProt) and in SEQ ID No 227 (MIF_human: SwissProt). Three subunits form a homotrimer that is not stabilized by disulfide bonds. The X-ray structure has been solved and shows three free cysteines (Sun et al., *PNAS* 93: 5191–96 (1996)), while some literature data claim the presence of a disulfide bond. Nonetheless, none of the cysteines are exposed enough for optimal interaction with a possible first attachment site present on the carrier. Thus, as the C-terminus of the protein is exposed in the trimer structure, an amino acid linker containing a free cysteine residue is, preferably, added at the C-terminus of the protein, for generation of the second attachment site in this preferred embodiment of the invention, as exemplarily described in EXAMPLE 4 for rat-MIF.

There is only one amino acid change between mouse- and rat-MIF, and similarly a very high sequence homology (about 90% sequence identity) between human- and rat-MIF or human- and mouse-MIF. Human- and mouse-MIF constructs according to the invention are described and can be generated as disclosed in EXAMPLE 4. In order to demonstrate the high potency to induce a self-specific immune response of MIF protein, or fragments thereof, associated to a core particle in accordance with the present invention, rat-MIF constructs coupled to Qβ capsid protein were injected in mice. The high antibody titers obtained by immunizing mice with rat-MIF show that tolerance towards immunization with self-antigens was overcome by immunizing with MIF constructs coupled to virus-like particles, and in particular to Qβ capsid protein (EXAMPLE 4). Therefore, compositions in accordance with the present invention comprising human-MIF protein associated to a core particle, preferably to pili or a virus-like particle, and more preferably to a virus-like particle of a RNA-phage, and even more preferably to RNA-phage Qβ or fr, represent very preferred embodiments of the present invention.

However, an amino acid linker containing a free cysteine that is added at the N-terminus of the sequence of MIF leads to further preferred embodiments of the present invention.

MIF has been expressed in *E.coli*, purified and shown to be fully functional (Bernhagen et al., *Biochemistry* 33: 14144–155 (1994). Thus, MIF may be, preferably, expressed in *E. coli* for generating the preferred embodiments of the invention.

Tautomerase activity of MIF is inhibited, if the start methionine is not cleaved from the construct. MIF constructs expressed in *E.coli* and described in EXAMPLE 4 show tautomerase activity. Mutants of MIF where the start methionine is cleaved and where the proline residue right after the start methionine in the sequence is mutated to alanine also do not show tautomerase activity represent further embodiments of the invention and are intended to be encompassed within the scope of the invention. In some specific embodiments, immunization with MIF mutants devoid of tautomerase activity is envisaged.

In another preferred embodiment of the invention, the antigenic determinant is Interleukin-17 (IL-17). Human IL-17 is a 32-kDa, disulfide-linked, homodimeric protein with variable glycosylation (Yao, Z. et al., *J. Immunol.* 155: 5483–5486 (1995); Fossiez, F. et al., *J. Exp. Med.* 183: 2593–2603 (1996)). The protein comprises 155 amino acids and includes an N-terminal secretion signal peptide of 19–23 residues. The amino acid sequence of IL-17 is similar only to a Herpesvirus protein (HSV13) and is not similar to other cytokines or known proteins. The amino acid sequence of human IL-17 is shown in SEQ ID No: 228 (ACCESSION #: AAC50341), The mouse protein sequence is shown in SEQ ID No: 229 (ACCESSION #: AAA37490). Of the large number of tissues and cell lines evaluated, the mRNA transcript encoding IL-17 has been detected only in activated T cells and phorbol 12-myristate 13-acetate/ionomycin-stimulated peripheral blood mononuclear cells (Yao, Z. et al:, *J. Immunol.* 155: 5483–5486 (1995); Fossiez, F. et al., *J. Exp. Med.* 183: 2593–2603 (1996)). Both human and mouse sequences contain 6 cysteine residues.

The receptor for IL-17 is widely expressed in many tissues and cell types (Yao, Z. et al., *Cytokine* 9: 794–800 (1997)). Although the amino acid sequence of the human IL-17 receptor (866 aa) predicts a protein with a single trans-membrane domain and a long, 525 aa intracellular domain, the receptor sequence is unique and is not similar to that of any of the receptors from the cytokine/growth factor receptor family. This coupled with the lack of similarity of IL-17 itself to other known proteins indicates that IL-17 and its receptor may be part of a novel family of signalling protein and receptors. Clinical studies indicate IL-17 may be involved in many inflammatory diseases. IL-17 is secreted by synovial T cells from rheumatoid arthritis patients and stimulates the production of inflammatory mediators (Chabaud, M. et al., *J. Immunol.* 161: 409–414 (1998); Chabaud, M. et al., *Arthritis Rheum.* 42: 963–970 (1999)). High levels of IL-17 have been reported in patients with rheumatoid arthritis (Ziolkowska M. et al., *J. Immunol.* 164:2832–8 (2000)).

Interleukin 17 has been shown to have an effect on proteoglycan degradation in murine knee joints (Dudler J. et al., *Ann Rheum Dis.* 59: 529–32 (2000)) and contribute to destruction of the synovium matrix (Chabaud M. et al., *Cytokine.* 12:1092–9 (2000)). There are relevant arthritis models in animals for testing the effect of an immunization against MIF (Chabaud M. et al., *Cytokine.* 12:1092–9 (2000)). Elevated levels of IL-17 mRNA have been found in mononuclear cells from patients with multiple sclerosis (Matusevicius, D. et al., *Mult. Scler.* 5: 101–104 (1999)). Elevated serum levels of IL-17 are observed in patients suffering Systemic Lupus Erythematosus (Wong C. K. et al., *Lupus* 9: 589–93 (2000)). In addition, IL-17 mRNA levels are increased in T cells isolated from lesional psoriatic skin (Teunissen, M. B. et al., *J. Invest. Dermatol.* 111: 645–649 (1998)).

The involvement of IL-17 in rejection of kidney graft has also been demonstrated (Fossiez F. et al., *Int. Rev. Immunol.*16:541–51 (1998)). Evidence for a role of IL-17 in organ allograft rejection has also been presented by Antonysamy et al. (*J. Immunol.* 162:577–84 (1999)) who showed IL-17 promotes the functional differentiation of dendritic cell progenitors. Their findings suggest a role for IL-17 in allogeneic T cell proliferation that may be mediated in part via a maturation-inducing effect on DCs. Furthermore the same group reports (Tang J. L. et al., *Transplantation* 72:348–50 (2001)) a role for IL-17 in the immunopathogenesis of acute vascular rejection where Interleukin-17 antagonism inhibits acute but not chronic vascular rejection. IL-17 appears to have potential as a novel target for therapeutic intervention in allograft rejection.

The above findings suggest IL-17 may play a pivotal role in the initiation or maintenance of an inflammatory response (Jovanovic, D. V. et al., *J. Immunol.* 160: 3513–3521 (1998)).

The anti-IL-17 monoclonal antibody mAb5 (Schering-Plough Research Institute) was able to completely inhibit the production of IL-6 from rheumatoid arthritis (RA) synovium supernatants following induction by 50 ng/ml of IL-17. An irrelevant mAb MX1 had no effect in this assay. mAb5 is a mouse IgG1 obtained after immunization with human rIL-17 (r=recombinant). A concentration of 1 µg/ml of mAb5 was able to completely inhibit the IL-6 production in the assay system (Chabaud, M. et al., *J. Immunol.* 161: 409–414 (1998)). Thus, immunization against IL-17 provides a way of treatment for the various conditions described above.

In another preferred embodiment of the invention, thus, the composition comprises a linker containing a second attachment site and being fused to the C-terminus of recombinant IL-17. In further preferred embodiments of the invention, however, an amino acid linker containing a free cysteine is fused to the N-terminus of the sequence corresponding to the sequence of the processed protein, or inserted at the N-terminus of the sequence of the mature form of the protein, C-terminally of the signal peptide. For eukaryotic expression systems, the signal peptide of the IL-17 gene, as it is the case for the other self-antigens indicated herein, may be replaced by another signal peptide if required. For expression in bacteria, the signal peptide is either replaced by a bacterial signal peptide for soluble expression in the periplasm, or deleted for expression in the cytoplasm. Constructs of human IL-17 devoid of signal peptide will preferably comprise residues 24–155, 22–155, 21–155 or 20–155. Constructs of mouse IL-17 devoid of signal peptide will preferably comprise residues 26–158, 25–158, 24–158 or 27–155. Human IL-17 may be expressed in CV1/EBNA cells; recombinant hIL-17 has been shown to be secreted in both glycosylated and nonglycosylated forms (Yao, Z. et al., *J. Immunol.* 155: 5483–5486 (1995)). 1L-17 can also be expressed as hIL-17/Fc fusion protein, with subsequent cleavage of the IL-17 protein from the fusion protein. IL-17 may also be expressed in the yeast *Pichia pastoris* (Murphy K. P. et. al., *Protein Expr Purif.* 12: 208–14 (1998)). Human IL-17 may also be expressed in *E. coli*. When expression of IL-17 in *E. coli* is directed to the periplasm, the signal peptide of IL-17 is replaced by a bacterial signal peptide. For expression of the protein in the cytoplasm of *E. coli*, IL-17 constructs are devoid of signal peptide.

In another preferred embodiment of the invention the antigenic determinant is Interleukin-13 (IL-13). IL-13 is a cytokine that is secreted by activated T lymphocytes and primarily impacts monocytes, macrophages, and B cells. The amino acid sequence of precursor human IL-13 is shown in SEQ ID No: 230 and the amino acid sequence of processed human IL-13 is shown in SEQ ID No: 231. The first 20 amino acids of the precursor protein correspond to the signal peptide, and are absent of the processed protein. The mouse sequence has also been described, and the processed amino acid sequence is shown in SEQ ID No: 232 (Brown K. D. et al., *J. Immunol.* 142:679–687 (1989)). Depending on the expression host, the IL-13 construct will comprise the sequence of the precursor protein, e.g. for expression and secretion in eukaryotic hosts, or consist of the mature protein, e.g. for cytoplasmic expression in *E.coli*. For expression in the periplasm of *E. coli*, the signal peptide of IL-13 is replaced by a bacterial signal peptide.

IL-13 is a T helper 2-derived cytokine (like IL-4, IL-5) that has recently been implicated in allergic airway responses (asthma). Upregulation of IL-13 and IL-13 receptor has been found in many tumour types (e.g. Hodgkin lymphoma). Interleukin 13 is secreted by and stimulates the growth of Hodgkin and Reed-Sternberg cells (Kapp U et al., *J Exp Med.* 189:1939–46 (1999)). Thus, immunization against IL-13 provides a way of treating among others the conditions described above, such as Asthma or Hodgkins Lymphoma.

Preferably, the composition comprises an amino acid linker containing a free cysteine residue and being fused to the N or C-terminus of the sequence of mature IL-13 to introduce a second attachment site within the protein. In further preferred embodiments, an amino acid linker containing a free cysteine is added to the N-terminus of the mature form of IL-13, since it is freely accessible according to the NMR structure of IL-13 (Eisenmesser, E. Z. et al., *J. Mol. Biol.* 310: 231 (2001)). In again further preferred embodiments, the amino acid linker containing a free cysteine is fused to the N-terminus of the sequence corresponding to the sequence of the processed protein, or inserted at the N-terminus of the sequence of the mature form of the protein, C-terminally of the signal peptide. In still further preferred embodiments, an amino acid linker containing a free cysteine residue is added to the C-terminus of the protein.

IL-13 may be expressed in *E.coli* (Eisenmesser E. Z. et al., *Protein Expr. Purif.* 20:186–95 (2000)), or in NS-0 cells (eukaryotic cell line) (Cannon-Carlson S. et al., *Protein Expr. Purif.* 12:239–48 (1998)). EXAMPLE 9 describes constructs and expression of constructs of murine IL-13, fused to an amino acid linker containing a cysteine residue, in bacterial and eukaryotic hosts. Human IL-13 constructs can be generated according to the teachings of EXAMPLE 9 and yielding the proteins human C-IL-13-F (SEQ ID NO:330) and human C-IL-13-S (SEQ ID NO:331) after expression of the fusion proteins and cleavage with Factor Xa, and enterokinase respectively. The so generated proteins can be coupled to VLPs and Pili, leading to preferred embodiments of the invention.

In yet another embodiment of the invention, the antigenic determinant is Interleukin-5 (IL-5). IL-5 is a lineage-specific cytokine for eosinophilopoiesis and plays an important part in diseases associated with increased number of eosinophils, such as asthma. The sequence of precursor and processed human IL-5 is provided in SEQ ID No: 233 and in SEQ ID No: 234, respectively, and the processed mouse amino acid sequence is shown in SEQ ID No: 235.

The biological function of IL-5 has been shown in several studies (Coffman R. L. et al., *Science* 245: 308–10 (1989); Kopf et al., *Immunity* 4:15–24 (1996)), which point to a beneficial effect of inhibiting IL-5 function in diseases mediated through eosinophils. Inhibition of the action of IL-S provides thus a way of treatment against asthma and other diseases associated with eosinophils.

IL-5 forms a dimer, covalently linked by a disulfide bridge. A single chain (sc) construct has been reported wherein two monomers of IL-5 are linked by a peptide linker.

In preferred embodiments of the invention, a peptide linker containing a free cysteine is added at the N-terminus of the sequence of the processed form of IL-5. Addition of a linker containing a free cysteine is also, preferably, envisaged at the N-terminus of the sequence of the processed form of a scIL-5. In further preferred embodiments, the amino acid linker containing a free cysteine is fused to the N-terminus of the sequence corresponding to the sequence of the processed protein, or inserted at the N-terminus of the sequence of the mature form of the protein, C-terminally of the signal peptide.

In again further preferred embodiments, a linker containing a free cysteine is fused to the C-terminus of the sequence of IL-5, or to the C-terminus of a scIL-5 sequence.

A number of expression systems have been described for IL-5 and can be used in preparing the compositions of the invention. A bacterial expression system using *E.coli* has been described by Proudfoot et al., (*Biochem J.* 270:357–61 (1990)). In the case where IL-5 is expressed in the cytoplasm of *E. coli*, the IL-5 construct is devoid of a signal peptide. Insect cells may also be used for producing IL-5 constructs for making the compositions of the invention (Pierrot C. et al., *Biochem. Biophys. Res. Commun.* 253:756–60 (1998)). Likewise, Baculovirus expression systems (sf9 cells; Ingley E. et al., *Eur. J. Biochem.* 196:623–9 (1991) and Brown P. M. et al., *Protein Expr. Purif.* 6: 63–71 (1995)) can also be used. Finally, mammalian expression systems have also been reported (CHO cells) and can be used in preparing these compositions of the invention (Kodama S et al., J. Biochem. (Tokyo) 110:693–701 (1991)).

Baculovirus expression systems (Mitchell et al., *Biochem. Soc. Trans.* 21:332S (1993); Kunimoto D Y et al., *Cytokine* 3:224–30 (1991)) and a mammalian cell expression system using CHO cells (Kodama S et al., *Glycobiology* 2:419–27 (1992)) have also been described for mouse IL-5. EXAMPLE 10 describes the expression of murine IL-5 constructs wherein the IL-5 sequence is fused at its N-terminus to amino acid linkers containing a cysteine residue for coupling to VLPs and Pili. Human constructs can be generated according to the teaching of EXAMPLE 10 and yield the proteins human C-IL-5-E (SEQ ID NO:335), human C-IL-5-F (SEQ ID NO:336) and human C-IL-5-S: (SEQ ID NO:337) suitable for coupling to VLPs and Pili and leading to preferred embodiments of the invention.

In another preferred embodiment of the invention, the antigenic determinant is CCL-21. CCL-21 is a chemokine of the CC subfamily that is also known as small inducable cytokine A21, as exodus-2, as SLD (secondary lymphocyte cytokine), as TCA4 (thymus-derived chemotactic agent 4) or 6Ckine.

CCL21 inhibitis hemopoiesis and stimulates chemotaxis for thymocytes, activated T-cells and dendritic cells, but not for B cells, macrophages or neutrophiles. It shows preferential activity towards naive T cells. It is also a potent mesangial cell chemoattractant. CCL21 binds to chemokine receptors CCR7 and to CXCR3 (dependent on species). It can trigger rapid integrin-dependent arrest of lymphocytes rolling under physiological shear and is highly expressed by high endothelial venules.

Murine CCL21 inhibited tumor growth and angiogenesis in a human lung cancer SCID mouse model (Arenberg et al., *Cancer Immunol. Immunother.* 49: 587–92 (2001)) and a colon carcinoma tumor model in mice (Vicari et al., *J. Immunol.* 165: 1992–2000 (2001)). The angiostatic activity of murine CCL21 was also detected in a rat corneal micropocket assay (Soto et al., *Proc. Natl. Acad. Sci. USA* 95: 8205–10(1998).

It has been shown that chemokine receptors CCR7 and CXCR4 are upregulated in breast cancer cells and that CCL21 and CXCL12, the respective ligands, are highly expressed in organs representing the first destinations of breast cancer metastasis Müller et al. (*Nature* 410: 50–6 (2001)). In vitro CCL21-mediated chemotaxis could be blocked by neutralizing anti-CCL21 antibodies as was CXCR4-mediated chemotaxis by the respective antibodies. Thus, immunization against CCL21 provides a way of treatment against metastatis spread in cancers, more specifically in breast cancer.

Secreted CCL21 consist of 110 or 111 aa in mice and humans, respectively. The respective sequences are shown in SEQ ID No: 236 (Swissprot: SY21_human) and in SEQ ID No: 237 (Swissprot: SY21_mouse). In contrast to other CC cytokines does CCL21 contain two more cysteines within an extended region at the C-terminus. It is assumed that all cysteines are engaged in disulfide bonds.

In the following, constructs and expression systems are described for making compositions of the invention comprising the CCL21 antigenic determinant. In the NMR structure of the homologous protein eotaxin, both N- and C-terminus are exposed to the solvent. In some specific embodiments, an amino acid linker containing a free cysteine residue as a second attachment site is added at the C-terminus of the protein. A fusion protein with alkaline phosphatase (at the C-terminus of CCL21) has been expressed and was shown to be functional, showing that fusions at the C-terminus of CCL21 are compatible with receptor binding. In other specific embodiments, the amino acid linker containing a free cysteine is fused to the N-terminus of the sequence corresponding to the sequence of the processed protein, or inserted at the N-terminus of the sequence of the mature form of the protein, C-terminally of the signal peptide.

Several expression systems have been described for production of CCL21 (e.g. Hedrick et al., *J. Immunol.* 159: 1589–93 (1997)). For example, it may expressed in a baculovirus system (Nagira et al., *J. Biol. Chem.* 272: 19518–24 (1997)).

In a related preferred embodiment, the antigenic determinant is Stromal derived factor-1 (SDF-1), now termed CXCL12. CXCL12 is a chemokine produced by bone marrow stromal cells and was originally identified as a stimulatory factor for pre-B cells.

As already stated above, it has been shown that chemokine receptors CCR7 and CXCR4 are upregulated in breast cancer cells and that CCL21 and SDF-1, the respective ligands, are highly expressed in organs representing the first destinations of breast cancer metastasis Müller et al. (*Nature* 410: 50–6 (2001)). In vitro SDF-1/CXCR4-mediated chemotaxis could be inhibited by neutralizing anti-SDF-1 and anti-CXCR4 antibodies.

In a breast cancer metastasis model in SCID mice using the human MDA-MB-231 breast cancer cell line, a significant decrease in lung metastasis was observed when mice were treated with anti-CXCR4 antibodies. In the draining lymph nodes a reduction of metastasis to the inguinal and axillary lymph nodes (38% instead of 100% metastasis in controls) was observed. Thus, immunization against CXCL12 provides a way of treatment against metastatis of cancers, more specifically of breast cancers.

The SDF-1/CXCR4 chemokine-receptor pair has been shown to increase the efficacy of homing of more primitive hematopoietic progenitor cells to be bone marrow. In addition, CXCR4 and SDF-1 are supposed to influence the distribution of chronic lymphocytic leukemia cells. These cells invariably infiltrate the bone marrow of patients and it was shown that their migration in the bone marrow was CXCR4 dependent. Chronic lymphocytic leukemia cells undergo apoptosis unless they are cocultured with stromal cells. SDF-1 blocking antibodies could inhibit this protective effect of stromal cells (Burger et al., *Blood* 96: 2655–63 (2000)). Immunizing against CXCL12 thus provides a way of treatment against chronic lymphocytic leukemia.

CXCR4 has been shown to be a coreceptor for entry of HIV into T-cells. SDF-1 inhibits infection of CD4+ cells by X4 (CXCR4-dependent) MV strains (Oberlin et al., *Nature* 382:833–5 (1996); Bleul et al., *Nature* 382:829–33 (1996), Rusconi et al., *Antivir. Ther.* 5:199–204 (2000)). Synthetic peptide analogs of SDF-1 have been shown to effectively inhibit HIV-1 entry and infection via the CXCR4 receptor (WO059928A1). Thus, immunization against CXCL12 provides a way to block HIV entry in T-cells, and therefore a way of treating AIDS.

SDF-1-CXCR4 interactions were also reported to play a central role in CD4+ T cell accumulation in rheumatoid arthritis synovium (Nanki et al., 2000). Immunization against SDF-1 thus provides a way of treatment against rheumatoid arthritis.

Human and murine SDF-1 are known to arise in two forms, SDF-1α and SDF-1β, by differential splicing from a single gene. They differ in four C-terminal amino acids that are present in SDF-1β (74 aa) and absent in SDF-1α (70 aa). The sequence of human is shown in SEQ ID No: 238 (Swissprot: SDF1_human) and the sequence mouse SDF-1 is shown in SEQ ID No: 239 (Swissprot: SDF1_mouse). SDF-1 contains four conserved cysteines that form two intra-molecular disulfide bonds. The crystal structure of SDF shows a non covalently-linked dimer (Dealwis et al., *PNAS* 95: 6941–46 (1998)). The SDF-1 structure also shows a long N-terminal extension.

Alanine-scanning mutagenesis was used to identify (part of) the receptor-binding site on SDF-1 (Ohnishi et al., *J. Interferon Cytokine Res.* 20: 691–700 (2000)) and Elisseeva et al. (*J. Biol. Chem.* 275:26799–805 (2000)) and Heveker et al. (*Curr. Biol.* 8:369–76 (1998)) described SDF-1 derived peptides inhibiting receptor binding (and HIV entry).

In the following, constructs and expression systems suitable in the generation of the compositions of the invention related to SDF-1 are described. The N- and C-terminus of SDF-1 are exposed to the solvent. In specific embodiments, an amino acid linker containing a cysteine as second attachment site is thus fused to the C-terminus of the protein sequence, while in other specific embodiments an amino acid linker containing a cysteine as second attachment site is fused to the N-terminus of the protein sequence. The amino acid linker containing a free cysteine is fused to the N-terminus of the sequence corresponding to the sequence of the processed protein, or inserted at the N-terminus of the sequence of the mature form of the protein, C-terminally of the signal peptide. The genes coding for these specific constructs may be cloned in a suitable expression vector.

Expression of SDF-1 in a sendai virus system in chicken embryonic fibroblasts (Moriya et al., *FEBS Lett.* 425:105–11 (1998)) has been described as well as expression in *E.coli* (Holmes et al., *Prot. Expr. Purif* 21: 367–77 (2001)) and chemical synthesis of SDF-1 (Dealwis et al., *PNAS* 95: 6941–46 (2001)).

In yet another embodiment of the invention, the antigenic determinant is BLC. B-lymphocyte chemoattractant (BLC, CXCL13) is expressed in the spleen, Peyer's patches and lymph nodes (Gunn et al., 1998). Its expression is strongest in the germinal centres, where B cells undergo somatic mutation and affinity maturation. It belongs to the CXC chemokine family, and its closest homolog is GROα_(Gunn et al., *Nature* 391:799–803 (1998)). Human BLC is 64% homologous to murine BLC. Its receptor is CXCR5. BLC also shares homology with IL-8. BLC recruits B-cells to follicles in secondary lymphoid organs such as the spleen and peyer's patches. BLC is also required for recruitment of B-cells to compartment of the lymph nodes rich in follicular Dendritic Cells (FDCs) (Ansel et al., *Nature* 406:309–314 (2000)). BLC also induces increased expression of Lymphotoxinα1β2 (LT?α1β2) on the recruited B-cells. This provides a positive feed-back loop, since LT?α1β2 promotes BLC expression (Ansel et al., *Nature* 406:309–314 (2000)). BLC has also been shown to be able to induce lymphoid neogenesis (Luther et al., *Immunity* 12:471–481(2000)). It appears that FDCs also express BLC. Thus immunization against BLC may provide a way of treatment against autoimmune diseases where lymphoid neogenesis is involved, such as Rheumatoid synovitis and Rheumatoid arthritis or Type I diabetes. A construct of BLC bearing a C-terminal his-tag has been described, and is functional (Ansel, K. M. et al., *J. Exp. Med.* 190: 1123–1134 (1999)).

Thus, in a preferred embodiment of the present invention, the composition comprises a linker containing a cysteine residue as second attachment site and being fused at the C-terminus of the BLC sequence.

In IL-8, which is homologous to BLC, both N- and C-termini are free. In a further preferred embodiment, addition of an amino acid linker containing a cysteine residue as second attachment site is, therefore, done to the N-terminus of BLC for generation of this specific composition of the invention.

In further preferred embodiments of the present invention, the composition comprises an amino acid linker containing a free cysteine and being fused to the N-terminus of the sequence corresponding to the sequence of the processed protein, or inserted at the N-terminus of the sequence of the mature form of the protein, C-terminally of the signal peptide. The genes coding for these specific constructs may be cloned in a suitable expression vector and expressed accordingly. The sequence of human BLC is shown in SEQ ID No: 240 (Accession: NP_006410). Amino acids 1–22 of the sequence are the signal peptide. The mouse sequence is shown in SEQ ID No: 241 (Accession NP_061354). Amino acids 1–21 are the signal peptide. Compositions of the invention with BLC as the antigenic determinant, preferably, use the mature form of the protein for generating the compositions of the invention.

In another specific embodiment, the antigenic determinant is Eotaxin. Eotaxin is a chemokine specific for Chemokine receptor 3, present on eosinophils, basophils and Th2 cells. Eotaxin seems however to be highly specific for Eosinophils (Zimmerman et al., *J. Immunol.* 165: 5839–46 (2000)). Eosinophil migration is reduced by 70% in the eotaxin-1 knock-out mouse, which however can still develop eosinophilia (Rothenberg et al., *J. Exp. Med.* 185: 785–90 (1997)). IL-5 seems to be responsible for the migration of eosinophils from bone-marrow to blood, and eotaxin for the local migration in the tissue (Humbles et al., *J. Exp. Med.* 186: 601–12 (1997)).

The human genome contains 3 eotaxin genes, eotaxin1–3. They share 30% homology to each other. Two genes are known so far in the mouse: eotaxin 1 and eotaxin 2 (Zimmerman et al., *J. Immunol.* 165: 5839–46 (2000)). They share 38% homology. Murine eotaxin-2 shares 59% homology with human eotaxin-2. In the mouse, eotaxin-1 seems to be ubiquitously expressed in the gastrointestinal tract, while eotaxin-2 seems to be predominantly expressed in the jejunum (Zimmerman et al., *J. Immunol.* 165: 5839–46 (2000)). Eotaxin-1 is present in broncho-alveolar fluid (Teixeira et al., *J. Clin. Invest.* 100: 1657–66 (1997)). The sequence of human eotaxin-1 is shown in SEQ ID No. 242 (aa 1–23 corresponds to the signal peptide), the sequence of human eotaxin-2 is shown in SEQ ID No. 243 (aa 1–26 corresponds to the signal peptide), the sequence of human eotaxin-3 is shown in SEQ ID No. 244 (aa 1–23 corresponds to the signal peptide), the sequence of mouse eotaxin-1 is shown in SEQ ID No. 245 (aa 1–23 corresponds to the signal peptide), and the sequence of mouse eotaxin-2 is shown in SEQ ID No. 246 (aa 1–23 corresponds to the signal peptide).

Eotaxin has a MW of 8.3 kDa. It is in equilibrium between monomers and dimers over a wide range of conditions, with an estimated Kd of 1.3 mM at 37° C. (Crump et al., *J. Biol. Chem.* 273: 22471–9 (1998)). The monomer form is however predominant. The structure of Eotaxin has been elucidated by NMR spectroscopy. Binding site to its receptor CCR3 is at the N-terminus, and the region preceding the first cysteine is crucial (Crump et al., *J. Biol. Chem.* 273: 22471–9 (1998)). Peptides of chemokine receptors bound to Eotaxin confirmed this finding. Eotaxin has four cysteines forming two disulfide bridges. Therefore, in a preferred embodiment, the inventive composition comprises an amino-acid linker containing a cysteine residue as second attachment site and being, preferably, fused to the C-terminus of the Eotaxin sequence. In other preferred embodiments, an amino acid linker containing a free cysteine is fused to the N-terminus of the sequence corresponding to the sequence of the processed protein, or inserted at the N-terminus of the sequence of the mature form of the protein, C-terminally of the signal peptide. The genes coding for these specific constructs are cloned in a suitable expression vector.

Eotaxin can be chemically synthesized (Clark-Lewis et al., *Biochemistry* 30:3128–3135 (1991)). Expression in *E. coli* has also been described for Eotaxin-1, in the cytoplasm (Crump et al., *J. Biol. Chem.* 273: 22471–9 (1998)). Expression in *E. coli* as inclusion bodies with subsequent refolding (Mayer et al., *Biochemistry* 39: 8382–95 (2000)), and Insect cell expression (Forssmann et al., *J. Exp. Med.* 185: 2171–6 (1997)) have been described for Eotaxin-2, and may, moreover, be used to arrive at the specific embodiments of the invention.

In yet another specific embodiment of the invention, the antigenic determinant is Macrophage colony-stimulating factor (M-CSF or CSF-1). M-CSF or CSF-1 is a regulator of proliferation, differentiation and survival of macrophages and their bone-marrow progenitors. The receptor for M-CSF is a cell surface tyrosine kinase receptor, encoded by the protooncogene cfms. An elevated expression of M-CSF and its receptor has been associated with poor prognosis in several epithelial cancers such as breast, uterine and ovarian cancer. Tumor progression has been studied in a mouse strain resulting from the crossing of a transgenic mouse susceptible to mammary cancer (PyMT) with a mouse containing a recessive null mutation in csf-1 gene. These mice show attenuated late stage invasive carcinoma and pulmonary metastasis compared to the PyMT mouse (Lin et al., *J. Exp. Med.* 193:727–739 (2001)). The cause seems to be the absence of macrophage recruitment to neoplastic tissues. Subcutaneous growth of Lewis lung cancer is also impaired in csf.1 null mice. It is postulated that the mechanism of macrophage enhancement of tumor growth would be through angiogenic factors, growth factors and proteases produced by the macrophages.

Structural data on the soluble form of M-CSF are available (crystal structure: Pandit et al., *Science* 258:1358–62 (1992)), and show that both the N- and C-termini of the protein are accessible. However, the N-terminus is close to the site of interaction with the receptor. In addition, M-CSF is present both in a soluble and cell surface form, where the transmembrane region is at its C-terminus. Therefore, in a preferred embodiment of the present invention, the inventive composition comprises an amino acid linker containing a cysteine and being, preferably, added at the C-terminus of M-CSF or fragments thereof, or preferably at the C-terminus of the soluble form of M-CSF. In further preferred embodiments, the amino acid linker containing a free cysteine is fused to the N-terminus of the sequence corresponding to the sequence of the processed protein or of the soluble form of the protein, or inserted at the N-terminus of the sequence of the mature form of the protein or of the soluble form of the protein, C-terminally of the signal peptide. M-CSF is a dimer, where the two monomers are linked via an interchain disulfide bridge.

An expression system in *E. coli* has been described for an N-terminal 149 amino acid fragment (functional) of M-CSF (Koths et al., *Mol. Reprod. Dev.* 46:31–37 (1997)). This fragment of M-CSF, preferably modified as outlined above, represents a preferred antigenic determinant in accordance with the invention.

The human sequence is shown in SEQ ID No: 247 (Accession: NP_000748). Further preferred antigenic determinants of the present invention comprise the N-terminal fragment consisting of residue 33–181 or 33–185 of SEQ ID No: 247, corresponding to the soluble form of the receptor.

The mouse sequence (Accession. NP_031804) is shown in sequence ID No: 248. The mature sequence starts at amino acid 33. Thus, a preferred antigenic determinant in accordance with the present invention comprises amino-acid 33–181 or 33–185.

In another specific embodiment, the antigenic determinant is Resistin (Res). Passive immunization studies were performed with a rabbit polyclonal antibodies generated against a fusion protein of mouse Resistin (mRes) fused to GST, expressed in bacteria. This passive immunization lead to improved glucose uptake in an animal obesity/Type II diabetes model (Steppan et al., *Nature* 409: 307–12 (2001)).

Resistin (Res) is a 114 aa peptide hormone of approximately 12 KD. It contains 11 cysteine of which the most N-terminal one was shown to be responsible for the dimerisation of the protein and the other 10 are believed to be involved in intramolecular disulfide bonds (Banerjee and Lazar, *J. Biol. Chem.* 276: 25970–3 (2001)). Mutation of the first cysteine to alanine abolishes the dimerisation of mRes.

It was shown, that mRes with a FLAG tag at its C-terminus still remains active in an animal model (Steppan et al., *Nature* 409: 307–12 (2001)), similarly a C-terminally HA taged (Haemagglutinin tag) version of resistin was shown to be active in a tissue culture assay (Kim et al., *J. Biol. Chem.* 276: 11252–6 (2001)), suggesting that the C-terminus is not very sensitive to introduced modifications. Thus, in a preferred embodiment, the inventive composition comprises an amino-acid linker containing a cysteine residue as second attachment site and being fused at the C-terminus of the resistin sequence. In further preferred embodiments, the amino acid linker containing a free cysteine is fused to the N-terminus of the sequence corresponding to the sequence of the processed protein, or inserted at the N-terminus of the sequence of the mature form of the protein, C-terminally of the signal peptide.

For a preferred embodiment of the present invention, MRes or huRes may also be expressed as Fc fusion molecules with a protease cleavage site inserted between Resistin and the Fc part of the construct, preferably C-terminally of one or more cysteine residues of the hinge region of the Fc part of the fusion protein in a eukaryotic expression system, or more preferably according to the descriptions and disclosures of EXAMPLE 2. Cleavage of the fusion protein releases Resistin additionally comprising either an aminoacid linker containing a cysteine residue as described in EXAMPLE 2, or part or all of the hinge region of the Fc part of the fusion protein which comprises a cysteine residue at its C-terminus, which is suitable for coupling to VLPs or Pili. The human Resistin sequence is shown in SEQ ID No: 249 (Accession AF323081). The mouse sequence is shown in SEQ ID No: 250 (Accession AF323080). A favored embodiment of the invention is human resistin protein fused at its C-terminus to an amino acid linker containing a cysteine residue. Human resistin construct can be generated according to the teachings disclosed in EXAMPLE 2, and by comparing murine and human Resistin sequences in a protein sequence alignment to identify the part of the sequence of human Resistin to be cloned in the vectors described in EXAMPLE 1 and EXAMPLE 2 according to the teachings of EXAMPLE 2, or in other suitable expression vectors. Example of human resistin constructs suitable for generating compositions of the inventions are human resistin-C-Xa: (SEQ ID NO:325), human resistin-C-EK: (SEQ ID NO:326) and human resistin-C: (SEQ ID NO:327).

Human Resistin constructs so generated are a preferred embodiment of the invention. Vaccination against Resistin using the aforementioned compositions of the invention may thus provide a way of treating Type II Diabetes and obesity.

In another embodiment the antigenic determinant is Lymphotoxin-β. Immunization against lymphotoxin-β may be useful in treating Prion mediated disease. Scrapie (a prion-mediated disease) agent replication is believed to take mainly place in lymphoid tissues and was shown to depend on prion-protein expressing follicular dendritic cells (FDCs) (Brown et al., *Nature Med.* 11: 1308–1312 (1999)). It was subsequently shown that mice lacking functional follicular dendrite cells show an impaired prion replication in spleens and a (small) retardation of neuroinvasion (Montrasio et al., *Science* 288: 1257–1259 (2000)). This was achieved by injecting the mice with a soluble lymphotoxin-β receptor-Fc-fusion protein (LTβR-Fc). This soluble receptor construct inhibits the development of FDCs by interfering with the crucial interaction of lymphotoxin-β on T, B or NK cells with the lymphotoxin-β receptor on the FDC precursor cells. Thus, vaccination against lymphotoxin-β (also called TNFγ) may provide a vaccine for treatment or prevention of Creutzfeld-Jakob (variant form) or other prion-mediated diseases and thus prevent prion replication and neuroinvasion.

Immunization against Lymphotoxin-β may also provide a way of treating diabetes. Transgene expression of soluble LTβR-Fc fusion protein in nonobese diabetic NOD mice blocked diabetes development but not insulitis (Ettinger et al., *J. Exp. Med.* 193: 1333–40 K (2001)). Wu et al. (*J. Exp. Med.* 193: 1327–32 (2001)) also used NOD mice to study the involvement of lymphotoxin-β, but instead of transgenic animals they did inject the LTβR-Fc fusion protein. They saw a strong inhibition of diabetes development and inhibition of insulitis. Most interestingly, they could even reverse preexisting insulitis by the fusion protein treatment. In the pancreas the formation of lymphoid follicular structures could thus be reversed. Vaccination against lymphotoxin-β may thus provide a way of treatment against type-I diabetes.

The sequence of the extracellular domain of human lymphotoxin-β is shown in SEQ ID No: 250 (TNFC_human) and the sequence of the extracellular domain of murine lymphotoxin-β is shown in SEQ ID No: 251 (TNFC_mouse).

In a further preferred embodiment, the inventive composition comprises an amino acid linker containing a free cysteine and being added to the N-terminus of the sequence corresponding to the processed form of lymphotoxin-β, or inserted between the N-terminus of the sequence corresponding to the mature form of the protein, and the signal peptide, C-terminally to the signal peptide. In further preferred embodiments of the invention, the extracellular part of lymphotoxin-β is expressed as a fusion protein either with Glutathione-S-transferase, fused N-terminally to lymphotoxin-β, or with a 6 histidine-tag followed by a myc-tag, fused again N-terminally to the extracellular part of lymphotoxin-β. An amino acid spacer containing a protease cleavage site as well as a linker sequence containing a free cysteine as attachment site, C-terminally to the protease cleavage site, are fused to the N-terminus of the sequence of the extracellular part of lymphotoxin-β. Preferably, the extracellular part of lymphotoxin-β consists of fragments corresponding to amino acids 49–306 or 126–306 of lymphotoxin-β. These specific compositions of the invention may be cloned and expressed in the pCEP-Pu eukaryotic vector. In further preferred embodiments, the inventive compositions comprise an amino acid linker containing a free cysteine residue suitable as second attachment site, and being fused to the C-terminus of lymphotoxin-β or lymphotoxin-β fragments. In a particularly favored embodiment, the amino acid sequence LACGG (SEQ ID NO:415), comprising the amino acid linker ACGG (SEQ ID NO:416) which itself contains a cysteine residue for coupling to VLPS and Pili is fused to the N-terminus of the extracellular part of lymphotoxin-β: or of a fragment of the extracellular part of lymphotoxin-β, yielding the proteins human C-LTβ$_{49-306}$ (SEQ ID NO:346) and human C-LTβ$_{126-306}$ (SEQ ID NO:347) after cleavage with enterokinase of the corresponding fusion proteins expressed either in vector pCEP-SP-GST-EK or vector pCP-SP-his-myc-EK as described in EXAMPLE 3.

In a preferred embodiment, the antigen or antigenic determinant is the prion protein, fragments thereof and in particular peptides of the prion protein. In one embodiment the prion protein is the human prion protein. Guidance on how to modify human prion protein for association with the core particle is given throughout the application and in particular in EXAMPLE 7. Mouse prion protein constructs are disclosed, and human prion protein constructs can also be generated and have, for example, the sequence of SEQ ID NO:348. Further constructs comprise the whole human prion protein sequence, and other fragments of the human prion protein, which are further composition of the invention. Immunization against prion protein may provide a way of treatment or prevention of Creutzfeldt-Jakob (variant form) or other prion-mediated diseases. Immunization using the compositions of the invention comprising the prion protein may provide a way of treatment against prion mediated diseases in other animals, and the corresponding sequences of bovine and sheep prion protein constructs are given in SEQ ID NO:349 and SEQ ID NO:350, respectively. The peptides of the human prion protein corresponding to the murine peptides described in EXAMPLE 8, and of amino acid sequence CSAMSRPIIHFGSDYEDRYYREN-MHR ("human cprplong"; SEQ ID NO:356) and CGS-DYEDRYYRENMHR ("human cprpshort"; SEQ ID NO:357) lead to preferred embodiments of the invention. These peptides comprise an N-terminal cysteine residue added for coupling to VLPs and Pili. Corresponding bovine and sheep peptides are CSAMSRPLIHF-GNDYEDRYYRENMHR ("bovine cprplong"; SEQ ID NO:401) and CGNDYEDRYYRENMHR ("bovine cprpshort"; SEQ ID NO:402) CSAMSRPLIHF-GNDYEDRYYRENMYR ("sheep cprplong"; SEQ ID NO:403) and CGNDYEDRYYRENMYR ("sheep cprpshort"; SEQ ID NO:404), all leading to embodiments of the invention.

In a further preferred embodiment of the invention, the antigenic determinant is tumor necrosis factor α (TNF-α), fragments thereof or peptides of TNF-α. In particular, peptides or fragments of TNF-α can be used to induce a self-specific immune response directed towards the whole protein by immunizing a human or an animal with vaccines and compositions, respectively, comprising such peptides or fragments in accordance with the invention. Preferably, VLPs, bacteriophages or bacterial pili are used as core particle, to which TNF-α, peptides or fragments thereof are attached according to the invention.

The following murine peptides are the murine homologs to human peptides that have been shown to be bound by antibodies neutralizing the activity of TNF-α_(Yone et al. *J. Biol. Chem.* 270: 19509–19515) and were, in a further preferred embodiment of the invention, modified with cysteine residues for coupling to VLPs, bacteriophages or bacterial pili.

MuTNFa peptide: the sequence CGG was added at the N-terminus of the epitope consisting of amino acid residues 22–32 of mature murine TNF-α: CGGVEEQLEWLSQR (SEQ ID NO:35 8).

3'TNF II peptide: the sequence GGC was fused at the C-terminus of the epitope consisting of amino acid residues 4–22 of mature murine TNF-α and glutamine 21 was mutated to glycine. The sequence of the resulting peptide is: SSQNSSDKPVAHVVANHGVGGC (SEQ ID NO:359).

5'TNF II peptide: a cysteine residue was fused to the N-terminus of the epitope consisting of amino acid residues 4–22 of mature murine TNF-α and glutamine 21 was mutated to glycine. The sequence of the resulting peptide is: CSSQNSSDKPVAHVVANHGV (SEQ ID NO:360).

The corresponding human sequence of the 4–22 epitope is SSRTPSDKPVAHVVANPQAEGQ (SEQ ID NO:361). Like for the murine sequence a cysteine is, preferably, fused at the N-terminus of the epitope, or the sequence GGC is fused at the C-terminus of the epitope for covalent coupling to VLPs, bacteriophages or bacterial pili according to the invention. It is, however, within the scope of the present invention that other cysteine containing sequences are fused at the N- or C-termini of the epitopes. In general, one or two glycine residues are preferably inserted between the added cysteine residue and the sequence of the epitope. Other amino acids may, however, also be inserted instead of glycine residues, and these amino acid residues will preferably be small amino acids such as seine.

The human sequence corresponding to amino acid residues 22–32 is QLQWLNRRANA (SEQ ID NO:362). Preferably, the sequence CGG is fused at the N-terminus of the epitope for covalent coupling to VLPs or bacterial pili according to the invention. Other TNF-α epitopes suitable for using in the present invention have been described and are disclosed for example by Yone et al. (*J. Bid. Chem.*270: 19509–19515).

The invention further includes compositions which contain mimotopes of the antigens or antigenic determinants described herein.

The specific composition of the invention comprises an antibody or preferably an antibody fragment presented on a virus-like particle or pilus for induction of an immune response against said antibody. Antibodies or antibody fragments which are produced by lymphoma cells, may be selected for attachment to the virus-like particle and immunization, in order to induce a protective immune response against the lymphoma.

In other further embodiments, an antibody or antibody fragment mimicking an antigen is attached to the particle. The mimicking antibody or antibody fragment may be generated by immunization and subsequent isolation of the mimicking antibody or antibody fragment by any known method known to the art such as e.g. hybridoma technology (Gherardi, E. et al., J. Immunol. Methods 126: 61–68 (1990)), phage display (Harrison et al., *Methods Enzymol.* 267: 83–109 (1996)), ribosome display (Hanes, J. et al., *Nat. Biotechnol.* 18: 1287–1292 (2000)), yeast two-hybrid (Visintin, M. et al., *Proc. Natl. Acad. Sci. USA* 96: 11723–11728 (1999)), yeast surface display (Boder, E T. & Wittrup, K D. *Methods. Enzym.* 328: 430–444 (2000)), bacterial surface display (Daugherty, P S. et al., *Protein Eng.* 12: 613–621 (1999)). The mimicking antibody may also be isolated from an antibody library or a naive antibody library using methods known to the art such as the methods mentioned above, for example.

In a further embodiment, an antibody recognizing the combining site of another antibody, i.e. an anti-idiotypic antibody, further called the immunizing antibody, may be used. The antibody recognized by the anti-idiotypic antibody will be further referred to as the neutralizing antibody. Thus, by immunizing against the anti-idiotypic antibody, molecules with the specificity of the neutralizing antibody are generated in situ; we will further refer to these generated antibodies as the induced antibodies. In another preferred embodiment, the immunizing antibody is selected to interact with a ligand molecule of the target molecule against which immunization is seeked. The ligand molecule may be any molecule interacting with the target molecule, but will preferentially interact with the site of the target molecule against which antibodies should be generated for inhibition of its function. The ligand molecule may be a natural ligand of the target molecule, or may be any engineered, designed or isolated ligand having suitable binding properties.

The immunizing antibodies may be of human origin, such as isolated from a naive or immune human antibody library, or may have been isolated from a library generated from another animal source, for example of murine origin.

Coupling of the antibody or antibody fragment to the VLP or pilus is achieved either by limited reduction of exposed disulfide bridges (for example of the interchain disulfide bridge between CH1 and Cκ or Cλ in a Fab fragment) or by fusion of a linker containing a free cysteine residue at the C-terminus of the antibody or antibody fragment. In a further embodiment, a linker containing a free cysteine residue is fused to the N-terminus of the antibody or antibody fragment for attachment to a VLP or pilus protein.

A number of vaccine compositions which employ mimotopes are known in the art, as are methods for generating and identifying mimotopes of particular epitopes. For example, Arnon et al., *Immunology* 101:555–562 (2000), the entire disclosure of which is incorporated herein by reference, describe mimotope peptide-based vaccines against *Schistosoma mansoni*. The mimotopes uses in these vaccines were obtained by screening a solid-phase 8mer random peptide library to identify mimotopes of an epitope recognized by a protective monoclonal antibody against *Schistosoma mansoni*. Similarly, Olszewska et al., *Virology* 272:98–105 (2000), the entire disclosure of which is incorporated herein by reference, describe the identification of synthetic peptides which mimic an epitope of the measles virus fusion protein and the use of these peptides for the immunization of mice. In addition, Zuercher et al., *Eur. J. Immunol.* 30:128–135 (2000), the entire disclosure of which is incorporated herein by reference, describe compositions and methods for oral anti-IgE immunization using epitope-displaying phage. In particular, epitope-displaying M13 bacteriophages are employed as carriers for an oral anti-IgE vaccine. The vaccine compositions tested contain mimotopes and epitopes of the monoclonal anti-IgE antibody BSW17.

The invention thus includes vaccine compositions which contain mimotopes that elicit immunological responses against particular antigens, as well as individual mimotope/core particle conjugates and individual mimotope/non-naturally occurring molecular scaffold conjugates which make up these vaccine compositions, and the use of these vaccine compositions to elicit immunological responses against specific antigens or antigenic determinants. Mimotopes may also be polypeptides, such as anti-idiotypic antibodies. Therefore, in a further preferred embodiment of the invention, the antigen or antigenic determinant is an anti-idiotypic antibody or anti-idiotypic antibody fragment.

The invention further includes compositions which contain mimotopes of the antigens or antigenic determinants described herein.

Mimotopes of particular antigens may be generated and identified by any number of means including the screening of random peptide phage display libraries (see, e.g., PCT Publication No. WO 97/31948, the entire disclosure of which is incorporated herein by reference). Screening of such libraries will often be performed to identify peptides which bind to one or more antibodies having specificity for a particular antigen.

Mimotopes suitable for use in vaccine compositions of the invention may be linear or circular peptides. Mimotopes which are linear or circular peptides may be linked to non-natural molecular scaffolds or core particles by a bond which is not a peptide bond.

As suggested above, a number of human IgE mimotopes and epitopes have been identified which elicit immunological responses against human IgE molecules. (See, e.g., PCT Publication No. WO 97/31948.) Thus, in certain embodiments, vaccine compositions of the invention include compositions which elicit an immunological response against immunoglobin molecules (e.g., IgE molecules).

Peptides which can be used to elicit such immunological responses include proteins, protein subunits, domains of IgE molecules, and mimotopes which are capable of eliciting production of antibodies having specificity for IgE molecules. Generally, portions of IgE molecules used to prepare vaccine compositions will be derived from IgE molecules of the species from which the composition is to be administered. For example, a vaccine composition intended for administration to humans will often contain one or more portions of the human IgE molecule, and/or one or more mimotopes which are capable of eliciting immunological responses against human IgE molecules.

In specific embodiments, vaccine compositions of the invention intended for administration to humans will contain at least one portion of the constant region of the IgE heavy chain set out in SEQ ID NO:176; Accession No. AAB59424 (SEQ ID NO: 176). In more specific embodiments, IgE peptides used to prepare vaccine compositions of the invention comprise, or alternatively consist of, peptides having the following amino acid sequences: CGGVNLTWSRASG (SEQ ID NO:178).

In additional specific embodiments, vaccine compositions of the invention will contain at least one mimotope which is capable of eliciting an immune response that results in the production of antibodies having specificity for a particular antigen.

Examples of mimotopes of IgE suitable for use in the preparation of vaccine compositions of the invention include peptides having the following amino acid sequences:

| Mimotope | SEQ ID NO |
|---|---|
| INHRGYWV | 179 |
| RNHRGYWV | 180 |
| RSRSGGYWLW | 181 |
| VNLTWSRASG | 182 |
| C. H₃ epitope | |
| VNLPWSRASG | 183 |
| VNLTWSFGLE | 184 |
| VNLPWSFGLE | 185 |
| C. H₃ mimotope | |
| VNRPWSFGLE | 186 |
| VKLPWRFYQV | 187 |
| VWTACGYGRM | 188 |
| GTVSTLS | 189 |
| LLDSRYW | 190 |
| QPAHSLG | 191 |
| LWGMQGR | 192 |
| LTLSHPHWVLNHFVS | 193 |
| SMGPDQTLR | 194 |
| VNLTWS | 195 |
| GEFCINHRGYWVCGDPA | 216 |

C. Preparation of the AlphaVaccine Particles

The invention provides novel compositions and methods for the construction of ordered and repetitive antigen arrays. As one of skill in the art would know, the conditions for the assembly of the ordered and repetitive antigen array depend to a large extent on the specific choice of the first attachment site of the non-natural molecular scaffold and the specific choice of the second attachment site of the antigen or antigenic determinant. Thus, practitioner choice in the design of the composition (i.e., selection of the first and second attachment sites, antigen and non-natural molecular scaffold) will determine the specific conditions for the assembly of the AlphaVaccine particle (the ordered and repetitive antigen array and non-natural molecular scaffold combined). Information relating to assembly of the AlphaVaccine particle is well within the working knowledge of the practitioner, and numerous references exist to aid the practitioner (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Celis, J., ed., CELL BIOLOGY, Academic Press, 2$^{nd}$ edition, (1998); Harlow, E. and Lane, D., "Antibodies: A Laboratory Manual," Cold Spring Harbor Laboratory, Cold Spring Harbor, N.Y. (1988), all of which are incorporated herein by reference.

In a specific embodiment of the invention, the JUN and FOS leucine zipper protein domains are utilized for the first and second attachment sites of the invention, respectively. In the preparation of AlphaVaccine particles, antigen must be produced and purified under conditions to promote assembly of the ordered and repetitive antigen array onto the non-natural molecular scaffold. In the particular JUN/FOS leucine zipper protein domain embodiment, the FOS-antigen or FOS-antigenic determinant should be treated with a reducing agent (e.g., Dithiothreitol (DTT)) to reduce or eliminate the incidence of disulfide bond formation (Example 15).

For the preparation of the non-natural molecular scaffold (i.e., recombinant Sinbis virus) of the JUN/FOS leucine zipper protein domain embodiment, recombinant E2-JUN viral particles should be concentrated, neutralized and treated with reducing agent (see Example 16).

Assembly of the ordered and repetitive antigen array in the JUN/FOS embodiment is done in the presence of a redox shuffle. E2-JUN viral particles are combined with a 240 fold molar excess of FOS-antigen or FOS-antigenic determinant for 10 hours at 4° C. Subsequently, the AlphaVaccine particle is concentrated and purified by chromatography (Example 16).

1 In another embodiment of the invention, the coupling of the non-natural molecular scaffold to the antigen or antigenic determinant may be accomplished by chemical cross-linking. In a specific embodiment, the chemical agent is a heterobifunctional cross-linking agent such as ∈-maleimidocaproic acid N-hydroxysuccinimide ester (Tanimori et al., J. Pharm. Dyn. 4:812 (1981); Fujiwara et al., J. Immunol. Meth. 45:195 (1981)), which contains (1) a succinimide group reactive with amino groups and (2) a maleimide group reactive with SH groups. A heterologous protein or polypeptide of the first attachment site may be engineered to contain one or more lysine residues that will serve as a reactive moiety for the succinimide portion of the heterobifunctional cross-linking agent. Once chemically coupled to the lysine residues of the heterologous protein, the maleimide group of the heterobifunctional cross-linking agent will be available to react with the SH group of a cysteine residue on the antigen or antigenic determinant. Antigen or antigenic determinant preparation in this instance may require the engineering of a cysteine residue into the protein or polypeptide chosen as the second attachment site so that it may be reacted to the free maleimide function on the cross-linking agent bound to the non-natural molecular scaffold first attachment sites. Thus, in such an instance, the heterobifunctional cross-linking agent binds to a first attachment site of the non-natural molecular scaffold and connects the scaffold to a second binding site of the antigen or antigenic determinant.

3. Compositions, Vaccines, and the Administration Thereof, and Methods of Treatment The invention provides vaccine compositions which may be used for preventing and/or attenuating diseases or conditions. The invention further provides vaccination methods for preventing and/or attenuating diseases or conditions in individuals.

In one embodiment, the invention provides vaccines for the prevention of infectious diseases in a wide range of species, particularly mammalian species such as human, monkey, cow, dog, cat, horse, pig, etc. Vaccines may be designed to treat infections of viral etiology such as HIV, influenza, Herpes, viral hepatitis, Epstein Bar, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

In another embodiment, the invention provides vaccines for the prevention of cancer in a wide range of species, particularly mammalian species such as human, monkey, cow, dog, cat, horse, pig, etc. Vaccines may be designed to treat all types of cancer: lymphomas, carcinomas, sarcomas, melanomas, etc.

In another embodiment of the invention, compositions of the invention may be used in the design of vaccines for the treatment of allergies. Antibodies of the IgE isotype are important components in allergic reactions. Mast cells bind IgE antibodies on their surface and release histamines and other mediators of allergic response upon binding of specific antigen to the IgE molecules bound on the mast cell surface. Inhibiting production of IgE antibodies, therefore, is a promising target to protect against allergies. This should be possible by attaining a desired T helper cell response. T helper cell responses can be divided into type 1 ($T_H1$) and type 2 ($T_H2$) T helper cell responses (Romagnani, *Immunol. Today* 18:263–266 (1997)). $T_H1$ cells secrete interferon-gamma and other cytokines which trigger B cells to produce IgG1–3 antibodies. In contrast, a critical cytokine produced by $T_H2$ cells is IL-4, which drived B cells to produce IgG4 and IgE. In many experimental systems, the development of $T_H1$ and $T_H2$ responses is mutually exclusive since $T_H1$ cells suppress the induction of $T_H2$ cells and vice versa. Thus, antigens that trigger a strong $T_H1$ response simultaneously suppress the development of $T_H2$ responses and hence the production of IgE antibodies. Interestingly, virtually all viruses induce a $T_H1$ response in the host and fail to trigger the production of IgE antibodies (Coutelier et al., *J. Exp. Med.* 165:64–69 (1987)). This isotype pattern is not restricted to live viruses but has also been observed for inactivated or recombinant viral particles (Lo-Man et al., *Eur. J. Immunol.* 28:1401–1407 (1998)). Thus, by using the processes of the invention (e.g., AlphaVaccine Technology), viral particles can be decorated with various allergens and used for immunization. Due to the resulting "viral structure" of the allergen, a $T_H1$ response will be elicited, "protective" IgG1–3 antibodies will be produced, and the production of IgE antibodies which cause allergic reactions will be prevented. Since the allergen is presented by viral particles which are recognized by a different set of helper T cells than the allergen itself, it is likely that the allergen-specific IgG1–3 antibodies will be induced even in allergic individuals harboring pre-existing $T_H2$ cells specific for the allergen. The presence of high concentrations of IgG antibodies may prevent binding of allergens to mast cell bound IgE, thereby inhibiting the release of histamine. Thus, presence of IgG antibodies may protect from IgE mediated allergic reactions. Typical substances causing allergies include: grass, ragweed, birch or mountain cedar pollens, house dust, mites, animal danders, mold, insect venom or drugs (e.g., penicillin). Thus, immunization of individuals with allergen-decorated viral particles should be beneficial not only before but also after the onset of allergies.

In specific embodiments, the invention provides methods for preventing and/or attenuating diseases or conditions which are caused or exacerbated by "self" gene products (e.g., tumor necrosis factors), i.e. "self antigens" as used herein. In related embodiments, the invention provides methods for inducing immunological responses in individuals which lead to the production of antibodies that prevent and/or attenuate diseases or conditions are caused or exacerbated by "self" gene products. Examples of such diseases or conditions include graft versus host disease, IgE-mediated allergic reactions, anaphylaxis, adult respiratory distress syndrome, Crohn's disease, allergic asthma, acute lymphoblastic leukemia (ALL), non-Hodgkin's lymphoma (NHL), Graves' disease, inflammatory autoimmune diseases, myasthenia gravis, systemic lupus erythematosus (SLE), immunoproliferative disease lymphadenopathy (IPL), angioimmunoproliferative lymphadenopathy (AIL), immunoblastive lymphadenopathy (IBL), rheumatoid arthritis, diabetes, multiple sclerosis, osteoporosis and Alzheimer's disease.

As would be understood by one of ordinary skill in the art, when compositions of the invention are administered to an individual, they may be in a composition which contains salts, buffers, adjuvants, or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1990)).

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention may be administered by various methods known in the art, but will normally be administered by injection, infusion, inhalation, oral administration, or other suitable physical methods. The compositions may alternatively be administered intramuscularly, intravenously, or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Prion-mediated diseases are an increasing threat for society. Specifically, prion-induced BSE in cattle represents a disease that has long been neglected and may affect a great number of animals throughout Europe. Moreover, a variant form of CJD is attributed to infection of humans after consumption of meat of prion-infected cattle. Although the number of infected people has been relatively low so far, it seems possible that the disease may become epidemic. However, long-term prognosis for the development of vCJD may be particular difficult, since incubation times between infection and overt disease are very long (an estimated 10 years).

Prions are cellular proteins existing in most mammalian species. Prion proteins exist in two forms, a normally folded form that is usually present in healthy individuals ($PrP^c$) and a misfolded form that causes disease ($Prp^{Sc}$). The current prion hypotheses postulates that the misfolded prion form PrP$^{Sc}$ can catalyse the refolding of healthy prion PrP$^c$ into disease causing PrP$^{Sc}$ (A. Aguzzi, *Haematologica* 85, 3–10 (2000)). In some rare instances, this transition may also occur spontaneously, causing classical CJD in humans. Some mutations in PrP$^c$ are associated with an increase in this spontaneous transition, causing the various forms of familial CJD. However, PrP$^{Sc}$ may also be infectious and may be transmitted by blood transfusion or via the food chain. The latter form of prion mediated disease is known as Kuru Kuru and used to occur in human cannibals. However, since species that are feeding on their own individuals are not abundant, this form of orally transmitted disease was too rare to be documented for other species.

The massive feeding of cows with beef-products throughout Europe now changed the situation and numbers of cows infected with a transmissible form of BSE-causing PrP$^{Sc}$, dramatically increased in recent years, afflicting hundreds of thousands of cows. This sudden appearance of massive numbers of BSE-diseased cows caused great fear in the human population that a similar disease may be induced in humans. Indeed, in 1996, the first case of a variant form of CJD was reported that could be attributed to the consumption of PrP$^{Sc}$ infected beef. Until now, this fear has further increased, since the number of infected humans has constantly increased during the following years and no cure is in sight. Moreover, since sheep succumb to a prion-mediated disease called scrapie and since other mammalian species can be infected with PrP$^{Sc}$ Experimentally, it is possible that BSE-like diseases may occur also in other species. The mechanism of prion transmission has been studied in great detail. It is now clear that prions first replicate in the lymphoid organs of infected mice and are subsequently transported to the central nervous system. Follicular dendritic cells (FDCs), a rare cell population in lymphoid organs, seems to be essential for both replication of prion proteins in the lymphoid organs and transport into the central nervous system (S. Brandner, M. A. Klein, A. Aguzzi, *Transfus Clin Biol* 6, 17–23 (1999); F. Montrasio, et al., *Science* 288, 1257–9 (2000)). FDCs are a poorly studied cell type but it is now clear that they depend upon the production of lymphotoxin and/or TNF by B cells for their development (F. Mackay, J. L. Browning, *Nature* 395, 26–27 (1998)). Indeed, mice deficient for lymphotoxin do not exhibit FDCs (M. S. Matsumoto, et al., *Science* 264, 703–707 (1996)). Moreover, they fail to be productively infected with prions and do not succumb to disease. In addition to FDCs, antibodies may also play a role in disease progression (S. Brandner, M. A. Klein, A. Aguzzi, *Transfus Clin Biol* 6, 17–23 (1999)).

Recently, it was shown that blocking the LTb pathway using a Ltb receptor Fc fusion molecule not only eliminates FDCs in mice but also blocks infection with PrP$^{Sc}$ (F. Montrasio, et al., *Science* 288, 1257–9 (2000). Thus, a vaccine that induces antibodies specific for LTb or its receptor may be able to block transmission of PrP$^{Sc}$ from one individual to another or from the periphery to the central nervous system.

However, it is usually difficult if not impossible to induce antibody responses to self-molecules by conventional vaccination. One way to improve the efficiency of vaccination is to increase the degree of repetitiveness of the antigen applied: Unlike isolated proteins, viruses induce prompt and efficient immune responses in the absence of any adjuvants both with and without T-cell help (Bachmann & Zinkemagel, Ann. Rev. Immunol: 15:235–270 (1991)). Although viruses often consist of few proteins, they are able to trigger much stronger immune responses than their isolated components. For B-cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann & Zinkernagel, Immunol. Today 17:553–558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann & Zinkernagel, Ann. Rev. Immunol. 15:235–270 (1997)). Viral structure is even linked to the generation of anti-antibodies in autoimmune disease and as a part of the natural response to pathogens (see Fehr, T., et al., J. Exp. Med. 185:1785–1792 (1997)). Thus, antibodies presented by a highly organized viral surface are able to induce strong anti-antibody responses.

The immune system usually fails to produce antibodies against self-derived structures. For soluble antigens present at low concentrations, this is due to tolerance at the Th cell level. Under these conditions, coupling the self-antigen to a carrier that can deliver T help may break tolerance. For soluble proteins present at high concentrations or membrane proteins at low concentration, B and Th cells may be tolerant. However, B cell tolerance may be reversible (anergy) and can be broken by administration of the antigen in a highly organized fashion coupled to a foreign carrier (Bachmann & Zinkernagel, Ann. Rev. Immunol. 15:235–270 (1997). Thus, LTb, LTa or LTb receptor as highly organized as a virus, a virus like particle or a bacterial pilus may be able to break B cell tolerance and to induce antibodies specific for these molecules.

The present invention is related to the fields of molecular biology, virology, immunology and medicine. The invention provides a method that facilitates induction of antibodies specific for endogenous lymphotoxin (LT)b, LTa or LTb receptor. The invention also provides a process for producing an antigen or antigenic determinant that is able to elicit antibodies specific for LTb, LTa or LTb receptor which is useful for the prevention and therapy of prion-mediated diseases such as variant Creutzfeld-Jacob disease (vCJD) or bovine spongioform encephalopathy (BSE) and elimination of lymphoid organ like structures in autoimmune diseased tissues.

The object of the invention is to provide a vaccine that is able to induce antibodies specific for LTb, LTa or LTb receptor thereby eliminating FDCs from lymphoid organs. This treatment may allow preventing infection with PrP$^{Sc}$ or spread of PrP$^{Sc}$ from the periphery to the central nervous system. In addition, this treatment blocks generation of lymphoid organ like structures in organs targeted by autoimmune disease and may even dissolve such existing structures, ameliorating disease symptoms.

LTb, LTa or LTb receptor or fragments thereof are coupled to a protein carrier that is foreign to the host. In a preferred embodiment of the invention, LTb, LTa or LTb receptor or fragments thereof will be coupled to a highly organized structure in order to render these molecules highly repetitive and organized. The highly organized structure may be a bacterial pilus, a virus like particle (VLP) generated by recombinant proteins of the bacteriophage Qβ, recombinant proteins of Rotavirus, recombinant proteins of Norwalkvirus, recombinant proteins of Alphavirus, recombinant proteins of Foot and Mouth Disease virus, recombinant proteins of Retrovirus, recombinant proteins of Hepatitis B virus, recombinant proteins of Tobacco mosaic virus, recombinant proteins of Flock House Virus, and recombinant proteins of human Papillomavirus. In order to optimize the three-dimensional arrangement of LTb, LTa or LTb receptor or fragments thereof on the highly organized structure, an attachment site, such as a chemically reactive amino-acid, is introduced into the highly organized structure (unless it is naturally there) and a binding site, such as a chemically reactive amino acid, will be introduced on the LTb, LTa or LTb receptor or fragments (unless it is naturally there). The presence of an attachment site on the highly organized structure and a binding site on the LTb, LTa or LTb receptor or fragments thereof will allow to couple these molecules to the repetitive structure in an oriented and ordered fashion which is essential for the induction of efficient B cell responses.

In an equally preferred embodiment, the attachment site introduced in the repetitive structure is biotin that specifically binds streptavidin. Biotin may be introduced by chemical modification. LTb, LTa or LTb receptor or fragments thereof may be fused or linked to streptavidin and bound to the biotinylated repetitive structure.

Other embodiments of the invention include processes for the production of the compositions of the invention and methods of medical treatment using said compositions. It is to be understood that both the foregoing general description and the following detailed description are exemplary and explanatory only and are intended to provide further explanation of the invention as claimed.

In addition to vaccine technologies, other embodiments of the invention are drawn to methods of medical treatment for cancer and allergies.

All patents and publications referred to herein are expressly incorporated by reference in their entirety.

EXAMPLES

Enzymes and reagents used in the experiments that follow included: T4 DNA ligase obtained from New England Biolabs; Taq DNA Polymerase, QIAprep Spin Plasmid Kit, QIAGEN Plasmid Midi Kit, QiaExII Gel Extraction Kit, QIAquick PCR Purification Kit obtained from QIAGEN; QuickPrep Micro mRNA Purification Kit obtained from Pharmacia; SuperScript One-step RT PCR Kit, fetal calf serum (FCS), bacto-tryptone and yeast extract obtained from Gibco BRL; Oligonucleotides obtained from Microsynth (Switzerland); restriction endonucleases obtained from Boehringer Mannheim, New England Biolabs or MBI Fermentas; Pwo polymerase and dNTPs obtained from Boehringer Mannheim. HP-1 medium was obtained from Cell culture technologies (Glattbrugg, Switzerland). All standard chemicals were obtained from Fluka-Sigma-Aldrich, and all cell culture materials were obtained from TPP.

DNA manipulations were carried out using standard techniques. DNA was prepared according to manufacturer instruction either from a 2 ml bacterial culture using the QIAprep Spin Plasmid Kit or from a 50 ml culture using the QIAGEN Plasmid Midi Kit. For restriction enzyme digestion, DNA was incubated at least 2 hours with the appropriate restriction enzyme at a concentration of 5–10 units (U) enzyme per mg DNA under manufacturer recommended conditions (buffer and temperature). Digests with more than one enzyme were performed simultaneously if reaction conditions were appropriate for all enzymes, otherwise consecutively. DNA fragments isolated for further manipulations were separated by electrophoresis in a 0.7 to 1.5% agarose gel, excised from the gel and purified with the QiaExII Gel Extraction Kit according to the instructions provided by the manufacturer. For ligation of DNA fragments, 100 to 200 pg of purified vector DNA were incubated overnight with a threefold molar excess of the insert fragment at 16° C. in the presence of 1 U T4 DNA ligase in the buffer provided by the manufacturer (total volume: 10–20 µl). An aliquot (0.1 to 0.5 µl) of the ligation reaction was used for transformation of $E.$ $coli$ XL1-Blue (Stratagene). Transformation was done by electroporation using a Gene Pulser (BioRAD) and 0.1 cm Gene Pulser Cuvettes (BioRAD) at 200 Ohm, 25 µF, 1.7 kV. After electroporation, the cells were incubated with shaking for 1 h in 1 ml S.O.B. medium (Miller, 1972) before plating on selective S.O.B. agar.

Example 1

Modular Eukaryotic Expression System for Coupling of Antigens to VLPs

This system was generated in order to add various amino acid linker sequences containing a cysteine residue to antigens for chemical coupling to VLPs.

A. Construction of an EBNA Derived Expression System Encoding a Cysteine-containing Amino Acid Linker and Cleavable Fc-Tag:

pCep-Pu (Wuttke et al. $J.$ $Biol.$ $Chem.$ 276: 36839–48 (2001)) was digested with Kpn I and Bam HI and a new multiple cloning site was introduced with the annealed oligonucleotides PH37 (SEQ ID NO:270) and PH38 (SEQ ID NO:271) leading to pCep-MCS.

A modular system containing a free cysteine flanked by several glycines, a protease cleavage site and the constant region of the human IgG1 was generated as follows. pSec2/Hygro B (Invitrogen Cat. No. V910-20) was digested with Bsp120I and Hind III and ligated with the annealed oligonucleotides SU7 (SEQ ID NO:278) and SU8 (SEQ ID NO:279) leading to construct pSec-B-MCS. pSec-B-MCS was then digested with Nhe I and Hind III and ligated with the annealed oligonucleotides PH29 (SEQ ID NO:264) and PH30 (SEQ ID NO:265) leading to construct pSec 29/30. The construct pSec-FL-EK-Fc* was generated by a three fragment ligation of the following fragments; first pSec 29/30 digested with Eco RI and Hind III, the annealed oligonucleotides PH31 (SEQ ID NO:266) and PH32 (SEQ ID NO:267) and the Bgl I/EcoRI fragment of a plasmid (pSP-Fc*-C1) containing a modified version of the human IgG1 constant region (for details of the hu IgG1 sequence see the sequence of the final construct pCep-Xa-Fc* see FIG. 1A–1C, SEQ ID NOS:426, 427 and 428, respectively). The complete sequence of pCep-Xa-Fc* is given in SEQ ID NO:283. The resulting construct was named pSec-FL-EK-Fc*. From this plasmid the linker region and the human IgG1 Fc part was excised by Nhe I, Pme I digestion and cloned into pCep-MCS digested with Nhe I and Pme I leading to construct pCep-FL-EK-Fc*. Thus a modular vector, was created where the linker sequence and the protease cleavage site, which are located between the Nhe I and Hind III sites, can easily be exchanged with annealed oligonucleotides. For the generation of cleavable fusion protein vectors pCep-FL-EK-Fc* was digested with Nhe I and Hind III and the Factor Xa cleavage site N-terminally flanked with amino acids GGGGCG (SEQ ID NO:413) was introduced with the annealed oligonucleotides PH35 (SEQ ID NO:268) and PH36 (SEQ ID NO:269) and the enterokinase site flanked n-terminally with GGGGCG (SEQ ID NO:413) was introduced with the annealed oligonucleotides PH39 (SEQ ID NO:272) and PH40 (SEQ ID NO:273) leading to the constructs pCep-Xa-Fc* (see FIG. 1A, SEQ ID NO:426) and pCep-EK-Fc* (see FIG. 1B, SEQ ID NO:427) respectively. The construct pCep-SP-EK-Fc* (see FIG. 1C, SEQ ID NO:428) which in addition contains a eukaryotic signal peptide was generated by a three fragment ligation of pCep-EK-Fc* digested Kpn I/Bam HI, the annealed oligos PH41 (SEQ ID NO:274) and PH42 (SEQ ID NO:275) and the annealed oligos PH43 (SEQ ID NO:276) and PH44 (SEQ ID NO:277).

B. Large Scale Production of Fusion Proteins:

For the large scale production of the different fusion proteins 293-EBNA cells (Invitrogen) were transfected with the different pCep expression plasmids with Lipofectamine 2000 reagent (life technologies) according to the manufacturer's recommendation. 24–36 h post transfection the cells were split at a 1 to 3 ratio under puromycin selection (1 μg/ml) in DMEM supplemented with 10% FCS. The resistant cells were then expanded in selective medium. For the harvesting of the fusion proteins the resistant cell population were passed onto poly-L-lysine coated dishes. Once the cells had reached confluence, they were washed 2 times with PBS and serum free medium (DMEM) was added to the plates. The tissue culture supernatant were harvested every 2 to 4 days and replaced with fresh DMEM medium during a period of up to one month. The harvested supernatants were kept at 4° C.

C. Purification of the Fusion Proteins:

The recombinant Fc-fusion proteins were purified by affinity chromatography using protein A sepharose CL-4B (Amersham Pharmacia Biotech AG). Briefly chromatography columns were packed with 1–3 ml protein A resin and the tissue culture supernatants containing the recombinant proteins were applied to the column with a peristaltic pump at a flow rate of 0.5–1.5 ml/min. The column was then washed with 20–50 ml PBS. Depending on the fusion protein the protease cleavage was performed on the column or the protein was eluted as described below. Recombinant fusion proteins were eluted with a citrate/phosphate buffer (pH 3.8) supplemented with 150 mM NaCl and the fractions containing the protein were pooled and concentrated with ultrafree centrifugal filters (Millipore).

D. Protease Cleavage of Recombinant Fusion Proteins (Factor Xa, Enterokinase):

Eluted recombinant fusion proteins containing the enterokinase (EK) cleavage site were cleaved using the EKmax system (Invitrogen) according to the manufacturer's recommendation. The cleaved Fc part of the fusion protein was removed by incubation with protein A. The enterokinase was then removed with the EK-Away system (Invitrogen) according to the manufacturers recommendation. Similarly fusion proteins containing the factor Xa (Xa) cleavage site were cleaved using the restriction protease factor Xa cleavage and removal kit (Roche) according to the manufacturer's recommendation. The cleaved Fc part was removed by incubation with protein A and the protease was removed with the streptavidin resin provided with the kit.

The different fusion proteins were concentrated with ultrafree centrifugal filters (Millipore), quantitated by UV spectrophotometrie and used for subsequent coupling reactions.

Figure 1C:
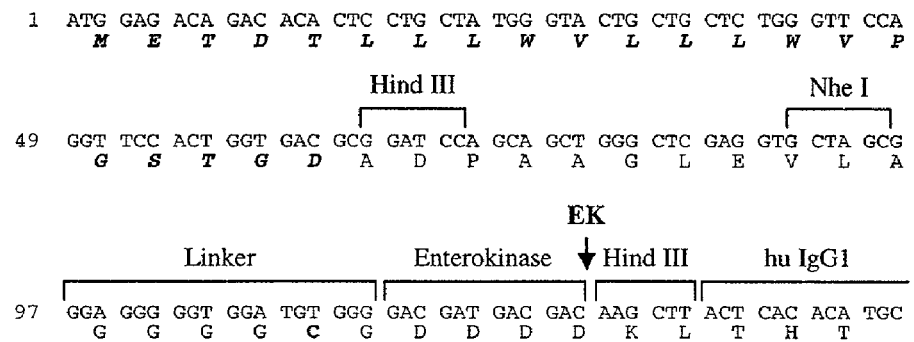

FIG. 1A–1C (SEQ ID NOS:426, 427 and 428, respectively) shows partial sequences of the different eukaryotic expression vectors used. Only the modified sequences are shown.

FIG 1A (SEQ ID NO:426): pCep-Xa-Fc*: the sequence is shown from the Bam HI site onwards and different features are shown above the translated sequence. The arrow indicates the cleavage site of the factor Xa protease.

FIG 1B (SEQ ID NO:427): pCep-EK-Fc*: the sequence is shown from the Bam HI site onwards and different features are shown above the translated sequence. The arrow indicates the cleavage site of the enterokinase. The sequence downstream of the Hind III site is identical to the one shown in FIG 1A.

FIG 1C (SEQ ID NO:428): pCep-SP-EK-Fc*: the sequence is shown from the beginning of the signal peptide on and different features are shown above the translated sequence. The signal peptide sequence which is cleaved of by the signal peptidase is shown in bold The arrow indicates the cleavage site of the enterokinase. The sequence downstream of the Hind III site is identical to the one shown in FIG 1A (SEQ ID NO:426).

Example 2

Eukaryotic Expression and Coupling of Mouse Resistin to VLPs and Pili

A. Cloning of Mouse Resistin:

Total RNA was isolated from 60 mg mouse adipose tissue using a Qiagen RNeasy kit according to the manufacturer's recommendation. The RNA was eluted in 40 μl H$_2$O. This total RNA was than used for the reverse transcription with an oligo dT primer using the ThermoScript™ RT-PCR System (Life Technologies) according to the manufacturer's recommendation. The sample was incubated at 50° C. for 1 h, heated to 85° C. for 5 minutes and treated for 20 minutes at 37° C. with RNAseH.

2 μl of the RT reaction were used for the PCR amplification of mouse resistin. The PCR was performed using Platinium TAQ (Life Technologies) according to the manufacturer's recommendation using primers PH19 (SEQ ID NO:260) and PH20 (SEQ ID NO:261). Primer PH19 (SEQ ID NO:260) corresponds to positions 58–77 and primer PH$_2$0 (SEQ ID NO:261) to positions 454–435 of the mouse Resistin sequence. The PCR mix was first denatured at 94° C. for 2 minutes and than 35 cycles were performed as follows: 30 seconds 94° C., 30 seconds 56° C. and 1 minute 72° C., at the end the samples were left for 10 minutes at 72° C. The PCR fragment was purified and subcloned by TA cloning into the pGEMTeasy vector (Invitrogen) leading to pGEMT-mRes. In order to add appropriate restriction sites a second PCR was performed on pGEMT-mRes with the primers PH21 (SEQ ID NO:262) and PH22 (SEQ ID NO. 263) primers using the same cycling program as described above. The forward primer (PH21 (SEQ ID NO:262)) contains a Bam HI site and nucleotides 81–102 of the mouse Resistin sequence. The reverse primer (PH22 (SEQ ID NO:263)) contains an Xba I site and nucleotides 426–406 of the mouse Resistin sequence. The indicated positions refer to the mouse resistin sequence Gene Accession No. AF323080. The PCR product was purified and digested with Bam HI and Xba I and subcloned into pcmv-Fc*-C1 digested with Bam HI and Xba I leading to the construct pcmv-mRes-Fc*.

The Resistin open reading frame was excised from pcmv-Res-Fc* by Bam HI/Xba I digestion and cloned into pCep- Xa-Fc* and pCep-EK-Fc* (see EXAMPLE 1, section B) digested with Bam HI and Nhe I leading to the constructs pCep-mRes-Xa-Fc* and pCep-mRes-EK-Fc* respectively.

B. Production, Purification and Cleavage of Resistin pCep-mRes-Xa-Fc* and pCep-mRes-EK-Fc* constructs were then used to transfect 293-EBNA cells for the production of recombinant proteins as described in EXAMPLE 1, section B. The tissue culture supernatants were purified as described in EXAMPLE 1, section C. The purified proteins were then cleaved as described in EXAMPLE 1, section D. The resulting recombinant proteins were termed "resistin-C-Xa" or "Res-C-Xa" and "resistin-C-BK" or "Res-C-EK" according to the vector used (see FIG. 2A and FIG. 2B, SEQ ID NOS:429 and 430, respectively).

FIG. 2A and FIG. 2B (SEQ ID NOS:429 and 430, respectively) show sequence of recombinant mouse Resistin proteins used for expression and further coupling. Res-C-Xa (FIG. 2A SEQ ID NO:429) and Res-C-EK (FIG. 2B, SEQ ID NO:430) are shown as a translated DNA sequences. The resistin signal sequence which is cleaved upon protein secretion by the signal peptidase is shown in italic. The amino acid sequences which result form signal peptidase and specific protease (factor Xa or enterokinase) cleavage are shown bold. The bold sequences correspond to the actual protein sequence which was used for coupling, i.e. SEQ ID NO:280, SEQ ID NO:281, SEQ ID NO:282 corresponds to an alternative resistin protein construct, which can also be used for coupling to virus-like particles and pili in accordance with the invention.

C. Coupling of Resistin-C-Xa and Resistin-C-EK to Qβ Capsid Protein

A solution of 0.2 ml of 2 mg/ml Qβ capsid protein in 20 mM Hepes, 150 mM NaCl pH 7.4 was reacted for 30 minutes with 5.6 µl of a solution of 100 mM SMPH (Pierce) in DMSO at 25° C. on a rocking shaker. The reaction solution was subsequently dialyzed twice for 2 hours against 1 L of 20 mM Hepes, 150 mM NaCl, pH 7.4 at 4° C. 8 µl of the dialyzed Qβ reaction mixture was then reacted with 32 µl of resistin-C-Xa solution (resulting in a final concentration of resistin of 0.39 mg/ml) and 13 µl of the Qβ reaction mixture was reacted with 27 µl resistin-C-EK solution (resulting in a final concentration of resistin of 0.67 mg/ml) for four hours at 25° C. on a rocking shaker. Coupling products were analysed by SDS-PAGE (see FIG. 2C). An additional band of 24 kDa is present in the coupling reaction, but not in derivatized Qβ and resistin, respectively. The size of 24 kDa corresponds to the expected size of 24 kDa for the coupled product (14 kDa for Qβ plus 10 kDa for resistin-C-Xa and resistin-C-EK, respectively).

Figure 2C:
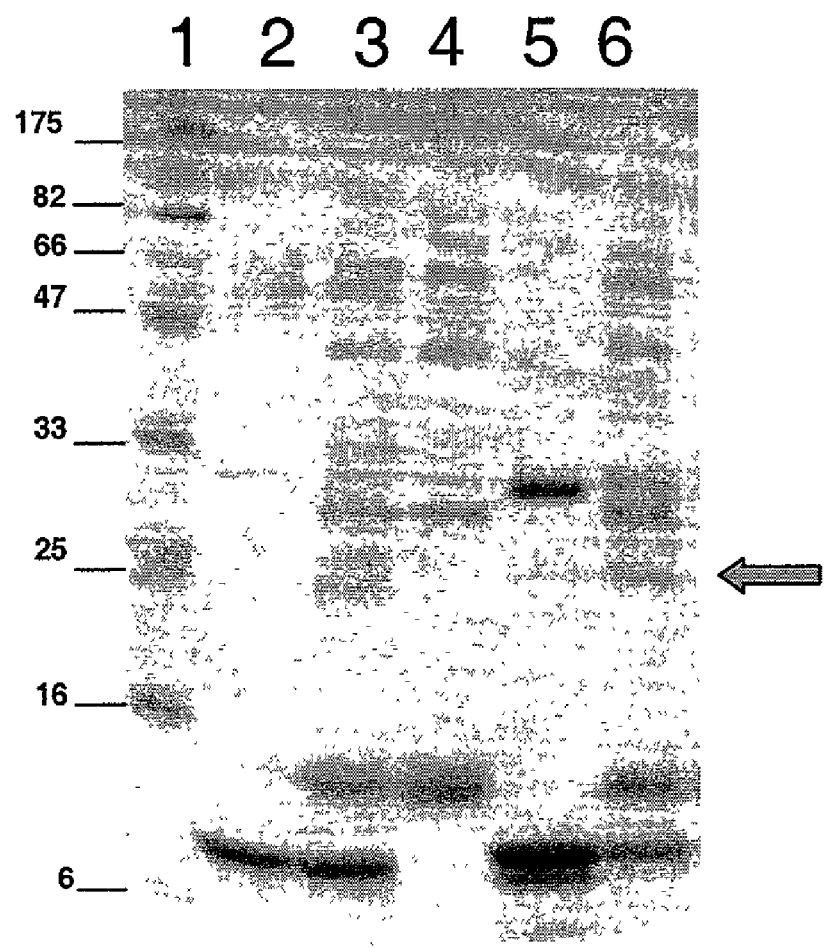

FIG. 2C shows coupling results of resistin-C-Xa and resistin-C-EK to Qβ. Coupling products were analysed on 16% SDS-PAGE gels under reducing conditions. Lane 1: Molecular weight marker. Lane 2: resistin-C-EK before coupling. Lane 3: resistin-C-EK- Qβ after coupling. Lane 4: Qβ derivatized. Lane 5: resistin-C-Xa before coupling. Lane 6: resistin-C-Xa- Qβ after coupling. Molecular weights of marker proteins are given on the left margin. Coupled band is indicated by the arrow.

D. Coupling of Resistin-C-Xa and Resistin-C-EK to fr Capsid Protein

A solution of 0.2 ml of 2 mg/ml fr capsid protein in 20 mM Hepes, 150 mM NaCl pH 7.4 is reacted for 30 minutes with 5.6 µl of a solution of 100 mM SMPH (Pierce) in DMSO at 25° C. on a rocking shaker. The reaction solution is subsequently dialyzed twice for 2 hours against 1 L of 20 mM Hepes, 150 mM NaCl, pH 7.4 at 4° C. 8 µl of the dialyzed fr capsid protein reaction mixture is then reacted with 32 µl of resistin-C-Xa solution (resulting in a final concentration of resistin of 0.39 mg/ml) and 13 µl of the fr capsid protein reaction mixture is reacted with 27 µl resistin-C-EK solution (resulting in a final concentration of resistin of 0.67 mg/mil) for four hours at 25° C. on a rocking shaker. Coupling products are analysed by SDS-PAGE under reducing conditions.

E. Coupling of Resistin-C-Xa and Resistin-C-EK to HBcAg-Lys-2cys-Mut

A solution of 0.2 ml of 2 mg/ml HBcAg-Lys-2cys-Mut in 20 mM Hepes, 150 mM NaCl pH 7.2 is reacted for 30 minutes with 5.6 µl of a solution of 100 nM SMPH (Pierce) in DMSO at 25° C. on a rocking shaker. The reaction solution is subsequently dialyzed twice for 2 hours against 1 L of 20 mM Hepes, 150 mM NaCl, pH 7.2 at 4° C. 8 µl of the dialyzed HBcAg-Lys-2cys-Mut reaction mixture is then reacted with 32 µl of resistin-C-Xa solution and 13 µl of the HBcAg-Lys-2cys-Mut reaction mixture is reacted with 27 µl resistin-C-EK solution for four hours at 25° C. on a rocking shaker. Coupling products are analysed by SDS-PAGE.

F. Coupling of Resistin-C-Xa and Resistin-C-EK to Pili

A solution of 400 µl of 2.5 mg/ml Type-1 pili of *E.coli* in 20 mM Hepes, pH 7.4, is reacted for 60 minutes with a 50-fold molar excess of cross-linker SMPH diluted from a stock solution in DMSO (Pierce) at RT on a rocking shaker. The reaction mixture is desalted on a PD-10 column (Amersham-Pharmacia Biotech). The protein-containing fractions eluating from the column are pooled, and 8 µl of the desalted derivatized pili protein is reacted with 32 µl of resistin-C-Xa solution and 13 µg of the desalted derivatized pili protein is reacted with 27 µl resistin-C-EK solution for four hours at 25° C. on a rocking shaker. Coupling products are analysed by SDS-PAGE.

Example 3

A. Introduction of Cys-containing Linkers, Expression and Purification of Mouse Lymphotoxin-β

The extracellular part of mouse lymphotoxin-β (LT-β) was recombinantly expressed with a CGG amino acid linker at its N-terminus. The linker contained one cysteine for coupling to VLP. A long (aa 49–306) and a short version (aa 126–306) of the protein were fused at their N-terminus to either glutathione S-transferase (GST) or a histidine-myc tag for purification. An enterokinase (EK) cleavage-site was inserted for cleavage of the tag.

Construction of C-LTβ$_{49-306}$ and C-LTβ$_{126-306}$.

Mouse LTβ$_{49-306}$ was amplified by PCR with oligos 5'LTβ and 3'LTβ from a mouse spleen cDNA library inserted into pFB-LIB. For the PCR reaction, 0.5 µg of each primer and 200 ng of the template DNA was used in the 50 µl reaction mixture (1 unit of PFX Platinum polymerase, 0.3 mM dNTPs and 2 mM MgSO$_4$). The temperature cycles were as follows: 94° C. for 2 minutes, followed by 25 cycles of 94° C. (15 seconds), 68° C. (30 seconds), 68° C. (1 minute) and followed by 68° C. for 10 minutes. The PCR product was phosphorylated with T4 Kinase and ligated into pEntry1A (Life technologies) which has been cut with EcoRV and has been dephosphorylated. The resulting plasmid was named pEntry1A-LTβ$_{49-306}$.

A second PCR reaction was performed with oligos 5'LTβlong-NheI and 3'LTβstop-NotI resp. 5'LTβshort-NheI and 3'LTβstop-NotI using pEntry1A-LTβ$_{49-306}$ as a template. Oligos 5'LTβlong-NheI and 5'LTβshort-NheI had an internal NheI site and contained codons for a Cys-Gly-Gly linker and 3'LTβstop-NotI had an internal NotI site and contained a stop codon. For the second PCR reaction, 0.5 µg of each primer and 150 ng of the template DNA was used in the 50 µl reaction mixture (1 unit of PFX Platinum polymerase, 0.3 mM dNTPs and 2 mM MgSO$_4$). The temperature cycles were as follows: 94° C. for 2 minutes, followed by 5 cycles of 94° C. (15 seconds), 50° C. (30 seconds), 68° C. (1 minute), followed by 20 cycles cycles of 94° C. (15 seconds), 64° C. (30 seconds), 68° C. (1 minute) and followed by 68° C. for 10 minutes.

The PCR products were digested with NheI and NotI and inserted into either pCEP-SP-GST-EK or pCEP-SP-his-myc-EK (Wuttke et al. J. Biol. Chem. 276: 36839–48 (2001)). Resulting plasmids were named pCEP-SP-GST-EK-C-LTβ$_{49-306}$, pCEP-SP-GST-EK-C-LTβ$_{126-306}$, pCEP-SP-his-myc-EK-C-LTβ$_{49-306}$, pCEP-SP-his-myc-EK-C-LTβ$_{126-306}$, respectively. GST stands for glutathione-S-transferase, EK for enterokinase, his for a hexahistidine tag and myc for anti c-myc epitope. The C indicates the CGG linker containing the additional cysteine.

All other steps were performed by standard molecular biology protocols.

Sequence of the oligonucleotides:

Expression and production of GST-EK-C-LTβ$_{49-306}$, GST-EK-C-LTβ$_{126-306}$, his-myc-EK-C-LTβ$_{49-306}$ and his-myc-EK-C-LTβ$_{126-306}$ The plasmids pCEP-SP-GST-EK-C-LTβ$_{49-306}$, pCEP-SP-GST-EK-C-LTβ$_{126-306}$, pCEP-SP-his-myc-EK-C-LTβ$_{49-306}$ and pCEP-SP-his-myc-EK-C-LTβ$_{126-306}$ were transfected into 293-EBNA cells (Invitrogen) for protein production as described in EXAMPLE 1. The resulting proteins were named GST-EK-C-LTβ$_{49-306}$, GST-EK-C-LTβ$_{126-306}$, his-myc-EK-C-LTβ$_{49-306}$ and his-myc-EK-C-LTβ$_{126-306}$.

The protein sequences of the LTβ fusion proteins were translated from the cDNA sequences:

GST-EK-C-LTβ$_{49-306}$: SEQ ID NO :289
GST-EK-C-LTβ$_{126-306}$: SEQ ID NO:290
his-myc-EK-C-LTβ$_{49-306}$: SEQ ID NO:291
his-myc-EK-C-LTβ$_{126-306}$: SEQ ID NO :292

The fusion proteins were analysed on 12% SDS-PAGE gels under reducing conditions. Gels were blotted onto nitrocellulose membranes. Membranes were blocked, incubated with a monoclonal mouse anti-myc antibody or with an anti-GST antibody. Blots were subsequently incubated with horse radish peroxidase-conjugated goat anti-mouse IgG or horse radish peroxidase-conjugated rabbit anti-goat IgG. The results are shown in FIG. 3. GST-EK-C-LTβ$_{49-306}$ and GST-EK-C-LTβ$_{126-306}$ could be detected with the anti-GST antibody at a molecular weight of 62 kDa and 48 kDa, respectively. his-myc-EK-C-LTβ$_{49-306}$ and his-myc-EK-C-

```
primerMCS-1F:
5'-TAT GGA TCC GGC TAG CGC TCG AGG GTT AAA ACG CGC GCC GCA T-3'     (SEQ ID NO:293)

primerMCS-1R:
5'-TCG AAT GCG GCC GCC GTT AAA ACC CTC GAG CGC TAG CCG GAT CCA-3'   (SEQ ID NO:294)

Bamhis6-EK-Nhe-F:
5'-GAT CCA CAC CAC CAC CAC CAC CAC GGT TCT GGT GAC GAC GAT          (SEQ ID NO:295)
GAC AAA GCG CTA GCC C-3'

Bamhis6-EK-Nhe-R:
5'-TCG AGG GCT AGC GCT TTG TCA TCG TCG TCA CCA GAA CCG TGG          (SEQ ID NO:296)
TGG TGG TGG TGG TGT G-3' oligo1F-C-glycine-linker:
5'-TCG AGG GTG GTG GTG GTG GTT GCG GTT AAT AAG TTT AAA CGC-3'       (SEQ ID NO:297)

oligo1R-C-glycine-linker:
5'-GGC GCG TTA AAC TTA TTA ACC GCA ACC ACC ACC ACC CCC-3'           (SEQ ID NO:298)

oligo1F-C-gamma1-linker:
5'-TCG AGG ATA AAA CCC ACA CCT CTC CGC CGT GTG GTT AAT AAG          (SEQ ID NO:299)
TTT AAA CGC-3' oligo1R-C-gamma1-linker:
5'-GGC GCG TTA AAC TTA TTA ACC ACA CGG CGG AGA GGT GTG GGT TTA TCC-3'  (SEQ ID NO:300)

oligo1FA-C-gamma3-linker:
5'-TCG AGC CGA AAC GTT CTA CCC GCG CGG GTT CTT CTG-3'               (SEQ ID NO:301)

oligo1RA-C-gamma3-linker:
5'-CAC CAC CAG AAG AAC CCG CGC GGG TAG ACG GTT TCG GC-3'            (SEQ ID NO:302)

oligo2FB-C-gamma3-linker:
5'-GTG GTG CTC CGG GTG GTT GCG GTT AAT AAG TTT AAA CGC-3'           (SEQ ID NO:303)

oligo2RB-C-gamma3-linker:
5'-GGC GCG TTA AAC TTA TTA ACC GCA ACC ACC CCC GGA G-3'             (SEQ ID NO 304)

rMIF-F:
5'-GGA ATT CCA TAT GCC TAT GTT CAT CGT GAA CAC-3'                   (SEQ ID NO:305)

rMIF-Xho-R:
5'-CCC GCT CGA GAG CGA AGG TGG AAC CGT TC-3'                        (SEQ ID NO:306)
```

LTβ$_{126-306}$ could be detected with the anti-myc antibody at 40–56 kDa and 33–39 kDa, respectively.

Figure 3A:
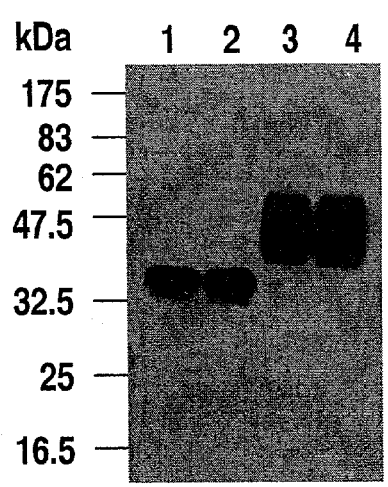
FIGS. 3A–3B Cloning and expression of lymphotoxin-β constructs for coupling to virus-like particles and pili.
Figure 3B:
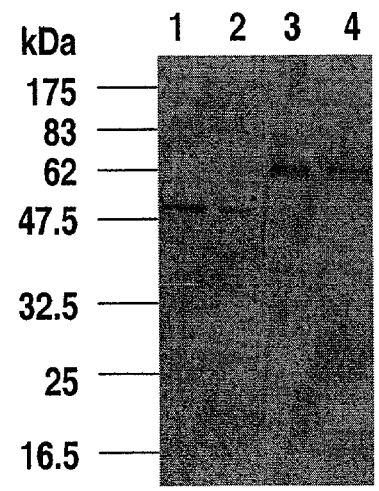

FIG. 3A and FIG. 3B show the result of the expression of LTβ fusion proteins. LTβ fusion proteins were analysed on 12% SDS-PAGE gels under reducing conditions. Gels were blotted onto nitrocellulose membranes. Membranes were blocked, incubated either with a monoclonal mouse anti-myc antibody (dilution 1:2000) (FIG. 3A) or with an anti-GST antibody (dilution 1:2000) (FIG. 3B). Blots were subsequently incubated with horse radish peroxidase-conjugated goat anti-mouse IgG (dilutions 1:4000) (FIG. 3A) or horse radish peroxidase-conjugated rabbit anti-goat IgG (dilutions 1:4000) (FIG. 3B).

A: Lane 1 and 2: his-myc-EK-C-LTβ$_{126-306}$. Lane 3 and 4: his-myc-EK-C-LTβ$_{49-306}$.

B: Lane 1 and 2: GST-EK-C-LTβ$_{126-306}$. Lane 3 and 4: GST-EK-C-LTβ$_{49-306}$.

Molecular weights of marker proteins are given on the left margin.

B. Purification of GST-EK-C-LTβ$_{49-306}$, GST-EK-C-LTβ$_{126-306}$, his-myc-EK-C-LTβ$_{49-306}$ and his-myc-EK-C-LTβ$_{126-306}$ GST-EK-C-LTβ$_{49-306}$ and GST-EK-C-LTβ$_{126-306}$ are purified on glutathione-sepharose column and his-myc-EK-C-LTβ$_{49-306}$ and his-myc-EK-C-LTβ$_{126-306}$ are purified on Ni-NTA sepharose column using standard purification protocols. The purified proteins are cleaved with enterokinase and analysed on a 16% SDS-PAGE gel under reducing conditions C. Coupling of C-LTβ$_{49-306}$ and C-LTβ$_{126-306}$ to Qβ Capsid Protein A solution of 120 μM Qβ capsid protein in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed Qβ reaction mixture is then reacted with the C-LTβ$_{49-306}$ and C-LTβ$_{126-306}$ solution (end concentrations: 60 μM Qβ, 60 μM C-LTβ$_{49-306}$ and C-LTβ$_{126-306}$) for four hours at 25° C. on a rocking shaker. Coupling products are analysed by SDS-PAGE.

D. Coupling of C-LTβ$_{49-306}$ and C-LTβ$_{126-306}$ to ft Capsid Protein

A solution of 120 μM fr capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr capsid protein reaction mixture is then reacted with the C-LTβ$_{49-306}$ and C-LTβ$_{126-306}$ solution (end concentrations: 60 μM fr, 60 μM C-LTβ$_{49-306}$ and C-LTβ$_{126-306}$) for four hours at 25° C. on a rocking shaker. Coupling products are analysed by SDS-PAGE under reducing conditions.

E. Coupling of C-LTβ$_{49-306}$ and C-LTβ$_{126-306}$ to HBcAg-Lys-2cys-Mut

A solution of 120 μM HBcAg-Lys-2cys-Mut capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with the C-LTβ$_{49-306}$ and C-LTβ$_{126-306}$ solution (end concentrations: 60 μM HBcAg-Lys-2cys-Mut, 60 μM C-LTβ$_{49-306}$ and C-LTβ$_{126-306}$) for four hours at 25° C. on a rocking shaker. Coupling products are analysed by SDS-PAGE.

F. Coupling of C-LTβ$_{49-306}$ and C-LTβ$_{126-306}$ to Pili

A solution of 125 μM Type-1 pili of *E.coli* in 20 mM Hepes, pH 7.4, is reacted for 60 minutes with a 50-fold molar excess of cross-linker SMPH, diluted from a stock solution in DMSO (Pierce), at RT on a rocking shaker. The reaction mixture is desalted on a PD-10 column (Amersham-Pharmacia Biotech). The protein-containing fractions eluting from the column are pooled, and the desalted derivatized pili protein is reacted with the C-LTβ$_{49-306}$ and C-LTβ$_{126-306}$ solution (end concentrations: 60 μM pili, 60 μM C-LTβ$_{49-306}$ and C-LTβ$_{126-306}$) for four hours at 25° C. on a rocking shaker. Coupling products are analysed by SDS-PAGE under reducing conditions.

EXAMPLE 4

A. Introduction of Cys-containing Linkers, Expression, Purification and Coupling of Rat Macrophage Migration Inhibitory Factor MIF to Qβ

Rat macrophage migration inhibitory factor (rMIF) was recombinantly expressed with three different amino acid linkers C1, C2 and C3 fused at its C-terminus. Each of the linker contained one cysteine for coupling to VLP.

Construction of rMIF-C1, rMIF-C2, and rMIF-C3.

The MCS of pET22b(+) (Novagen, Inc.) was changed to GTTTAACTTT AAGAAGGAGATATACATATGGATC-CGGCTAGCGCTCGAGGGTTTAAACGGCGGC CGCATGCACC (SEQ ID NO:363) by replacing the original sequence from the NdeI site to XhoI site with annealed oligos primerMCS-1F and primerMCS-1R (annealing in 15 mM TrisHC1 pH 8 buffer). The resulting plasmid was termed pMod00, which had NdeI, BamHI, NheI, XhoI, PmeI and NotI restriction sites in its MCS. The annealed pair of oligos Bamhis6-EK-Nhe-F and Bamhis6-EKNhe-R and the annealed pair of oligo1F-C-glycine-linker and oligo1R-C-glycine-linker were together ligated into BamHI-NotI digested pMod00 plasmid to get pModEC 1, which had an N terminal hexahistidine tag, an enterokinase cleavage site and a C-terminal amino acid glycine linker containing one cysteine residue. The annealed pair of oligos Bamhis6-EK-Nhe-F and Bamhi6-EKNhe R together with the annealed pair of oligo1F-C-gamma1-linker and oligo1R-C-gamma1-linker were ligated into BamHI-NotI digested pMod00 plasmid to get pModEC2, which had an N terminal hexahistidine tag, an enterokinase cleavage site and a C-terminal 1 linker, derived from the hinge region of human immunoglobulin γ1, containing one cysteine residue. The annealed pair of oligos Bamhis6-EK-Nhe-F and Bamhis6-EK-Nhe-R, the annealed pair of oligo1FA-C-gamma3-linker and oligo1RA-C-gamma3-linker, and the annealed pair of oligo1FB-C-gamma3-linker and oligo1RB-C-gamma3-linker were together ligated into BamHI-NotI digested pMod00 to get pModEC3, which had an N terminal hexahistidine tag, an enterokinase cleavage site and a C terminal γ3 linker, containing one cysteine residue, derived from the hinge region of mouse immunoglobulin γ3.

pBS-rMIF, which contains the rat MIF cDNA, was amplified by PCR with oligos rMIF-F and rMIF-Xho-R. rMIF-F had an internal NdeI site and rMIF-Xho-R had an internal XhoI site. The PCR product was digested with NdeI and XhoI and ligated into pModEC1, pModEC2 and pModEC3 digested with the same enzymes. Resulting plasmids were named pMod-rMIF-C1, pMod-rMIG-C2 and pMod-rMIF-C3, respectively.

For the PCR reaction, 15 pmol of each oligo and 1 ng of the template DNA was used in the 50 µl reaction mixture (2 units of PFX polymerase, 0.3 mM dNTPs and 2 mM MgSO4). The temperature cycles were as follows: 94° C. for 2 minutes, followed by 30 cycles of 94° C. (30 seconds), 60° C. (30 seconds), 68° C. (30 seconds) and followed by 68° C. for 2 minutes.

Expression and Purification of rMIF-Cs

Competent E. coli BL21 (DE3) cells were transformed with plasmids pMod-rMIF-C1, pMod-rMIF-C2 and pMod-rMIF-C3. Single colonies from ampicillin (Amp)-containing agar plates were expanded in liquid culture (SB with 150 mM MOPS, pH 7.0, 200 ug/ml Amp, 0.5% glucose) and incubated at 30° C. with 220 rpm shaking overnight. 1 l of SB (150 mM MOPS, pH 7.0, 200 ug/ml Amp) was then inoculated 1:50 v/v with the overnight culture and grown to OD600=2.5 at 30° C. Expression was induced with 2 mM IPTG. Cells were harvested after overnight culture and centrifuged at 6000 rpm. Cell pellet was suspended in lysis buffer (10 mM $Na_2HPO_4$, 30 mM NaCl, 10 mM EDTA and 0.25% Tween-20) with 0.8 mg/ml lysozyme, sonicated and treated with benzonase. 2 ml of the lysate was then run through a 20 ml Q XL- and a 20 ml SP XL-column. The proteins rMIF-C1, rMIF-C2 and rMIF-C3 were in the flow through.

The Protein Sequences of the rMIF-Cs were Translated from the cDNA Sequences.

rMIF-C1: SEQ ID NO:307
rMIF-C2: SEQ ID NO:308
rMIF-C3: SEQ ID NO:309

Coupling of rMIF-C1 to Qβ Capsid Protein

A solution of 1.48 ml of 6 mg/ml Qβ capsid protein in 20 mM Hepes, 150 mM NaCl pH 7.2 was reacted for 30 minutes with 14.8 µl of a SMPH (Pierce) (from a 100 mM stock solution dissolved in DMSO) at 25° C. The reaction solution was subsequently dialyzed twice for 3 hours against 2 l of 20 mM Hepes, 150 mM NaCl, pH 7.0 at 4° C. A solution of 1.3 ml of 3.6 mg/ml rMIF-C1 protein in 20 mM Hepes, 150 mM NaCl pH 7.2 was reacted for 1 hour with 9.6 µl of a TCEP (Pierce) (from a 36 mM stock solution dissolved in H2O ) at 25° C. 130 µl of the derivatized and dialyzed Qβ was then reacted with 129 µl of reduced rMIF-C1 in 241 µl of 20 mM Hepes, 150 mM NaCl, pH 7.0 over night at 25° C.

Coupling of rMIF-C2 to Qβ Capsid Protein

A solution of 0.9 ml of 5.5 mg/ml Qβ capsid protein in 20 mM Hepes, 150 mM NaCl pH 7.2 was reacted for 30 minutes with 9 µl of a SMPH (Pierce) (from a 100 mM stock solution dissolved in DMSO) at 25° C. The reaction solution was subsequently dialyzed twice for 2 hours against 2 l of 20 mM Hepes, 150 mM NaCl, pH 7.2 at 4° C. A solution of 850 µl of 5.80 mg/ml rMIF-C2 protein in 20 mM Hepes, 150 mM NaCl pH 7.2 was reacted for 1 hour with 8.5 µl of a TCEP (Pierce) (from a 36 mM stock solution dissolved in H2O) at RT. 80 µl of the derivatized and dialyzed Qβ was then reacted with 85 µl of reduced rMIF-C2 in 335 µl of 20 mM Hepes, 150 mM NaCl pH 7.2 over night at 25° C.

Coupling of rMIF-C3 to Qβ Capsid Protein

A solution of 1.48 ml of 6 mg/ml Qβ capsid protein in 20 mM Hepes, 150 mM NaCl pH 7.2 was reacted for 30 minutes with 14.8 µl of a SMPH (Pierce) (from a 100 mM stock solution dissolved in DMSO) at 25° C. The reaction solution was subsequently dialyzed twice for 3 hours against 2 l of 20 mM Hepes, 150 mM NaCl, pH 7.0 at 4° C. A solution of 720 µl of 5.98 mg/ml rMIF-C3 protein in 20 mM Hepes, 150 mM NaCl pH 7.2 was reacted for 1 hour with 9.5 µl of a TCEP (Pierce) (from a 36 mM stock solution dissolved in H2O) at 25° C. 130 µl of the derivatized and dialyzed Qβ was then reacted with 80 µl of reduced rMIF-C3 in 290 µl of 20 mM Hepes, 150 mM NaCl, pH 7.0 over night at 25° C.

Figure 4A:
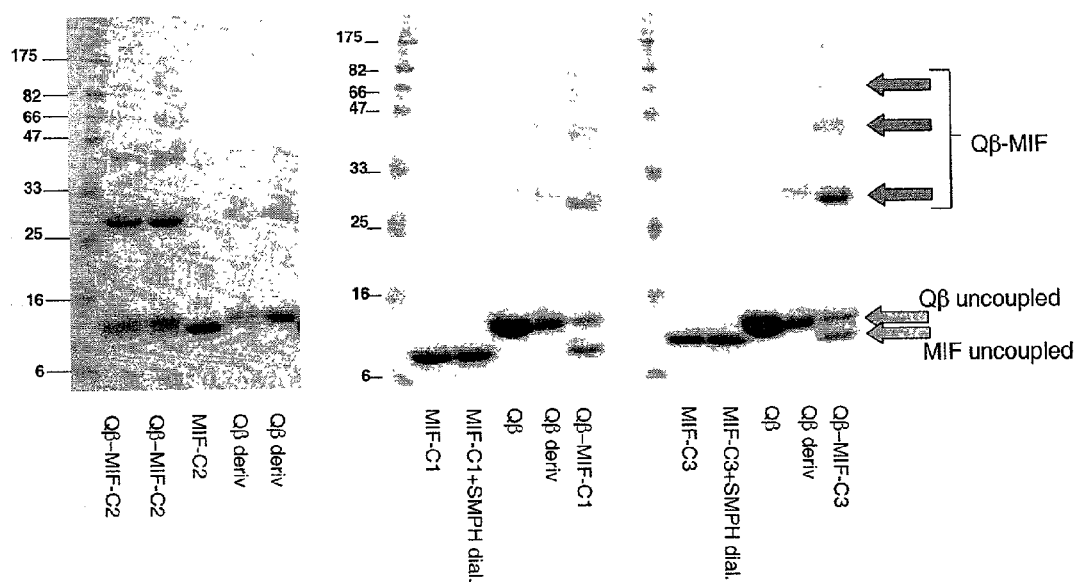
FIGS. 4A–4B Cloning, expression and coupling of MIF constructs to Qβ capsid protein.
Figure 4B:
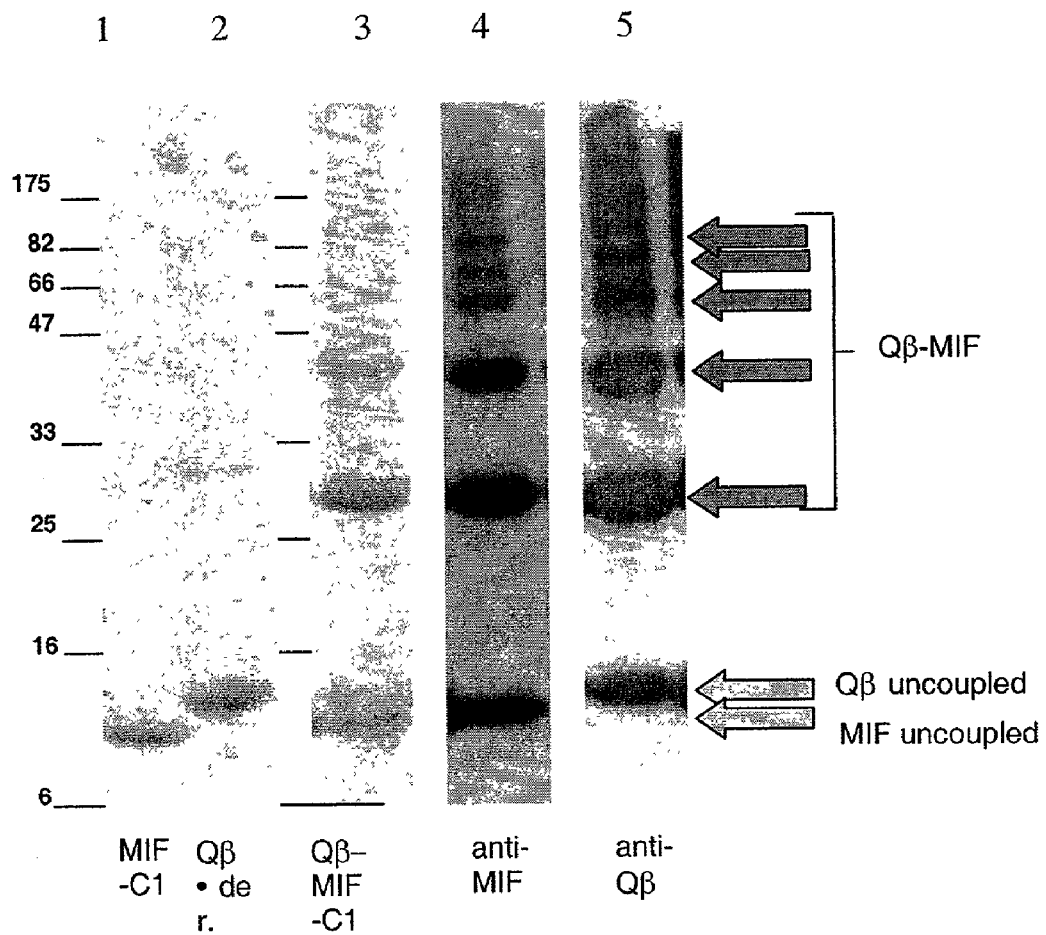

All three coupled products were analysed on 16% SDS-PAGE gels under reducing conditions. Gels were either stained with Coomassie Brilliant Blue or blotted onto nitrocellulose membranes. Membranes were blocked, incubated with a polyclonal rabbit anti-Qβ antiserum (dilution 1:2000) or a purified rabbit anti-MW antibody (Torrey Pines Biolabs, Inc.) (dilution 1:2000). Blots were subsequently incubated with horse radish peroxidase-conjugated goat anti-rabbit IgG (dilutions 1:2000). The results are shown in FIG. 4A and FIG. 4B. Coupled products could be detected in the Coomassie-stained gels (FIG. 4A) and by both anti-Qβ antiserum and the anti-MIF antibody (FIG. 4B) clearly demonstrated the covalent coupling of all three rMIF variants to Qβ capsid protein.

FIG. 4A shows the coupling of the MIF constructs to Qβ. Coupling products were analysed on 16% SDS-PAGE gels under reducing conditions. The gel was stained with Coomassie Brilliant Blue. Molecular weights of marker proteins are given on the left margin.

FIG. 4B shows the coupling of MIF-C1 to Qβ. Coupling products were analysed on 16% SDS-PAGE gels under reducing conditions. Lane 1: MIF-C1 before coupling Lane 2: derivatized Qβ before coupling. Lane 3–5: Qβ-MIF-C1 Lanes 1–3 were stained with Coomassie Brilliant Blue. Lanes 4 and 5 represent western blots of the coupling reaction developed with an anti-MIF antiserum and an anti-Qβ antiserum, respectively. Molecular weights of marker proteins are given on the left margin.

B. Immunization of Mice with MIF-C1 Coupled to Qβ Capsid Protein

Female Balb/c mice were vaccinated with MIF-C1 coupled to Qβ capsid protein without the addition of adjuvants. 25 µg of total protein of each sample was diluted in PBS to 200 ul and injected subcutaneously (100 ml on two ventral sides) on day 0 and day 14. Mice were bled retroorbitally on day 31 and their serum was analyzed using a MIF-specific ELISA.

C. ELISA

Figure 4C:
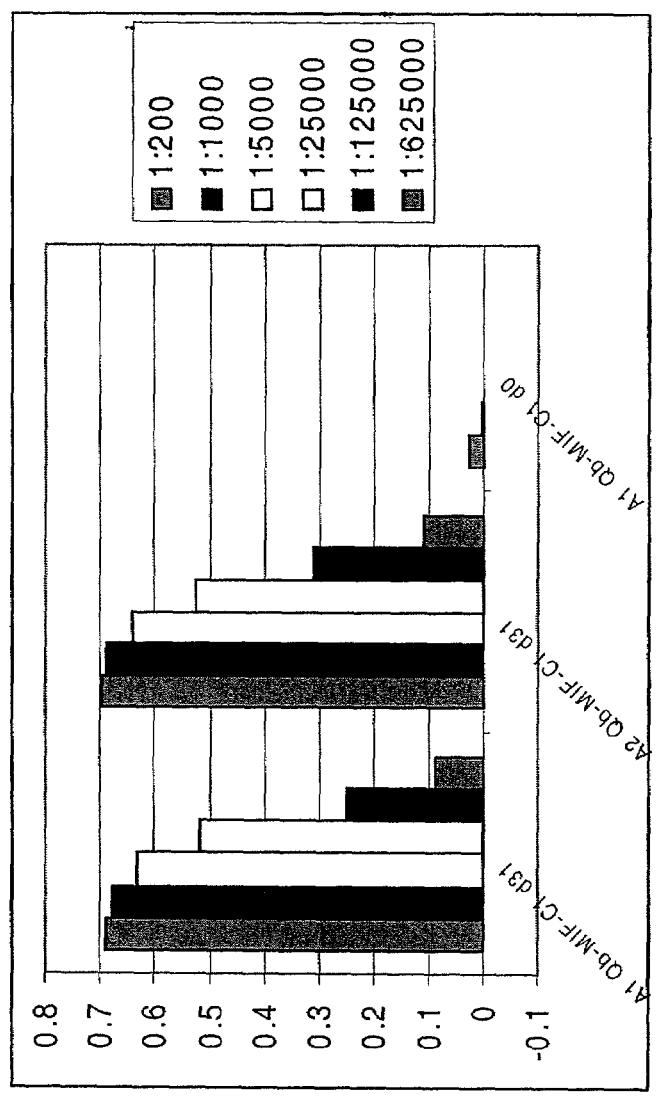
FIG. 4C ELISA analysis of IgG antibodies specific for MIF in sera of mice immunized against MIF proteins coupled to Qβ capsid protein.

ELISA plates were coated with MIF-C1 at a concentration of 5 µg/ml. The plates were blocked and then incubated with serially diluted mouse sera. Bound antibodies were detected with enzymatically labeled anti-mouse IgG antibody. As a control, preimmune serum of the same mice was also tested. The results are shown in FIG. 4C. There was a clear reactivity of the mouse sera raised against MIF-C1 coupled to Qβ capsid protein, while the pre-immune sera did not react with MIF (FIG. 4C and data not shown). From the dilution series with the antisera against MIF-C1 coupled to Qβ capsid protein, a half-maximal titer was reached at 1:84000.

Shown on FIG. 4C are the ELISA signals obtained with the sera of the mice vaccinated with MIF-C1 coupled to Qβ capsid protein. Female Balb/c mice were vaccinated subcutaneously with 25 µg of vaccine in PBS on day 0 and day 14. Serum IgG against MIF-C1 were measured on day 31. As a control, pre-immune sera from one of the mice were analyzed. Results for indicated serum dilutions are shown as optical density at 450 nm. All vaccinated mice made high IgG antibody titers. No MIF-specific antibodies were detected in control (pre-immune mouse).

Example 5

Coupling of rMIF-C1 to fr Capsid Protein and HBcAg-lys-2cys-Mut Capsid Protein

Coupling of rMIF-C1 to fr Capsid Protein

A solution of 100 µl of 3.1 mg/ml fr capsid protein in 20 mM Hepes, 150 mM NaCl pH 7.2 was reacted for 30 minutes with 3 µl of a 100 mM stock solution of SMPH (Pierce) dissolved in DMSO at 25° C. In a parallel reaction, fr capsid protein was first alkylated using iodoacetamide and then reacted with SMPH using the same reaction conditions described above. The reaction solutions were subsequently dialyzed twice for 2 hours against 2 l of 20 mM Hepes, 150 mM NaCl, pH 7.2 at 4° C. A solution of 80 µl of 5.7 mg/ml rMIF-C1 protein in 20 mM Hepes, 150 mM NaCl pH 7.2, was reacted for 1 hour with 1 µl of a 36 mM TCEP (Pierce) stock solution dissolved in H$_2$O, at 25° C. 50 µl of the derivatized and dialyzed fr capsid protein and 50 µl of the derivatized, alkylated and dialyzed fr capsid protein were then reacted each with 17 µl of reduced rMIF-C1 for two hours at 25° C.

Figure 5:
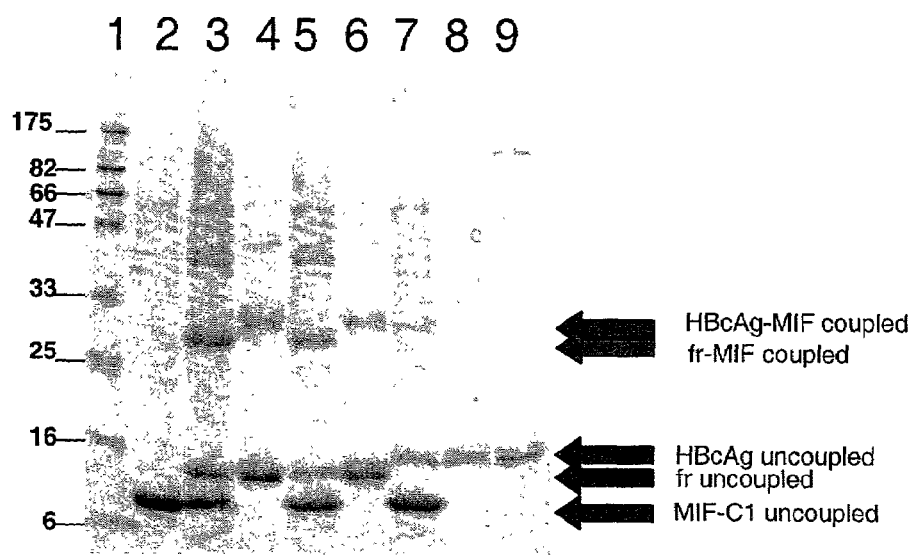
FIG. 5 Coupling of MIF constructs to fr capsid protein and to HBcAg-lys-2cys-Mut capsid protein analyzed by SDS-Page.

Coupling products were analysed on 16% SDS-PAGE gels (FIG. 5). An additional band of the expected size of 27 kDa (rMIF-C1: apparent MW 13 kDa, fr capsid protein apparent MW 14 kDa) and 29 kDa (rMIF-C1: apparent MW 13 kDa, HBcAg-lys-2cys-Mut: apparent MW 15 kDa) can be detected in the coupling reaction but not in the fr capsid protein and rMIF-C1 solutions, clearly demonstrating coupling.

Coupling of rMIF-C1 to Hepatitis HBcAg-lys-2cys-Mut Capsid Protein:

A solution of 100 µl of 1.2 mg/ml HBcAg-lys-2cys-Mut capsid protein in 20 mM Hepes, 150 mM NaCl pH 7.2 was reacted for 30 minutes with 1.4 µl of a SMPH (Pierce) (from a 100 mM stock solution dissolved in DMSO) at 25° C. The reaction solution was subsequently dialyzed twice for 2 hours against 2 l of 20 mM Hepes, 150 mM NaCl, pH 7.2 at 4° C. A solution of 80 µl of 5.7 mg/ml rMIF-C1 protein in 20 mM Hepes, 150 mM NaCl, pH 7.2 was reacted for 1 hour with 1 µl of a TCEP (Pierce) (from a 36 mM stock solution dissolved in H$_2$O) at 25° C. 60 µl of the derivatized and dialyzed HBcAg-lys-2cys-Mut capsid protein was then reacted with 20 µl of reduced rMIF-Cl for two hours at 25° C.

Coupling products were analysed on 16% SDS-PAGE gels (FIG. 5) under reducing conditions. An additional band of the expected size of about 28 kDa (rMIF-C1: apparent MW 13 kDa, HBcAg-lys-2cys-Mut: apparent MW 15 kDa) can be detected in the coupling reaction but not in derivatized HBcAg-lys-2cys-Mut or rMIF-C1, clearly demonstrating coupling.

The samples loaded on the gel of FIG. 5 were the following:

Lane 1: Molecular weight marker. Lane 2: rMIF-C1 before coupling. Lane 3: rMIF-C1-fr capsid protein after coupling. Lane 4: derivatized fr capsid protein. Lane 5: rMIF-C1-fr after coupling to alkylated fr capsid protein. Lane 6: alkylated and derivatized fr capsid protein. Lane7: rMIF-HBcAg-lys-2cys-Mut after coupling. Lane 8 and 9: derivatized HBcAg-lys-2cys-Mut. The gel was stained with Coomassie Brilliant Blue. Molecular weights of marker proteins are given on the left margin.

Example 6

A. Introduction of Amino Acid Linkers Containing a Cysteine Residue, Expression and Purification of Mouse RANKL A fragment of the receptor activator of nuclear factor kappa b ligand (RANKL), which has also been termed osteoclast differentiation factor, osteoprotegerin ligand and tumor necrosis factor-related activation-induced cytokine was recombinantly expressed with an N-terminal linker containing one cysteine for coupling to VLP.

Construction of Expression Plasmid

The C-terminal coding region of the RANKL gene was amplified by PCR with oligos RANKL-UP and RANKL-DOWN. RANKL-UP had an internal ApaI site and RANKL-DOWN had an internal XhoI site. The PCR product was digested with ApaI and XhoI and ligated into pGEX-6p1 (Amersham Pharmacia). The resulting plasmid was named pGEX-RANKL. All steps were performed by standard molecular biology protocols and the sequence was verified. The plasmid pGEX-RANKL codes for a fusion protein of a glutathione S-transferase-Prescission cleavage site-cysteine-containing amino acid linker-RANKL (GST-PS-C-RANKL). The cysteine-containing amino acid linker had the sequence GCGGG. The construct also contains a hexa-histidine tag between the cysteine containing amino acid linker and the RANKL sequence.

```
Oligos:
RANKL-UP:
5'CTGCCAGGGGCCCGGGTGCGGCGGTGGCCATCATCACCACCATCACCAGCGCTTCTCAGGAG-3'      (SEQ ID NO:316)

RANKL-DOWN:
5'-CCGCTCGAGTTAGTCTATGTCCTGAACTTTGAAAG-3'                                (SEQ ID NO:317)
```

Protein of GST-PS-C-RANKL (SEQ ID NO:318) and cDNA Sequence of GST-PS-C-RANKL (SEQ ID NO:319)

```
 1  M  S  P  I  L  G  Y  W  K  I  K  G  L  V  Q  P  T  R  L  L  L  E  Y  L  E 1  atgtccctatactaggttattggaaaattaagggccttgtgcaacccactcgacttcttttggaatatcttgaa 26  E  K  Y  E  E  H  L  Y  E  R  D  E  G  D  K  W  R  N  K  K  F  E  L  G  L
```

-continued

```
  76 gaaaaatatgaagagcatttgtatgagcgcgatgaaggtgataaatggcgaaacaaaaagtttgaattgggtttg
  51  E  F  P  N  L  P  Y  Y  I  D  G  D  V  K  L  T  Q  S  M  A  I  I  R  Y  I 151 gagtttcccaatcttccttattatattgatggtgatgttaaattaacacagtctatggccatcatacgttatata
  76  A  D  K  H  N  M  L  G  G  C  P  K  E  R  A  E  I  S  M  L  E  G  A  V  L 226 gctgacaagcacaacatgttgggtggttgtccaaaagagcgtgcagagatttcaatgcttgaaggagcggttttg
 101  D  I  R  Y  G  V  S  R  I  A  Y  S  K  D  F  E  T  L  K  V  D  F  L  S  K 301 gatattagatacggtgtttcgagaattgcatatagtaaagactttgaaactctcaaagttgattttcttagcaag
 126  L  P  E  M  L  K  M  F  E  D  R  L  C  H  K  T  Y  L  N  G  D  H  V  T  H 376 ctacctgaaatgctgaaaatgttcgaagatcgtttatgtcataaaacatatttaaatggtgatcatgtaacccat
 151  P  D  F  M  L  Y  D  A  L  D  V  V  L  Y  M  D  P  M  C  L  D  A  F  P  K 451 cctgacttcatgttgtatgacgctcttgatgttgttttatacatggacccaatgtgcctggatgcgttcccaaaa
 176  L  V  C  F  K  K  R  I  E  A  I  P  Q  I  D  K  Y  L  K  S  S  K  Y  I  A 526 ttagtttgttttaaaaaacgtattgaagctatcccacaaattgataagtacttgaaatccagcaagtatatagca
 201  W  P  L  Q  G  W  Q  A  T  F  G  G  G  D  H  P  P  K  S  D  L  E  V  L  F 601 tggcctttgcagggctggcaagccacgtttggtggtggcgaccatcctccaaaatcggatctggaagttctgttc
 226  Q  G  P  G     G  G  G  H  H  H  H  H  H  Q  R  F  S  G  A  P  A  M  M  E 676 cagGGGCCCGGGTGCGGCGGTGGCCATCATCACCACCATCACCAGCGCTTCTCAGGAGCTCCAGCTATGATGGAA
 251  G  S  W  L  D  V  A  Q  R  G  K  P  F  A  Q  P  F  A  H  L  T  I  N  A  A 751 GGCTCATGGTTGGATGTGGCCCAGCGAGGCAAGCCTGAGGCCCAGCCATTTGCACACCTCACCATCAATGCTGCC
 276  S  I  P  S  G  S  H  K  V  T  L  S  S  W  Y  H  D  R  G  W  A  K  I  S  N 826 AGCATCCCATCGGGTTCCCATAAAGTCACTCTGTCCTCTTGGTACCACGATCGAGGCTGGGCCAAGATCTCTAAC
 301  M  T  L  S  N  G  K  L  R  V  N  Q  D  G  P  Y  Y  L  Y  A  N  L  C  F  R 901 ATGACGTTAAGCAACGGAAAACTAAGGGTTAACCAAGATGGCTTCTATTACCTGTACGCCAACATTTGCTTTCGG
 326  H  H  E  T  S  G  S  V  P  T  D  Y  L  Q  L  M  V  Y  V  V  K  T  S  I  K 976 CATCATGAAACATCGGGAAGCGTACCTACAGACTATCTTCAGCTGATGGTGTATGTCGTTAAAACCAGCATCAAA
 351  I  P  S  S  H  N  L  M  K  G  G  S  T  K  N  W  S  G  N  S  E  F  H  F  Y 1051 ATCCCAAGTTCTCATAACCTGATGAAAGGAGGGAGCACGAAAAACTGGTCGGGCAATTCTGAATTCCACTTTTAT
 376  S  I  N  V  G  G  F  F  K  L  R  A  G  E  E  I  S  I  Q  V  S  N  P  S  L 1126 TCCATAAATGTTGGGGGATTTTTCAAGCTCCGAGCTGGTGAAGAAATTAGCATTCAGGTGTCCAACCCTTCCCTG
 401  L  D  P  D  Q  D  A  T  Y  F  G  A  F  K  V  Q  D  I  D

1201 CTGGATCCGGATCAAGATGCGACGTACTTTGGGGCTTTCAAAGTTCAGGACATAGACTAACTCGAGCGG
```

Expression and Purification of C-RANKL

Competent *E. coli* BL21 (DE3) Gold pLys cells were transformed with the plasmid pGEX-RANKL. Single colonies from kanamycin and chloramphenicol-containing agar plates were expanded in liquid culture (LB medium, 30 μg/ml kanamycin, 50 μg/ml chloramphenicol) and incubated at 30° C. with 220 rpm shaking overnight. 1 l of LB (with 30 ug/ml kanamycin) was then inoculated 1:100 v/v with the overnight culture and grown to OD600=1 at 24° C. Expression was induced with 0.4 mM IPTG. Cells were harvested after 16 h and centrifuged at 5000 rpm. Cell pellet was suspended in lysis buffer (50 mM Tris-HCl, pH=8; 25% sucrose; 1 mM EDTA, 1% NaN$_3$; 10 mM DTT; 5 mM MgCl$_2$; 1 mg/ml Lysozyme; 0.4 u/ml DNAse) for 30 min. Then 2.5 volumes of buffer A (50 mM Tris-HCl, pH=8.0; 1% Triton X100; 100 mM NaCl; 0,1% NaN$_3$; 10 mM DTT;1 mM PMSF) were added and incubated at 37° C. for 15 min. The cells were sonicated and pelleted at 9000 rpm for 15 min. The supernatant was immediately used for GST-affinity chromatography.

A column GST-Trap FF of 5 ml (Amersham Pharmacia) was equilibrated in PBS, pH 7.3 (140 mM NaCl, 2.7 mM KCl, 10 mM Na$_2$HPO$_4$, 1.8 mM KH$_2$PO$_4$). The supernatant was loaded on the 5 ml GST-Trap FF column and subsequently the column was rinsed with 5 column volumes of PBS. The protein GST-PS-C-RANKL was eluted with 50 mM Tris-HCl, pH=8.0 containing GSH 10 mM.

The purified GST-PS-C-RANKL protein was digested using the protease PreScission (Amersham Pharmacia). The digestion was performed at 37° C. for 1 hour using a molar ratio of 500/1 of GST-PS-C-RANKL to PreScission.

Furthermore, the reaction of protease digestion was buffer exchanged using a HiPrep 26/10 desalting column (Amersham Pharmacia), the fractions containing the proteins were pooled and immediately used for another step of GST affinity chromatography using the same conditions reported before. Purification of C-RANKL was analysed on a SDS-PAGE gel under reducing conditions, shown in FIG. 6. Molecular weights of marker proteins are given on the left margin of the gel in the figure. The gel was stained with Coomassie Brilliant Blue. The cleaved C-RANKL is present in the flow-through (unbound fraction) while the uncleaved GST-PS-C-RANKL, the cleaved GST-PS and the PreScission remain bound to the column. C-RANKL protein of the expected size of 22 kDa was obtained in high purity.

Figure 6:
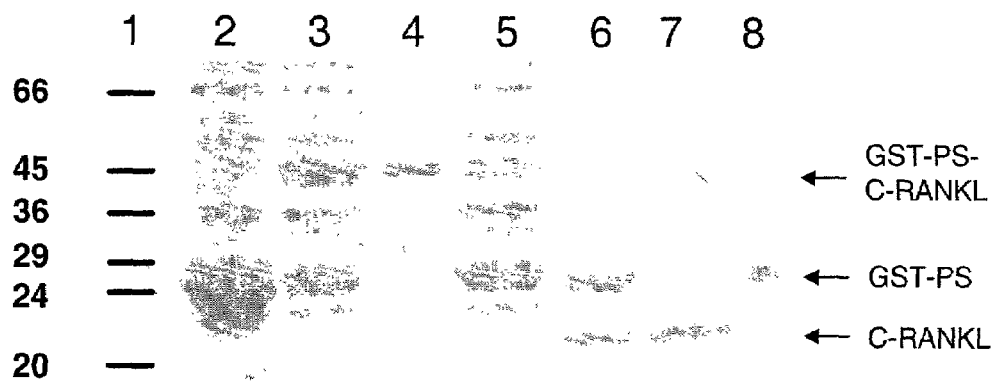
FIG. 6 Cloning and expression of human-C-RANKL.

The samples loaded on the gel of FIG. 6 were the following:

Lane 1: Low molecular weight marker. Lanes 2 and 3: the supernatant of the cell lysates of the BL21/DE3 cells transformed with the empty vector pGEX6p1 and pGEX-RANKL respectively, after sixteen hours of induction with IPTG 0.4 mM. Lane 4: the purified GST-PS-C-RANKL protein after GST-Trap FF column. Lane 5: the GST-Trap FF column unbound fraction. Lane 6: the purified GST-PS-C-RANKL protein after the cleavage with the PreScission protease. Lane 7: the unbound fraction of the GST-Trap FF column loaded with the GST-RANKL digestion, which contains the purified C-RANKL. Lane 8: the bound fraction of the GST-Trap FF column loaded with the GST-PS-C-RANKL digestion and eluted with GSH.

B. Coupling of C-RANKL to Qβ Capsid Protein

A solution of 120 μM Qβ capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed Qβ reaction mixture is then reacted with the C-RANKL solution (end concentrations: 60 μM Qβ, 60 μM C-RANKL) for four hours at 25° C. on a rocking shaker. Coupling products are analysed by SDS-PAGE.

C. Coupling of C-RANKL to fr Capsid Protein

A solution of 120 μM fr capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr capsid protein reaction mixture is then reacted with the C-RANKL solution (end concentrations: 60 μM fr capsid protein, 60 μM C-RANKL) for four hours at 25° C. on a rocking shaker. Coupling products are analysed by SDS-PAGE.

D. Coupling of C-RANKL to HBcAg-Lys-2cys-Mut

A solution of 120 μM HBcAg-Lys-2cys-Mut capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with the C-RANKL solution (end concentrations: 60 μM HBcAg-Lys-2cys-Mut, 60 μM C-RANKL) for four hours at 25° C. on a rocking shaker. Coupling products are analysed by SDS-PAGE.

E. Coupling of C-RANKL to Pili

A solution of 125 μM Type-1 pili of *E.coli* in 20 mM Hepes, pH 7.4, is reacted for 60 minutes with a 50-fold molar excess of cross-linker SMPH, diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with the C-RANKL solution (end concentrations: 60 μM pili, 60 μM C-RANKL) for four hours at 25° C. on a rocking shaker. Coupling products are analysed by SDS-PAGE.

Example 7

A. Introduction of Amino Acid Linker Containing a Cysteine Residue, Expression and Purification of a Truncated Form of the Mouse Prion Protein A truncated form (aa 121–230) of the mouse prion protein (termed miPrPt) was recombinantly expressed with a GGGGCG (SEQ ID NO:413) amino acid linker fused at its C-terminus for coupling to VLPs and Pili. The protein was fused to the N-terminus of a human Fc-fragment for purification. An enterokinase (EK) cleavage-site was introduced behind the EK cleavage site to cleave the Fc- part of the fusion protein after purification.

Construction of mPrPt-EK-Fc*.

Mouse PrPt was amplified by PCR with the primer 5PrP-BamHI and 3PrP-NheI using the plasmid pBPCM-VPrP-Fc as a template. pBPCMVPrP-Fc contained the wild-type sequence of the mouse prion protein. 5PrP-BamHI had an internal BamHI site and contained an ATG and 3 PrP-NheI had an internal NheI site.

For the PCR reaction, 0.5 μg of each primer and 200 ng of the template DNA was used in the 50 μl reaction mixture (1 unit of PFX Platinum polymerase, 0.3 mM dNTPs and 2 mM MgSO4). The temperature cycles were as follows: 94□C for 2 minutes, followed by 5 cycles of 94° C. (15 seconds), 50° C. (30 seconds), 68° C. (45 seconds), followed by 20 cycles of 94° C. (15 seconds), 64° C. (30 seconds), 68° C. (45 seconds) and followed by 68° C. for 10 minutes.

The PCR product was digested with BamHI and NheI and inserted into pCEP-SP-EK-Fc* containing the GGGGCG (SEQ ID NO:413) linker sequence at the 5'end of the BK cleavage sequence. The resulting plasmid was named pCEP-SP-mPrPt-EK-Fc*.

All other steps were performed by standard molecular biology protocols.

Oligos:
Primer 5'PrP-BamHI
5'-CGG GAT CCC ACC ATG GTG GGG GGC CTT GG-3' (SEQ ID NO:321)
Primer 3'PrP-NheI
5'-CTA GCT AGC CTG GAT CTT CTC CCG-3' (SEQ ID NO:322)

Expression and Purification of mPrP$_t$-EK-Fc*

Plasmid pCEP-SP-mPrP$_t$-EK-Fc* was transfected into 293-EBNA cells (Invitrogen) and purified on a Protein A-sepharose column as described in EXAMPLE 1.

The protein sequence of the mPrPt-EK-Fc* is identified in SEQ ID NO:323. mPrPt after cleavage has the sequence as identified in SEQ ID NO:324 with the GGGGCG (SEQ ID NO:413) linker at its C-terminus.

Figure 7:
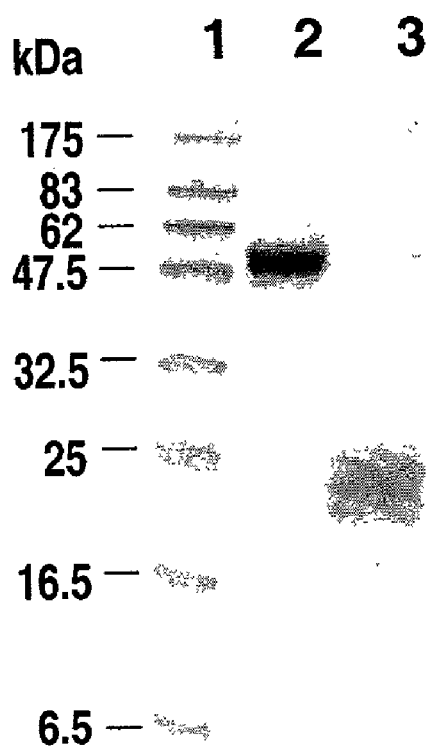
FIG. 7 Cloning and expression of prion protein.

The purified fusion protein mPrPt-EK-Fc* was cleaved with enterokinase and analysed on a 16% SDS-PAGE gel under reducing conditions before and after enterokinase cleavage. The gel was stained with Coomassie Brilliant Blue. The result is shown in FIG. 7. Molecular weights of marker proteins are given on the left margin of the gel in the figure. The mPrPt-EK-Fc* fusion protein could be detected as a 50 kDa band. The cleaved mPrPt protein containing the GGGGCG (SEQ ID NO:413) amino acid linker fused to its C-terminus could be detected as a broad band between 18 and 25 kDa. The identity of mPrPt was confirmed by western blotting (data not shown). Thus, mPrPt with a C-terminal amino acid linker containing a cysteine residue, could be expressed and purified to be used for coupling to VLPs and Pili.

The samples loaded on the gel of FIG. 7 were the following.

Lane 1: Molecular weight marker. Lane 2: mPrP$_t$-EK-Fc* before cleavage. Lane 3: mPrP$_t$ after cleavage.

B. Coupling of mPrP$_t$ to Qβ Capsid

A solution of 120 μM Qβ capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed Qβ reaction mixture is then reacted with the mPrP$_t$ solution (end concentrations: 60 μM Qβ, 60 μM mPrP$_t$) for four hours at 25° C. on a rocking shaker. Coupling products are analysed by SDS-PAGE.

C. Coupling of mPrP$_t$ to fr Capsid Protein

A solution of 120 μM fr capsid protein in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 MM NaCl, pH 7.2 at 4° C. The dialyzed fr reaction mixture is then reacted with the mPrP$_t$ solution (end concentrations: 60 μM fr, 60 μM mPrP$_t$) for four hours at 25° C. on a rocking shaker. Coupling products are analysed by SDS-PAGE.

D. Coupling of mPrP$_t$ to HBcAg-Lys-2cys-Mut

A solution of 120 μM HBcAg-Lys-2cys-Mut capsid in 20 MM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with the mPrP$_t$ solution (end concentrations: 60 μM HBcAg-Lys-2cys-Mut, 60 μM mPrP$_t$) for four hours at 25° C. on a rocking shaker. Coupling products are analysed by SDS-PAGE.

E. Coupling of mPrP$_t$ to Pili

A solution of 125 μM Type-1 pili of *E.coli* in 20 mM Hepes, pH 7.4, is reacted for 60 minutes with a 50-fold molar excess of cross-linker SMPH (Pierce), diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with the mPrP$_t$ solution (end concentrations: 60 μM pili, 60 μM mPrP$_t$) for four hours at 25° C. on a rocking shaker. Coupling products are analysed by SDS-PAGE.

Example 8

A. Coupling of Prion Peptides to Qβ Capsid Protein: Prion Peptide Vaccines

The following prion peptides were chemically synthesized: CSAMSRPMIHFGNDWEDRYYRENMYR ("cprplong"; SEQ ID NO:364) and CGNDWEDRYYRENMYR ("cprpshort"; SEQ ID NO:365), which comprise an added N-terminal cysteine residue for coupling to VLPs and Pili, and used for chemical coupling to Qβ as described in the following.

A solution of 5 ml of 140 μM Qβ capsid protein in 20 mM Hepes. 150 mM NaCl pH 7.4 was reacted for 30 minutes with 108 μl of a 65 mM solution of SMPH (Pierce) in H2O at 25° C. on a rocking shaker. The reaction solution was subsequently dialyzed twice for 2 hours against 5 L of 20 mM Hepes, 150 mM NaCl, pH 7.4 at 4° C. 100 μl of the dialyzed reaction mixture was then reacted either with 1.35 μl of a 2 mM stock solution (in DMSO) of the peptide cprpshort (1:2 peptide/Qβ capsid protein ratio) or with 2.7 μl of the same stock solution (1:1 peptide/Qβ ratio). 1 μl of a 10 mM stock solution (in DMSO) of the peptide cprplong was reacted with 100 μl of the dialyzed reaction mixture. The coupling reactions were performed over night at 15° C. in a water bath. The reaction mixtures were subsequently dialyzed 24 h against 2×5 L of 20 mM Hepes, 150 mM NaCl, pH 7.4 at 4° C.

Figure 16:
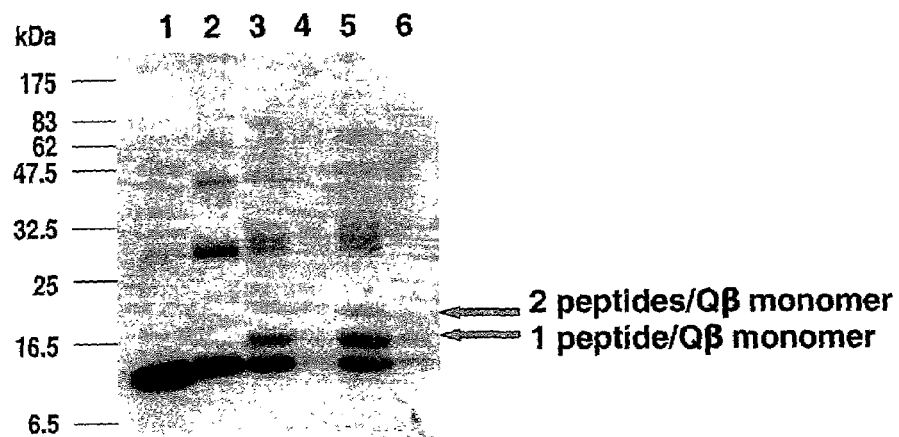
FIG. 16 Coupling of prion peptides to Qβ capsid protein; SDS-Page analysis.
Figure 16:
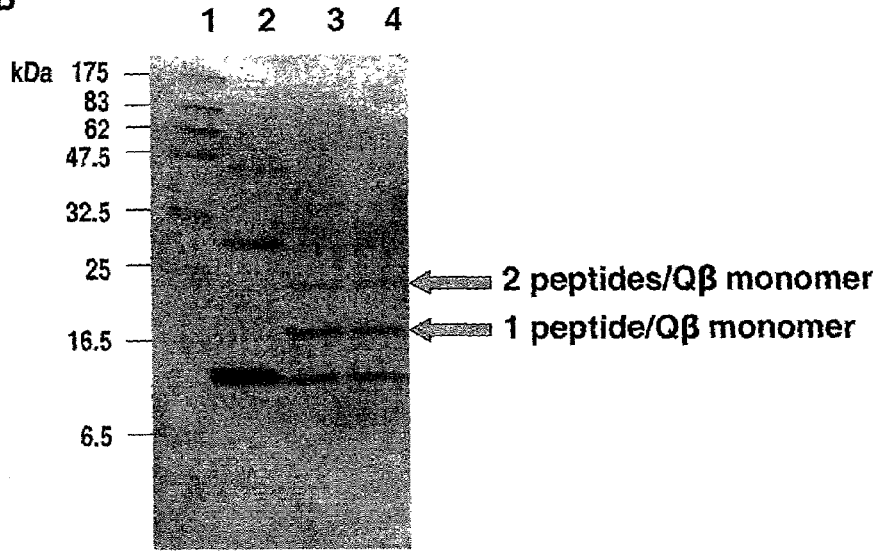

The coupled products were centrifuged and supernatants and pellets were analysed on 16% SDS-PAGE gels under reducing conditions. Gels were stained with Coomassie Brilliant Blue. The results are shown in FIG. 16. Molecular weights of marker proteins are given on the left margin of the gel in the figure. The bands at a molecular weight between 16.5 and 25 kDa clearly demonstrated the covalent coupling of the peptides cprpshort and cprplong to Qβ capsid protein.

The samples loaded on the gel of FIG. 16A were the following:

Lane 1: purified Qβ capsid protein. Lane 2: derivatized Qβ capsid protein before coupling. Lanes 3–6: Qβ capsid protein-cprpshort couplings with a 1:2 peptide/Qβ ratio (lanes 3 and 4) and 1:1 peptide/Qβ ratio (lanes 5 and 6). Soluble fractions (lanes 3 and 5) and insoluble fractions (lanes 4 and 6) are shown.

The samples loaded on the gel of FIG. 16B were the following:

Lane 1; Molecular weight marker. Lane 2: derivatized Qβ capsid protein before coupling. Lane 3 and 4: Qβ capsid protein-cprplong coupling reactions. Soluble fraction (lane 3) and insoluble fraction (lane 4) are shown.

B. Coupling of Prion Peptides to fr Capsid Protein

A solution of 120 μM fr capsid protein in 20 mM Hepes, 150 mM NaCl pH 7.2 is reacted for 30 minutes with a 10 fold molar excess of SMPH (Pierce)), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr reaction mixture is then reacted with equimolar concentration of peptide cprpshort or a ration of 1:2 cprplong/fr over night at 16° C. on a rocking shaker. Coupling products are analysed by SDS-PAGE.

C. Coupling of Prion Peptides to HBcAg-Lys-2cys-Mut

A solution of 120 μM HBcAg-Lys-2cys-Mut in 20 mM Hepes, 150 mM NaCl pH 7.2 is reacted for 30 minutes with a 10 fold molar excess of SMPH (Pierce)), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with equimolar concentration of peptide cprp-short or a ration of 1:2 cprplong/HBcAg-Lys-2cys-Mut over night at 16° C. on a rocking shaker. Coupling products are analysed by SDS-PAGE.

D. Coupling of Prion Peptides to Pili

A solution of 125 μM Type-1 pili of E.coli in 20 mM Hepes, pH 7.4, is reacted for 60 minutes with a 50-fold molar excess of cross-linker SMPH (Pierce), diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with the prion peptides in equimolar or in a ratio of 1:2 peptide pili over night at 16° C. on a rocking shaker. Coupling products are analysed by SDS-PAGE.

Example 9

Cloning, Expression and Purification of IL-13 to VLPs and Pili

A. Cloning and Expression of Interleukin 13 (IL-13) with an N-Terminal Amino Acid Linker Containing a Cysteine Residue for Coupling to VLPs and Pili a) Cloning of Mouse IL-13 (HEK-293T) for Expression in Mammalian Cells as Fc Fusion Protein The DNA for the cloning of IL-13 was isolated by RT-PCR from in vitro activated splenocytes, which were obtained as following: CD4+ T cells were isolated from mouse spleen cells and incubated 3 days in IMDM (+5% FCS+10 ng/ml IL4) in 6 well plates which have been previously coated with anti-CD3 and anti-CD28 antibodies. The RNA from these cells was used to amplify IL13 by one-step RT-PCR (Qiagen one-step PCR kit). Primer XhoIL13-R was used for the reverse transcription of the RNA and the primers NheIL13-F (SEQ ID NO:338) and XhoIL13-R (SEQ ID NO:339) were used for the PCR amplification of the IL13 cDNA. Amplified IL13 cDNA was ligated in a pMOD vector using the NheI/XhoI restriction sites (giving the vector pMODB1-IL13). pMODB1-I113 was digested BamHI/XhoI and the fragment containing IL13 was ligated in the pCEP-SP-XA-Fc*(Δxho) vector, an analogue of pCEP-SP-XA-Fc* where a XhoI site at the end of the Fc sequence has been removed, which had been previously digested with BamHI/XhoI. The plasmid resulting from this ligation (pCEP-SP-IL13-Fc) was sequenced and used to transfect HEK-293T cells. The resulting IL 13 construct encoded by this plasmid had the amino acid sequence ADPGCGGGGGLA fused at the N-terminus of the IL-13 mature sequence. This sequence comprises the amino acid linker sequence GCGGGGG flanked by additional amino acids introduced during the cloning procedure. IL13-Fc could be purified with Protein-A resin from the supernatant of the cells transfected with pCEP-SP-IL13-Fc. The result of the expression is shown on FIG. 17B (see EXAMPLE 10 for description of the samples). Mature IL-13 fused at its N-terminus with the aforementioned amino acid sequence is released upon cleavage of the fusion protein with Factor-Xa, leading to a protein called hereinafter "mouse C-IL-13-F" and having a sequence of SEQ ID NO:328. The result of FIG. 17B clearly demonstrates expression of the IL-13 construct.

b) Cloning of Mouse IL-13 (HEK-293T) for Expression in Mammalian Cells with GST (Glutathion-S-transferase) Fused at its N-terminus The cDNA used for cloning IL-13 with an N-terminal GST originated from the cDNA of TH2 activated T-cells as described above (a.). IL-13 was amplified from this cDNA using the primers Nhelink1IL13-F and IL13StopXhoNot-R. The PCR product was digested with NheI and XhoI and ligated in the pCEP-SP-GST-EK vector previously digested with NheI/XhoI. The plasmid which could be isolated from the ligation (pCEP-SP-GST-IL13) was used to transfect HEK-293T cells. The resulting IL 13 construct encoded by this plasmid had the amino acid sequence LACGGGGG (SEQ ID NO:417) fused at the N-terminus of the IL-13 mature sequence. This sequence comprises the amino acid linker sequence ACGGGGG (SEQ ID NO:418) flanked by an additional amino acid introduced during the cloning procedure. The culture supernatant of the cells transfected with pCEP-SP- GST-IL13 contained the fusion protein GST-IL13 which could be purified by Glutathione affinity chromatography according to standard protocols. Mature IL-13 fused at its N-terminus with aforementioned amino acid sequence is released upon cleavage of the fusion protein with enterokinase, leading to a protein called hereinafter "mouse C-IL-13-S" and having a sequence of SEQ ID NO:329.

B. Coupling of Mouse C-IL-13-F, Mouse C-IL-13-S to Qβ Capsid Protein

A solution of 120 μM Qβ capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed Qβ reaction mixture is then reacted with the mouse C-IL-13-F or mouse C-IL-13-S solution (end concentrations: 60 μM Qβ capsid protein, 60 μM mouse C-IL-13-F or mouse C-IL-13-S) for four hours at 25° C. on a rocking shaker. Coupling products are analysed by SDS-PAGE.

C. Coupling of Mouse C-IL-13-F, Mouse C-IL-13-S to fr Capsid Protein

A solution of 120 μM fr capsid protein in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr reaction mixture is then reacted with the the mouse C-IL-13-F or mouse C-IL-13-S solution (end concentrations: 60 μM fr capsid protein, 60 μM mouse C-IL-13-F or mouse C-IL-13-S) for four hours at 25° C. on a rocking shaker. Coupling products are analysed by SDS-PAGE.

D. Coupling of Mouse C-IL-13-F or Mouse C-IL-13-S solution to HBcAg-Lys-2cys-Mut A solution of 120 μM HBcAg-Lys-2cys-Mut capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with the mouse C-IL-13-F or mouse C-IL-13-S solution (end concentrations: 60 µM HBcAg-Lys-2cys-Mut, 60 µM mouse C-IL-13-F or mouse C-IL-13-S) for four hours at 25° C. on a rocking shaker. Coupling products are analysed by SDS-PAGE.

E. Coupling of Mouse C-IL-13-F or Mouse C-IL-13-S Solution to Pili

A solution of 125 µM Type-1 pili of *E.coli* in 20 mM Hepes, pH 7.4, is reacted for 60 minutes with a 50-fold molar excess of cross-linker SMPH, diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with the mouse C-IL-13-F or mouse C-IL-13-S solution (end concentrations: 60 µM pili, 60 µM mouse C-IL-13-F or mouse C-IL-13-S) for four hours at 25° C. on a rocking shaker. Coupling products are analysed by SDS-PAGE.

Example 10

Cloning and Expression of Interleukin 5 (IL-5) with an N-Terminal Amino Acid Linker Containing a Cysteine Residue for Coupling to VLPs and Pili A. Cloning of IL-5 for Expression as Inclusion Bodies in *E. coli*

IL-5 was amplified from an ATCC clone (pmIL5–4G; ATCC number: 37562) by PCR using the following two primers: Spelinker3-F1 (SEQ ID NO:340) and I15StopXho-R (SEQ ID NO:342). The product of this PCR was used as template for a second PCR with the primers SpeNlinker3-F2 (SEQ ID NO:341) and I15StopXho-R. The insert was digested with SpeI and NotI. This insert was ligated into a pET vector derivative (pMODEC3–8 vector), previously digested with NheI and NotI (not dephosphorylated), and transformed into *E.coli* TG1 cells. The IL5 construct generated by cloning into pMODEC3–8 vector contains at its N-terminus a hexa-histidine tag, followed by an enterokinase site, an N-terminal gamma 3 amino acid linker containing a cysteine residue, flanked C-terminally by the sequence AS and N-terminally by the sequence ALV, and the mature form of the IL 5 gene. The protein released by cleavage with enterokinase is called "mouse C-IL-5-E" (SEQ ID NO:332). Plasmid DNA of resulting clone pMODC6-IL5.2 (also called pMODC6-IL5), whose sequence had been confirmed by DNA sequencing, was transformed into *E.coli* strain BL21.

Clone pMODC6-IL5/BL21 was grown over night in 5 ml LB containing 1 mg/L Ampicillin. 2 ml of this culture were diluted in 100 ml terrific broth (TB) containing 1 mg/L Ampicillin. The culture was induced by adding 0.1 ml of a 1M solution of Ispropyl β-D-Thiogalactopyranoside (IPTG) when the culture reached an optical density OD600=0.7. 10 ml samples were taken every 2 h. The samples were centrifugated 10 min at 4000×g. The pellet was resuspended in 0.5 ml Lysis buffer containing 50 mM Tris-HCl, 2 mM EDTA, 0.1% triton X-100 (pH 8). After having added 20 ul of Lysozyme (40 mg/ml) and having incubated the tube 30 min at 4° C., the cells were sonicated for 2 min. 100 µl of a 50 mM $MgCl_2$ solution and 1 ml of benzonase were added. The cells were then incubated 30 min at room temperature and centrifugated 15 min at 13000×g.

Figure 17:
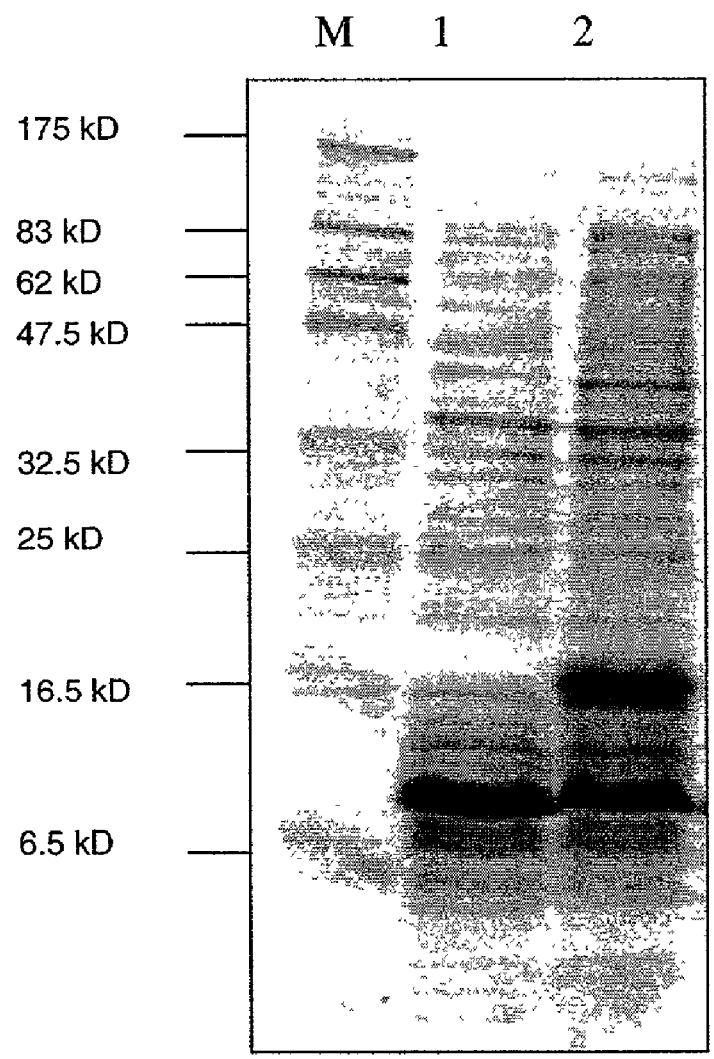
FIG. 17A. SDS-PAGE analysis of expression of IL-5 in bacteria
FIG. 17B. Western-Blot analysis of expression of IL-5 and IL-13 in eukaryotic cells FIG. 18A. SDS-PAGE analysis of coupling of murine VEGFR-2 peptide to Pili.
Figure 17:
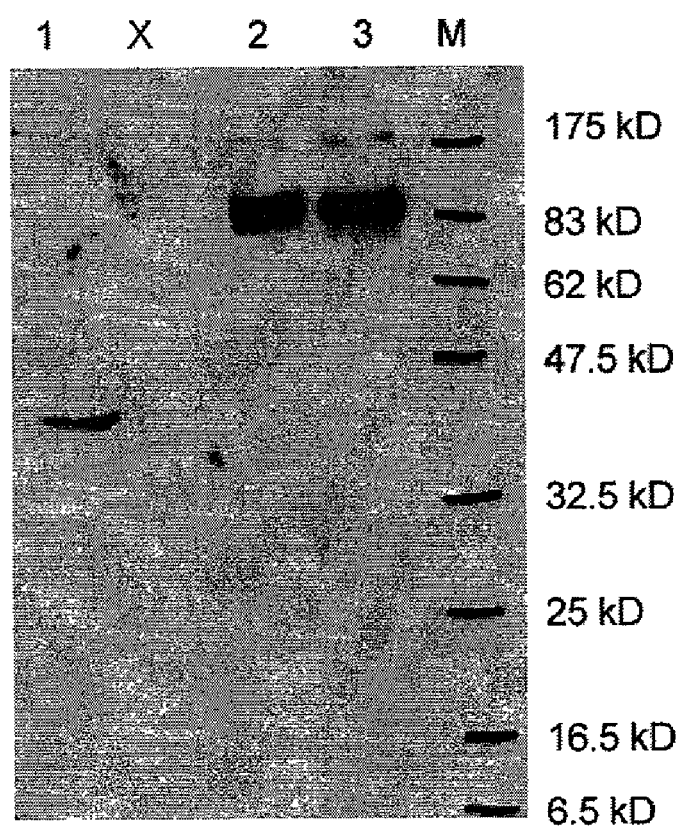

The supernatant was discarded and the pellet was boiled 5 min at 98° C. in 100 µl of SDS loading buffer. 10 µl of the samples in loading buffer were analyzed by SDS-PAGE under reducing conditions (FIG. 17A). The gel of FIG. 17A clearly demonstrates expression of the IL-5 construct. The samples loaded on the gel of FIG. 17A were the following: Lane M: Marker (NEB, Broad range prestained marker).

Lane 1: cell extract of 1 ml culture before induction. Lane 2: cell extract of 1 ml culture 4 h after induction.

B. Cloning of IL-5 for Expression in Mammalian Cells (HEK-293T)

a) IL-5 Fused at its N-Terminus to an Amino Acid Linker Containing a Cysteine Residue and Fused at its C-Terminus to the Fc Fragment The template described under (A) (ATCC clone 37562) was used for the cloning of the following construct. The plasmid pMODB1-IL5 (a pET derivative) was digested with BamHI/XhoI to yield a small fragment encoding IL5 fused to an N terminal amino acid linker containing a cysteine. This fragment was ligated in the vector pCEP-SP-XA-Fc* (ΔXho) which had previously been digested with BamHI and XhoI. The ligation was electroporated into *E.coli* strain TG1 and plasmid DNA of resulting clone pCEP-SP-IL5-Fc.2, whose sequence had been confirmed by DNA sequencing, was used to transfect HEK-293T cells. The resulting IL-5 construct encoded by this plasmid had the amino acid sequence ADPGCGGGGGLA (SEQ ID NO:419) fused at the N-terminus of the IL-5 mature sequence. This sequence comprises the amino acid linker sequence GCGGGGG (SEQ ID NO:420) containing a cysteine and flanked by additional amino acids introduced during the cloning procedure. The IL-5 protein released by cleavage of the fusion protein with Factor-Xa is named hereinafter "mouse C-IL-5-F" (SEQ ID NO:333).

After transfection and selection on Puromycin the culture supernatant was analyzed by Western-Blot (FIG. 17B) using an anti-His (mouse) and an anti-mouse IgG antibody conjugated to Horse raddish peroxidase. The anti-mouse IgG antibody conjugated to Horse raddish peroxidase also detects Fc-fusion proteins. Purification of the protein was performed by affinity chromatography on Protein-A resin. The result of FIG. 17B clearly demonstrates expression of the IL-5 construct.

The samples loaded on the Western-Blot of FIG. 17B were the following:

Lane 1: supernatant of HEK culture expressing IL5-Fc (20%1). SDS-PAGE was performed under reducing conditions. Lane 2: supernatant of HEK culture expressing IL13-Fc (20 µl). SDS-PAGE was performed under non reducing conditions. Lane 3: supernatant of HEK culture expressing IL5-Fc (20 µl). SDS-PAGE was performed under non reducing conditions.

b) IL-5 Cloned with GST (Glutathion-S-Transferase) and an Amino Acid Linker Containing a Cysteine Residue Fused at its N-Terminus IL-5 (ATCC 37562) was amplified with the primers Nhe-link1-IL13-F and IL5StopXho-R. After digestion with NheI and XhoI the insert was ligated into pCEP-SP-GST-EK which had been previously digested with NheI and XhoI. The resulting plasmid pCEP-SP-GST-IL5 was sequenced and used for transfection of HEK-293T cells. The resulting IL-5 construct encoded by this plasmid had the amino acid sequence LACGGGGG (SEQ ID NO:417) fused at the N-terminus of the IL-5 mature sequence. This sequence comprises the amino acid linker sequence ACGGGGG (SEQ ID NO:418) containing a cysteine residue and flanked by additional amino acids introduced during the cloning procedure. The protein released by cleavage with enterokinase was named hereinafter "mouse C-IL-5-S" (SEQ ID NO:334). The purification of the resulting protein was performed by affinity chromatography on Glutathione affinity resin.

C. Coupling of Mouse C-IL-5-F or Mouse C-IL-5-S to Qβ Capsid Protein

A solution of 120 μM Qβ capsid protein in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed Qβ reaction mixture is then reacted with the mouse C-IL-5-F or mouse C-IL-5-S solution (end concentrations: 60 μM Qβ capsid protein, 60 μM mouse C-IL-5-F or mouse C-IL-5-S) for four hours at 25° C. on a rocking shaker. Coupling products are analysed by SDS-PAGE.

D. Coupling of Mouse Mouse C-IL-5-F or Mouse C-IL-5-S to fr Capsid Protein

A solution of 120 μM fr capsid protein in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr reaction mixture is then reacted with the the mouse C-IL-5-F or mouse C-IL-5-S solution (end concentrations: 60 μM fr capsid protein, 60 μM mouse C-IL-5-F or mouse C-IL-5-S) for four hours at 25° C. on a rocking shaker. Coupling products are analysed by SDS-PAGE.

E. Coupling of Mouse C-IL-5-F or Mouse C-IL-5-S Solution to HBcAg-Lys-2cys-Mut

A solution of 120 μM HBcAg-Lys-2cys-Mut capsid in 20 mM Hepes, 150 mM NaCl pH 7.2 is reacted for 30 minutes with a 25 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with the mouse mouse C-1L-5-F or mouse C-IL-5-S solution (end concentrations: 60 μM HBcAg-Lys-2cys-Mut, 60 μM mouse C-IL-5-F or mouse C-IL-5-S) for four hours at 25° C. on a rocking shaker. Coupling products are analysed by SDS-PAGE.

F. Coupling of Mouse C-IL-5-F or Mouse C-IL-5-S Solution to Pili

A solution of 125 μM Type-1 pili of E.coli in 20 mM Hepes, pH 7.4, is reacted for 60 minutes with a 50-fold molar excess of cross-linker SMPH, diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with the mouse mouse C-IL-5-F or mouse C-IL-5-S solution (end concentrations: 60 μM pili, 60 μM mouse C-IL-5-F or mouse C-IL-5-S) for four hours at 25° C. on a rocking shaker. Coupling products are analysed by SDS-PAGE.

Example 11

Introduction of an Amino Acid Linker Containing a Cysteine Residue, Expression, Purification and Coupling of a Murine Vascular Endothelial Growth Factor-2 (mVEGFR-2, FLK1) Fragment A construct of the murine vascular endothelial growth factor-2 (mVEGFR-2, FLK-1) comprising its second and third extracellular domains was recombinantly expressed as a Fc-fusion protein with an amino acid linker containing a cysteine residue at its C-terminus for coupling to VLPs and Pili. The protein sequences of the mVEGFR-2(2–3) was translated from the cDNA sequences of mouse FLK-1 ((Matthews et al., *Proc. Natl. Acad. Sci. USA* 88: 9026–9030 (1991)): Accession no.: X59397; Ig-like C2-type domain 2: amino acid 143–209; Ig-like C2-type domain 3: amino acid 241–306). The mVEGFR-2 (2–3) construct comprises the sequence of mVEGFR-2 from amino acid proline126 to lysine329 (in the numbering of the precursor protein). The construct also comprises, in addition to the immunoglobulin-like C2-type domains 2 and 3, flanking regions preceding domain 2 and following domain 3 in the sequence of mVEGFR-2, to add amino acid spacer moieties. An amino acid linker containing a cysteine residue was fused to the C-terminus of the mVEGFR-2 sequence through cloning into pCEP-SP-EK-Fc* vector (EXAMPLE 1). The fragment of mVEGFR-2 cloned into pCEP-SP-EK-Fc* vector encoded the following amino acid sequence (SEQ ID NO:345):

PFIAS VSDQHGIVYI TENKNKTVVI PCRGSISNLN VSLCARYPEK RFVPDGNRIS WDSEIGFTLP SYMISYAGMV FCEAKINDET YQSIMYIVVV VGYRIYDVIL SPPHEIELSA GEKLVLNCTA RTELNVGLDF TWHSPPSKSH HKKIVNRDVK PFPGTVAKMF LSTLTIESVT KSDQGEYTCV ASSGRMIKRN RTFVRVHTKP

Expression of Recombinant mVEGFR-2(2–3) in Eukaryotic Cells

Recombinant mVEGFR-2(2–3) was expressed in EBNA 293 cells using the pCEP-SP-EK-Fc* vector. The pCEP-SP-EK-Fc* vector has a BamHI and an NheI sites, encodes an amino acid linker containing one cysteine residue, an enterokinase cleavage site, and C-terminally a human Fc region. The mVEGFR-2(2–3) was amplified by PCR with the primer pair BamHI-FLK1-F and NheI-FLK1-B from a mouse 7-day embryo cDNA (Marathon-Ready cDNA, Clontech). For the PCR reaction, 10 pmol of each oligo and 0.5 ng of the cDNA (mouse 7-day embryo cDNA Marathon-Ready cDNA, Clontech) was used in the 50 μl reaction mixture (1 μl of Advantage 2 polymerase mix (50×), 0.2 mM dNTPs and 5 μl 10× cDNA PCR reaction buffer). The temperature cycles were as follows: 5 cycles a 94° C. for 1 minute, 94° C. for 30 seconds, 54° C. for 30 seconds, 72° C. for 1 minute followed by 5 cycles of 94° C. (30 seconds), 54° C. (30 seconds), 70° C. (1 minute) and followed by 30 cycles 94° C. (20 seconds), 54° C. (30 seconds) and 68° C. (1 minute). The PCR product was digested with BamHI and NheI and inserted into the pCEP-SP-EK-Fc* vector digested with the same enzymes. Resulting plasmid was named mVEGFR-2(2–3)-pCep-EK-Fc. All other steps were performed by standard molecular biology protocols.

```
Oligos:
1. Primer BamH1-FLK1-F
5'-CGCGGATCCATTCATCGCCTCTGTC-3'    (SEQ ID NO:343)

2. Primer Nhe1-FLK1-B
5'-CTAGCTAGCTTTGTGTGAACTCGGAC-3'   (SEQ ID NO:344)
```

Transfection and expression of recombinant mVEGFR-2 (2–3)

EBNA 293 cells were transfected with the mVEGFR-2 (2–3)-pCep-Ek-Fc construct described above and serum free supernatant of cells was harvested for purification as described in EXAMPLE 1.

Purification of recombinant mVEGFR-2(2–3)

Protein A purification of the expressed Fc-EK-mVEGFR-2(2–3) proteins was performed as described in EXAMPLE 1. Subsequently, after binding of the fusion protein to Protein A, mVEGFR-2(2–3) was cleaved from the Fc portion bound to protein A using enterokinase (Enterokinase-Max, Invitrogen). Digestion was conducted over night at 37° C. (2,5 units enterokinase/100 μl Protein A beads with bound fusion protein). The released VEGFR-2(2–3) was separated from the Fc-portion still bound to protein A beads by short centrifugation in chromatography columns (Micro Bio Spin, Biorad). In order to remove the enterokinase the flow through was treated with enterokinase away (Invitrogen) according to the instructions of the manufacturer.

Example 12

Coupling of Murine VEGFR-2 Peptide to Qβ Capsid Protein, HbcAg-lys-2cys-Mut and Pili and Immunization of Mice with VLP-peptide and Pili-peptide Vaccines A. Coupling of Murine VEGFR-2 Peptides to VLPs and Pili The following peptide was chemically synthesized (by Eurogentec, Belgium): murine VEGFR-2 peptide CTART-ELNVGLDFTWHSPPSKSHHKK (SEQ ID NO:366) and used for chemical coupling to Pili as described below.

Figure 18:
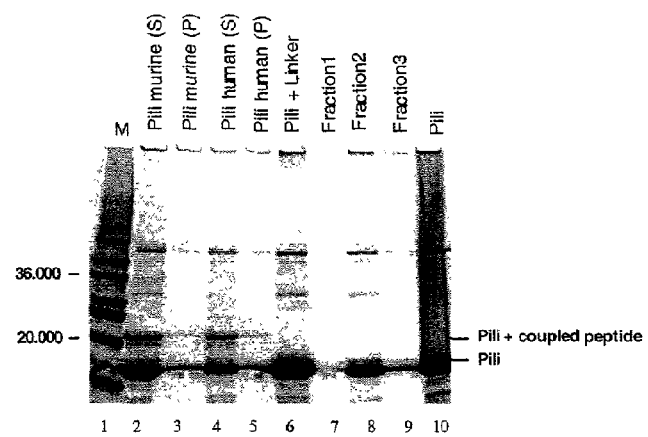
FIG. 18B. SDS-PAGE analysis of coupling of murine VEGFR-2 peptide to Qβ capsid protein.
FIG. 18C. SDS-PAGE analysis of coupling of murine VEGFR-2 peptide to HBcAg-lys-2cys-Mut.
FIG. 18D. ELISA analysis of IgG antibodies specific for murine VEGFR-2 peptide in sera of mice immunized against murine VEGFR-2 peptide coupled to Pili.
FIG. 18E. ELISA analysis of IgG antibodies specific for murine VEGFR-2 peptide in sera of mice immunized against murine VEGFR-2 peptide coupled to Qβ capsid protein.
FIG. 18F. ELISA analysis of IgG antibodies specific for murine VEGFR-2 peptide in sera of mice immunized against murine VEGFR-2 peptide coupled to HBcAg-lys-2cys-Mut.
Figure 18:
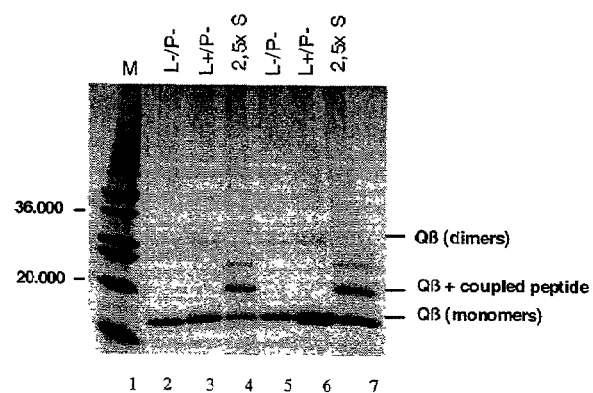
Figure 18:
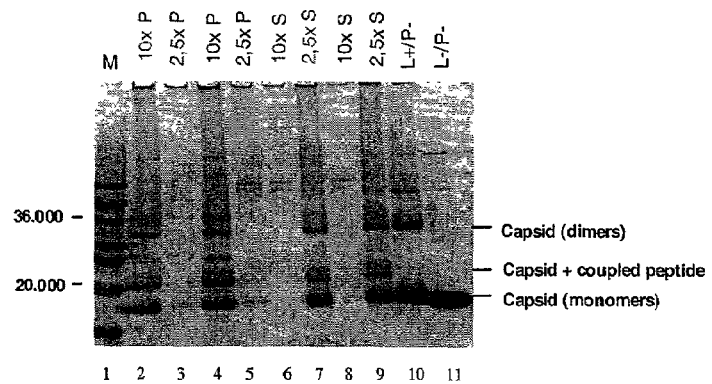
Figure 18:
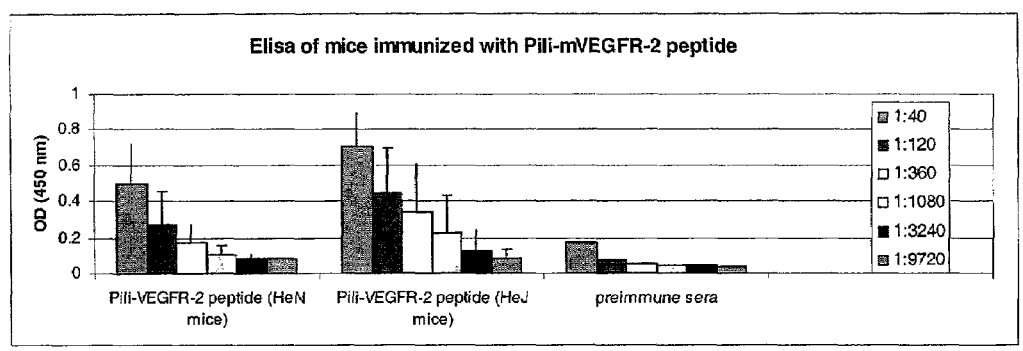
Figure 18:
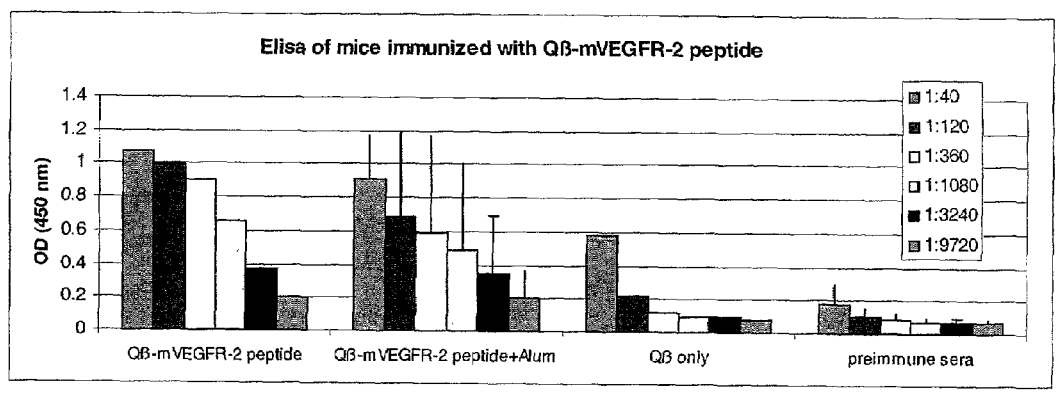
Figure 18:
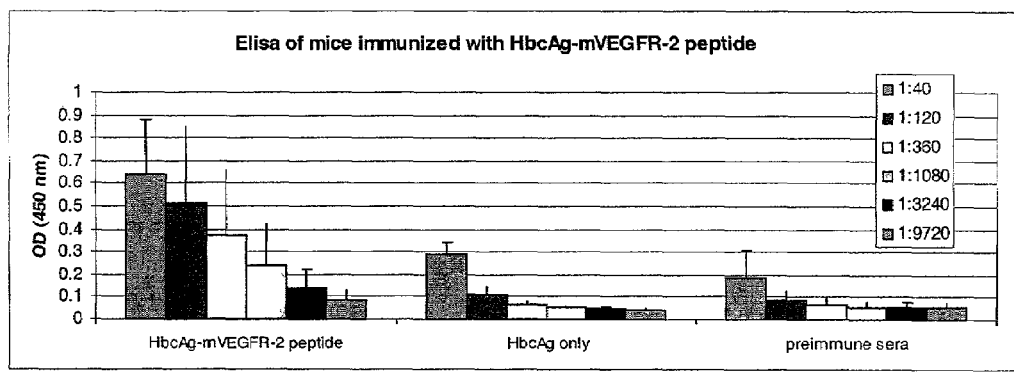

Coupling of murine VEGFR-2 peptides to pili: A solution of 1400 μl of 1 mg/ml pili protein in 20 mM Hepes, pH 7.4, was reacted for 60 minutes with 85 μl of a 100 mM Sulfo-MBS (Pierce) solution in (H2O) at RT on a rocking shaker. The reaction mixture was desalted on a PD-10 column (Amersham-Pharmacia Biotech), The protein-containing fractions eluting from the column were pooled (containing approximately 1,4 mg protein) and reacted with a 2.5-fold molar excess (final volume) of murine VEGFR-2 peptide respectively. For example, to 200 μl eluate containing approximately 0.2 mg derivatized pili, 2,4 μl of a 10 mM peptide solution (in DMSO) were added. The mixture was incubated for four hours at 25° C. on a rocking shaker and subsequently dialyzed against 2 liters of 20 mM Hepes, pH 7.2 overnight at 4° C. Coupling results were analyzed by SDS-PAGE under reducing conditions and are shown in FIG. 18A. Supernatant (S) and pellet (P) of each sample were loaded on the gel, as well pili and pili derivatized with Sulfo-MBS cross-linker (Pierce). The samples loaded on the gel of FIG. 18A were the following:

Lane 1: Marker proteins; lane 2–5: coupled samples (Pili murine: Pili coupled to murine peptide; Pili human: Pili coupled to human peptide); lane 6: pili derivatized with Sulfo-MBS cross-linker; lane 7–9: three fractions of the eluate of the PD-10 column. Fraction 2 is the peak fraction, fraction 1 and 3 are fractions taken at the border of the peak. Coupling bands were clearly visible on the gel, demonstrating the successful coupling of murine VEGFR-2 to pili.

Coupling of murine VEGFR-2 peptide to Qβ capsid protein: A solution of 1 ml of 1 mg/ml Qβ capsid protein in 20 mM Hepes, 150 mM NaCl pH 7.4 was reacted for 45 minutes with 20 μl of 100 mM Sulfo-MBS (Pierce) solution in (H2O) at RT on a rocking shaker. The reaction solution was subsequently dialyzed twice for 2 hours against 2 L of 20 mM Hepes, pH 7.4 at 4° C. 1000 μl of the dialyzed reaction mixture was then reacted with 12 μl of a 10 mM peptide solution (in DMSO) for four hours at 25° C. on a rocking shaker. The reaction mixture was subsequently dialyzed 2×2 hours against 2 liters of 20 mM Hepes, pH 7.4 at 4° C. Coupling results were analyzed by SDS-PAGE under reducing conditions and are shown in FIG. 18B. Supernatant (S) of each sample was loaded on the gel, as well as Qβ capsid protein and Qβ capsid protein derivatized with Sulfo-MBS cross-linker. Coupling was done in duplicate. The following samples were loaded on the gel:

Lane 1: Marker proteins; lane 2, 5: Qβ capsid protein; lane 3, 6 Qβ capsid protein derivatized with Sulfo-MBS; lane 4, 7: Qβ capsid protein coupled to murine VEGFR-2 peptide. Coupling bands were clearly visible on the gel, demonstrating the successful coupling of murine VEGFR-2 to Qβ capsid protein.

Coupling of murine VEGFR-2 peptide to HbcAg-lys-2cys-Mut: A solution of 3 ml of 0.9 mg/ml cys-free HbcAg capsid protein (EXAMPLE 31) in PBS, pH 7.4 was reacted for 45 minutes with 37.5 μl of a 100 mM Sulfo-MBS (Pierce) solution in (H2O) at RT on a rocking shaker. The reaction solution was subsequently dialyzed overnight against 2 L of 20 mM Hepes, pH 7.4. After buffer exchange the reaction solution was dialyzed for another 2 hours against the same buffer. The dialyzed reaction mixture was then reacted with 3 μl of a 10 mM peptide solution (in DMSO) for 4 hours at 25° C. on a rocking shaker. The reaction mixture was subsequently dialyzed against 2 liters of 20 mM Hepes, pH 7.4 overnight at 4° C. followed by buffer exchange and another 2 hours of dialysis against the same buffer. Coupling results were analyzed by SDS-PAGE under reducing conditions and are shown in FIG. 18C. The supernatant (S) of each sample was loaded on the gel, as well as HbcAg-lys-2cys-Mut protein and HbcAg-lys-2cys-Mut protein derivatized with Sulfo-MBS cross-linker. Coupling was done in duplicate. Coupling reactions were conducted in a 2.5 fold and 10 fold molar excess of peptide. The following samples were loaded on the gel:

Lane 1: Marker proteins; lane 2, 4, 6, 8: Supernatant (S) and pellet (P) of coupling reactions performed with 10 fold molar excess of peptide; lane 3, 5, 7, 9: Supernatant (S) and pellet (P) of coupling reactions performed with 2.5 fold molar excess of peptide; lane 10: HbcAg-lys-2cys-Mut derivatized with Sulfo-MBS; lane 11: HbcAg-lys-2cys-Mut.

Coupling bands were clearly visible on the gel, demonstrating the successful coupling of murine VEGFR-2 to HbcAg-lys-2cys-Mut protein.

B. Immunization of Mice:

Pili-peptide Vaccine:

Female C3H-HeJ (Toll-like receptor 4 deficient) and C3H-HeN (wild-type) mice were vaccinated with the murine VEGFR-2 peptide coupled to pili protein without the addition of adjuvants. Approximately 100 μg of total protein of each sample was diluted in PBS to 200 μl and injected subcutaneously on day 0, day 14 and day 28. Mice were bled retroorbitally on day 14, 28 and day 42 and serum of day 42 was analyzed using a human VEGFR-2 specific ELISA.

Qβ Capsid Protein-peptide Vaccine:

Female Black 6 mice were vaccinated with the murine VEGFR-2 peptide coupled to QB capsid protein with and without the addition of adjuvant (Aluminiumhydroxid). Approximately 100 μg of total protein of each sample was diluted in PBS to 200 μl and injected subcutaneously on day 0, day 14 and day 28. Mice were bled retroorbitally on day 14, 28 and day 42 and serum of day 42 was analyzed using a human VEGFR-2 specific ELISA.

HbcAg-lys-2cys-Mut Vaccines:

Female Black 6 mice were vaccinated with the murine VEGFR-2 peptide coupled to HbcAg-lys-2cys-Mut protein with and without the addition of adjuvant (Aluminiumhydroxid). Approximately 100 μg of total protein of each sample was diluted in PBS to 200 μl and injected subcutaneously on day 0, day 14 and day 28. Mice were bled retroorbitally on day 14, 28 and day 42 and serum of day 42 was analyzed using a human VEGFR-2 specific ELISA.

C. ELISA

Sera of immunized mice were tested in ELISA with immobilized murine VEGFR-2 peptide. Murine VEGFR-2 peptide was coupled to bovine RNAse A using the chemical cross-linker Sulfo-SPDP. ELISA plates were coated with coupled RNAse A at a concentration of 10 µg/ml. The plates were blocked and then incubated with serially diluted mouse sera. Bound antibodies were detected with enzymatically labeled anti-mouse IgG antibody. As a control, preimmune sera of the same mice were also tested. Control ELISA experiments using sera from mice immunized with uncoupled carrier showed that the antibodies detected were specific for the respective peptide. The results are shown in FIGS. 4–6.

Pili-peptide Vaccine:

The result of the ELISA is shown in FIG. 18D. Results for indicated serum dilutions are shown as optical density at 450 nm. The average of three mice each (including standard deviations) are shown. All vaccinated mice made IgG antibody titers against the murine VEGFR-2 peptide. No difference was noted between mice deficient for the Toll-like receptor 4 and wild-type mice, demonstrating the immunogenicity of the self-antigen murine VEGFR-2 peptide, when coupled to pili, in mice. The vaccines injected in the mice are designating the corresponding analyzed sera.

Qβ Capsid Protein-peptide Vaccine:

Results for indicated serum dilutions are shown in FIG. 18E as optical density at 450 nm. The average of two mice each (including standard deviations) are shown. All vaccinated mice made IgG antibody titers against the murine VEGFR-2 peptide, demonstrating the immunogenicity of the self-antigen murine VEGFR-2 peptide, when coupled to Qβ capsid protein, in mice. The vaccines injected in the mice are designating the corresponding analyzed sera.

HbcAg-lys-2cys-Mut Vaccine:

Results for indicated serum dilutions are shown in FIG. 18F as optical density at 450 nm. The average of three mice each (including standard deviations) are shown. All vaccinated mice made IgG antibody titers against the murine VEGFR-2 peptide, demonstrating the immunogenicity of the self-antigen murine VEGFR-2 peptide, when coupled to Qβ capsid protein, in mice. The vaccines injected in the mice are designating the corresponding analyzed sera.

Example 13

Coupling of Aβ 1–15 Peptides to HBc-Ag-lys-2cys-Mut and fr Capsid Protein

The following Aβ peptide was chemically synthesized (DAEFRHDSGYEVHHQGGC (SEQ ID NO:367)), a peptide which comprises the amino acid sequence from residue 1–15 of human Aβ, fused at its C-terminus to the sequence GGC for coupling to VLPs and Pili.

A. a.) Coupling of A13 1–15 peptide to HBc-Ag-lys-2cys-Mut using the cross-linker SMPH.

A solution of 833.3 µl of 1.2 mg/ml HBc-Ag-lys-2cys-Mut protein in 20 mM Hepes 150 mM NaCl pH 7.4 was reacted for 30 minutes with 17 µl of a solution of 65 mM SMPH (Pierce) in H2O, at 25° C. on a rocking shaker. The reaction solution was subsequently dialyzed twice for 2 hours against 1 L of 20 mM Hepes, 150 mM NaCl, pH 7.4 at 4° C. in a dialysis tubing with Molecular Weight cutoff 10000 Da. 833.3 µl of the dialyzed reaction mixture was then reacted with 7.1 µl of a 50 mM peptide stock solution (peptide stock solution in DMSO) for two hours at 15° C. on a rocking shaker. The reaction mixture was subsequently dialyzed overnight against 1 liters of 20 mM Hepes, 150 mM NaCl, pH 7.4 at 4° C. The sample was then frozen in aliquots in liquid Nitrogen and stored at −80° C. until immunization of the mice.

b) Coupling of Aβ 1–15 peptide to fr capsid protein using the cross-linker SMPH.

A solution of 500 µl of 2 mg/ml fr capsid protein in 20 mM Hepes 150 mM NaCl pH 7.4 was reacted for 30 minutes with 23 µl of a solution of 65 mM SMPH (Pierce) in H2O, at 25° C. on a rocking shaker. The reaction solution was subsequently dialyzed twice for 2 hours against 1 L of 20 mM Hepes, 150 mM NaCl, pH 7.4 at 4° C. in a dialysis tubing with Molecular Weight cutoff 10000 Da. 500 µl of the dialyzed reaction mixture was then reacted with 5.7 µl of a 50 mM peptide stock solution (peptide stock solution in DMSO) for two hours at 15° C. on a rocking shaker. The reaction mixture was subsequently dialyzed overnight against 1 liter of 20 mM Hepes, 150 mM NaCl, pH 7.4 at 4° C. The sample was then frozen in aliquots in liquid Nitrogen and stored at −80° C. until immunization of the mice. Samples of the coupling reaction were analyzed by SDS-PAGE under reducing conditions.

Figure 19:
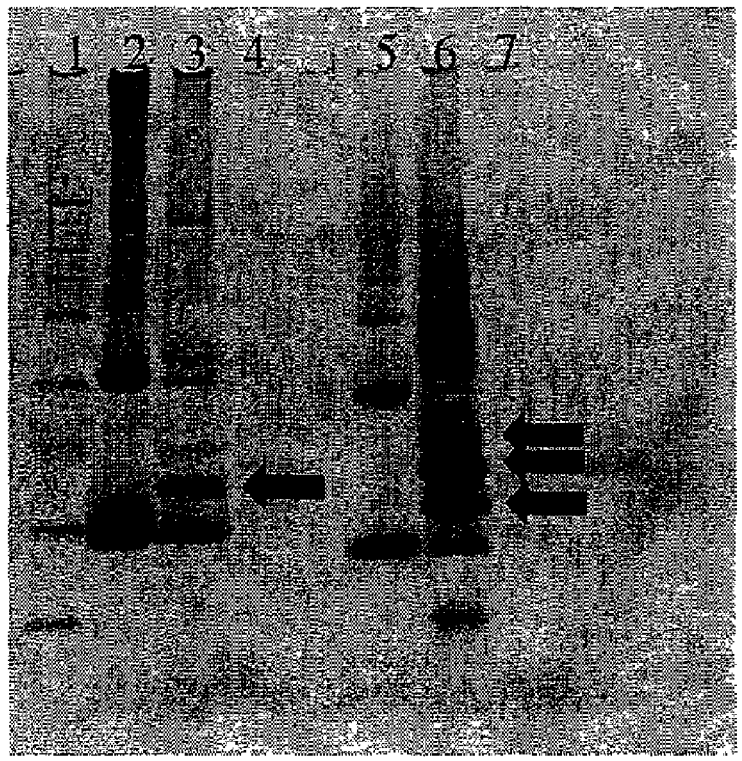
FIG. 19A. SDS-PAGE analysis of coupling of Aβ 1–15 peptide to HBcAg-lys-2cys-Mut and fr capsid protein.
FIG. 19B. ELISA analysis of IgG antibodies specific for Aβ 1–15 peptide in sera of mice immunized against Aβ 1–15 peptide coupled to HBcAg-lys-2cys-Mut or fr capsid protein.
Figure 19:
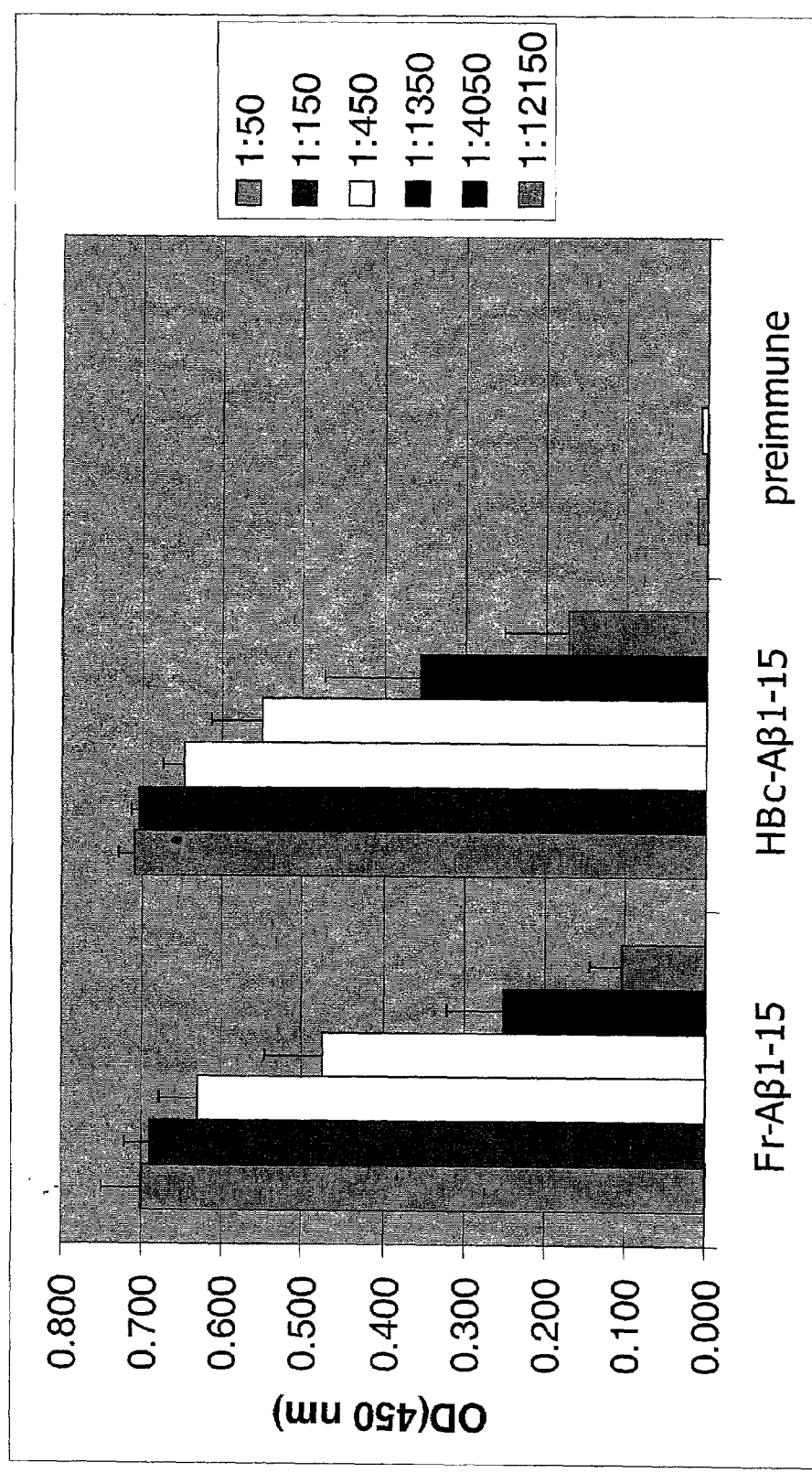

The results of the coupling experiments were analyzed by SDS-PAGE, and are shown in FIG. 19A. Clear coupling bands corresponding to the coupling of Aβ 1–15 either to fr capsid protein or to HBc-Ag-lys-2cys-Mut were visible on the gel, and are indicated by arrows in the figure, demonstrating successful coupling of Aβ 1–15 to fr capsid protein and to HBc-Ag-lys-2cys-Mut capsid protein. Multimple coupling bands were visible for the coupling to fr capsid protein, while mainly one coupling band was visible for HBc-Ag-lys-2cys-Mut.

The following samples were loaded on the gel of FIG. 19A.

1: Protein Marker (kDa Marker 7708S BioLabs. Molecular weight marker bands from the top of the gel: 175, 83, 62, 47.5, 32.5, 25, 16.5, 6.5 kDa). 2: derivatized HBc-Ag-lys-2cys-Mut. 3: HBc-Ag-lys-2cys-Mut coupled with Aβ1–15, supernatant of the sample taken at the end of the coupling reaction, and centrifuged. 4: HBc-Ag-lys-2cys-Mut coupled with Aβ1–15, pellet of the sample taken at the end of the coupling reaction, and centrifuged. 5: derivatized fr capsid protein. 6: fr capsid protein coupled with Aβ1–15, supernatant of the sample taken at the end of the coupling reaction, and centrifuged. 4: fr capsid protein coupled with Aβ1–15, pellet of the sample taken at the end of the coupling reaction, and centrifuged.

B. Immunization of Balb/c Mice

Female Balb/c mice were vaccinated twice on day 0 and day 14 subcutaneously with either 10 µg of fr capsid protein coupled to Aβ1–15 (Fr-Aβ 1–15) or 10 µg of HBc-Ag-lys-2cys-Mut coupled to to Aβ 1–15 (HBc-Aβ1–15) diluted in sterile PBS. Mice were bled retroorbitally on day 22 and sera were analysed in an Aβ-1–15-specific ELISA.

C. ELISA

The Aβ 1–15 peptide was coupled to bovine RNAse A using the chemical cross-linker sulfo-SPDP. ELISA plates were coated with Aβ 1–15-RNAse conjugate at a concentration of 10 µg/ml. The plates were blocked and then incubated with serially diluted serum samples. Bound antibodies were detected with enzymatically labeled anti-mouse IgG. As a control, serum from a naive mouse was also tested.

Shown on FIG. 19B are the ELISA signals obtained on day 22 with the sera of the mice immunized with vaccines Fr-Aβ 3 1–15, and HBc-Aβ1–15 respectively. A control serum from a naive mouse (preimmune serum) was also included. Results from different serum dilutions are shown as optical density at 450 nm. Average results from three vaccinated mice each are shown. All vaccinated mice had Aβ 1–15-specific IgG antibodies in their serum.

Example 14

Coupling of Aβ 1–15, Aβ 1–27 and Aβ 33–42 Peptides to Type I Pili

Coupling of Aβ 1–15, Aβ 1–27 and Aβ 33–42 peptides to Pili using the cross-linker SMPH.

The following Aβ peptides were chemically synthesized: DAEFRHDSGYEVHHQGGC ("Aβ 1–15"; SEQ ID NO:367), a peptide which comprises the amino acid sequence from residue 1–15 of human Aβ fused at its C-terminus to the sequence GGC for coupling to Pili and VLPs, DAEFRHDSGYEVHHQKLVFFAEDVGSNGGC ("Aβ 1–27": SEQ ID NO:368) a peptide which comprises the amino acid sequence from residue 1–27 of human Aβ fused, at its C-terminus to the sequence GGC for coupling to Pili and VLPs, and CGHGNKSGLMVGGVVIA ("Aβ 33–42"; SEQ ID NO:369) a peptide which comprises the amino acid sequence from residue 33–42 of Aβ, fused at its N-terminus to the sequence CGHGNKS (SEQ ID NO:405) for coupling to Pili and VLPs. All three peptides were used for chemical coupling to Pili as described in the following.

A solution of 2 ml of 2 mg/ml Pili in 20 mM Hepes 150 mM NaCl pH 7.4 was reacted for 45 minutes with 468 μl of a solution of 33.3 mM SMPH (Pierce) in H2O, at 25° C. on a rocking shaker. The reaction solution was loaded on a PD10 column (Pharmacia) and eluted with 6×500 μl of 20 mM Hepes 150mM NaCl pH 7.4. Fractions were analyzed by dotting on a Nitrocellulose (Schleicher & Schuell) and stained with Amidoblack. Fractions 3–6 were pooled. The samples were then frozen in aliquots in liquid Nitrogen and stored at –80° C. until coupling.

200 μl of the thawed desalted reaction mixture was then mixed with 200 μl DMSO and 2.5 μl of each of the corresponding 50 mM peptide stock solutions in DMSO, for 3.5 hours at RT on a rocking shaker. 400 μl of the reaction mixture was subsequently dialyzed three times for one hour against 1 liter of 20 mM Hepes, 150 mM NaCl, pH 7.4 at 4° C. in a dialysis tubing with Molecular Weight cutoff 10000 Da. The samples were then frozen in aliquots in liquid Nitrogen and stored at –80° C.

Sample preparation for SDS-Page was performed as follows: 100 μl of the dialyzed coupling reaction was incubated for 10 minutes in 10% TCA on ice and subsequently centrifuged. The pellet was resuspended in 50 μl 8.5 M Guanidine-HCl solution and incubated for 15 minutes at 70° C. The samples were then precipitated with ethanol and after a second centrifugation step, the pellet was resuspended in sample buffer.

The results of the coupling experiments were analyzed by SDS-PAGE under reducing conditions. Clear coupling bands were visible for all three peptides, demonstrating coupling of Aβ peptides to Pili.

Example 15

Vaccination of APP23 Mice with Aβ Peptides Coupled to Qβ Capsid Protein

A. Immunization of APP23 Mice

Three different Aβ peptides (Aβ 1–27-Gly-Gly-Cys-NH2 (SEQ ID NO:421); H-Cys-Gly-His-Gly-Asn-Lys-Ser-Aβ 33–42 (SEQ ID NO:422); Aβ 1–15-Gly-Gly-Cys-NH2 (SEQ ID NO:422)) were coupled to Qβ capsid protein. The resulting vaccines were termed "Qb-Ab 1–15", "Qb-Ab 1–27" and "Qb-Ab 33–42". 8 months old female APP23 mice which carry a human APP transgene (Sturchler-Pierrat et al., Proc. Natl. Acad.Sci. USA 94: 13287–13292 (1997)) were used for vaccination. The mice were injected subcutaneously with 25 μg vaccine diluted in sterile PBS and 14 days later boosted with the same amount of vaccine. Mice were bled from the tail vein before the start of immunization and 7 days after the booster injection. The sera were analyzed by ELISA.

B. ELISA

Figure 20:
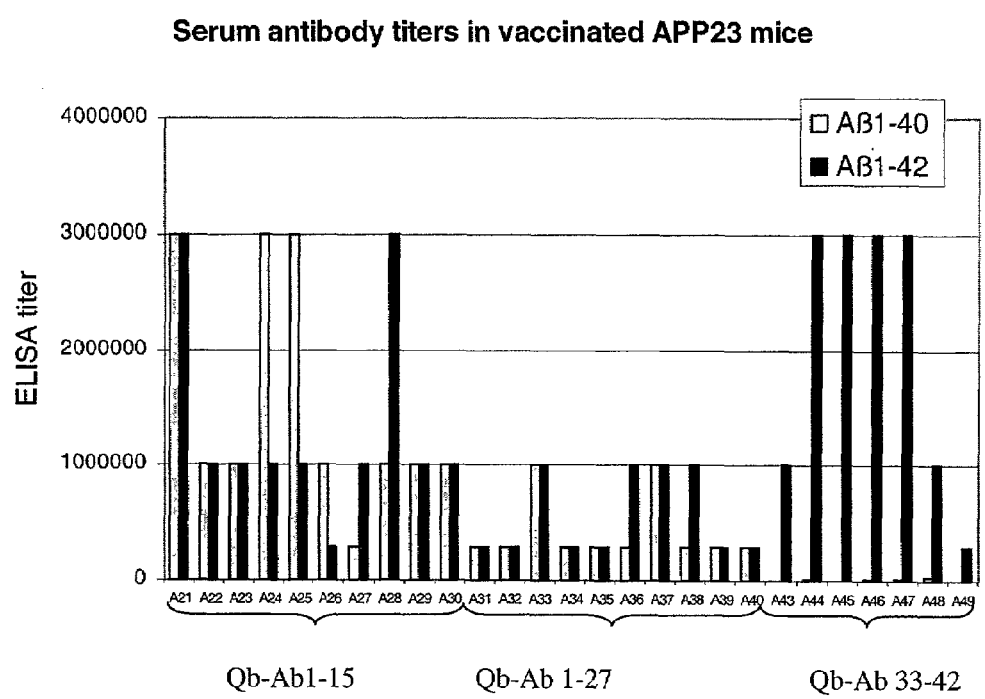
FIG. 20 ELISA analysis of IgG antibodies specific for human Aβ in sera of transgenic APP23 mice immunized with human Aβ peptides coupled to Qβ capsid protein.

Aβ 1–40 and Aβ 1–42 peptide stocks were made in DMSO and diluted in coating buffer before use. ELISA plates were coated with 0.1 μg/well Aβ 1–40 or Aβ 1–42 peptide. The plates were blocked and then incubated with serially diluted mouse serum. Bound antibodies were detected with enzymatically labeled anti-mouse IgG antibody. As a control, sera obtained before vaccination were also included. The serum dilution showing a mean three standard deviations above baseline was calculated and defined as "ELISA titer". All three vaccines tested were immunogenic in APP23 mice and induced high antibody titers against the Aβ peptides 1–40 and/or Aβ 1–42. The results are shown in FIG. 20. No specific antibodies were detected in preimmune sera of the same mice (not shown).

Shown on FIG. 20 are the ELISA signals obtained on day 22 with the sera of the mice immunized with vaccines Fr-Aβ 1–15, and HBc-Aβ1–15 respectively. A control serum from a naïve mouse (preimmune serum) was also included. Results from different serum dilutions are shown as optical density at 450 nm. Average results from three vaccinated mice each are shown.

Mice A21-A30 received the vaccine Qb-Ab 1–15, mice A31-A40 received Qb-Ab 1–27 and mice A41-49 received Qb-Ab 33–42. For each mouse, Aβ 1–40 and Aβ 1–42 peptide-specific serum antibody titers were determined on day 21 by ELISA. The ELISA titers defined as the serum dilution showing a mean three standard deviations above baseline are shown for individual mice. Mice vaccinated with Qb-Ab 1–15 or Qb-Ab 1–27 made high antibody titers against both Aβ 1–40 and Aβ 1–42 whereas mice vaccinated with Qb-Ab 33–42 had only high antibody titers against the Aβ 1–42 peptide.

Example 16

Coupling of Fab Antibody Fragments to Qβ Capsid Protein

A solution of 4.0 mg/ml Qβ capsid protein in 20 mM Hepes, 150 mM NaCl pH 7.2 was reacted for 30 minutes with a 2.8 mM SMPH (Pierce) (from a stock solution dissolved in DMSO) at 25° C. on a rocking shaker. The reaction solution was subsequently dialyzed twice for 2 hours against 2 l of 20 mM Hepes, 150 mM NaCl, pH 7.2 at 4° C.

The Fab fragment of human IgG, produced by papain digestion of human IgG, was purchased from Jackson Immunolab. This solution (11.1 mg/ml) was diluted to a concentration of 2.5 mg/ml in 20 mM Hepes, 150 mM NaCl pH 7.2 and allowed to react with different concentrations (0–1000 μM) of either dithiothreitol (DTT) or tricarboxyethylphosphine (TCEP) for 30 minutes at 25° C.

Coupling was induced by mixing the derivatized and dialysed Qβ capsid protein solution with non-reduced or reduced Fab solution (final concentrations: 1.14 mg/ml Qβ and 1.78 mg/ml Fab) and proceeded overnight at 25° C. on a rocking shaker.

Figure 21:
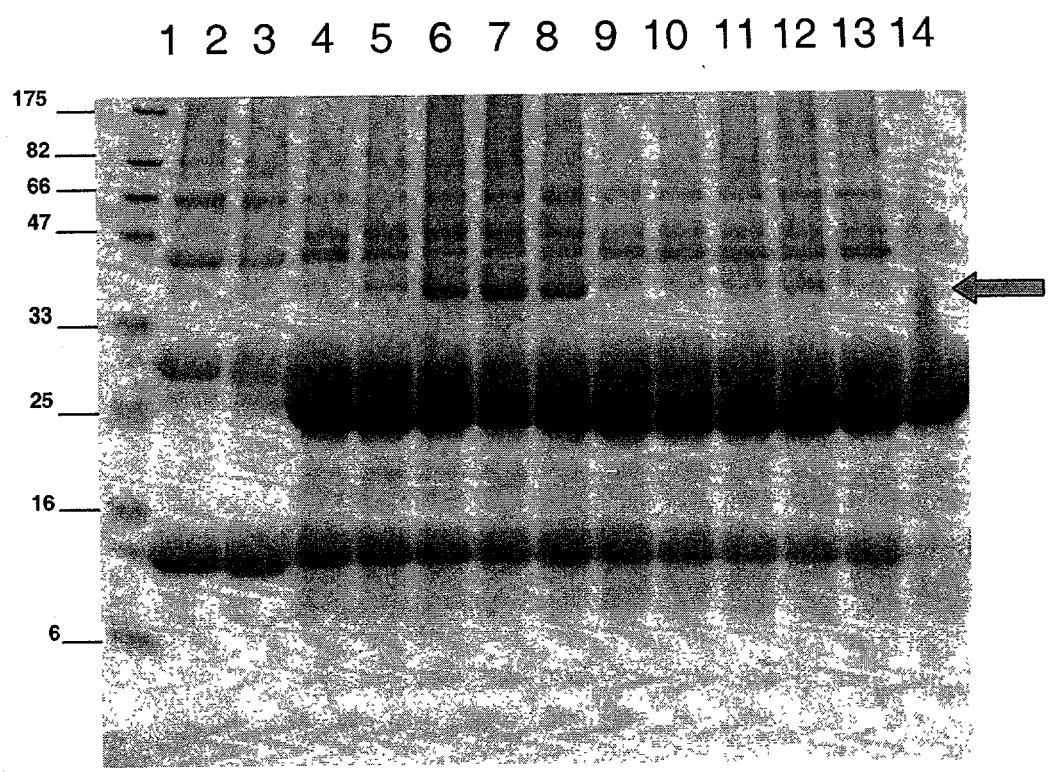
FIG. 21 SDS-PAGE analysis of coupling of an Fab antibody fragment to Qβ capsid protein.

The reaction products were analysed on 16% SDS-PAGE gels under reducing conditions. Gels were stained with Coomassie Brilliant Blue. The results are shown in FIG. 21. A coupling product of about 40 kDa could be detected in samples in which the Fab had been reduced before coupling by 25–1000 μM TCEP and 25–100 μM DTT (FIG. 21, arrow), but not at 10 μM TCEP, 10 μM DTT or 1000 μM DTT. The coupled band also reacted with an anti-Qβ antiserum (data not shown) clearly demonstrating the covalent coupling of the Fab fragment to Qβ capsid protein.

The samples loaded on the gel of FIG. 21 were the following:.

Lane 1: Molecular weight marker. Lane 2 and 3: derivatized Qβ capsid protein before coupling. Lane 4–13: Qβ-Fab coupling reactions after reduction of Fab with 4: Qβ-Fab coupling reactions after reduction of Fab with 10 μM TCEP. 5: Qβ-Fab coupling reactions after reduction of Fab with 25 μM TCEP. 6: Qβ-Fab coupling reactions after reduction of Fab with 50 μM TCEP, 7: Qβ-Fab coupling reactions after reduction of Fab with 100 μM TCEP. 8: Qβ-Fab coupling reactions after reduction of Fab with 1000 μM TCEP. 9: Qβ-Fab coupling reactions after reduction of Fab with 10 μM DTT. 10: Qβ-Fab coupling reactions after reduction of Fab with 25 μM DTT. 11: Qβ-Fab coupling reactions after reduction of Fab with 50 μM DTT. 12: Qβ-Fab coupling reactions after reduction of Fab with 100 μM DTT. 13: Qβ-Fab coupling reactions after reduction of Fab with 1000 μM DTT. Lane 14: Fab before coupling. The gel was stained with Coomassie Brilliant Blue. Molecular weights of marker proteins are given on the left margin. The arrow indicates the coupled band.

Example 17

Vaccination of APP23 Mice with Aβ Peptides Coupled to Qβ Capsid Protein

A. Immunization of APP23 Mice

Three different Aβ peptides (Aβ 1–27-Gly-Gly-Cys-NH2; H-Cys-Gly-His-Gly-Asn-Lys-Ser-Aβ 33–42; Aβ 1–15-Gly-Gly-Cys-NH2) were coupled to Qβ capsid protein. The resulting vaccines were termed "Qb-Ab 1–15", "Qb-Ab 1–27" and "Qb-Ab 33–42". 8 months old female APP23 mice which carry a human APP transgene (Sturchler-Pierrat et al., Proc. Natl. Acad. Sci. USA 94: 13287–13292 (1997)) were used for vaccination. The mice were injected subcutaneously with 25 μg vaccine diluted in sterile PBS and 14 days later boosted with the same amount of vaccine. Mice were bled from the tail vein before the start of immunization and 7 days after the booster injection. The sera were analyzed by ELISA.

B. ELISA

Aβ 1–40 and Aβ 1–42 peptide stocks were made in DMSO and diluted in coating buffer before use. ELISA plates were coated with 0.1 μg/well Aβ 1–40 or Aβ 1–42 peptide. The plates were blocked and then incubated with serially diluted mouse serum. Bound antibodies were detected with enzymatically labeled anti-mouse IgG antibody. As a control, sera obtained before vaccination were also included. The serum dilution showing a mean three standard deviations above baseline was calculated and defined as "ELISA titer". All three vaccines tested were immunogenic in APP23 mice and induced high antibody titers against the Aβ peptides 1–40 and/or Aβ 1–42. The results are shown in FIG. 20. No specific antibodies were detected in preimmune sera of the same mice (not shown).

Shown on FIG. 20 are the ELISA signals obtained on day 22 with the sera of the mice immunized with vaccines Qb-Ab 1–15, Qb-Ab 1–27 and Qb-Ab 33–42, respectively. Mice A21-A30 received the vaccine Qb-Ab 1–15, mice A31-A40 received Qb-Ab 1–27 and mice A41-49 received Qb-Ab 33–42. For each mouse, Aβ 1–40 and Aβ 1–42 peptide-specific serum antibody titers were determined on day 21 by ELISA. The ELISA titers defined as the serum dilution showing a mean three standard deviations above baseline are shown for individual mice. Mice vaccinated with Qb-Ab 1–15 or Qb-Ab 1–27 made high antibody titers against both Aβ 1–40 and Aβ 1–42 whereas mice vaccinated with Qb-Ab 33–42 had only high antibody titers against the Aβ 1–42 peptide. The very strong immune responses obtained with the human Aβ peptides in the transgenic mice expressing human Aβ transgene, demonstrate that by coupling Aβ peptides to Qβ capsid protein, tolerance towards the self-antigen can be overcome.

Example 18

Construction, Expression and Purification of Mutant Qβ Coat Proteins Construction of pQβ-240

The plasmid pQβ10 (Kozlovska, T M, et al., Gene 137: 133–137) was used as an initial plasmid for the construction of pQβ-240. The mutation Lys13→Arg was created by inverse PCR. The inverse primers were designed in inverted tail-to-tail directions:

```
                                              (SEQ ID NO:370)
5'-GGTAACATCGGTCGAGATGGAAAACAAACTCTGGTCC-3' and (SEQ ID NO:371)
5'-GGACCAGAGTTTGTTTTCCATCTCGACCGATGTTACC-3'.
```

The products of the first PCR were used as templates for the second PCR reaction, in which an upstream primer 5'-AGCTCGCCCGGGGATCCTCTAG-3' (SEQ ID NO:372) and a downstream primer 5'-CGATGCATTTCATCCTTAGTTAT-CAATACGCTGGGTTCAG-3' (SEQ ID NO:373) were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. E.coli cells harbouring pQβ-240 supported efficient synthesis of 14-kD protein co migrating upon PAGE with control Qβ coat protein isolated from Qβ phage particles.

Resulting amino acid sequence: (SEQ ID NO:255)

```
AKLETVTLGNIGRDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY
```

The plasmid pQβ10 was used as an initial plasmid for the construction of pQβ-243. The mutation Asn10→Lys was created by inverse PCR. The inverse primers were designed in inverted tail-to-tail directions:

5'-GGCAAAATTAGAGACTGTTACTTTAGGTAAGATCGG-3' (SEQ ID NO:374)

and

5'-CCGATCTTACCTAAAGTAACAGTCTCTAATTTTGCC-3'. (SEQ ID NO:375)

The products of the first PCR were used as templates for the second PCR reaction, in which an upstream primer 5'-AGCTCGCCCGGGGATCCTCTAG-3' (SEQ ID NO:372) and a downstream primer 5'-CGATGCATTTCATCCTTAGTTATCAATACGCTGGGTTCAG-3' (SEQ ID NO:373) were used. The product of the second PCR was digested with XbaI and Mph 1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. E.coli cells harbouring pQβ243 supported efficient synthesis of 14-kD protein co migrating upon PAGE with control Qβ coat protein isolated from Qβ phage particles.

Resulting amino acid sequence: (SEQ ID NO:256)

AKLETVTLGKIGKDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY

The plasmid pQβ-240 was used as an initial plasmid for the construction of pQβ-250. The mutation Lys2→Arg was created by site-directed mutagenesis. An upstream primer 5'-GGCCATGGCACGACTCGAGACTGTTACTTTAGG-3' (SEQ ID NO:376) and a downstream primer 5'-GATTTAGGTGACACTATAG-3' (SEQ ID NO:377) were used for the synthesis of the mutant PCR-fragment, which was introduced into the pQβ-185 expression vector at the unique restriction sites NcoI and HindIII. The PCR reactions were performed with PCR kit reagents and according to producer protocol (MBI Fermentas, Vilnius, Lithuania).

Sequencing using the direct label incorporation method verified the desired mutations. E.coli cells harbouring pQβ-250 supported efficient synthesis of 14-kD protein co migrating upon PAGE with control Qβ coat protein isolated from Qβ phage particles.

Resulting amino acid sequence: (SEQ ID NO:257)

ARLETVTLGNIGRDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY

The plasmid pQβ10 was used as an initial plasmid for the construction of pQβ-251. The mutation Lys16→Arg was created by inverse PCR. The inverse primers were designed in inverted tail-to-tail directions:
5'-GATGGACGTCAAACTCTGGTCCTCAATCCGCGTGGGG -3' (SEQ ID NO:378) and 5'-CCCCACGCGGATTGAGGACCAGAGTTTGACGTCCATC -3' (SEQ ID NO:379).

The products of the first PCR were used as templates for the second PCR reaction, in which an upstream primer 5'-AGCTCGCCCGGGGATCCTCTAG-3' (SEQ ID NO:372) and a downstream primer 5'-CGATGCATTTCATCCTTAGTTATCAATACGCTGGGTTCAG-3' (SEQ ID NO:3 73) were used. The product of the second PCR was digested with XbaI and Mph 1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. E. coli cells harbouring pQβ-251 supported efficient synthesis of 14-kD protein co migrating upon PAGE with control Qβ coat protein isolated from Qβ phage particles. The resulting amino acid sequence encoded by this construct is shown in SEQ ID NO:259.

Construction of pQβ-259

The plasmid pQβ-251 was used as an initial plasmid for the construction of pQβ-259. The mutation Lys2→Arg was created by site-directed mutagenesis. An upstream primer 5'-GGCCATGGCACGACTCGAGACTGTTACTTTAGG-3' (SEQ ID NO:376) and a downstream primer 5'-GATTTAGGTGACACTATAG-3' (SEQ ID NO:377) were used for the synthesis of the mutant PCR-fragment, which was introduced into the pQβ-185 expression vector at the unique restriction sites NcoI and HindIII. The PCR reactions were performed with PCR kit reagents and according to producer protocol (MBI Fermentas, Vilnius, Lithuania).

Sequencing using the direct label incorporation method verified the desired mutations. E.coli cells harbouring pQβ-259 supported efficient synthesis of 14-k1 protein co migrating upon PAGE with control Qβ coat protein isolated from Qβ phage particles.

Resulting amino acid sequence: (SEQ ID NO: 258)

AKLETVTLGNIGKDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY

General Procedures for Expression and Purification of Qβ and Qβ Mutants

Expression

Transform E.coli JM109 with Q-beta expression plasmids. Inoculate 5 ml of LB liquid medium with 20 µg/ml ampicillin with clones transformed with Q-beta expression plasmids. Incubate at 37° C. for 16–24 h without shaking.

Inoculate 100–300 ml of LB medium, containing 20 µg/ml, 1:100 with the prepared inoculum. Incubate at 37° C. overnight without shaking. Inoculate M9+1% Casamino acids+0.2% glucose medium in flasks with the prepared inoculum 1:50, incubate at 37° C. overnight under shaking.

Purification

Solutions and Buffers for the Purification Procedure:
1. Lysis Buffer LB
   50 mM Tris-HCl pH 8,0 with 5 mM EDTA, 0,1% tritonX100 and fresh! prepared PMSF till 5 micrograms per ml. Without lysozyme and DNAse.
2. SAS
   Saturated ammonium sulphate in water 3. Buffer NET.
  20 mM Tris-HCl, pH 7.8 with 5 mM EDTA and 150 mM NaCl.
4. PEG
  40% (w/v) polyethylenglycol 6000 in NET
  Disruption and Lyses
  Frozen cells were resuspended in LB at 2 ml/g cells. The mixture was sonicated with 22 kH five times for 15 seconds, with intervals of 1 min to cool the solution on ice. The lysate was then centrifuged at 14 000 rpm, for 1 h using a Janecki K 60 rotor. The centrifugation steps described below were all performed using the same rotor, except otherwise stated. The supernatant was stored at 4° C., while cell debris were washed twice with LB. After centrifugation, the supernatants of the lysate and wash fractions were pooled.
  Fractionation
  A saturated ammonium sulphate solution was added dropwise under stirring to the above pooled lysate. The volume of the SAS was adjusted to be be one fifth of total volume, to obtain 20% of saturation. The solution was left standing overnight, and was centrifuged the next day at 14 000 rpm, for 20 min. The pellet was washed with a small amount of 20% ammonium sulphate, and centrifuged again. The obtained supernatants were pooled, and SAS was added dropwise to obtain 40% of saturation. The solution was left standing overnight, and was centrifuged the next day at 14 000 rpm, for 20 min. The obtained pellet was solubilised in NET buffer.
  Chromatography
  The capsid protein resolubilized in NET buffer was loaded on a Sepharose CL-4B column. Three peaks eluted during chromatography. The first one mainly contained membranes and membrane fragments, and was not collected. Capsids were contained in the second peak, while the third one contained other E.coli proteins.
  The peak fractions were pooled, and the NaCl concentration was adjusted to a final concentration of 0.65 M. A volume of PEG solution corresponding to one half of the pooled peak fraction was added dropwise under stirring. The solution was left to stand overnight without stirring. The capsid protein was sedimented by centrifugation at 14 000 rpm for 20 min. It was then solubilized in a minimal volume of NET and loaded again on the Sepharose CL-4B column. The peak fractions were pooled, and precipitated with ammonium sulphate at 60% of saturation (w/v). After centrifugation and resolubilization in NET buffer, capsid protein was loaded on a Sepharose CL-6B column for rechromatography.
  Dialysis and Drying
  The peak fractions obtained above were pooled and extensively dialysed against sterile water, and lyophilized for storage.
  Expression and Purification Qβ-240
  Cells (*E. coli* JM 109, transformed with the plasmid pQβ-240) were resuspended in LB, sonicated five times for 15 seconds (water ice jacket) and centrifuged at 13000 rpm for one hour. The supernatant was stored at 4° C. until further processing, while the debris were washed 2 times with 9 ml of LB, and finally with 9 ml of 0,7 M urea in LB. All supernatants were pooled, and loaded on the Sepharose CL-4B column. The pooled peak fractions were precipitated with ammonium sulphate and centrifuged. The resolubilized protein was then purified further on a Sepharose 2B column and finally on a Sepharose 6B column. The capsid peak was finally extensively dialyzed against water and lyophilized as described above. The assembly of the coat protein into a capsid was confirmed by electron microscopy.

Expression and Purification Qβ-243
  Cells (*E. coli* RR1) were resuspended in LB and processed as described in the general procedure. The protein was purified by two successive gel filtration steps on the sepharose CL-4B column and finally on a sepharose CL-2B column. Peak fractions were pooled and lyophilized as described above. The assembly of the coat protein into a capsid was confirmed by electron microscopy.
  Expression and Purification of Qβ-250
  Cells (*E. coli* JM 109, transformed with pQβ-250) were resuspended in LB and processed as described above. The protein was purified by gel filtration on a Sepharose CL-4B and finally on a Sepharose CL-2B column, and lyophilized as described above. The assembly of the coat protein into a capsid was confirmed by electron microscopy.
  Expression and Purification of Qβ-259
  Cells (*E. coli* JM 109, transformed with pQβ-259) were resuspended in LB and sonicated. The debris were washed once with 10 ml of LB and a second time with 10 ml of 0,7 M urea in LB. The protein was purified by two gel-filtration chromatography steps, on a Sepharose CL-4 B column. The protein was dialyzed and lyophilized, as described above. The assembly of the coat protein into a capsid was confirmed by electron microscopy.

Example 19

Desensitization of Allergic Mice with PLA2 Coupled to Qβ Capsid Protein

Figure 25:
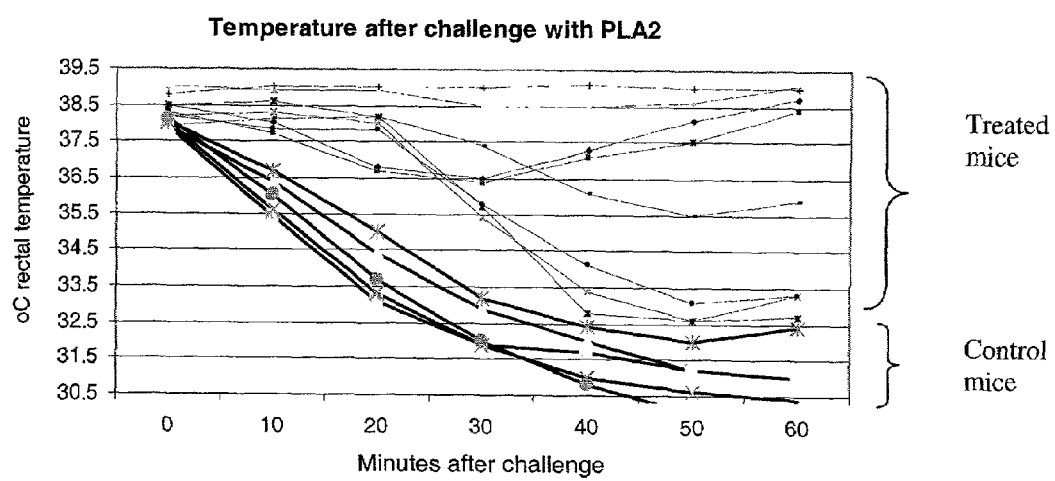
Figure 25:
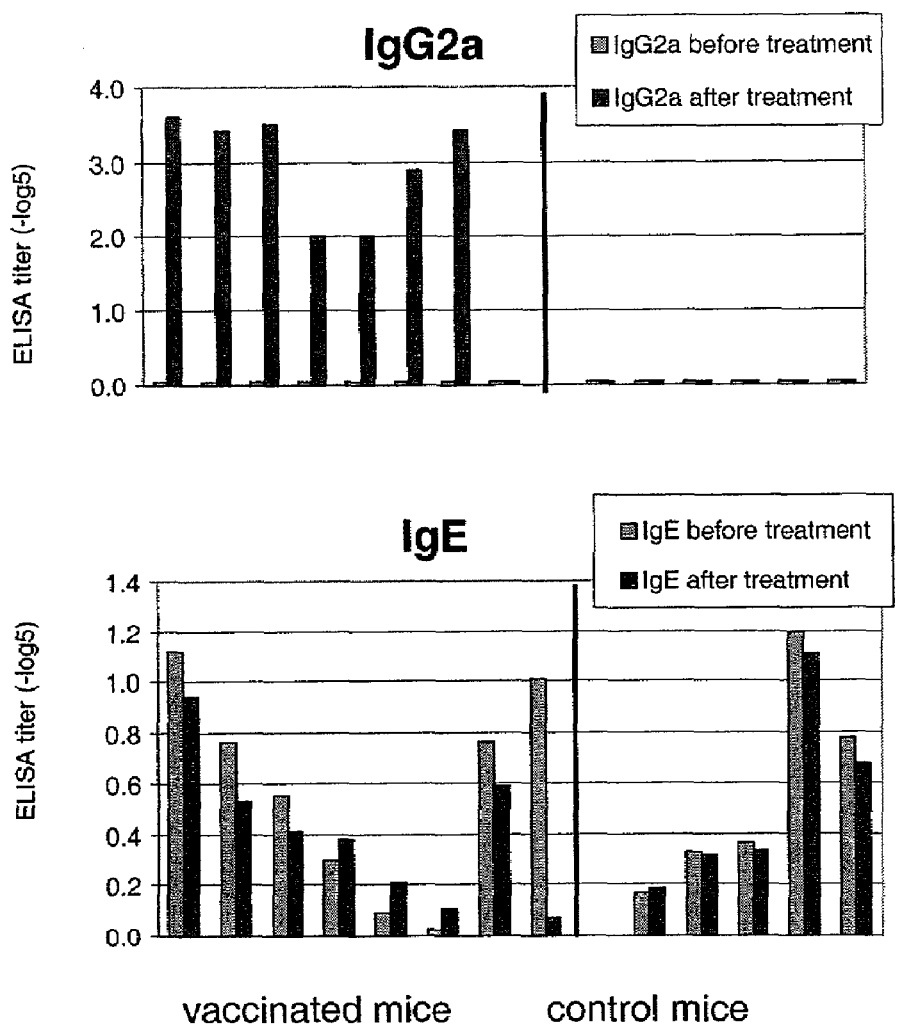

C. Desensitization of Allergic Mice by Vaccination
  Female CBA/J mice (8 weeks old) were sensitized with PLA2: Per mouse, 0.1 ug PLA2 from Latoxan (France) was adsorbed to 1 mg Alum (Imject, Pierce) in a total volume of 66 ul by vortexing for 30 min and then injected subcutaneously. This procedure was repeated every 14 days for a total of four times. This treatment led to the development of PLA2-specific serum IgE but no IgG2a antibodies. 1 month after the last sensitization, mice were injected subcutaneously with 10 ug vaccine consisting of recombinant PLA2 coupled to Qβ capsid protein. One and 2 weeks later they were again treated with the same amount of vaccine. One week after the last treatment, mice were bled and then challenged intraperitoneally with 25 µg PLA2 (Latoxan) and rectal temperature was measured for 60 min using a calibrated digital thermometer. As a control sensitized mice which had not been treated with Qβ capsid protein-PLA2 were used. Whereas all control mice experienced an anaphylactic response reflected in a dramatic drop in rectal temperature after PLA2 challenge, vaccinated mice were fully or at least partially protected. Results are shown in FIG. 25 A.
  B. ELISA
  ELISA plates (Maxisorp, Nunc) were coated with PLA2 (Latoxan) at 5 µg/ml. The plates were blocked and then incubated with serially diluted serum. For the detection of IgE antibodies, serum was pretreated with protein G beads (Pharmacia) for 60 min on a shaker at room temperature. The beads were removed by centrifugation and the supernatant was used for ELISA. Antibodies bound to PLA2 were detected with enzymatically labeled anti-mouse IgG2a or IgE antibodies. ELISA titers were determined at half maximal optical density (OD50%) and expressed as −log5 of 100-fold prediluted sera for IgG2a and as −log5 of 10-fold prediluted sera for IgE. For all mice, PLA2-specific IgG2a and IgE in serum were determined before and at the end of the vaccine treatment. Vaccination led to a dramatic increase of PLA2-specific IgG2a whereas no consistent changes in IgE titers were noted. These results indicate that the vaccination led to an induction of a Th1-like immune response (reflected by the production of IgG2a). Results are shown in FIG. 25B.

The Anaphylactic response in vaccinated and non-vaccinated mice is shown in FIG. 25A.

Mice were sensitized to PLA2 and then treated 3×subcutaneously with 10 ug vaccine consisting of PLA2 coupled to Qβ capsid protein. Control mice were sensitized but not vaccinated. One week after the last vaccination all mice were challenged intraperitoneally with 25 μg PLA2 and the anaphylactic response was monitored by measuring the rectal temperature for 60 min. Whereas all control mice showed a dramatic drop in body temperature, vaccinated mice were fully or at least partially protected from an anaphylactic reaction.

The induction of PLA2-specific IgG2a by vaccination is shown in FIG. 25B.

Mice were sensitized to PLA2 and then treated 3× with 10 ug vaccine consisting of PLA2 coupled to Qβ capsid protein. Control mice were sensitized but not vaccinated. Serum was taken from sensitized mice before the start of the treatment and after completion of treatment, before challenge. In vaccinated mice (left hand of panel) a dramatic increase of PLA2-specific IgG2a was observed.

Example 20

Expression, Refolding, Purification and Coupling of Pla$_2$-Cys (Also Called PLA$_2$ Fusion Protein)

Expression and Preparation of Inclusion Bodies

The pET11a Plasmid containing the PLA$_2$-Cys gene Of example xxx was transformed into *E. coli* BL21DE3Rill (Stratagene). An overnight culture was grown in dYT medium containing 100 μg/ml Ampicillin and 15 μg/ml Chloramphenicol. The culture was diluted in fresh dYT medium containing Ampicillin and Chloramphenicol, and grown at 37° C. until $OD_{600\ nm}=1$ was reached. The culture was induced with 1 mM IPTG, and grown for another 4 hours. Cells were collected by centrifugation, and resuspended in PBS buffer containing 0.5 mg/ml Lysozyme. After incubation on ice, cells were sonicated on ice, and MgCl$_2$ added to a concentration of 10 mM. 6 μl of Benzonase (Merck) were added to the cell lysate, and the lysate was incubated 30 minutes at RT. Triton was added to a final concentration of 1%, and the lysate was further incubated for 30 minutes on ice. The inclusion body (IB) pellet was collected by centrifugation for 10 minutes at 13000 g. The inclusion body pellet was washed in wash buffer containing 20 mM Tris, 23% sucrose, 1 mM EDTA, pH 8.0. The IBs were solubilized in 6 M Guanidinium-HCl, 20 mM Tris, pH 8.0, containing 200 mM DTT. The solubilized IBs were centrifuged at 50000 g and the supernatant dialyzed against 6 M Guanidinium-HCl, 20 mM Tris, pH 8.0 and subsequently against the same buffer containing 0.1 mM DTT. Oxidized glutathion was added to a final concentration of 50 mM, and the solubilized IBs were incubated for 1 h. at RT. The solubilized IBs were dialyzed against 6 M Guanidinium-HCL, 20 mM Tris, pH 8.0. The concentration of the IB solution was estimated by Bradford analysis and SDS-PAGE.

B. Refolding and Purification

The IB solution was added slowly in three portions, every 24 h., to a final concentration of 3 μM, to the refolding buffer containing 2 mM EDTA, 0.2 mM Benzamidin, 0.2 mM 6 aminocapronic acid, 0.2 mM Guanidinium-HCl, 0.4 M L-Arginin, pH 6.8, to which 5 mM reduced Glutathion and 0.5 mM oxidized Glutathion were added prior to initiation of refolding at 4° C. The refolding solution was concentrated to one half of its volume by Ultrafiltration using a YM10 membrane (Millipore) and dialyzed against PBS, pH 7.2, containing 0.1 mM DTT. The protein was further concentrated by ultrafiltration and loaded onto a Superdex G-75 column (Pharmacia) equilibrated in 20 mM Hepes, 150 mM NaCl, 0.1 mM DTT, 4° C. for purification. The pH of the equilibration buffer was adjusted to 7.2 at RT. The monomeric fractions were pooled.

C. Coupling

A solution of 1.5 mg Qβ in 0.75 mL 20 mM Hepes, 150 mM NaCl, pH 7.4 was reacted with 0.06 mL Sulfo-SMPB (Pierce; 31 mM Stock in H2O) for 45 min. at RT. The reaction mixture was dialyzed overnight against 20 mM Hepes, 150 mM NaCl, pH 7.4 and 0.75 mL of this solution were mixed with 1.5 mL of a PLA$_2$-Cys solution in 0.1 mM DTT (62 μM) and 0.43 mL of 20 mM Hepes, 150 mM NaCl, 137 μM DTT, pH 7.4 adjusted at RT. The coupling reaction was left to proceed for 4 h. at RT, and the reaction mixture was dialyzed overnight against 20 mM Hepes, 150 mM NaCl, pH 7.4 using Spectra Por dialysis tubing, MW cutoff 300 000 Da (Spectrum). The coupling reaction was analyzed by SDS-PAGE and coomassie staining, and Western blotting, using either a rabbit anti-bee venom antiserum (diluted 1:10000), developed with a goat anti-rabbit alkaline phosphatase conjugate (diluted 1:10000), or a rabbit anti-Qβ antiserum (1:5000), developed with a goat anti-rabbit alkaline phosphatase conjugate (diluted 1:10000). Samples were run in both cases under reducing conditions.

Figure 26:
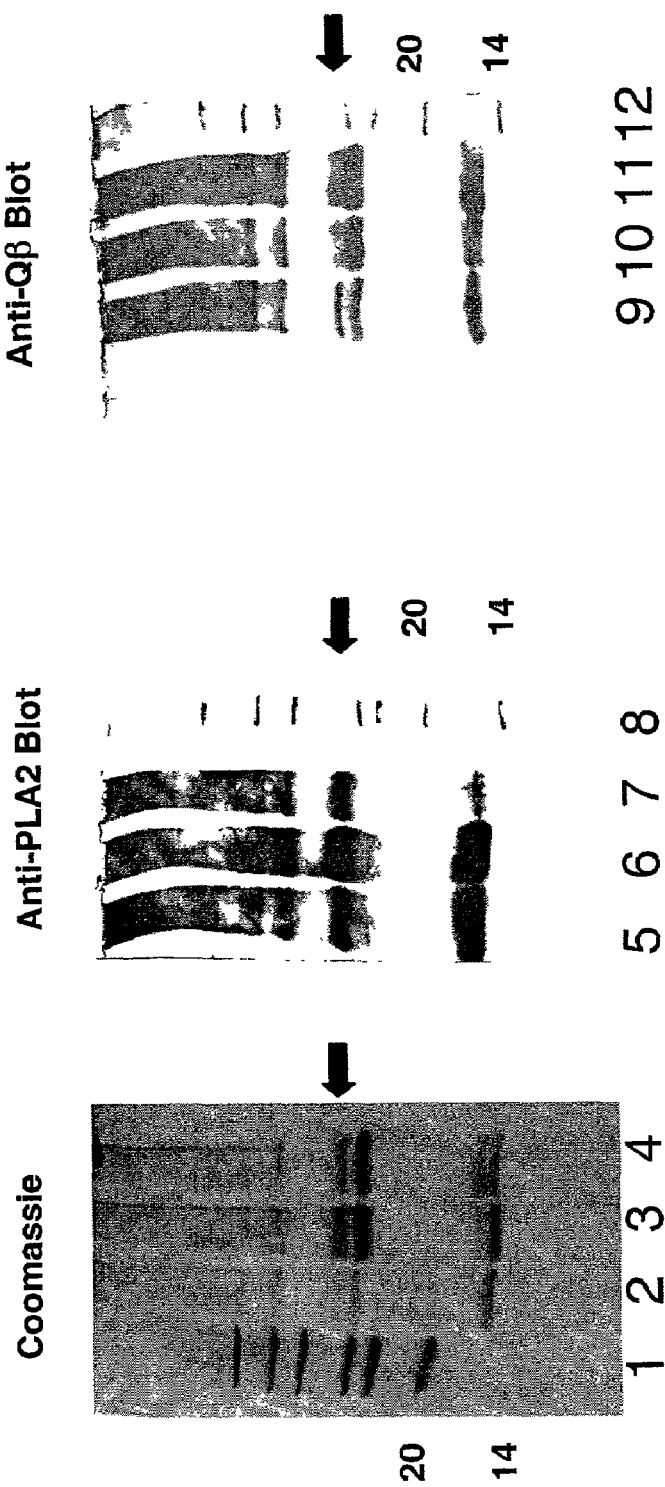

The result of the coupling reaction is shown in FIG. 26. Bands corresponding to the coupling product of Qβ capsid protein to PLA$_2$-Cys are clearly visible in the coomassie stained SDS-PAGE (left panel), the anti-Qβ Western Blot (center panel) and the anti-PLA2 Western blot (right panel) of the coupling reactions between Qβ capsid protein and PLA$_2$-Cys, and are indicated by an arrow in the figure. 15 μl of the coupling reactions and 50 μl of the dialyzed coupling reactions were loaded on the gel.

Lane 1: Protein marker. 2: Dialyzed coupling reaction 1. 3: Coupling reaction 1. 4: Coupling reaction 2. 5: coupling reaction 2. 6: Coupling reaction 1. 7: Dialyzed coupling reaction 1. 8: Protein Marker. 9: Coupling reaction 2. 10: Coupling reaction 1. 11: Dialyzed coupling reaction 1. 12: Protein Marker.

Example 21

Coupling of Anti-Idiotypic IgE Mimobody VAE051 to Qβ, Immunization of Mice and Testing of Antisera A solution of 4.0 mg/ml Qβ capsid protein in 20 mM Hepes, 150 mM NaCl pH 7.2 was reacted for 30 minutes with 10 fold molar excess SMPH (Pierce) (from a 100 mM stock solution dissolved in DMSO) at 25° C. on a rocking shaker. The reaction solution was subsequently dialyzed twice for 2 hours against 2 l of 20 mM Hepes, 150 mM NaCl, pH 7.2 at 4° C. The VAEO5 1 solution (2.4 mg/ml) was reduced with an equimolar concentration of TCEP for 60 min at 25° C.

46 μl of the dialyzed Qβ reaction mixture was then reacted with 340 μl of the TCEP-treated VAE051 solution (2.4 mg/ml) in a total volume of 680 μl of 50 mM sodium acetate buffer at 16° C. for 2 h on a rocking shaker.

Figure 28:
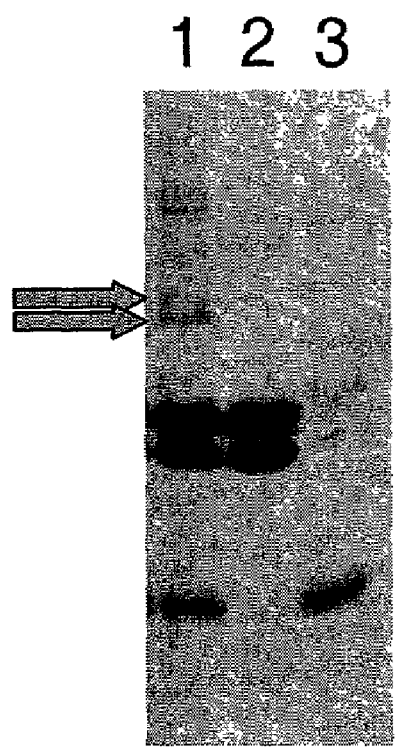
Figure 28:
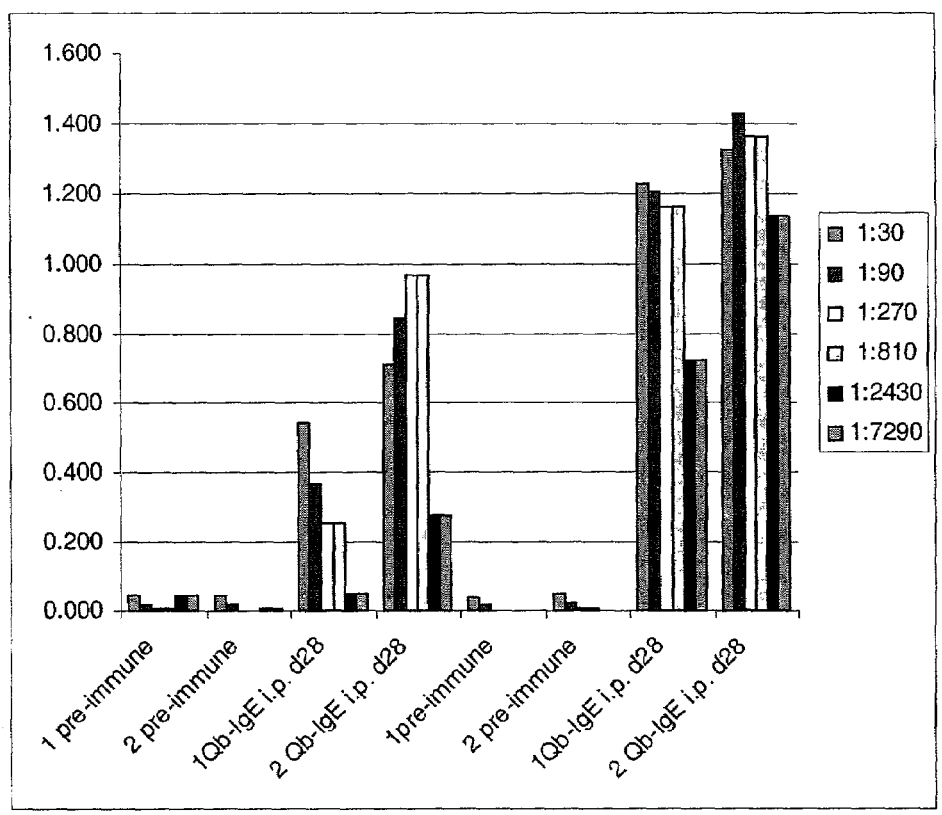

The reaction products were analysed on 16% SDS-PAGE gels under reducing conditions. Gels were either stained with Coomassie Brilliant Blue. The two additional band in the coupling reactions (which are absent in VAE or Qβ solutions) represent the heavy chain and the light chain of the VAE051 coupled to Qβ (FIG. 28 A). Identity of the bands were confirmed by Western blotting with antibodies specific for heavy and light chains, respectively.

Immunization of Mice

The Qβ-VAE051 coupling solution was dialysed against 20 mM Hepes, 150 mM NaCl, pH 7.2 using a membrane with a cut-off of 300000 Da. 50 µg of the Qβ-VAE051 were injected intraperitoneal in two female Balb/c mice at day 0 and day 14. Mice were bled retroorbitally on day 28 and their serum was analyzed using IgE- and VAE051-specific ELISAs.

ELISA

ELISA plates were coated with human IgE at a concentration of 0.8 µg/ml or with 10 µg/ml VAE051. The plates were blocked and then incubated with serially diluted mouse sera. Bound antibodies were detected with enzymatically labeled anti-mouse IgG antibody (FIG. 28B).

Both mice showed high reactivity to VAE051 as well as the human IgE. Preimmune sera of the same mice did not show any reactivity against VAE051 and IgE (FIG. 28B). This demonstrates that antibodies against the anti-idiotypic IgE mimobody VAE051 have been produced which also recognize the "parent" molecule IgE.

Example 22

High Occupancy Coupling of DerpI Peptide to wt Qβ Capsid Protein Using the Cross-linker SMPH The Derp 1,2 peptide, to which a cysteine was added N-terminally for coupling, was chemically synthesized and had the following sequence: H2N-CQIYPPNANKIRE-ALAQTHSA-COOH (SEQ ID NO:385). This peptide was used for chemical coupling to wt Qβ capsid protein and as described in the following.

D. Coupling of Flag peptide to Qβ Capsid Protein

Qβ capsid protein in 20 mM Hepes, 150 mM NaCl, pH 7.2, at a concentration of 2 mg/ml, was reacted with a 5- or 20-fold excess of the cross-linker SMPH (Pierce) for 30 min. at 25° C. on a rocking shaker. The reaction solution was subsequently dialyzed twice for 2 hours against 2 L of 20 mM Hepes, 150 mM NaCl, pH 7.2 at 4° C. The dialyzed reaction mixture was then reacted with a 5-fold excess of Derp 1,2 peptide for two hours at 25° C. on a rocking shaker.

Figure 24:
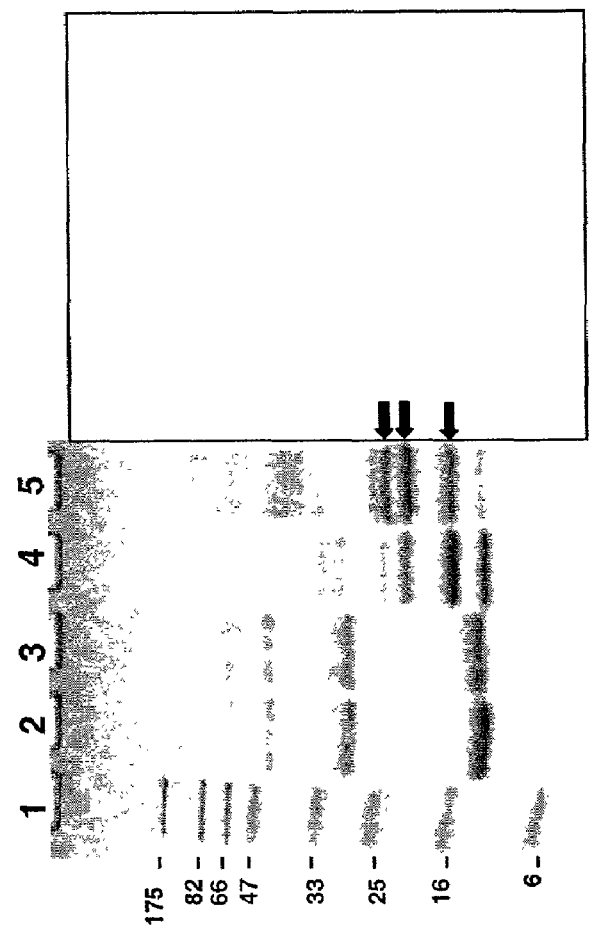

The result of the coupling reaction can be seen on FIG. 24. Coupling bands corresponding to 1, 2 and 3 peptides per subunit, respectively, are clearly visible on the gel, and are indicated by arrows. An average of two peptides per subunit were displayed on the capsid.

The samples loaded on the gel of FIG. 24 were the following:

Lane 1: Protein Marker. 2: Qβ capsid protein derivatized with a 5-fold excess of SMPH. 3: Qβ capsid protein derivatized with a 20-fold excess of SMPH. 4: Coupling reaction of 5-fold derivatized Qβ capsid protein. 5: Coupling reaction of 20-fold derivatized Qβ capsid protein.

Example 23

Insertion of a Peptide Containing a Lysine Residue Into the c/e1 Epitope of HBcAg(1–149)

The c/e1 epitope (residues 72 to 88) of HBcAg is located in the tip region on the surface of the Hepatitis B virus capsid (HBcAg). A part of this region (Proline 79 and Alanine 80) was genetically replaced by the peptide Gly-Gly-Lys-Gly-Gly (HBcAg-Lys construct; SEQ ID NO:406). The introduced Lysine residue contains a reactive amino group in its side chain that can be used for intermolecular chemical crosslinking of HBcAg particles with any antigen containing a free cysteine group.

HBcAg-Lys DNA, having the amino acid sequence shown in SEQ ID NO:158, was generated by PCRs: The two fragments encoding HBcAg fragments (amino acid residues 1 to 78 and 81 to 149) were amplified separately by PCR. The primers used for these PCRs also introduced a DNA sequence encoding the Gly-Gly-Lys-Gly-Gly (SEQ ID NO:406) peptide. The HBcAg (1 to 78) fragment was amplified from pEco63 using primers EcoRIHBcAg(s) and Lys-HBcAg(as). The HBcAg (81 to 149) fragment was amplified from pEco63 using primers Lys-HBcAg(s) and HBcAg(1–149)Hind(as). Primers Lys-HBcAg(as) and Lys-HBcAg(s) introduced complementary DNA sequences at the ends of the two PCR products allowing fusion of the two PCR products in a subsequent assembly PCR. The assembled fragments were amplified by PCR using primers EcoRIHBcAg(s) and HbcAg(1–149)Hind(as).

For the PCRs, 100 pmol of each oligo and 50 ng of the template DNAs were used in the 50 ml reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (1 minute), 50° C. (1 minute), 72° C. (2 minutes).

```
Primer sequences:
EcoRIHBcAg(s):
(5'-CCGGAATTCATGGACATTGACCCTTATAAAG-3');                              (SEQ ID NO:79)

Lys-HBcAg(as):
(5'-CCTAGAGCCACCTTTGCCACCATCTTCTAAATTAGTACCCACCCAGGTAGC-3');          (SEQ ID NO:80)

Lys-HBcAg(s):
(5'-GAAGATGGTGGCAAAGGTGGCTCTAGGGACCTAGTAGTCAGTTATGTC-3');             (SEQ ID NO:81)

HBcAg(1-149)Hind(as):
(5'-CGCGTCCCAAGCTTCTAAACAACAGTAGTCTCCGGAAG-3').                       (SEQ ID NO:82)
```

For fusion of the two PCR fragments by PCR 100 pmol of primers EcoRIHBcAg(s) and HBcAg(1–149)Hind(as) were used with 100 ng of the two purified PCR fragments in a 50 ml reaction mixture containing 2 units of Pwo polymerase, 0.1 mM dNTPs and 2 mM MgSO$_4$. PCR cycling conditions were: 94° C. for 2 minutes; 30 cycles of 94° C.

(1 minute), 50° C. (1 minute), 72° C. (2 minutes). The assembled PCR product was analyzed by agarose gel electrophoresis, purified and digested for 19 hours in an appropriate buffer with EcoRI and HindIII restriction enzymes. The digested DNA fragment was ligated into EcoRI/HindIII-digested pKK vector to generate pKK-HBcAg-Lys expression vector. Insertion of the PCR product into the vector was analyzed by EcoRI/HindIII restriction analysis and DNA sequencing of the insert.

Example 24

Expression and Partial Purification of HBcAg-Lys

E. coli strain XL-1 blue was transformed with pKK-HBcAg-Lys. 1 ml of an overnight culture of bacteria was used to innoculate 100 ml of LB medium containing 100 µg/ml ampicillin. This culture was grown for 4 hours at 37° C. until an OD at 600 nm of approximately 0.8 was reached. Induction of the synthesis of HBcAg-Lys was performed by addition of IPTG to a final concentration of 1 mM. After induction, bacteria were further shaken at 37° C. for 16 hours. Bacteria were harvested by centrifugation at 5000×g for 15 minutes. The pellet was frozen at −20° C. The pellet was thawed and resuspended in bacteria lysis buffer (10 mM $Na_2HPO_4$, pH 7.0, 30 mM NaCl, 0.25% Tween-20, 10 mM EDTA, 10 mM DTT) supplemented with 200 µg/ml lysozyme and 10 µl of Benzonase (Merck). Cells were incubated for 30 minutes at room temperature and disrupted using a French pressure cell. Triton X-100 was added to the lysate to a final concentration of 0.2%, and the lysate was incubated for 30 minutes on ice and shaken occasionally. E. coli cells harboring pKK-HBcAg-Lys expression plasmid or a control plasmid were used for induction of HBcAg-Lys expression with IPTG. Prior to the addition of IPTG, a sample was removed from the bacteria culture carrying the pKK-HBcAg-Lys plasmid and from a culture carrying the control plasmid. Sixteen hours/after addition of IPTG, samples were again removed from the culture containing pKK-HBcAg-Lys and from the control culture. Protein expression was monitored by SDS-PAGE followed by Coomassie staining.

The lysate was then centrifuged for 30 minutes at 12,000×g in order to remove insoluble cell debris. The supernatant and the pellet were analyzed by Western blotting using a monoclonal antibody against HBcAg (YVS1841, purchased from Accurate Chemical and Scientific Corp., Westbury, N.Y., USA), indicating that a significant amount of HBcAg-Lys protein was soluble. Briefly, lysates from E. coli cells expressing HBcAg-Lys and from control cells were centrifuged at 14,000×g for 30 minutes. Supernatant (=soluble fraction) and pellet (=insoluble fraction) were separated and diluted with SDS sample buffer to equal volumes. Samples were analyzed by SDS-PAGE followed by Western blotting with anti-HBcAg monoclonal antibody YVS 1841.

The cleared cell lysate was used for step-gradient centrifugation using a sucrose step gradient consisting of a 4 ml 65% sucrose solution overlaid with 3 ml 15% sucrose solution followed by 4 ml of bacterial lysate. The sample was centrifuged for 3 hrs with 100,000×g at 4° C. After centrifugation, 1 ml fractions from the top of the gradient were collected and analyzed by SDS-PAGE followed by Coomassie staining. The HBcAg-Lys protein was detected by Coomassie staining.

The HBcAg-Lys protein was enriched at the interface between 15 and 65% sucrose indicating that it had formed a capsid particle. Most of the bacterial proteins remained in the sucrose-free upper layer of the gradient, therefore step-gradient centrifugation of the HBcAg-Lys particles led both to enrichment and to a partial purification of the particles.

Example 25

Chemical Coupling of FLAG Peptide to HbcAg-Lys Using the Heterobifunctional Cross-linker SPDP Synthetic FLAG peptide with a Cysteine residue at its amino terminus (amino acid sequence CGGDYKDDDDK (SEQ ID NO:147)) was coupled chemically to purified HBcAg-Lys particles in order to elicit an immune response against the FLAG peptide. 600 ml of a 95% pure solution of HBcAg-Lys particles (2 mg/ml) were incubated for 30 minutes at room temperature with the heterobifunctional cross-linker N-Succinimidyl 3-(2-pyridyldithio) propionate (SPDP) (0.5 mM). After completion of the reaction, the mixture was dialyzed overnight against 1 liter of 50 mM Phosphate buffer (pH 7.2) with 150 mM NaCl to remove free SPDP. Then 500 ml of derivatized HBcAg-Lys capsid (2 mg/ml) were mixed with 0.1 mM FLAG peptide (containing an amino-terminal cysteine) in the presence of 10 mM EDTA to prevent metal-catalyzed sulfhydryl oxidation. The reaction was monitored through the increase of the optical density of the solution at 343 nm due to the release of pyridine-2-thione from SPDP upon reaction with the free cysteine of the peptide. The reaction of derivatized Lys residues with the peptide was complete after approximately 30 minutes.

The FLAG decorated particles were injected into mice.

Example 26

Construction of pMPSV-gp140cys

The gp140 gene was amplified by PCR from pCytTSgp140FOS using oligos gp140CysEcoRI and SalIgp140. For the PCRs, 100 pmol of each oligo and 50 ng of the template DNAs were used in the 50 ml reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (0.5 minutes), 55° C. (0.5 minutes), 72° C. (2 minutes).

The PCR product was purified using QiaEXII kit, digested with SalI/EcoRI and ligated into vector pMPSVHE cleaved with the same enzymes.

```
Oligo
sequences:
Gp140CysEcoRI:                  (SEQ ID NO:83)
5'-GCCGAATTCCTAGCAGCTAGCACCGAATTTATCTAA-3';

SalIgp140:                      (SEQ ID NO:84)
5'- GGTTAAGTCGACATGAGAGTGAAGGAGAAATAT-3'.
```

Example 27

Expression of pMPSVgp140Cys pMPSVgp140Cys (20 µg) was linearized by restriction digestion. The reaction was stopped by phenol/chloroform extraction, followed by an isopropanol precipitation of the linearized DNA. The restriction digestion was evaluated by agarose gel electrophoresis. For the transfection, 5.4 µg of linearized pMPSVgp140-Cys was mixed with 0.6 µg of linearized pSV2Neo in 30 µl H$_2$O and 30 µl of 1 M CaCl$_2$ solution was added. After addition of 60 µl phosphate buffer (50 mM HEPES, 280 mM NaCl, 1.5 mM Na$_2$ HPO$_4$, pH 7.05), the solution was vortexed for 5 seconds, followed by an incubation at room temperature for 25 seconds. The solution was immediately added to 2 ml HP-1 medium containing 2% FCS (2% FCS medium). The medium of an 80% confluent BHK21 cell culture (6-well plate) was then replaced by the DNA containing medium. After an incubation for 5 hours at 37° C. in a CO$_2$ incubator, the DNA containing medium was removed and replaced by 2 ml of 15% glycerol in 2% FCS medium. The glycerol containing medium was removed after a 30 second incubation phase, and the cells were washed by rinsing with 5 ml of HP-1 medium containing 10% FCS. Finally 2 ml of fresh HP-1 medium containing 10% FCS was added.

Stably transfected cells were selected and grown in selection medium (HP-1 medium supplemented with G418) at 37° C. in a CO$_2$ incubator. When the mixed population was grown to confluency, the culture was split to two dishes, followed by a 12 h growth period at 37° C. One dish of the cells was shifted to 30° C. to induce the expression of soluble GP140-FOS. The other dish was kept at 37° C.

The expression of soluble GP140-Cys was determined by Western blot analysis. Culture media (0.5 ml) was methanol/chloroform precipitated, and the pellet was resuspended in SDS-PAGE sample buffer. Samples were heated for 5 minutes at 95° C. before being applied to a 15% acrylamide gel. After SDS-PAGE, proteins were transferred to Protan nitrocellulose membranes (Schleicher & Schuell, Germany) as described by Bass and Yang, in Creighton, T. E., ed., *Protein Function: A Practical Approach*, 2nd Edn., IRL Press, Oxford (1997), pp. 29–55. The membrane was blocked with 1% bovine albumin (Sigma) in TBS (10×TBS per liter: 87.7 g NaCl, 66.1 g Trizma hydrochloride (Sigma) and 9.7 g Trizma base (Sigma), pH 7.4) for 1 hour at room temperature, followed by an incubation with an anti-GP140 or GP-160 antibody for 1 hour. The blot was washed 3 times for 10 minutes with TBS-T (TBS with 0.05% Tween20), and incubated for 1 hour with an alkaline-phosphatase-antimouse/rabbit/monkey/human IgG conjugate. After washing 2 times for 10 minutes with TBS-T and 2 times for 10 minutes with TBS, the development reaction was carried out using alkaline phosphatase detection reagents (10 ml AP buffer (100 mM Tris/HCl, 100 mM NaCl, pH 9.5) with 50 µl NBT solution (7.7% Nitro Blue Tetrazolium (Sigma) in 70% dimethylformamide) and 37 µl of X-Phosphate solution (5% of 5-bromo-4-chloro-3-indolyl phosphate in dimethylformamide).

Example 28

Purification of gp140Cys

An anti-gp120 antibody was covalently coupled to a NHS/EDC activated dextran and packed into a chromatography column. The supernatant, containing GP140Cys is loaded onto the column and after sufficient washing, GP140Cys was eluted using 0.1 M HCl. The eluate was directly neutralized during collection using 1 M Tris pH 7.2 in the collection tubes.

Disulfide bond formation might occur during purification, therefore the collected sample is treated with 10 mM DTT in 10 mM Tris pH 7.5 for 2 hours at 25° C.

DTT is remove by subsequent dialysis against 10 mM Mes; 80 mM NaCl pH 6.0. Finally GP140Cys is mixed with alphavirus particles containing the JUN residue in E2 as described in Example 16.

Example 29

Construction of PLA$_2$-Cys

The PLA$_2$ gene was amplified by PCR from pAV3PLAfos using oligos EcoRIPLA and PLA-Cys-hind. For the PCRs, 100 pmol of each oligo and 50 ng of the template DNAs were used in the 50 ml reaction mixtures with 2 units of Pwo polymerase, 0.1 mM dNTPs and 2 mM MgSO$_4$. For the reaction, temperature cycling was carried out as follows: 94° C. for 2 minutes; 30 cycles of 94° C. (0.5 minutes), 55° C. (0.5 minutes), 72° C. (2 minutes).

The PCR product was purified using QiaEXII kit, digested with EcoRI/HindIII and ligated into vector pAV3 cleaved with the same enzymes.

```
Oligos
EcoRIPLA:                              (SEQ ID NO:85)
5'-TAACCGAATTCAGGAGGTAAAAAGATATGG-3'

PLA Cys-hind:                          (SEQ ID NO:86)
5'-GAAGTAAAGCTTTTAACCACCGCAACCACCAGAAG-3'.
```

Example 30

Expression and Purification of PLA$_2$-Cys

For cytoplasmic production of Cys tagged proteins, *E. coli* XL-1-Blue strain was transformed with the vectors pAV3::PLA and pPLA-Cys. The culture was incubated in rich medium in the presence of ampicillin at 37° C. with shaking. At an optical density (550 nm) of, 1 mM IPTG was added and incubation was continued for another 5 hours. The cells were harvested by centrifugation, resuspended in an appropriate buffer (e.g., Tris-HCl, pH 7.2, 150 mM NaCl) containing DNase, RNase and lysozyme, and disrupted by passage through a french pressure cell. After centrifugation (Sorvall RC-5C, SS34 rotor, 15000 rpm, 10 min, 4° C.), the pellet was resuspended in 25 ml inclusion body wash buffer (20 mM tris-HCl, 23% sucrose, 0.5% Triton X-100, 1 mM EDTA, pH 8) at 4° C. and recentrifuged as described above. This procedure was repeated until the supernatant after centrifugation was essentially clear. Inclusion bodies were resuspended in 20 ml solubilization buffer (5.5 M guanidinium hydrochloride, 25 mM tris-HCl, pH 7.5) at room temperature and insoluble material was removed by centrifugation and subsequent passage of the supernatant through a sterile filter (0.45 µm). The protein solution was kept at 4° C. for at least 10 hours in the presence of 10 mM EDTA and 100 mM DTT and then dialyzed three times against 10 volumes of 5.5 M guanidinium hydrochloride, 25 mM tris-HCl, 10 mM EDTA, pH 6. The solution was dialyzed twice against 51 2 M urea, 4 mM EDTA, 0.1 M NH$_4$Cl, 20 mM sodium borate (pH 8.3) in the presence of an appropriate redox shuffle (oxidized glutathione/reduced glutathione; cystine/cysteine). The refolded protein was then applied to an ion exchange chromatography. The protein was stored in an appropriate buffer with a pH above 7 in the presence of 2–10 mM DTT to keep the cysteine residues in a reduced form. Prior to coupling of the protein with the

Example 31

Construction of a HBcAg Devoid of Free Cysteine Residues and Containing an Inserted Lysine Residue A Hepatitis core Antigen (HBcAg), referred to herein as HBcAg-lys-2cys-Mut, devoid of cysteine residues at positions corresponding to 48 and 107 in SEQ ID NO:134 and containing an inserted lysine residue was constructed using the following methods.

The two mutations were introduced by first separately amplifying three fragments of the HBcAg-Lys gene prepared as described above in Example 23 with the following PCR primer combinations. PCR methods essentially as described in Example 1 and conventional cloning techniques were used to prepare the HBcAg-lys-2cys-Mut gene.

In brief, the following primers were used to prepare fragment 1:

```
In brief, the following primers were used to
prepare fragment 1:
Primer 1: EcoRIHBcAg(s)           (SEQ ID NO:148)
CCGGAATTCATGGACATTGACCCTTATAAAG Primer 2: 48as                    (SEQ ID NO:149)
GTGCAGTATGGTGAGGTGAGGAATGCTCAGGAGACTC The following primers were used to prepare fra-
gment 2:
Primer 3: 48s                     (SEQ ID NO:150)
GSGTCTCCTGAGCATTCCTCACCTCACCATACTGCAC Primer 4: 107as                   (SEQ ID NO:151)
CTTCCAAAAGTGAGGGAAGAAATGTGAAACCAC The following primers were used to prepare fra-
gment 3:
Primer 5: HBcAg149hind-as         (SEQ ID NO:152)
CGCGTCCCAAGCTTCTAAACAACAGTAGTCTCCGGAAGCGTTGATA
G Primer 6: 107s                    (SEQ ID NO:153)
GTGGTTTCACATTTCTTCCCTCACTTTTGGAAG
```

Fragments 1 and 2 were then combined with PCR primers EcoRIHBcAg(s) and 107 as to give fragment 4. Fragment 4 and fragment 3 were then combined with primers EcoRIHBcAg(s) and HBcAg149hind-as to produce the full length gene. The full length gene was then digested with the EcoRI (GAATTC) and HindIII (AAGCTT) enzymes and cloned into the pKK vector (Pharmacia) cut at the same restriction sites.

Example 32

Blockage of Free Cysteine Residues of a HBcAg Followed by Cross-linking

The free cysteine residues of the HBcAg-Lys prepared as described above in Example 23 were blocked using Iodacetamide. The blocked HBcAg-Lys was then cross-linked to the FLAG peptide with the hetero-bifunctional cross-linker m-maleimidonbenzoyl-N-hydroxysuccinimide ester (Sulfo-MBS).

The methods used to block the free cysteine residues and cross-link the HBcAg-Lys are as follows. HBcAg-Lys (550 µg/ml) was reacted for 15 minutes at room temperature with Iodacetamide (Fluka Chemie, Brugg, Switzerland) at a concentration of 50 mM in phosphate buffered saline (PBS) (50 mM sodium phosphate, 150 mM sodium chloride), pH 7.2, in a total volume of 1 ml. The so modified HBcAg-Lys was then reacted immediately with Sulfo-MBS (Pierce) at a concentration of 330 µM directly in the reaction mixture of step 1 for 1 hour at room temperature. The reaction mixture was then cooled on ice, and dialyzed against 1000 volumes of PBS pH 7.2. The dialyzed reaction mixture was finally reacted with 300 µM of the FLAG peptide (CGGDYKD-DDDK (SEQ ID NO:147)) containing an N-terminal free cysteine for coupling to the activated HBcAg-Lys, and loaded on SDS-PAGE for analysis.

The resulting patterns of bands on the SDS-PAGE gel showed a clear additional band migrating slower than the control HBcAg-Lys derivatized with the cross-linker, but not reacted with the FLAG peptide. Reactions done under the same conditions without prior derivatization of the cysteines with Iodacetamide led to complete cross-linking of monomers of the HBcAg-Lys to higher molecular weight species.

Example 33

Isolation and Chemical Coupling of FLAG Peptide to Type-1 Pili of *Escherichia coli* Using a Heterobifunctional Cross-linker A. Introduction Bacterial pili or fimbriae are filamentous surface organelles produced by a wide range of bacteria. These organelles mediate the attachment of bacteria to surface receptors of host cells and are required for the establishment of many bacterial infections like cystitis, pyelonephritis, new born meningitis and diarrhea.

Pili can be divided in different classes with respect to their receptor specificity (agglutination of blood cells from different species), their assembly pathway (extracellular nucleation, general secretion, chaperone/usher, alternate chaperone) and their morphological properties (thick, rigid pili; thin, flexible pili; a typical structures including capsule; curli; etc). Examples of thick, rigid pili forming a right handed helix that are assembled via the so called chaperone/usher pathway and mediate adhesion to host glycoproteins include Type-1 pili, P-pili, S-pili, F1C-pili, and 987P-pili). The most prominent and best characterized members of this class of pili are P-pili and Type-1 pili (for reviews on adhesive structures, their assembly and the associated diseases see Soto, G. E. & Hultgren, S. J., *J. Bacteriol.* 181:1059–1071 (1999); Bullitt & Makowski, *Biophys. J.* 74:623–632 (1998); Hung, D. L. & Hultgren, S. J., *J. Struct, Biol.* 124:201–220 (1998)).

Type-1 pili are long, filamentous polymeric protein structures on the surface of *E. coli*. They possess adhesive properties that allow for binding to mannose-containing receptors present on the surface of certain host tissues. Type-1 pili can be expressed by 70–80% of all *E. coli* isolates and a single *E. coli* cell can bear up to 500 pili. Type-pili reach a length of typically 0.2 to 2 µM with an average number of 1000 protein subunits that associate to a right-handed helix with 3.125 subunits per turn with a diameter of 6 to 7 nm and a central hole of 2.0 to 2.5 nm.

The main Type-1 pilus component, FimA, which represents 98% of the total pilus protein, is a 15.8 kDa protein. The minor pilus components FimF, FimG and FimH are incorporated at the tip and in regular distances along the pilus shaft (Klemm, P. & Krogfelt, K. A., "Type I fimbriae of *Escherichia coli*," in: Fimbriae. Klemm, P. (ed.), CRC Press Inc., (1994) pp. 9–26). FimH, a 29.1 kDa protein, was shown to be the mannose-binding adhesin of Type-1 pili (Krogfelt, K. A., et al., *Infect. Immun.* 58:1995–1998 (1990); Klemm, P., et al., *Mol. Microbiol.* 4:553–560 (1990); Hanson, M. S. & Brinton, C. C. J., *Nature* 17:265–268 (1988)), and its incorporation is probably facilitated by FimG and FimF (Klemm, P. & Christiansen, G., *Mol. Gen. Genetics* 208:439–445 (1987); Russell, P. W. & Orndorff, P. E., *J. Bacteriol.* 174:5923–5935 (1992)). Recently, it was shown that FimH might also form a thin tip-fibrillum at the end of the pili (Jones, C. H., et al., *Proc. Nat. Acad. Sci. USA* 92:2081–2085 (1995)). The order of major and minor components in the individual mature pili is very similar, indicating a highly ordered assembly process (Soto, G. E. & Hultgren, S. J., *J. Bacteriol.* 181:1059–1071 (1999)).

P-pili of *E. coli* are of very similar architecture, have a diameter of 6.8 nm, an axial hole of 1.5 nm and 3.28 subunits per turn (Bullitt & Makowski, *Biophys. J.* 74:623–632 (1998)). The 16.6 kDa PapA is the main component of this pilus type and shows 36% sequence identity and 59% similarity to FimA (see Table 1). As in Type-1 pili the 36.0 kDa P-pilus adhesin PapG and specialized adapter proteins make up only a tiny fraction of total pilus protein. The most obvious difference to Type-1 pili is the absence of the adhesin as an integral part of the pilus rod, and its exclusive localization in the tip fibrillium that is connected to the pilus rod via specialized adapter proteins that Type-1 pili lack (Hultgren, S. J., et al., *Cell* 73:887–901 (1993)).

TABLE 1

Similarity and identity between several structural pilus proteins of Type-1 and P-pili (in percent). The adhesins were omitted.

| Identity | Similarity | | | | | | | | |
|---|---|---|---|---|---|---|---|---|---|
| | FimA | PapA | FimI | FimF | FimG | PapE | PapK | PapH | PapF |
| FimA | | 59 | 57 | 56 | 44 | 50 | 44 | 46 | 46 |
| PapA | 36 | | 49 | 48 | 41 | 45 | 49 | 49 | 47 |
| FimI | 35 | 31 | | 56 | 46 | 40 | 47 | 48 | 48 |
| FimF | 34 | 26 | 30 | | 40 | 47 | 43 | 49 | 48 |
| FimG | 28 | 28 | 28 | 26 | | 39 | 39 | 41 | 45 |
| PapE | 25 | 23 | 18 | 28 | 22 | | 43 | 47 | 54 |
| PapK | 24 | 29 | 25 | 28 | 22 | 18 | | 49 | 53 |
| PapH | 22 | 26 | 22 | 22 | 23 | 24 | 23 | | 41 |
| PapF | 18 | 22 | 22 | 24 | 28 | 27 | 26 | 21 | |

Type-1 pili are extraordinary stable hetero-oligomeric complexes. Neither SDS-treatment nor protease digestions, boiling or addition of denaturing agents can dissociate Type-1 pili into their individual protein components. The combination of different methods like incubation at 100° C. at pH 1.8 was initially found to allow for the depolymerization and separation of the components (Eshdat, Y., et al., *J. Bacteriol.* 148:308–314 (1981); Brinton, C. C. J., *Trans, N.Y. Acad. Sci.* 27:1003–1054 (1965); Hanson, A. S., et al., *J. Bacteriol.*, 170:3350–3358 (1988); Klemm, P. & Krogfelt, K. A., "Type I fimbriae of *Escherichia coli*," in: Fimbriae. Klemm, P. (ed.), CRC Press Inc., (1994) pp. 9–26). Interestingly, Type-1 pili show a tendency to break at positions where FimH is incorporated upon mechanical agitation, resulting in fragments that present a FimH adhesin at their tips. This was interpreted as a mechanism of the bacterium to shorten pili to an effective length under mechanical stress (Klemm, P. & Krogfelt, K. A., "Type I fimbriae of *Escherichia coli*," in: Fimbriae. Klemm, P. (ed.), CRC Press Inc., (1994) pp. 9–26). Despite their extraordinary stability, Type-1 pili have been shown to unravel partially in the presence of 50% glycerol; they lose their helical structure and form an extended and flexible, 2 nm wide protein chain (Abraham, S. N., et al., *J. Bacteriol.* 174:5145–5148 (1992)).

P-pili and Type-1 pili are encoded by single gene clusters on the *E. coli* chromosome of approximately 10 kb (Klemm, P. & Krogfelt, K. A., "Type I fimbriae of *Escherichia coli*," in: Fimbriae. Klemm, P. (ed.), CRC Press Inc., (1994) pp. 9–26; Orndorff, P. E. & Falkow, S., *J. Bacteriol.* 160:61–66 (1984)). A total of nine genes are found in the Type-1 pilus gene cluster, and 11 genes in the P-pilus cluster (Hultgren, S. J., et al., *Adv. Prot. Chem.* 44:99–123 (1993)). Both clusters are organized quite similarly.

The first two fim-genes, fimB and fimE, code for recombinases involved in the regulation of pilus expression (McClain, M. S., et al., *J. Bacteriol.* 173:5308–5314 (1991)). The main structural pilus protein is encoded by the next gene of the cluster, fimA (Klemm, P., *Euro. J. Biochem.* 143:395–400 (1984); Orndorff, P. E. & Falkow, S., *J. Bacteriol.* 160:61–66 (1984); Orndorff, P. E. & Falkow, S., *J. Bacteriol.* 162:454–457 (1985)). The exact role of fimI is unclear. It has been reported to be incorporated in the pilus as well (Klemm, P. & Krogfelt, K. A., "Type I fimbriae of *Escherichia coli*," in: Fimbriae. Klemm, P. (ed.), CRC Press Inc., (1994) pp. 9–26). The adjacent fimC codes not for a structural component of the mature pilus, but for a so-called pilus chaperone that is essential for the pilus assembly (Klemm, P., *Res. Microbiol.* 143:831–838 (1992); Jones, C. H., et al., *Proc. Nat. Acad. Sci. USA* 90:8397–8401 (1993)).

The assembly platform in the outer bacterial membrane to which the mature pilus is anchored is encoded by fimD (Klemm, P. & Christiansen, G., *Mol. Gen, Genetics* 220:334–338 (1990)). The three minor components of the Type-1 pili, FimF, FimG and FimH are encoded by the last three genes of the cluster (Klemm, P. & Christiansen, G., *Mol. Gen. Genetics* 208:439–445 (1987)). Apart from fimB and fimE, all genes encode precursor proteins for secretion into the periplasm via the sec-pathway.

The similarities between different pili following the chaperone/usher pathway are not restricted to their morphological properties. Their genes are also arranged in a very similar manner. Generally the gene for the main structural subunit is found directly downstream of the regulatory elements at the beginning of the gene cluster, followed by a gene for an additional structural subunit (fimI in the case of Type-1 pili and papH in the case of P-pili). PapH was shown and FimI is supposed to terminate pilus assembly (Hultgren, S. J., et al., *Cell* 73:887–901 (1993)). The two proteins that guide the process of pilus formation, namely the specialized pilus chaperone and the outer membrane assembly platform, are located adjacently downstream. At the end of the clusters a variable number of minor pilus components including the adhesins are encoded. The similarities in morphological structure, sequence (see Table 1), genetic organization and regulation indicate a close evolutionary relationship and a similar assembly process for these cell organelles.

Bacteria producing Type-1 pili show a so-called phase-variation. Either the bacteria are fully piliated or bald. This is achieved by an inversion of a 314 bp genomic DNA fragment containing the fimA promoter, thereby inducing an "all on" or "all off" expression of the pilus genes (McClain, M. S., et al., *J. Bacteriol.* 173:5308–5314 (1991)). The coupling of the expression of the other structural pilus genes to fimA expression is achieved by a still unknown mechanism. However, a wide range of studies elucidated the mechanism that influences the switching between the two phenotypes.

The first two genes of the Type-1 pilus cluster, fimB and fimE encode recombinases that recognize 9 bp DNA segments of dyad symmetry that flank the invertable fimA promoter. Whereas FimB switches pilation "on", FimE turns the promoter in the "off" orientation. The up- or down-regulation of either fimB or fimE expression therefore controls the position of the so-called "fim-switch" (McClain, M. S., et al., *J. Bacteriol.* 173:5308–5314 (1991); Blomfield, I. C., et al., *J. Bacteriol.* 173:5298–5307 (1991)).

The two regulatory proteins fimB and fimE are transcribed from distinct promoters and their transcription was shown to be influenced by a wide range of different factors including the integration host factor (IHF) (Blomfield, I. C., et al., *Mol. Microbiol.* 23:705–717 (1997)) and the leucine-responsive regulatory protein (LRP) (Blomfield, I. C., et al., *J. Bacteriol.* 175:27–36 (1993); Gally, D. L., et al., *J. Bacteriol.* 175:6186–6193 (1993); Gally, D. L., et al., *Microbiol.* 21:725–738 (1996); Roesch, R. L. & Blomfield, I. C., *Mol. Microbiol,* 27:751–761 (1998)). Mutations in the former lock the bacteria either in "on" or "off" phase, whereas LRP mutants switch with a reduced frequency. In addition, an effect of leuX on pilus biogenesis has been shown. This gene is located in the vicinity of the fim-genes on the chromosome and codes for the minor leucine tRNA species for the UUG codon. Whereas fimB contains five UUG codons, fimE contains only two, and enhanced leuX transcription might favor FimB over FimE expression (Burghoff, R. L., et al., *Infect. Immun.* 61:1293–1300 (1993); Newman, J. V., et al., *FEMS Microbiol. Lett.* 122: 281–287 (1994); Ritter, A., et al., *Mol. Microbial,* 25:871–882 (1997)).

Furthermore, temperature, medium composition and other environmental factors were shown to influence the activity of FimB and FimE. Finally, a spontaneous, statistical switching of the fimA promoter has been reported. The frequency of this spontaneous switching is approximately $10^{-3}$ per generation (Eisenstein, B. I., *Science* 214:337–339 (1981); Abraham, S. M., et al., *Proc. Nat. Acad. Sci, USA* 82:5724–5727 (1985)), but is strongly influenced by the above mentioned factors.

The genes fimI and fimC are also transcribed from the fimA promoter, but directly downstream of fimA a DNA segment with a strong tendency to form secondary structure was identified which probably represents a partial transcription terminator (Klemm, P., *Euro. J. Biochem.* 143:395–400 (1984)); and is therefore supposed to severely reduce fimI and fimC transcription. At the 3' end of fimC an additional promoter controls the fimD transcription; at the 3' end of fimD the last known fim promoter is located that regulates the levels of FimF, FimG, and FimH. Thus, all of the minor Type-1 pili proteins are transcribed as a single mRNA (Klemm, P. & Krogfelt, K. A., "Type I fimbriae of *Escherichia coli*," in: Fimbriae. Klemm, P. (ed.), CRC Press Inc., (1994) pp. 9–26). This ensures a 1:1:1 stoichiometry on mRNA-level, which is probably maintained on the protein level.

In the case of P-pili additional regulatory mechanisms were found when the half-life of mRNA was determined for different P-pilus genes. The mRNA for papA was extraordinarily long-lived, whereas the mRNA for papB, a regulatory pilus protein, was encoded by short-lived mRNA (Naureckiene, S. & Uhlin. B. E., *Mol. Microbiol.* 21:55–68 (1996); Nilsson, P., et al., *J. Bacterial.* 178:683–690 (1996)).

In the case of Type-1 pili, the gene for the Type-1 pilus chaperone FimC starts with a GTG instead of an ATG codon, leading to a reduced translation efficiency. Finally, analysis of the fimH gene revealed a tendency of the fimH mRNA to form a stem-loop, which might severely hamper translation. In summary, bacterial pilus biogenesis is regulated by a wide range of different mechanisms acting on all levels of protein biosynthesis.

Periplasmic pilus proteins are generally synthesized as precursors, containing a N-terminal signal-sequence that allows translocation across the inner membrane via the Sec-apparatus. After translocation the precursors are normally cleaved by signal-peptidase I. Structural Type-1 pilus subunits normally contain disulfide bonds, their formation is catalyzed by DsbA and possibly DsbC and DsbG gene products.

The Type-1 pilus chaperone FimC lacks cysteine residues. In contrast, the chaperone of P-pili, PapD, is the only member of the pilus chaperone family that contains a disulfide bond, and the dependence of P-pili on DsbA has been shown explicitly (Jacob-Dubuisson, F., et al., *Proc. Nat. Acad. Sci. USA* 91:11552–11556 (1994)). PapD does not accumulate in the periplasm of a ΔdsbA strain, indicating that the disturbance of the P-pilus assembly machinery is caused by the absence of the chaperone (Jacob-Dubuisson, F., et al., *Proc. Nat. Acad. Sci. USA* 91:11552–11556 (1994)). This is in accordance with the finding that Type-1 pili are still assembled in a ΔdsbA strain, albeit to reduced level (Hultgren, S. J., et al., "Bacterial Adhesion and Their Assembly", in: *Escherichia coli* and Salmonella, Neidhardt, F. C. (ed.) ASM Press, (1996) pp. 2730–2756).

Type-1 pili as well as P-pili are to 98% made of a single or main structural subunit termed FimA and PapA, respectively. Both proteins have a size of ~15.5 kDa. The additional minor components encoded in the pilus gene clusters are very similar (see Table 1). The similarities in sequence and size of the subunits with the exception of the adhesins suggest that all share an identical folding motif, and differ only with respect to their affinity towards each other. Especially the N- and C-terminal regions of these proteins are well conserved and supposed to play an important role in chaperone/subunit interactions as well as in subunit/subunit interactions within the pilus (Soto, G. E. & Hultgren, S. J., *J. Bacteriol.* 181:1059–1071 (1999)). Interestingly, the conserved N-terminal segment can be found in the middle of the pilus adhesins, indicating a two-domain organization of the adhesins where the proposed C-terminal domain, starting with the conserved motif, corresponds to a structural pilus subunit whereas the N-terminal domain was shown to be responsible for recognition of host cell receptors (Hultgren, S. J., et al., *Proc. Nat. Acad. Sci. USA* 86:4357–4361 (1989); Haslam, D. B., et al., *Mol. Microbiol.* 14:399–409 (1994); Soto, G. E., et al., *EMBO J.* 17:6155–6167 (1998)). The different subunits were also shown to influence the morphological properties of the pili. The removal of several genes was reported to reduce the number of Type-1 or P-pili or to increase their length, (fimH, papG, papK, fimF, fimG) (Russell, P. W. & Orndorff, P. E., *J. Bacteriol.* 174:5923–5935 (1992); Jacob-Dubuisson, R., et al., *EMBO J.* 12:837–847 (1993); Soto, G. E. & Hultgren, S. J., *J. Bacteriol.* 181: 1059–1071 (1999)); combination of the gene deletions amplified these effects or led to a total loss of pilation (Jacob-Dubuisson, R., et al., *EMBO J.* 12:837–847 (1993)).

In non-fimbrial adhesive cell organelles also assembled via chaperones/usher systems such as Myf fimbriae and CS3 pili, the conserved C-terminal region is different. This indirectly proves the importance of these C-terminal subunit segments for quaternary interactions (Hultgren, S. J., et al., "Bacterial Adhesion and Their Assembly", in: *Escherichia coli* and Salmonella, Neidhardt, F. C. (ed.) ASM Press, (1996) pp. 2730–2756).

Gene deletion studies proved that removal of the pilus chaperones leads to a total loss of piliation in P-pili and Type-1 pili (Lindberg, F., et al., *J. Bacteriol.* 171:6052–6058 (1989); Klemm, P., *Res. Microbiol.* 143:831–838 (1992); Jones, C. H., et al., *Proc. Nat. Acad. Sci. USA* 90:8397–8401 (1993)). Periplasmic extracts of a ΔfimC strain showed the accumulation of the main subunit FimA, but no pili could be detected (Klemm, P., *Res. Microbiol.* 143:831–838 (1992)). Attempts to over-express individual P-pilus subunits failed and only proteolytically degraded forms could be detected in the absence of PapD; in addition, the P-pilus adhesin was purified with the inner membrane fraction in the absence of the chaperone (Lindberg, F., et al., *J. Bacteriol.* 171:6052–6058 (1989)). However, co-expression of the structural pilus proteins and their chaperone allowed the detection of chaperone/subunit complexes from the periplasm in the case of the FimC/FimH complex as well as in the case of different Pap-proteins including the adhesin PapG and the main subunit PapA (Tewari, R., et al., *J. Biol. Chem.* 268:3009–3015 (1993); Lindberg, F., et al., *J. Bacteriol.* 171:6052–6058 (1989)). The affinity of chaperone/subunit complexes towards their assembly platform has also been investigated in vitro and was found to differ strongly (Dodson et al., *Proc. Natl. Acad. Sci. USA* 90:3670–3674 (1993)). From these results the following functions were suggested for the pilus chaperones.

They are assumed to recognize unfolded pilus subunits, prevent their aggregation and to provide a "folding template" that guides the formation of a native structure.

The folded subunits, which after folding display surfaces that allow subunit/subunit interactions, are then expected to be shielded from interacting with other subunits, and to be kept in a monomeric, assembly-competent state.

Finally, the pilus chaperones are supposed to allow a triggered release of the subunits at the outer membrane assembly location, and, by doing so with different efficiency, influence the composition and order of the mature pili (see also the separate section below).

After subunit release at the outer membrane, the chaperone is free for another round of substrate binding, folding assistance, subunit transport through the periplasm and specific delivery to the assembly site. Since the periplasm lacks energy sources, like ATP, the whole pilus assembly process must be thermodynamically driven (Jacob-Dubuisson, F., et al., *Proc. Nat. Acad. Sci. USA* 91:11552–11556 (1994)). The wide range of different functions attributed to the pilus chaperones would implicate an extremely fine tuned cascade of steps.

Several findings, however, are not readily explained with the model of pilus chaperone function outlined above. One example is the existence of multimeric chaperone/subunit complexes (Striker, R. T., et al., *J. Biol. Chem.* 269:12233–12239 (1994)), where one chaperone binds subunit dimers or trimers. It is difficult to imagine a folding template that can be "double-booked". The studies on the molecular details of chaperone/subunit interaction (see below) partially supported the functions summarized above, but also raised new questions.

All 31 periplasmic chaperones identified by genetic studies or sequence analysis so far are proteins of approximately 25 kDa with conspicuously high pI values around 10. Ten of these chaperones assist the assembly of rod-like pili, four are involved in the formation of thin pili, ten are important for the biogenesis of a typically thin structures (including capsule-like structures) and two adhesive structures have not been determined so far (Holmgren, A., et al., *EMBO J.* 11:1617–1622 (1992); Bonci, A., et al., *J. Mol. Evolution* 44:299–309 (1997); Smyth, C. J., et al., *FEMS Immun. Med Microbiol.* 16:127–139 (1996); Hung, D. L. & Hultgren, S. J., *J. Struct. Biol.* 124:201–220 (1998)). The pairwise sequence identity between these chaperones and PapD ranges from 25 to 56%, indicating an identical overall fold (Hung, D. L., et al., *EMBO J.* 15:3792–3805 (1996)).

The first studies on the mechanism of chaperone/substrate recognition was based on the observation that the C-termini of all known pilus chaperones are extremely similar. Synthetic peptides corresponding to the C-termini of the P-pilus proteins were shown to bind to PapD in ELISA assays (Kuehn, M. J., et al., *Science* 262:1234–1241 (1993)). Most importantly, the X-ray structures of two complexes were solved in which PapD was co-crystallized with 19-residue peptides corresponding to the C-termini of either the adhesin PapG or the minor pilus component PapK (Kuehn, M. J., et al., *Science* 262:1234–1241 (1993); Soto, G. E., et al., *EMBO J.* 17:6155–6167 (1998)). Both peptides bound in an extended conformation to a β-strand in the N-terminal chaperone domain that is oriented towards the inter-domain cleft, thereby extending a β-sheet by an additional strand. The C-terminal carboxylate groups of the peptides were anchored via hydrogen-bonds to Arg8 and Lys112, these two residues are invariant in the family of pilus chaperones. Mutagenesis studies confirmed their importance since their exchange against alanine resulted in accumulation of non-functional pilus chaperone in the periplasm (Slonim, L. N., et al., *EMBO J.* 11:4747–4756 (1992)). The crystal structure of PapD indicates that neither Arg8 nor Lys112 is involved in stabilization of the chaperone, but completely solvent exposed (Holmgren, A. & Branden, C. I., *Nature* 342:248–251 (1989)). On the substrate side the exchange of C-terminal PapA residues was reported to abolish P-pilus formation, and similar experiments on the conserved C-terminal segment of the P-pilus adhesin PapG prevented its incorporation into the P-pilus (Hultgren, S. J., et al., "Bacterial Adhesion and Their Assembly", in: *Escherichia coli* and *Salmonella*, Neidhardt, F. C. (ed.) ASM Press, (1996) pp. 2730–2756). All evidence therefore indicated pilus subunit recognition via the C-terminal segments of the subunits.

A more recent study on C-terminal amino acid exchanges of the P-pilus adhesin PapG gave a more detailed picture. A range of amino acid substitutions at the positions −2, 4, −6, and −8 relative to the C-terminus were tolerated, but changed pilus stability (Soto, G. E., et al., *EMBO J.* 17:6155–6167 (1998)).

Still, certain problems arise when this model is examined more closely. Adhesive bacterial structures not assembled to rigid, rod-like pili lack the conserved C-terminal segments (Hultgren, S. J., et al., "Bacterial Adhesion and Their Assembly", in: *Escherichia coli* and *Salmonella*, Neidhardt, F. C. (ed.) ASM Press, (1996) pp. 2730–2756), even though they are also dependent on the presence of related pilus chaperones. This indicates a different general role for the C-terminal segments of pilus subunits, namely the mediation of quaternary interactions in the mature pilus. Moreover, the attempt to solve the structure of a C-terminal peptide in complex with the chaperone by NMR was severely hampered by the weak binding of the peptide to the chaperone (Walse, B., et al., *FEBS Lett.* 412:115–120 (1997)); whereas an essential contribution of the C-terminal segments for chaperone recognition implies relatively high affinity interactions.

An additional problem arises if the variability between the different subunits are taken into account. Even though the C-terminal segments are conserved, a wide range of conservative substitutions is found. For example, 15 out of 19 amino acid residues differ between the two peptides co-crystallized with PapD (Soto, G. E., et al., *EMBO J.* 17:6155–6167 (1998)). This has been explained by the kind of interaction between chaperone and substrate, that occurs mainly via backbone interactions and not specifically via side-chain interactions. Then again, the specificity of the chaperone for certain substrates is not readily explained. On the contrary to the former argument, the conserved residues have been taken as a proof for the specificity (Hultgren, S. J., et al., "Bacterial Adhesion and Their Assembly", in: *Escherichia coli* and Salmonella, Neidhardt, F. C. (ed.) ASM Press, (1996) pp. 2730–2756).

The outer membrane assembly platform, also termed "usher" in the literature, is formed by homo-oligomers of FimD or PapC, in the case of Type-1 and P-pili, respectively (Klemm, P. & Christiansen, G., *Mol. Gen, Genetics* 220: 334–338 (1990); Thanassi, D. G., et al., *Proc. Nat. Acad. Sei. USA* 95:3146–3151 (1998)). Studies on the elongation of Type-1 fimbriae by electron microscopy demonstrated an elongation of the pilus from the base (Lowe, M. A., et al., *J. Bacteriol.* 169:157–163 (1987)). In contrast to the secretion of unfolded subunits into the periplasmic space, the fully folded proteins have to be translocated through the outer membrane, possibly in an oligomeric form (Thanassi, D. G., et al., *Proc. Nat. Acad. Sei. USA* 95:3146–3151 (1998)). This requires first a membrane pore wide enough to allow the passage and second a transport mechanism that is thermodynamically driven (Jacob-Dubuisson, F., et al., *J. Biol. Chem.* 269:12447–12455 (1994)).

FimD expression alone was shown to have a deleterious effect on bacterial growth, the co-expression of pilus subunits could restore normal growth behavior (Klemm, P. & Christiansen, G., *Mol. Gen, Genetics* 220:334–338 (1990)). Based on this it can be concluded that the ushers probably form pores that are completely filled by the pilus. Electron microscopy on membrane vesicles in which PapC had been incorporated confirmed a pore-forming structure with an inner diameter of 2 nm (Thanassi, D. G., et al., *Proc. Nat. Acad. Sei. USA* 95:3146–3151 (1998)). Since the inner diameter of the pore is too small to allow the passage of a pilus rod, it has been suggested that the helical arrangement of the mature pilus is formed at the outside of the bacterial surface. The finding that glycerol leads to unraveling of pili which then form a protein chain of approximately 2 nm is in good agreement with this hypothesis, since an extended chain of subunits might be formed in the pore as a first step (Abraham, S. N., et al., *J. Bacteriol.* 174:5145–5148 (1992); Thanassi, D. G., et al., *Proc. Nat. Acad. Sei. USA* 95:3146–3151 (1998)). The formation of the helical pilus rod at the outside of the bacterial membrane might then be the driving force responsible for translocation of the growing pilus through the membrane.

It has also been demonstrated that the usher proteins of Type-1 and P-pili form ternary complexes with chaperone/subunit complexes with different affinities (Dodson, K. W., et al., *Proc. Nat. Acad. Sci. USA* 90:3670–3674 (1993); Saulino, E. T., et al., *EMBO J.* 17:2177–2185 (1998)). This was interpreted as "kinetic partitioning" that allows a defined order of pilus proteins in the pilus. Moreover, it has been suggested that structural proteins might present a binding surface only compatible with one other type of pilus protein; this would be another mechanism to achieve a highly defined order of subunits in the mature pilus (Saulino, E. T., et al., *EMBO J.* 17:2177–2185 (1998)).

B. Production of Type-1 Pili From *Escherichia coli*

*E. coli* strain W3110 was spread on LB (10 g/L tryptone, 5 g/L yeast extract, 5 g/L NaCl, pH 7.5, 1% agar (w/v)) plates and incubated at 37° C. overnight. A single colony was then used to inoculate 5 ml of LB starter culture (10 g/L tryptone, 5 g/L yeast extract, 5 g/L NaCl, pH 7.5). After incubation for 24 hours under conditions that favor bacteria that produce Type-1 pili (37° C., without agitation) 5 shaker flasks containing 1 liter LB were inoculated with one milliliter of the starter culture. The bacterial cultures were then incubated for additional 48 to 72 hours at 37° C. without agitation. Bacteria were then harvested by centrifugation (5000 rpm, 4° C., 10 minutes) and the resulting pellet was resuspended in 250 milliliters of 10 mM Tris/HCl, pH 7.5. Pili were detached from the bacteria by 5 minutes agitation in a conventional mixer at 17.000 rpm. After centrifugation for 10 minutes at 10,000 rpm at 4° C. the pili containing supernatant was collected and 1 M $MgCl_2$ was added to a final concentration of 100 mM. The solution was kept at 4° C. for 1 hour, and the precipitated pili were then pelleted by centrifugation (10,000 rpm, 20 minutes, 4° C.). The pellet was then resuspended in 10 mM HEPES, pH 7.5, and the pilus solution was then clarified by a final centrifugation step to remove residual cell debris.

C. Coupling of FLAG to Purified Type-1 Pili of *E. coli* Using m-Maleimidonbenzoyl-N-hydroxysulfosuccinimide Ester (Sulfo-MBS)

600 µl of a 95% pure solution of bacterial Type-1 pili (2 mg/ml) were incubated for 30 minutes at room temperature with the heterobifunctional cross-linker sulfo-MBS (0.5 mM). Thereafter, the mixture was dialyzed overnight against 1 liter of 50 mM Phosphate buffer (pH 7.2) with 150 mM NaCl to remove free sulfo-MBS. Then 500 µl of the derivatized pili (2 mg/ml) were mixed with 0.5 mM FLAG peptide (containing an amino-terminal Cysteine) in the presence of 10 MM EDTA to prevent metal-catalyzed sufhydryloxidation. The non-coupled peptide was removed by size-exclusion-chromatography.

Example 34

Construction of an Expression Plasmid for the Expression of Type-1 Pili of *Escherichia coli*

The DNA sequence disclosed in GenBank Accession No. U14003, the entire disclosure of which is incorporated herein by reference, contains all of the *Escherichia coli* genes necessary for the production of type-1 pili from nucleotide number 233947 to nucleotide number 240543 (the fim gene cluster). This part of the sequences contains the sequences for the genes fimA, fimI, fimC, fimD, fimF, fimG, and fimH. Three different PCRs were employed for the amplification of this part of the *E. coli* genome and subsequent cloning into pUC19 (GenBank Accession Nos. L09137 and X02514) as described below.

The PCR template was prepared by mixing 10 ml of a glycerol stock of the *E. coli* strain W3110 with 90 ml of water and boiling of the mixture for 10 minutes at 95° C., subsequent centrifugation for 10 minutes at 14,000 rpm in a bench top centrifuge and collection of the supernatant.

Ten ml of the supernatant were then mixed with 50 pmol of a PCR primer one and 50 pmol of a PCR primer two as defined below. Then 5 ml of a 10×PCR buffer, 0.5 ml of Taq-DNA-Polymerase and water up to a total of 50 ml were added. All PCRs were carried out according to the following scheme: 94° C. for 2 minutes, then 30 cycles of 20 seconds at 94° C., 30 seconds at 55° C., and 2 minutes at 72° C. The PCR products were then purified by 1% agarose gel-electrophoresis.

Oligonucleotides with the following sequences with were used to amplify the sequence from nucleotide number 233947 to nucleotide number 235863, comprising the fimA, fimI, and fimC genes:

TAGATGATTACGCCAAGCTTATAATAGAAATAGTTTTTTGAAAGGAAAGCAGCATG (SEQ ID NO:196)
and

GTCAAAGGCCTTGTCGACGTTATTCCATTACGCCCGTCATTTTGG (SEQ ID NO:197)

These two oligonucleotides also contained flanking sequences that allowed for cloning of the amplification product into puc19 via the restriction sites HindIII and SalI. The resulting plasmid was termed pFIMAIC (SEQ ID NO:198).

Oligonucleotides with the following sequences with were used to amplify the sequence from nucleotide number 235654 to nucleotide number 238666, comprising the fimD gene:

(SEQ ID NO:199)
AAGATCTTAAGCTAAGCTTGAATTCTCTGACGCTGATTAACC
and (SEQ ID NO:200)
ACGTAAAGCATTTCTAGACCGCGGATAGTAATCGTGCTATC.

These two oligonucleotides also contained flanking sequences that allowed for cloning of the amplification product into puc19 via the restriction sites HindIII and XbaI, the resulting plasmid was termed pFIMD (SEQ ID NO:201).

Oligonucleotides with the following sequences with were used to amplify the sequence from nucleotide number 238575 nucleotide number 240543, comprising the fimF, fimG, and fimH gene:

(SEQ ID NO:202)
AATTACGTGAGCAAGCTTATGAGAAACAAACCTTTTTATC
and (SEQ ID NO:203)
GACTAAGGCCTTTCTAGATTATTGATAAACAAAAGTCACGC.

These two oligonucleotides also contained flanking sequences that allowed for cloning of the amplification product into puc19 via the restriction sites HindIII and XbaI; the resulting plasmid was termed pFIMFGH. (SEQ ID NO:204).

The following cloning procedures were subsequently carried out to generate a plasmid containing all the above-mentioned fim-genes:
pFIMAIC was digested EcoRI and HindIII (2237–3982), pFIMD was digested EcoRI and SstII (2267–5276), pFIMFGH was digested SstII and HindIII (2327–2231). The fragments were then ligated and the resulting plasmid, containing all the fim-genes necessary for pilus formation, was termed pFIMAICDFGH (SEQ ID NO:205).

Example 35

Construction of an Expression Plasmid for Escherichia coli Type-1 Pili that Lacks the Adhesion FimH The plasmid pFIMAICDFGH (SEQ ID NO:205) was digested with Kpnl, after which a fragment consisting of nucleotide numbers 8895–8509 was isolated by 0.7% agarose gelelectrophoresis and circularized by self-ligation. The resulting plasmid was termed pFIMAICDFG (SEQ ID NO: 206), lacks the fimH gene and can be used for the production of FIMH-free type-1 pili.

Example 36

Expression of Type-1 Pili Using the Plasmid pFIMAICDFGH

E. coli strain W3110 was transformed with pFIMAICDFGH (SEQ ID NO:205) and spread on LB (10 g/L tryptone, 5 g/L yeast extract, 5 g/L NaCl, pH 7.5, 1% agar (w/v)) plates containing 100 g/ml ampicillin and incubated at 37° C. overnight. A single colony was then used to inoculate 50 ml of LB-glucose starter culture (10 µL tryptone, 5 µL yeast extract, 1% (w/v) glucose, 5 g/L NaCl, pH 7.5, 100 mg/ml ampicillin). After incubation for 12–16 hours at 37° C. at 150 rpm, a 5 liter shaker flasks containing 2 liter LB-glucose was inoculated with 20 milliliter of the starter culture. The bacterial cultures were then incubated for additional 24 at 37° C. with agitation (150 rpm). Bacteria were then harvested by centrifugation (5000 rpm, 4° C., 10 minutes) and the resulting pellet was resuspended in 250 milliliters of 10 mM Tris/HCl, pH 8. Pili were detached from the bacteria by agitation in a conventional mixer at 17,000 rpm for 5 minutes. After centrifugation for 10 minutes at 10,000 rpm, 1 hour, ° C. the supernatant containing pili was collected and 1 M $MgCl_2$ was added to a final concentration of 100 mM. The solution was kept at 4° C. for 1 hour, and precipitated pili were then pelleted by centrifugation (10,000 rpm, 20 minutes, 4° C.). The pellet was then resuspended in 10 mM HEPES, 30 mM EDTA, pH 7.5, for 30 minutes at room temperature, and the pilus solution was then clarified by a final centrifugation step to remove residual cell debris. The preparation was then dialyzed against 20 mM HEPES, pH 7.4.

Example 37

Coupling of IgE Epitopes and Mimotopes to Type-1 Pili of Escherichia coli

A 66 µl aliquot of a 100 uM solution of the heterobifunctional cross-linker sulfa-MBS was added to 400 µl of a 95% pure solution of bacterial Type-1 pili (2.5 mg/ml, 20 mM HEPES, pH 7.4) and subsequently incubated for 45 minutes at room temperature with agitation. Thereafter, the excess of sulfa-MBS was removed by size exclusion chromatography using a PD-10 column. Alternatively, the cross-linker can be removed by dialysis. Then either 1.3 µl of a solution containing 1.1 mg/ml peptide Ce3epi (CGGVNLTWSRA SG (SEQ ID NO:207)), or peptide Ce3Mim (CGGVNLPWSFGLE (SEQ ID NO:208) was added to 1 ml aliquots of the derivatized pili (1–1.25 mg/ml, 20 mM HEPES pH 7.4). The samples were incubated at room temperature for 4 h and non-coupled peptide was removed by dialysis against 2 times 2 l of a buffer containing 20 mM HEPES (pH 7.4). Alternatively, the non-coupled peptide can be removed by size-exclusion chromatography.

Example 38

Immunization of Mice with a Bee Venom Phospholipase $A_2$ ($PLA_2$) Fusion Protein Coupled to Qβ Capsid Protein A. Preparation of an Alternative Vector for Cytoplasmic Expression of the Catalytically Inactive Variant of the $PLA_2$ Gene Fused to the Amino Acid Sequence AAASGGCGG (SEQ ID NO: 209)

The $PLA_2$ gene construct of example 9 was amplified by PCR from pAV3PLAfos using oligos ecori_NdeI_pla (sequence below) and PLA-Cys-hind (Example 29). For the reaction, 100 pmol of each oligo, and about 1 μg of PAV3PLAfos DNA were used in the 50 μl reaction mixtures with 1.2 units of Pfx DNA polymerase (Gibco), 1 mM $MgSO_4$, 200 μM dNTPS and Pfx enhancer solution (Gibco) diluted ten times. For the reaction, temperature cycling was carried out as follows: 94° C. for 2 minutes, 5 cycles of 92° C. (0.5 minutes), 58° C. (0.5 minutes), 68° C. (1 minute); 25 cycles of 92° C. (0.5 minutes), 63° C. (0.5 minutes), 68° C. (1 minute). The PCR product was purified by agarose gel electrophoresis and subsequent isolation of the fragment using the Qiagen Qiaquick Kit, digested with enzymes NdeI and HindIII, and cloned into the PET1la vector (Novagen) digested with the same enzymes.

```
Oligos: ecorl_Ndel_pla:       (SEQ ID NO: 214)
TAACCGAATTCAGGAGGTAAAAACATATGGC TATCATCTACC.
```

The vector encoded a fusion protein having the amino acid sequence MAIIYPGTLWCGHGNKSSGPNELGR-FKHTDACCRTQDMCPDVMSAG ESKHGLTNTASH-TRLSCDCDDKFYDCLKNSADTISSY-FVGKMYFNLIDTK CYKLEHPVTGCGERTEGRCLHYTVDK-SKPKVYQWFDLRKYAAASGGCG G (SEQ ID NO:210).

Coupling of $PLA_2$ Fusion Protein to Qβ Capsid Protein

A solution of 600 μl of Qβ capsid protein (2 mg/ml in 20 mM Hepes, pH 7.4) was reacted with 176 μl Sulfo-MBS (13 mg/ml in $H_2O$) for 60 minutes at room temperature, and dialyzed against 1 L of 20 mM Hepes pH 7.4 O/N at 4° C. The next day, 500 μl of a PLA2 solution (2.5 mg/ml) containing 0.1 mM DTT were desalted over a 5 ml Hi-Trap column (Pharmacia). Reduced and desalted $PLA_2$ (60 μl, of a solution of approx. 0.5 mg/ml) was mixed with activated and dialyzed Qβ capsid (25 μl of a 1.5 mg/ml solution) and reacted for four hours at room temperature.

1 Capsids of 25–30 nm Diameter are Clearly Visible in Electron Microscopy Images of Qβ Capsid Protein Taken Both Before and After Coupling to $PLA_2$.

C. Immunization of Mice with $PLA_2$ Coupled to Qβ Capsid Protein

Female Balb/c mice were immunized intravenously on day 0 with 50 μg Qβ capsid coupled to $PLA_2$, and boosted on day 14 with the same amount of antigen. Mice were bled on day 20 and sera analyzed in an ELISA. A titer of 1:5000 against $PLA_2$ was obtained.

Example 39

Coupling of IgE Mimotopes and Epitopes to Qβ Capsid Protein

Human IgE epitopes having the following amino acid sequences were coupled to Qβ capsid protein using the N-terminal cysteine residue:
Ce3epitope: CGGVNLTWSRASG (SEQ ID NO:207)
Ce3mimotope: CGGVNLPWSFGLE (SEQ ID NO:208)

The coupling reaction was performed using Qβ capsid protein activated with Sulfo-MBS and subsequently dialyzed to remove excess crosslinker. The respective epitope or mimotope was diluted into the reaction mixture containing the activated Qβ capsid, and left to react for 4 hours at room temperature. The reaction mixture was finally dialyzed for 4 hours against PBS, and injected into mice.

The following circular mimotope was also coupled to Qβ capsid protein: Ce4mimotope: GEFCINHRGYWVCGDPA (SEQ ID NO:211).

The mimotope was first reacted with the chemical group N-succinimidyl-S-acetylthioacetate (SATA), in order to introduce a protected sulfhydryl group into the mimotope. The protecting group was subsequently removed by treatment with hydroxylamine, and immediately reacted with activated Qβ capsid protein, for 4 hours at room temperature. The reaction mixture was finally dialyzed for 4 hours, and injected into mice.

Example 40

Immunization of Mice with HBcAg-Lys Coupled to M2 Peptide

A. Coupling of M2 Peptide to HBcAg-Lys Capsid Protein

Synthetic M2 peptide, corresponding to an N-terminal fragment of the Influenza M2 protein with a cysteine residue at its C-terminus (SLLTEVETPIRNEWGCRCNGSS-DGGGC (SEQ ID NO:212)) was chemically coupled to purified HBcAg-Lys particles in order to elicit an immune response against the M2 peptide. Sulfo-MBS (232 μl, 3 mM) was reacted with a solution of 1.4 ml HBcAg-Lys (1.6 mg/ml) in PBS. The mixture was dialyzed overnight against phosphate buffered saline (PBS). M2 peptide was diluted to a concentration of 24 mg/ml in DMSO; 5 μl of this solution was diluted in 300 μl PBS, 188 μl of which was added to 312 μl of the dialyzed activated HBcAg-Lys solution. EDTA (10 μl of a 1 M solution) was also added to the reaction mixture, after which the reaction was allowed to proceed for 4 hours at room temperature.

Immunization of Mice with HBcAg-Lys Coupled to M2 Peptide

Female Balb/c mice were immunized intravenously on day 0 with 50 μg HBcAg-Lys-M2 or M2 peptide alone and boosted 10 days later with the same amount of antigen. After another 10 days, the mice were infected intranasally with Influenza virus (50 pfu, PR/8) and survival of infected mice was monitored. In addition, viral titers were determined in the lung. Mice primed with M2-HBcAg-Lys were fully protected and had eliminated the virus by day 7.

Example 41

Coupling of M2 Peptide to Pili, Qβ and Cys-Free HbcAg-Capsid Protein and Comparison of the Antibody Titer Obtained by Immunization of Mice with These Coupled Pili and Capsids with the Titer Obtained by Immunizing Mice with an N-Terminal Fusion Protein of the M2 Peptide to HbcAg1–183

A. Coupling of M2 Peptide to Pili, Qβ- and Cys-Free HbcAg-capsid Protein

Qβ: A solution of 1 ml of 1 mg/ml Qβ capsid protein in 20 mM Hepes. 150 mM NaCl pH 7.2 was reacted for 30 minutes with 93 μl of a solution of 13 mg/ml Sulfo-MBS (Pierce) in $H_2O$ at RT on a rocking shaker. The reaction solution was subsequently dialyzed overnight against 2 L of 20 mM hepes, 150 mM NaCl, pH 7.2. The dialyzed reaction mixture was then reacted with 58.8 μl of a 25 mM stock solution of M2 peptide (SEQ ID NO:212) in DMSO for four hours at RT on a rocking shaker. The reaction mixture was subsequently dialyzed against 2 liters of 20 mM Hepes, 150 mM NaCl, pH 7.2 overnight at 4° C.

Cys-free HbcAg: A solution of 1.25 ml of 0.8 mg/ml cys-free HbcAg capsid protein (example 31) in PBS, pH 7.2 was reacted for 30 minutes with 93 μl of a solution of 13 mg/ml Sulfo-MBS (Pierce) in $H_2O$ at RT on a rocking shaker. The reaction solution was subsequently dialyzed overnight against 2 L of 20 mM Hepes, 150 mM NaCl, pH 7.2. The dialyzed reaction mixture was then reacted with 58.8 μl of a 25 mM stock solution of M2 peptide (SEQ ID NO:212) in DMSO for four hours at RT on a rocking shaker. The reaction mixture was subsequently dialyzed against 2 liters of 20 mM hepes, 150 mM NaCl, ph 7.2 overnight at 4° C.

Pili: A solution of 400 μl of 2.5 mg/ml pili protein in 20 mM Hepes, pH 7.4, was reacted for 45 minutes with 60 μl of a 100 mM Sulfo-MBS (Pierce) solution in ($H_2O$) at RT on a rocking shaker. The reaction mixture was desalted on a PD-10 column (Amersham-Pharmacia Biotech), and the second fraction of 500 μl protein elating from the column (containing approximately 1 g protein) was reacted with 58.8 μl of a 25 mM stock solution of M2 peptide (SEQ ID NO:212) in DMSO for four hours at RT on a rocking shaker. The reaction mixture was subsequently dialyzed against 2 liters of 20 mM Hepes, 150 mM NaCl, pH 7.2 overnight at 4° C.

Genetic Fusion of the M2 Peptide to HbcAg1–183

M2 genetically fused to Hbc: M2 was cloned at the N-terminus of Hbc as published by Neirynck et. al. *Nature Medicine* 5: 1157 (1999). MD-HBc was expressed in *E. coli* and purified by gel chromatography. The presence of the M2 peptide at the N-terminus of M2-HBc was confirmed by Edman sequencing.

Immunization of Mice:

Female Balb/c mice were vaccinated with M2 peptide coupled to pili, Qβ and cys-free HbcAg protein and with M2 peptide genetically fused to Hbc immunogen without the addition of adjuvants. 35 μg protein of each sample were injected intraperitoneally on day 0 and day 14. Mice were bled on day 27 and their serum analyzed using a M2-peptide specific ELISA.

ELISA

Figure 27:
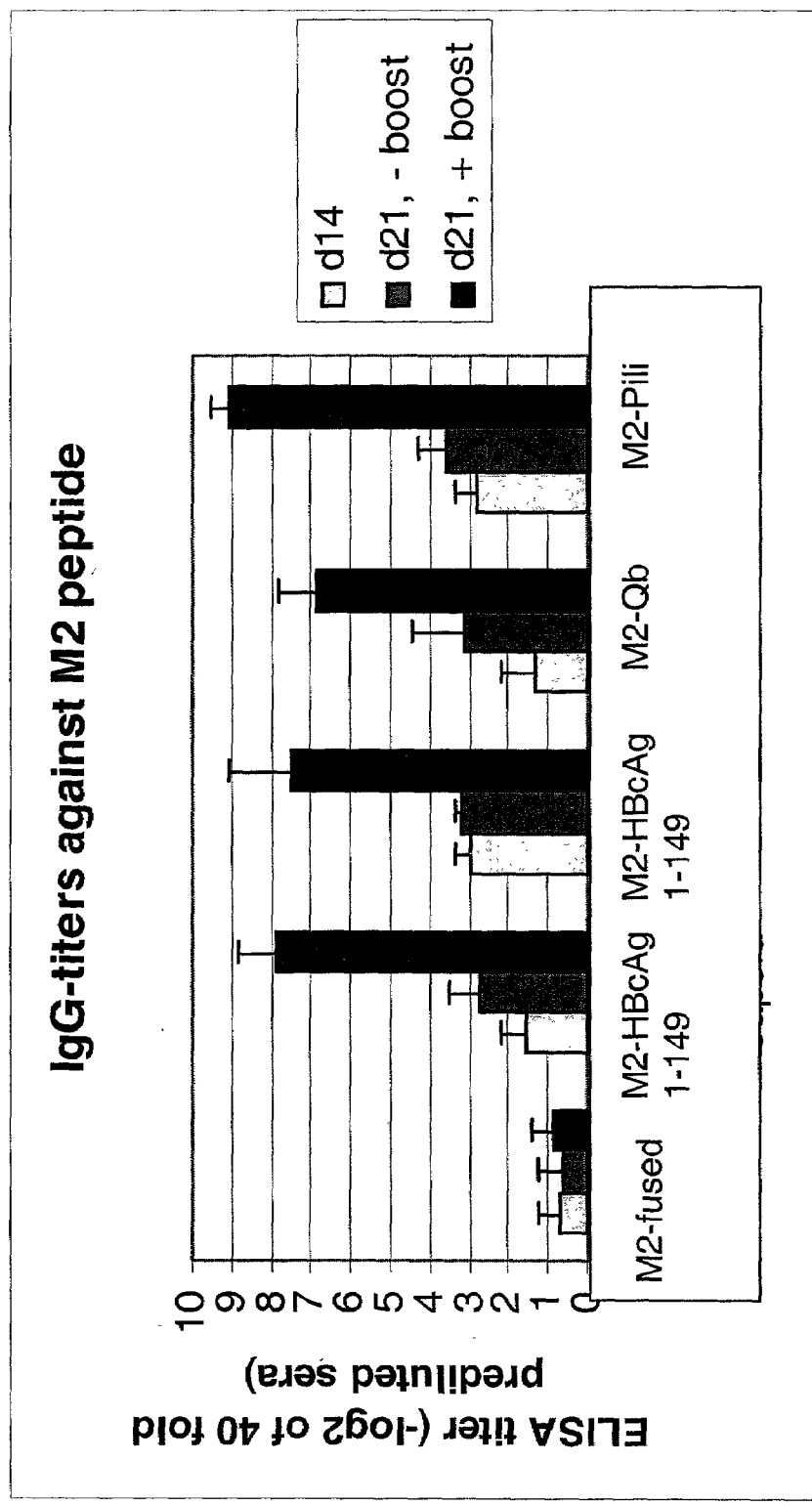
FIG. 27B Survival of mice vaccinated intravenously by a lethal influenza A challenge FIG. 28A SDS-PAGE Analysis of coupling of anti-idiotypic IgE mimobody VAE051 to Qβ capsid protein FIG. 28B. ELISA analysis of IgG antibodies specific for anti-idiotypic antibody VAE051 and Human IgE in sera of mice immunized against VAE051 coupled to Qβ capsid protein
Figure 27:
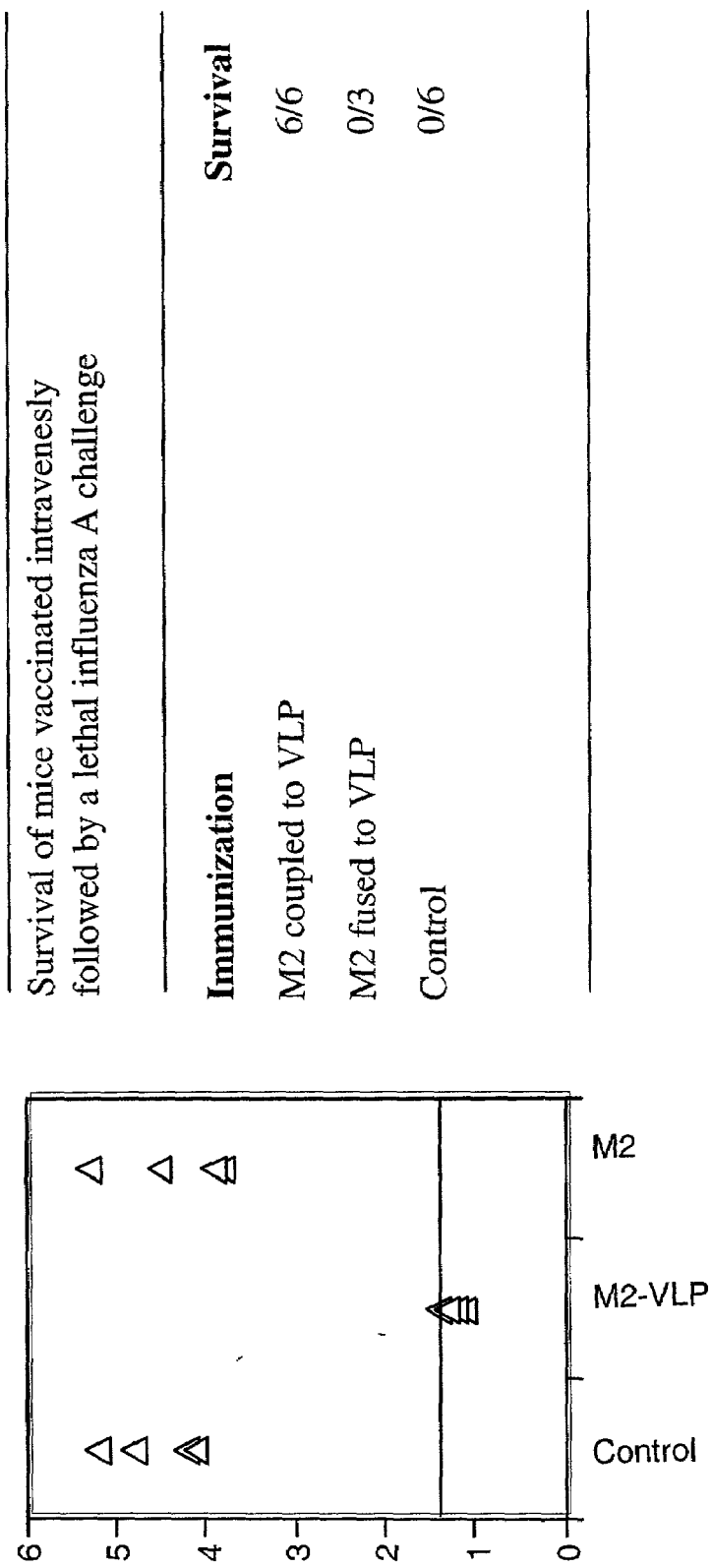

10 μg/ml M2 peptide coupled to RNAse was coated on an ELISA plate. The plate was blocked then incubated with serially diluted mouse sera. Bound antibodies were detected with enzymatically labeled anti-mouse IgG antibody. As a control, preimmune sera were also tested. Control ELISA experiments using sera from mice immunized with unrelated peptides crosslinked to Hbc or other carriers showed the antibodies detected were specific for the M2 peptide. The results are shown in FIGS. 27A and B.

Example 42

Coupling of Angiotensin I and Angiotensin II Peptides to Qβ and Immunization of Mice with Qβ—Angiotensin Peptide Vaccines A. Coupling of Angiotensin I and Angiotensin II Peptides to Qβ Capsid Protein The following angiotensin peptides were chemically synthesized: CGGDRVYIHPF ("Angio I"; SEQ ID NO:380), CGGDRVYIHPFHL ("Angio II"; SEQ ID NO:381), DRVYIHPFHLGGC ("Angio III"; SEQ ID NO:382), CDRVYIHPFHL ("Angio IV"; SEQ ID NO:383) and used for chemical coupling to Qβ as described in the following.

A solution of 5 ml of 2 mg/ml Qβ capsid protein in 20 mM Hepes. 150 mM NaCl pH 7.4 was reacted for 30 minutes with 507 μl of a solution of 13 mg/ml Sulfo-MBS (Pierce) in $H_2O$ at 25° C. on a rocking shaker. The reaction solution was subsequently dialyzed twice for 2 hours against 2 L of 20 mM Hepes, 150 mM NaCl, pH 7.4 at 4° C. 665 ml of the dialyzed reaction mixture was then reacted with 2.8 ml of each of the corresponding 100 mM peptide stock solution (in DMSO) for two hours at 25° C. on a rocking shaker. The reaction mixture was subsequently dialyzed 2×2 hours against 2 liters of 20 mM Hepes, 150 mM NaCl, pH 7.4 at 4° C.

Immunization of Mice:

Female Balb/c mice were vaccinated with one of the four angiotensin peptides coupled to Qβ capsid protein without the addition of adjuvants. 50 μg of total protein of each sample was diluted in PBS to 200 ml and injected subcutaneously (100 ml on two ventral sides) on day 0 and day 14. Mice were bled retroorbitally on day 21 and their serum was analyzed using a angiotensin-specific ELISA.

ELISA

All four angiotensin peptides were individually coupled to bovine RNAse A using the chemical cross-linker sulfo-SPDP. ELISA plates were coated with coupled RNAse preparations at a concentration of 10 mg/ml. The plates were blocked and then incubated with serially diluted mouse sera. Bound antibodies were detected with enzymatically labeled anti-mouse IgG antibody. As a control, preimmune sera of the same mice were also tested. Control ELISA experiments using sera from mice immunized with unrelated peptides crosslinked to Qβor other carriers showed that the antibodies detected were specific for the respective peptide. The results are shown in FIGS. 8A–8D.

FIGS. 8A, 8B, 8C and 8D, respectively, show ELISA analyses of IgG antibodies specific for "Angio I", "Angio II", "Angio III", and "Angio IV", respectively, in sera of mice immunized against Angio I-IV coupled to Qβcapsid protein. Qβ-Angio I, Qβ-Angio II, Qβ-Angio III and Qβ-Angio IV, as used in the figures, stand for the vaccine injected in the mice, from which the sera are derived in accordance with above definition of the angiotensin peptides.

Figure 8A:
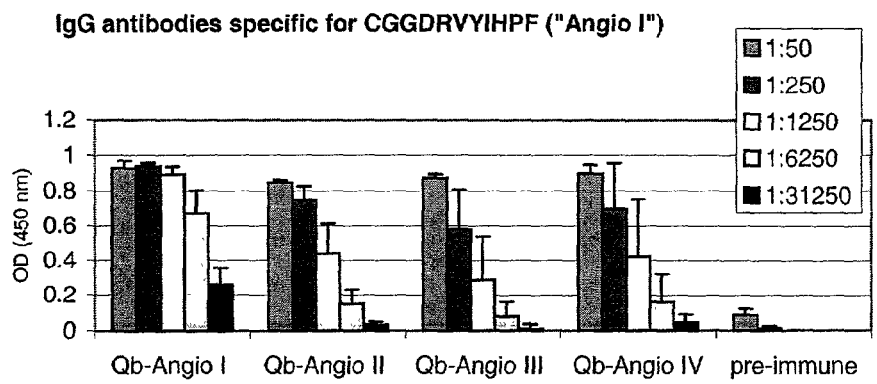
FIG. 8A. ELISA analysis of IgG antibodies specific for "Angio I" in sera of mice immunized against angiotensin peptides coupled to Qβ capsid protein.
Figure 8B:
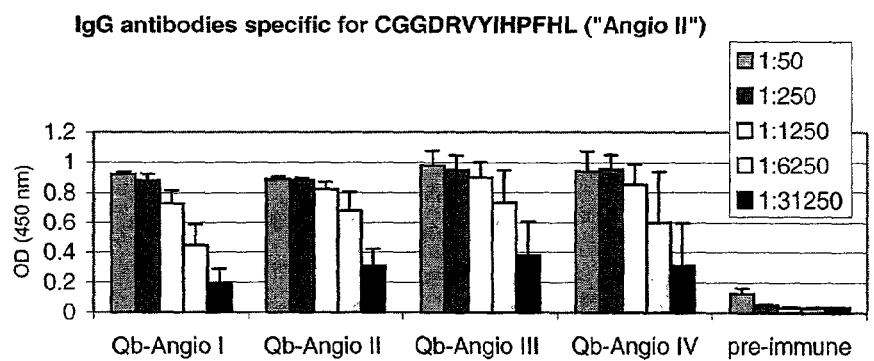
FIG. 8B. ELISA analysis of IgG antibodies specific for "Angio II" in sera of mice immunized against angiotensin peptides coupled to Qβ capsid protein.
Figure 8C:
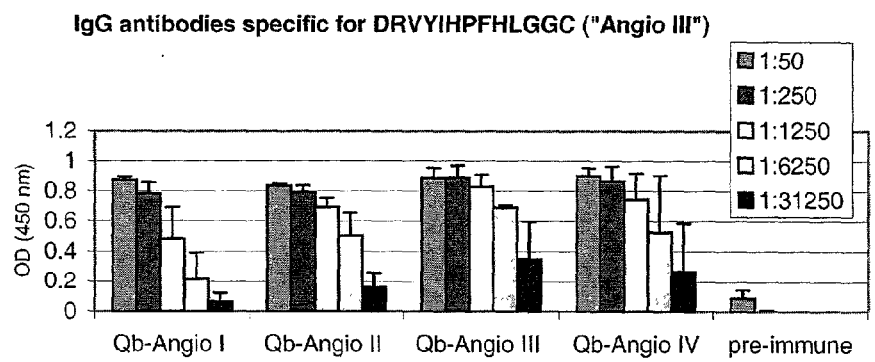
FIG. 8C. ELISA analysis of IgG antibodies specific for "Angio III" in sera of mice immunized against angiotensin peptides coupled to Qβ capsid protein.
Figure 8D:
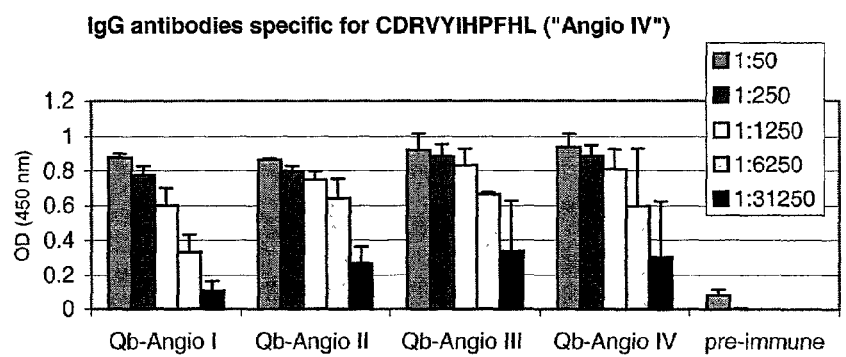
FIG. 8D. ELISA analysis of IgG antibodies specific for "Angio IV" in sera of mice immunized against angiotensin peptides coupled to Qβ capsid protein.

Female Balb/c mice were vaccinated subcutaneously with 50 mg of vaccine in PBS on day 0 and day 14. IgG antibodies in sera of mice vaccinated with Qβ-Angio I, Qβ-Angio II, Qβ-Angio III and Qβ-Angio IV were measured on day 21 against all four peptides (coupled to RNAse A), i.e. against "Angio I" (FIG. 8A), "Angio II" (FIG. 8B), "Angio III" (FIG. 8C), and "Angio IV" (FIG. 8D). As a control, pre-immune sera from the same mice were analyzed. Results for indicated serum dilutions are shown as optical density at 450 nm. The average of three mice each (including standard deviations) is shown. All vaccinated mice made high IgG antibody titers against all four peptides tested. No angiotensin-specific antibodies were detected in the controls (pre-immune mice).

Example 43

Coupling of Angiotensin I and Angiotensin II Peptides to HBcAg-149-lys-2cys-Mut, i.e. cys-Free HBcAg The following angiotensin peptides were chemically synthesized: CGGDRVYIHPF ("Angio I"; SEQ ID NO:380), CGGDRVYIHPFHL ("Angio II"; SEQ ID NO:381), DRVYIHPFHLGGC ("Angio III"; SEQ ID NO:382), CDRVYIHPFHL ("Angio IV"; SEQ ID NO:383) and are used for chemical coupling to HBcAg-149-lys-2cys-Mut, i.e. cys-free HBcAg.

A solution of 1.25 ml of 0.8 mg/ml HBcAg-149-lys-2cys-Mut capsid protein (cf. Example 31) in PBS, pH 7.4 is reacted for 30 minutes with 93 μl of a solution of 13 mg/ml Sulfo-MBS (Pierce) in H$_2$O at 25° C. on a rocking shaker. The reaction solution is subsequently dialyzed overnight against 2 L of 20 mM Hepes, 150 mM NaCl, pH 7.4. After buffer exchange the reaction solution is dialyzed for another 2 hours. The dialyzed reaction mixture is then reacted with 1.8 μl of a 100 mM peptide stock solution (in DMSO) for 2 hours at 25° C. on a rocking shaker. The reaction mixture is subsequently dialyzed against 2 liters of 20 mM Hepes, 150 mM NaCl, ph 7.4 overnight at 4° C. followed by buffer exchange and another 2 hours of dialysis.

Example 44

Coupling of Angiotensin I and Angiotensin II Peptides to Type-1 Pili of *E.coli*

The following angiotensin peptides were chemically synthesized: CGGDRVYIHPF ("Anglo I"; SEQ ID NO:380), CGGDRVYIHPFHL ("Anglo II"; SEQ ID NO:381), DRVYIHPFHLGGC ("Angio III"; SEQ ID NO:382), CDRVYIHPFHL ("Angio IV"; SEQ ID NO:383) and are used for chemical coupling to Type-1 pili of *E.coli*.

A solution of 400 μl of 2.5 mg/ml Type-1 pili of *E.coli* in 20 mM Hepes, pH 7.4, is reacted for 60 minutes with 60 μl of a 100 mM Sulfo-MBS (Pierce) solution in (H$_2$O) at RT on a rocking shaker. The reaction mixture is desalted on a PD-10 column (Amersham-Pharmacia Biotech), The protein-containing fractions eluating from the column are pooled (containing approximately 1 mg protein, i.e. derivatized pili) and reacted with a three-fold molar excess of peptide. For example, to 500 ul eluate containing approximately 1 mg derivatized pili, 2.34 ul of a 100 mM peptide stock solution (in DMSO) is added. The mixture is incubated for four hours at 25° C. on a rocking shaker and subsequently dialyzed against 2 liters of 20 mM Hepes, 150 mM NaCl, pH 7.2 overnight at 4° C.

Example 45

Coupling of Der p I Peptides to Qβ and Immunization of Mice with Qβ-Der p I Vaccines Coupling of Der p I Peptides to Qβ Capsid Protein The following peptides derived from the house dust mite allergen Der p I were chemically synthesized: CGNQSLDLAEQELVDCASQHGCH ("Der p I p52"; aa 52–72, with an additional cysteine-glycine linker at the N terminus: SEQ ID NO:384), CQIYPPNANKIREALAQTHSA ("Der p1 p117"; aa 117–137; SEQ ID NO:385). These peptides were used for chemical coupling to Qβ as described below.

1 ml of a solution consisting of 2 mg/ml Qβ capsid protein in 20 mM Hepes, 150 mM NaCl, pH 7.4 was reacted for 30 minutes with 102 μl of a solution of 13 mg/ml Sulfo-MBS (Pierce) in H$_2$O at 25° C. on a rocking shaker. The reaction solution was subsequently dialyzed twice for 2 hours against 2 L of 20 mM Hepes, 150 mM NaCl, pH 7.4 at 4° C. 440 μl of the dialyzed reaction mixture was then reacted with 1.9 μl of a 100 mM peptide stock solution (in DMSO) for two hours at 25° C. on a rocking shaker. The reaction mixture was subsequently dialyzed 2×2 hours against 2 liters of 20 mM Hepes, 150 mM NaCl, pH 7.4 at 4° C.

Immunization of Mice:

Female Balb/c mice were vaccinated with one of the two Der p I peptides coupled to Qβ capsid protein without the addition of adjuvants. Two mice for each vaccine were used. 30 μg of total protein of each sample was diluted in PBS to 200 μl and injected subcutaneously on day 0 and day 14. Mice were bled retroorbitally on day 21 and their serum was analyzed using a Der p I peptide-specific ELISA.

ELISA

The Der p I peptides "Der p I p52" and "Der p I p117" were individually coupled to bovine RNAse A using the chemical cross-linker sulfo-SPDP. ELISA plates were coated with coupled RNAse preparations at a concentration of 10 mg/ml. The plates were blocked and then incubated with serially diluted mouse sera. Bound antibodies were detected with enzymatically labeled anti-mouse IgG antibody. As a control, preimmune sera of the same mice were also tested. Control ELISA experiments using sera from mice immunized with unrelated peptides crosslinked to Qβ or other carriers showed that the antibodies detected were specific for the respective peptide. The results are shown in FIGS. 9A and 9B.

Figure 9A:
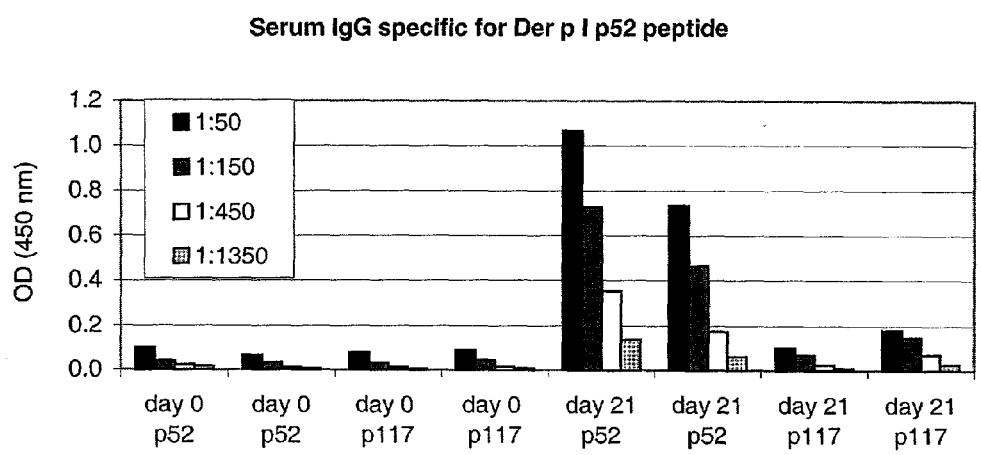
FIG. 9A. ELISA analysis of IgG antibodies specific for "Der p I p52" in sera of mice immunized against Der p I peptides coupled to Qβ capsid protein.
Figure 9B:
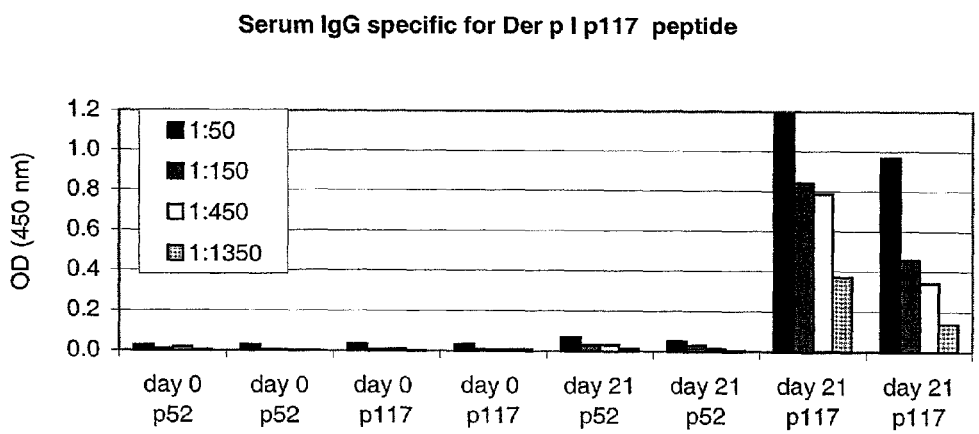
FIG. 9B. ELISA analysis of IgG antibodies specific for for "Der p I p117" in sera of mice immunized against Der p I peptides coupled to Qβ capsid protein.

FIG. 9A and FIG. 9B show ELISA analyses of IgG antibodies specific for "Der p I p52" (FIG. 9A) and specific for "Der p I p117" (FIG. 9B) in sera of mice immunized against the Der p I peptides coupled to Qβ capsid protein. "p52" and "p117", as used in FIGS. 9A and 9B, stand for the vaccine injected in the mice, from which the sera are derived.

As a control, pre-immune sera from the same mice were analyzed (day 0). Results for indicated serum dilutions are shown as optical density at 450 nm. On day 21, all vaccinated mice made specific IgG antibodies against the Der p I peptide they were vaccinated with but not against the other Der p I peptide. No Der p I peptide-specific antibodies were detected before vaccination (day 0).

Both Der p I peptide vaccines were highly immunogenic in the absence of adjuvants. All vaccinated mice made good antibody responses specific for the peptide in the vaccine preparation.

Example 46

Coupling of Der p 1 Peptides to HBcAg-149-lys-2cys-Mut, i.e. Cys-free HBcAg

The following peptides derived from the house dust mite allergen Der p1 were chemically synthesized: Der p I p52 (aa 52–72, with an additional cysteine-glycine linker at the N terminus): CGNQSLDLAEQELVDCASQHGCH (SEQ ID NO:384), Der p I p117 (aa 117–137): CQIYPPNANKIREALAQTHSA (SEQ ID NO:385). These peptides are used for chemical coupling to HBcAg-149-lys-2cys-Mut, i.e. cys-free HBcAg.

A solution of 1.25 ml of 0.8 mg/ml HBcAg-149-lys-2cys-Mut capsid protein (Example 31) in PBS, pH 7.4 is reacted for 30 minutes with 93 μl of a solution of 13 mg/ml Sulfo-MBS (Pierce) in H2O at 25° C. on a rocking shaker. The reaction solution is subsequently dialyzed overnight against 2 L of 20 mM Hepes, 150 mM NaCl, pH 7.4. After buffer exchange the reaction solution is dialyzed for another 2 hours. The dialyzed reaction mixture is then reacted with 1.8 μl of a 100 mM peptide stock solution (in DMSO) for 2 hours at 25° C. on a rocking shaker. The reaction mixture is subsequently dialyzed against 2 liters of 20 mM Hepes, 150 mM NaCl, ph 7.4 overnight at 4° C. followed by buffer exchange and another 2 hours of dialysis.

The following peptides derived from the house dust mite allergen Der p I were chemically synthesized: Der p I p52 (an 52–72, with an additional cysteine-glycine linker at the N terminus) and CGNQSLDLAEQELVDCASQHGCH (SEQ ID NO:384), Der p I p117 (an 117–137): CQIYPP-NANKIREALAQTHSA (SEQ ID NO:385). These peptides are used for chemical coupling to Type-1 pili of E.coli.

A solution of 400 µl of 2.5 mg/ml Type-1 pili of E.coli in 20 mM Hepes, pH 7.4, is reacted for 60 minutes with 60 µl of a 100 mM Sulfo-MBS (Pierce) solution in (H$_2$O) at RT on a rocking shaker. The reaction mixture is desalted on a PD-10 column (Amersham-Pharmacia Biotech), The protein-containing fractions eluating from the column are pooled (containing approximately 1 mg protein, i.e. derivatized pili) and reacted with a three-fold molar excess of peptide. For example, to 500 ul eluate containing approximately 1 mg derivatized pili, 2.34 ul of a 100 mM peptide stock solution (in DMSO) is added. The mixture is incubated for four hours at 25° C. on a rocking shaker and subsequently dialyzed against 2 liters of 20 mM Hepes, 150 mM NaCl, pH 7.2 overnight at 4° C.

Example 48

Coupling of HumanVEGFR-II Peptide to Type-1 Pili of E.coli and Immunization of Mice with Vaccines Comprising Type-1 Pili-HumanVEGFR-II Peptide Arrays Coupling of HumanVEGFR-II Peptide to Type-1 Pili of E.coli The human VEGFR II peptide with the sequence CTARTELNVGIDFNWEYPSSKHQHKK (SEQ ID NO:351) was chemically synthesized and used for chemical coupling to Type-1 pili of E.coli.

A solution of 1400 µl of 1 mg/ml pili protein in 20 mM Hepes, pH 7.4, was reacted for 60 minutes with 85 µl of a 100 mM Sulfo-MBS (Pierce) solution in (H$_2$O) at RT on a rocking shaker. The reaction mixture was desalted on a PD-10 column (Amersham-Pharmacia Biotech). The protein-containing fractions eluting from the column were pooled (containing approximately 1,4 mg protein) and reacted with a 2.5-fold molar excess (final volume) of human VEGFR II peptide. For example, to 200 µl eluate containing approximately 0,2 mg derivatized pili, 2.4 µl of a 10 mM peptide solution (in DMSO) was added. The mixture was incubated for four hours at 25° C. on a rocking shaker and subsequently dialyzed against 2 liters of 20 mM Hepes, pH 7.2 overnight at 4° C.

Immunization of Mice

Female C3H-HeJ (Toll-like receptor 4 deficient, LPS non-responder mice) and C3H-HeN (wild-type) mice were vaccinated with the human VEGFR-II peptide coupled to Type-1 pili protein without the addition of adjuvants. Approximately 100 µg of total protein of each sample was diluted in PBS to 200 µl and injected subcutaneously on day 0, day 14 and day 28. Mice were bled retroorbitally on day 14, 28 and day 42 and serum of day 42 was analyzed using a human VEGFR-II specific ELISA

ELISA

Sera of immunized mice were tested in ELISA with immobilized human VEGFR-II peptide and the extracellular domain of the human VEGFR-II (R&D Systems GmbH, Wiesbaden).

Figure 10A:
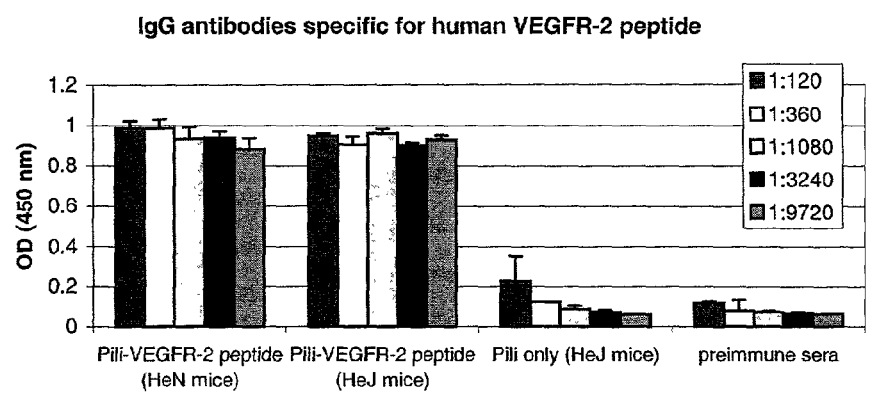
FIG. 10A. ELISA analysis of IgG antibodies specific for human VEGFR II peptide in sera of mice immunized against human VEGFR II peptide and the extracellular domain of human VEGFR II both coupled to Type-1 pili protein.
Figure 10B:
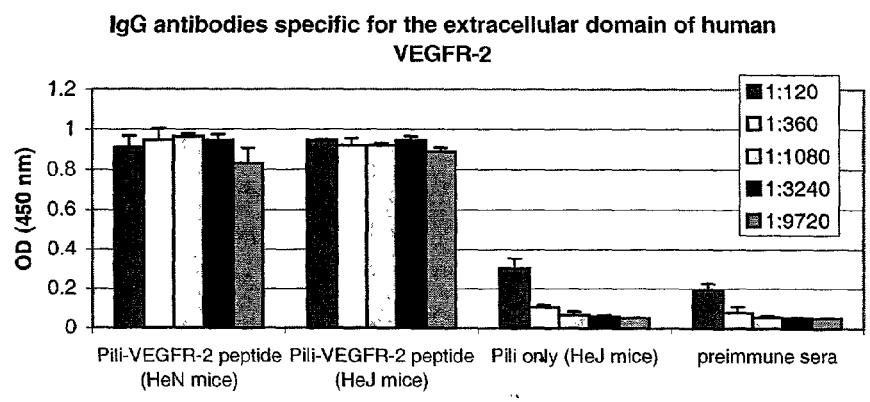
FIG. 10B. ELISA analysis of IgG antibodies specific for the extracellular domain of human VEGFR II in sera of mice immunized against human VEGFR II peptide and extracellular domain of human VEGFR II both coupled to Type-1 pili protein.
Figure 11:
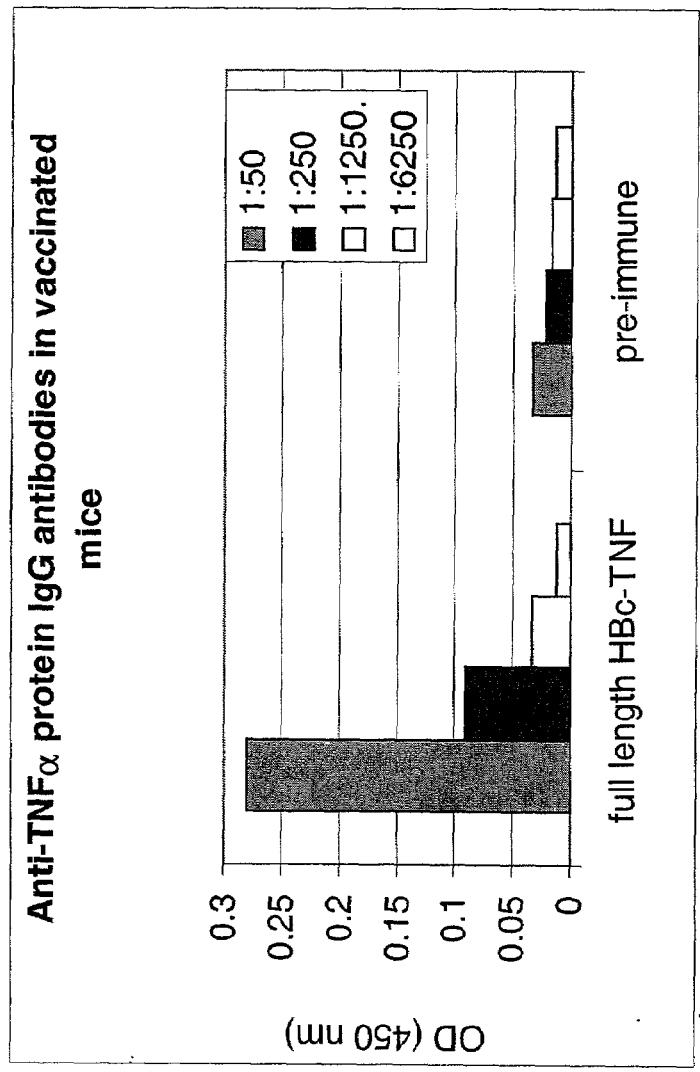
FIG. 11. ELISA analysis of IgG antibodies specific for anti-TNFα protein in sera of mice immunized against full length HBc-TNF.
Figure 12:
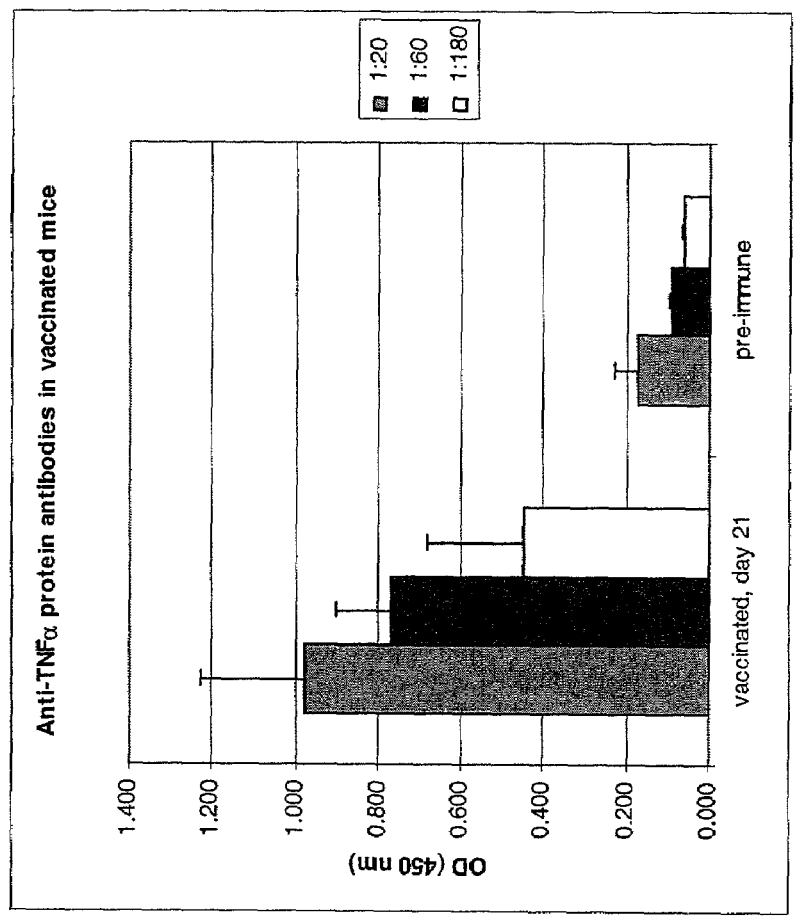
FIG. 12. ELISA analysis of IgG antibodies specific for anti-TNFα protein in sera of mice immunized against 2cysLys-mut HBcAg1–149 coupled to the 3'TNF II peptide FIG. 13A. SDS-PAGE analysis of coupling of "AβB1–15" to Qβ capsid protein using the cross-linker SMPH.

Human VEGFR-II peptide was coupled to bovine RNAse A using the chemical cross-linker sulfo-SPDP. ELISA plates were coated with coupled RNAse A at a concentration of 10 µg/ml. The human extracellular domain of VEGFR-II was adsorbed to the plates at a concentration of 2 µg/ml. The plates were blocked and then incubated with serially diluted mouse sera. Bound antibodies were detected with enzymatically labeled anti-mouse IgG antibody. As a control, preimmune sera of the same mice were also tested. Control ELISA experiments using sera from mice immunized with uncoupled carrier showed that the antibodies detected were specific for the respective peptide. The results for human VEGFR II peptide coupled to Type-1 pili are shown in FIG. 10. In particular, FIG. 10A. and FIG. 10B show ELISA analyses of IgG antibodies specific for human VEGFR II peptide and extracellular domain of human VEGFR II, respectively, in sera of mice immunized against human VEGFR II peptide and the extracellular domain of human VEGFR II each coupled to Type-1 pili protein.

Female C3H-HeJ (Toll-like receptor 4 deficient, LPS-nonresponder) and C3H-HeN (wild-type) mice were vaccinated subcutaneously with 100 ug of vaccine in PBS on day 0, 14 and 28. Serum IgG against the peptide (coupled to RNAse A) and the extracellular domain of human VEGFR II were measured on day 42. As a control, preimmune sera from the same mice were analyzed. Results for indicated serum dilutions are shown as optical density at 450 nm. The average of three mice each (including standard deviations) are shown. All vaccinated mice made high IgG antibody titers against the human VEGFR-II peptide as well as the extracellular domain of human VEGFR-II (KDR) and no difference was noted between mice deficient for the Toll-like receptor 4 and wild-type mice. The latter is remarkable since it demonstrates that formation of high IgG antibody titers against the human VEGFR-II peptide as well as the extracellular domain of human VEGFR-II is independent of endotoxin contaminations.

Example 49

Coupling of HumanVEGFR-II Peptide to Qβ Capsid Protein and Immunization of Mice with Vaccines Comprising Qβ Capsid Protein—HumanVEGFR-II Peptide Arrays Coupling of HumanVEGFR-II Peptide to Qβ Capsid Protein The human VEGFR II peptide with the sequence CTARTELNVGIDFNWEYPSSKRQHKK (SEQ ID NO:351) was chemically synthesized and is used for chemical coupling to Qβ capsid protein.

A solution of 1 ml of 1 mg/ml Qβ capsid protein in 20 mM Hepes, 150 mM NaCl pH 7.4 was reacted for 45 minutes with 20 µl of 100 mM Sulfo-MBS (Pierce) solution in (H$_2$O) at RT on a rocking shaker. The reaction solution was subsequently dialyzed twice for 2 hours in 2 L of 20 mM Hepes, pH 7.4 at 4° C. 1000 µl of the dialyzed reaction mixture was then reacted with 12 µl of a 10 mM human VEGFR II peptide solution (in DMSO) for four hours at 25° C. on a rocking shaker. The reaction mixture was subsequently dialyzed 2×2 hours against 2 liters of 20 mM Hepes, pH 7.4 at 4° C.

1 ml of a solution consisting of 2 mg/ml Qβ capsid protein in 20 mM Hepes, 150 mM NaCl, pH 7.4 was reacted for 30 minutes with 102 µl of a solution of 13 mg/ml Sulfo-MBS (Pierce) in H$_2$O at 25° C. on a rocking shaker. The reaction solution was subsequently dialyzed twice for 2 hours against 2 L of 20 mM Hepes, 150 mM NaCl, pH 7.4 at 4° C. 440 µl of the dialyzed reaction mixture was then reacted with 1.9 µl of a 100 mM peptide stock solution (in DMSO) for two hours at 25° C. on a rocking shaker. The reaction mixture was subsequently dialyzed 2×2 hours against 2 liters of 20 mM Hepes, 150 mM NaCl, pH 7.4 at 4° C.

Immunization of Mice

C57BL/6 mice are vaccinated with the human VEGFR-II peptide coupled to Qβ protein without the addition of adjuvants. Approximately 50 µg of total protein of each sample is diluted in PBS to 200 ul and injected subcutaneously on day 0, day 14 and day 28. Mice are bled retroorbitally on day 14, 28 and day 42 and serum of day 42 is analyzed using a human VEGFR-II specific ELISA Example 50

Coupling of HumanVEGFR-II Peptide to HBcAg-149-lys-2cys-Mut Capsid Protein, i.e. Cys-Free HBcAg, and Immunization of Mice with Vaccines Comprising HBcAg-149-lys-2cys-Mut Capsid Protein—HumanVEGFR-II Peptide Arrays Coupling of HumanVEGFR-II Peptide to HBcAg-149-lys-2cys-Mut Capsid Protein The human VEGFR II peptide with the sequence CTARTELNVGIDFNWEYPSSKHQHKK (SEQ ID NO:351) was chemically synthesized and is used for chemical coupling to HBcAg-149-lys-2cys-Mut capsid protein.

A solution of 3 ml of 0.9 mg/ml cys-free HbcAg capsid protein (cf. Example 31) in PBS, pH 7.4 is reacted for 45 minutes with 37.5 µl of 100 mM Sulfo-MBS (Pierce) solution in (H$_2$O) at RT on a rocking shaker. The reaction solution is subsequently dialyzed overnight against 2 L of 20 mM Hepes, pH 7.4. After buffer exchange the reaction solution is dialyzed for another 2 hours. The dialyzed reaction mixture is then reacted with 3 µl of a 10 mM human VEGFR II peptide solution (in DMSO) for 4 hours at 25° C. on a rocking shaker. The reaction mixture is subsequently dialyzed against 2 liters of 20 mM Hepes, pH 7.4 overnight at 4° C. followed by buffer exchange and another 2 hours of dialysis.

Example 51

Construction of HBcAg1-183Lys

Hepatitis core Antigen (HBcAg) 1–183 was modified as described in Example 23. A part of the c/e1 epitope (residues 72 to 88) region (Proline 79 and Alanine 80) was genetically replaced by the peptide Gly-Gly-Lys-Gly-Gly (HBcAg1-183Lys construct; SEQ ID NO:406). The introduced Lysine residue contains a reactive amino group in its side chain that can be used for intermolecular chemical crosslinking of HBcAg particles with any antigen containing a free cysteine group. PCR methods essentially as described in Example 1 and conventional cloning techniques were used to prepare the HBcAg1-183Lys gene.

The Gly-Gly-Lys-Gly-Gly (SEQ ID NO:406) sequence was inserted by amplifying two separate fragments of the HBcAg gene from pEco63, as described above in Example 23 and subsequently fusing the two fragments by PCR to assemble the full length gene. The following PCR primer combinations were used:
fragment 1:
 Primer 1: EcoRIHBcAg(s) (see Example 23)
 Primer 2: Lys-HBcAg(as) (see Example23)
fragment 2:
 Primer 3: Lys-HEcAg(s) (see Example23)
 Primer 4: HBcAgwtHindIIII

CGCGTCCCAAGCTTCTAACATTGAGATTCCCGAGATTG (SEQ ID NO:386)

Assembly:
 Primer 1: EcoRIHBcAg(s) (see example 23)
 Primer 2: HBcAgwtHindIIII

The assembled full length gene was then digested with the EcoRI (GAATTC) and HindIII (AAGCTT) enzymes and cloned into the pKK vector (Pharmacia) cut at the same restriction sites.

Example 52

Coupling of muTNFa Peptide to HBcAg1-183Lys and Immunization of Mice with Vaccines Comprising HBcAg1-183Lys-muTNFa Peptide Arrays A. Coupling of muTNFa Peptide to HBcAg1-183Lys HBcAg1-183Lys at a concentration of 0.6 mg/ml (29 µM) was treated with iodacetamide as described in Example 32. HBcAg1-183Lys was then reacted with a fifty-fold excess of the cross-linker Sulfo-MBS, as described in Example 32, and dialyzed overnight against 20 mN Hepes, pH 7.2, at 4° C. Activated (derivatized) HBcAg1-183Lys was reacted with a five-fold molar excess of the peptide muTNFa (sequence: CGGVEEQLEWLSQR (SEQ ID NO:387)), diluted directly into the HBcAg1-183Lys solution from a 100 mM stock solution in DMSO) at RT for 4 hours. The coupling reaction (about 1 ml solution) was dialyzed against 2×2 liters of 20 mM HEPES pH 7.2, at 40C, for 4 hours. The dialyzed coupling reaction was frozen in aliquots in liquid nitrogen and stored at −80° C. until immunization of the mice.

Immunization

Two mice (female Balb/c) were immunized intravenously at day 0 and 14 with 100 µg HBcAg1-183Lys coupled to the muTNFa peptide, per animal, without adjuvant. Antibodies specific for the muTNFa peptide (coated as a Ribonuclease A conjugate) and for native TNFα protein (Sigma) in the serum were determined at day 21 by ELISA.

ELISA

Murine TNFα protein (Sigma) was coated at a concentration of 2 µg/ml. As a control, preimmune sera from the same mice used for immunization were tested. FIG. 14 shows the result of the ELISA experiment, demonstrating that immunization with HBcAg1-183Lys coupled to the muTNFa peptide (Full length HBc-TNF) generated an immune response specific for the murine TNFα protein. The sera from mice bled on day 0 (preimmune) and 21 were tested at three different dilutions. Each bar is the average of the signal obtained with sera from two mice. Thus, vaccination with HBcAg1-183Lys coupled to the muTNFa peptide induced an immune response against a self-antigen, since the amino acid sequence of the muTNFa peptide is derived from the sequence of mouse TNFα protein.

Example 53

Coupling of 3'TNF II Peptide to 2cysLys-mut HBcAg1–149 and Immunization of Mice with Vaccines Comprising 2cysLys-mut HBcAg1–149-3'TNF II Peptide Arrays Coupling of the 3'TNF II Peptide to 2cysLys-mut HBcAg1–149

2cysLys-mut HBcAg1–149 was reacted at a concentration of 2 mg/ml for 30 min. at RT with a fifty-fold excess of cross-linker in 20 mM Hepes, 150 mM NaCl, pH 7.2. Excess cross-linker was removed by dialysis overnight, and activated (derivatized) 2cysLys-mut HBcAg1–149 capsid protein was reacted with a ten-fold excess of 3'TNF II peptide (SEQ: SSQNSSDKPVAHVVANHGVGGC (SEQ ID NO:359), diluted from a 100 mM stock solution in DMSO) for 4 hours at RT. The reaction mixture was then dialyzed overnight in a dialysis tubing with a molecular weight cutoff of 50000 Da, frozen in liquid nitrogen and stored at −80° C. until immunization of the mice.

Immunization of Mice

3 Female C3H/HeN mice, 8 weeks of age were vaccinated with the 3'TNF II peptide coupled to 2cysLys-mut HBcAg1–149 without the addition of adjuvants. 50 μg of total protein was diluted in PBS to 200 μl and injected subcutaneously (100 μl on two inguinal sides) on day 0 and day 14. Mice were bled retroorbitally on day 0 and 21, and their serum were analyzed in an ELISA specific for murine TNFα protein.

ELISA

Figure 15A:
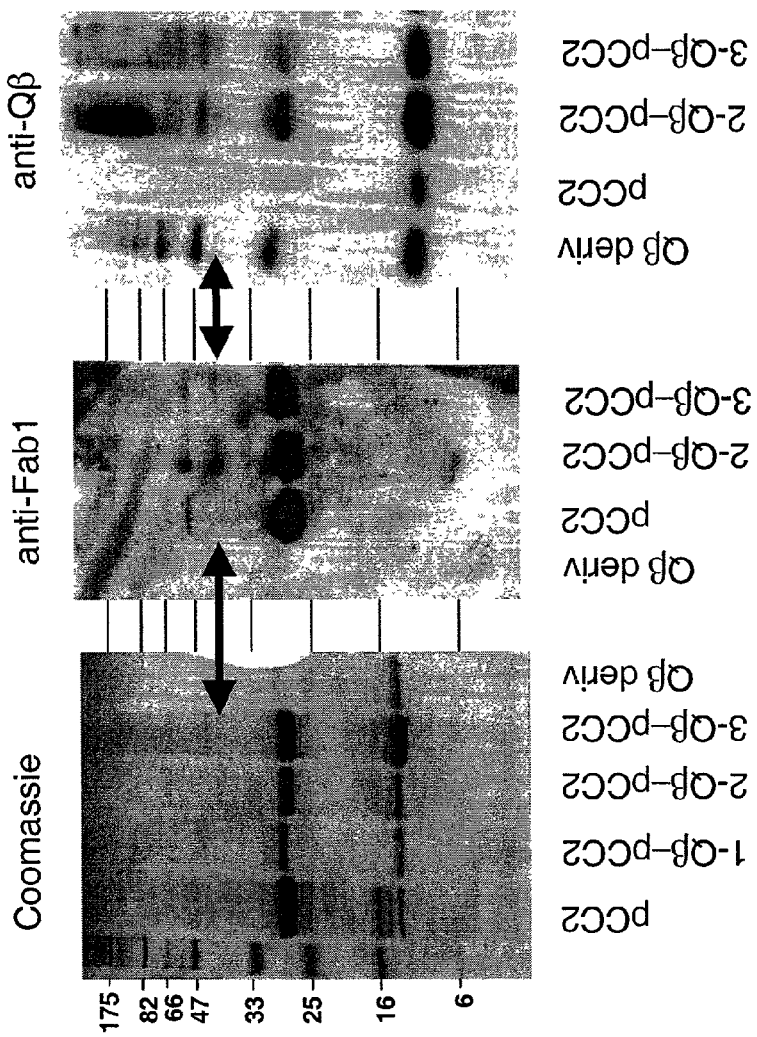
FIG. 15A. SDS-PAGE analysis of coupling of pCC2 to Qβ capsid protein.

Murine TNFα protein (Sigma) was coated at a concentration of 2 μg/ml. As a control, preimmune sera from the same mice used for immunization were tested. FIG. 15 shows the result of the ELISA, demonstrating that immunization with 2cysLys-mut HBcAg1–149 coupled to the 3'TNF II peptide generated an immune response specific for the murine TNFα protein. The sera from mice bled on day 0 (preimmune) and 21 were tested at three different dilutions. Each bar is the average of the signal obtained with sera from 3 mice. Thus, vaccination with 2cysLys-mut HBcAg1–149 coupled to the 3'TNF II peptide induced an immune response specific for a self-antigen, since the amino acid sequence of the 3'TNF II peptide is derived from the sequence of murine TNFα protein.

Example 54

Coupling of Aβ 1–15, Aβ 1–27 and Aβ 33–42 Peptides to Qβ and Immunization of Mice with Vaccines Comprising Qβ-Aβ Peptide Arrays A. Coupling of Aβ 1–15 and Aβ 33–42 Peptides to Qβ Capsid Protein Using the Cross-linker SMPH.

The following Aβ peptides were chemically synthesized: DAEFRHDSGYEVHHQGGC (abbreviated as "Aβ 1–15"; SEQ ID NO:367), a peptide which comprises the amino acid sequence from residue 1–15 of human Aβ, fused at its C-terminus to the sequence GGC for coupling to Qβ capsid protein and CGHGNKSGLMVGGVVIA (abbreviated as "Aβ 33–42"; SEQ ID NO:369) a peptide which comprises the amino acid sequence from residue 33–42 of Aβ fused at its N-terminus to the sequence CGHGNKS (SEQ ID NO:405) for coupling to Qβ capsid protein. Both peptides were used for chemical coupling to Qβ as described in the following.

A solution of 1.5 ml of 2 mg/ml Qβ capsid protein in 20 mM Hepes 150 mM NaCl pH 7.4 was reacted for 30 minutes with 16.6 μl of a solution of 65 mM SMPH (Pierce) in H₂O, at 25° C. on a rocking shaker. The reaction solution was subsequently dialyzed twice for 2 hours against 2 L of 20 mM Hepes, 150 mM NaCl, pH 7.4 at 4° C. in a dialysis tubing with Molecular Weight cutoff 10000 Da. 450 μl of the dialyzed reaction mixture, which contains activated (derivatized) Qβ, was then reacted with 6.5 μl of each of the corresponding 50 mM peptide stock solution (in DMSO) for two hours at 15° C. on a rocking shaker. 200 μl of the reaction mixture was subsequently dialyzed overnight against 2 liters of 20 mM Hepes, 150 mM NaCl, pH 7.4 at 4° C., and the next morning for another two hours after change of buffer. The reaction mixture was then frozen in aliquots in liquid Nitrogen and stored at −80° C. until immunization of the mice.

Figure 13A:
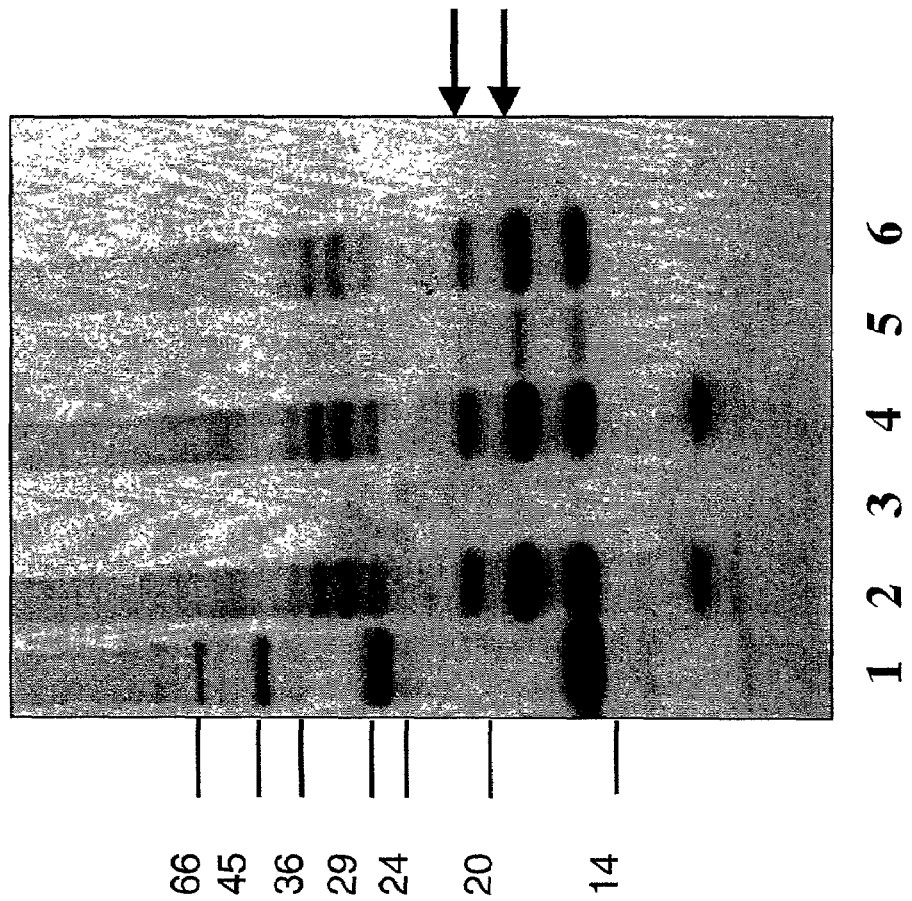
FIG. 13B. SDS-PAGE analysis of coupling of "Aβ33–42" to Qβ capsid protein using the cross-linker SMPH.
FIG. 13C. SDS-PAGE analysis of coupling of "Aβ1–27" to Qβ capsid protein using the cross-linker SMPH.
FIG. 13D. SDS-PAGE analysis of coupling of "Aβ1–15" to Qβ capsid protein using the cross-linker Sulfo-GMBS.
FIG. 13E. SDS-PAGE analysis of coupling of "Aβ1–15" to Qβ capsid protein using the cross-linker Sulfo-MBS.
Figure 13B:
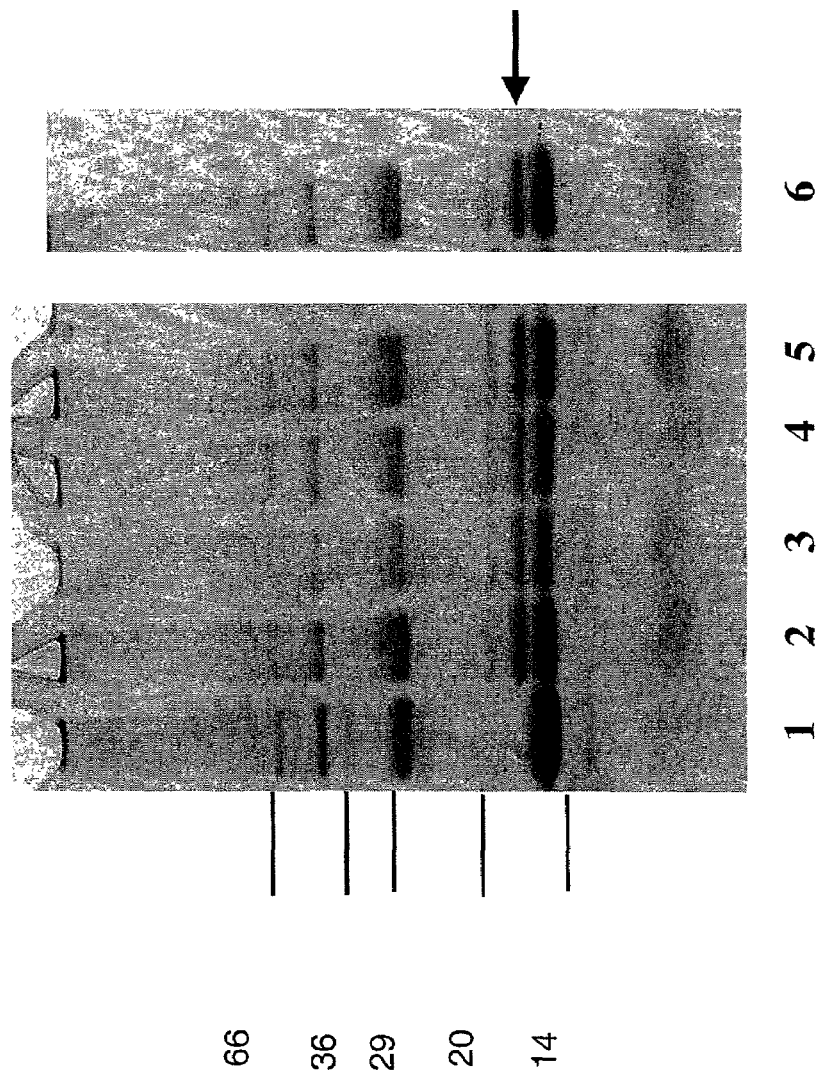

The results of the coupling experiments were analyzed by SDS-PAGE, and are shown in FIG. 13A and FIG. 13B. The arrows point to the band corresponding to one, respectively two peptides coupled to one Qβ subunit (FIG. 13A), or one peptide coupled to one Qβ subunit (FIG. 13B). Molecular weights of marker proteins are given on the left margin of FIG. 13A and FIG. 13B.

The samples loaded on the gel of FIG. 13A are the following:

1: derivatized Qβ; 2: Qβ coupled with "Aβ1–15", supernatant of the sample taken at the end of the coupling reaction, and centrifuged; 3: Qβ coupled with "Aβ1–15", pellet of the sample taken at the end of the coupling reaction, and centrifuged. 4: Qβ coupled with "Aβ1–15", supernatant of a sample left to stand 24 hours at 4° C., undialyzed and centrifuged. 5: Qβ coupled with "Aβ1–15", pellet of a sample left to stand 24 hours at 4° C., undialyzed and centrifuged. 6: Qβ coupled with "Aβ1–15", supernatant of the sample taken after dialysis of the coupling reaction, and centrifuged.

The samples loaded on the gel of FIG. 13B are the following:

1: derivatized Qβ 2: Qβ coupled with "Aβ33–42", supernatant of the sample taken at the end of the coupling reaction, and centrifuged. 3: Qβ coupled with "Aβ33–42", pellet of the sample taken at the end of the coupling reaction, and centrifuged. 4: Qβ coupled with "Aβ33–42", supernatant of a sample left to stand 24 hours at 4° C., undialyzed and centrifuged. 5: Qβ coupled with "Aβ33–42", pellet of a sample left to stand 24 hours at 4° C., undialyzed and centrifuged. 6: Qβ coupled with "Aβ33–42", supernatant of the sample taken after dialysis of the coupling reaction, and centrifuged.

B. Coupling of "Aβ 1–27" Peptide to Qβ Capsid Protein Using the Cross-linker SMPH.

The following Aβ peptide ("Aβ 1–27"; SEQ ID NO:368) was chemically synthesized DAEFRHDSGYEVH-HQKLVFFAEDVGSNGGC . This peptide comprises the amino acid sequence from residue 1–27 of human Aβ, fused at its C-terminus to the sequence GGC for coupling to Qβ capsid protein.

A first batch of "Aβ1–27" coupled to Qβ capsid protein, in the following abbreviated as "Qβ-Aβ1–27 batch 1" was prepared as follows:

A solution of 1.5 ml of 2 mg/ml Qβ capsid protein in 20 mM Hepes 150 mM NaCl pH 7.4 was reacted for 30 minutes with 16.6 μl of a solution of 65 mM SMPH (Pierce) in H₂O, at 25° C. on a rocking shaker. The reaction solution was subsequently dialyzed twice for 2 hours against 2 L of 20 mM Hepes, 150 mM NaCl, pH 7.4 at 4° C. in a dialysis tubing with Molecular Weight cutoff 10000 Da. 450 μl of the dialyzed reaction mixture was then reacted with 6.5 μl of a 50 mM peptide stock solution (in DMSO) for two hours at 15° C. on a rocking shaker. 200 μl of the sample was then aliquoted, frozen in liquid Nitrogen and stored at −80° C. until immunization of the mice.

A second batch of "Aβ 1–27" coupled to Qβ capsid protein, in the following abbreviated as "Qβ-Aβ 1–27 batch 2" was prepared as follows:

500 μl of Qβ capsid protein in 20 mM Hepes 150 mM NaCl pH 7.4 was reacted for 30 minutes with 11.3 μl of a solution of 32.5 MM SMPH (Pierce) in H$_2$O, at 25° C. on a rocking shaker. The reaction solution was subsequently dialyzed twice for 2 hours against 2 L of 20 mM Hepes, 150 mM NaCl, pH 7.4 at 4° C. in a dialysis tubing with Molecular Weight cutoff 3500 Da (SnakeSkin, Pierce). The dialyzed reaction mixture was then reacted with 3.6 μl of a 50 mM peptide stock solution (in DMSO) for two hours at 15° C. on a rocking shaker. The reaction mixture was then dialyzed 2× against 1 l 20 mM Hepes, 150 mM NaCl, pH 7.4 for 1 hour and overnight after a last change of buffer, using a dialysis membrane with a 50000 Da cutoff (Spectrapor, spectrum). The reaction mixture was then frozen in aliquots in liquid nitrogen and stored at −80° C. until immunization of the mice. "Qβ-Aβ 1–27 batch 1" was used for the first immunization, while "Qβ-Aβ 1–27 batch 2" was used for the boost.

Figure 13C:
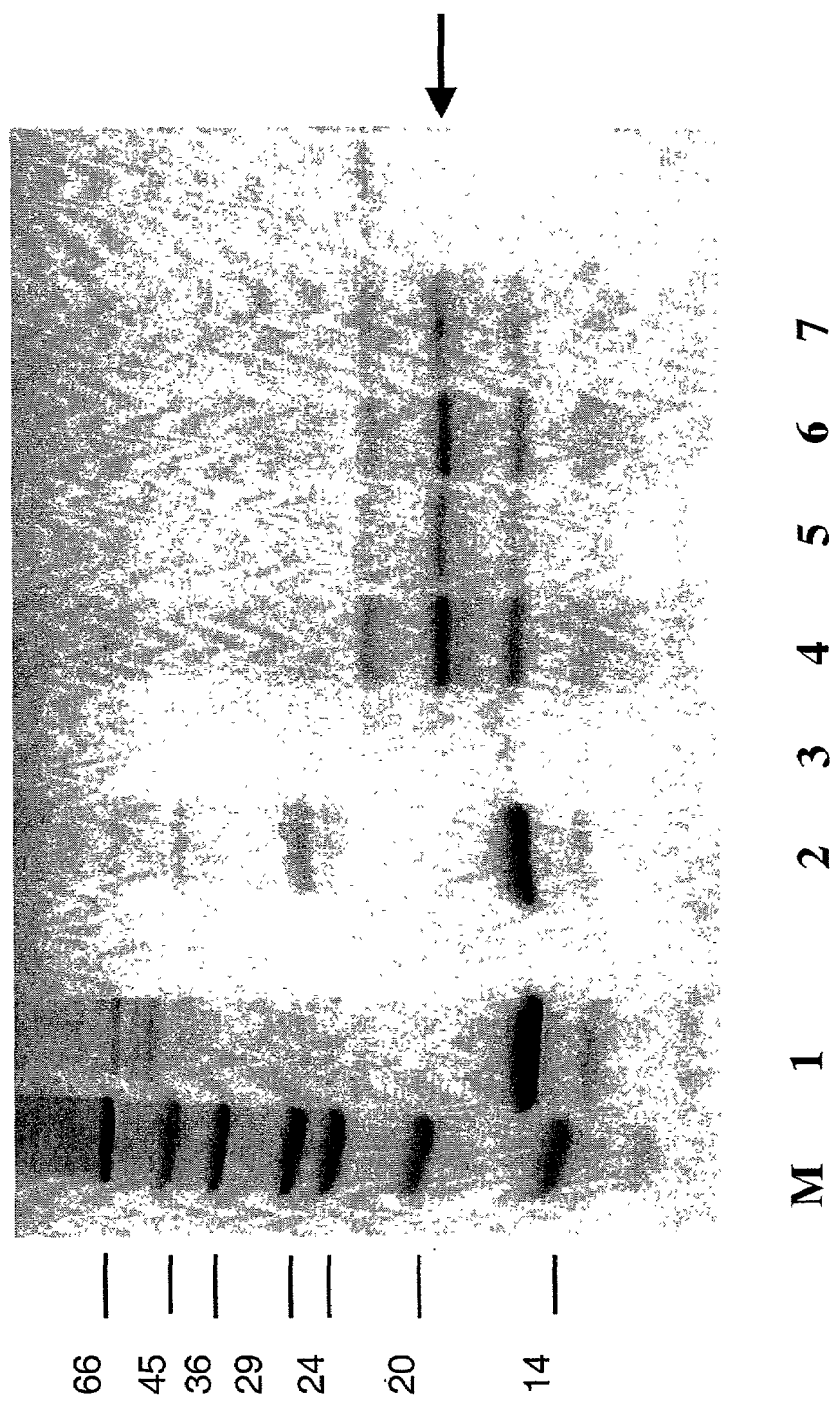

The result of the coupling experiment was analyzed by SDS-PAGE, and is shown in FIG. 13C. The arrow points to the band corresponding to one peptide coupled to one Qβ subunit.

The samples loaded on the gel of FIG. 13C are the following:

M: protein marker. 1: Qβ capsid protein 2: derivatized Qβ, supernatant of the sample taken at the end of the derivatization reaction, and centrifuged. 3: derivatized Qβ, pellet of the sample taken at the end of the derivatization reaction, and centrifuged. 4: Qβ coupled with "Aβ1–27", supernatant of the sample taken at the end of the coupling reaction, and centrifuged. 5: Qβ coupled with "Aβ1–27", pellet of the sample taken at the end of the coupling reaction, and centrifuged. 6: Qβ coupled with "Aβ1–27", supernatant of the sample taken after dialysis of the coupling reaction, and centrifuged. 7: Qβ coupled with "Aβ1–27", pellet of the sample taken after dialysis of the coupling reaction, and centrifuged.

C. Coupling of "Aβ 1–15" Peptide to Qβ Capsid Protein Using the Cross-linker Sulfo-GMBS A solution of 500 μl of 2 mg/ml Qβ capsid protein in 20 mM Hepes 150 mM NaCl pH 7.4 was reacted for 30 minutes with 5.5 μl of a solution of 65 mM SMPH (Pierce) in H$_2$O, at 25° C. on a rocking shaker. The reaction solution was subsequently dialyzed twice for 2 hours against 2 L of 20 mM Hepes, 150 mM NaCl, pH 7.4 at 4° C. in a dialysis tubing with Molecular Weight cutoff 10 000 Da. 500 μl of the dialyzed reaction mixture was then reacted with 6.5 μl of the 50 mM peptide stock solution (in DMSO) for two hours at 15° C. on a rocking shaker. 200 μl of the reaction mixture was subsequently dialyzed overnight against 2 liters of 20 mM Hepes, 150 mM NaCl, pH 7.4 at 4° C., and the next morning for another two hours after change of buffer. The reaction mixture was then frozen in aliquots in liquid Nitrogen and stored at −80° C. until immunization of the mice.

Figure 13D:
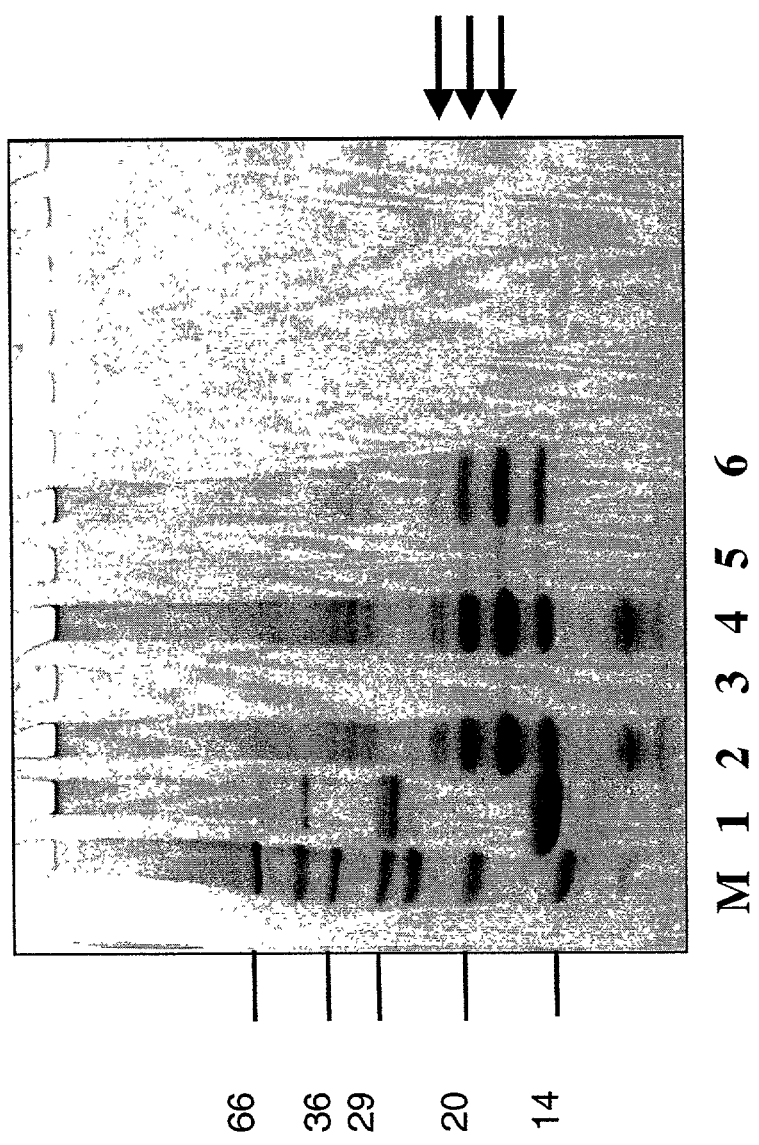

The result of the coupling experiment was analyzed by SDS-PAGE, and is shown in FIG. 13D. The arrow points to the band corresponding to one, two and three peptides, respectively, coupled to one Qβ subunit.

The samples loaded on the gel of FIG. 13D are the following:

M: protein marker. 1: derivatized Qβ 2: Qβ coupled with "Aβ1–15", supernatant of the sample taken at the end of the coupling reaction, and centrifuged. 3: Qβ coupled with "Aβ1–15", pellet of the sample taken at the end of the coupling reaction, and centrifuged. 4: Qβ coupled with "Aβ1–15", supernatant of a sample left to stand 24 hours at 4° C., undialyzed and centrifuged. 5: Qβ coupled with "Aβ1–15", pellet of a sample left to stand 24 hours at 4° C., undialyzed and centrifuged. 6: Qβ coupled with "Aβ1–15", supernatant of the sample taken after dialysis of the coupling reaction, and centrifuged.

D. Coupling of "Aβ 1–15" to Qβ Capsid Protein Using the Cross-linker Sulfo-MBS.

500 μl of Qβ capsid protein in 20 mM Hepes 150 mM NaCl pH 7.4 was reacted for 30 minutes with 14.7 μl of a solution of 100 mM Sulfo-MBS (Pierce) in H$_2$O, at 25° C. on a rocking shaker. The reaction solution was subsequently dialyzed twice for 2 hours against 2 L of 20 mM Hepes, 150 mM NaCl, pH 7.4 at 4° C. in a dialysis tubing (SnakeSkin, Pierce) with Molecular Weight cutoff 3500 Da. The dialyzed reaction mixture was then reacted with 7.2 μl of a 50 mM peptide stock solution (in DMSO) for two hours at 15° C. on a rocking shaker. The reaction mixture was then dialyzed 3× over 4 hours against 2 l 20 mM Hepes, 150 mM NaCl, pH 7.4 using a dialysis membrane with a 50000 Da cutoff (Spectrapor, spectrum). The reaction mixture was then frozen in aliquots in liquid nitrogen and stored at −80° C. until immunization of the mice.

Figure 13E:
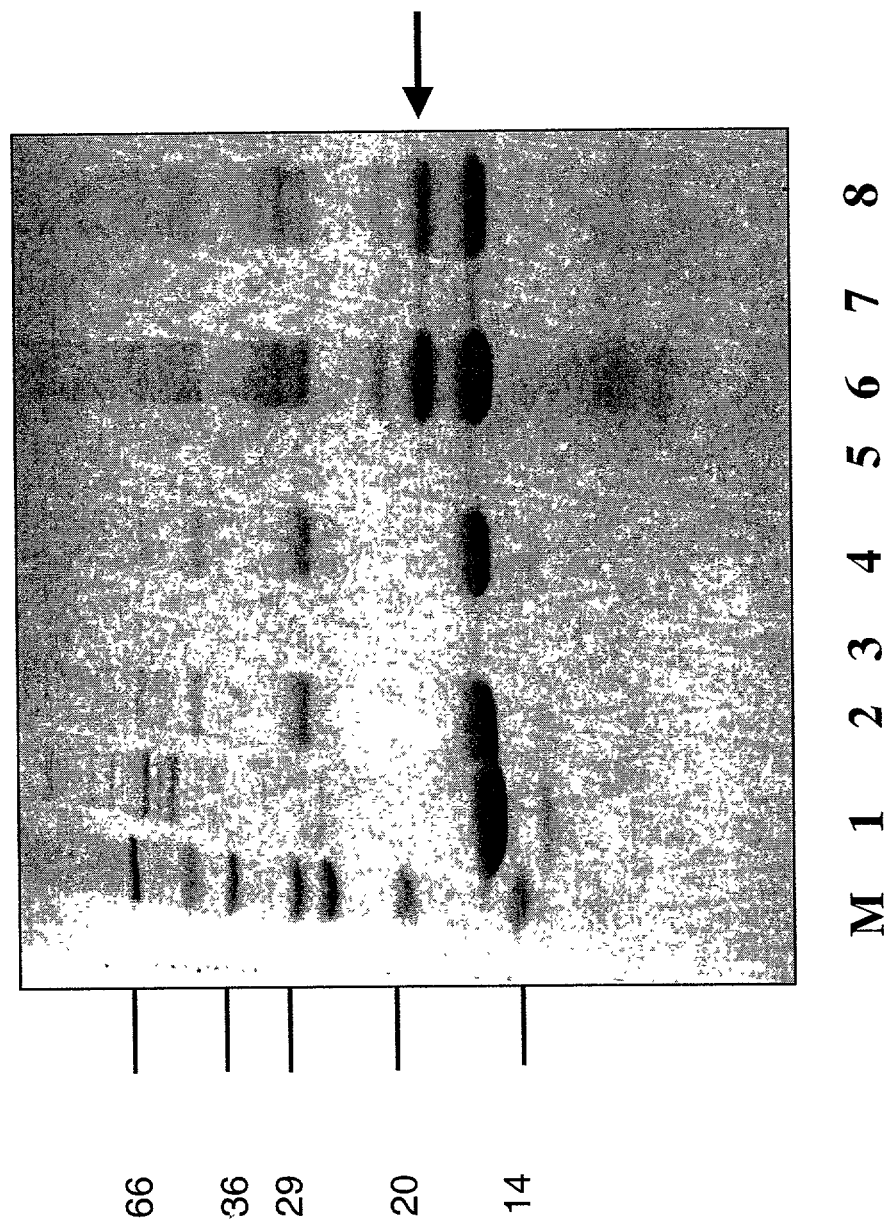

The result of the coupling experiment was analyzed by SDS-PAGE, and is shown in FIG. 13E. The arrow points to the band corresponding to one peptide coupled to one Qβ subunit.

The samples loaded on the gel of FIG. 13E are the following:

1: Qβ capsid protein 2: derivatized Qβ, supernatant of the sample taken at the end of the derivatization reaction, and centrifuged. 3: derivatized Qβ, pellet of the sample taken at the end of the derivatization reaction, and centrifuged. 4: derivatized Qβ, supernatant of the sample taken at the end of the dialysis of the derivatization reaction, and centrifuged. 5: derivatized Qβ, pellet of the sample taken at the end of the dialysis of the derivatization reaction, and centrifuged. 6: Qβ coupled with "Aβ1–15", supernatant of the sample taken at the end of the coupling reaction, and centrifuged. 7: Qβ coupled with "Aβ1–15", pellet of the sample taken at the end of the coupling reaction, and centrifuged. 8: Qβ coupled with "Aβ1–15", supernatant of the sample taken after dialysis of the coupling reaction, and centrifuged.

E. Immunization of Mice:

Five groups of female C57BL/6 mice, three mice per group, 8 weeks of age were vaccinated each with one of the five Aβ peptide-Qβ capsid protein conjugates without the addition of adjuvant. 25 μg of total protein of each sample was diluted in PBS to 200 μl and injected subcutaneously on day 0 and day 14. Mice were bled retroorbitally on day 0 (preimmune) and 21 and their serum was analyzed in an ELISA. "Aβ 1–15" peptide was coupled to Qβ with three different cross-linkers, resulting in three different vaccine preparations ("Qb-Aβ1–15 SMPH", "Qβ-Ab1–15 SMBS", "Qb-Aβ1–15 SGMBS"; see ELISA section for the results).

F. ELISA

All three Aβ peptides were individually coupled to bovine RNAse A using the chemical cross-linker SPDP as follows: a solution of 10 mg RNAse A in 2 mL PBS (50 mM Phoshate buffer, 150 mM NaCl pH 7.2) was reacted with 100 μl of a 20 mM SPDP solution in DMSO, at 25° C. for 60 min. on a rocking shaker. Excess cross-linker was separated from activated (derivatized) RNAse A by gel filtration using a PD 10 column (Pharmacia). The protein containing fractions were pooled and concentrated to a volume of 2 ml using centrifugal filters (5000 MWCO). A sample of 333 μl of the derivatized RNAse A solution was reacted with 2 μl of the peptide stock solution (50 mM in DMSO). The coupling reaction was followed spectrophotometrically.

Figure 14A:
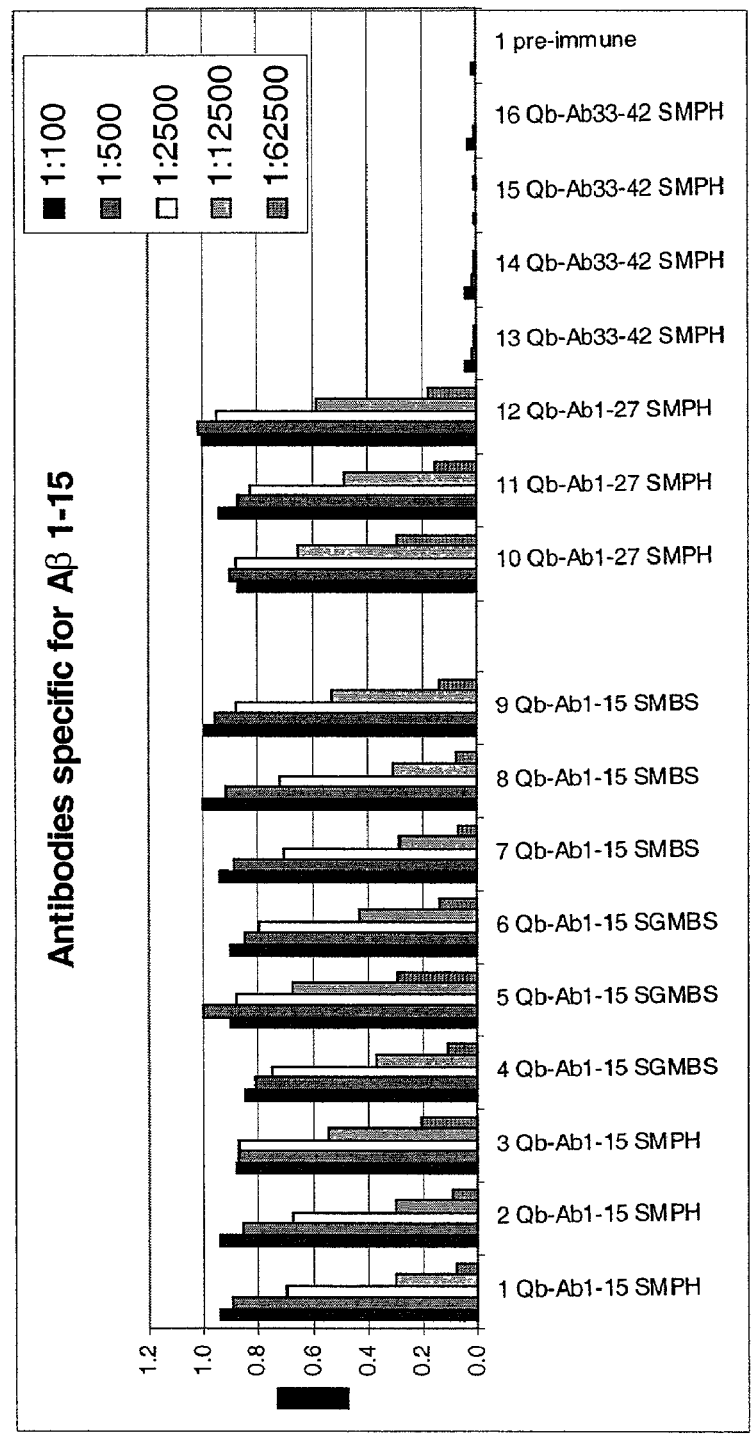
FIG. 14A. ELISA analysis of IgG antibodies specific for "Aβ1–15" in sera of mice immunized against "Aβ1–15" coupled to Qβ capsid protein.
Figure 14B:
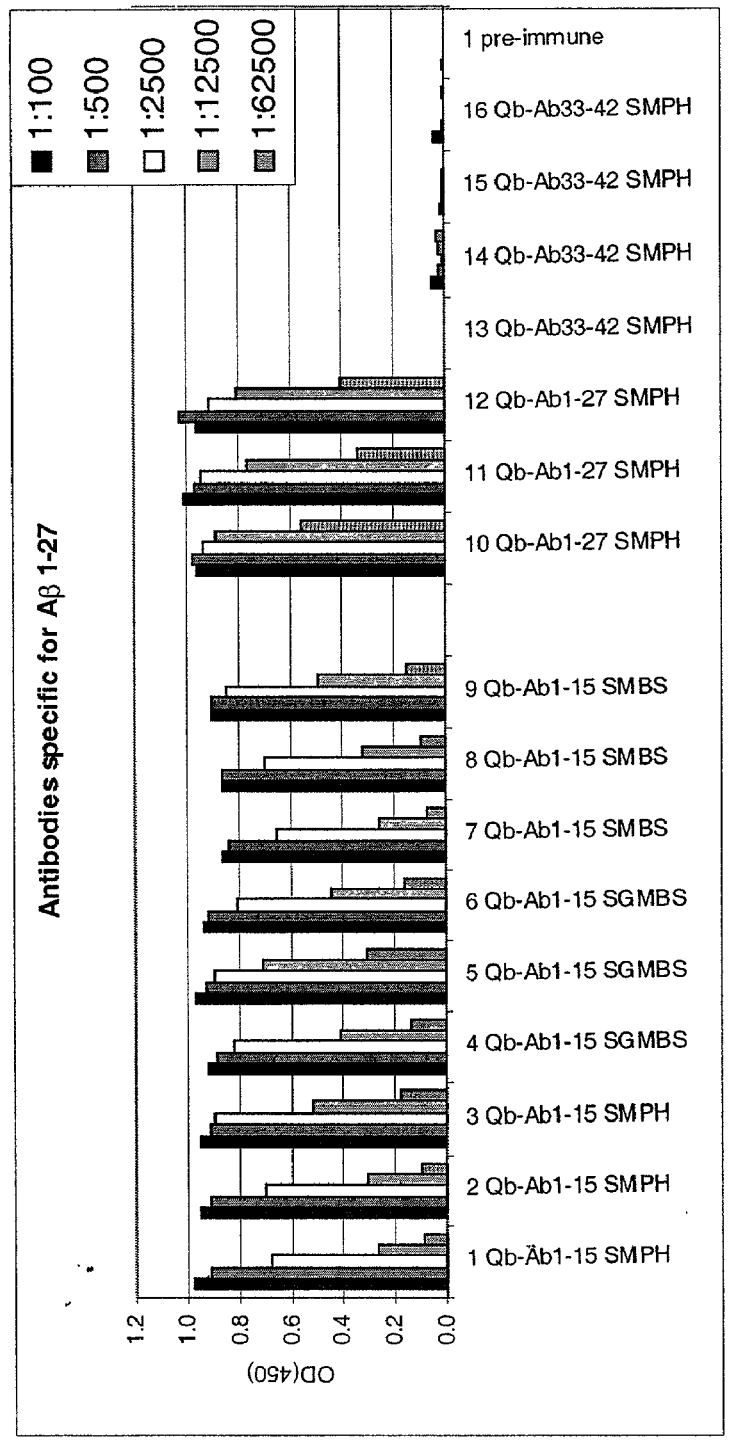
FIG. 14B. ELISA analysis of IgG antibodies specific for "Aβ1–27" in sera of mice immunized against "Aβ1–27" coupled to Qβ capsid protein.
Figure 14C:
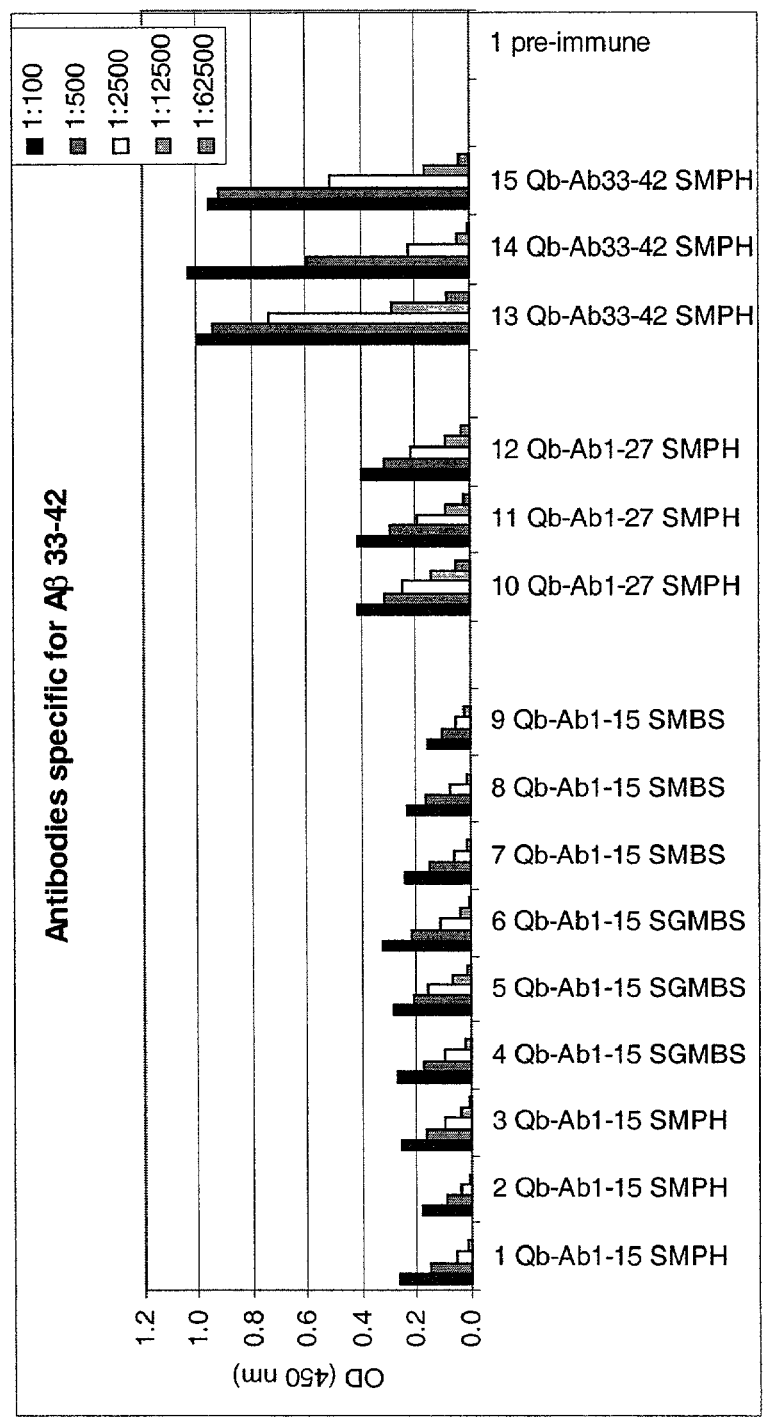
FIG. 14C. ELISA analysis of IgG antibodies specific for "Aβ33–42" in sera of mice immunized against "Aβ33–42" coupled to Qβ capsid protein.

ELISA plates were coated with RNAse A coupled to peptide at a concentration of 10 μg/ml. The plates were blocked and then incubated with serially diluted mouse sera. Bound antibodies were detected with enzymatically labeled anti-mouse IgG antibody. Preimmune sera or control sera from mice immunized with unrelated peptides conjugated to Qβ, showed that the antibodies detected were specific for the respective peptide. FIG. 14A, FIG. 14B and FIG. 14C, respectively, show ELISA analyses of IgG antibodies specific for "Aβ 1–15", "Aβ 1–27" and "Aβ 33–42", respectively, in sera of mice immunized against "Aβ 1–15", "Aβ 1–27" and "Aβ 33–42", respectively, coupled to Qβ capsid protein. The denominations on the abscissa stand for the vaccine injected in the mice from which the sera are derived, and describe the peptide and the cross-linker used to make the respective vaccine. All sera were measured against the three peptides coupled to RNAse A, and the results show that while there is cross-reactivity between the antibodies raised against peptide 1–15 and 1–27, no such cross reactivity is observed against peptide 33–42, demonstrating the specificity of the immune response. Likewise, The ELISA titers obtained, expressed as the dilution of the serum yielding an ELISA signal three standard deviations above background, were very high, and ranged from 60,000 to 600,000. No Aβ peptide-specific antibodies were detected in the controls (pre-immune mice).

Example 55

Introduction of Cys-containing Linkers, Expression, and Purification of Anti-idiotypic IgE Mimobodies and Their Coupling to Qβ Capsid Protein A. Construction of Plasmids for the Expression of Mimobodies for Coupling to Qβ Capsid Protein Plasmids were based on the expression plasmid VAE051-pASK116. This plasmid contains the coding regions for the heavy chain and for the light chain of the mimobody. The following primers were used to introduce cys-containing linkers at the C-terminus of the heavy chain:

(SEQ ID NO:388)
Primer CA2F:
CGGCTCGAGCATCACCATCACCATCACGGTGAAGTTAAACTGCAGCTG
GAGTCG (SEQ ID NO:389)
Primer CA1R:
CATGCCATGGTTAACCACAGGTGTGGGTTTTATCACAAGATTTGGGCT
CAAC (SEQ ID NO:390)
Primer CB1R:
CATGCCATGGTTAACCACACGGCGGAGAGGTGTGGGTTTTATCACAAG
ATTTGGGCTCAAC (SEQ ID NO:391)
Primer CC1R:
CCAGAAGAACCCGGCGGGGTAGACGGTTTCGGGCTAGCACAAGATTT
GGGCTCAACTC (SEQ ID NO:392)
Primer CC1F:
CGCCGGGTTCTTCTGGTGGTGCTCCGGGTGGTTGCGGTTAACCATGGA
GAAAATAAAGTG (SEQ ID NO:393)
Primer CCR2:
CTCCCGGGTAGAAGTCAC A.1. Construction of pCA2:

Primers CA2F and CA1R were used to amplify a 741 bp fragment encoding part of the heavy chain with an extension encoding the cys-containing linker sequence. VAE-pASK116 served as template for the Pfx polymerase (Roche) in the PCR cycler (Robo) at (initial denaturation at 92° C., cycling: 92° C., 30 s; 48° C., 30 s; 68° C., 60s) for 5 cycles followed by 30 cycles with 92° C., 30 s; 58° C., 30 s; 68° C., 1 min. The PCR product of the appropriate size was purified using the Qiagen PCR purification kit and digested with XhoI and NcoI according to the recommendation of the manufacturer (Gibco). The product was purified from an agarose gel with the Qiagen gel extraction kit. Plasmid VAE-pASKI 16 was in parallel cleaved with XhoI and NcoI and a 3.7 kb band purified from agarose gels. Appropriate aliquots of the XhoI-NcoI digested PCR product and the plasmid were ligated overnight at 16° C. using T4 DNA ligase according to the manufacturer's protocoll (Gibco). The ligation product was transformed into competent E.coli XL-1 cells which were plated on agarose plates containing chloramphenicol. Single colonies were expanded in LB/chloramphenicol medium, plasmid was prepared (Qiagen mini plasmid kit) and tested for the presence of the appropriate XhoI-NcoI insert size after digestion with the corresponding enzymes. A correspondingly positive plasmid termed pCA2 was sent for sequencing on both strands which confirmed the identity of the plasmid including the cys-containing linker.

A.2. Construction of pCB2:

Primers CA2F and CB1R were used to introduce linker 2 at the 5' end of the heavy chain coding sequence and the same conditions as described in section A1. The resulting PCR product was 750 bp and cloned into VAE051-pASK116 as described in section A.1.

A.3. Construction of pCC2:

Plasmid pCC2 was constructed in a two step procedure: A first PCR product of 754 bp was amplified using primers CA2F and CC1R. A second PCR product of 560 bp was produced using primers CC IF and CC2R. For both PCRs VAE051-pASK116 was used as template and conditions were as described in section A1. Both PCR products were isolated from agarose gels, mixed with primers CA2F and CC2R and a third PCR was performed that resulted in a 1298 bp fragment. This fragment was isolated and digested with XhoI and NcoI. The resulting 780 bp fragment was cloned into VAE-pASK100 as described in section A.1.

B. Expression of Mimobodies

Competent E. coli W3110 cells were transformed with plasmids pCA2, pCB2 and pCC2. Single colonies from chloramphenical agarose plates were expanded in liquid culture (LB+15 μg/ml chloramphenicol) overnight at 37° C. 1 l of TB medium was then inoculated 1.50 v/v with the overnight culture and grown to OD600=3 at 28° C. Expression was induced with 1 mg/l anhydrotetracyclin. Cells were harvested after overnight culture and centrifuged at 6000 rpm. Periplasma was isolated from cell pellets by incubation in lysis buffer supplemented with polymyxin B sulfate for 2 h at 4° C. Spheroblasts were separated by centrifugation at 6000 rpm. The resulting supernatant contained the mimobody and was dialysed against 20 mM Tris, pH 8.0.

C. Purification of Mimobodies

The introduced his6-tag allowed the purification of mimobody pCA2 and pCB2 by chromatography on Ni-NTA fast flow (Qiagen) according the recommendations of the manufacturer. If necessary, a polishing step on a protein G fast flow column (Amersham Pharmacia Biotech) followed. Mimobodies were eluted with 0.1 M glycine pH 2.7, immediately neutralized by addition of NaOH and dialysed against 20 mM Hepes, 150 mM NaCl, pH 7.2.

pCC2 was purified by affinity chromatography on protein G only. Purity was analysed by SDS-PAGE.

The protein sequences of the mimobodies were translated from the cDNA sequences. N-terminal sequences were confirmed by Edman sequencing of pCA2 and pCB2.

The sequence of the light chains of pCA2, pCB2 and pCC2 is the

DIELVVTQPASVSGSPGQSITISCTGTRSDVGGYNYVSWYQQHPGKAPKL

MIYDVSNRPSGVSNRFSGSKSGNTASLTISGLQAEDEADYYCSSYTSSST

LGVFGGGTKLTVLGQPKAAPSVTLFPPSSEELQANKATLVCLISDFYPGA

VTVAWKADSSPVKAGVETTTPSKQSNNKYAASSYLSLTPEQWKSHKSYSC

QVTHEGSTVEKTVAPTECS (SEQ ID NO:394)

The sequence of the heavy chain of pCA2 is:

EVKLQLEHHHHHHGEVKLQLESGPGLVKPSETLSLTCTVSGGSISSGGYY

WTWIRQRPGKGLEWIGYIYYSGSTSYNPSLKSRVTMSVDTSKNQFSLRLT

SVTAADTAVYYCARERGETGLYYPYYYIDVWGTGTTVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCDKTHTC

G (SEQ ID NO:395)

The sequence of the heavy chain of pCB2 is:

EVKLQLEHHHHHHGEVKLQLESGPGLVKPSETLSLTCTVSGGISSGGYYW

TWIRQRPGKGLEWIGYIYYSGSTSYNPSLKSRVTMSVDTSKNQFSLRLTS

VTAADTAVYYCARERGETGLYYPYYYIDVWGTGTTVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTSP

PCG (SEQ ID NO:396)

The sequence of the heavy chain of pCC2 is:

EVKLQLEHHHHHHGEVKLQLESGPGLVKPSETLSLTCTVSGGSISSGGYY

WTWIRQRPGKGLEWIGYIYYSGSTSYNPSLKSRVTMSVDTSKNQFSLRLT

SVTAADTAVYYCARERGETGLYYPYYYIDVWGTGTTVTVSSSASTKGPSV

FPLAPSSKSTSGGTAALGCLVKDYFPEPVTVSWNSGALTSGVHTFPAVLQ

SSGLYSLSSVVTVPSSSLGTQTYICNVNHKPSNTKVDKRVEPKSCASPKP

STPPGSSGGAPGGC (SEQ ID NO:397)

same and as follows:

D. Coupling of Mimobodies to Qβ Capsid Protein

D.1. Coupling of Mimobody pCC2 to Qβ Capsid Protein:

A solution of 1.25 ml of 4.5 mg/ml Qβ capsid protein in 20 mM Hepes, 150 mM NaCl pH 7.2 was reacted for 30 minutes with 40 µl of a SMPH solution (Pierce) (from a 100 mM stock solution dissolved in DMSO) at 25° C. on a rocking shaker. The reaction solution was subsequently dialyzed twice for 2 hours against 2 l of 20 mM Hepes, 150 mM NaCl, pH 7.2 at 4° C. 6 µl of the dialyzed reaction mixture was then reacted with 30 µl of the pCC2 solution (2.88 mg/ml) for at 25° C. over night on a rocking shaker.

The reaction products were analysed on 16% SDS-PAGE gels under reducing conditions. Gels were either stained with Coomassie Brilliant Blue or blotted onto nitrocellulose membranes. Membranes were blocked, incubated with a polyclonal rabbit anti-Qb antiserum (dilution 1:2000) or a mouse monoclonal anti-Fab-mAb (Jackson ImmunoResearch) (dilution 1:2000). Blots were subsequently incubated with horse radish peroxidase-conjugated goat anti-rabbit IgG or horse radish peroxidase-conjugated goat anti-mouse IgG (dilutions 1:7000), respectively The results are shown in FIG. 13A. Coupling products and educts were analysed on 16% SDS-PAGE gels under reducing conditions. In FIG. 13A "pCC2" corresponds to the mimobody before coupling. "Qβ deriv" stands for derivatized Qβ before coupling, "Qβ-pCC2" for the product of the coupling reaction. Gels were either stained with Coomassie Brilliant Blue or blotted onto nitrocellulose membranes. Membranes were blocked, incubated with a polyclonal rabbit anti-Qβ antiserum (dilution 1:2000) or an mouse monoclonal anti-Fab-mAb (Jackson ImmunoResearch) (dilution 1:2000). Blots were subsequently incubated with horse radish peroxidase-conjugated goat anti-rabbit IgG or horse radish peroxidase-conjugated goat anti-mouse IgG (dilutions 1:7000), respectively. Enhanced chemoluminescence (Amersham Pharmacia ELC kit) was used to visualize the immunoreactive bands. Molecular weights of marker proteins are given on the left margin.

A coupling product of about 40 kDa could be detected (FIG. 13A, arrows). Its reactivity with the anti-Qβ antiserum and the anti-Fab antibody recognizing the mimobody clearly demonstrated the covalent coupling of the mimobody to Qβ.

D.2. Coupling of Mimobodies pCA2 and pCB2 to Qβ Capsid Protein:

A solution of 1.25 ml of 4.5 mg/ml Qβ capsid protein in 20 mM Hepes, 150 mM NaCl pH 7.4 was reacted for 30 minutes with 40 µl of a SMPH (Pierce) (from a 100 mM stock solution dissolved in DMSO) at 25° C. on a rocking shaker. The reaction solution was subsequently dialyzed twice for 2 hours against 2 l of 20 mM Hepes, 150 mM NaCl, pH 7.2 at 4° C. pCA2 (1.2 mg/ml) was reduced with 20 mM TCEP for 30 min at 25° C., pCB2 (4.2 mg/ml) with 50 mM mercaptoethylamine at 37° C. Both mimobodies were then dialyzed twice against 20 mM Hepes, 150 mM NaCl, pH 7.2 at 4° C. Coupling was performed by adding 6 µl of derivatized Qβ to 30 µl of mimobody at 25° C. over night on a rocking shaker.

The reaction products were analysed on 16% SDS-PAGE gels under reducing conditions. Gels were either stained with Coomassie Brilliant Blue or blotted onto nitrocellulose membranes. Membranes were blocked, incubated with a polyclonal rabbit anti-Qb antiserum (Cytos, dilution 1:2000) or an mouse monoclonal anti-his6-mAb (Qiagen) (dilution 1:5000). Blots were subsequently incubated with horse radish peroxidase-conjugated goat anti-rabbit IgG or horse radish peroxidase-conjugated goat anti-mouse IgG (dilutions 1:5000), respectively.

The results are shown in FIG. 13B and FIG. 13C. Coupling products and educts were analysed on 16% SDS-PAGE gels under reducing conditions. In FIG. 15A and FIG.

15B "pCA2" and "pCB2" corresponds to the mimobodies before coupling. "Qb deriv" stands for derivatized Qβ before coupling and "Qβ-pCA2" and "Qβ-pCA2" for the products of the coupling reaction. Gels were either stained with Coomassie Brilliant Blue or blotted onto nitrocellulose membranes. Membranes were blocked, incubated with a polyclonal rabbit anti-Qb antiserum (dilution 1:2000) or an mouse monoclonal anti-his6-mAb (Qiagen) (dilution 1:5000). Blots were subsequently incubated with horse radish peroxidase-conjugated goat anti-rabbit IgG or horse radish peroxidase-conjugated goat anti-mouse IgG (dilutions 1:5000), respectively. Enhanced chemoluminescence (Amersham Pharmacia ECL kit) was used to visualize the immunoreactive bands. Molecular weights of marker proteins are given on the left margin.

Figure 15B:
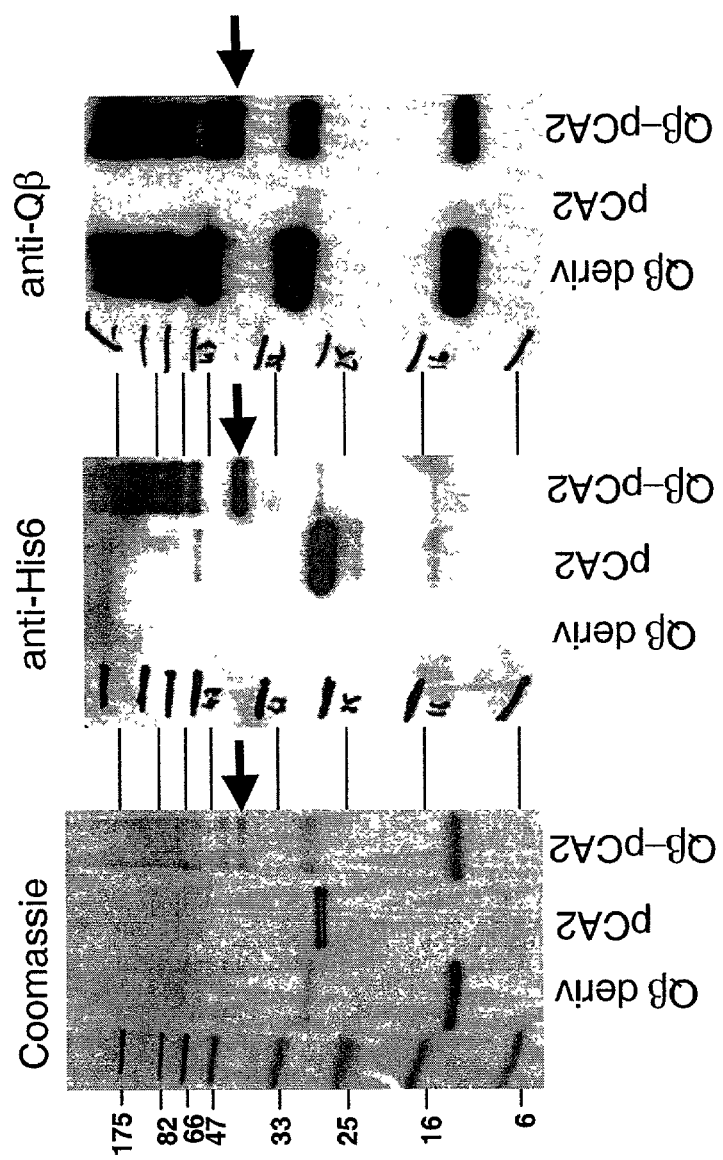
FIG. 15B. SDS-PAGE analysis of coupling of pCA2 to Qβ capsid protein.
Figure 15C:
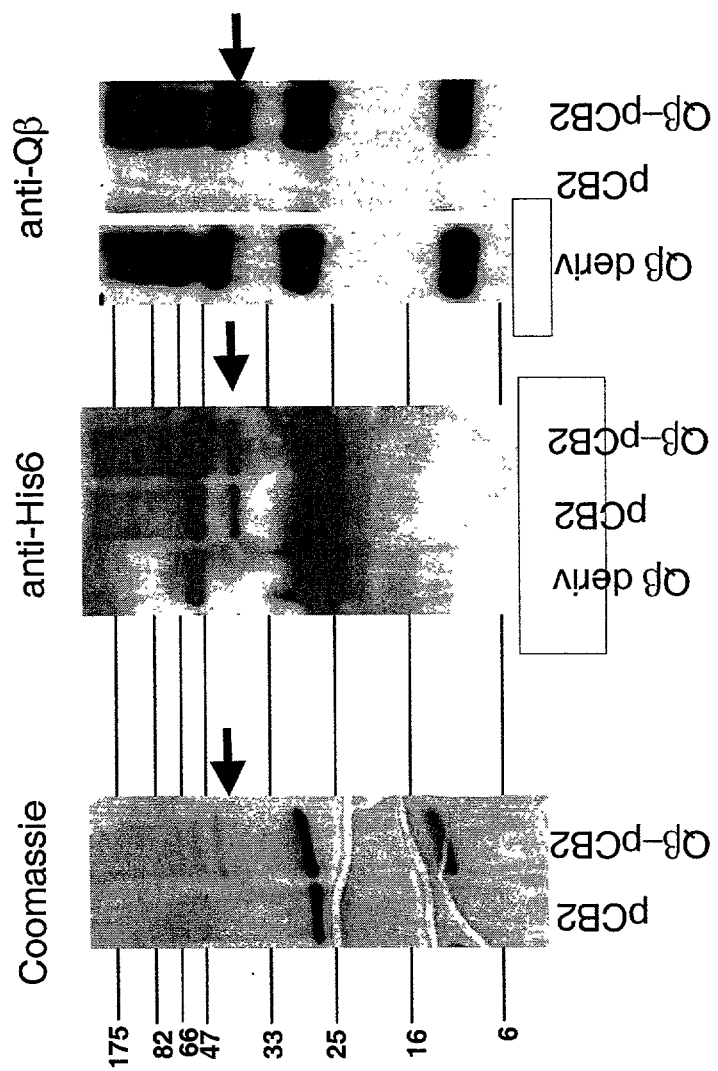
FIG. 15C. SDS-PAGE analysis of coupling of pCB2 to Qβ capsid protein.

Coupling products of about 40 kDa could be detected for both the pCA2 and the pCB2 coupling (FIG. 15A and FIG. 15B, arrows). Its reactivity with the anti-Qβ antiserum and the anti-his6 antibody recognizing the heavy chain of the mimobody clearly demonstrated the covalent coupling of the mimobody to Qβ.

Example 56

Coupling of Flag Peptides to wt and Mutant Qβ Capsid Protein Using the Cross-linker Sulfo-GMBS The Flag peptide, to which a CGG sequence was added N-terminally for coupling, was chemically synthesized and had the following sequence: CGGDYKDDDDK (SEQ ID NO:147). This peptide was used for chemical coupling to wt Qβ capsid protein and the Qβ mutant capsid protein as described in the following.

A. Coupling of Flag Peptide to Qβ Capsid Protein
A solution of 100 μl of 2 mg/ml Qβ capsid protein in 20 mM Hepes. 150 mM NaCl pH 7.2 was reacted for 60 minutes with 7 μl of a solution of 65 mM Sulfo-GMBS (Pierce) in H2O at 25° C. on a rocking shaker. The reaction solution was subsequently dialyzed twice for 2 hours against 2 L of 20 mM Hepes, 150mM NaCl, pH 7.2 at 4° C. 100 μl of the dialyzed reaction mixture was then reacted with 0.58 μl of 100 mM Flag peptide stock solution (in H2O) for two hours at 25° C. on a rocking shaker. The reaction mixture was subsequently dialyzed 2×2 hours against 2 liters of 20 mM Hepes, 150 mM NaCl, pH 7.4 at 4° C.

B. Coupling of Flag Peptide to Qβ-240 Capsid Protein
A solution of 100 μl of 2 mg/ml Qβ-240 capsid protein in 20 mM Hepes. 150 mM NaCl pH 7.2 was reacted for 60 minutes with 7 μl of a solution of 65 mM Sulfo-GMBS (Pierce) in H2O at 25° C. on a rocking shaker. The reaction solution was subsequently dialyzed twice for 2 hours against 2 L of 20 mM Hepes, 150 mM NaCl, pH 7.2 at 4° C. 100 μl of the dialyzed reaction mixture was then reacted with 0.58 μl of 100 mM Flag peptide stock solution (in H2O) for two hours at 25° C. on a rocking shaker. The reaction mixture was subsequently dialyzed 2×2 hours against 2 liters of 20 mM Hepes, 150 mM NaCl, pH 7.2 at 4° C.

C. Coupling of Flag Peptides to Qβ-250 Capsid Protein
A solution of 100 μl of 2 mg/ml Qβ-250 capsid protein in 20 mM Hepes. 150 mM NaCl pH 7.4 was reacted for 60 minutes with 7 μl of a solution of 65 mM Sulfo-GMBS (Pierce) in H2O at 25° C. on a rocking shaker. The reaction solution was subsequently dialyzed twice for 2 hours against 2 L of 20 mM Hepes, 150 mM NaCl, pH 7.2 at 4° C. 100 μl of the dialyzed reaction mixture was then reacted with 0.58 μl of 00 mM Flag peptide stock solution (in H2O) for two hours at 25° C. on a rocking shaker. The reaction mixture was subsequently dialyzed 2×2 hours against 2 liters of 20 mM Hepes, 150 mM NaCl, pH 7.2 at 4° C.

D. Coupling of Flag Peptides to Qβ3259 Capsid Protein
A solution of 100 μl of 2 mg/ml Qβ-259 Capsid Protein in 20 mM Hepes. 150 mM NaCl pH 7.4 was reacted for 60 minutes with 7 μl of a solution of 65 mM Sulfo-GMBS (Pierce) in H2O at 25° C. on a rocking shaker. The reaction solution was subsequently dialyzed twice for 2 hours against 2 L of 20 mM Hepes, 150 mM NaCl, pH 7.4 at 4° C. 100 μl of the dialyzed reaction mixture was then reacted with 0.58 μl of 100 mM Flag peptide stock solution (in H2O) for two hours at 25° C. on a rocking shaker. The reaction mixture was subsequently dialyzed 2×2 hours against 2 liters of 20 mM Hepes, 150 mM NaCl, pH 7.4 at 4° C.

Figure 22:
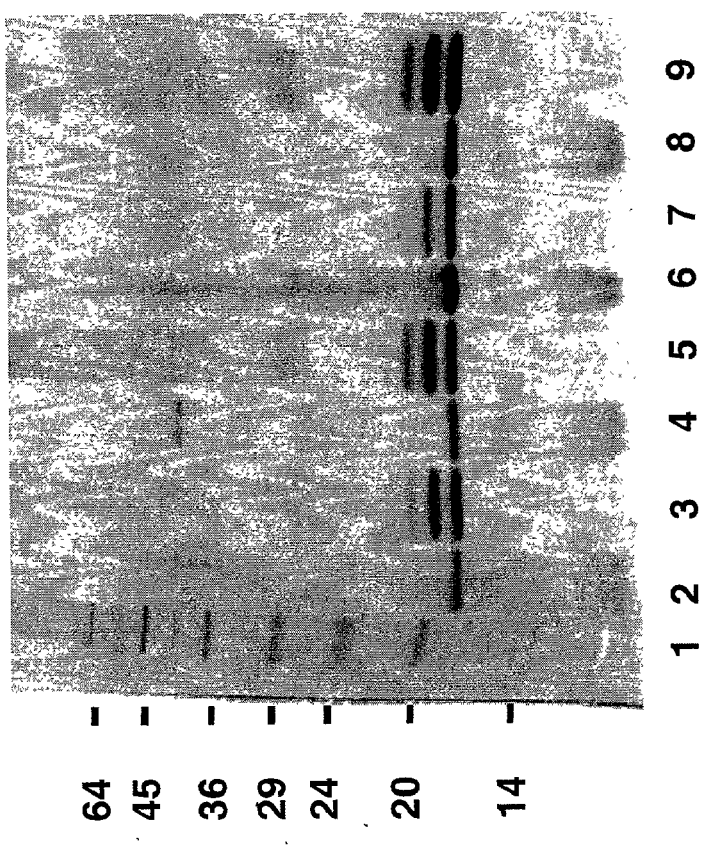
FIG. 22A. SDS-PAGE analysis of coupling of flag peptide coupled to mutant Qβ capsid protein with cross-linker sulfo GMBS FIG. 22B. SDS-PAGE analysis of coupling of flag peptide coupled to mutant Qβ capsid protein with cross-linker sulfo MBS FIG. 22C. SDS-PAGE analysis of coupling of flag peptide coupled to mutant Qβ capsid protein with cross-linker SMPH FIG. 22D. SDS-PAGE analysis of coupling of $PLA_2$-cys protein coupled to mutant Qβ capsid protein with cross-linker SMPH FIG. 23 ELISA analysis of immunization with M2 peptide coupled to mutant Qβ capsid protein and fr capsid FIG. 24 SDS-PAGE analysis of coupling of DER p1,2 peptide coupled to mutant Qβ capsid protein FIG. 25A Desensitization of allergic mice with PLA2 coupled to Qβ capsid protein: temperature measurements FIG. 25B Desensitization of allergic mice with PLA2-cys coupled to Qβ capsid protein: IgG 2A and Ig E titers FIG. 26 SDS-PAGE Analysis and Western-blot analysis of coupling of $PLA_2$-cys to Qβ capsid protein FIG. 27A ELISA analysis of IgG antibodies specific for M2 peptide in sera of mice immunized against M2 peptide coupled to HBcAg-lys-2cys-Mut, Qβ capsid protein, fr capsid protein, HBcAg-lys-1–183 and M2 eptide fused to HBcAg 1–183
Figure 22:
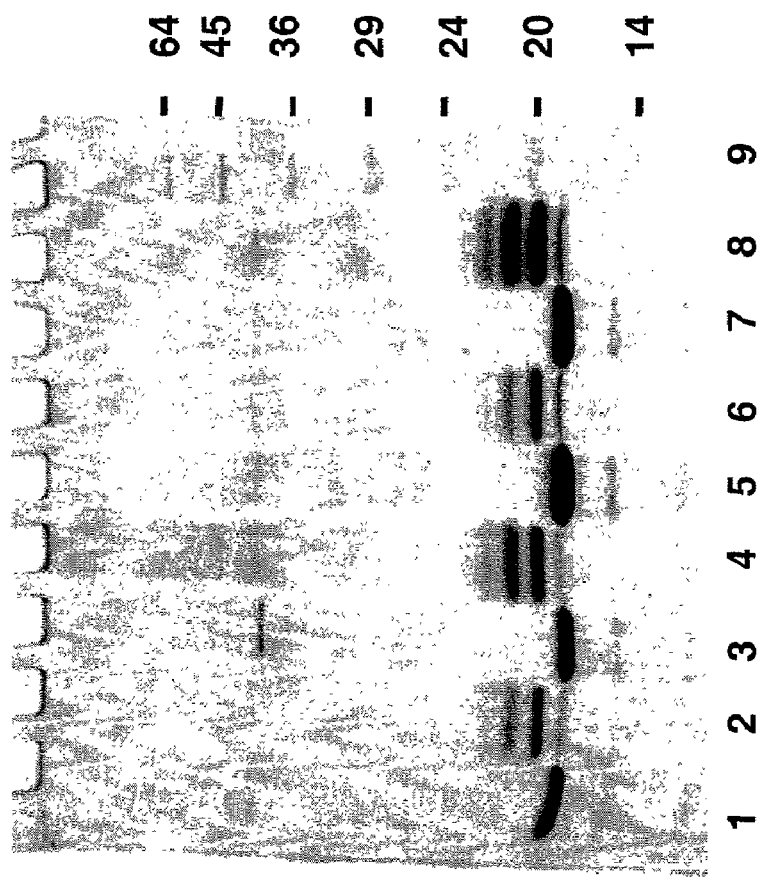
Figure 22:
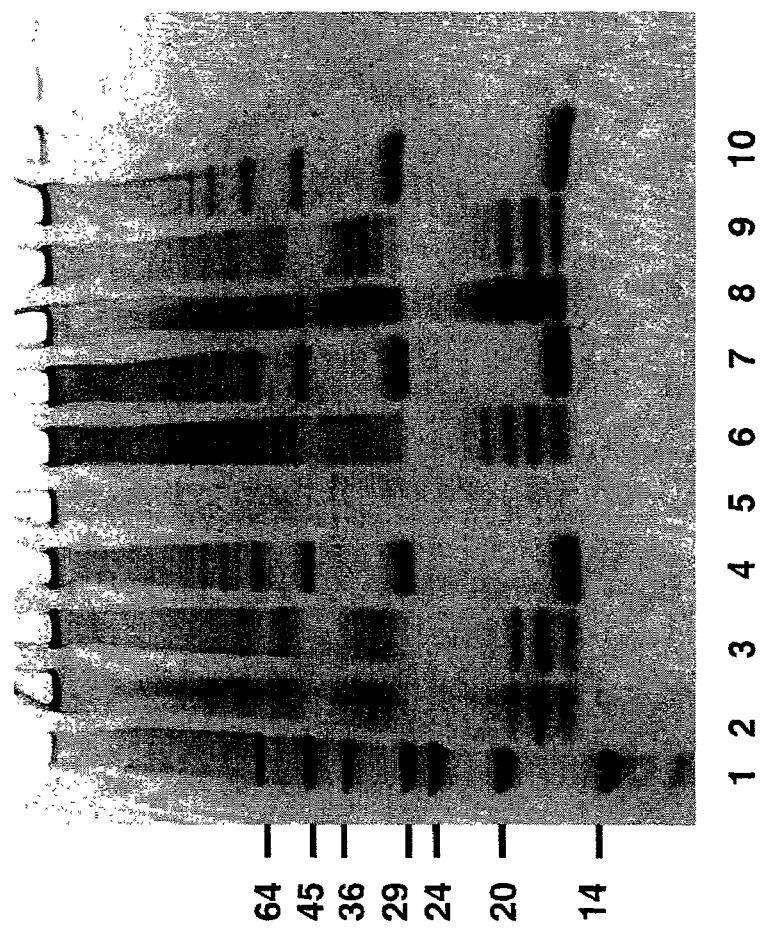
Figure 22:
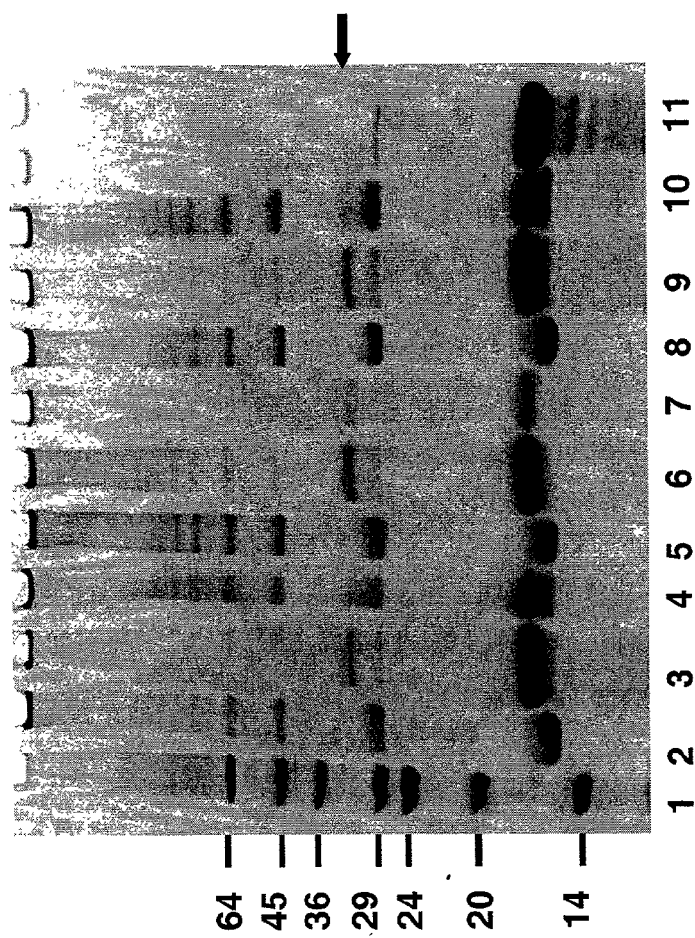
Figure 23:
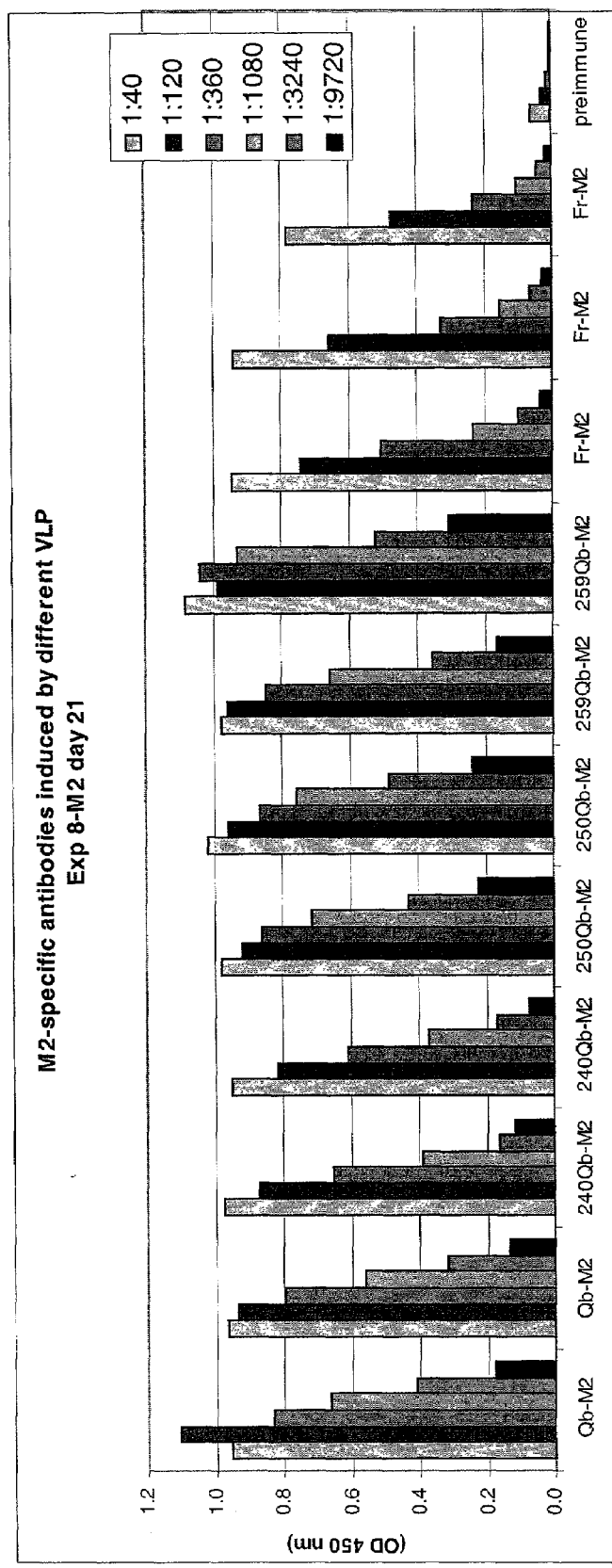

The results of the coupling reactions of the Qβ mutants 240, 250 and 259 to Flag peptide analyzed by SDS-PAGE are shown in FIG. 22A. The loading pattern was the following: 1. Derivatized Qβ-240 2. Qβ-240 coupled to the Flag peptide 3. Derivatized Qβ-250 4. Qβ-250 coupled to the Flag peptide 5. Derivatized Qβ-259 6. Qβ-259 coupled to the Flag peptide 7. Derivatized wt Qβ 8. wt Qβ coupled to the Flag peptide 9. Protein Marker.

Comparison of the derivatized reaction with the coupling reactions shows that for all the mutants and wt, coupling bands corresponding to 1 and 2 peptides per subunit are visible. The band corresponding to the uncoupled Qβ subunit is very weak, indicating that nearly all subunits have reacted with at least one Flag peptide. For the Qβ-250 mutant and wt Qβ, a band corresponding to three peptides per subunit is visible. The ratio of the intensities of the band corresponding to two peptides per subunit and the band corresponding to 1 peptide per subunit is strongest for wt, with a ratio of 1:1. this ratio is still high for the Qβ-250 mutant, while it is significantly weaker for the Qβ-240 mutant and weakest for the Qβ-259 mutant.

Example 57

Coupling of Flag Peptide to Qβ Capsid Protein Using the Cross-linker Sulfo-MBS

The Flag peptide, to which a CGG sequence was added N-terminally for coupling, was chemically synthesized and had the following sequence: CGGDYKDDDDK (SEQ ID NO:147). This peptide was used for chemical coupling to wt Qβ capsid protein and the Qβ mutant capsid protein as described in the following.

A. Coupling of Flag Peptides to Qβ Capsid Protein
A solution of 100 μl of 2 mg/ml Qβ capsid protein in 20 mM Hepes. 150 mM NaCl pH 7.2 was reacted for 60 minutes with 7 μl of a solution of 65 mM Sulfo-MBS (Pierce) in H2O at 25° C. on a rocking shaker. The reaction solution was subsequently dialyzed twice for 2 hours against 2 L of 20 mM Hepes, 150 mM NaCl, pH 7.2 at 4° C. 100 μl of the dialyzed reaction mixture was then reacted with 0.58 μl of 100 mM Flag peptide stock solution (in H2O) for two hours at 25° C. on a rocking shaker. The reaction mixture was subsequently dialyzed 2×2 hours against 2 liters of 20 mM Hepes, 150 mM NaCl, pH 7.2 at 4° C.

B. Coupling of Flag Peptide to Qβ-240 Capsid Protein
A solution of 100 μl of 2 mg/ml Qβ-240 capsid protein in 20 mM Hepes. 150 mM NaCl pH 7.2 was reacted for 60 minutes with 7 μl of a solution of 65 mM Sulfo-MBS (Pierce) in H2O at 25° C. on a rocking shaker. The reaction solution was subsequently dialyzed twice for 2 hours against 2 L of 20 mM Hepes, 150 mM NaCl, pH 7.2 at 4° C. 100 μl of the dialyzed reaction mixture was then reacted with 0.58 μl of 100 mM Flag peptide stock solution (in H2O) for two hours at 25° C. on a rocking shaker. The reaction mixture was subsequently dialyzed 2×2 hours against 2 liters of 20 mM Hepes, 150 mM NaCl, pH 7.4 at 4° C.

C. Coupling of Flag Peptide to Qβ-250 Capsid Protein

A solution of 100 μl of 2 mg/ml Qβ-250 capsid protein in 20 mM Hepes. 150 mM NaCl pH 7.2 was reacted for 60 minutes with 7 μl of a solution of 65 mM Sulfo-MBS (Pierce) in H2O at 25° C. on a rocking shaker. The reaction solution was subsequently dialyzed twice for 2 hours against 2 L of 20 mM Hepes, 150 mM NaCl, pH 7.2 at 4° C. 100 μl of the dialyzed reaction mixture was then reacted with 0.58 μl of 100 mM Flag peptide stock solution (in H2O) for two hours at 25° C. on a rocking shaker. The reaction mixture was subsequently dialyzed 2×2 hours against 2 liters of 20 mM Hepes, 150 mM NaCl, pH 7.2 at 4° C.

D. Coupling of Flag Peptides to Qβ-259 Capsid Protein

A solution of 100 μl of 2 mg/ml Qβ-259 capsid protein in 20 mM Hepes. 150 mM NaCl pH 7.2 was reacted for 60 minutes with 7 μl of a solution of 65 mM Sulfo-MBS (Pierce) in H2O at 25° C. on a rocking shaker. The reaction solution was subsequently dialyzed twice for 2 hours against 2 L of 20 mM Hepes, 150 mM NaCl, pH 7.2 at 4° C. 100 μl of the dialyzed reaction mixture was then reacted with 0.58 μl of 100 mM Flag peptide stock solution (in H2O) for two hours at 25° C. on a rocking shaker. The reaction mixture was subsequently dialyzed 2×2 hours against 2 liters of 20 mM Hepes, 150 mM NaCl, pH 7.2 at 4° C.

The results of the coupling reactions of the Qβ mutants 240, 250 and 259 to Flag peptide analyzed by SDS-PAGE are shown in FIG. 1. The loading pattern was the following:
1. Protein Marker 2. Derivatized Qβ-240 3. Qβ-240 coupled to the Flag peptide 4. Derivatized Qβ-250 5. Qβ-250 coupled to the Flag peptide 6. Derivatized Qβ-259 7. Qβ-259 coupled to the Flag peptide 8. Derivatized wt Qβ 9. wt Qβ coupled to the Flag peptide.

Comparison of the derivatized reaction with the coupling reactions shows that for all the mutants and wt, a coupling band corresponding to 1 peptide per subunit is visible. Bands corresponding to 2 peptides per subunit are also visible for the mutant Qβ-250 and wt Qβ. The ratio of the intensities of the band corresponding to 1 peptide per subunit and to the uncoupled subunit, respectively, is higher for the Qβ-250 mutant and wt Qβ. A weak band corresponding to two peptides per subunit is visible for the Qβ-240 mutant.

Example 58

Coupling of Flag Peptides to CGG Mutants Using the Cross-linker SMPH

The Flag peptide, to which a CGG sequence was added N-terminally for coupling, was chemically synthesized and had the following sequence: CGGDYKDDDDK (SEQ ID NO: 147). This peptide was used for chemical coupling to the Qβ mutants as described in the following.

A Coupling of Flag Peptides to Qβ-240 Capsid Protein

A solution of 100 μl of 2 mg/ml Qβ-240 capsid protein in 20 mM Hepes. 150 mM NaCl pH 7.4 was reacted for 30 minutes with 2.94 μl of a solution of 100 mM SMPH (Pierce) in DMSO at 25° C. on a rocking shaker. The reaction solution was subsequently dialyzed twice for 2 hours against 2 L of 20 mM Hepes, 150 mM NaCl, pH 7.4 at 4° C. 90 μl of the dialyzed reaction mixture was then reacted with 1.3 μl of 50 mM Flag peptide stock solution (in DMSO) for two hours at 25° C. on a rocking shaker. The reaction mixture was subsequently dialyzed 2×2 hours against 2 liters of 20 mM Hepes, 150 mM NaCl, pH 7.4 at 4° C.

B. Coupling of Flag Peptides to Qβ-250 Capsid Protein

A solution of 100 μl of 2 mg/ml Qβ-250 capsid protein in 20 mM Hepes. 150 mM NaCl pH 7.4 was reacted for 30 minutes with 2.94 μl of a solution of 100 mM SMPH (Pierce) in DMSO at 25° C. on a rocking shaker. The reaction solution was subsequently dialyzed twice for 2 hours against 2 L of 20 mM Hepes, 150 mM NaCl, pH 7.4 at 4° C. 90 μl of the dialyzed reaction mixture was then reacted with 1.3 μl of 50 mM Flag peptide stock solution (in DMSO) for two hours at 25° C. on a rocking shaker. The reaction mixture was subsequently dialyzed 2×2 hours against 2 liters of 20 mM Hepes, 150 mM NaCl, pH 7.4 at 4° C.

C. Coupling of Flag Peptide to Qβ-259 Capsid Protein

A solution of 100 μl of 2 mg/ml Qβ-259 capsid protein in 20mM Hepes. 150 mM NaCl pH 7.4 was reacted for 30 minutes with 2.94 μl of a solution of 100 mM SMPH (Pierce) in DMSO at 25° C. on a rocking shaker. The reaction solution was subsequently dialyzed twice for 2 hours against 2 L of 20 mM Hepes, 150 mM NaCL, pH 7.4 at 4° C. 90 μl of the dialyzed reaction mixture was then reacted with 1.3 μl of 50 mM Flag peptide stock solution (in DMSO) for two hours at 25° C. on a rocking shaker. The reaction mixture was subsequently dialyzed 2×2 hours against 2 liters of 20 mM Hepes, 150 mM NaCl, pH 7.4 at 4° C. Qβ-250 coupled to Flag, pellet of the coupling reaction 6. Qβ-250 coupled to Flag, supernatant of the coupling reaction 7. Qβ-250 derivatized with SMPH 8. Qβ-259 coupled to Flag, pellet of the coupling reaction 9. Qβ-259 coupled to Flag, supernatant of the coupling reaction 10. Qβ-259 derivatized with SMPH.

Comparison of the derivatized reaction with the coupling reactions shows that for all the mutants, coupling bands corresponding to 1, respectively 2 peptides per subunits are visible. Bands corresponding to three, respectively four peptides per subunit are also visible for the mutant Qβ-250.

Example 59

Coupling of PLA$_2$-Cys Protein to Mutant Qβ Capsid Proteins

Lyophilized mutant Qβ capsid proteins were swollen overnight in 20 mM Hepes, 150 mM NaCl, pH 7.4.

A. Coupling of PLA2-Cys Protein to Qβ-240 Capsid Protein

A solution of 100 μl of 2 mg/ml Qβ-240 capsid protein in 20 mM Hepes. 150 mM NaCl pH 7.4 was reacted for 30 minutes with 2.94 μl of a solution of 100 mM SMPH (Pierce) in DMSO at 25° C. on a rocking shaker. The reaction solution was subsequently dialyzed twice for 2 hours against 2 L of 20 mM Hepes, 150 mM NaCl, pH 7.4 at 4° C. 90 μl of the dialyzed reaction mixture was mixed with 146 μl 20 mM Hepes, 150 mM NaCl, pH 7.4 and reacted with 85.7 μl of 2.1 mg/ml PLA$_2$-Cys stock solution for four hours at 25° C. on a rocking shaker. The reaction mixture was subsequently dialyzed 2×2 hours against 2 liters of 20 mM Hepes, 150 mM NaCl, pH 7.4 at 4° C.

B. Coupling of PLA2-Cys Protein to Qβ-250 Capsid Protein

A solution of 100 μl of 2 mg/ml Qβ-250 capsid protein in 20 mM Hepes. 150 mM NaCl pH 7.4 was reacted for 30 minutes with 2.94 pi of a solution of 100 mM SMPH (Pierce) in DMSO at 25° C. on a rocking shaker. The reaction solution was subsequently dialyzed twice for 2 hours against 2 L of 20 mM Hepes, 150 mM NaCl, pH 7.4 at 4° C. 90 µl of the dialyzed reaction mixture was mixed with 146 µl 20 mM Hepes, 150 mM NaCl, pH 7.4 and reacted with 85.7 µl of 2.1 mg/ml PLA2-Cys stock solution for four hours at 25° C. on a rocking shaker. The reaction mixture was subsequently dialyzed 2×2 hours against 2 liters of 20 mM Hepes, 150 mM NaCl, pH 7.4 at 4° C.

C. Coupling of PLA2-Cys Protein to Qβ-259 Capsid Protein

A solution of 100 µl of 2 mg/ml Qβ-j259 capsid protein in 20 mM Hepes. 150 mM NaCl pH 7.4 was reacted for 30 minutes with 2.94 µl of a solution of 100 mM SMPH (Pierce) in DMSO at 25° C. on a rocking shaker. The reaction solution was subsequently dialyzed twice for 2 hours against 2 L of 20 mM Hepes, 150 mM NaCl, pH 7.4 at 4° C. 90 µl of the dialyzed reaction mixture was mixed with 146 µl 20 mM Hepes, 150 mM NaCl, pH 7.4 and reacted with 85.7 µl of 2.1 mg/ml PLA$_2$-Cys stock solution for four hours at 25° C. on a rocking shaker. The reaction mixture was subsequently dialyzed 2×2 hours against 2 liters of 20 mM Hepes, 150 mM NaCl, pH 7.4 at 4° C.

The results of the coupling experiment analyzed by SDS-PAGE are shown in FIG. 1. The loading pattern was the following: 1. Protein Marker 2. derivatized Qβ-240 3. Qβ-240 coupled to Pla2Cys, supernatant of the coupling reaction 4. Qβ-240 coupled to PLA$_2$-Cys, pellet of the coupling reaction 5. derivatized Qβ-250 6. Qβ-250 coupled to PLA$_2$-Cys, supernatant of the coupling reaction 7. Qβ-250 coupled to PLA$_2$-Cys, pellet of the coupling reaction 8. derivatized Qβ-259 9. Qβ-259 coupled to PLA$_2$-Cys, supernatant of the coupling reaction 10. Qβ-259 coupled to PLA$_2$-Cys, pellet of the coupling reaction 11. PLA$_2$-Cys.

Coupling bands (indicated by the arrow in the figure) were visible for all the mutants, showing that PLA$_2$-Cys protein could be coupled to all of the mutant Qβ capsid proteins.

1 All patents and publications referred to herein are expressly incorporated by reference.

2 The entire disclosure of U.S. application Ser. No. 09/449,631 and WO 00/3227, both filed Nov. 30, 1999, are herein incorporated by reference in their entirety. All publications and patents mentioned hereinabove are hereby incorporated in their entireties by reference.

What is claimed is:

1. A composition comprising:
   (a) a non-natural molecular scaffold comprising:
      (i) a core particle comprising a virus-like particle of an RNA bacteriophage; and
      (ii) an organizer comprising at least one first attachment site, wherein said organizer is connected to said core particle by at least one covalent bond; and wherein said first attachment site is not a sulfhydryl group; and
   (b) an antigen or antigenic determinant with at least one second attachment site,
   wherein said antigen or antigenic determinant is at least one self antigen, a peptide thereof, or fragment thereof, wherein said self antigen is not amyloid β or a peptide of fragment thereof;
   wherein said second attachment site is capable of association through at least one non-peptide bond to said first attachment site; and
   wherein said antigen or antigenic determinant and said scaffold interact through said association to form an ordered and repetitive antigen array.

2. The composition of claim 1, wherein said RNA bacteriophage is selected from the group consisting of:
   (a) bacteriophage Qβ;
   (b) bacteriophage R17;
   (c) bacteriophage fr;
   (d) bacteriophage GA;
   (e) bacteriophage SP;
   (f) bacteriophage MS2;
   (g) bacteriophage M11;
   (h) bacteriophage MX1;
   (i) bacteriophage NL95;
   (j) bacteriophage f2; and
   (k) bacteriophage PP7.

3. The composition of claim 1, wherein said bacteriophage is bacteriophage Qβ.

4. The composition of claim 1, wherein said bacteriophage is bacteriophage fr.

5. The composition of claim 1, wherein said bacteriophage is bacteriophage GA.

6. The composition of claim 1, wherein said virus-like particle of an RNA bacteriophage comprises recombinant proteins, or fragments thereof, of an RNA bacteriophage.

7. The composition of claim 6, wherein said bacteriophage is bacteriophage Qβ.

8. The composition of claim 6, wherein said bacteriophage is bacteriophage fr.

9. The composition of claim 6, wherein said bacteriophage is bacteriophage GA.

10. The composition of claim 6, wherein said virus-like particle of an RNA bacteriophage consists essentially of recombinant proteins, or fragments thereof, of an RNA bacteriophage.

11. The composition of claim 1, wherein said virus-like particle of an RNA bacteriophage comprises recombinant coat proteins comprising an amino acid sequence selected from the group consisting of:
   (a) SEQ ID NO:159;
   (b) SEQ ID NO:160;
   (c) SEQ ID NO:161;
   (d) SEQ ID NO:162;
   (e) SEQ ID NO:163;
   (f) SEQ ID NO:164;
   (g) SEQ ID NO:165;
   (h) SEQ ID NO:166;
   (i) SEQ ID NO:167;
   (j) SEQ ID NO:215;
   (k) SEQ ID NO:253;
   (l) SEQ ID NO:217; and
   (m) SEQ ID NO:254.

12. The composition of claim 1, wherein said virus-like particle of an RNA bacteriophage consists essentially of recombinant coat proteins comprising an amino acid sequence selected from the group consisting of:
   (a) SEQ ID NO:159;
   (b) SEQ ID NO:160;
   (c) SEQ ID NO:161;
   (d) SEQ ID NO:162;
   (e) SEQ ID NO:163;
   (f) SEQ ID NO:164;
   (g) SEQ ID NO:165;
   (h) SEQ ID NO:166;
   (i) SEQ ID NO:167;
   (j) SEQ ID NO:215;
   (k) SEQ ID NO:253;
   (l) SEQ ID NO:217; and
   (m) SEQ ID NO:254.

13. The composition of claim 1, wherein said virus-like particle of an RNA bacteriophage comprises coat proteins having an amino acid sequence of SEQ ID NO:159, or a mixture of coat proteins having amino acid sequences of SEQ ID NO:159 and of SEQ ID NO:217.

14. The composition of claim 1, wherein said virus-like particle of an RNA bacteriophage consists essentially of coat proteins having an amino acid sequence of SEQ ID NO:159, or consists essentially of a mixture of coat proteins having amino acid sequences of SEQ ID NO:217 and of SEQ ID NO:159.

15. The composition of claim 1, wherein said virus-like particle of an RNA bacteriophage comprises one or more coat proteins of said RNA bacteriophage that have been modified by deletion or substitution to remove at least one naturally occurring lysine residue, or that have been modified by insertion or substitution to add at least one lysine residue.

16. The composition of claim 15, wherein said RNA bacteriophage is Qβ.

17. The composition of claim 1, wherein said virus-like particle of an RNA bacteriophage comprises one or more coat proteins comprising an amino acid sequence selected from the group consisting of:
(a) SEQ ID NO:255;
(b) SEQ ID NO:256;
(c) SEQ ID NO:257;
(d) SEQ ID NO:258;
(e) SEQ ID NO:259; and
(f) a mixture of any one of (a)–(e) and the corresponding A1 protein.

18. The composition of claim 1, wherein said virus-like particle of an RNA bacteriophage comprises one or more coat proteins consisting essentially of an amino acid sequence selected from the group consisting of:
(a) SEQ ID NO:255;
(b) SEQ ID NO:256;
(c) SEQ ID NO:257;
(d) SEQ ID NO:258;
(e) SEQ ID NO:259; and
(f) a mixture of any one of (a)–(e) and the corresponding A1 protein.

19. The composition of claim 1, wherein said organizer is an integral part of said RNA bacteriophage.

20. The composition of claim 1, wherein said organizer is a polypeptide or residue thereof and said second attachment site is a polypeptide or residue thereof.

21. The composition of claim 1, wherein said association is by way of at least one covalent bond.

22. The composition of claim 1, further comprising an amino acid linker.

23. The composition of claim 22, wherein said amino acid linker is bound to said antigen or said antigenic determinant by way of at least one covalent bond.

24. The composition of claim 23, wherein said covalent bond is a peptide bond.

25. The composition of claim 22, wherein said amino acid linker comprises said second attachment site.

26. The composition of claim 22, wherein said amino acid linker is selected from the group consisting of:
(a) CGG;
(b) an N-terminal gamma 1-linker;
(c) an N-terminal gamma 3-linker;
(d) an Ig hinge region;
(e) an N-terminal glycine linker;
(f) $(G)_k C(G)_n$ with n=0–12 and k=0–5;
(g) an N-terminal glycine-serine linker;
(h) $(G)_k C(G)_m (S)_l (GGGGS)_n$ with n=0–3, k=0–5, m=0–10, l=0–2 (SEQ ID NO: 424);
(i) GGC;
(j) GGC-NH2;
(k) a C-terminal gamma 1-linker;
(l) a C-terminal gamma 3-linker;
(m) a C-terminal glycine linker;
(n) $(G)_n C(G)_k$ with n=0–12 and k=0–5;
(o) a C-terminal glycine-serine linker; and
(p) $(G)_m (S)_l (GGGGS)_n (G)_o C(G)_k$ with n=0–3, k=0–5, m=0–10, l=0–2, and o=0–8 (SEQ ID NO: 425).

27. The composition of claim 22, wherein said amino acid linker comprises a sulfhydryl group or a cysteine residue.

28. The composition of claim 1, wherein said first and said second attachment sites comprise an interacting pair selected from the group consisting of:
(a) an antigen and an antibody or antibody fragment thereto;
(b) biotin and avidin;
(c) streptavidin and biotin;
(d) a receptor and its ligand;
(e) a ligand-binding protein and its ligand;
(f) interacting leucine zipper polypeptides;
(g) an amino group and a chemical group reactive thereto;
(h) a carboxyl group and a chemical group reactive thereto; and
(i) a combination thereof of any of (a)–(h).

29. The composition of claim 1, wherein said first attachment site and said second attachment site are associated through a heterobifunctional linker.

30. The composition of claim 29, wherein said heterobifunctional linker is selected from the group consisting of:
(a) a maleimidocaproic acid N-hydroxysuccinimide ester;
(b) N-Succinimidyl 3-(2-pyridyldithio) propionate (SPDP); and
(c) Sulfo-MBS.

31. The composition of claim 1, wherein said first attachment site comprises an amino group and said second attachment site comprises a sulfhydryl group.

32. The composition of claim 1, wherein said first attachment site is an amino group and said second attachment site is a sulfhydryl group.

33. The composition of claim 1, wherein said first attachment site is a lysine residue and said second attachment site is a cysteine residue.

34. The composition of claim 1, wherein said first attachment site comprises a lysine residue.

35. The composition of claim 1, wherein said first attachment site is a lysine residue.

36. The composition of claim 1, wherein said second attachment site does not naturally occur within said antigen or antigenic determinant.

37. The composition of claim 1, wherein said second attachment site comprises a sulfhydryl group or a cysteine residue.

38. The composition of claim 1, wherein said second attachment site is a sulfhydryl group or is a cysteine residue.

39. The composition of claim 1, wherein said self antigen is selected from the group consisting of:
(a) a lymphotoxin;
(b) a lymphotoxin receptor;
(c) RANKL;
(d) VEGF;
(e) VEGFR;
(f) Interleukin-5;
(g) Interleukin-17;
(h) Interleukin-13;
(i) Angiotensin;
(j) CCL21;
(k) CXCL12;

(l) SDF-1;
(m) MCP-1;
(n) Endoglin;
(o) Resistin;
(p) GHRH;
(q) LHRH;
(r) TRH;
(s) MIF;
(t) Eotaxin;
(u) Bradykinin;
(v) BLC;
(w) Tumor Necrosis Factor-α (TNF-α);
(x) a human IgE; and
(y) peptides or fragments of any of (a) through (x).

40. The composition of claim 1, wherein said self antigen is angiotensin.

41. The composition of claim 40, wherein said second attachment site does not naturally occur within said antigen or antigenic determinant.

42. The composition of claim 40, wherein said second attachment site comprises a sulfhydryl group or a cysteine residue.

43. The composition of claim 40, wherein said composition further comprises an amino acid linker, and wherein said amino acid linker comprises said second attachment site, and wherein said amino acid linker comprises a sulfhydryl group or a cysteine residue.

44. The composition of claim 40, wherein said self antigen with said second attachment site comprises an amino acid sequence selected from the group consisting of:
    (a) CGGDRVYIHPF (SEQ ID NO: 380);
    (b) CGGDRVYIHPFHL (SEQ ID NO. 381)
    (c) DRVYIHPFHLGGC (SEQ ID NO: 382); and
    (d) CDRVYIHPFHL (SEQ ID NO: 383).

45. The composition of claim 40, wherein said self antigen with said second attachment site consists of an amino acid sequence selected from the group consisting of:
    (a) CGGDRVYIHPF (SEQ ID NO: 380);
    (b) CGGDRVYIIHPFHL (SEQ ID NO. 381)
    (c) DRVYIHPFHLGGC (SEQ ID NO: 382); and
    (d) CDRVYIHPFHL (SEQ ID NO: 383).

46. The composition of claim 40, wherein said self antigen with said second attachment site consists of the amino acid sequence CGGDRVYIHPF (SEQ ID NO: 380).

47. The composition of claim 1, wherein said self antigen is VEGFR-II.

48. The composition of claim 47, wherein said self antigen is human VEGFR-II.

49. The composition of claim 47, wherein said second attachment site does not naturally occur within said antigen or antigenic determinant.

50. The composition of claim 47, wherein said second attachment site comprises a sulfhydryl group or a cysteine residue.

51. The composition of claim 47, wherein said composition further comprises an amino acid linker, and wherein said amino acid linker comprises said second attachment site, and wherein said amino acid linker comprises a sulfhydryl group or a cysteine residue.

52. The composition of claim 47, wherein said self antigen with said second attachment site comprises the amino acid sequence CTARTELNVGIDFN-WEYPSSKHQHKK (SEQ ID NO:351).

53. The composition of claim 47, wherein said self antigen with said second attachment site consists of the amino acid sequence CTARTELNVGIDFN-WEYPSSKHQHKK (SEQ ID NO:351).

54. The composition of claim 1, wherein said self antigen is tumor necrosis factor-α (TNF-α).

55. The composition of claim 54, wherein said second attachment site does not naturally occur within said antigen or antigenic determinant.

56. The composition of claim 54, wherein said second attachment site comprises a sulfhydryl group or a cysteine residue.

57. The composition of claim 54, wherein said composition further comprises an amino acid linker, and wherein said amino acid linker comprises said second attachment site, and wherein said amino acid linker comprises a sulfhydryl group or a cysteine residue.

58. The composition of claim 54, wherein said self antigen with said second attachment site comprises an amino acid sequence selected from the group consisting of:
    (a) CSSRTPSDKPVAHVVANPQAEGQ (SEQ ID NO:398);
    (b) SSRTPSDKPVAHVVANPQAEGQGGC (SEQ ID NO:399); and
    (c) CGGQLQWLNRRANA (SEQ ID NO:400).

59. The composition of claim 54, wherein said self antigen with said second attachment site consists of an amino acid sequence selected from the group consisting of:
    (a) CSSRTPSDKPVAHVVANPQAEGQ (SEQ ID NO:398);
    (b) SSRTPSDKPVAHVVANPQAEGQGGC (SEQ ID NO:399); and
    (c) CGGQLQWLNRRANA (SEQ ID NO:400).

60. The composition of claim 1, wherein said self antigen is resistin.

61. The composition of claim 60, wherein said self antigen with said second attachment site consists of an amino acid sequence selected from the group consisting of:
    (a) SEQ ID NO:325
    (b) SEQ ID NO:326; and
    (c) SEQ ID NO:327.

62. The composition of claim 1, wherein said self antigen is a lymphotoxin.

63. The composition of claim 62, wherein said lymphotoxin is selected from the group consisting of:
    (a) lymphotoxin α (LTα);
    (b) lymphotoxin β (LTβ); and
    (c) a mixture or combination of LTα and LTβ.

64. The composition of claim 62, wherein said second attachment site does not naturally occur within said antigen or antigenic determinant.

65. The composition of claim 62, wherein said second attachment site comprises a sulfhydryl group or a cysteine residue.

66. The composition of claim 62, wherein said composition further comprises an amino acid linker, and wherein said amino acid linker comprises said second attachment site, and wherein said amino acid linker comprises a sulfhydryl group or a cysteine residue.

67. The composition of claim 62, wherein said lymphotoxin is lymphotoxin β and wherein said lymphotoxin β with said second attachment site comprises an amino acid sequence selected from the group consisting of:
    (a) SEQ ID NO:346; and
    (b) SEQ ID NO:347.

68. The composition of claim 62, wherein said lymphotoxin is lymphotoxin β and wherein said lymphotoxin β with said second attachment site consists of an amino acid sequence selected from the group consisting of:
    (a) SEQ ID NO:346; and
    (b) SEQ ID NO:347.

69. The composition of claim 1, wherein said self antigen is MIF.

70. The composition of claim 69 wherein self antigen is human-MIF.

71. The composition of claim 69, wherein said second attachment site does not naturally occur within said antigen or antigenic determinant.

72. The composition of claim 69, wherein said second attachment site comprises a sulfhydryl group or a cysteine residue.

73. The composition of claim 69, wherein said composition further comprises an amino acid linker, and wherein said amino acid linker comprises said second attachment site, and wherein said amino acid linker comprises a sulfhydryl group or a cysteine residue.

74. The composition of claim 69, wherein said self antigen with said second attachment site comprises an amino acid sequence selected from the group consisting of:
    (a) SEQ ID NO:310;
    (b) SEQ ID NO:311;
    (c) SEQ ID NO:312;
    (d) SEQ ID NO:313;
    (e) SEQ ID NO:314; and
    (f) SEQ ID NO:315.

75. The composition of claim 69, wherein said self antigen with said second attachment site consists of an amino acid sequence selected from the group consisting of:
    (a) SEQ ID NO:310;
    (b) SEQ ID NO:311;
    (c) SEQ ID NO:312;
    (d) SEQ ID NO:313;
    (e) SEQ ID NO:314; and
    (f) SEQ ID NO:315.

76. The composition of claim 1, wherein said self antigen is RANKL.

77. The composition of claim 76, wherein said self antigen is human-RANKL.

78. The composition of claim 76, wherein said self antigen is an extracellular domain of RANKL.

79. The composition of claim 76, wherein said second attachment site does not naturally occur within said antigen or antigenic determinant.

80. The composition of claim 76, wherein said second attachment site comprises a sulfhydryl group or a cysteine residue.

81. The composition of claim 76, wherein said composition further comprises an amino acid linker, and wherein said amino acid linker comprises said second attachment site, and wherein said amino acid linker comprises a sulfhydryl group or a cysteine residue.

82. The composition of claim 76, wherein said self antigen with said second attachment site comprises the amino acid sequence of SEQ ID NO:320.

83. The composition of claim 76, wherein said self antigen with said second attachment site consists of the amino acid sequence of SEQ ID NO:320.

84. The composition of claim 1, wherein said self antigen is IgE.

85. The composition of claim 84, wherein said second attachment site does not naturally occur within said antigen or antigenic determinant.

86. The composition of claim 84, wherein said second attachment site comprises a sulfhydryl group or a cysteine residue.

87. The composition of claim 84, wherein said composition further comprises an amino acid linker, and wherein said amino acid linker comprises said second attachment site, and wherein said amino acid linker comprises a sulfhydryl group or a cysteine residue.

88. The composition of claim 84, wherein said IgE with said second attachment site comprises the amino acid sequence of SEQ ID NO:176.

89. The composition of claim 84, wherein said IgE with said second attachment site consists of the amino acid sequence of SEQ ID NO:176.

90. The composition of claim 1, wherein said self antigen is a lymphotoxin receptor.

91. The composition of claim 1, wherein said self antigen is VEGF.

92. The composition of claim 1, wherein said self antigen is Interleukin-5.

93. The composition of claim 1, wherein said self antigen is Interleukin-17.

94. The composition of claim 1, wherein said self antigen is Interleukin-13.

95. The composition of claim 1, wherein said self antigen is CCL21.

96. The composition of claim 1, wherein said self antigen is CXCL12.

97. The composition of claim 1, wherein said self antigen is SDF-1.

98. The composition of claim 1, wherein said self antigen is MCP-1.

99. The composition of claim 1, wherein said self antigen is Endoglin.

100. The composition of claim 1, wherein said self antigen is GHRH.

101. The composition of claim 1, wherein said self antigen is LHRH.

102. The composition of claim 1, wherein said self antigen is TRH.

103. The composition of claim 1, wherein said self antigen is Eotaxin.

104. The composition of claim 1, wherein said self antigen is Bradykinin.

105. The composition of claim 1, wherein said self antigen is BLC.

106. The composition of claim 1, wherein said self antigen is suitable to induce an immune response against cancer cells.

107. The composition of claim 106, wherein said self antigen is:
    (a) a protein of breast cancer cells;
    (b) a protein of kidney cancer cells;
    (c) a protein of prostate cancer cells;
    (d) a protein of skin cancer cells;
    (e) a protein of brain cancer cells; or
    (f) a protein of leukemia cells.

108. A pharmaceutical composition comprising:
    (a) the composition of claim 1; and
    (b) an acceptable pharmaceutical carrier.

109. A method of immunization of an animal comprising administering to said animal the composition of claim 1, wherein an immune response against said antigen or antigenic determinant is produced in said animal.

110. An immunogenic composition comprising the composition of claim 1 and an adjuvant.

111. A method of immunization of an animal comprising administering to said animal the composition of claim 110, wherein an immune response against said antigen or antigenic determinant is produced in said animal.

112. A process for producing a non-naturally occurring, ordered and repetitive antigen array comprising:
(a) providing a non-natural molecular scaffold comprising:
(i) a core particle comprising a virus-like particle of an RNA bacteriophage; and
(ii) an organizer comprising at least one first attachment site, wherein said organizer is connected to said core particle by at least one covalent bond, and wherein said first attachment site is not a sulfhydryl group; and
(b) providing an antigen or antigenic determinant with at least one second attachment site,
wherein said antigen or antigenic determinant is at least one self antigen, a peptide thereof, or a fragment thereof, and wherein said self antigen is not amyloid β or a peptide or fragment thereof;
wherein said second attachment site is capable of association through at least one non-peptide bond to said first attachment site; and
(c) combining said non-natural molecular scaffold and said antigen to form an ordered and repetitive antigen array.

113. The process of claim 112, wherein said organizer is a polypeptide or residue thereof; and wherein said second attachment site is a polypeptide or residue thereof.

114. The process of claim 112, wherein said association is by way of at least one covalent bond.

115. A composition comprising:
(a) a non-natural molecular scaffold comprising:
(i) a core particle comprising a virus-like particle of an RNA bacteriophage; and
(ii) an organizer comprising at least one first attachment site, wherein said organizer is connected to said core particle by at least one covalent bond; and
(b) an antigen or antigenic determinant with at least one second attachment site,
wherein said antigen or antigenic determinant is at least one self antigen, a peptide thereof, or fragment thereof;
wherein said second attachment site is capable of association through at least one non-peptide bond to said first attachment site; and
wherein said antigen or antigenic determinant and said scaffold interact through said association to form an ordered and repetitive antigen array, and
wherein said self antigen, peptide or fragment thereof is selected from the group consisting of:
(a) a lymphotoxin;
(b) a lymphotoxin receptor;
(c) RANKL;
(d) VEGF;
(e) VEGFR;
(f) Interleukin-5;
(g) Interleukin-17;
(h) Interleukin-13;
(i) Angiotensin;
(j) CCL21;
(k) CXCL12;
(l) SDF-1;
(m) MCP-1;
(n) Endoglin;
(o) Resistin;
(p) GHRH;
(q) TRH;
(r) MIF;
(s) Eotaxin;
(t) Bradykinin;
(u) BLC; and
(v) Tumor Necrosis Factor-α (TNF-α).

116. The composition of claim 115, wherein said RNA bacteriophage is selected from the group consisting of:
(a) bacteriophage Qβ;
(b) bacteriophage R17;
(c) bacteriophage fr;
(d) bacteriophage GA;
(e) bacteriophage SP;
(f) bacteriophage MS2;
(g) bacteriophage M11;
(h) bacteriophage MX1;
(i) bacteriophage NL95;
(j) bacteriophage f2; and
(k) bacteriophage PP7.

117. The composition of claim 115, wherein said bacteriophage is bacteriophage Qβ.

118. The composition of claim 115, wherein said bacteriophage is bacteriophage fr.

119. The composition of claim 115, wherein said bacteriophage is bacteriophage GA.

120. The composition of claim 115, wherein said virus-like particle of an RNA bacteriophage comprises recombinant proteins, or fragments thereof, of an RNA bacteriophage.

121. The composition of claim 120, wherein said bacteriophage is bacteriophage Qβ.

122. The composition of claim 120, wherein said bacteriophage is bacteriophage fr.

123. The composition of claim 120, wherein said bacteriophage is bacteriophage GA.

124. The composition of claim 120, wherein said virus-like particle of an RNA bacteriophage consists essentially of recombinant proteins, or fragments thereof, of an RNA bacteriophage.

125. The composition of claim 115, wherein said virus-like particle of an RNA bacteriophage comprises recombinant coat proteins comprising an amino acid sequence selected from the group consisting of:
(a) SEQ ID NO:159;
(b) SEQ ID NO:160;
(c) SEQ ID NO:161;
(d) SEQ ID NO:162;
(e) SEQ ID NO:163;
(f) SEQ ID NO:164;
(g) SEQ ID NO:165;
(h) SEQ ID NO:166;
(i) SEQ ID NO:167;
(J) SEQ ID NO:215;
(k) SEQ ID NO:253;
(l) SEQ ID NO:217; and
(m) SEQ ID NO:254.

126. The composition of claim 115, wherein said virus-like particle of an RNA bacteriophage consists essentially of recombinant coat proteins comprising an amino acid sequence selected from the group consisting of:
(a) SEQ ID NO:159;
(b) SEQ ID NO:160;
(c) SEQ ID NO:161;
(d) SEQ ID NO:162;
(e) SEQ ID NO:163;
(f) SEQ ID NO:164;
(g) SEQ ID NO:165;
(h) SEQ ID NO:166;
(i) SEQ ID NO:167;
(j) SEQ ID NO:215;
(k) SEQ ID NO:253;

(l) SEQ ID NO:217; and
(m) SEQ ID NO:254.

127. The composition of claim 115, wherein said virus-like particle of an RNA bacteriophage comprises recombinant coat proteins having an amino acid sequence of SEQ ID NO:159, or a mixture of coat proteins having amino acid sequences of SEQ ID NO:159 and of SEQ ID NO:217.

128. The composition of claim 115, wherein said virus-like particle of an RNA bacteriophage consists essentially of coat proteins having an amino acid sequence of SEQ ID NO:159, or consists essentially of a mixture of coat proteins having amino acid sequences of SEQ ID NO:217 and of SEQ ID NO:159.

129. The composition of claim 115, wherein said virus-like particle of an RNA bacteriophage comprises one or more coat proteins of said RNA bacteriophage that have been modified by deletion or substitution to remove at least one naturally occurring lysine residue, or that have been modified by insertion or substitution to add at least one lysine residue.

130. The composition of claim 129, wherein said RNA bacteriophage is Qβ.

131. The composition of claim 115, wherein said virus-like particle of an RNA bacteriophage comprises one or more coat proteins comprising an amino acid sequence selected from the group consisting of:
 (a) SEQ ID NO:255;
 (b) SEQ ID NO:256;
 (c) SEQ ID NO:257;
 (d) SEQ ID NO:258;
 (e) SEQ ID NO:259; and
 (f) a mixture of any one of (a)–(e) and the corresponding A1 protein.

132. The composition of claim 115, wherein said virus-like particle of an RNA bacteriophage comprises one or more coat proteins consisting essentially of an amino acid sequence selected from the group consisting of:
 (a) SEQ ID NO:255;
 (b) SEQ ID NO:256;
 (c) SEQ ID NO:257;
 (d) SEQ ID NO:258;
 (e) SEQ ID NO:259; and
 (f) a mixture of any one of (a)–(e) and the corresponding A1 protein.

133. The composition of claim 115, wherein said organizer is an integral part of said RNA bacteriophage.

134. The composition of claim 115, wherein said organizer is a polypeptide or residue thereof and said second attachment site is a polypeptide or residue thereof.

135. The composition of claim 115, wherein said association is by way of at least one covalent bond.

136. The composition of claim 115, further comprising an amino acid linker.

137. The composition of claim 136, wherein said amino acid linker is bound to said antigen or said antigenic determinant by way of at least one covalent bond.

138. The composition of claim 137, wherein said covalent bond is a peptide bond.

139. The composition of claim 136, wherein said amino acid linker comprises said second attachment site.

140. The composition of claim 136, wherein said amino acid linker is selected from the group consisting of:
 (a) CGG;
 (b) an N-terminal gamma 1-linker;
 (c) an N-terminal gamma 3-linker;
 (d) an Ig hinge region;
 (e) an N-terminal glycine linker;
 (f) $(G)_kC(G)_n$ with n=0–12 and k=0–5;
 (g) an N-terminal glycine-serine linker;
 (h) $(G)_kC(G)_m(S)_l(GGGGS)_n$ with n=0–3, k=0–5, m=0–10, l=0–2 (SEQ ID NO: 424);
 (i) GGC;
 (j) GGC-NH2;
 (k) a C-terminal gamma 1-linker;
 (l) a C-terminal gamma 3-linker;
 (m) a C-terminal glycine linker;
 (n) $(G)_nC(G)_k$ with n=0–12 and k=0–5;
 (o) a C-terminal glycine-serine linker; and
 (p) $(G)_m(S)_l(GGGGS)_n(G)_oC(G)_k$ with n=0–3, k=0–5, m=0–10, l=0–2, and o=0–8 (SEQ ID NO: 425).

141. The composition of claim 136, wherein said amino acid linker comprises a sulfhydryl group or a cysteine residue.

142. The composition of claim 115, wherein said first and said second attachment sites comprise an interacting pair selected from the group consisting of:
 (a) an antigen and an antibody or antibody fragment thereto;
 (b) biotin and avidin;
 (c) streptavidin and biotin;
 (d) a receptor and its ligand;
 (e) a ligand-binding protein and its ligand;
 (f) interacting leucine zipper polypeptides;
 (g) an amino group and a chemical group reactive thereto;
 (h) a carboxyl group and a chemical group reactive thereto; and
 (i) a combination thereof of any of (a)–(h).

143. The composition of claim 115, wherein said first attachment site and said second attachment site are associated through a heterobifunctional linker.

144. The composition of claim 143, wherein said heterobifunctional linker is selected from the group consisting of:
 (a) a maleimidocaproic acid N-hydroxysuccinimide ester;
 (b) N-Succinimidyl 3-(2-pyridyldithio) propionate (SPDP); and
 (c) Sulfo-MBS.

145. The composition of claim 115, wherein said first attachment site comprises an amino group and said second attachment site comprises a sulfhydryl group.

146. The composition of claim 115, wherein said first attachment site is an amino group and said second attachment site is a sulfhydryl group.

147. The composition of claim 115, wherein said first attachment site is a lysine residue and said second attachment site is a cysteine residue.

148. The composition of claim 115, wherein said first attachment site comprises a lysine residue.

149. The composition of claim 115, wherein said first attachment site is a lysine residue.

150. The composition of claim 115, wherein said second attachment site does not naturally occur within said antigen or antigenic determinant.

151. The composition of claim 115, wherein said second attachment site comprises a sulfhydryl group or a cysteine residue.

152. The composition of claim 115, wherein said second attachment site is a sulfhydryl group or is a cysteine residue.

153. The composition of claim 115, wherein said first attachment site does not comprise a sulfhydryl group.

154. The composition of claim 115, wherein said first attachment site is not a sulfhydryl group.

155. The composition of claim 1, wherein said first attachment site does not comprise a sulfhydryl group.

156. The composition of claim 115, wherein said association does not comprise a disulfide bond.

157. The composition of claim 1, wherein said association does not comprise a disulfide bond.

158. The composition of claim 115, wherein said self antigen is angiotensin.

159. The composition of claim 158, wherein said second attachment site does not naturally occur within said antigen or antigenic determinant.

160. The composition of claim 158, wherein said second attachment site comprises a sulfhydryl group or a cysteine residue.

161. The composition of claim 158, wherein said composition further comprises an amino acid linker, and wherein said amino acid linker comprises said second attachment site, and wherein said amino acid linker comprises a sulfhydryl group or a cysteine residue.

162. The composition of claim 158, wherein said self antigen with said second attachment site comprises an amino acid sequence selected from the group consisting of:
  (a) CGGDRVYIHPF (SEQ ID NO: 380);
  (b) CGGDRVYIHPFHL (SEQ ID NO. 381)
  (c) DRVYIHPFHLGGC (SEQ ID NO: 382); and
  (d) CDRVYIHIPFHL (SEQ ID NO: 383).

163. The composition of claim 158, wherein said self antigen with said second attachment site consists of an amino acid sequence selected from the group consisting of:
  (a) CGGDRVYIHPF (SEQ ID NO: 380);
  (b) CGGDRVYIHPFHL (SEQ ID NO. 381)
  (c) DRVYIIHPFHLGGC (SEQ ID NO: 382); and
  (d) CDRVYIHPFHL (SEQ ID NO: 383).

164. The composition of claim 158, wherein said self antigen with said second attachment site consists of the amino acid sequence CGGDRVYIHPF (SEQ ID NO: 380).

165. The composition of claim 115, wherein said self antigen is VEGFR-II.

166. The composition of claim 165, wherein said self antigen is human VEGFR-II.

167. The composition of claim 165, wherein said second attachment site does not naturally occur within said antigen or antigenic determinant.

168. The composition of claim 165, wherein said second attachment site comprises a sulfhydryl group or a cysteine residue.

169. The composition of claim 165, wherein said composition further comprises an amino acid linker, and wherein said amino acid linker comprises said second attachment site, and wherein said amino acid linker comprises a sulfhydryl group or a cysteine residue.

170. The composition of claim 165, wherein said self antigen with said second attachment site comprises the amino acid sequence CTARTELNVGIDFN-WEYPSSKHQHKK (SEQ ID NO:351).

171. The composition of claim 165, wherein said self antigen with said second attachment site consists of the amino acid sequence CTARTELNVGIDFN-WEYPSSKHQHKK (SEQ ID NO:351).

172. The composition of claim 115, wherein said self antigen is tumor necrosis factor-α (TNF-α).

173. The composition of claim 172, wherein said second attachment site does not naturally occur within said antigen or antigenic determinant.

174. The composition of claim 172, wherein said second attachment site comprises a sulfhydryl group or a cysteine residue.

175. The composition of claim 172, wherein said composition further comprises an amino acid linker, and wherein said amino acid linker comprises said second attachment site, and wherein said amino acid linker comprises a sulfhydryl group or a cysteine residue.

176. The composition of claim 172, wherein said self antigen with said second attachment site comprises an amino acid sequence selected from the group consisting of:
  (a) CSSRTPSDKPVAHVVANPQAEGQ (SEQ ID NO:398);
  (b) SSRTPSDKPVAHVVANPQAEGQGGC (SEQ ID NO:399); and
  (c) CGGQLQWLNRRANA (SEQ ID NO:400).

177. The composition of claim 172, wherein said self antigen with said second attachment site consists of an amino acid sequence selected from the group consisting of:
  (a) CSSRTPSDKPVAHVVANPQAEGQ (SEQ ID NO:398);
  (b) SSRTPSDKPVAHVVANPQAEGQGGC (SEQ ID NO:399); and
  (c) CGGQLQWLNRRANA (SEQ ID NO:400).

178. The composition of claim 115, wherein said self antigen is resistin.

179. The composition of claim 178, wherein said self antigen with said second attachment site consists of an amino acid sequence selected from the group consisting of:
  (a) SEQ ID NO:325
  (b) SEQ ID NO:326; and
  (c) SEQ ID NO:327.

180. The composition of claim 115, wherein said self antigen is a lymphotoxin.

181. The composition of claim 180, wherein said lymphotoxin is selected from the group consisting of:
  (a) lymphotoxin α (LTα);
  (b) lymphotoxin β (LTβ); and
  (c) a mixture or combination of LTα and LTβ.

182. The composition of claim 180, wherein said second attachment site does not naturally occur within said antigen or antigenic determinant.

183. The composition of claim 180, wherein said second attachment site comprises a sulfhydryl group or a cysteine residue.

184. The composition of claim 180, wherein said composition further comprises an amino acid linker, and wherein said amino acid linker comprises said second attachment site, and wherein said amino acid linker comprises a sulfhydryl group or a cysteine residue.

185. The composition of claim 180, wherein said lymphotoxin is lymphotoxin β and wherein said lymphotoxin β with said second attachment site comprises an amino acid sequence selected from the group consisting of:
  (a) SEQ ID NO:346; and
  (b) SEQ ID NO:347.

186. The composition of claim 180, wherein said lymphotoxin is lymphotoxin β and wherein said lymphotoxin β with said second attachment site consists of an amino acid sequence selected from the group consisting of:
  (a) SEQ ID NO:346; and
  (b) SEQ ID NO:347.

187. The composition of claim 115, wherein said self antigen is MIF.

188. The composition of claim 187, wherein said self antigen with said second attachment site consists of an amino acid sequence selected from the group consisting of:
  (a) SEQ ID NO:310;
  (b) SEQ ID NO:311;
  (c) SEQ ID NO:312;
  (d) SEQ ID NO:313;
  (e) SEQ ID NO:314; and
  (f) SEQ ID NO:315.

189. The composition of claim 115, wherein said self antigen is RANKL.

190. The composition of claim 189, wherein said self antigen is human-RANKL.

191. The composition of claim 189, wherein said self antigen is an extracellular domain of RANKL.

192. The composition of claim 189, wherein said second attachment site does not naturally occur within said antigen or antigenic determinant.

193. The composition of claim 189, wherein said second attachment site comprises a sulfhydryl group or a cysteine residue.

194. The composition of claim 189, wherein said composition further comprises an amino acid linker, and wherein said amino acid linker comprises said second attachment site, and wherein said amino acid linker comprises a sulfhydryl group or a cysteine residue.

195. The composition of claim 189, wherein said self antigen with said second attachment site comprises the amino acid sequence of SEQ ID NO:320.

196. The composition of claim 189, wherein said self antigen with said second attachment site consists of the amino acid sequence of SEQ ID NO:320.

197. The composition of claim 115, wherein said self antigen is a lymphotoxin receptor.

198. The composition of claim 115, wherein said self antigen is VEGF.

199. The composition of claim 115, wherein said self antigen is Interleukin-5.

200. The composition of claim 115, wherein said self antigen is Interleukin-17.

201. The composition of claim 115, wherein said self antigen is Interleukin-13.

202. The composition of claim 115, wherein said self antigen is CCL21.

203. The composition of claim 115, wherein said self antigen is CXCL12.

204. The composition of claim 115, wherein said self antigen is SDF-1.

205. The composition of claim 115, wherein said self antigen is MCP-1.

206. The composition of claim 115, wherein said self antigen is Endoglin.

207. The composition of claim 115, wherein said self antigen is GHRH.

208. The composition of claim 115, wherein said self antigen is TRH.

209. The composition of claim 115, wherein said self antigen is Eotaxin.

210. The composition of claim 115, wherein said self antigen is Bradykinin.

211. The composition of claim 115, wherein said self antigen is BLC.

212. A pharmaceutical composition comprising:
(a) the composition of claim 115; and
(b) an acceptable pharmaceutical carrier.

213. A method of immunization of an animal comprising administering to said animal the composition of claim 115, wherein an immune response against said antigen or antigenic determinant is produced in said animal.

214. An immunogenic composition comprising the composition of claim 115 and an adjuvant.

215. A method of immunization of an animal comprising administering to said animal the composition of claim 214, wherein an immune response against said antigen or antigenic determinant is produced in said animal.

216. A process for producing a non-naturally occurring, ordered and repetitive antigen array comprising:
(a) providing a non-natural molecular scaffold comprising:
(i) a core particle comprising a virus-like particle of an RNA bacteriophage; and
(ii) an organizer comprising at least one first attachment site, wherein said organizer is connected to said core particle by at least one covalent bond;
(b) providing an antigen or antigenic determinant with at least one second attachment site,
wherein said antigen or antigenic determinant is at least one self antigen, a peptide thereof, or a fragment thereof;
wherein said second attachment site is capable of association through at least one non-peptide bond to said first attachment site; and
wherein said self antigen, peptide or fragment thereof is selected from the group consisting of:
(a) a lymphotoxin;
(b) a lymphotoxin receptor;
(c) RANKL;
(d) VEGF;
(e) VEGFR;
(f) Interleukin-5;
(g) Interleukin-17;
(h) Interleukin-13;
(i) Angiotensin;
(j) CCL21;
(k) CXCL12;
(l) SDF-1;
(m) MCP-1;
(n) Endoglin;
(o) Resistin;
(p) GHRH;
(q) TRH;
(r) MIF;
(s) Eotaxin;
(t) Bradykinin;
(u) BLC;
(v) Tumor Necrosis Factor-α (TNF-α);
(c) combining said non-natural molecular scaffold and said antigen to form an ordered and repetitive antigen array.

217. The process of claim 216, wherein said organizer is a polypeptide or residue thereof; and wherein said second attachment site is a polypeptide or residue thereof.

218. The process of claim 216, wherein said association is by way of at least one covalent bond.

* * * * *